(12) United States Patent
Ding et al.

(10) Patent No.: US 10,087,186 B2
(45) Date of Patent: Oct. 2, 2018

(54) COMPOUNDS AS LRRK2 KINASE INHIBITORS

(71) Applicant: GLAXOSMITHKLINE INTELLECTUAL PROPERTY DEVELOPMENT LIMITED, Brentford, Middlesex (GB)

(72) Inventors: Xiao Ding, Shanghai (CN); Luigi Piero Stasi, Shanghai (CN); Zehong Wan, Shanghai (CN); Colin Michael Edge, Shanghai (CN)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 15/114,858

(22) PCT Filed: Jan. 28, 2015

(86) PCT No.: PCT/CN2015/000055
§ 371 (c)(1),
(2) Date: Jul. 28, 2016

(87) PCT Pub. No.: WO2015/113452
PCT Pub. Date: Aug. 6, 2015

(65) Prior Publication Data
US 2017/0015668 A1  Jan. 19, 2017

(30) Foreign Application Priority Data
Jan. 29, 2014 (WO) ................ PCT/CN2014/000139

(51) Int. Cl.
*C07D 487/04* (2006.01)
*A61K 31/519* (2006.01)

(52) U.S. Cl.
CPC .......... *C07D 487/04* (2013.01); *A61K 31/519* (2013.01)

(58) Field of Classification Search
CPC ........................... C07D 487/04; A61K 31/519
See application file for complete search history.

(56) References Cited

U.S. PATENT DOCUMENTS

| | | |
|---|---|---|
| 7,855,205 B2 | 12/2010 | Huang et al. |
| 7,998,978 B2 | 8/2011 | Huang et al. |
| 9,156,775 B2 | 10/2015 | Thiele et al. |
| 9,315,449 B2 | 4/2016 | Thiele et al. |
| 9,353,116 B2 | 5/2016 | Garske et al. |
| 9,815,841 B2 | 11/2017 | Ding et al. |
| 2005/0070542 A1 | 3/2005 | Hodgetts et al. |
| 2007/0275984 A1 | 11/2007 | Imogai et al. |
| 2008/0004295 A1 | 1/2008 | Gore et al. |
| 2009/0325964 A1 | 12/2009 | Bursavich et al. |
| 2012/0094999 A1 | 4/2012 | Gray et al. |
| 2012/0122838 A1 | 5/2012 | Ren et al. |
| 2012/0165329 A1 | 6/2012 | Ibrahim et al. |
| 2013/0079324 A1 | 3/2013 | Cheng et al. |
| 2014/0018540 A1 | 1/2014 | Sheridan et al. |
| 2014/0031547 A1 | 1/2014 | Sheridan et al. |
| 2015/0209368 A1 | 7/2015 | Sheridan et al. |
| 2016/0058745 A1 | 3/2016 | Sheridan et al. |

FOREIGN PATENT DOCUMENTS

| | | |
|---|---|---|
| CN | 102482277 A | 5/2012 |
| CN | 103492389 A | 1/2014 |
| WO | WO2009/036066 | 3/2009 |
| WO | 2012045195 A1 | 9/2010 |
| WO | 2010129053 A1 | 11/2010 |
| WO | WO2011/038572 | 4/2011 |
| WO | WO2012/009258 | 1/2012 |
| WO | WO2012/062783 | 5/2012 |
| WO | 2012143144 A1 | 10/2012 |
| WO | 2013042006 A1 | 3/2013 |
| WO | WO2013/079496 | 6/2013 |
| WO | WO2013/139882 | 9/2013 |
| WO | 2013164321 A1 | 11/2013 |
| WO | 2013164323 A1 | 11/2013 |
| WS | WO2014/001973 | 1/2014 |

OTHER PUBLICATIONS

Chan et al., Discovery of a Highly Selective, Brain-Penetrant Aminopyrazole LRRK2 Inhibitor. ACS Med Chem Lett. Nov. 23, 2012;4(1):85-90.
Deng et al., Leucine-rich repeat kinase 2 inhibitors: a patent review (2006-2011). Expert Opin Ther Pat. Dec. 2012;22(12):1415-26.
Estrada et al., Discovery of highly potent, selective, and brain-penetrable leucine-rich repeat kinase 2 (LRRK2) small molecule inhibitors. J Med Chem. Nov. 26, 2012;55(22):9416-33.
Estrada et al., Discovery of highly potent, selective, and brain-penetrant aminopyrazole leucine-rich repeat kinase 2 (LRRK2) small molecule inhibitors. J Med Chem. Feb. 13, 2014;57(3):921-36.
Kethiri et al., Leucine-rich repeat kinase 2 inhibitors: a review of recent patents (2011-2013). Expert Opin Ther Pat. Jul. 2014;24(7):745-57.
Extended European Search Report 15743797.1 dated May 15, 2017.

*Primary Examiner* — Susanna Moore
(74) *Attorney, Agent, or Firm* — Nora L. Stein; Kathryn A. Lutomski

(57) ABSTRACT

The present invention relates to novel compounds that inhibit LRRK2 kinase activity, processes for their preparation, to compositions containing them and to their use in the treatment of or prevention of diseases characterized by LRRK2 kinase activity, for example Parkinson's disease, Alzheimer's disease and amyotrophic lateral sclerosis (ALS).

15 Claims, No Drawings

COMPOUNDS AS LRRK2 KINASE INHIBITORS

This application is a 371 of International Application No. PCT/CN2015/000055, filed 28 Jan. 2015, which claims priority to PCT/CN2014/000139, filed 29 Jan. 2014.

RELATED APPLICATION

The present application claims priority from PCT International Application No. PCT/CN2014/000139 filed on Jan. 29, 2014 at the State Intellectual Property Office of the People's Republic of China, the entire contents of which is incorporated herein by reference.

FIELD OF THE INVENTION

The present invention relates to novel compounds that inhibit LRRK2 kinase activity, processes for their preparation, compositions containing them and their use in the treatment of diseases characterized by LRRK2 kinase activity, for example, Parkinson's disease, amyotrophic lateral sclerosis (ALS) and Alzheimer's disease.

BACKGROUND OF THE INVENTION

Parkinson's disease (PD) is a neurodegenerative disorder characterized by selective degeneration and cell death of dopaminergic neurons in the substantial nigra region of the brain. Parkinson's disease was generally considered to be sporadic and of unknown etiology, but, in the last 15 years, there has been an important development of the understanding of the genetic basis of this disease and associated pathogenic mechanisms. One area of the development is the understanding of leucine rich repeat kinase 2 (LRRK2) protein. A number of mis-sense mutations in the LRRK2 gene have been strongly linked with autosomal dominant Parkinson's disease in familial studies (See WO2006068492 and WO2006045392; Trinh and Farrer 2013, Nature Reviews in Neurology 9: 445-454; Paisan-Ruiz et al., 2013, J. Parkinson's Disease 3: 85-103). The G2019S mutation in LRRK2 is the most frequent mis-sense mutation and is associated with a clinical phenotype that closely resembles sporadic Parkinson's disease. The LRRK2 G2019S mutation is also present in approximately 1.5% of sporadic Parkinson's disease cases (See Gilks et al., 2005, Lancet, 365: 415-416). In addition to the known pathogenic coding mutations in LRRK2, additional amino acid coding variants of LRRK2 have been identified that are also associated with risk of developing Parkinson's disease (See Ross et al., 2011 Lancet Neurology 10: 898-908). Furthermore, genome-wide association studies (GWAS) have identified LRRK2 as a Parkinson's disease susceptibility locus, which indicates that LRRK2 may be also relevant to sporadic Parkinson's disease cases without mutations that cause amino acid substitutions in the LRRK2 protein. (See Satake et al., 2009 Nature Genetics 41:1303-1307; Simon-Sanchez et al 2009 Nature Genetics 41: 1308-1312)

LRRK2 is a member of the ROCO protein family and all members of this family share five conserved domains. The most common pathogenic mutation G2019S occurs in the highly conserved kinase domain of LRRK2. This mutation confers an increase in the LRRK2 kinase activity in in vitro enzyme assays of recombinant LRRK2 proteins (See Jaleel et al., 2007, Biochem J, 405: 307-317) and in LRRK2 proteins purified from G2019S PD patient-derived cells (See Dzamko et al., 2010 Biochem. J. 430: 405-413). A less frequent LRRK2 pathogenic mutation that confers amino acid substitution at a different residue, R1441, has also been shown to elevate LRRK2 kinase activity by decreasing the rate of GTP hydrolysis by the GTPase domain of LRRK2 (See Guo et al., 2007 Exp Cell Res. 313: 3658-3670; West et al., 2007 Hum. Mol Gen. 16: 223-232). Therefore, the evidence indicates that the kinase and GTPase activities of LRRK2 are Important for pathogenesis, and that the LRRK2 kinase domain may regulate overall LRRK2 function (See Cookson, 2010 Nat. Rev. Neurosci. 11: 791-797).

There is evidence to show that the increased LRRK2 kinase activity is associated with neuronal toxicity in cell culture models (See Smith et al., 2006 Nature Neuroscience 9: 1231-1233) and kinase inhibitor compounds protect against LRRK2-mediated cell death (See Lee et al., 2010 Nat. Med. 16: 998-1000).

Induced pluripotent stem cells (iPSCs) derived from LRRK2 G2019S Parkinson's disease patients have been found to exhibit defects in neurite outgrowth and increased susceptibility to rotenone, that may be ameliorated by either genetic correction of the G2019S mutation or treatment of cells with small molecule inhibitors of LRRK2 kinase activity (See Reinhardt et al., 2013 Cell Stem Cell 12: 354-367). Increased mitochondrial damage associated with LRRK2 G2019S mutation in ISPCs is also blocked by genetic correction of the G2019S mutation (See Sanders et al., 2013 Neurobiol. Dis. 62: 381-386).

Additional evidence links LRRK2 function and dysfunction with autophagy-lysosomal pathways (See Manzoni and Lewis, 2013 Faseb J. 27:3234-3429). LRRK2 proteins confer defects in chaperone-mediated autophagy that negatively impact the ability of cells to degrade alpha-synuclein (Orenstein et al., 2013 Nature Neurosci. 16 394-406). In other cell models, selective LRRK2 inhibitors have been shown to stimulate macroautophagy (See Manzoni et al., 2013 BBA Mol. Cell Res. 1833: 2900-2910). These data suggest that small molecule inhibitors of LRRK2 kinase activity may have utility in the treatment of diseases characterized by defects in cellular proteostasis that result from aberrant autophagy/lysosomal degradation pathways including forms of Parkinson's disease associated with GBA mutations (See Swan and Saunders-Pullman 2013 Curr. Neurol. Neurosci Rep. 13: 368), other alpha-synucleinopathies, tauopathies, Alzheimer's disease (See Li et al., 2010 Neurodegen. Dis. 7: 265-271) and other neurodegenerative diseases (See Nixon 2013 Nat. Med. 19: 983-997) and Gaucher disease (See Westbroek et al., 2011 Trends. Mol. Med. 17: 485-493). Further, significantly elevated levels of LRRK2 mRNA have also been observed in fibroblasts of Niemann-Pick Type C (NPC) disease patients compared with fibroblasts of normal subjects, which indicates that aberrant LRRK2 function may play a role in lysosomal disorders (See Reddy et al., 2006 PLOS One 1 (1):e19 doi: 10.1371/journal.pone.0000019—supporting information Dataset S1). This observation suggests that LRRK2 inhibitors may have utility for treatment of NPC.

The PD-associated G2019S mutant form of LRRK2 has also been reported to enhance phosphorylation of tubulin-associated Tau (See Kawakami et al., 2012 PLoS ONE 7: e30834, doi 10.1371), and disease models have been proposed in which LRRK2 acts upstream of the pathogenic effects of Tau and alpha-synuclein (See Taymans & Cookson, 2010, BioEssays 32: 227-235). In support of this, LRRK2 expression has been associated with increased aggregation of insoluble Tau, and increased Tau phosphorylation, in a transgenic mouse model (See Bailey et al., 2013 Acta Neuropath. 126:809-827). Over-expression of the PD pathogenic mutant protein LRRK2 R1441G is reported to cause symptoms of Parkinson's disease and hyperphosphorylation of Tau in transgenic mouse models (See Li, Y. et al. 2009, Nature Neuroscience 12: 826-828). Therefore, these data suggest that LRRK2 inhibitors of kinase catalytic activity may be useful for the treatment of tauopathy diseases characterized by hyperphosphorylation of Tau such as argyrophilic grain disease, Pick's disease, corticobasal degeneration, progressive supranuclear palsy and inherited frontotemporal dementia and parkinsonism linked to chromosome 17 (FTDP-17) (See Goedert, M and Jakes, R (2005) Biochemica et Biophysica Acta 1739, 240-250). In addition, LRRK2 inhibitors may have utility in treatment of other diseases characterized by diminished dopamine levels such as withdrawal symptoms/relapse associated with drug addiction (See Rothman et al., 2008, Prog. Brain Res, 172: 385).

Other studies have also shown that overexpression of the G2019S mutant form of LRRK2 confers defects in subventricular zone (SVZ) neuroprogenitor cell proliferation and migration in transgenic mouse models (See Winner et al., 2011 Neurobiol. Dis. 41: 706-716) and reduces neurite length and branching cell culture models (See Dachsel et al., 2010 Parkinsonism & Related Disorders 16: 650-655). Moreover, it was reported that agents that promote SVZ neuroprogenitor cell proliferation and migration also improve neurological outcomes following ischemic injury in rodent models of stroke (See Zhang et al., 2010 J. Neurosci. Res. 88: 3275-3281). These findings suggest that compounds that inhibit aberrant activity of LRRK2 may have utility for the treatments designed to stimulate restoration of CNS functions following neuronal injury, such as ischemic stroke, traumatic brain injury, spinal cord injury.

Mutations in LRRK2 have also been identified that are clinically associated with the transition from mild cognitive impairment (MCI) to Alzheimer's disease (See WO2007149798). These data suggest that inhibitors of LRRK2 kinase activity may be useful for the treatment diseases such as Alzheimer's disease, other dementias and related neurodegenerative disorders.

Aberrant regulation of normal LRRK2 proteins is also observed in some disease tissues and models of disease. Normal mechanisms of translational control of LRRK2 by miR-205 are perturbed in some sporadic PD cases, where significant decreases in miR-205 levels in PD brain samples concur with elevated LRRK2 protein levels in those samples (See Cho at al., (2013) Hum. Mol. Gen. 22: 608-620). Therefore, LRRK2 inhibitors may be used in treatment of sporadic PD patients who have elevated levels of normal LRRK2 proteins.

In an experimental model of Parkinson's disease in marmosets, an elevation of LRRK2 mRNA is observed in a manner that correlates with the level of L-Dopa induced dyskinesia (See Hurley, M. J et al., 2007 Eur. J. Neurosci. 26: 171-177). This suggests that LRRK2 inhibitors may have a utility in amelioration of such dyskinesias.

Significantly elevated levels of LRRK2 mRNA have been reported in ALS patient muscle biopsy samples (See Shtilbans et al., 2011 Amyotrophic Lateral Sclerosis 12: 250-256) It is suggested that elevated levels of LRRK2 kinase activity may be a characteristic feature of ALS. Therefore, this observation indicated that LRRK2 inhibitor may have utility for treatment of ALS.

There is also evidence indicating that LRRK2 kinase activity may play a role in mediating microglial proinflammatory responses (See Moehle et al., 2012, J. Neuroscience 32: 1602-1611). This observation suggests a possible utility of LRRK2 inhibitors for treatment of aberrant neuroinflammatory mechanisms that contribute a range of neurodegenerative diseases, including Parkinson's disease, Alzheimer's disease, multiple sclerosis, HIV-induced dementia, amyotrophic lateral sclerosis, ischemic stroke, traumatic brain injury and spinal cord injury. Some evidence also indicates that LRRK2 plays a role in regulating neuronal progenitor differentiation in vitro (See Milosevic, J. et al., 2009 Mol. Neurodegen. 4: 25). This evidence suggests that inhibitors of LRRK2 may have a utility in production of neuronal progenitor cells in vitro for consequent therapeutic application in cell based-treatment of CNS disorders.

It has been reported that Parkinson's disease patients bearing LRRK2 G2019S mutation display increased frequency of non-skin cancers, including renal, breast, lung, prostate cancers as well as acute myelogenous leukemia (AML). Since there is evidence to show that G2019S mutation in LRRK2 increases catalytic activity of the LRRK2 kinase domain, small molecule inhibitors of LRRK2 may have a utility in treatment of cancers, for example kidney cancer, breast cancer, lung cancer, prostate cancer (e.g. solid tumors) and blood cancer (See. AML; Saunders-Pullman et al., 2010, Movement Disorders, 25:2536-2541; Inzelberg et al., 2012 Neurology 78: 781-786). Amplification and over-expression of LRRK2 has also been reported in papillary renal and thyroid carcinomas, where co-operativity between LRRK2 and the MET oncogene may promote tumor cell growth and survival (See Looyenga et al., 2011 PNAS 108: 1439-1444.)

Some studies suggested that genetic association of common LRRK2 variants with susceptibility to ankylosing spondylitis (See Danoy P, et al., 2010. PLoS Genet.; 6(12): e1001195; and leprosy infection. (See Zhang F R, et al. 2009, N Engl J Med. 361:2609-18.) These findings suggest that inhibitors of LRRK2 may have a utility in the treatment of ankylosing spondylitis and leprosy infection.

Meta-analysis of three genome wide associated scans for Crohn's disease identified a number of loci associated with the disease, including the locus containing the LRRK2 gene (See Barrett et al., 2008, Nature Genetics, 40: 955-962). Evidence has also emerged that LRRK2 is an IFN-γ target gene that may be involved in signaling pathways relevant to Crohn's disease pathogenesis (See Gardet et al., 2010, J. Immunology, 185: 5577-5585). These findings suggest that inhibitors of LRRK2 may have utility in the treatment of Crohn's disease.

As an IFN-γ target gene, LRRK2 may also play a role in T cell mechanisms that underlie other diseases of the immune system such as multiple sclerosis and rheumatoid arthritis. Further potential utility of LRRK2 inhibitors comes from the reported finding that B lymphocytes constitute a major population of LRRK2 expressing cells (See Maekawa et al. 2010, BBRC 392: 431-435). This suggests that LRRK2 inhibitors may be effective in treatment of diseases of the immune system for which B cell depletion is, or may be, effective in diseases such as lymphomas, leukemias, multiple sclerosis (See Ray et al., 2011 J. Immunol. 230: 109), rheumatoid arthritis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease and inflammatory myopathies (See Engel et al., 2011 Pharmacol. Rev. 63: 127-156; Homam et al., 2010 J. Clin. Neuromuscular Disease 12: 91-102).

SUMMARY OF THE INVENTION

The present invention provides, in a first aspect, a compound of Formula (I) or a pharmaceutically acceptable salt thereof

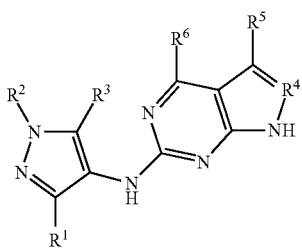

(I)

wherein
$R^1$ is selected from the group consisting of H, $C_{1-3}$alkoxyl, $C_{1-3}$alkyl, and halo;
$R^2$ is $C_{1-5}$alkyl optionally substituted with one or more substituents independently selected from the group consisting of OH, $C_{1-3}$alkoxyl, halo, and CN
or $R^2$ is —$(CR_aR_b)_n$—Y, wherein
n is 0, 1, or 2,
each occurrence of $R_a$ and $R_b$ are independently H or methyl,
Y is
1) a four to six-membered heterocyclyl optionally substituted with one or more substituents independently selected from the group consisting of $C_{1-3}$alkyl, halo, OH, oxetanyl, $C_{1-3}$haloalkyl, and morpholinyl;
2) $C_{3-6}$cycloalkyl optionally substituted with one or more substituents independently selected from the group consisting of $C_{1-3}$alkyl, halo, OH, oxetanyl, $C_{1-3}$haloalkyl, and morpholinyl, or
3)

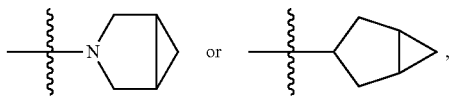

either of which is optionally substituted with one OH group;
$R^3$ is selected from the group consisting of H, $C_{1-3}$alkoxyl, $C_{1-3}$alkyl, $C_{3-6}$cycloalkyl, and halo;
$R^4$ is CH or N;
$R^5$ is H, CN or methyl; and
$R^6$ is selected from the group consisting of $C_{1-3}$alkoxy, and —O—CH—C cycloalkyl.

In a further aspect of the Invention, the invention provides a pharmaceutical composition comprising a compound of Formula (I) or a pharmaceutically acceptable salt thereof and a pharmaceutically acceptable carrier.

A further aspect, the invention provides a compound of Formula (I) or a pharmaceutically acceptable salt thereof for use in the treatment or prevention of Parkinson's disease or Alzheimer's disease.

DETAILED DESCRIPTION OF THE INVENTION

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are Intended to Include the plural forms as well, unless the context clearly indicates otherwise. Also, as used herein, "and/or" refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Generally, the nomenclature used herein and the laboratory procedures in organic chemistry, medicinal chemistry, biology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

All patents, patent applications and publications referred to herein are Incorporated by reference in their entirety. In case of a conflict in terminology, the present specification is controlling.

A. Definitions

As used herein, "alkyl" refers to a monovalent, saturated hydrocarbon chain having a specified number of carbon atoms. For example, $C_{1-3}$ alkyl refers to an alkyl group having from 1 to 3 carbon atoms. $C_1$ alkyl refers to an alkyl group having from 1 to 5 carbon atoms. Alkyl groups may be straight or branched. In some embodiments, branched alkyl groups may have one, two, or three branches. Exemplary alkyl groups include, but are not limited to, methyl, methylethyl, ethyl, propyl (n-propyl and isopropyl), methylpropyl, butyl (n-butyl, isobutyl, and t-butyl), pentyl (n-pentyl, isopentyl, and neopentyl), and hexyl.

As used herein, "alkoxy" refers to the group —O-alkyl. For example, $C_{1-5}$ alkoxyl groups contain from 1 to 5 carbon atoms. $C_{1-3}$ alkoxyl groups contain from 1 to 3 carbon atoms. Exemplary alkoxy groups include, but are not limited to, methoxy, ethoxy, propoxy, butoxyl, and pentyloxy.

As used herein, "cycloalkyl" refers to a saturated monocyclic hydrocarbon ring of 3 to 10 carbon atoms as member atoms in the ring. For example, $C_{3-6}$ cycloalkyl contains 3 to 6 carbon atoms as member atoms in the ring. For example, $C_{4-6}$ cycloalkyl contains 4 to 6 carbon atoms as member atoms in the ring. Examples of cycloalkyl include cyclopropyl, cyclobutyl, cyclopentyl and cyclohexyl.

As used herein, "enantiomeric excess" or "ee" is the excess of one enantiomer over the other expressed as a percentage. As a result, since both enantiomers are present in equal amounts in a racemic mixture, the enantiomeric excess is zero (ee=0%). However, if one enantiomer is enriched such that it constitutes 95% of the product, the enantiomeric excess is 90% (the amount of the enriched enantiomer, 95%, minus the amount of the other enantiomer, 5%).

As used herein, "halogen" refers to fluorine (F), chlorine (Cl), bromine (Br), or iodine (I). "Halo" refers to the halogen radicals: fluoro (—F), chloro (—Cl), bromo (—Br), or iodo (—I).

As used herein, "haloalkyl" refers to an alkyl group, as defined above, having one or more halogen atoms selected from F, Cl, Br, and I, which are substituted on any or all of the carbon atoms of the alkyl group by replacing hydrogen atoms attached to the carbon atoms. For example, $C_{1-3}$haloalkyl refers to a $C_{1-3}$alkyl group substituted with one or more halogen atoms. In some embodiments, "haloalkyl" refers to an alkyl group substituted with one or more halogen atoms independently selected from F and Cl. Exemplary haloalkyl groups include, but are not limited to, chloromethyl, bromoethyl, trifluoromethyl, dichloromethyl, difluoromethyl and difluoroethyl.

As used herein, "four to six-membered heterocyclyl" refers to a four to six-membered monoheterocyclic ring which is saturated and which contains one or two heteroatoms independently selected from N, S and O. Examples of four to six-membered heterocycyl include, but are not limited to, tetrahydro-2H-pyranyl, tetrahydrofuranyl, pyrrolidinyl, piperidinyl, oxetanyl, morpholinyl, and azetidinyl.

As used herein, "substituted" in reference to a group indicates that one or more hydrogen atom attached to a member atom (e.g., carbon atom) within the group is replaced with a substituent selected from the group of defined substituents. It should be understood that the term "substituted" includes the implicit provision that such substitution is in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituent, one or more (as appropriate) member atom within the group may be substituted. In addition, a single member atom within the group may be substituted with more than one substituent as long as such substitution is in accordance with the permitted valence of the atom. Exemplary substituents include, but are not limited to, alkyl, alkoxyl, halo, haloalkyl, OH, CN, morpholinyl and oxetanyl. Suitable substituents are defined herein for each substituted or optionally substituted group.

As used herein, "optionally substituted" indicates that a group, such as alkyl, heterocyclyl cycloalkyl,

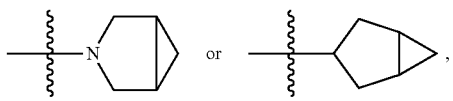

may be unsubstituted or may be substituted with one or more substituent as defined.

As used herein, the term "disease" refers to any alteration in state of the body or of some of the organs, interrupting or disturbing the performance of the functions and/or causing symptoms such as discomfort, dysfunction, distress, or even death to the person afflicted or those in contact with a person. A disease can also include a distemper, ailing, ailment, malady, disorder, sickness, illness, complain, interdisposition and/or affectation.

As used herein, "treat", "treating" or "treatment" in reference to a disease means: (1) to ameliorate the disease or one or more of the biological manifestations of the disease, (2) to interfere with (a) one or more points in the biological cascade that leads to or is responsible for the disease or (b) one or more of the biological manifestations of the disease, (3) to alleviate one or more of the symptoms or effects associated with the disease, (4) to slow the progression of the disease or one or more of the biological manifestations of the disease, and/or (5) to diminish the likelihood of severity of a disease or biological manifestations of the disease.

As used herein, "prevent", "preventing" or "prevention" means the prophylactic administration of a drug to diminish the likelihood of the onset of or to delay the onset of a disease or biological manifestation thereof.

As used herein, "subject" means a mammalian subject (e.g., dog, cat, horse, cow, sheep, goat, monkey, etc.), and human subjects including both male and female subjects, and including neonatal, infant, juvenile, adolescent, adult and geriatric subjects, and further including various races and ethnicities including, but not limited to, white, black, Asian, American Indian and Hispanic.

As used herein, "pharmaceutically acceptable salt(s)" refers to salt(s) that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively.

As used herein, "therapeutically effective amount" in reference to a compound of the invention or other pharmaceutically-active agent means an amount of the compound sufficient to treat or prevent the patient's disease but low enough to avoid serious side effects (at a reasonable benefit/risk ratio) within the scope of sound medical judgment. A therapeutically effective amount of a compound will vary with the particular compound chosen (e.g. consider the potency, efficacy, and half-life of the compound); the route of administration chosen; the disease being treated; the severity of the disease being treated; the age, size, weight, and physical disease of the patient being treated; the medical history of the patient to be treated; the duration of the treatment; the nature of concurrent therapy; the desired therapeutic effect; and like factors, but can nevertheless be routinely determined by the skilled artisan.

B. Compounds

This invention provides, in a first aspect, a compound of Formula (I) or a pharmaceutically acceptable salt thereof

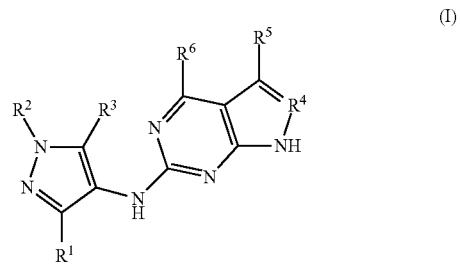

wherein
$R^1$ is selected from the group consisting of H, $C_{1-3}$alkoxyl, $C_{1-3}$alkyl, and halo;
$R^2$ is $C_{1-5}$alkyl optionally substituted with one or more substituents independently selected from the group consisting of OH, $C_{1-3}$alkoxyl, halo, and CN or R² is —(CRₐRᵦ)ₙ—Y, wherein
  n is 0, 1, or 2,
  each occurrence of Rₐ and Rᵦ are independently H or methyl,
  Y is
    1) a four to six-membered heterocyclyl optionally substituted with one or more substituents independently selected from the group consisting of $C_{1-3}$ alkyl, halo, OH, oxetanyl, $C_{1-3}$haloalkyl, and morpholinyl;
    2) $C_{3-6}$cycloalkyl optionally substituted with one or more substituents independently selected from the group consisting of $C_{1-3}$alkyl, halo, OH, oxetanyl, $C_{1-3}$haloalkyl, and morpholinyl, or
    3)

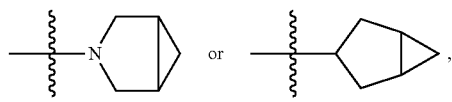

either of which is optionally substituted with one OH group;
$R^3$ is selected from the group consisting of H, $C_{1-3}$alkoxyl, $C_{1-3}$alkoxyl, $C_{3-6}$cycloalkyl, and halo;
$R^4$ is CH or N;
$R^5$ is H, CN or methyl; and
$R^6$ is selected from the group consisting of $C_{1-3}$alkoxy, and —O—$CH_2$—$C_{3-6}$cycloalkyl.

In one embodiment, the present invention relates to a compound of Formula (I) or a pharmaceutically acceptable salt thereof (I)

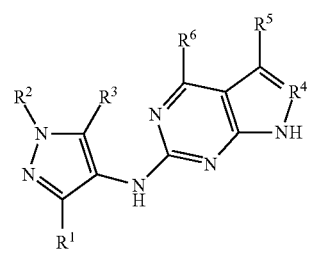

wherein
  $R^1$ is independently selected from the group consisting of H, $C_{1-3}$alkyl, and halo;
  $R^2$ is $C_{1-5}$alkyl optionally substituted with one or more substituents independently selected from the group consisting of OH, $C_{1-3}$alkoxyl, halo, and CN,
  or $R^2$ is —(CH₂)ₙ—Y, wherein
    n is 0, 1, or 2,
    Y is
      1) a four to six-membered heterocyclyl optionally substituted with one or two (or one, two or three) substituents independently selected from the group consisting of $C_{1-3}$alkyl, halo, OH and oxetanyl,
      2) a $C_{3-6}$cycloalkyl optionally substituted with one or two (or one, two or three) substituents independently selected from the group consisting of $C_{1-3}$alkyl, halo and OH, or
    3)

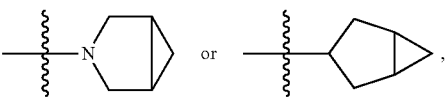 [SMILES: *N1CC2CC2C1 ; *C1CC2CC2C1]

either of which is optionally substituted with one OH group;
$R^3$ is selected from the group consisting of H, $C_{1-3}$alkoxyl, $C_{1-3}$alkyl, $C_{3-6}$cycloalkyl, and halo;
$R^4$ is CH or N;
$R^5$ is H, CN or methyl; and
$R^6$ is selected from the group consisting of $C_{1-3}$alkoxyl, and —O—$CH_2$—$C_{3-6}$cycloalkyl.

In one embodiment, the present invention relates to a compound of Formula (I) or a pharmaceutically acceptable salt thereof (I)

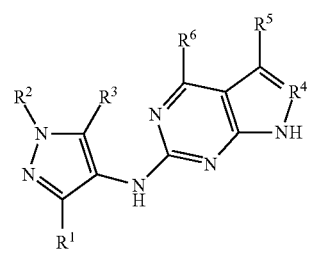

wherein
  $R^1$ is independently selected from the group consisting of H, $C_{1-3}$alkoxyl, $C_{1-3}$alkyl, and halo;
  $R^2$ is C alkyl optionally substituted with one or more substituents independently selected from the group consisting of OH, $C_{1-3}$alkoxyl, halo, and CN
  or $R^2$ is —(CRₐRᵦ)ₙ—Y, wherein
    n is 0, 1, or 2,
    each occurrence of Rₐ and Rᵦ are independently H or methyl,
    Y is
      1) $C_{3-6}$cycloalkyl optionally substituted with one or more substituents Independently selected from the group consisting of $C_{1-3}$alkyl, halo, OH, oxetanyl, $C_{1-3}$haloalkyl, and morpholinyl, or
    2)

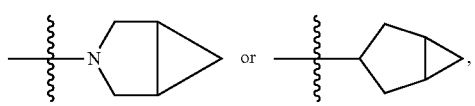

either of which is optionally substituted with one OH group;
$R^3$ is selected from the group consisting of H, $C_{1-3}$alkoxyl, $C_{1-3}$alkyl, $C_{3-6}$cycloalkyl, and halo;
$R^4$ is CH or N;
$R^5$ is H, CN or methyl; and
$R^6$ is selected from the group consisting of $C_{1-3}$alkoxy, and —O—$CH_2$—$C_{3-6}$cycloalkyl.

In one embodiment, this invention relates to compounds of Formula (I), wherein $R^1$ is selected from the group consisting of H, $C_{1-3}$alkyl, and halo, or pharmaceutically acceptable salts thereof.

In one embodiment, this invention relates to compounds of Formula (I), wherein $R^1$ is H, methyl or Cl, or pharmaceutically acceptable salts thereof.

In one embodiment, this invention relates to compounds of Formula (I), wherein $R^1$ is H or methyl, or pharmaceutically acceptable salts thereof.

In one embodiment, this invention relates to compounds of Formula (I), wherein $R^1$ is H, or pharmaceutically acceptable salts thereof.

In another embodiment, this invention relates to compounds of Formula (I) and any of the above applicable embodiments, wherein $R^2$ is $C_{1-5}$alkyl optionally substituted with one or more substituents independently selected from the group consisting of OH, $C_{1-3}$alkoxyl, halo, and CN, or pharmaceutically acceptable salts thereof.

In one embodiment, this invention relates to compounds of Formula (I) and any of the above applicable embodiments, wherein $R^2$ is $C_{1-5}$alkyl optionally substituted with one or more substituents independently selected from the group consisting of OH, methoxyl, Cl, F and CN, or pharmaceutically acceptable salts thereof.

In one embodiment, this invention relates to compounds of Formula (I) and any of the above applicable embodiments, wherein $R^2$ is $C_{1-5}$alkyl optionally substituted with one, two, or three substituents independently selected from the group consisting of OH, methoxyl, Cl, F and CN, or pharmaceutically acceptable salts thereof.

In one embodiment, this invention relates to compounds of Formula (I) and any of the above applicable embodiments, wherein $R^2$ is —$(CR_aR_b)_n$—Y, wherein Y is a four to six-membered heterocyclyl optionally substituted with one or more substituents independently selected from the group consisting of $C_{1-3}$alkyl, halo, OH, oxetanyl, $C_{1-3}$haloalkyl, and morpholinyl.

In another embodiment, this invention relates to compounds of Formula (I) and any of the above applicable embodiments, wherein $R^2$ is —$(CH_2)_n$—Y, n is 0, 1, or 2, and Y is a four to six-membered heterocyclyl optionally substituted with one or two substituents independently selected from the group consisting of $C_{1-3}$alkyl, halo, OH and oxetanyl, or pharmaceutically acceptable salts thereof.

In one embodiment, this invention relates to compounds of Formula (I) and any of the above applicable embodiments, wherein $R^2$ is —$(CH_2)_n$—Y, n is 0, 1, or 2, and Y is a four to six-membered heterocyclyl selected from the group consisting of tetrahydro-2H-pyranyl, tetrahydrofuranyl, pyrrolidinyl, piperidinyl, oxetanyl, and morpholinyl, wherein the heterocyclyl is optionally substituted with one, two or three substituents independently selected from the group consisting of $C_{1-3}$alkyl, halo, OH and oxetanyl, or pharmaceutically acceptable salts thereof.

In one embodiment, this invention relates to compounds of Formula (I) and any of the above applicable embodiments, wherein $R^2$ is —$(CH_2)_n$—Y, n is 0, 1, or 2, and Y is a four to six-membered heterocyclyl selected from the group consisting of tetrahydro-2H-pyranyl, tetrahydrofuranyl, pyrrolidinyl, piperidinyl, oxetanyl, and morpholinyl, wherein the heterocyclyl is optionally substituted with one or two substituents independently selected from the group consisting of $C_{1-3}$alkyl, halo, OH and oxetanyl, or pharmaceutically acceptable salts thereof.

In another embodiment, this invention relates to compounds of Formula (I) and any of the above applicable embodiments, wherein $R^2$ is —$(CH_2)_n$—Y, n is 0, 1 or 2 and Y is a four to six-membered heterocyclyl selected from the group consisting of azetidinyl, tetrahydro-2H-pyranyl, tetrahydrofuranyl, pyrrolidinyl, piperidinyl, oxetanyl, and morpholinyl, wherein the heterocyclyl is optionally substituted with one, two or three substituents independently selected from the group consisting of $C_{1-3}$alkyl, halo, OH and oxetanyl, or pharmaceutically acceptable salts thereof.

In another embodiment, this invention relates to compounds of Formula (I) and any of the above applicable embodiments, wherein $R^2$ is —$(CH_2)_n$—Y, n is 0 and Y is a four to six-membered heterocyclyl selected from the group consisting of tetrahydro-2H-pyranyl, piperidinyl, and morpholinyl, wherein the heterocyclyl is optionally substituted with one, two or three substituents independently selected from the group consisting of $C_{1-3}$alkyl, halo, OH and oxetanyl, or pharmaceutically acceptable salts thereof.

In certain embodiment, this invention relates to compounds of Formula (I) and any of the above applicable embodiments, wherein $R^2$ is —$(CH_2)_n$—Y, n is 0 or 2 and Y is a four to six-membered heterocyclyl selected from the group consisting of azetidin-1-yl, tetrahydro-2H-pyran-4-yl, tetrahydro-2H-pyran-3-yl, tetrahydrofuran-3-yl, pyrrolidin-1-yl, pyrrolidin-3-yl, piperidin-3-yl, piperidin-4-yl, oxetan-3-yl, morpholin-2-yl, and morpholin-4-yl, wherein the heterocyclyl is optionally substituted with one, two or three substituents independently selected from the group consisting of $C_{1-3}$alkyl, halo, OH and oxetanyl, or pharmaceutically acceptable salts thereof.

In certain embodiment, this invention relates to compounds of Formula (I) and any of the above applicable embodiments, wherein $R^2$ is —$(CH_2)_n$—Y, n is 0, 1, or 2, and Y is a four to six-membered heterocyclyl selected from the group consisting of tetrahydro-2H-pyran-4-yl, tetrahydro-2H-pyran-3-yl, tetrahydrofuran-3-yl, pyrrolidin-1-yl, pyrrolidin-3-yl, piperidin-4-yl, oxetan-3-yl, and morpholin-4-yl, wherein the heterocyclyl is optionally substituted with one, two or three substituents independently selected from the group consisting of $C_{1-3}$alkyl, halo, OH and oxetanyl, or pharmaceutically acceptable salts thereof.

In certain embodiment, this invention relates to compounds of Formula (I) and any of the above applicable embodiments, wherein $R^2$ is —$(CH_2)_n$—Y, n is 0, 1, or 2, and Y is a four to six-membered heterocycyl selected from the group consisting of tetrahydro-2H-pyran-4-yl, tetrahydro-2H-pyran-3-yl, tetrahydrofuran-3-yl, pyrrolidin-1-yl, pyrrolidin-3-yl, piperidin-4-yl, oxetan-3-yl, and morpholin-4-yl, wherein the heterocyclyl is optionally substituted with one or two substituents independently selected from the group consisting of $C_{1-3}$alkyl, halo, OH and oxetanyl, or pharmaceutically acceptable salts thereof.

In one embodiment, this invention relates to compounds of Formula (I) and any of the above applicable embodiments, wherein $R^2$ is —$(CH_2)_n$—Y, n is 0 or 2, and Y is a four to six-membered heterocyclyl selected from the group consisting of pyrrolidin-3-yl, piperidin-4-yl, tetrahydro-2H-pyran-4-yl and morpholin-4-yl, wherein the heterocyclyl is optionally substituted with one substituent selected from the group consisting of methyl, OH and oxetanyl, or pharmaceutically acceptable salts thereof.

In one embodiment, this invention relates to compounds of Formula (I) and any of the above applicable embodiments, wherein $R^2$ is —$(CH_2)_n$—Y, n is 0, and Y is a four to six-membered heterocyclyl selected from the group consisting of pyrrolidin-3-yl, piperidin-4-yl, tetrahydro-2H-pyran-4-yl and morpholin-4-yl, wherein the heterocyclyl is optionally substituted with one substituent selected from the group consisting of methyl, OH and oxetanyl, or pharmaceutically acceptable salts thereof.

In another embodiment, this invention relates to compounds of Formula (I) and any of the above applicable embodiments, wherein $R^2$ is —$(CH_2)_n$—Y, n is 0, 1, or 2, and Y is $C_{3-6}$cycloalkyl optionally substituted with one, two or three substituents independently selected from the group consisting of $C_{1-3}$ alkyl, halo and OH, or pharmaceutically acceptable salts thereof.

In another embodiment, this invention relates to compounds of Formula (I) and any of the above applicable embodiments, wherein $R^2$ is —$(CH_2)_n$—Y, n is 0, 1, or 2, and Y is $C_{3-6}$ cycloalkyl optionally substituted with one or two substituents independently selected from the group consisting of $C_{1-3}$alkyl, halo and OH, or pharmaceutically acceptable salts thereof.

In another embodiment, this Invention relates to compounds of Formula (I) and any of the above applicable embodiments, wherein $R^2$ is —$(CH_2)_n$—Y, n is 0 or 2, and Y is $C_{4-6}$cycloalkyl optionally substituted with one, two or three substituents independently selected from the group consisting of $C_{1-3}$alkyl, halo and OH, or pharmaceutically acceptable salts thereof.

In another embodiment, this invention relates to compounds of Formula (I) and any of the above applicable embodiments, wherein $R^2$ is —$(CH_2)_n$—Y, n is 0 or 2, and Y is $C_{4-6}$cycloalkyl optionally substituted with one or two substituents independently selected from the group consisting of $C_{1-3}$alkyl, halo and OH, or pharmaceutically acceptable salts thereof.

In one embodiment, this invention relates to compounds of Formula (I) and any of the above applicable embodiments, wherein $R^2$ is —$(CH_2)_n$—Y, n is 0, and Y is selected from the group consisting of cyclobutanyl, cyclopentanyl, and cyclohexyl, wherein cyclobutanyl, cyclopentanyl, or cyclohexyl is optionally substituted with one, two or three substituents independently selected from the group consisting of methyl and OH, or pharmaceutically acceptable salts thereof.

In one embodiment, this invention relates to compounds of Formula (I) and any of the above applicable embodiments, wherein $R^2$ is —$(CH_2)_n$—Y, n is 0, and Y is selected from the group consisting of cyclobutanyl, cyclopentanyl, and cyclohexyl, wherein cyclobutanyl, cyclopentanyl, or cyclohexyl is optionally substituted with one or two substituents independently selected from the group consisting of methyl and OH, or pharmaceutically acceptable salts thereof.

In one embodiment, this invention relates to compounds of Formula (I) and any of the above applicable embodiments, wherein $R^2$ is —$(CH_2)_n$—Y, n is 0, and Y is selected from the group consisting of cyclobutanyl, cyclopentanyl, and cyclohexyl, wherein cyclobutanyl, cyclopentanyl or cyclohexyl is optionally substituted with one substituent of OH, or pharmaceutically acceptable salts thereof.

In certain embodiment, this invention relates to compounds of Formula (I), and any of the above applicable embodiments, wherein $R^2$ is —$(CH_2)_n$—Y, n is 0 and Y is a four to six-membered heterocyclyl selected from the group consisting of tetrahydro-2H-pyran-4-yl, tetrahydro-2H-pyran-3-yl, tetrahydrofuran-3-yl, pyrrolidin-1-yl, pyrrolidin-3-yl, piperidin-3-yl, piperidin-4-yl, oxetan-3-yl, morpholin-2-yl, and morpholin-4-yl, wherein the heterocyclyl is optionally substituted with one, two or three substituents independently selected from the group consisting of $C_{1-3}$alkyl, halo, OH and oxetanyl, or pharmaceutically acceptable salts thereof.

In certain embodiment, this invention relates to compounds of Formula (I, and any of the above applicable embodiments, wherein $R^2$ is —$(CH_2)_n$—Y, n is 0 and Y is a four to six-membered heterocyclyl selected from the group consisting of tetrahydro-2H-pyran-4-yl, tetrahydro-2H-pyran-3-yl, tetrahydrofuran-3-yl, piperidin-3-yl, piperidin-4-yl, morpholin-2-yl, and morpholin-4-yl, wherein the heterocyclyl is optionally substituted with one, two or three substituents independently selected from the group consisting of halo and oxetanyl, or pharmaceutically acceptable salts thereof.

In one embodiment, this invention relates to compounds of Formula (I) and any of the above applicable embodiments, wherein $R^2$ is

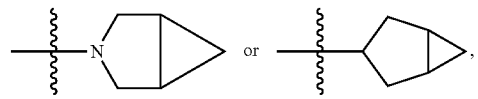

either of which is optionally substituted with one OH group, or pharmaceutically acceptable salts thereof.

In another embodiment, this invention relates to compounds of Formula (I), and any of the above applicable embodiments, wherein $R^3$ is selected from the group consisting of $C_{1-3}$alkyl and halo, or pharmaceutically acceptable salts thereof.

In one embodiment, this invention relates to compounds of Formula (I) and any of the above applicable embodiments, wherein $R^3$ is selected from the group consisting of H, methyl, cyclopropyl and Cl, or pharmaceutically acceptable salts thereof.

In certain embodiment, this Invention relates to compounds of Formula (I) and any of the above applicable embodiments, wherein $R^3$ is selected from the group consisting of methyl, cyclopropyl and Cl, or pharmaceutically acceptable salts thereof.

In certain embodiment, this invention relates to compounds of Formula (I) and any of the above applicable embodiments, wherein $R^3$ is Cl or methyl or pharmaceutically acceptable salts thereof.

In certain embodiment, this invention relates to compounds of Formula (I) and any of the above applicable embodiments, wherein $R^3$ is methyl or pharmaceutically acceptable salts thereof.

In another embodiment, this invention relates to compounds of Formula (I) and any of the above applicable embodiments, wherein $R^4$ is CH, or pharmaceutically acceptable salts thereof.

In one embodiment, this invention relates to compounds of Formula (I) and any of the above applicable embodiments, wherein $R^4$ is N, or pharmaceutically acceptable salts thereof.

In another embodiment, this invention relates to compounds of Formula (I) and any of the above applicable embodiments, wherein $R^5$ is H or methyl, or pharmaceutically acceptable salts thereof.

In another embodiment, this invention relates to compounds of Formula (I) and any of the above applicable embodiments, wherein $R^5$ is H, or pharmaceutically acceptable salts thereof.

In another embodiment, this invention relates to compounds of Formula (I), and any of the above applicable embodiments, wherein $R^6$ is $C_{1-3}$alkoxy, or pharmaceutically acceptable salts thereof.

In another embodiment, this invention relates to compounds of Formula (I) and any of the above applicable embodiments, wherein $R^6$ is ethoxy or —O—$CH_2$-cyclopropyl, or pharmaceutically acceptable salts thereof.

In one embodiment, this invention relates to compounds of Formula (I) and any of the above applicable embodiments, wherein $R^6$ is ethoxy, or pharmaceutically acceptable salts thereof.

In one embodiment, this invention relates to compounds of Formula (I) and any of the above applicable embodiments, wherein
$R^1$ is selected from the group consisting of H, methyl, and Cl;
$R^2$ is $C_{1-5}$alkyl optionally substituted with one or two substituents independently selected from the group consisting of OH, $C_{1-3}$alkoxyl, halo, and CN and
or $R^2$ is —$(CH_2)_n$—Y, wherein
n is 0 or 2,
Y is
(1) a four to six-membered heterocyclyl selected from the group consisting of tetrahydro-2H-pyranyl, tetrahydrofuranyl, pyrrolidinyl, piperidinyl, oxetanyl, and morpholinyl, wherein the heterocyclyl is optionally substituted with one or two substituents independently selected from the group consisting of $C_{1-3}$alkyl, halo, OH and oxetanyl,
(2) a $C_{4-6}$cycloalkyl optionally substituted with one or two substituents independently selected from the group consisting of $C_{1-3}$alkyl, halo and OH, or
(3)

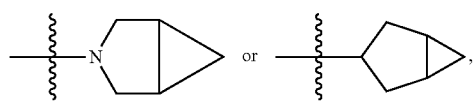 [SMILES: *N1CC2CC2C1 ; *C1CC2CC2C1]

either of which is optionally substituted with one OH group;
$R^3$ is selected from the group consisting of H, Cl, $C_{1-3}$alkyl, and cyclopropyl;
$R^4$ is CH;
$R^5$ is H or methyl; and
$R^6$ is ethoxy;
or pharmaceutically acceptable salts thereof.

In one embodiment, this invention relates to compounds of Formula (I) and any of the above applicable embodiments, wherein
$R^1$ is H;
$R^2$ is $C_{4-5}$ alkyl optionally substituted with one or more substituents independently selected from the group consisting of OH, methoxy, Cl, F and CN,
or $R^2$ is —$(CH_2)_n$—Y, wherein
n is 0 or 2,
Y is
(1) a four to six-membered heterocyclyl selected from the group consisting of pyrrolidin-3-yl, piperidin-4-yl, tetrahydro-2H-pyran-4-yl and morpholin-4-yl, wherein the heterocyclyl is optionally substituted with one substituent selected from the group consisting of methyl, OH and oxetanyl, or
(2) a $C_{4-6}$cycloalkyl selected from the group consisting of cyclobutanyl, cyclopentanyl and cyclohexyl, wherein the cycloalkyl is optionally substituted with one substituent of OH,
$R^3$ is methyl;
$R^4$ is CH;
$R^5$ is H; and
$R^6$ is ethoxy;
or pharmaceutically acceptable salts thereof.

In one embodiment, this invention relates to compounds of Formula (I) and any of the above applicable embodiments, wherein
$R^1$ is H,
$R^2$ is —$(CH_2)_n$—Y, wherein n is 0, and Y is a four to six-membered heterocyclyl selected from the group consisting of piperidin-4-yl, piperidin-3-yl, and morpholin-2-yl, wherein the heterocyclyl is optionally substituted with one, two or three substituent selected from the group consisting of methyl, OH, halo and oxetanyl,
$R^3$ is halo,
$R^4$ is CH,
$R^5$ is H, and
$R^6$ is $C_{1-3}$alkoxyl,
or a pharmaceutically acceptable salt thereof.

In one embodiment, this invention relates to compounds of Formula (I), wherein $R^1$ is H, $R^3$ is $C_{1-3}$alkyl, $R^4$ is CH, and $R^5$ is H, or pharmaceutically acceptable salts.

In one embodiment, the compound of Formula (I) is a compound of any one of Examples 1 to 80, a free base form, a free acid form, or a salt (e.g., a pharmaceutically acceptable salt) thereof.

In one embodiment, the compound of Formula (I) is a compound of any one of Examples 81 to 151, a free base form, a free acid form, or a salt (e.g., a pharmaceutically acceptable salt) thereof.

In one embodiment, the compound of Formula (I) is a compound of any one of Examples 1 to 151, or a pharmaceutically acceptable salt thereof.

In one embodiment, the compound of Formula (I) is

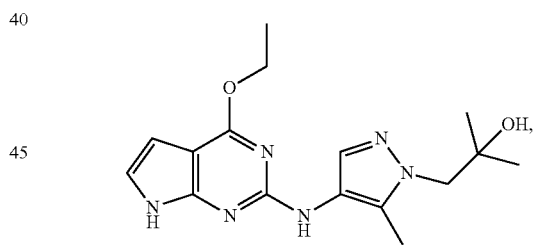

or a pharmaceutically acceptable salt thereof.

In one embodiment, the compound of Formula (I) is

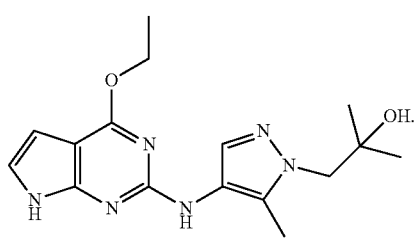 [SMILES: CCOc1nc(Nc2cnn(CC(C)(C)O)c2C)nc2[nH]ccc12]

In one embodiment, the compound of Formula (I) is

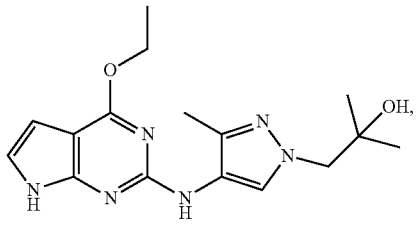 [SMILES: CCOc1nc(Nc2cn(CC(C)(C)O)nc2C)nc2[nH]ccc12]

or a pharmaceutically acceptable salt thereof.

In one embodiment, the compound of Formula (I) is

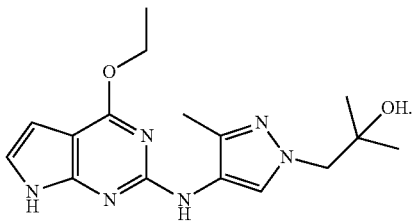 [SMILES: CCOc1nc(Nc2cn(CC(C)(C)O)nc2C)nc2[nH]ccc12]

In one embodiment, the compound of Formula (I) Is a mixture of

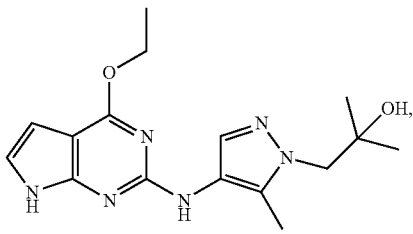 [SMILES: CCOc1nc(Nc2cnn(CC(C)(C)O)c2C)nc2[nH]ccc12]

or a pharmaceutically acceptable salt thereof, and

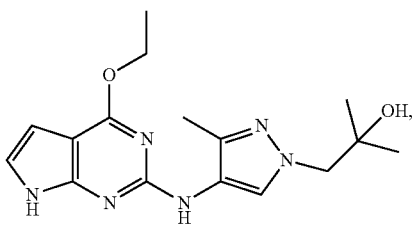 [SMILES: CCOc1nc(Nc2cn(CC(C)(C)O)nc2C)nc2[nH]ccc12]

or a pharmaceutically acceptable salt thereof.

In one embodiment, the compound of Formula (I) has the structure of Formula (IA)

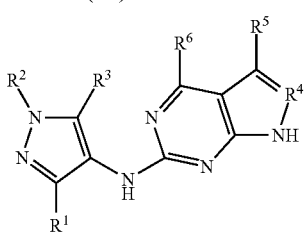

(I)

$R^1$ is independently selected from the group consisting of H, $C_{1-3}$alkoxyl, $C_{1-3}$alkyl, and halo;

$R^2$ is —$(CR_aR_b)_n$—Y, wherein n is 0, 1, or 2, each occurrence of $R_a$ and $R_b$ are independently H or methyl, and Y is a four to six-membered heterocyclyl optionally substituted with one or more substituents independently selected from the group consisting of $C_{1-3}$alkyl, halo, OH, oxetanyl, $C_{1-3}$haloalkyl, and morpholinyl;

$R^3$ is selected from the group consisting of H, $C_{1-3}$alkoxyl, $C_{1-3}$alkyl, $C_{3-6}$cycloalkyl, and halo;

$R^4$ is CH or N;

$R^b$ is H, CN or methyl; and $R^6$ is selected from the group consisting of $C_{1-3}$alkoxy and —O—$CH_2$—$C_{3-6}$cycloalkyl, or a pharmaceutically acceptable salt thereof.

In one embodiment, this invention relates to compounds of Formula (IA), wherein $R^1$ is H, methyl or Cl, or pharmaceutically acceptable salts thereof.

In one embodiment, this invention relates to compounds of Formula (IA), wherein $R^1$ is H, or pharmaceutically acceptable salts thereof.

In another embodiment, this invention relates to compounds of Formula (IA), and any of the above applicable embodiments, wherein $R^2$ is —$(CH_2)_n$—Y, n is 0, 1 or 2 and Y is a four to six-membered heterocyclyl selected from the group consisting of azetidinyl, tetrahydro-2H-pyranyl, tetrahydrofuranyl, pyrrolidinyl, piperidinyl, oxetanyl, and morpholinyl, wherein the heterocyclyl is optionally substituted with one, two or three substituents independently selected from the group consisting of $C_{1-3}$alkyl, halo, OH and oxetanyl, or pharmaceutically acceptable salts thereof.

In another embodiment, this invention relates to compounds of Formula (IA), and any of the above applicable embodiments, wherein $R^2$ is —$(CH_2)_n$—Y, n is 0 and Y is a four to six-membered heterocyclyl selected from the group consisting of tetrahydro-2H-pyranyl, piperidinyl, and morpholinyl, wherein the heterocyclyl is optionally substituted with one, two or three substituents independently selected from the group consisting of $C_{1-3}$alkyl, halo, OH and oxetanyl, or pharmaceutically acceptable salts thereof.

In certain embodiment, this Invention relates to compounds of Formula (IA), and any of the above applicable embodiments, wherein $R^2$ is —$(CH_2)_n$—Y, n is 0 or 2 and Y is a four to six-membered heterocyclyl selected from the group consisting of azetidin-1-yl, tetrahydro-2H-pyran-4-yl, tetrahydro-2H-pyran-3-yl, tetrahydrofuran-3-yl, pyrrolidin-1-yl, pyrrolidin-3-yl, piperidin-3-yl, piperidin-4-yl, oxetan-3-yl, morpholin-2-yl, and morpholin-4-yl, wherein the heterocyclyl is optionally substituted with one, two or three substituents independently selected from the group consisting of $C_{1-3}$alkyl, halo, OH and oxetanyl, or pharmaceutically acceptable salts thereof.

In certain embodiment, this invention relates to compounds of Formula (IA), and any of the above applicable embodiments, wherein $R^2$ is —$(CH_2)_n$—Y, n is 0 and Y is a four to six-membered heterocyclyl selected from the group consisting of tetrahydro-2H-pyran-4-yl, tetrahydro-2H-pyran-3-yl, tetrahydrofuran-3-yl, pyrrolidin-1-yl, pyrrolidin-3-yl, piperidin-3-yl, piperidin-4-yl, oxetan-3-yl, morpholin-2-yl, and morpholin-4-yl, wherein the heterocyclyl is optionally substituted with one, two or three substituents independently selected from the group consisting of $C_{1-3}$alkyl, halo, OH and oxetanyl, or pharmaceutically acceptable salts thereof.

In certain embodiment, this invention relates to compounds of Formula (IA), and any of the above applicable embodiments, wherein $R^2$ is —$(CH_2)_n$—Y, n is 0 and Y is a four to six-membered heterocyclyl selected from the group consisting of tetrahydro-2H-pyran-4-yl, tetrahydro-2H-pyran-3-yl, tetrahydrofuran-3-yl, piperidin-3-yl, piperidin-4-yl, morpholin-2-yl, and morpholin-4-yl, wherein the heterocyclyl is optionally substituted with one, two or three substituents independently selected from the group consisting of halo and oxetanyl, or pharmaceutically acceptable salts thereof.

In another embodiment, this invention relates to compounds of Formula (IA), and any of the above applicable embodiments, wherein $R^3$ is selected from the group consisting of $C_{1-3}$alkyl and halo, or pharmaceutically acceptable salts thereof.

In certain embodiment, this invention relates to compounds of Formula (IA), and any of the above applicable embodiments, wherein $R^3$ is selected from the group consisting of methyl and Cl, or pharmaceutically acceptable salts thereof.

In certain embodiment, this invention relates to compounds of Formula (IA), and any of the above applicable embodiments, wherein $R^3$ is methyl, or pharmaceutically acceptable salts thereof.

In another embodiment, this invention relates to compounds of Formula (IA), and any of the above applicable embodiments, wherein $R^4$ is CH, or pharmaceutically acceptable salts thereof.

In another embodiment, this invention relates to compounds of Formula (IA), and any of the above applicable embodiments, wherein $R^5$ is H or methyl, or pharmaceutically acceptable salts thereof.

In another embodiment, this invention relates to compounds of Formula (IA), and any of the above applicable embodiments, wherein $R^5$ is H, or pharmaceutically acceptable salts thereof.

In another embodiment, this invention relates to compounds of Formula (IA), and any of the above applicable embodiments, wherein $R^6$ is $C_{1-3}$alkoxy, or pharmaceutically acceptable salts thereof.

In another embodiment, this invention relates to compounds of Formula (IA), and any of the above applicable embodiments, wherein $R^6$ is ethoxy, or pharmaceutically acceptable salts thereof.

In one embodiment, this invention relates to compounds of Formula (IA) and any of the above applicable embodiments, wherein
$R^1$ is H,
$R^2$ is —$(CH_2)_n$—Y, wherein n is 0, and Y is a four to six-membered heterocyclyl selected from the group consisting of piperidin-4-yl, piperidin-3-yl, and morpholin-2-yl, wherein the heterocyclyl is optionally substituted with one, two or three substituent selected from the group consisting of methyl, OH, halo and oxetanyl,
$R^3$ is halo,
$R^4$ is CH,
$R^5$ is H, and
$R^6$ is $C_{1-3}$alkoxyl,
or a pharmaceutically acceptable salt thereof.

In one embodiment, the compound of Formula (I) or Formula (IA) is

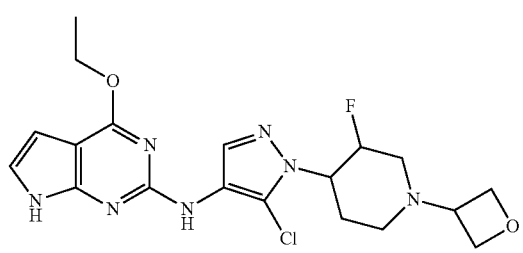 [SMILES: CCOc1nc(Nc2cnn(C3CCN(C4COC4)CC3F)c2Cl)nc2[nH]ccc12]

or a pharmaceutically acceptable salt thereof.

In one embodiment, the compound of Formula (I) or Formula (IA) is

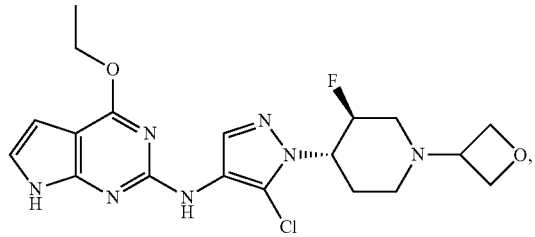

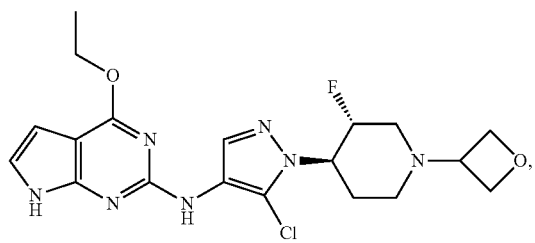

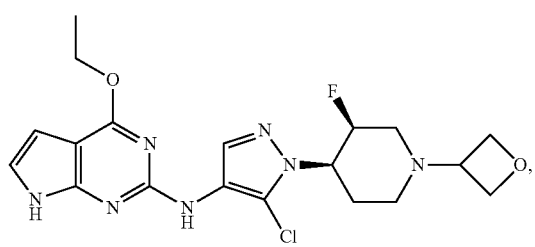

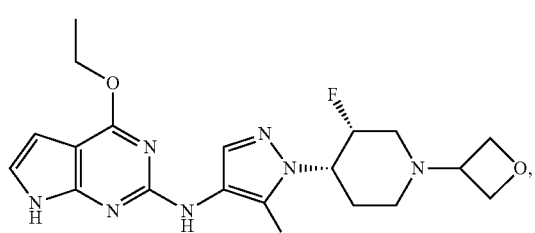

or a pharmaceutically acceptable salt thereof.

In one embodiment, the compound of Formula (I) or Formula (IA) is

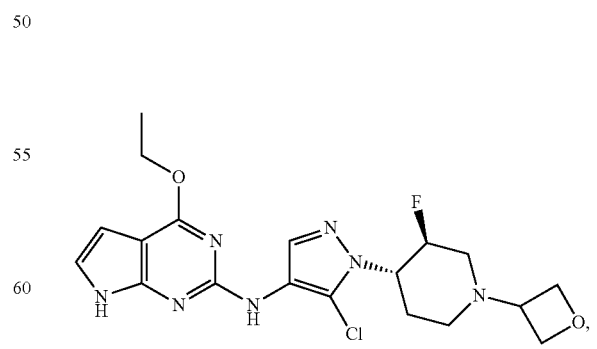

or a pharmaceutically acceptable salt thereof.

In one embodiment, the compound of Formula (I) or Formula (IA) is

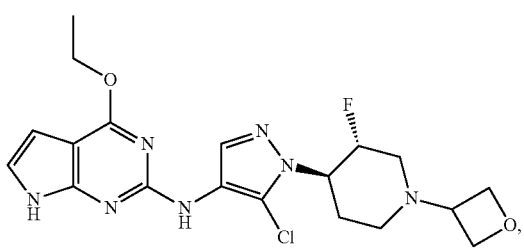 [SMILES: CCOc1nc(Nc2cnn([C@@H]3CCN(C4COC4)C[C@H]3F)c2Cl)nc2[nH]ccc12]

or a pharmaceutically acceptable salt thereof.

In one embodiment, the compound of Formula (I) or Formula (IA) is

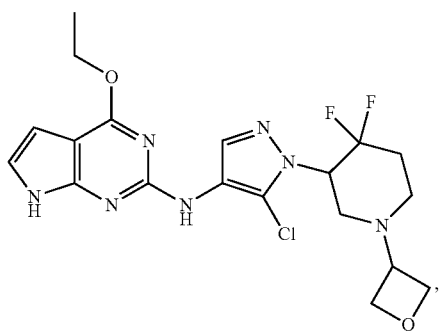 [SMILES: CCOc1nc(Nc2cnn(C3CN(C4COC4)CCC3(F)F)c2Cl)nc2[nH]ccc12]

or a pharmaceutically acceptable salt thereof.

In one embodiment, the compound of Formula (I) or Formula (IA) is

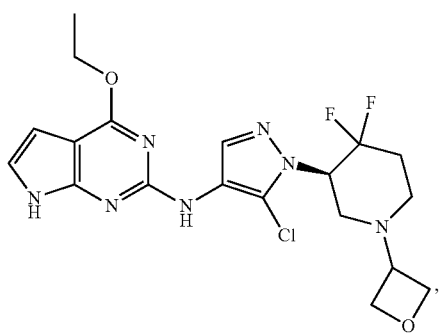 [SMILES: CCOc1nc(Nc2cnn([C@@H]3CN(C4COC4)CCC3(F)F)c2Cl)nc2[nH]ccc12]

or a pharmaceutically acceptable salt thereof.

In one embodiment, the compound of Formula (I) or Formula (IA) is

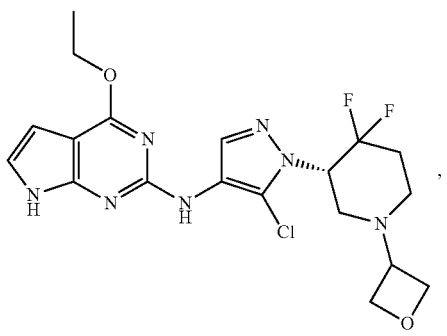 [SMILES: CCOc1nc(Nc2cnn([C@H]3CN(C4COC4)CCC3(F)F)c2Cl)nc2[nH]ccc12]

or a pharmaceutically acceptable salt thereof.

In one embodiment, the compound of Formula (I) or Formula (IA) is

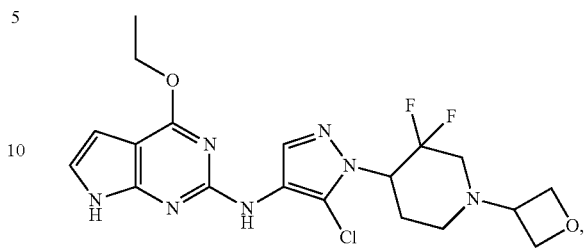

or a pharmaceutically acceptable salt thereof.

In one embodiment, the compound of Formula (I) or Formula (IA) is

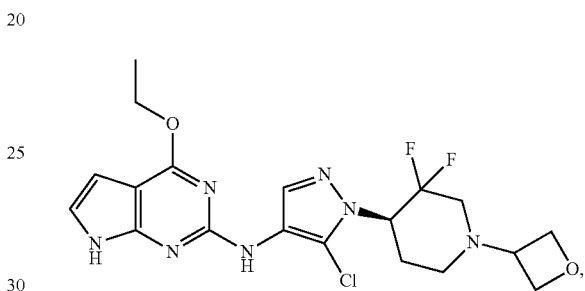

or a pharmaceutically acceptable salt thereof.

In one embodiment, the compound of Formula (I) or Formula (IA) is

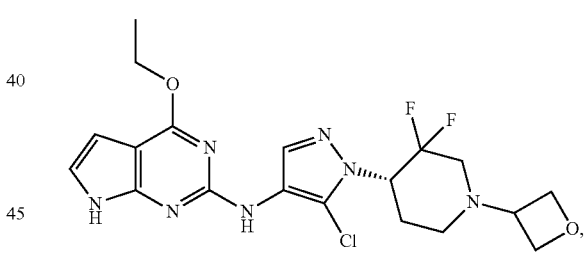

or a pharmaceutically acceptable salt thereof.

In one embodiment, the compound of Formula (I) or Formula (IA) is

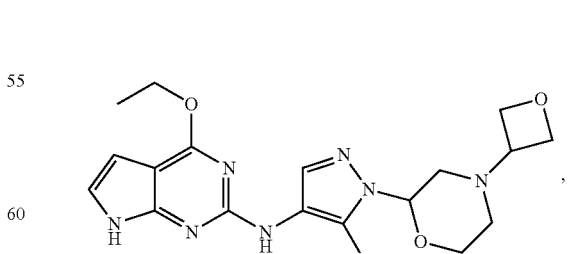

or a pharmaceutically acceptable salt thereof.

In one embodiment, the compound of Formula (I) or Formula (IA) is

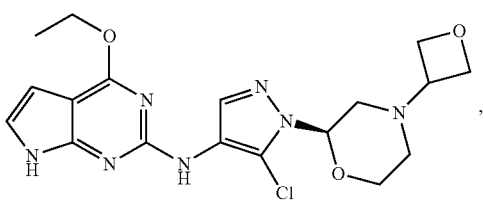 [SMILES: CCOc1nc(Nc2cnn([C@H]3CN(C4COC4)CCO3)c2Cl)nc2[nH]ccc12]

or a pharmaceutically acceptable salt thereof.

In one embodiment, the compound of Formula (I) or Formula (IA) is

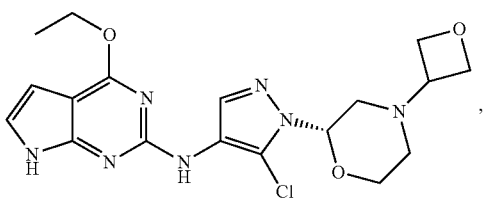 [SMILES: CCOc1nc(Nc2cnn([C@@H]3CN(C4COC4)CCO3)c2Cl)nc2[nH]ccc12]

or a pharmaceutically acceptable salt thereof.

In addition to the free base form or free acid form of the compounds described herein, the salt form of the compounds is also within the scope of the present invention. The salts or pharmaceutically-acceptable salts of the compounds described herein may be prepared in situ during the final isolation and purification of the compound, or by separately reacting the purified compound in its free acid form or free base form with a suitable base or acid, respectively. For reviews on suitable pharmaceutical salts see Berge et al, J. Pharm, Sci., 66, 1-19, 1977; P L Gould, International Journal of Pharmaceutics, 33 (1986), 201-217; and Bighley et al, Encyclopedia of Pharmaceutical Technology, Marcel Dekker Inc, New York 1996, Volume 13, page 453-497.

In certain embodiments, compounds of the present invention may contain an acidic functional group, which is acidic enough to form salts. Representative salts include pharmaceutically-acceptable metal salts such as sodium, potassium, lithium, calcium, magnesium, aluminum, and zinc salts; carbonates and bicarbonates of a pharmaceutically-acceptable metal cation such as sodium, potassium, lithium, calcium, magnesium, aluminum, and zinc; pharmaceutically-acceptable organic primary, secondary, and tertiary amines including aliphatic amines, aromatic amines, aliphatic diamines, and hydroxy alkylamines such as methylamine, ethylamine, diethylamine, triethylamine, ethylenediamine, ethanolamine, diethanolamine, and cyclohexylamine.

In certain embodiments, compounds of the present invention may contain a basic group and are therefore capable of forming pharmaceutically-acceptable acid addition salts by treatment with a suitable acid. Suitable acids include pharmaceutically-acceptable Inorganic acids and pharmaceutically-acceptable organic acids. These salts may be crystalline or amophorus. Exemplary pharmaceutically-acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicylate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate. In some embodiments, the pharmaceutically acceptable salts include the L-tartrate, ethanedisulfonate (edisylate), sulfate, phosphate, p-toluenesulfonate (tosylate), hydrochloride salt, methanesulfonate, citrate, fumarate, benzenesulfonate, maleate, hydrobromate, L-lactate, malonate, and S-camphor-10-sulfonate. In certain embodiments, some of these salts form solvates. In certain embodiments, some of these salts are crystalline.

The compounds of Formula (I), salts (e.g., pharmaceutically acceptable salts) thereof may exist in stereoisomeric forms (e.g., it contains one or more asymmetric carbon atoms). The individual stereoisomers (enantiomers and diastereomers) and mixtures of these are included within the scope of the present invention. The invention also covers the individual isomers of the compounds of Formula (I), salts (e.g., pharmaceutically acceptable salts) thereof as mixtures with isomers thereof in which one or more chiral centers are inverted. Likewise, it is understood that the compounds of Formula (I), salts (e.g., pharmaceutically acceptable salts) thereof may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures.

Also included within the scope of the invention are individual isomers of the compounds of Formula (I), salts (e.g., pharmaceutically acceptable salts) thereof, as well as any wholly or partially equilibrated mixtures thereof. The present invention also includes the individual isomers of the compounds of Formula (I), salts (e.g., pharmaceutically acceptable salts) thereof as well as mixtures with isomers thereof in which one or more chiral centers are inverted. It is to be understood that the present invention includes all combinations and subsets of the particular groups defined hereinabove. The different isomeric forms may be separated or resolved one from the other by conventional methods, or any given isomer may be obtained by conventional synthetic methods or by stereospecific or asymmetric syntheses.

The invention also includes isotopically-labelled compounds and salts, which are identical to compounds of Formula (I) or salts thereof, but for the fact that one or more atoms are replaced by an atom having an atomic mass or mass number different from the atomic mass or mass number most commonly found in nature. Examples of Isotopes that can be incorporated into compounds of Formula (I) or salts thereof isotopes of hydrogen, carbon, nitrogen, fluorine, such as $^{3}H$, $^{11}C$, $^{14}C$ and $^{18}F$. Such isotopically-labelled compound of Formula (I) or salts thereof are useful in drug and/or substrate tissue distribution assays. For example, $^{11}C$ and $^{18}F$ isotopes are useful in PET (positron emission tomography). PET is useful in brain imaging. Isotopically-labelled compounds of Formula (I) and salts thereof can generally be prepared by carrying out the procedures disclosed below, by substituting a readily available isotopically-labelled reagent for a non-isotopically labelled reagent. In one embodiment, compounds of Formula (I) or salts thereof are not isotopically labelled.

Certain compounds of Formula (I) or salts thereof may exist in solid or liquid form. In the solid state, compounds of Formula (I) or salts may exist in crystalline or noncrystalline form, or as a mixture thereof. For compounds of Formula (I) or salts that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of Formula (I), pharmaceutically acceptable salts or solvates thereof that exist in crystalline form, including the various solvates thereof, may exhibit polymorphism (i.e. the capacity to occur in different crystalline structures). These different crystalline forms are typically known as "polymorphs." Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions. The invention includes all such polymorphs.

The skilled artisan also appreciates that this invention may contain various deuterated forms of compounds of Formula (I), or pharmaceutically acceptable salts thereof. Each available hydrogen atom attached to a carbon atom may be independently replaced with a deuterium atom. A person of ordinary skill in the art will know how to synthesize deuterated forms of compounds of Formula (I), or pharmaceutically acceptable salts thereof. Commercially available deuterated starting materials may be employed in the preparation of deuterated forms of compounds of Formula (I) or pharmaceutically acceptable salts thereof, or they may be synthesized using conventional techniques employing deuterated reagents (e.g. lithium aluminum deuteride).

The compounds described herein, their salts (e.g., pharmaceutically acceptable salts), deuterated form, solvates or hydrates thereof, may exist in one or more polymorphic form. Therefore, in a further aspect, the invention provides a polymorph of a compound defined herein, their salts (e.g., pharmaceutically acceptable salts), or a polymorph of a solvate or hydrate of a compound described herein or a salt (e.g., pharmaceutically acceptable salt) thereof.

As used herein, the terms "compound(s) of the invention" or "compound(s) of the present invention" mean a compound of Formula (I), as defined herein, in any form, i.e., any salt or non-salt form (e.g., as a free acid or base form, or as a salt, for example, a pharmaceutically acceptable salt thereof), deuterated form and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi-hydrates)), and mixtures of various forms.

Accordingly, a compound of the invention includes a compound of Formula (I), or a salt thereof, for example a pharmaceutically acceptable salt thereof. Representative compounds of this invention include the specific compounds described.

C. Methods of Use

The compounds of Formula (I) or pharmaceutically acceptable salts thereof are inhibitors of LRRK2 kinase activity and are thus believed to be of potential use in the treatment of or prevention of neurological diseases. Exemplary neurological diseases include, but are not limited to, Parkinson's disease, Alzheimer's disease, dementia (including Lewy body dementia and vascular dementia, HIV-induced dementia), amyotrophic lateral sclerosis (ALS), age related memory dysfunction, mild cognitive impairment, argyrophilic grain disease, Pick's disease, corticobasal degeneration, progressive supranuclear palsy, inherited frontotemporal dementia and parkinsonism linked to chromosome 17 (FTDP-17), withdrawal symptoms/relapse associated with drug addiction, L-Dopa induced dyskinesia, ischemic stroke, traumatic brain injury, and spinal cord injury. Other disorders include, but are not limited to, lysosomal disorders (for example, Niemann-Pick Type C disease, Gaucher disease), Crohn's disease, thyroid, renal (including papillary renal), breast, lung and prostate cancers, leukemias (including acute myelogenous leukemia (AML)), lymphomas, leukemias, multiple sclerosis, rheumatoid arthritis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease and inflammatory myopathies.

One aspect of the invention provides a compound of Formula (I) or a pharmaceutically acceptable salt thereof for use in therapy. In one embodiment, the invention provides a compound of Formula (I) or a pharmaceutically acceptable salt thereof for use in the treatment of or prevention of Parkinson's disease. In one embodiment, the invention provides a compound of Formula (I) or a pharmaceutically acceptable salt thereof for use in the treatment of Parkinson's disease.

A further aspect of the invention provides the use of a compound of Formula (I) or a pharmaceutically acceptable salt thereof in the manufacture of a medicament for the treatment of or prevention of Parkinson's disease. A further aspect of the invention provides the use of a compound of Formula (I) or a pharmaceutically acceptable salt thereof in the manufacture of a medicament for the treatment of Parkinson's disease.

One embodiment of the invention provides methods of treatment of or prevention of Parkinson's disease, which comprises administering to a subject in need thereof a therapeutically effective amount of a compound of Formula (I) or a pharmaceutically acceptable salt thereof. In certain embodiment, the subject is human.

In the context of the present invention, treatment of Parkinson's disease refers to the treatment of sporadic Parkinson's disease, and/or familial Parkinson's disease. In one embodiment, familial Parkinson's disease includes patients expressing LRRK2 kinase bearing the G2019S mutation or the R1441G mutation. In a further embodiment, familial Parkinson's disease includes patients expressing LRRK2 kinase bearing G2019S mutation, N1437H mutation, R1441G mutation, R1441C mutation, R1441H mutation, Y1699C mutation, S1761R mutation, or I2020T mutation for Parkinson's disease. In another embodiment, sporadic Parkinson's disease includes patients expressing LRRK2 kinase bearing G2019S mutation, N1437H mutation, R1441G mutation, R1441C mutation, R1441H mutation, Y1699C mutation, S1761R mutation, or I2020T mutation for Parkinson's disease. In another embodiment, Parkinson's disease includes patients expressing LRRK2 kinase bearing other coding mutations such as G2385R or non-coding single nucleotide polymorphisms at the LRRK2 locus that are associated with Parkinson's disease. In one embodiment, treatment of Parkinson's disease refers to the treatment of familial Parkinson's disease includes patients expressing LRRK2 kinase bearing G2019S mutation. In another embodiment, Parkinson's disease includes patients expressing aberrantly high levels of normal LRRK2 kinase. Treatment of Parkinson's disease may be symptomatic or may be disease modifying. In one embodiment, treatment of Parkinson's disease refers to symptomatic treatment. In one embodiment, treatment of Parkinson's disease refers to disease modifying.

Compounds of the present invention may also be useful in treating patients identified as susceptible to progression to severe Parkinsonism by means of one or more subtle features associated with disease progression such as family history, olfaction deficits, constipation, cognitive defects, gait or biological indicators of disease progression gained from molecular, biochemical, immunological or imaging technologies. In this context, treatment may be symptomatic or disease modifying.

In the context of the present invention, treatment of Alzheimer's disease refers to the treatment of sporadic Alzheimer's disease and/or familial Alzheimer's disease. Treatment of Alzheimer's disease may be symptomatic or may be disease modifying. In one embodiment, treatment of Alzheimer's disease refers to symptomatic treatment. Similarly, treatment of dementia (including Lewy body dementia vascular dementia, and HIV-induced dementia), age related memory dysfunction, mild cognitive impairment argyrophilic grain disease, amyotrophic lateral sclerosis (ALS), Pick's disease, corticobasal degeneration, progressive supranuclear palsy, inherited frontotemporal dementia and parkinsonism linked to chromosome 17 (FTDP-17), ischemic stroke, traumatic brain injury, spinal cord injury, lysosomal disorders (for example, Niemann-Pick Type C disease, Gaucher disease) Crohn's disease, thyroid, renal (including papillary renal), breast, lung and prostate cancers, leukemias (including acute myelogenous leukemia (AML)), lymphomas, leukemias, multiple sclerosis, rheumatoid arthritis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease and inflammatory myopathies may be symptomatic or disease modifying. In some embodiments, treatment of dementia (including Lewy body dementia, vascular dementia and HIV-induced dementia), age related memory dysfunction, mild cognitive impairment, argyrophilic grain disease, amyotrophic lateral sclerosis (ALS), Pick's disease, corticobasal degeneration, progressive supranuclear palsy, inherited frontotemporal dementia and parkinsonism linked to chromosome 17 (FTDP-17), ischemic stroke, traumatic brain injury, spinal cord injury, lysosomal disorders (for example, Niemann-Pick Type C disease, Gaucher disease), Crohn's disease, thyroid, renal (including papillary renal), breast, lung and prostate cancers, leukemias (including acute myelogenous leukemia (AML)), lymphomas, leukemias, multiple sclerosis, rheumatoid arthritis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease and inflammatory myopathies refers to symptomatic treatment.

In one embodiment, the invention also provides methods of treatment of ankylosing spondylitis and/or leprosy infection, which comprises administering to a subject in need thereof a therapeutically effective amount of a compound of Formula (I) or a pharmaceutically acceptable salt thereof. In some embodiments, the subject is human.

In the context of the present invention, treatment of withdrawal symptoms/relapse associated with drug addiction and L-Dopa induced dyskinesia refers to symptomatic treatment. In a further aspect, the invention provides a compound of Formula (I) or a pharmaceutically acceptable salt thereof for use in the treatment of the above disorders, for example Parkinson's disease. In some embodiments, the invention provides a compound of Formula (I) or a pharmaceutically acceptable salt thereof for use in the prevention of Parkinson's disease, Alzheimer's disease, of dementia (including Lewy body dementia vascular dementia and HIV-induced dementia), age related memory dysfunction, mild cognitive impairment, argyrophilic grain disease, amyotrophic lateral sclerosis (ALS), Pick's disease, corticobasal degeneration, progressive supranuclear palsy, inherited frontotemporal dementia or parkinsonism linked to chromosome 17 (FTDP-17), lysosomal disorders (e.g., Niemann-Pick Type C disease, Gaucher disease) or renal, breast, lung, prostate cancers as well as acute myelogenous leukemia (AML). In one embodiment, the invention provides a compound of Formula (I) or a pharmaceutically acceptable salt thereof for use in the prevention of Parkinson's disease.

The invention further provides a method of treatment of the above disorders, for example Parkinson's disease in mammals including humans, which comprises administering to a subject in need thereof a therapeutically effective amount of a compound of Formula (I) or a pharmaceutically acceptable salt thereof.

The invention also provides the use of the compound of Formula (I) or a pharmaceutically acceptable salt thereof in the manufacture of a medicament for use in the treatment of the above disorders, for example, Parkinson's disease. The invention also provides the use of the compound of Formula (I) or a pharmaceutically acceptable salt thereof in the manufacture of a medicament for use in the prevention of Parkinson's disease, Alzheimer's disease, of dementia (including Lewy body dementia and vascular dementia), age related memory dysfunction, mild cognitive impairment, argyrophilic grain disease, amyotrophic lateral sclerosis (ALS), Pick's disease, corticobasal degeneration, progressive supranuclear palsy, inherited frontotemporal dementia or parkinsonism linked to chromosome 17 (FTDP-17), or renal, breast, lung, prostate cancers as well as acute myelogenous leukemia (AML), lysosomal disorders (for example, Niemann-Pick Type C disease, Gaucher disease). In some embodiments, the invention provides the use of the compound of Formula (I) or a pharmaceutically acceptable salt thereof in the manufacture of a medicament for use in the prevention of Parkinson's disease.

The invention also provides the use of inhibitors of LRRK2 in the production of neuronal progenitor cells in vitro for consequent therapeutic application in cell based-treatment of CNS disorders.

The invention further provides the use of inhibitors of LRRK2 to stimulate restoration of CNS functions following neuronal injury including, but not limited to, ischemic stroke, traumatic brain injury, and/or spinal cord injury.

The invention also provides the use of inhibitors of LRRK2 to treat aberrant neuroinflammatory mechanisms that contribute a range of neurodegenerative diseases, including Parkinson's disease, Alzheimer's disease, multiple sclerosis, HIV-induced dementia, amyotrophic lateral sclerosis, ischemic stroke, traumatic brain injury and spinal cord injury.

When used in therapy, a compound of Formula (I) or pharmaceutically acceptable salt thereof is usually formulated in a standard pharmaceutical composition. Such compositions can be prepared using standard procedures.

The present invention further provides a pharmaceutical composition which comprises the compound of Formula (I) or a pharmaceutically acceptable salt thereof and a pharmaceutically acceptable carrier.

When a compound of Formula (I) or a pharmaceutically acceptable salt thereof is intended for use in the treatment of Parkinson's disease, it may be used in combination with medicaments claimed to be useful as symptomatic treatments of Parkinson's disease. Suitable examples of such other therapeutic agents include L-dopa, and dopamine agonists (e.g. pramipexole, ropinirole).

When a compound of Formula (I) or a pharmaceutically acceptable salt thereof is intended for use in the treatment of Alzheimer's disease, it may be used in combination with medicaments claimed to be useful as either disease modifying or symptomatic treatments of Alzheimer's disease. Suitable examples of such other therapeutic agents may be symptomatic agents, for example those known to modify cholinergic transmission such as M1 muscarinic receptor agonists or allosteric modulators, M2 muscarinic antagonists, acetylcholinesterase inhibitors (such as tetrahydroaminoacridine, donepezil hydrochloride and rivastigmine), nicotinic receptor agonists or allosteric modulators (such as α7 agonists or allosteric modulators or α4β2 agonists or allosteric modulators), PPAR agonists (such as PPARγ agonists), 5-HT$_4$ receptor partial agonists, 5-HT$_6$ receptor antagonists or 5HT1A receptor antagonists and NMDA receptor antagonists or modulators, or disease modifying agents such as β or γ-secretase inhibitors, mitochondrial stabilisers, microtubule stabilisers or modulators of Tau pathology such as Tau aggregation inhibitors (e.g. methylene blue and REMBER™).

When a compound of Formula (I) or a pharmaceutically acceptable salt thereof is used in combination with other therapeutic agents, the compounds may be administered either sequentially or simultaneously by any convenient route.

The invention also provides, in a further aspect, a combination comprising a compound of Formula (I) or a pharmaceutically acceptable salt thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of Formula (I) or a pharmaceutically acceptable salt thereof is used in combination with a second therapeutic agent active against the same disease state the dose of each compound may differ from that when the compound is used alone. Appropriate doses will be readily appreciated by those skilled in the art.

D. Composition

The compounds of the present invention may be formulated into pharmaceutical compositions prior to administration to a subject. According to one aspect, the invention provides a pharmaceutical composition comprising a compound of the invention and one or more pharmaceutically acceptable excipients. According to another aspect, the invention provides a process for the preparation of a pharmaceutical composition comprising admixing a compound of the Formula (I), or a salt (e.g., pharmaceutically acceptable salt) thereof, solvates etc thereof, with one or more pharmaceutically acceptable excipient.

Pharmaceutical compositions may be presented in unit dose forms containing a predetermined amount of active ingredient per unit dose. Such a unit may contain, for example, 0.1 mg, 0.5 mg, or 1 mg to 50 mg, 100 mg, 200 mg, 250 mg, 500 mg, 750 mg or 1 g of a compound of the present invention, depending on the disease being treated, the route of administration and the age, weight and condition of the subject, or pharmaceutical compositions may be presented in unit dose forms containing a predetermined amount of active ingredient per unit dose. In other embodiments, the unit dosage compositions are those containing a daily dose or sub-dose as described herein, or an appropriate fraction thereof, of an active ingredient. Furthermore, such pharmaceutical compositions may be prepared by any of the methods well-known to one skilled in the art.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, a therapeutically effective amount of a compound of present invention for the treatment of diseases described in the present invention will generally be in the range of 0.1 to 100 mg/kg body weight of recipient per day and more usually in the range of 1 to 10 mg/kg body weight per day. Thus, for a 70 kg adult mammal, the actual amount per day would usually be from 70 to 700 mg and this amount may be given in a single dose per day or in a number of sub-doses per day as such as two, three, four, five or six doses per day. Or the dosing can be done intermittently, such as once every other day, once a week or once a month. A therapeutically effective amount of a salt or solvate, etc., may be determined as a proportion of the therapeutically effective amount of the compound of Formula (I) per se. It is envisaged that similar dosages would be appropriate for treatment of the other diseases referred to above.

The pharmaceutical compositions of the invention may contain one or more compounds of the invention. In some embodiments, the pharmaceutical compositions may contain more than one compound of the invention. For example, in some embodiments, the pharmaceutical compositions may contain two or more compounds of the invention. In addition, the pharmaceutical compositions may optionally further comprise one or more additional pharmaceutically active compounds.

As used herein, "pharmaceutically acceptable excipient" means a pharmaceutically acceptable material, composition or vehicle involved in giving form or consistency to the pharmaceutical composition. Each excipient may be compatible with the other ingredients of the pharmaceutical composition when commingled such that interactions which would substantially reduce the efficacy of the compound of the invention when administered to a subject and interactions which would result in pharmaceutical compositions that are not pharmaceutically acceptable are avoided.

The compounds of the invention and the pharmaceutically acceptable excipient or excipients may be formulated into a dosage form adapted for administration to the subject by the desired route of administration. For example, dosage forms include those adapted for (1) oral administration (including buccal or sublingual) such as tablets, capsules, caplets, pills, troches, powders, syrups, elixers, suspensions, solutions, emulsions, sachets, and cachets; (2) parenteral administration (including subcutaneous, intramuscular, Intravenous or intradermal) such as sterile solutions, suspensions, and powders for reconstitution; (3) transdermal administration such as transdermal patches; (4) rectal administration such as suppositories; (5) nasal inhalation such as dry powders, aerosols, suspensions, and solutions; and (6) topical administration (including buccal, sublingual or transdermal) such as creams, ointments, lotions, solutions, pastes, sprays, foams, and gels. Such compositions may be prepared by any methods known in the art of pharmacy, for example by bringing into association a compound of Formula (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Suitable pharmaceutically-acceptable excipients may vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically acceptable excipients may be chosen for their ability to facilitate carrying or transporting the compound or compounds of the invention once administered to the subject from an organ, or a portion of the body, to another organ, or a portion of the body. Certain pharmaceutically-acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a therapeutically effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

In certain embodiment, the present invention is directed to a pharmaceutical composition comprising 0.01 to 1000 mg of one or more compounds described herein or a pharmaceutically acceptable salt thereof and 0.01 to 5 g of one or more pharmaceutically acceptable excipients.

E. Process of Preparing Compounds

The process to be utilized in the preparation of the compounds described herein depends upon the desired compounds. Such factors as the selection of the specific substituent and various possible locations of the specific substituent all play a role in the path to be followed in the preparation of the specific compounds of this invention. Those factors are readily recognized by one of ordinary skill in the art.

In general, the compounds of the present invention may be prepared by standard techniques known in the art and by known processes analogous thereto. General methods for preparing compounds of the present invention are set forth below. All starting material and reagents described in the below general experimental schemes are commercially available or can be prepared by methods known to one skilled in the art. The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

General Schemes 1-3 provide exemplary processes of synthesis for preparing compounds of the present invention.

as $Na_2CO_3$ in appropriate solvents such as 1,4-dioxane under suitable temperatures such as 90° C. to 130° C.

Intermediates IV reacts with suitable alkylating reagents in step (iii) in the presence of suitable bases such as NaH in appropriate solvents such as DMF under suitable temperatures such as 25° C. to 90° C. may provide intermediates III. Amino intermediates V may be obtained by reacting intermediates III with suitable reducing reagents such as hydrogen in the presence of suitable catalysts such as Pd/C in polar solvents such as methanol at appropriate temperatures such as 25° C. to 100° C. in step (iv).

Step (v) may be carried out by reacting intermediates VI with sodium alkoxys in the presence of suitable polar solvents such as EtOH under suitable temperatures such as 70° C. to 90° C. to provide intermediates VII. Intermediates

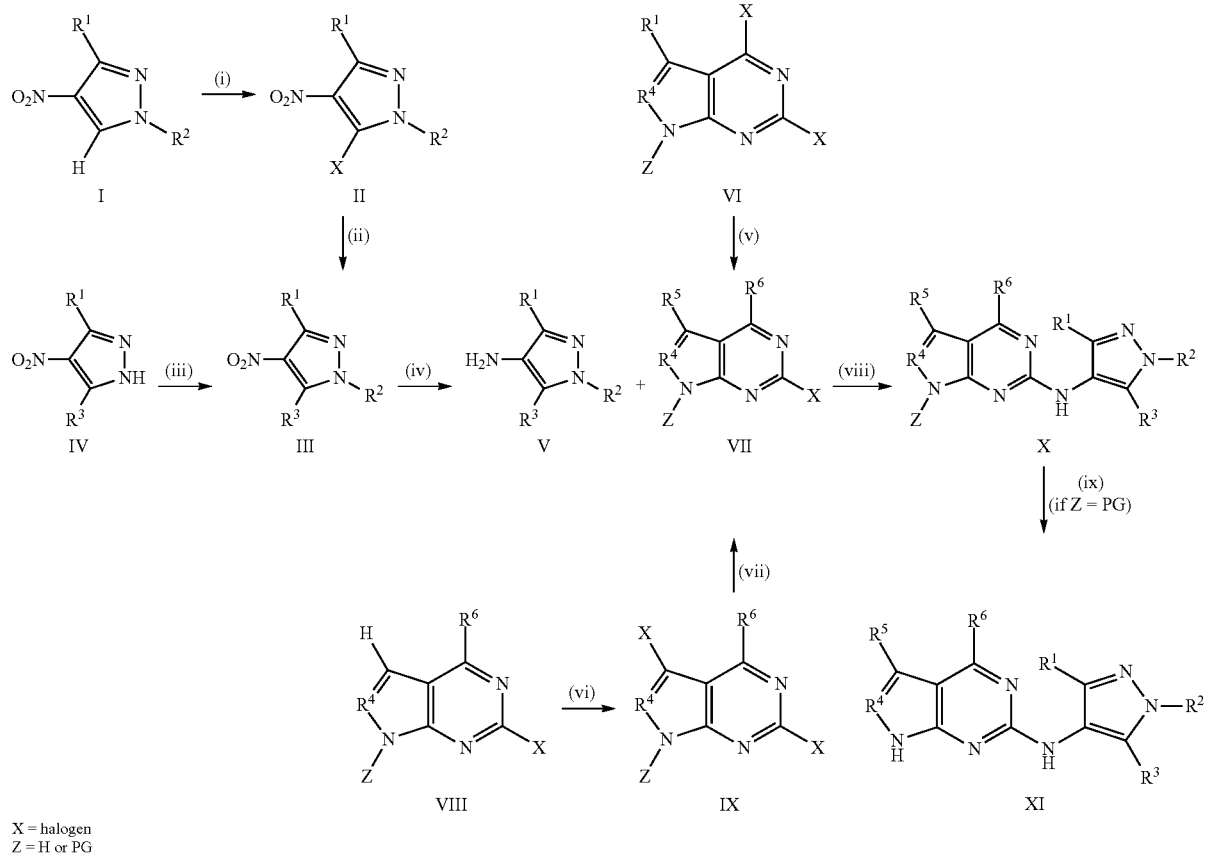

General scheme 1

X = halogen
Z = H or PG

General Scheme 1 provides an exemplary synthesis for preparing compounds X and XI. The protecting group can be any suitable protecting group (PG), such as 4-methylbenzene-1-sulfonyl (Ts) or tert-butyl carboxylate (Boc). In General Scheme 1, $R^1$, $R^2$, $R^3$, $R^4$, $R^5$, and $R^6$, are as defined in Formula (I).

Intermediates II may be obtained by reacting intermediates I with halogen reagents such as $C_2Cl_6$ in step (i) in the presence of suitable bases such as n-BuLi in appropriate solvents such as THF under suitable temperatures such as −78° C. to 0° C. Intermediates III may be obtained by Suzuki coupling reaction of intermediates II with boronic acids or boronic esters in step (ii) using appropriate palladium catalysts such as $Pd(PPh_3)_4$ in the presence of suitable bases such IX may be obtained by reacting intermediates VIII in step (vi) with suitable reagents such as NIS in suitable solvents such as DMF at suitable temperatures such as 0° C. to 25° C. Intermediates IX react with suitable reagents such as CuCN in the presence of suitable copper or palladium catalysts in suitable solvents such as DMF under suitable temperatures such as 90° C. to 130° C. may provide intermediates VII in step (vii).

Step (viii) may be Buchwald coupling reactions by reacting intermediates VII with intermediates V using appropriate palladium catalysts such as $Pd(dppf)Cl_2$ in the presence of suitable bases such as $K_2CO_3$ and suitable ligands such as X-Phos in appropriate solvents such as 1,4-dioxane under suitable temperatures such as 90° C. to 120° C. to provide compound X. If Z=PG, compound XI may be obtained by reacting compound X with suitable bases such as NaOH in suitable solvents such as MeOH at suitable temperatures such as 25° C. to 60° C. in step (ix).

such as −78° C. to 0° C. Intermediates XVI may be obtained by Suzuki coupling reaction from intermediates XV with boronic acids or boronic esters in step (xiii) using appropriate palladium catalysts such as Pd(PPhs)$_4$ in the presence of

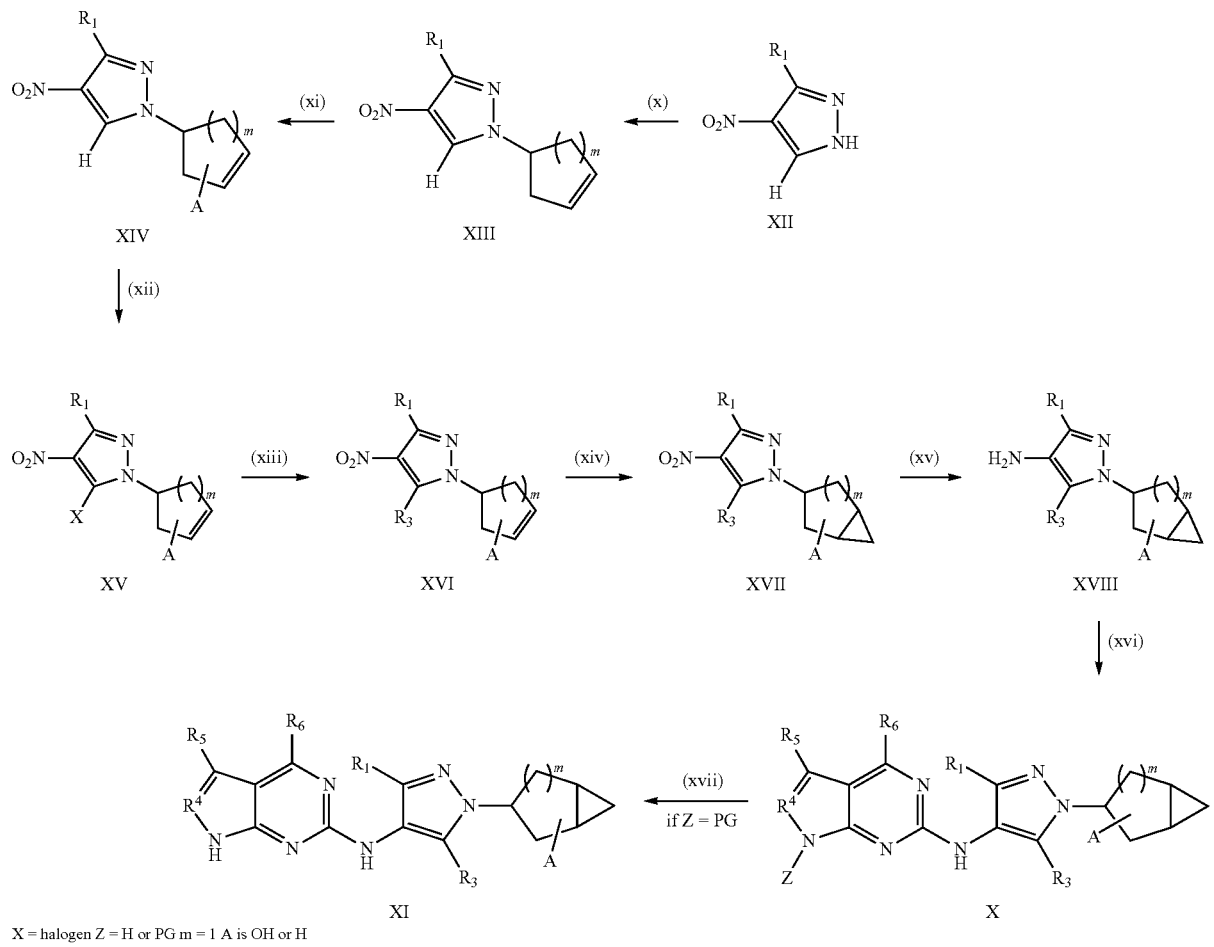

General scheme 2

X = halogen  Z = H or PG  m = 1  A is OH or H

General Scheme 2 provides an exemplary synthesis for preparing compounds X and XI. The protecting group can be any suitable protecting group, such as 4-methylbenzene-1-sulfonyl (Ts) or tert-butyl carboxylate (Boc). In General Scheme 2, R$^1$, R$^3$, R$^4$, R$^5$ and R$^6$ are as defined in Formula (I).

Intermediates XIII may be obtained by reacting intermediates XII with suitable alkylating reagents in step (x) In the presence of suitable bases such as K$_2$CO$_3$ in appropriate solvents such as CH$_3$CN under suitable temperatures such as 25° C. to 90° C. Step (xi) may be carried out by reacting intermediates XIII with oxidation reagents such as SeO$_2$ in appropriate solvents such as 1, 4-dioxane under suitable temperatures such as 80° C. to 100° C. to provide intermediates XIV.

Intermediates XV may be obtained by reacting intermediates XIV with halogen reagents such as C$_2$Cl$_6$ in step (xii) in the presence of suitable bases such as n-BuLi in appropriate solvents such as THF under suitable temperatures suitable bases such as Na$_2$CO$_3$ in appropriate solvents such as 1,4-dioxane under suitable temperatures such as 90° C. to 130° C.

Step (xiv) may be carried out by reacting intermediates XVI with carbenes in appropriate solvents such as DCM under suitable temperatures such as 0° C. to 25° C. to provide intermediates XVII. Amino intermediates XVIII may be obtained by reacting intermediates XVII with suitable reducing reagents such as hydrogen in the presence of suitable catalysts such as Pd/C in polar solvents such as methanol at appropriate temperatures such as 25° C. to 60° C. in step (xv). Step (xvi) may be Buchwald coupling reactions by reacting Intermediates XVIII with intermediates VII using appropriate palladium catalysts such as Pd(dppf)Cl$_2$ in the presence of suitable bases such as K$_2$CO$_3$ and suitable ligands such as X-Phos in appropriate solvents such as 1,4-dioxane under suitable temperatures such as 90° C. to 120° C. to provide compound X. If Z=PG, compound XI may be obtained by reacting compound X with suitable bases such as NaOH in suitable solvents such as MeOH at suitable temperatures such as 25° C. to 60° C. in step (xvii).

General scheme 3

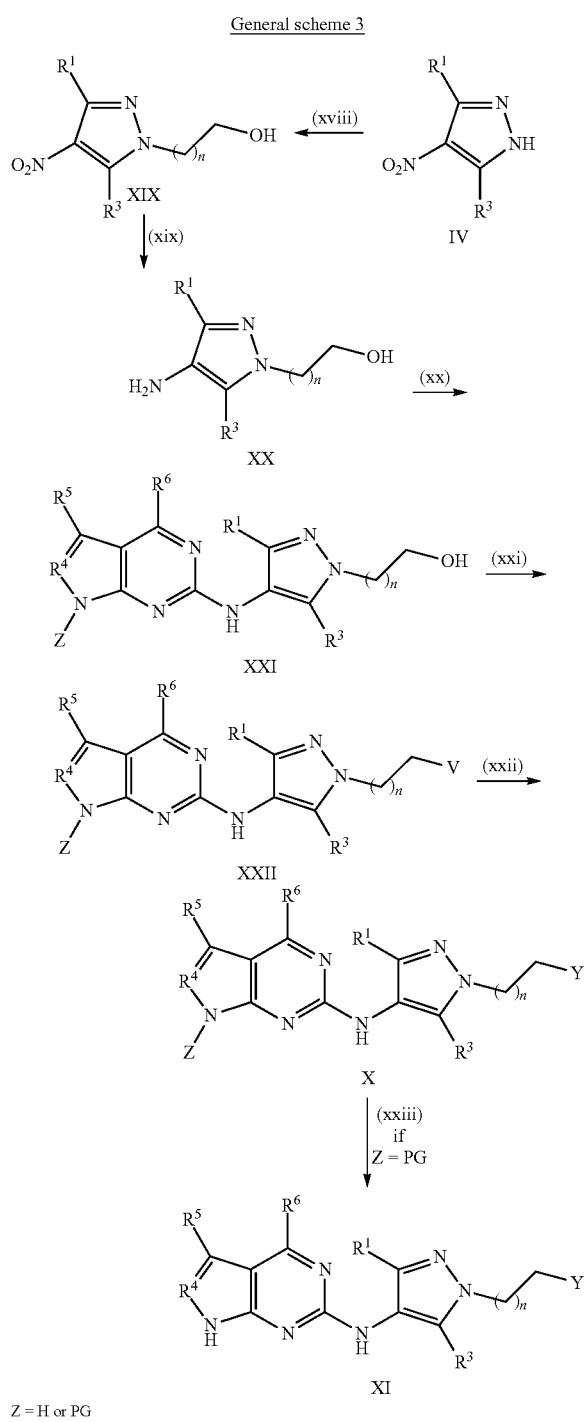

Z = H or PG
V = Leaving group
n is 0 or 1

General Scheme 3 provides an exemplary synthesis for preparing compounds X and XI. The protecting group can be any suitable protecting group, such as 4-methylbenzene-1-sulfonyl (Ts) or tert-butyl carboxylate (Boc). The leaving group can be any suitable leaving group, such as halogen (Cl, Br, I) or methanesulfonate. In General Scheme 3, $R^1$, $R^3$, $R^4$, $R^5$, $R^6$ and Y are as defined in Formula (I).

Intermediates XIX may be obtained by intermediates IV reacting with suitable alkylating reagents in step (xviii) in the presence of suitable bases such as $K_2CO_3$ in appropriate solvents such as DMF under suitable temperatures such as 25° C. to 90° C. Amino intermediates XX may be obtained by intermediates XIX reacting with suitable reducing reagents such as hydrogen in the presence of suitable catalysts such as Pd/C in polar solvents such as methanol at appropriate temperatures such as 25° C. to 60° C. in step (xix). Step (xx) may be Buchwald coupling reactions by reacting intermediates XX with intermediates VII in Scheme 1 using appropriate palladium catalysts such as $Pd(dppf)Cl_2$ in the presence of suitable bases such as $K_2CO_3$ and suitable ligands such as X-Phos in appropriate solvents such as 1,4-dioxane under suitable temperatures such as 90° C. to 120° C. to provide intermediate XXI. Intermediates XXI reacts with suitable halogen reagents such as MsCl in the presence of suitable bases such as $Et_3N$ in step (xxi) in appropriate solvents such as DCM under suitable temperatures such as 0° C. to 25° C. to provide intermediates XXII. Step (xxii) may be carried out by reacting intermediates XXII with different amines in the presence of suitable bases such as $K_2CO_3$ in appropriate solvents such as DMF under suitable temperatures such as 25° C. to 120° C. to provide compounds X. If Z=PG, compound XI may be obtained by reacting compound X with suitable bases such as NaOH in suitable solvents such as MeOH at suitable temperatures such as 25° C. to 60° C. in step (xxiii).

The starting material and reagents described in the above schemes are either commercially available or may be readily prepared from commercially available compounds using procedures known to a person of ordinary skill in the art.

EXAMPLES

General Experimental Procedures

The following descriptions and examples illustrate the invention. These examples are not intended to limit the scope of the present invention, but rather to provide guidance to the skilled chemist to prepare and use the compounds, compositions and methods of the present invention. While particular embodiments of the present invention are described, the skilled chemist will appreciate that various changes and modifications can be made without departing from the spirit and scope of the invention.

Microwave reactions were carried out on the following instruments: Smith Creator (purchased from Personal Chemistry, Forboro/MA, now owned by Biotage), Emrys Optimizer (purchased from Personal Chemistry) and CEM Explorer (provided by CEM Discover, Matthews/NC).

Conventional techniques may be used herein for work up of reactions and purification of the products of the Examples.

References in the Examples below relating to the drying of organic layers or phases may refer to drying the solution over magnesium sulfate or sodium sulfate and filtering off the drying agent in accordance with conventional techniques. Products may generally be obtained by removing the solvent by evaporation under reduced pressure.

Purification of the compounds in the examples may be carried out by conventional methods such as chromatography and/or re-crystallization using suitable solvents. Chromatographic methods are known to the skilled person and include e.g. column chromatography, flash chromatography, HPLC (high performance liquid chromatography), and MDAP (mass directed auto-preparation, also referred to as mass directed LCMS purification). MDAP is described in e.g. W. Goetzinger et al, *Int. J. Mass Spectrom.*, 2004, 238, 153-162.

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel. Preparative HPLC were performed using a Gilson Preparative System using a Luna 5u C18(2) 100A reverse phase column eluting with a 10-80 gradient (0.1% TFA in CH$_3$CN/0.1% aqueous TFA) or a 10-80 gradient (CH$_3$CN/water). The Combi-Flash system used for purification in this application was purchased from Isco, Inc. Combi-Flash purification was carried out using a pre-packed SiO$_2$ column, a detector with UV wavelength at 254 nm and mixed solvents.

The terms "Combi-Flash", "Biotage®", "Biotage 75" and "Biotage SP4®" when used herein refer to commercially available automated purification systems using pre-packed silica gel cartridges.

Final compounds were characterized with LCMS (conditions listed below) or NMR. The structures of regioisomers and stereoisomers were assigned based on NMR coupling constant and/or Nuclear Overhauser Effect studies (NOE) or other analytical methods known to one skilled in the art. 1H-NMR spectra were recorded using a Bruker Avance 400 MHz spectrometer. CDCl$_3$ is deuterlochloroform, DMSO-de is hexadeuteriodimethysulfoxide, and CD$_3$OD (or MeOD) is tetradeuteriomethanol. Chemical shifts are reported in parts per million (ppm) downfield from the internal standard tetramethylsilane (TMS) or the NMR solvent. Abbreviations for NMR data are as follows: s=singlet, d=doublet, t=triplet, q=quartet, m=multi-plet, dd=doublet of doublets, dt=doublet of triplets, app=apparent, br=broad. J indicates the NMR coupling constant measured in Hertz. Mass spectra were taken on instruments, using electro-spray (ES) ionization techniques. All temperatures are reported in degrees Celsius. All other abbreviations are as described in the ACS Style Guide (American Chemical Society, Washington, D.C., 1986).

Absolute stereochemistry can be determined by methods known to one skilled in the art, for example X-ray or Vibrational circular dichroism (VCD).

In the procedures that follow, after each starting material, reference to an intermediate is typically provided. This is provided merely for assistance to the skilled chemist. The starting material may not necessarily have been prepared from the batch referred to.

LCMS Conditions:
1) Acidic Conditions:
Mobile phase: water containing 0.05% TFA/0.05% CH$_3$CN
Column: Agilent SB-C18 4.6×30 mm-1.8 microns
Detection: MS and photodiode array detector (PDA)
2) Basic Conditions:
Mobile phase: water containing 10 mmol NH$_4$HCO$_3$/CH$_3$CN
Column: XBridge™ C18 4.6×50 mm-3.5 microns
Detection: MS and photodiode array detector (PDA)
3) Basic Conditions:
Mobile phase: water containing 0.02% NH$_4$OAc/CH$_3$CN
Column: Welch Ultimate XB-C18 5 μm 4.6*33 mm
Detection: MS and photodiode array detector (PDA)
MDAP Conditions:
1) Acidic Conditions:
Instrument: Waters instrument
Column: Sunfire Prep C18 column (5 um, 19×50 mm)
Mobile phase: water containing 0.05% TFA/CH$_3$CN.
2) Basic Conditions:
Instrument: Waters instrument
Column: Xbridge Prep C18 column (5 um, 19×50 mm)
Mobile phase: water containing 0.04% ammonia/CH$_3$CN.
Prep-HPLC Conditions
Instrument: Waters instrument
Column: Xbridge Prep C18 column OBD (10 um, 19×250 mm)
Mobile phase: water containing 0.08% ammonia/acetonitrile.
Chiral-HPLC Isolation Instruments:
1. Gilson Gx-281 Prep LC (Gilson 806 Manometric Module, Gilson 811D Dynamic Mixer, Gilson Gx-281 prep liquid handler, Gilson 306 Pump *2, Gilson 156 Detector),
2. Agilent 1200 series Prep LC (Agilent G1361A Prep pump *2, Agilent G2260A Prep ALS, Agilent G1315D DAD Detector, Agilent G1364B Prep FC),
3. Thar SFC Prep 80 (TharSFC ABPR1, TharSFC SFC Prep 80 CO$_2$ Pump, TharSFC Co-Solvent Pump, TharSFC Cooling Heat Exchanger and Circulating Bath, TharSFC Mass Flow Meter, TharSFC Static Mixer, TharSFC Injection Module, Gilson UV Detector, TharSFC Fraction Collection Module).
Chiral-HPLC Analysis Conditions:
Instrument: Agilent 1200 series HPLC or Thar Analytical SFC
Column and mobile phase: are described in below examples.
[α]$_D$ was obtained by using automatic polarimeter SGW$_®$-1.

Abbreviations and Resource Sources

The following abbreviations and resources are used herein below:
ACN Acetonitrile
Aq.—aqueous
Boc$_2$O—Di-tert-butyl dicarbonate
n-BuLi—Butyl
CbzCl—Benzyl chloroformate
DAST—Diethylaminosulfur trifluoride
dba—dibenzylideneacetone
DBU—1,8-Diazabicyclo[5.4.0]undec-7-ene
DCE—1,2-Dichloroethene
DCM—Dichloromethane
DIAD—Diisopropyl azodicarboxylate
DIPEA—N,N-Diisopropylethylamine
DMA—N,N-dimethylacetamide
DMF—Dimethylformamide
DMAP—4-Dimethylaminopyridine
DMSO—Dimethyl sulfoxide
dppf—1,1'-Bis(diphenylphosphino)ferrocene
EA—Ethyl acetate
Et—Ethyl
Et$_2$O—Diethyl ether
EtOAc—Ethyl acetate
LDA—Lithium diisopropylamide
LiAlH$_4$—Lithium aluminium hydride
LHMDS (or UHMDS)—Lithium bis(trimethylsilyl)amide
Me—Methyl
MsCl—Methanesulfonyl chloride
NIS—N-Iodosuccinimide
NaBH$_4$—Sodium borohydride
HOAc—Acetic acid
SEMCl—(2-(Chloromethoxy)ethyl)trimethylsilane
SOCl$_2$—Thionyl chloride
TBAF—Tetrabutylammonium fluoride
TEA—Triethylamine TFA—Trifluoroacetic acid
THF—Tetrahydrofuran
PE—Petroleum ether
X-Phos—4,5-Bis(diphenylphosphino)-9,9-dimethylxanthene Description D1

2-chloro-4-ethoxy-7H-pyrrolo[2,3-d]pyrimidine (D1)

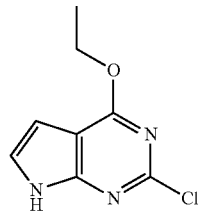

Method A:
A solution of 2,4-dichloro-7H-pyrrolo-[2,3-d]-pyrimidine (500 g, 2.66 mmol) and sodium ethoxide (181 g, 2.66 mmol) in ethanol (8 mL) and THF (8.00 mL) was stirred at 90° C. overnight. The mixture was cooled to room temperature and evaporated. The crude was purified via chromatography on silica gel (PE:EA=25:1) to give the title compound D1 (300 g, 1.214 mmol, 45.7% yield) as a white solid.
LCMS: 198 [M+1]$^+$. $t_R$=1523 min. (LCMS condition 2)
Method B:
A solution of 2,4-dichloro-7H-pyrrolo-[2,3-d]-pyrimidine (13 g, 69.1 mmol), sodium ethoxide (5.65 g, 83 mmol) in ethanol (100 mL) was heated overnight at 90° C. The mixture was cooled to room temperature and water was added. The formed solid was then filtered and dried to give the title compound D1 (10.0 g, 50.6 mmol, 73.2% yield) as a white solid.
LCMS: 198 [M+1]$^+$. $t_R$=1.871 min. (LCMS condition 2)
$^1$H NMR (400 MHz, DMSO-d$_6$): δ 12.23 (br. s., 1H), 7.38 (d, J=3.4 Hz, 1H), 6.50 (d, J=3.4 Hz, 1H), 4.51 (q, J=7.1 Hz, 2H), 1.39 (t, J=7.0 Hz, 3H).

Description D2

2-chloro-4-ethoxy-7-tosyl-7H-pyrrolo-[2,3-d]-pyrimidine (D2)

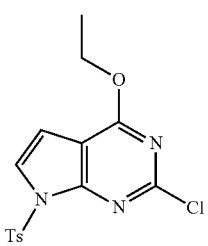 [SMILES: CCOc1nc(Cl)nc2c1ccn2S(=O)(=O)c1ccc(C)cc1]

To a solution of 2-chloro-4-ethoxy-7H-pyrrolo[2,3-d]pyrimidine (which may be prepared according to D1) (8 g, 40.5 mmol) in DMF (50 mL) was added sodium hydride (1.619 g, 40.5 mmol). The reaction mixture was stirred for 5 min at room temperature. Then 4-methylbenzene-1-sulfonyl chloride (7.72 g, 40.5 mmol) was added to this mixture. The reaction mixture was stirred for an additional 1 hour at room temperature. The reaction mixture was diluted with water (450 mL) and filtered. The filtered solid was washed with water (90 mL) and dried to give the title compound D2 (10 g, 26.2 mmol, 64.6% yield) as a white solid.
LCMS: 352 [M+H]$^+$. $t_R$=1.871 min. (LCMS condition 2)

Description D3

N-(1,3-dimethyl-1H-pyrazol-4-yl)-4-ethoxy-7-tosyl-7H-pyrrolo[2,3-d]pyrimidin-2-amine (D3)

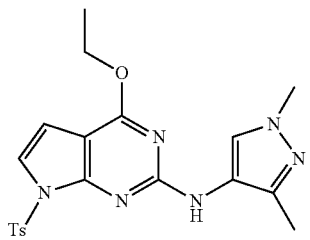 [SMILES: CCOc1nc(Nc2cn(C)nc2C)nc2c1ccn2S(=O)(=O)c1ccc(C)cc1]

To a solution of 2-chloro-4-ethoxy-7-tosyl-7H-pyrrolo-[2,3-d]-pyrimidine (which may be prepared according to D2) (200 g, 0.568 mmol), 1,3-dimethyl-1H-pyrazol-4-amine, hydrochloride (105 g, 0.568 mmol) and (9,9-dimethyl-9H-xanthene-4,5-diyl)bis(diphenylphosphine) (49.3 g, 0.085 mmol) in 1,4-dioxane (2.0 mL) and water (0.2 mL) was added potassium carbonate (157 g, 1.137 mmol) and PdCl$_2$ (pddf) (46.4 g, 0.057 mmol). The reaction mixture was stirred overnight at 90° C. The mixture was then cooled to room temperature and partitioned between EtOAc (25 mL) and water (20 mL). The organic layer was washed with water (20 mL), dried over Na$_2$SO$_4$ and evaporated. The crude was purified by column chromatography on silica gel (DCM:MeOH=25:1) to give the title compound D3 (100 g, 0.234 mmol, 41.2% yield) as a white solid.
LCMS: 427 [M+H]$^+$, $t_R$=1.75 min. (LCMS condition 2)

Description D4

N-(5-chloro-1-methyl-1H-pyrazol-4-yl)-4-ethoxy-7-tosyl-7H-pyrrolo-[2,3-d]-pyrimidin-2-amine (D4)

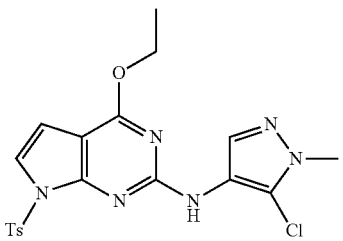 [SMILES: CCOc1nc(Nc2cnn(C)c2Cl)nc2c1ccn2S(=O)(=O)c1ccc(C)cc1]

A solution of 2-chloro-4-ethoxy-7-tosyl-7H-pyrrolo-[2,3-d]-pyrimidine (which may be prepared according to D2) (100 g, 0.284 mmol) and 3-chloro-1-methyl-1H-pyrazol-4-amine (44.9 g, 0.341 mmol), potassium carbonate (79 g, 0.568 mmol), PdCl$_2$(pddf)-CH$_2$Cl$_2$ (23.21 g, 0.028 mmol) and dicyclohexyl(2',4',6'-triisopropyl-[1,1'-biphenyl]-2-yl) phosphine (20.33 g, 0.043 mmol) in 1,4-dioxane (3 mL) and water (0.300 mL) was irradiated by microwave at 100° C. for 2 hours. Solvent was evaporated and the crude was purified via prep-HPLC to give the title compound D4 (100 g, 0.190 mmol, 66.9% yield) as a yellow solid.

LCMS: 447 [M+H]$^+$, $t_R$=1.542 min. (LCMS condition 2)

Description D5

1-(3,5-dimethyl-4-nitro-1H-pyrazol-1-yl)-2-methyl-propan-2-ol (D5)

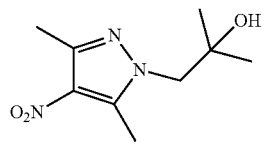

To a solution of 3,5-dimethyl-4-nitro-1H-pyrazole (1.0 g, 7.09 mmol) in acetonitrile (10 mL) was added 2,2-dimethyloxirane (1.788 g, 24.80 mmol) and DBU (2.136 mL, 14.17 mmol). The reaction was stirred at 60° C. for 20 hours. The mixture was quenched with water and extracted with DCM (20 mL×3). The combined organic layer was dried over Na$_2$SO$_4$, filtered and concentrated in vacuum. The crude was purified by column chromatography on silica gel (DCM:MeOH=20:1) to give the title compound D5 (800 g, 3.75 mmol, 52.9% yield).

LCMS: 214 [M+H]$^+$, $t_R$=1.06 min. (LCMS condition 2)

Description D6

1-(4-amino-3,5-dimethyl-1H-pyrazol-1-yl)-2-methylpropan-2-ol (D6)

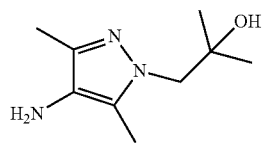

To a solution of 1-(3,5-dimethyl-4-nitro-1H-pyrazol-1-yl)-2-methylpropan-2-ol (which may be prepared according to D5) (800 g, 3.75 mmol) in methanol (15 mL) was added Pd/C (100 g, 0.094 mmol) under nitrogen. The mixture was stirred overnight under hydrogen at room temperature. The mixture was filtered through a pad of Celite and the filtrate was concentrated in vacuum. The crude was purified by column chromatography on silica gel (DCM:MeOH=20:1) to give the title compound D6 (680 g, 3.66 mmol, 98% yield).

LCMS: 184 [M+H]$^+$, $t_R$=0.74 min. (LCMS condition 2)

Description D7

1,3,5-trimethyl-4-nitro-1H-pyrazole (D7)

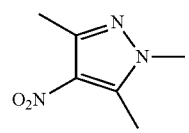

To a solution of 3,5-dimethyl-4-nitro-1H-pyrazole (1.0 g, 7.09 mmol) in THF (25 mL) was added formaldehyde (0.255 g, 8.50 mmol) at 0° C. After stirred for 30 min, NaCNBH$_3$ (0.668 g, 10.63 mmol) was added. The reaction was warmed up to room temperature and stirred overnight. The mixture was quenched with water and extracted with DCM (20 mL×3). The combined organic layer was dried over Na$_2$SO$_4$, filtered and concentrated in vacuum. The crude was purified by column chromatography on silica gel (DCM:MeOH=20:1) to give the title compound D7 (850 g, 4.99 mmol, 70.5% yield) as yellow oil.

LCMS: 156.1 [M+H]$^+$. $t_R$=1.35 mins. (LCMS condition 2)

$^1$H NMR (400 MHz, DMSO-d$_6$): δ 3.73 (3H, s), 2.54 (3H, s), 2.36 (3H, s).

Description D8

1,3,5-trimethyl-1H-pyrazol-4-amine (D8)

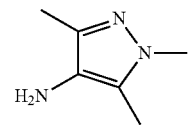

A solution of 1,3,5-trimethyl-4-nitro-1H-pyrazole (which may be prepared according to D7) (850 g, 5.48 mmol) and Pd/C (146 g, 0.137 mmol) in methanol (15 mL) was stirred overnight under hydrogen at room temperature. The suspension was filtered through Celite and the pad was washed with EtOH (10 mL×3). The filtrate was concentrated in vacuum. The crude was purified by column chromatography on silica gel (DCM:MeOH=20:1) to give the title compound D8 (650 g, 4.88 mmol, 89% yield) as yellow oil.

LCMS: 126.1 [M+H]$^+$, $t_R$=0.69 min. (LCMS condition 2)

Description D9 tert-butyl-(3-chloro-1H-pyrazol-4-yl)carbamate (D9)

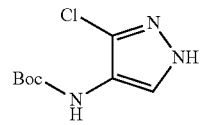 [SMILES: CC(C)(C)OC(=O)Nc1c[nH]nc1Cl]

To a solution of 3-chloro-1H-pyrazol-4-amine (1 g, 8.51 mmol) (which may be prepared as an example following PCT Int. Appl., WO2011048082), (Boc)$_2$O (2.043 g, 9.36 mmol) in THF (50 mL) and water (5 mL) at 20° C. was added sodium carbonate (1.984 g, 18.72 mmol). The reaction was stirred at 20° C. for 16 hours. The mixture was quenched with water, and then partitioned between ethyl acetate (50 mL) and NaHCO$_3$ solution (50 mL). The organic layer was evaporated in vacuum to give the title compound D9 (1.5 g, 6.89 mmol, 81% yield) as yellow oil.

LCMS: 218 [M+H]⁺. $t_R$=1.416 mins. (LCMS condition 2)
¹H NMR (400 MHz, CHLOROFORM-d): δ: 10.78-11.60 (m, 1H), 7.92 (s, 1H), 6.29 (br. s., 1H), 1.52 (s, 9H).

Description D10 tert-butyl-(3-chloro-1-(2-hydroxy-2-methylpropyl)-1H-pyrazol-4-yl)carbamate (D10)

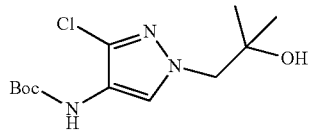 [SMILES: CC(C)(O)Cn1cc(NC(=O)OC(C)(C)C)c(Cl)n1]

To a solution of tert-butyl-(3-chloro-1H-pyrazol-4-yl)carbamate (which may be prepared according to D9) (320 g, 1.470 mmol) In acetonitrile (10 mL) was added DBU (0.443 mL, 2.94 mmol) and 2,2-dimethyloxirane (318 g, 4.41 mmol). The reaction was stirred at 60° C. for 20 hours. The reaction mixture was concentrated in vacuum. The residue was dissolved in ethyl acetate and washed with 1N HCl, water and brine. The organic layer was dried over Na₂SO₄, filtered and concentrated in vacuum. The crude was purified by column chromatography on silica gel (DCM:CH₃OH=20:1) to give the title compound D10 (260 g, 0.610 mmol, 41.5% yield).

LCMS: 290 [M+H]⁺. $t_R$=1.186 mins. (LCMS condition 2)
¹H NMR (400 MHz, METHANOL-d₄): δ 7.79 (br. s., 1H), 3.99 (s, 2H), 1.52 (s, 9H), 1.18 (s, 6H).

Description D11

1-(4-amino-3-chloro-1H-pyrazol-1-yl)-2-methylpropan-2-ol (D11)

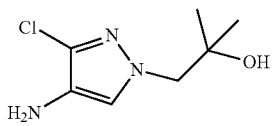

A solution of tert-butyl-(3-chloro-1-(2-hydroxy-2-methylpropyl)-1H-pyrazol-4-yl)carbamate (which may be prepared according to D10) (100 g, 0.345 mmol) and HCl (3 mL, 12.00 mmol, 4M in dioxane) was stirred at 35° C. for 12 hours. Solvent was evaporated in vacuum to give the title compound D11 (50 g, 0.264 mmol, 76% yield) as a white solid.

LCMS: 190 [M+H]⁺. $t_R$=1.046 mins. (LCMS condition 2)

Description D12 and D13

4-ethoxy-N-(1-(2-methoxyethyl)-3-methyl-1H-pyrazol-4-yl)-7-tosyl-7H-pyrrolo-[2,3-d]-pyrimidin-2-amine (D12)

4-ethoxy-N-(1-(2-methoxyethyl)-5-methyl-1H-pyrazol-4-yl)-7-tosyl-7H-pyrrolo-[2,3-d]-pyrimidin-2-amine (D13)

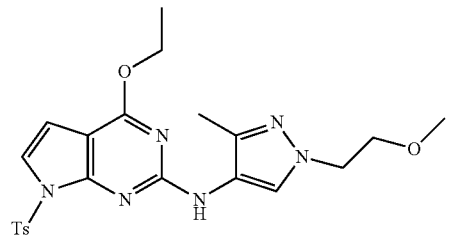

D12

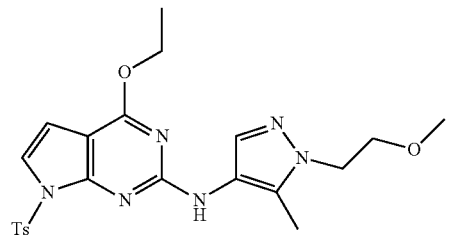

D13

A solution of 2-chloro-4-ethoxy-7-tosyl-7H-pyrrolo-[2,3-d]-pyrimidine (which may be prepared according to D2) (318 g, 2.047 mmol), a mixture of 1-(2-methoxyethyl)-3-methyl-1H-pyrazol-4-amine and 1-(2-methoxyethyl)-5-methyl-1H-pyrazol-4-amine (318 g, 2.047 mmol) (which may be prepared according to PCT Int Appl., 2012062783) dicyclohexyl(2',4',6'-triisopropyl-[1,1'-biphenyl]-2-yl)phosphine (148 g, 0.256 mmol), potassium carbonate (471 g, 3.41 mmol) and PdCl₂(dppf)-CH₂Cl₂ (139 g, 0.171 mmol) in 1,4-dioxane (2.0 mL) and water (0.2 mL) was stirred overnight at 90° C. Then mixture was diluted with water (100 mL) and extracted with ethyl acetate (2×40 mL). The combined organic layer was washed with brine (20 mL), dried with Na₂SO₄, filtered and concentrated. The crude was purified by column chromatography on silica gel (PE:EA=3:1) to give the mixture of the title compound D12 and D13 (650 g, 0.995 mmol, 58.3% yield) as oil.

LCMS: 471 [M+H]⁺. $t_R$=1.76 mins. (LCMS condition 2)

Description D14

2-(5-methyl-4-nitro-1H-pyrazol-1-yl)-ethanol (D14)

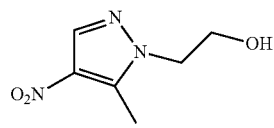

To a solution of 3-methyl-4-nitro-1H-pyrazole (2.0 g, 15.74 mmol) and 1, 3-dioxolan-2-one (6.93 g, 79 mmol) in acetonitrile (5 mL) was added sodium hydroxide (1.888 g, 47.2 mmol). The reaction mixture was stirred at 80° C. for 15 hours. The mixture was then diluted with water (100 ml) and extracted with EtOAc. The organic layer was dried over Na$_2$SO$_4$, filtered and concentrated. The crude was purified by pre-HPLC to give the title compound D14 (400 g, 2.337 mmol, 14.85% yield) as a white solid.

LCMS: 172 [M+H]$^+$. t$_R$=1.130 mins. (LCMS condition 2)

$^1$H NMR (400 MHz, CHLOROFORM-d): δ 8.11 (s, 1H), 4.17-4.26 (m, 2H), 3.99-4.13 (m, 2H), 2.77 (t, 1H), 2.68 (s, 3H).

Description D15

2-(5-methyl-4-nitro-1H-pyrazol-1-yl) ethyl-methanesulfonate (D15)

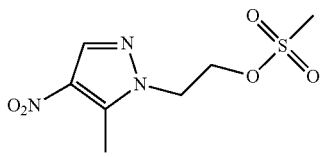 [SMILES: Cc1c([N+](=O)[O-])cnn1CCOS(C)(=O)=O]

To a solution of 2-(5-methyl-4-nitro-1H-pyrazol-1-yl)-ethanol (which may be prepared according to D14) (200 g, 1.169 mmol) and DIPEA (0.204 mL, 1.169 mmol) in THF (5 mL) was added hypochlorous methanesulfonic anhydride (0.210 mL, 1.169 mmol). The reaction was then stirred at 0° C. for 30 min. The mixture was diluted with aq. NaHCO$_3$ (20 mL), extracted with EtOAc. The organic layer was dried and concentrated to give the title compound D15 (300 g, 0.951 mmol, 81% yield) as oil.

LCMS: 250 [M+H]$^+$. t$_R$=1.316 mins. (LCMS condition 2)

Description D16

3-(2-(5-methyl-4-nitro-1H-pyrazol-1-yl)-ethyl)-3-azabicyclo-[3.1.0]hexane (D16)

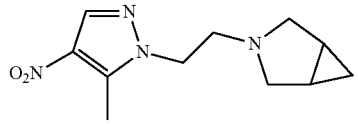

A solution of 2-(5-methyl-4-nitro-1H-pyrazol-1-yl) ethyl-methanesulfonate (which may be prepared according to D15) (288 g, 1.155 mmol), 3-azabicyclo[3.1.0]hexane (80 mg, 0.962 mmol) and potassium carbonate (399 g, 2.89 mmol) in acetonitrile (10 mL) was stirred overnight at 80° C. The mixture was concentrated and purified by column chromatography on silica gel (PE:EA=1:1) to give the title compound D16 (150 g, 0.552 mmol, 57.4% yield) as an oil.

LCMS: 237 [M+H]$^+$. t$_R$=1.612 mins. (LCMS condition 2)

$^1$H NMR (400 MHz, CHLOROFORM-d): δ 8.08 (s, 1H), 4.11 (t, J=6.4 Hz, 2H), 2.79-2.98 (m, 4H), 2.64 (s, 3H), 2.39 (d, J=7.8 Hz, 2H), 1.25-1.37 (m, 2H), 0.54 (q, J=3.8 Hz, 1H), 0.33 (td, J=7.7, 4.3 Hz, 1H)

Description D17

1-(2-(3-azabicyclo-[3.1.0]-hexan-3-yl)ethyl)-5-methyl-1H-pyrazol-4-amine (D17)

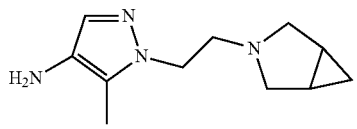 [SMILES: Cc1c([N+](=O)[O-])cnn1CCN1CC2CC2C1]

A solution of 3-(2-(5-methyl-4-nitro-1H-pyrazol-1-yl)-ethyl)-3-azabicyclo-[3.1.0]hexane (which may be prepared according to D16) (200 g, 0.846 mmol) and Pd/C (45.0 g, 0.042 mmol) in methanol (20 mL) was stirred overnight at 20° C. under hydrogen. The mixture was filtered and concentrated. The residue was purified by chromatography on silica gel (DCM:MeOH=10:1) to give the title compound D17 (150 g, 0.727 mmol, 86% yield) as oil.

LCMS: 151 [M+H]$^+$. t$_R$=1.207 mins. (LCMS condition 2)

Description D18

N-(1-(2-(3-azabicyclo-[3.1.0]-hexan-3-yl)ethyl)-5-methyl-1H-pyrazol-4-yl)-4-ethoxy-7-tosyl-7H-pyrrolo[2,3-d]pyrimidin-2-amine (D18)

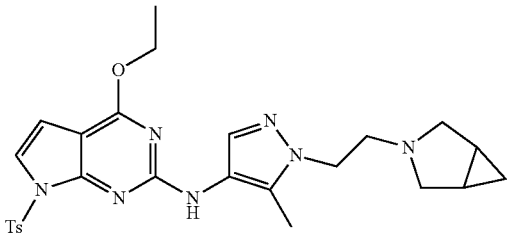 [SMILES: CCOc1nc(Nc2cnn(CCN3CC4CC4C3)c2C)nc2c1ccn2S(=O)(=O)c1ccc(C)cc1]

A solution of 2-chloro-4-ethoxy-7-tosyl-7H-pyrrolo-[2,3-d]-pyrimidine (which may be prepared according to D2) (200 g, 0.568 mmol), D17 (117 g, 0.568 mmol), PdCl$_2$(dppf) (46.4 g, 0.057 mmol), (9,9-dimethyl-9H-xanthene-4,5-diyl) bis(diphenylphosphine) (49.3 mg, 0.085 mmol) and potassium carbonate (157 g, 1.137 mmol) in 1,4-dioxane (2.0 mL) and water (0.2 mL) was stirred overnight at 90° C. The mixture was cooled to room temperature and partitioned between EtOAc (25 mL) and water (20 mL). The organic layer was dried over Na$_2$SO$_4$ and evaporated. The crude was purified by chromatography on silica gel (PE:EA=1:3) to give the title compound D18 (100 g, 0.165 mmol, 29.0% yield) as a white solid.

LCMS: 522 [M+H]$^+$. t$_R$=1.869 mins. (LCMS condition 2)

Description D19

(±)-4-ethoxy-N-(5-methyl-1-(1-methyl-pyrrolidin-3-yl)-1H-pyrazol-4-yl)-7-tosyl-7H-pyrrolo-[2,3-d]-pyrimidin-2-amine (D19)

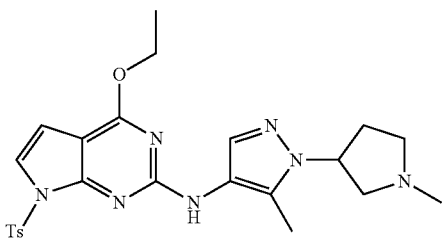 [SMILES: CCOc1nc(Nc2cnn(C3CCN(C)C3)c2C)nc2c1ccn2S(=O)(=O)c1ccc(C)cc1]

To a solution of 5-methyl-1-(1-methylpyrrolidin-3-yl)-1H-pyrazol-4-amine (237 mg, 1.313 mmol), 2-chloro-4-ethoxy-7-tosyl-7H-pyrrolo-[2,3-d]-pyrimidine (which may be prepared according to D2) (420 g, 1.194 mmol) and (9,9-dimethyl-9H-xanthene-4,5-diyl)bis-(diphenylphosphine) (104 g, 0.179 mmol) in 1,4-dioxane (2.0 mL) and water (0.2 mL) was added potassium carbonate (330 g, 2.388 mmol) and $PdCl_2(dppf)\text{-}CH_2Cl_2$ (97 mg, 0.119 mmol). The reaction was stirred overnight at 90° C. The mixture was diluted with water (100 mL) and extracted with ethyl acetate (2×40 mL). The combined organic layer was washed with brine (20 mL), dried with $Na_2SO_4$, filtered and concentrated. The residue was purified by chromatography on silica gel (DCM:MeOH=3:1) to give the title compound D19 (240 g, 0.498 mmol, 41.7% yield) as a black solid.

LCMS: 495.7 $[M+H]^+$. $t_R$=1.58 mins. (LCMS condition 2)

Description D20

1-(5-chloro-4-((4-ethoxy-7-tosyl-7H-pyrrolo-[2,3-d]-pyrimidin-2-yl)amino)-1H-pyrazol-1-yl)-2-methyl-propan-2-ol (D20)

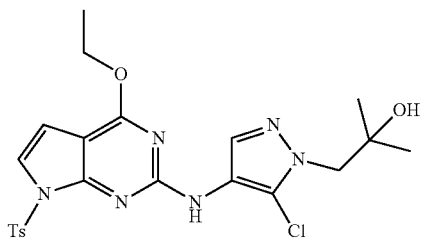 [SMILES: CCOc1nc(Nc2cnn(CC(C)(C)O)c2Cl)nc2c1ccn2S(=O)(=O)c1ccc(C)cc1]

To a solution of 2-chloro-4-ethoxy-7-tosyl-7H-pyrrolo-[2,3-d]-pyrimidine (which may be prepared according to D2) (224 g, 0.638 mmol), 1-(4-amino-5-chloro-1H-pyrazol-1-yl)-2-methyl propan-2-ol, (110 g, 0.580 mmol) (which may be prepared according to PCT Int. Appl. WO2012062783) and (9,9-dimethyl-9H-xanthene-4,5-diyl)bis(diphenylphosphine) in 1,4-dioxane (3 mL) and water (0.300 mL) was added $PdCl_2(dppf)\text{-}CH_2Cl_2$ (47.4 mg, 0.058 mmol) and sodium carbonate (123 g, 1.160 mmol). The mixture was irradiated by microwave at 90° C. for 45 min. The reaction was quenched with water and extracted with EtOAc (20 mL×3). The combined organic layer was dried over $Na_2SO_4$, filtered and concentrated in vacuum. The crude was purified by column chromatography on silica gel (DCM:MeOH=20:1) to give the title compound D20 (200 g, 0.285 mmol, 49.2% yield) as a yellow solid.

LCMS: 504.5 $[M+H]^+$. $t_R$=1.614 mins. (LCMS condition 2)

Description D21 and D22

4-ethoxy-N-(5-methyl-1-(1-methylpiperidin-4-yl)-1H-pyrazol-4-yl)-7-tosyl-7H-pyrrolo-[2,3-d]pyrimidin-2-amine (D21)

4-ethoxy-N-(3-methyl-1-(1-methylpiperidin-4-yl)-1H-pyrazol-4-yl)-7-tosyl-7H-pyrrolo-[2,3-d]pyrimidin-2-amine (D22)

D21
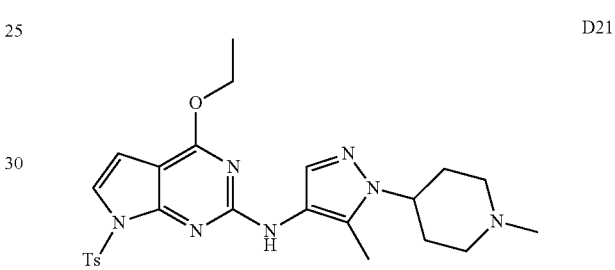

D22
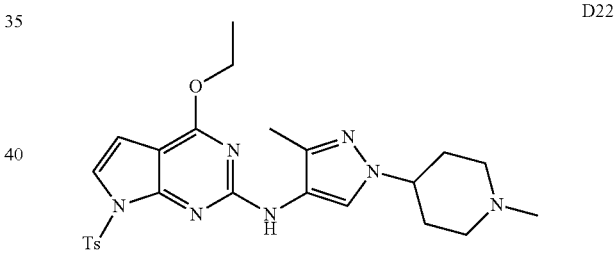

To a solution of 2-chloro-4-ethoxy-7-tosyl-7H-pyrrolo-[2,3-d]-pyrimidine (which may be prepared according to D2) (362 g, 1.029 mmol), a mixture of 5-methyl-1-(1-methylpiperidin-4-yl)-1H-pyrazol-4-amine and 3-methyl-1-(1-methylpiperidin-4-yl)-1H-pyrazol-4-amine (200 g, 1.029 mmol), (which may be prepared according to PCT Int. Appl. WO 2012062783), (9,9-dimethyl-9H-xanthene-4,5-diyl)bis(diphenylphosphine) (89 mg, 0.154 mmol) in 1,4-dioxane (2.0 mL) and water (0.2 mL) was added potassium carbonate (285 g, 2.059 mmol) and $PdCl_2(dppf)$ (84 g, 0.103 mmol). The reaction mixture was stirred at 90° C. overnight. The mixture was cooled to room temperature and partitioned between EtOAc (25 mL) and water (20 mL). The organic layer was washed with water (20 mL), dried over $Na_2SO_4$ and evaporated. The crude was purified by Biotage to give the mixture of the title compounds D11 and D12 (130 g, 0.140 mmol, 13.63% yield) as yellow oil.

LCMS: 510.1 $[M+H]^+$. $t_R$=1.45 mins. (LCMS condition 2)

Description D23

5-methoxy-4-nitro-1-(tetrahydro-2H-pyran-4-yl)-1H-pyrazole (D23)

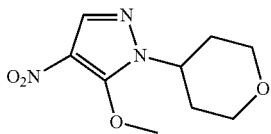 [SMILES: COc1c([N+](=O)[O-])cnn1C1CCOCC1]

To a solution of 5-chloro-4-nitro-1-(tetrahydro-2H-pyran-4-yl)-1H-pyrazole (200 mg, 0.863 mmol) (which may be prepared according to PCT Int. Appl., WO2012062783) in DMF (3 mL) was added sodium hydride (51.8 g, 2.159 mmol) slowly under nitrogen at 0° C. The mixture was stirred at 0° C. for 30 min. Methanol (41.5 g, 1.295 mmol) was added and the mixture was stirred at 0° C. for another 3 hours. The reaction was quenched with aq. NH$_4$Cl and evaporated. The crude was purified by Biotage to give the title compound D23 (140 g, 0.592 mmol, 68.5% yield) as a white solid.

LCMS: 228 [M+H]$^+$. $t_R$=1.503 mins. (LCMS condition 2)

Description D24

5-methoxy-1-(tetrahydro-2H-pyran-4-yl)-1H-pyrazol-4-amine (D24)

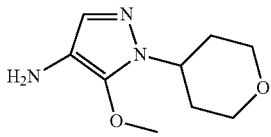

A solution of 5-methoxy-4-nitro-1-(tetrahydro-2H-pyran-4-yl)-1H-pyrazole (which may be prepared according to D23) (200 g, 0.880 mmol), ammonia hydrochloride (235 mg, 4.40 mmol) and iron (246 g, 4.40 mmol) in water (2 mL) and ethanol (2.000 mL) was stirred overnight at 70° C. under nitrogen. The mixture was concentrated and the residue was dissolved in ethanol and filtered. The filtrate was evaporated to give the title compound D24 (160 g, 0.811 mmol, 92% yield) as brown oil which was used in the next step directly.

LCMS: 198 [M+H]$^+$. $t_R$=0.896 mins. (LCMS condition 2)

Description D25

4-ethoxy-N-(5-methoxy-1-(tetrahydro-2H-pyran-4-yl)-1H-pyrazol-4-yl)-7-tosyl-7H-pyrrolo-[2,3-d]pyrimidin-2-amine (D25)

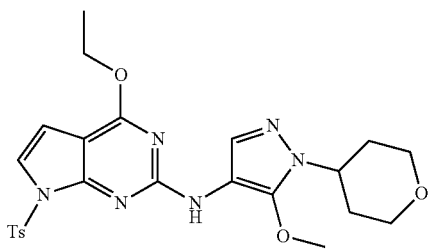 [SMILES: CCOc1nc(Nc2cnn(C3CCOCC3)c2OC)nc2c1ccn2S(=O)(=O)c1ccc(C)cc1]

To a solution of 2-chloro-4-ethoxy-7-tosyl-7H-pyrrolo-[2,3-d]-pyrimidine (which may be prepared according to D2) (241 g, 0.686 mmol), 5-methoxy-1-(tetrahydro-2H-pyran-4-yl)-1H-pyrazol-4-amine (which may be prepared according to D24) (123 g, 0.624 mmol) and dicyclohexyl-(2',4',6'-triisopropyl-[1,1'-biphenyl]-2-yl)phosphine (44.6 g, 0.094 mmol) in 1,4-dioxane (3 mL) and water (0.300 mL) was added PdCl$_2$(dppf)-CH$_2$Cl$_2$ (50.9 g, 0.062 mmol) and sodium carbonate (132 g, 1.247 mmol). The mixture was irradiated by microwave at 90° C. for 45 min. The reaction was quenched with water and extracted with EtOAc (20 mL×3). The combined organic layer was dried over Na$_2$SO$_4$, filtered and concentrated in vacuum. The crude was purified by column chromatography on silica gel (DCM:MeOH=20:1) to give the title compound D25 (80 g, 0.106 mmol, 17.02% yield).

LCMS: 513 [M+H]$^+$. $t_R$=1.961 mins. (LCMS condition 2)

Description D26

2-chloro-4-ethoxy-5-iodo-7H-pyrrolo-[2,3-d]-pyrimidine (D26)

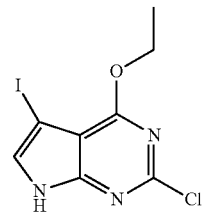

To a solution of 2-chloro-4-ethoxy-7H-pyrrolo[2,3-d]pyrimidine (which may be prepared according to D1) (500 g, 2.53 mmol) in DMF (5 mL) was added NIS (683 g, 3.04 mmol) in one portion. The reaction mixture was stirred at room temperature for 1 hour. The mixture was diluted with aq. Na$_2$S$_2$O$_3$ and extracted with ethyl acetate. The organic layer was dried and concentrated to give the title compound D26 (800 g, 2.473 mmol, 98% yield) as a brown solid.

LCMS: 324 [M+H]$^+$. $t_R$=3.210 mins. (LCMS condition 1)
$^1$H NMR (400 MHz, DMSO-d$_6$): δ 7.59 (d, J=2.4 Hz, 1H), 4.51 (q, J=7.1 Hz, 2H), 1.40 (t, 3H).

Description D27

2-chloro-4-ethoxy-7H-pyrrolo-[2,3-d]pyrimidine-5-carbonitrile (D27)

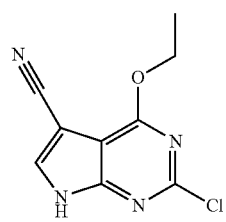

To a solution of 2-chloro-4-ethoxy-5-iodo-7H-pyrrolo-[2,3-d]-pyrimidine (which may be prepared according to D26) (610 g, 1.886 mmol) in DMA (5 mL) was added copper (I) cyanide (507 g, 5.66 mmol). The reaction was irradiated by microwave at 120° C. for 2 hours. The mixture was diluted with ethyl acetate and washed with water. The organic layer was washed with brine, dried over Na$_2$SO$_4$, filtered, and concentrated in vacuum. The crude was purified by column chromatography on silica gel (PE:EA=3:2) to give the title compound D27 (200 g, 0.898 mmol, 47.6% yield) as a white solid.

LCMS: 223 [M+H]$^+$. t$_R$=2.777 mins. (LCMS condition 1)

Description D28

6-chloro-4-ethoxy-3-methyl-1H-pyrazolo[3,4-d]pyrimidine (D28)

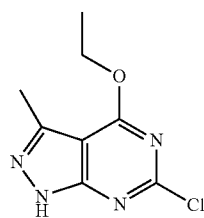

To a solution of ethanol (0.227 g, 4.93 mmol) in THF (60 mL) was added sodium hydride (0.591, 14.78 mmol) in ice bath. After 20 min, 4,6-dichloro-3-methyl-1H-pyrazolo-[3,4-d]-pyrimidine (19 g, 4.93 mmol) was added. The reaction mixture was gradually warmed to room temperature and then stirred overnight. Then, the mixture was diluted with water (20 mL), concentrated to remove solvent and diluted with ethyl acetate (220 mL). The organic layer was washed with water (60 mL×2), dried over Na$_2$SO$_4$, filtered and concentrated. The crude was used in next step without further purification. Yield: 86%.

LCMS: 213 [M+H]$^+$. t$_R$=2.775 mins. (LCMS condition 1)

Description D29

6-chloro-4-(cyclopropylmethoxy)-1H-pyrazolo[3,4-d]pyrimidine (D29)

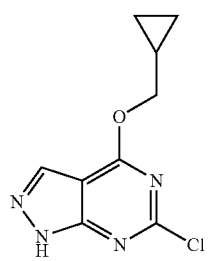 [SMILES: Clc1nc(OCC2CC2)c2cn[nH]c2n1]

To a solution of cyclopropylmethanol (1.908 g, 26.5 mmol) in THF (200 mL) was added sodium hydride (3.17 g, 79 mmol) in ice bath. After stirring for 30 min, 4,6-dichloro-1H-pyrazolo-[3,4-d]-pyrimidine (5 g, 26.5 mmol) was added. The reaction was gradually warmed to room temperature and stirred for overnight. Then, the mixture was diluted with water (80 mL), concentrated to remove solvent and diluted with ethyl acetate (220 mL). The organic layer was washed with water (80 mL×2), dried over Na$_2$SO$_4$, filtered and concentrated. The crude was used in next step without further purification. Yield: 84%.

LCMS: 225 [M+H]$^+$. t$_R$=2.918 mins. (LCMS condition 1)

Description D30 and D31

1-(2-fluoroethyl)-5-methyl-4-nitro-1H-pyrazole (D30)

1-(2-fluoroethyl)-3-methyl-4-nitro-1H-pyrazole (D31)

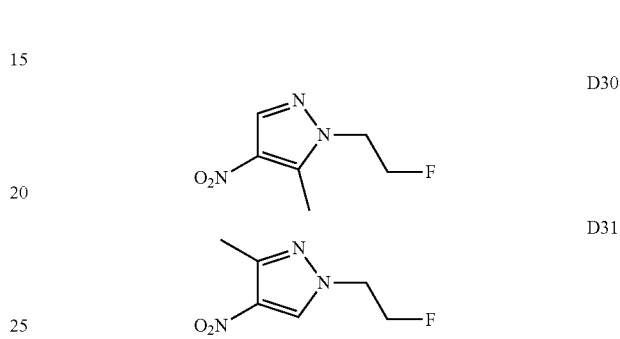

A solution of 5-methyl-4-nitro-1H-pyrazole (2.0 g, 15.74 mmol), 1-bromo-2-fluoroethane (2.197 g, 17.31 mmol) and Cs$_2$CO$_3$ (10.25 g, 31.5 mmol) in acetonitrile (100 mL) was stirred overnight at 60° C. The mixture was filtered and the solution was concentrated in vacuum to give the mixture of the title compounds D30 (2.6 g, 6.01 mmol, 38.2% yield) and D31 (2.6 g, 9.01 mmol, 57.3% yield) as yellow oil.

LCMS: 174 [M+H]$^+$. t$_R$=1.161 mins. (LCMS condition 2)

Description D32 and D33

1-(2-fluoroethyl)-5-methyl-1H-pyrazol-4-amine (D32)

1-(2-fluoroethyl)-3-methyl-1H-pyrazol-4-amine (D33)

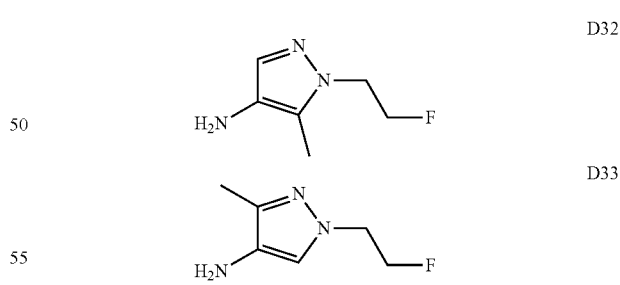

A solution of the mixture of 1-(2-fluoroethyl)-5-methyl-4-nitro-1H-pyrazole (which may be prepared according to D30) and 1-(2-fluoroethyl)-3-methyl-4-nitro-1H-pyrazole (which may be prepared according to D31) (D30 and D31 together, 1200 g, 2.772 mmol) and Pd/C (100 g, 0.940 mmol) in methanol (20 mL) was stirred under hydrogen at room temperature for 2 hours. The crude was then filtered and the solution was concentrated to give the mixture of the title compound D32 (500 g, 1.397 mmol, 50% yield) and D33 (500 g, 2.096 mmol, 75% yield) as yellow oil.

D32: LCMS: 144 [M+H]$^+$. $t_R$=0.64 mins. (LCMS condition 1)

D33: LCMS: 144 [M+H]$^+$. $t_R$=0.73 mins. (LCMS condition 1)

Description D34

5-chloro-1-(oxetan-3-yl-methyl)-1H-pyrazol-4-amine (D34)

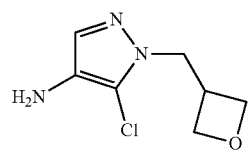 [SMILES: Nc1cnn(CC2COC2)c1Cl]

A solution of 5-chloro-4-nitro-1-(oxetan-3-ylmethyl)-1H-pyrazole (290 g, 1.333 mmol) (which may be prepared according to U.S. Pat. Appl. Publ., 20130079321) and iron (372 g, 6.66 mmol) in ethanol (2 mL) and water (2.000 mL) was stirred at 80° C. for 1 hour. The mixture was filtered and concentrated. The crude was purified by prep-HPLC to give the title compound D34 (140 g, 0.746 mmol, 56.0% yield) as a solid.

LCMS: 188 [M+H]$^+$. $t_R$=0.76 mins. (LCMS condition 2)

$^1$H NMR (400 MHz, DMSO-d$_6$): δ 7.07 (s, 1H), 4.54-4.70 (m, 2H), 4.38 (t, J=6.1 Hz, 2H), 4.25 (d, J=7.5 Hz, 2H), 3.90-4.08 (m, 2H), 3.33-3.37 (m, 1H).

Description D35

5-methyl-4-nitro-1-(oxetan-3-ylmethyl)-1H-pyrazole (D35)

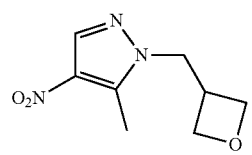

To a solution of methylboronic acid (413 g, 6.89 mmol), 5-chloro-4-nitro-1-(oxetan-3-yl-methyl)-1H-pyrazole (500 g, 2.298 mmol) and sodium carbonate (731 g, 6.89 mmol) in 1,4-dioxane (4 mL) and water (0.400 mL) was added PdCl$_2$(dppf)-CH$_2$Cl$_2$ adduct (188 g, 0.230 mmol). The reaction mixture was stirred at 75° C. under nitrogen for overnight. The mixture was cooled to room temperature, and concentrated. The crude was purified by column chromatography on silica gel (PE:EA=5:1) to give the title compound D35 (280 g, 1.278 mmol, 55.6% yield) as a white solid.

LCMS: 198 [M+H]$^+$. $t_R$=1.421 mins. (LCMS condition 2)

$^1$H NMR (400 MHz, CHLOROFORM-d): δ 8.06 (s, 1H), 4.79-4.91 (m, 2H), 4.52 (t, J=6.1 Hz, 2H), 4.39 (d, J=7.5 Hz, 2H), 3.42-3.62 (m, 1H), 2.59-2.73 (m, 3H).

Description D36

5-methyl-1-(oxetan-3-ylmethyl)-1H-pyrazol-4-amine (D36)

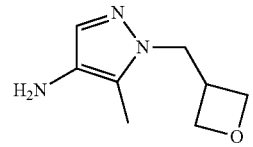

A solution of 5-methyl-4-nitro-1-(oxetan-3-ylmethyl)-1H-pyrazole (which may be prepared according to D35) (260 g, 1.319 mmol) and iron (368 g, 6.59 mmol) in ethanol (2 mL) and water (2.000 mL) was stirred at 80° C. for 1 hour. The mixture was filtered and the filtrate was concentrated. The crude was purified by prep-HPLC to get the title compound D36 (275 g, 0.822 mmol, 62.4% yield) as a yellow solid.

LCMS: 168 [M+H]$^+$. $t_R$=0.32 mins. (LCMS condition 2)

$^1$H NMR (400 MHz, DMSO-d$_6$): δ 7.65 (s, 1H), 5.23 (br. s., 1H), 4.71 (br. s., 2H), 4.43 (ddd, J=11.2, 8.3, 2.8 Hz, 2H), 4.15-4.25 (m, 2H), 3.55 (t, J=5.4 Hz, 2H), 2.25 (s, 3H).

Description D37 and D38

(±)-5-methyl-4-nitro-1-(tetra hydro-2H-pyran-3-yl)-1H-pyrazole (D37)

(±)-3-methyl-4-nitro-1-(tetrahydro-2H-pyran-3-yl)-1H-pyrazole (D38)

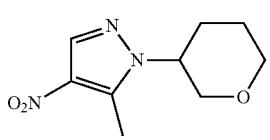

D37

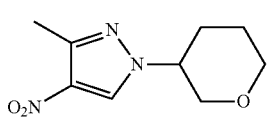

D38

A solution of 5-methyl-4-nitro-1H-pyrazole (1.5 g, 11.80 mmol) and tetrahydro-2H-pyran-3-yl methanesulfonate (3.19 g, 17.70 mmol) in DMF (15 mL) was added potassium carbonate (2.447 g, 17.70 mmol) was stirred overnight at 90° C. The mixture was diluted with water and extracted with EtOAc. The organic layer was concentrated in vacuum and purified by column chromatography on silica gel (PE:EA=2:1) and further purified with pre-HPLC to get the mixture of the title compounds D37 and D38 (500 mg, 50% yield) as a white solid.

LCMS: 212 [M+H]$^+$. $t_R$=1.266 mins. (LCMS condition 2)

Description D39 and D40

(±)-5-methyl-1-(tetrahydro-2H-pyran-3-yl)-1H-pyrazol-4-amine (D39)

(±)-3-methyl-1-(tetrahydro-2H-pyran-3-yl)-1H-pyrazol-4-amine (D40)

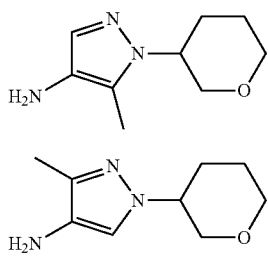

A solution of mixture of (±)-5-methyl-4-nitro-1-(tetrahydro-2H-pyran-3-yl)-1H-pyrazole (which may be prepared according to D37) and (±)-3-methyl-4-nitro-1-(tetrahydro-2H-pyran-3-yl)-1H-pyrazole (which may be prepared according to D38) (D37 and D38 together, 450 mg, 2.131 mmol) and iron (595 g, 10.65 mmol) in ethanol (2 mL) and water (2.000 mL) was stirred at 80° C. about 1 hours. The mixture was filtered and concentrated. The crude was purified by column chromatography on silica gel (PE:EA=1:1) to give the mixture of the title compounds D39 and D40 (150 g, 0.828 mmol, 38.8% yield) as a yellow solid.

LCMS: 182 [M+H]$^+$. $t_R$=0.98 mins. (LCMS condition 2)

Description D41

(±)-trans-2-(4-nitro-1H-pyrazol-1-yl)cyclopentanol (D41)

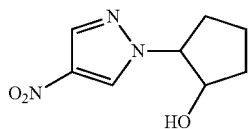 [SMILES: O=[N+]([O-])c1cnn(C2CCCC2O)c1]

A solution of 4-nitro-1H-pyrazole (5.0 g, 44.2 mmol), 6-oxabicyclo-[3.1.0]-hexane (4.46 g, 53.1 mmol) (which may be prepared according to Tetrahedron, 64(39), 9253-9257; 2008) and Cs$_2$CO$_3$ (18.73 g, 57.5 mmol) in DMF (40 mL) was heated overnight at 80° C. The mixture was added to water (300 mL), extracted with EA. The organic layer was concentrated and purified by column chromatography on silica gel (PE:EA=2:1) to give the title compound D41 (7.0 g, 33.4 mmol, 75% yield) as an oil.

LCMS: 198 [M+H]$^+$. $t_R$=1.118 mins. (LCMS condition 2)
$^1$H NMR (400 MHz, CHLOROFORM-d): δ 8.21 (s, 1H), 8.10 (s, 1H), 4.32-4.48 (m, 2H), 2.73 (d, J=3.3 Hz, 1H), 2.30-2.42 (m, 1H), 2.07-2.25 (m, 2H), 1.86-2.00 (m, 2H), 1.71-1.83 (m, 1H).

Description D42

(±)-trans-2-(5-chloro-4-nitro-1H-pyrazol-1-yl)cyclopentanol (D42)

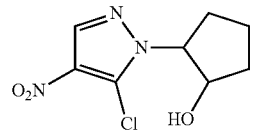 [SMILES: O=[N+]([O-])c1cnn(C2CCCC2O)c1Cl]

To a solution of (±)-trans-2-(4-nitro-1H-pyrazol-1-yl)cyclopentanol (which may be prepared according to D41)(3.5 g, 17.75 mmol) in dry THF (100 mL) stirred under nitrogen at −78° C. was added a solution of lithium bis(trimethylsilyl)amide (53.2 mL, 53.2 mmol) in THF dropwise during 15 min. The reaction mixture was stirred at −78° C. for 30 min. A solution of perchloroethane (10.50 g, 44.4 mmol) in THF (100 mL) was added and the mixture was stirred for 3 hours at −78° C. under nitrogen. The mixture was quenched with aq. NH$_4$Cl and extracted with EtOAc. The organic layer was concentrated and purified by chromatography on silica gel (PE:EA=1:1) to give the title compound D42 (1.3 g, 5.61 mmol, 31.6% yield) as oil.

LCMS: 232 [M+H]$^+$. $t_R$=1.258 mins. (LCMS condition 2)
$^1$H NMR (400 MHz, CHLOROFORM-d): δ 8.20 (s, 1H), 4.60-4.73 (m, 2H), 2.14-2.37 (m, 2H), 1.91-2.08 (m, 3H), 1.70-1.82 (m, 1H).

Description D43

(±)-trans-2-(4-amino-5-chloro-1H-pyrazol-1-yl)cyclopentanol (D43)

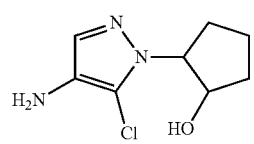 [SMILES: Nc1cnn(C2CCCC2O)c1Cl]

The mixture of (±)-trans-2-(5-chloro-4-nitro-1H-pyrazol-1-yl)cyclopentanol (which may be prepared according to D42) (500 g, 2.159 mmol) and iron (1205 g, 21.59 mmol) in ethanol (40 mL) and water (40.0 mL) was stirred overnight at 20° C. The mixture was filtered and concentrated. The crude was purified by chromatography on silica gel (DCM:MeOH=10:1) to give the title compound D43 (350 g, 1.649 mmol, 76% yield) as oil.

LCMS: 202 [M+H]$^+$. $t_R$=0.944 mins. (LCMS condition 2)

Description D44

(±)-trans-2-(5-methyl-4-nitro-1H-pyrazol-1-yl)cyclopentanol (D44)

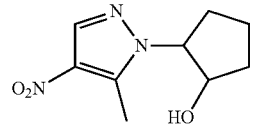

To a mixture of (±)-trans-2-(5-chloro-4-nitro-1H-pyrazol-1-yl)cyclopentanol (which may be prepared according to D42) (700 g, 3.02 mmol), methylboronic acid (543 g, 9.07 mmol) in 1,4-dioxane (20 mL) and water (2.000 mL) was added PdCl$_2$(dppf) (111 g, 0.151 mmol). The mixture was stirred overnight at 75° C. under nitrogen. The mixture was concentrated and purified by chromatography on silica gel (PE:EA=1:1) to give the title compound D44 (400 g, 1.515 mmol, 50.1% yield) as oil.

LCMS: 212 [M+H]$^+$. t$_R$=1.265 mins. (LCMS condition 2)
$^1$H NMR (400 MHz, CHLOROFORM-d): δ 8.10 (s, 1H), 4.56-4.68 (m, 1H), 4.32-4.46 (m, 1H), 2.69 (s, 3H), 2.08-2.24 (m, 3H), 1.86-1.98 (m, 2H), 1.68-1.82 (m, 1H).

Description D45

(±)-trans-2-(4-amino-5-methyl-1H-pyrazol-1-yl)cyclopentanol (D45)

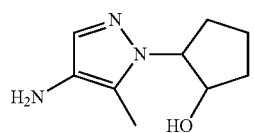

A solution of (±)-trans-2-(5-methyl-4-nitro-1H-pyrazol-1-yl)cyclopentanol (which may be prepared according to D44) (400 g, 1.894 mmol) and Pd/C (101 g, 0.095 mmol) in methanol (20 mL) was stirred overnight at 20° C. under hydrogen. The mixture was filtered and concentrated. The crude was purified by chromatography on silica gel (DCM:MeOH=10:1) to give the title compound D45 (300 g, 1.407 mmol, 74.3% yield) as an oil.

LCMS: 182 [M+H]$^+$. t$_R$=1.057 mins. (LCMS condition 2)

Description D46

(±)-trans-2-(5-chloro-4-((4-ethoxy-7-tosyl-7H-pyrrolo-[2,3-d]-pyrimidin-2-yl)amino)-1H-pyrazol-1-yl)cyclopentanol (D46)

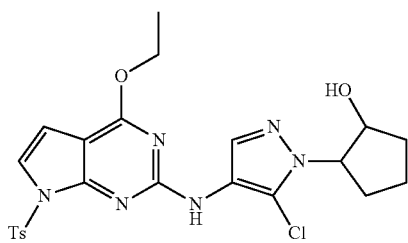 [SMILES: CCOc1nc(Nc2cnn(C3CCCC3O)c2Cl)nc2c1ccn2S(=O)(=O)c1ccc(C)cc1]

To a solution of 2-chloro-4-ethoxy-7-tosyl-7H-pyrrolo-[2,3-d]-pyrimidine (which may be prepared according to D2) (600 g, 1.705 mmol), (±)-trans-2-(4-amino-5-chloro-1H-pyrazol-1-yl)cyclopentanol (which may be prepared according to D43) (344 g, 1.705 mmol) and (9,9-dimethyl-9H-xanthene-4,5-diyl)bis(diphenylphosphine) (148 g, 0.256 mmol) in 1,4-dioxane (2.0 mL) and water (0.2 mL) was added potassium carbonate (471 g, 3.41 mmol) and Pd(dppf)Cl$_2$ (139 g, 0.171 mmol). The reaction mixture was stirred overnight at 90° C. The mixture was cooled to room temperature and partitioned between EtOAc (25 mL) and water (20 mL). The organic layer was washed with water (20 mL), dried over Na$_2$SO$_4$ and evaporated in vacuum. The crude was purified by column chromatography on silica gel (PE:EA=1:3) to give the title compound D46 (350 g, 0.555 mmol, 32.5% yield) as a white solid.

LCMS: 517 [M+H]$^+$. t$_R$=1.820 mins. (LCMS condition 2)
$^1$H NMR (400 MHz, CHLOROFORM-d): δ 8.36 (br. s., 1H), 7.97 (d, J=7.9 Hz, 1H), 7.23-7.32 (m, 5H), 6.46-6.57 (m, 1H), 4.72 (d, J=5.4 Hz, 1H), 4.54-4.62 (m, 1H), 4.49 (q, J=7.1 Hz, 2H), 4.15 (q, J=7.3 Hz, 1H), 2.39 (s, 3H), 2.30-2.37 (m, 1H), 2.18-2.27 (m, 1H), 2.08-2.15 (m, 1H), 1.90-1.99 (m, 2H), 1.72-1.83 (m, 1H), 1.43 (t, J=7.1 Hz, 3H).

Description D47

(±)-trans-2-(4-((4-ethoxy-7-tosyl-7H-pyrrolo-[2,3-d]-pyrimidin-2-yl)amino)-5-methyl-1H-pyrazol-1-yl)cyclopentanol (D47)

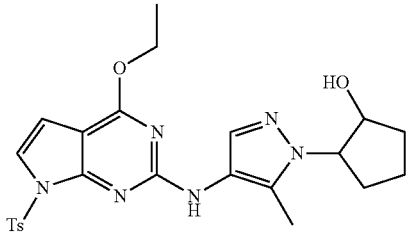

To a solution of 2-chloro-4-ethoxy-7-tosyl-7H-pyrrolo-[2,3-d]-pyrimidine (which may be prepared according to D2) (500 g, 1.421 mmol), (±)-trans-2-(4-amino-5-methyl-1H-pyrazol-1-yl)cyclopentanol (which may be prepared according to D45) (300 g, 1.655 mmol) and (9,9-dimethyl-9H-xanthene-4,5-diyl)bis(diphenylphosphine) (123 g, 0.213 mmol) in 1,4-dioxane (2.0 mL) and water (0.2 mL) was added potassium carbonate (393 g, 2.84 mmol) and Pd(dppf)Cl$_2$ (116 g, 0.142 mmol). The reaction mixture was stirred overnight at 90° C. The mixture was cooled to room temperature and partitioned between EtOAc (25 mL) and water (20 mL). The organic layer was washed with water (20 mL), dried over Na$_2$SO$_4$ and evaporated in vacuum. The crude was purified by chromatography on silica gel (PE:EA=1:3) to give the title compound D47 (250 g, 0.337 mmol, 23.73% yield) as a white solid.

LCMS: 497 [M+H]$^+$. t$_R$=1.547 mins. (LCMS condition 2)
$^1$H NMR (400 MHz, CHLOROFORM-d): δ 7.70-7.80 (m, 2H), 7.67 (s, 1H), 7.13-7.25 (m, 4H), 6.42 (d, J=3.8 Hz, 1H), 6.22 (br. s., 1H), 4.59-4.70 (m, 1H), 4.38-4.47 (m, 3H), 2.35 (s, 3H), 2.33 (s, 3H), 2.13-2.28 (m, 3H), 1.82-1.98 (m, 2H), 1.74 (dq, J=12.8, 8.2 Hz, 1H), 1.38 (t, J=7.0 Hz, 3H).

Description D48

(±)-2-methyl-tetrahydro-2H-pyran-4-yl-methanesulfonate (D48)

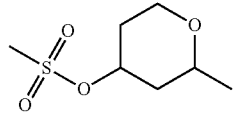

To a solution of 2-methyltetrahydro-2H-pyran-4-ol (1 g, 8.61 mmol) and DIPEA (2.255 mL, 12.91 mmol) in DCM (10 mL) stirred at 0° C. was added a solution of methanesulfonyl chloride (0.356 mL, 10.33 mmol) in DCM (2 mL) dropwise. The reaction mixture was stirred at room temperature for 1 hour. Saturated NaHCO$_3$ solution was added and the mixture was extracted with DCM (10 mL×3). The organic layer was dried over Na$_2$SO$_4$ and concentrated in vacuum to give D48 (1.1 g, 5.66 mmol, 65.8% yield) as colorless oil.

$^1$H NMR (400 MHz, CHLOROFORM-d): δ 4.70-4.87 (m, 1H), 4.04 (ddd, J=12.0, 4.9, 1.6 Hz, 1H), 3.31-3.52 (m, 2H), 3.03 (s, 3H), 2.01-2.20 (m, 2H), 1.73-1.87 (m, 1H), 1.44-1.57 (m, 1H), 1.20-1.26 (m, 3H).

Description D49

(±)-5-methyl-1-(2-methyl-tetrahydro-2H-pyran-4-yl)-4-nitro-1H-pyrazole (D49)

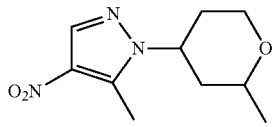 [SMILES: Cc1c([N+](=O)[O-])cnn1C1CCOC(C)C1]

A solution of 5-methyl-4-nitro-1H-pyrazole (3.04 g, 23.89 mmol), (±)-2-methyl-tetrahydro-2H-pyran-4-yl-methanesulfonate (which may be prepared according to D48) (5.8 g, 29.9 mmol) and Cs$_2$CO$_3$ (9.73 g, 29.9 mmol) in acetonitrile (50 mL) was stirred overnight at 80° C. The mixture was filtered and the solution was evaporated. The crude was purified by prep-HPLC to give the title compound D49 (870 g, 3.86 mmol, 16.1% yield) as colorless oil.

LCMS: 226 [M+H]$^+$. t$_R$=1.52 mins. (LCMS condition 2)

Description D50

(±)-5-methyl-1-(2-methyl-tetrahydro-2H-pyran-4-yl)-1H-pyrazol-4-amine (D50)

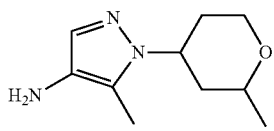

A solution of (±)-5-methyl-1-(2-methyl-tetrahydro-2H-pyran-4-yl)-4-nitro-1H-pyrazole (which may be prepared according to D49) (220 g, 0.977 mmol) and iron (545 g, 9.77 mmol) in ethanol (4 mL) and water (4.00 mL) was stirred overnight at room temperature. The mixture was filtered and the solution was concentrated. The crude was purified by chromatography on silica gel (DCM:MeOH=10:1) to give the title compound D50 (200 g, 0.727 mmol, 74.5% yield) as black oil.

LCMS: 196 [M+H]$^+$. t$_R$=1.16 mins. (LCMS condition 2)
$^1$H NMR (400 MHz, CHLOROFORM-d): δ 7.15 (s, 1H), 4.43 (m, J=4.5 Hz, 1H), 4.20-4.30 (m, J=9.3, 6.3, 6.3, 6.3, 3.0 Hz, 1H), 4.11 (td, J=10.9, 3.0 Hz, 2H), 3.76-3.89 (m, 2H), 2.17 (s, 3H), 1.98-2.09 (m, 2H), 1.88-1.97 (m, 1H), 1.74 (dt, J=9.2, 4.7 Hz, 1H), 1.20 (d, J=6.3 Hz, 3H).

Description D51

(±)-4-ethoxy-N-(5-methyl-1-(2-methyl-tetrahydro-2H-pyran-4-yl)-1H-pyrazol-4-yl)-7-tosyl-7H-pyrrolo[2,3-d]pyrimidin-2-amine (D51)

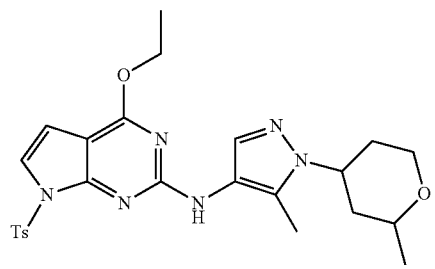 [SMILES: CCOc1nc(Nc2cnn(C3CCOC(C)C3)c2C)nc2c1ccn2S(=O)(=O)c1ccc(C)cc1]

To a solution of 2-chloro-4-ethoxy-7-tosyl-7H-pyrrolo-[2,3-d]-pyrimidine (which may be prepared according to D2) (541 g, 1.536 mmol), (±)-5-methyl-1-(2-methyl-tetrahydro-2H-pyran-4-yl)-1H-pyrazol-4-amine (which may be prepared according to D50) (200 mg, 1.024 mmol) and (9,9-dimethyl-9H-xanthene-4,5-diyl)bis(diphenylphosphine) (73.2 g, 0.154 mmol) in 1,4-dioxane (2.0 mL) and water (0.2 mL) was added potassium carbonate (283 mg, 2.049 mmol) and PdCl$_2$(dppf) (84 g, 0.102 mmol). The reaction mixture was stirred overnight at 90° C. The mixture was cooled to room temperature and partitioned between EtOAc (100 mL) and water (80 mL). The organic layer was washed with water (80 mL), dried over Na$_2$SO$_4$ and evaporated in vacuum. The crude was purified by chromatography on silica gel (PE:EA=3:1) to give the title compound D51 (300 g, 0.382 mmol, 37.3% yield) as a white solid.

LCMS: 511 [M+H]$^+$. t$_R$=1.62 mins. (LCMS condition 2)
$^1$H NMR (400 MHz, CHLOROFORM-d): δ 7.70-7.86 (m, 2H), 7.61 (s, 1H), 7.12-7.21 (m, 3H), 6.42 (d, J=4.0 Hz, 1H), 4.62 (t, J=4.4 Hz, 1H), 4.43 (q, J=7.2 Hz, 2H), 4.27-4.37 (m, 1H), 4.16-4.26 (m, 1H), 3.88 (dt, J=11.5, 4.4 Hz, 1H), 2.36 (s, 3H), 2.31 (s, 3H), 2.14-2.23 (m, 1H), 2.11 (dt, J=8.7, 4.5 Hz, 2H), 1.82 (ddd, J=13.9, 9.0, 5.0 Hz, 1H), 1.38 (t, J=7.0 Hz, 3H), 1.19 (d, J=6.3 Hz, 3H).

Description D52

5-cyclopropyl-4-nitro-1-(tetrahydro-2H-pyran-4-yl)-1H-pyrazole (D52)

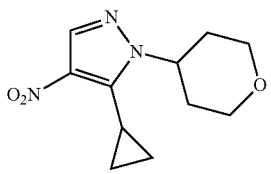 [SMILES: O=[N+]([O-])c1cnn(C2CCOCC2)c1C1CC1]

To a solution of cyclopropylboronic acid (556 g, 6.48 mmol), 5-chloro-4-nitro-1-(tetrahydro-2H-pyran-4-yl)-1H-pyrazole (500 g, 2.159 mmol) and sodium carbonate (458 mg, 4.32 mmol) in 1,4-dioxane (3 mL) and water (0.300 mL) was added PdCl$_2$(pddf) (176 mg, 0.216 mmol). The reaction mixture was stirred at 90° C. for 3 hours under nitrogen. Solvent was evaporated and the crude was purified by Biotage to give the title compound D52 (300 g, 1.151 mmol, 53.3% yield) as a white solid.

LCMS: 328 [M+H]⁺. $t_R$=1.304 mins. (LCMS condition 2)

Description D53

5-cyclopropyl-1-(tetrahydro-2H-pyran-4-yl)-1H-pyrazol-4-amine (D53)

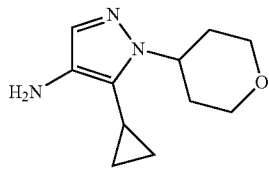

A solution of 5-cyclopropyl-4-nitro-1-(tetrahydro-2H-pyran-4-yl)-1H-pyrazole (which may be prepared according to D52) (200 g, 0.843 mmol), ammonia hydrochloride (225 mg, 4.21 mmol) and iron (235 g, 4.21 mmol) in water (2 mL) and ethanol (2.000 mL) was stirred at 70° C. under nitrogen overnight. Solvent was evaporated and the crude was dissolved in ethanol and filtered. The filtrate was concentrated to give the title compound D53 (150 g, 0.651 mmol, 77% yield) as brown oil.

LCMS: 208 [M+H]⁺. $t_R$=0.995 mins. (LCMS condition 2)

Description D54

N-(5-cyclopropyl-1-(tetrahydro-2H-pyran-4-yl)-1H-pyrazol-4-yl)-4-ethoxy-7-tosyl-7H-pyrrolo-[2,3-d]-pyrimidin-2-amine (D54)

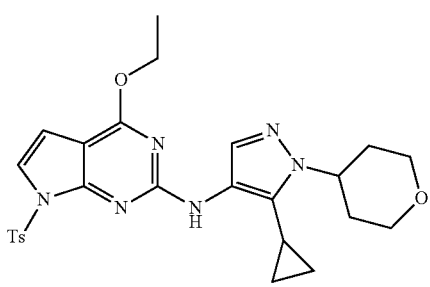 [SMILES: CCOc1nc(Nc2cnn(C3CCOCC3)c2C2CC2)nc2c1ccn2S(=O)(=O)c1ccc(C)cc1]

A solution of 2-chloro-4-ethoxy-7-tosyl-7H-pyrrolo-[2,3-d]-pyrimidine (which may be prepared according to D2) (18.67 g, 0.053 mmol), 5-cyclopropyl-1-(tetrahydro-2H-pyran-4-yl)-1H-pyrazol-4-amine (which may be prepared according to D53) (10 g, 0.048 mmol), sodium carbonate (10.23 g, 0.096 mmol), PdCl₂(pddf)·CH₂Cl₂ (3.94 mg, 4.82 μmol) and (9,9-dimethyl-9H-xanthene-4,5-diyl)bis(diphenylphosphine) (3.45 mg, 7.24 μmol) in 1,4-dioxane (3 mL) and water (0.300 mL) was irradiated by microwave at 120° C. for 45 min. The reaction mixture was quenched with water and extracted with EtOAc (20 mL×3). The combined organic layer was dried over Na₂SO₄, filtered and concentrated in vacuum. The crude was purified by chromatography on silica gel (DCM:MeOH=20:1) to give the title compound D54 (18 g, 0.024 mmol, 50.0% yield) as a white solid.

LCMS: 523 [M+H]⁺. $t_R$=1.834 mins. (LCMS condition 2)

Description D55

4-(2-(5-methyl-4-nitro-1H-pyrazol-1-yl)ethyl)-morpholine (D55)

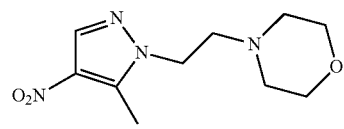 [SMILES: Cc1c([N+](=O)[O-])cnn1CCN1CCOCC1]

A solution of 2-(5-methyl-4-nitro-1H-pyrazol-1-yl)ethyl-methanesulfonate (which may be prepared according to D15) (200 g, 0.802 mmol), morpholine (80 g, 0.918 mmol) and potassium carbonate (381 g, 2.75 mmol) in acetonitrile (10 mL) was stirred overnight at 80° C. The mixture was concentrated and purified by chromatography on silica gel (PE:EA=1:1) to give the title compound D55 (150 g, 0.312 mmol, 34.0% yield) as oil.

LCMS: 241 [M+H]⁺. $t_R$=1.120 mins. (LCMS condition 2)
¹H NMR (400 MHz, CHLOROFORM-d): δ 8.10 (s, 1H), 4.16-4.24 (m, 2H), 3.62-3.74 (m, 4H), 2.80 (t, J=6.3 Hz, 2H), 2.69 (s, 3H), 2.44-2.52 (m, 4H).

Description D56

5-methyl-1-(2-morpholinoethyl)-1H-pyrazol-4-amine (D56)

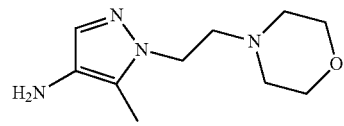

A solution of 4-(2-(5-methyl-4-nitro-1H-pyrazol-1-yl)ethyl)-morpholine (which may be prepared according to D55) (150 g, 0.624 mmol) and Pd/C (33.2 g, 0.031 mmol) in methanol (5 mL) was stirred overnight at 20° C. under hydrogen. The mixture was filtered and the solution was concentrated to give the title compound D56 (100 g, 0.476 mmol, 76% yield) as oil.

LCMS: 211 [M+H]⁺. $t_R$=1.008 mins. (LCMS condition 2)

Description D57

4-ethoxy-N-(5-methyl-1-(2-morpholinoethyl)-1H-pyrazol-4-yl)-7-tosyl-7H-pyrrolo[2,3-d]pyrimidin-2-amine (D57)

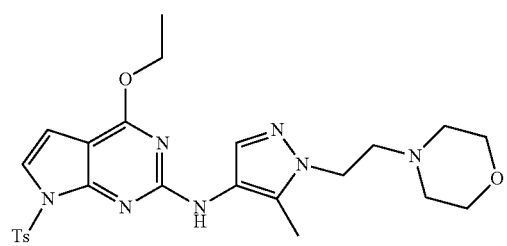 [SMILES: CCOc1nc(Nc2cnn(CCN3CCOCC3)c2C)nc2c1ccn2S(=O)(=O)c1ccc(C)cc1]

To a solution of 2-chloro-4-ethoxy-7-tosyl-7H-pyrrolo-[2,3-d]-pyrimidine (which may be prepared according to D2) (150 g, 0.426 mmol), 5-methyl-1-(2-morpholinoethyl)-1H-pyrazol-4-amine (which may be prepared according to D56) (100 g, 0.476 mmol) and (9,9-dimethyl-9H-xanthene-4,5-diyl)bis(diphenylphosphine) (37.0 g, 0.064 mmol) in 1,4-dioxane (2.0 mL) and water (0.2 mL) was added potassium carbonate (118 g, 0.853 mmol) and Pd(dppf)Cl$_2$ (34.8 g, 0.043 mmol). The reaction mixture was stirred overnight at 90° C. The mixture was cooled to room temperature and partitioned between EtOAc (25 mL) and water (20 mL). The organic layer was washed with water (20 mL), dried over Na$_2$SO$_4$ and evaporated in vacuum, was purified by column chromatography on silica gel (PE:EA=1:1) to give the title compound D57 (70 g, 0.109 mmol, 25.6% yield) as a yellow solid.

LCMS: 525 [M+H]$^+$. $t_R$=1.743 mins. (LCMS condition 2)

Description D58

3-benzyloxy-cyclobutyl methanesulfonate (D58)

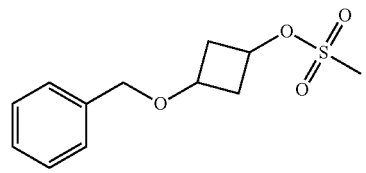 [SMILES: CS(=O)(=O)OC1CC(OCc2ccccc2)C1]

A solution of DIPEA (5.33 mL, 30.5 mmol) and 3-(benzyloxy)cyclobutanol (3.63 g, 20.34 mmol) in DCM (10 mL) was cooled to 0° C. and methanesulfonyl chloride (2.33 g, 20.34 mmol) was added. The mixture was then stirred at room temperature for 2 hours. The mixture was then diluted with EtOAc (50 mL) and washed with aq. NaHCO$_3$, dried over Na$_2$SO$_4$, filtered and concentrated to give the title compound D58 (3.3 g, 12.87 mmol, 63.3% yield) as colorless oil, which was used in next step without further purification LCMS: 257 [M+H]$^+$. $t_R$=1.460 mins. (LCMS condition 2)

Description D59

1-(3-(benzyloxy)-cyclobutyl)-4-nitro-1H-pyrazole (D59)

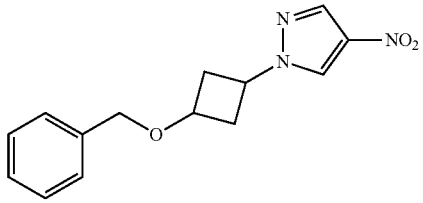 [SMILES: O=[N+]([O-])c1cnn(C2CC(OCc3ccccc3)C2)c1]

To a solution of 4-nitro-1H-pyrazole (765 g, 6.77 mmol) and 3-benzyloxy-cyclobutyl methanesulfonate (which may be prepared according to D58) (2601 g, 10.15 mmol) in DMF (15 mL) was added potassium carbonate (1403 g, 10.15 mmol). The mixture was stirred overnight at 90° C. The reaction mixture was extracted with EtOAc and the organic layer was concentrated. The crude was purified by column chromatography on silica gel (PE:EA=5:1) to give the title compound D59 (1.4 g, 5.12 mmol, 76% yield) as a yellow solid.

LCMS: 274 [M+H]$^+$. $t_R$=1.499 mins. (LCMS condition 2)

$^1$H NMR (400 MHz, DMSO-d$_6$): δ 8.98 (s, 1H), 8.32 (s, 1H), 7.25-7.44 (m, 5H), 5.01-5.18 (m, 1H), 4.44 (s, 2H), 4.30-4.40 (m, 1H), 2.64-2.75 (m, 2H), 2.48-2.61 (m, 2H).

Description D60

1-(3-(benzyloxy)cyclobutyl)-5-chloro-4-nitro-1H-pyrazole (D60)

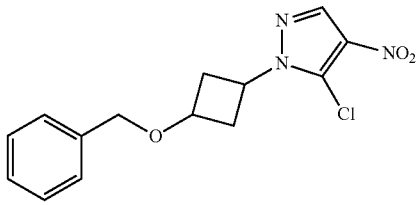 [SMILES: O=[N+]([O-])c1cnn(C2CC(OCc3ccccc3)C2)c1Cl]

To a solution of 1-(3-(benzyloxy)-cyclobutyl)-4-nitro-1H-pyrazole (which may be prepared according to D59) (1.4 g, 5.12 mmol) in dry THF (10 mL) stirred under nitrogen at −70° C. was added a solution of lithium bis(trimethylsilyl)amide (3.43 g, 20.49 mmol) in THF (10 mL) during 15 min. The reaction mixture was stirred at −78° C. for 30 min. A solution of perchloroethane (3.64 g, 15.37 mmol) in THF (10 mL) was added and the mixture was stirred at −78° C. under nitrogen for 2 hours. The mixture was quenched with aq. NH$_4$Cl solution and extracted with EtOAc (2×100 mL). The organic layer was washed with brine, dried with Na$_2$SO$_4$, filtered and concentrated. The crude was purified by chromatography on silica gel (PE:EA=10:1) to give the title compound D60 (700 g, 2.275 mmol, 44.4% yield) as oil.

LCMS: 308 [M+H]$^+$. $t_R$=1.79 mins. (LCMS condition 2)

$^1$H NMR (400 MHz, DMSO-d$_6$): δ 8.53 (s, 1H), 7.25-7.40 (m, 5H), 5.09-5.25 (m, 1H), 4.44 (s, 2H), 4.32-4.41 (m, 1H), 2.65-2.77 (m, 2H), 2.54-2.65 (m, 2H).

Description D61

1-(3-(benzyloxy)-cyclobutyl)-5-methyl-4-nitro-1H-pyrazole (D61)

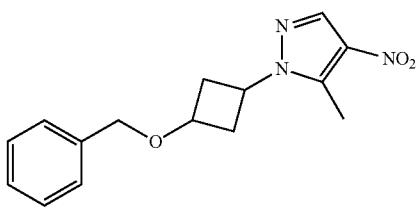 [SMILES: Cc1c([N+](=O)[O-])cnn1C1CC(OCc2ccccc2)C1]

To a solution of methylboronic acid (233 g, 3.90 mmol), 1-(3-(benzyloxy)cyclobutyl)-5-chloro-4-nitro-1H-pyrazole (which may be prepared according to D60) (400 g, 1.300 mmol) and sodium carbonate (413 g, 3.90 mmol) in 1,4-dioxane (3 mL) and water (0.300 mL) was added PdCl$_2$(dppf)-CH$_2$Cl$_2$ adduct (106 g, 0.130 mmol). The reaction mixture was stirred overnight at 75° C. under nitrogen. The mixture was then concentrated and the crude was purified by chromatography on silica gel (PE:EA=10:1) to give the title compound D61 (130 mg, 27.8%).

LCMS: 288 [M+H]$^+$. $t_R$=1.549 mins. (LCMS condition 2)

Description D62

3-(4-amino-5-methyl-1H-pyrazol-1-yl)cyclobutanol (D62)

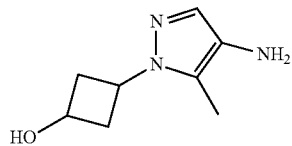

A solution of 1-(3-(benzyloxy)-cyclobutyl)-5-methyl-4-nitro-1H-pyrazole (which may be prepared according to D61) (200 g, 0.696 mmol) and Pd/C (50 g, 0.047 mmol) in methanol (20 mL) was stirred overnight at room temperature under hydrogen. The mixture was filtered and the filtrate was concentrated in vacuum to give the title compound D62 (100 g, 0.598 mmol, 86% yield) as a yellow solid.

LCMS: 168 [M+H]$^+$. $t_R$=0.693 mins. (LCMS condition 2)

Description D63

(±)-4-(5-methyl-4-nitro-1H-pyrazol-1-yl)cyclohexanol (D63)

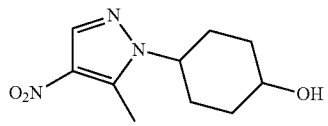

A solution of 5-methyl-4-nitro-1H-pyrazole (2.053 g, 16.16 mmol), cyclohexane-1,4-diyl dimethanesulfonate (5.5 g, 20.20 mmol) and Cs$_2$CO$_3$ (6.58 g, 20.20 mmol) in acetonitrile (50 mL) was heated at 90° C. for 40 hours. The mixture was concentrated and purified via chromatography on silica gel (PE:EA=10:1) to get a crude product (1.1 g, 2.502 mmol, 12.39% yield), which was further purified by prep-HPLC to give the title compound (180 mg, 0.757 mmol) as colorless oil.

LCMS: 226 [M+H]$^+$. $t_R$=1.02 mins. (LCMS condition 2)
$^1$H NMR (400 MHz, CHLOROFORM-d): 8.18 (s, 1H), 4.69-4.93 (m, 1H), 4.05-4.09 (m, 1H), 2.54 (s, 3H), 2.33-2.49 (m, 1H), 2.07-2.20 (m, 4H), 1.97-2.01 (m, 2H), 1.87-1.93 (m, 1H).

Description D64

(±)-4-(4-amino-5-methyl-1H-pyrazol-1-yl)cyclohexanol (D64)

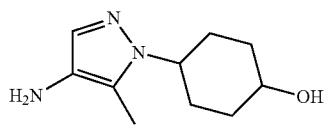 [SMILES: Cc1c([N+](=O)[O-])cnn1C1CCC(O)CC1]

A solution D63 (170 g, 0.755 mmol) and iron (421 g, 7.55 mmol) in ethanol (6 mL) and water (6.00 mL) was stirred overnight at room temperature. The mixture was filtered and concentrated to give the title compound D64 (160 g, 0.492 mmol, 65.1% yield) as black oil.

LCMS: 196 [M+H]$^+$. $t_R$=1.03 mins. (LCMS condition 2)

Description D65

(±)-4-(4-((4-ethoxy-7-tosyl-7H-pyrrolo-[2,3-d]pyrimidin-2-yl)amino)-5-methyl-1H-pyrazol-1-yl)cyclohexanol (D65)

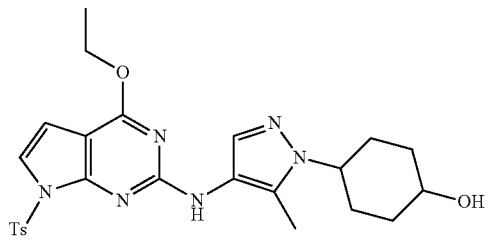 [SMILES: CCOc1nc(Nc2cnn(C3CCC(O)CC3)c2C)nc2c1ccn2S(=O)(=O)c1ccc(C)cc1]

To a solution of 2-chloro-4-ethoxy-7-tosyl-7H-pyrrolo-[2,3-d]-pyrimidine (which may be prepared according to D2) (432 g, 1.229 mmol), (±)-4-(4-amino-5-methyl-1H-pyrazol-1-yl)cyclohexanol (which may be prepared according to D64)(160 g, 0.819 mmol) and dicyclohexyl(2',4',6'-triisopropyl-[1,1'-biphenyl]-2-yl)phosphine (58.6 g, 0.123 mmol) in 1,4-dioxane (2.0 mL) and water (0.2 mL) was added potassium carbonate (226 g, 1.639 mmol) and PdCl$_2$(pddf) (66.9 g, 0.082 mmol). The reaction mixture was stirred overnight at 90° C. The mixture was cooled to room temperature and partitioned between EtOAc (25 mL) and water (20 mL). The organic layer was washed with water (20 mL), dried over Na$_2$SO$_4$ and evaporated in vacuum, was purified by chromatography on silica gel (DCM:MeOH=20:1) to give the title compound D65 (100 g, 0.143 mmol, 17.45% yield) as a yellow solid.

LCMS: 511 [M+H]$^+$. $t_R$=1.93 mins. (LCMS condition 2)

Description D66

(±)-3-(4-nitro-1H-pyrazol-1-yl)cyclopentanol (D66)

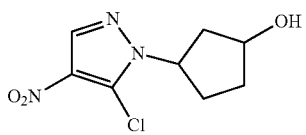 [SMILES: O=[N+]([O-])c1cnn(C2CCC(O)C2)c1Cl]

To a solution of 4-nitro-1H-pyrazole (1.3 g, 11.50 mmol), 3-hydroxycyclopentyl methanesulfonate (3 g, 16.65 mmol) and Cs$_2$CO$_3$ (7.49 g, 22.99 mmol) in DMF (20 mL) was stirred at 90° C. for 4 hours. The mixture was diluted with water and extracted with ethyl acetate. The organic layer was dried with Na$_2$SO$_4$ and concentrated. The crude was purified by chromatography on silica gel (PE:EA=1:1) to give the title compound D66 (1.3 g, 5.80 mmol, 50.5% yield) as oil.

LCMS: 198 [M+H]$^+$. $t_R$=1.39 mins. (LCMS condition 2)

Description D67

(±)-3-(5-chloro-4-nitro-1H-pyrazol-1-yl)-cyclopentanol (D67)

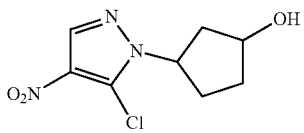 [SMILES: O=[N+]([O-])c1cnn(C2CCC(O)C2)c1Cl]

To a solution of (±)-3-(4-nitro-1H-pyrazol-1-yl)cyclopentanol (which may be prepared according to D66) (1.3 g, 6.59 mmol) in dry THF (20 mL) stirred under nitrogen at −70° C. was added a solution of lithium bis(trimethylsilyl)amide (19.78 mL, 19.78 mmol, 1M in THF) dropwise during 15 min. The reaction mixture was stirred at −78° C. for 30 min. A solution of perchloroethane (3.12 g, 13.19 mmol) in THF (20 mL) was added and the mixture was stirred for 2 hours at −78° C. under nitrogen. The mixture was quenched with aq. NH$_4$Cl. Then the mixture was extracted with EtOAc (2×100 mL), washed with brine, dried with Na$_2$SO$_4$, filtered and concentrated. The crude was purified by chromatography on silica gel (PE:EA=5:1) to give the title compound D67 (1.1 g, 4.23 mmol, 64.1% yield) as oil.

LCMS: 232 [M+H]$^+$. $t_R$=1.56 mins. (LCMS condition 2)

Description D68

(±)-3-(5-methyl-4-nitro-1H-pyrazol-1-yl)cyclopentanol (D68)

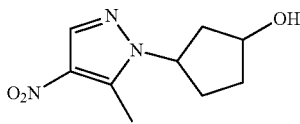

To a solution of methylboronic acid (0.775 g, 12.95 mmol), (±)-3-(5-chloro-4-nitro-1H-pyrazol-1-yl)-cyclopentanol (which may be prepared according to D67) (1 g, 4.32 mmol) and sodium carbonate (1.373 g, 12.95 mmol) in 1,4-dioxane (20 mL) and water (4.00 mL) was added PdCl$_2$(dppf)-CH$_2$Cl$_2$ adduct (0.353 g, 0.432 mmol). The reaction mixture was stirred overnight at 90° C. Then water (100 mL) was added and then extracted with ethyl acetate (2×50 mL). The combined organic phase was washed with brine (20 mL), dried with Na$_2$SO$_4$, filtered and concentrated. The crude was purified by chromatography on silica gel (PE:EA=3:1) to give the title compound D68 (500 g, 2.367 mmol, 54.8% yield) as a white solid.

LCMS: 212 [M+H]$^+$. $t_R$=1.12 mins. (LCMS condition 2)

Description D69 and D70

(±)-trans-3-(4-amino-5-methyl-1H-pyrazol-1-yl) cyclopentanol (D69)

(±)-cis-3-(4-amino-5-methyl-1H-pyrazol-1-yl)cyclopentanol (D70)

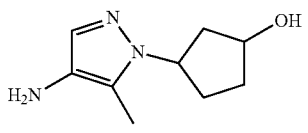

trans-isomer

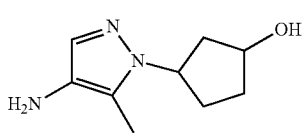

cis-isomer

A solution of (±)-3-(5-methyl-4-nitro-1H-pyrazol-1-yl) cyclopentanol (which may be prepared according to D68) (500 g, 2.367 mmol) and Pd/C (650 g, 6.11 mmol) in methanol (20 mL) was stirred under hydrogen at room temperature for 4 hours. The mixture was then filtered and the filtrate was concentrated. The crude was purified by chromatography on silica gel (PE:EA=3:1) to give the title compound D69 (50 g, 0.276 mmol, 11.65% yield) and D70 (270 g, 1.490 mmol, 62.9% yield) as white solids.

D69: LCMS: 182 [M+H]$^+$. $t_R$=0.82 mins. (LCMS condition 2)

D70: LCMS: 182 [M+H]$^+$. $t_R$=1.03 mins. (LCMS condition 2)

Description D71

(±)-tert-butyl 3-hydroxy-4-(5-methyl-4-nitro-1H-pyrazol-1-yl)pyrrolidine-1-carboxylate (D71)

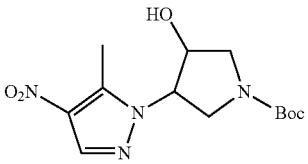 [SMILES: Cc1c([N+](=O)[O-])cnn1C1CN(C(=O)OC(C)(C)C)CC1O]

A solution of 5-methyl-4-nitro-1H-pyrazole (5.0 g, 39.3 mmol), tert-butyl 6-oxa-3-azabicyclo-[3.1.0]hexane-3-carboxylate (8.74 g, 47.2 mmol) (which may be prepared according to U.S. Pat. Appl. Publ., 20070037853), and Cs$_2$CO$_3$ (16.66 g, 51.1 mmol) in DMF (20 mL) was heated to 80° C. overnight. The mixture was added to water (300 mL) and extracted with EtOAc. The organic layer was concentrated and purified by chromatography on silica gel (PE:EA=2:1) to give the title compound (5.0 g, 11.21 mmol, 28.5% yield) as an oil.

LCMS: 313 [M+H]$^+$. $t_R$=1.543 mins. (LCMS condition 2)

Description D72

(±)-tert-butyl 3-fluoro-4-(5-methyl-4-nitro-1H-pyrazol-1-yl)pyrrolidine-1-carboxylate (D72)

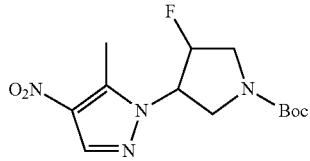 [SMILES: Cc1c([N+](=O)[O-])cnn1C1CN(C(=O)OC(C)(C)C)CC1F]

To a solution of DAST (7.61 mL, 57.6 mmol) in DCM (30 mL) was added a solution of (±)-tert-butyl3-hydroxy-4-(5-methyl-4-nitro-1H-pyrazol-1-yl)pyrrolidine-1-carboxylate (which may be prepared according to D71) (6.0 g, 19.21 mmol) in DCM (200 mL) at 0° C. The mixture was then warmed to room temperature and stirred for 4 hours. The mixture was diluted with 10% NaHCO$_3$ and extracted with DCM. The organic layer was washed with 10% NaHCO$_3$, dried over Na$_2$SO$_4$, filtered and concentrated. The crude was purified by chromatography on silica gel (PE:EA=4:1) to give the title compound D72 (500 g, 1.432 mmol, 7.45% yield) as oil.

LCMS: 315 [M+H]$^+$. $t_R$=1.683 mins. (LCMS condition 2)

Description D73

(±)-1-(4-fluoro-1-methylpyrrolidin-3-yl)-5-methyl-1H-pyrazol-4-amine (D73)

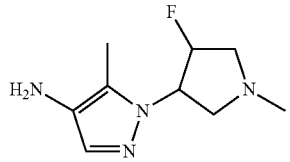

A solution of LiAlH$_4$ (72.5 g, 1.909 mmol, 1M in THF) and (±)-tert-butyl 3-fluoro-4-(5-methyl-4-nitro-1H-pyrazol-1-yl)pyrrolidine-1-carboxylate (which may be prepared according to D72) (200 g, 0.636 mmol) in THF (5 mL) was stirred overnight at 60° C. overnight under nitrogen. The mixture was quenched by water, concentrated and purified by chromatography on silica gel (EA:MeOH=20:1) to give the title compound D73 (100 g, 0.444 mmol, 69.8% yield).

LCMS: 199 [M+H]$^+$. $t_R$=1.093 mins. (LCMS condition 2)

Description D74

(±)-4-ethoxy-N-(1-(4-fluoro-1-methylpyrrolidin-3-yl)-5-methyl-1H-pyrazol-4-yl)-7-tosyl-7H-pyrrolo[2,3-d]pyrimidin-2-amine (D74)

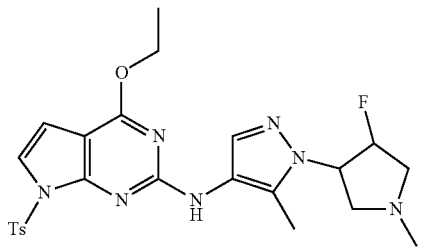 [SMILES: CCOc1nc(Nc2cnn(C3CN(C)CC3F)c2C)nc2c1ccn2S(=O)(=O)c1ccc(C)cc1]

A solution of 2-chloro-4-ethoxy-7-tosyl-7H-pyrrolo-[2,3-d]-pyrimidine (which may be prepared according to D2) (150 g, 0.426 mmol), (±)-1-(4-fluoro-1-methylpyrrolidin-3-yl)-5-methyl-1H-pyrazol-4-amine (which may be prepared according to D73)(90 g, 0.454 mmol), potassium carbonate (118 g, 0.853 mmol), (9,9-dimethyl-9H-xanthene-4,5-diyl)bis(diphenylphosphine) (37.0 g, 0.064 mmol) and Pd(dppf)Cl$_2$ (34.8 g, 0.043 mmol) in 1,4-dioxane (2.0 mL) and water (0.2 mL) was stirred at 90° C. for 6 hours. The mixture was cooled to room temperature and partitioned between EtOAc (25 mL) and water (20 mL). The organic layer was washed with water (20 mL), dried over Na$_2$SO$_4$ and evaporated in vacuum. The crude was purified by column chromatography on silica gel (PE:EA=1:3) to give the title compound D74 (70 g, 0.061 mmol, 14.39% yield) as a white solid.

LCMS: 514 [M+H]$^+$. $t_R$=1.595 mins. (LCMS condition 2)

Description D75

2-cyano-2-methylpropyl methanesulfonate (D75)

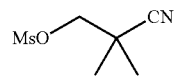

To a solution of 3-hydroxy-2,2-dimethylpropanenitrile (1.3 g, 13.11 mmol) and DIPEA (2.290 mL, 13.11 mmol) at 0° C. in THF (50 mL) was added hypochlorous methanesulfonic anhydride (2.358 mL, 13.11 mmol) and the mixture was then stirred at 0° C. for 30 min. The reaction mixture was diluted with aq. NaHCO$_3$ (20 mL), extracted with EtOAc. The organic layer was dried over Na$_2$SO$_4$ and concentrated to give the title compound D75 (2.0 g, 10.16 mmol, 77% yield) as oil, which was used in next step without further purification.

$^1$H NMR (400 MHz, CHLOROFORM-d): δ 4.13 (s, 2H), 3.13 (s, 3H), 1.45 (s, 6H).

Description D76

2,2-dimethyl-3-(5-methyl-4-nitro-1H-pyrazol-1-yl)propanenitrile (D76)

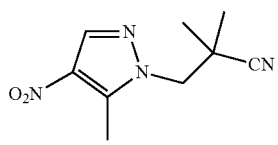

A solution of 5-methyl-4-nitro-1H-pyrazole (1.2 g, 9.44 mmol) and 2-cyano-2-methylpropyl methanesulfonate (which may be prepared according to D75) (1.8 g, 10.16 mmol) and K$_2$CO$_3$ (3.91 g, 28.3 mmol) in DMF (20 mL) was stirred overnight at 80° C. The mixture was concentrated and purified by pre-HPLC to give the title compound D76 (230 g, 1.005 mmol, 10.65% yield) as a white solid.

LCMS: 209 [M+H]$^+$. $t_R$=1.465 mins. (LCMS condition 2)

$^1$H NMR (400 MHz, DMSO-d$_6$): δ 8.33 (s, 1H), 4.40 (s, 2H), 2.68 (s, 3H), 1.38 (s, 6H).

Description D77

3-(4-amino-5-methyl-1H-pyrazol-1-yl)-2,2-dimethylpropanenitrile (D77)

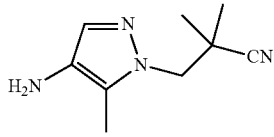

A solution of 2,2-dimethyl-3-(5-methyl-4-nitro-1H-pyrazol-1-yl)propanenitrile (which may be prepared according to D76) (150 g, 0.720 mmol) and iron (402 g, 7.20 mmol) in ethanol (4 mL) and water (4.00 mL) was stirred overnight at 20° C. The mixture was concentrated and purified by chromatography on silica gel (PE:EA=3:1) to give the title compound D77 (100 g, 0.561 mmol, 78% yield) as oil.

LCMS: 179 [M+H]$^+$. $t_R$=0.934 mins. (LCMS condition 2)

$^1$H NMR (400 MHz, DMSO-d$_6$): δ 6.96 (s, 1H), 4.03 (s, 2H), 3.63 (br. s., 2H), 2.13 (s, 3H), 1.31 (s, 6H).

Description D78

3-(4-((4-ethoxy-7-tosyl-7H-pyrrolo-[2,3-d]-pyrimidin-2-yl)amino)-5-methyl-1H-pyrazol-1-yl)-2,2-dimethylpropanenitrile (D78)

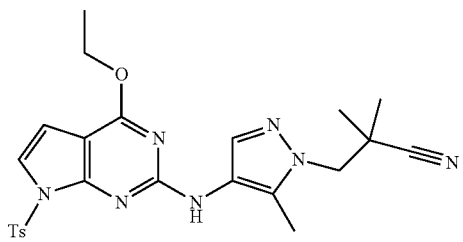 [SMILES: CCOc1nc(Nc2cnn(CC(C)(C)C#N)c2C)nc2c1ccn2S(=O)(=O)c1ccc(C)cc1]

To a solution of 2-chloro-4-ethoxy-7-tosyl-7H-pyrrolo-[2,3-d]-pyrimidine (which may be prepared according to D2) (150 g, 0.426 mmol), 3-(4-amino-5-methyl-1H-pyrazol-1-yl)-2,2-dimethylpropanenitrile (which may be prepared according to D77) (100 g, 0.561 mmol) and (9,9-dimethyl-9H-xanthene-4,5-diyl)bis(diphenylphosphine) (37.0 g, 0.064 mmol) in 1,4-dioxane (2.0 mL) and water (0.2 mL) was added potassium carbonate (118 g, 0.853 mmol) and Pd(dppf)Cl$_2$ (34.8 g, 0.043 mmol). The reaction mixture was stirred at 90° C. for 6 hours. The mixture was cooled to room temperature and partitioned between EtOAc (25 mL) and water (20 mL). The organic layer was washed with water (20 mL), dried over Na$_2$SO$_4$ and evaporated in vacuum. The crude was purified by column chromatography on silica gel (PE:EA=3:1) to give the title compound D78 (80 g, 0.128 mmol, 30.0% yield) as a white solid.

LCMS: 494 [M+H]$^+$. $t_R$=1.613 mins. (LCMS condition 2)

$^1$H NMR (400 MHz, DMSO-d$_6$): δ 8.73 (s, 1H), 7.78-7.95 (m, 2H), 7.22-7.37 (m, 4H), 6.53 (d, J=3.8 Hz, 1H), 4.28 (br. s., 2H), 3.98-4.08 (m, 2H), 2.30 (s, 3H), 1.99 (s, 2H), 1.41 (s, 6H), 1.18 (t, J=7.2 Hz, 3H).

Description D79

2-(4-((4-ethoxy-7-tosyl-7H-pyrrolo-[2,3-d]-pyrimidin-2-yl)amino)-5-methyl-1H-pyrazol-1-yl)-ethanol (D79)

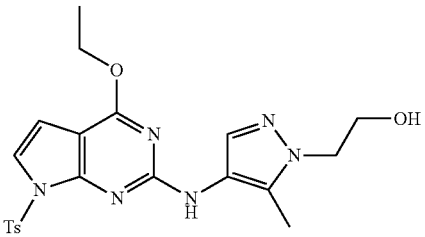 [SMILES: CCOc1nc(Nc2cnn(CCO)c2C)nc2c1ccn2S(=O)(=O)c1ccc(C)cc1]

A solution of 2-chloro-4-ethoxy-7-tosyl-7H-pyrrolo-[2,3-d]-pyrimidine (which may be prepared according to D2) (600 g, 1.705 mmol), 2-(4-amino-5-methyl-1H-pyrazol-1-yl)ethanol (289 g, 2.047 mmol)(which may be prepared according to PCT Int. Appl., WO2012062783), potassium carbonate (707 g, 5.12 mmol), X-Phos (122 g, 0.256 mmol) and PdCl$_2$(dppf)-CH$_2$C$_2$ adduct (139 g, 0.171 mmol) in 1,4-dioxane (16 mL) and water (4 mL) was stirred overnight at 90° C. The mixture was concentrated and the crude was purified by column chromatography on silica gel (EA) to give the title compound D79 (500 g, 0.931 mmol, 54.6% yield) as yellow oil.

LCMS: 457 [M+H]$^+$. $t_R$=1.464 mins. (LCMS condition 2)

Description D80

2-(4-((4-ethoxy-7-tosyl-7H-pyrrolo-[2,3-d]-pyrimidin-2-yl)amino)-5-methyl-1H-pyrazol-1-yl)-ethyl methanesulfonate (D80)

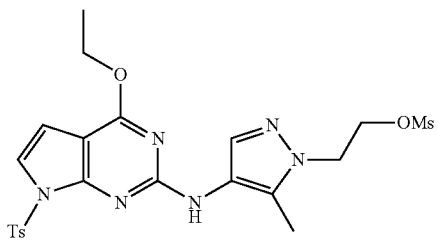 [SMILES: CCOc1nc(Nc2cnn(CCOS(C)(=O)=O)c2C)nc2c1ccn2S(=O)(=O)c1ccc(C)cc1]

A solution of 2-(4-((4-ethoxy-7-tosyl-7H-pyrrolo-[2,3-d]-pyrimidin-2-yl)amino)-5-methyl-1H-pyrazol-1-yl)-ethanol (which may be prepared according to D79) (500 g, 1.095 mmol) and DIPEA (212 g, 1.643 mmol) in DCM (10 mL) was cooled to 0° C. and methanesulfonyl chloride (125 g, 1.095 mmol) was added and stirred for 2 hours. The mixture was added EtOAc (50 mL) and washed with aq. NaHCO$_3$, dried over Na$_2$SO$_4$, filtered and concentrated to give the title compound D80 (550 g, 1.029 mmol, 94% yield) as colorless oil.

LCMS: 534 [M+H]$^+$. $t_R$=1.531 mins. (LCMS condition 2)

Description D81

(R)-4-ethoxy-N-(1-(2-(3-fluoropyrrolidin-1-yl)ethyl)-5-methyl-1H-pyrazol-4-yl)-7-tosyl-7H-pyrrolo[2,3-d]pyrimidin-2-amine (D81)

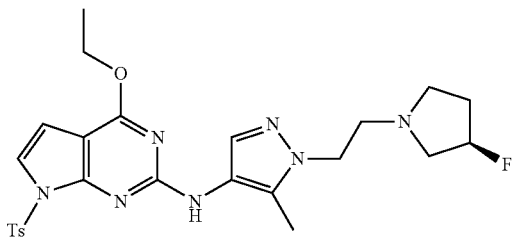 [SMILES: CCOc1nc(Nc2cnn(CCN3CC[C@@H](F)C3)c2C)nc2c1ccn2S(=O)(=O)c1ccc(C)cc1]

A solution of (R)-3-fluoropyrrolidine (23.66 g, 0.266 mmol), 2-(4-((4-ethoxy-7-tosyl-7H-pyrrolo-[2,3-d]-pyrimidin-2-yl)amino)-5-methyl-1H-pyrazol-1-yl)-ethyl methanesulfonate (which may be prepared according to D80) (95 g, 0.177 mmol) in acetonitrile (3 mL) was stirred overnight at 80° C. The mixture was concentrated and purified by column chromatography by using EtOAc to give the title compound D81 (50 g, 0.087 mmol, 49.1% yield) as yellow oil.

LCMS: 528 [M+H]$^+$. $t_R$=1.578 mins. (LCMS condition 2)

Description D82

(S)-4-ethoxy-N-(1-(2-(3-fluoropyrrolidin-1-yl)ethyl)-5-methyl-1H-pyrazol-4-yl)-7-tosyl-7H-pyrrolo[2,3-d]pyrimidin-2-amine (D82)

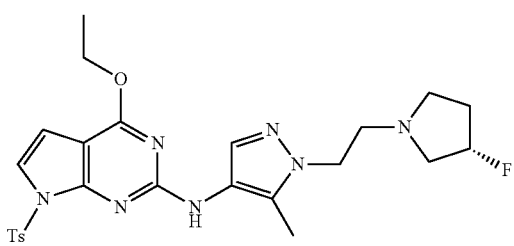 [SMILES: CCOc1nc(Nc2cnn(CCN3CC[C@H](F)C3)c2C)nc2c1ccn2S(=O)(=O)c1ccc(C)cc1]

A solution of (S)-3-fluoropyrrolidine (37.5 g, 0.421 mmol), 2-(4-((4-ethoxy-7-tosyl-7H-pyrrolo-[2,3-d]-pyrimidin-2-yl)amino)-5-methyl-1H-pyrazol-1-yl)-ethyl methanesulfonate (which may be prepared according to D80) (150 g, 0.281 mmol) in acetonitrile (4 mL) was stirred overnight at 80° C. The mixture was concentrated and the crude was purified by column chromatography on silica gel (EtOAc) to give the title compound D82 (90 mg, 0.162 mmol, 57.8% yield) as yellow oil.

LCMS: 528 [M+H]$^+$. $t_R$=1.539 mins. (LCMS condition 2)

Description D83

1-(2-methyl-1-((2-(trimethylsilyl)ethoxy)methoxy)propan-2-yl)-4-nitro-1H-pyrazole (D83)

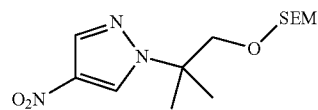

A solution of 2-methyl-2-(4-nitro-1H-pyrazol-1-yl)propan-1-ol (2 g, 10.80 mmol)(which may be prepared according to PCT Int. Appl. WO2012062783) and sodium hydride (0.864 g, 21.60 mmol) in DMF (30 mL) was stirred in an ice-bath for 30 min. SEMCl (2.299 mL, 12.96 mmol) was added and then the mixture was stirred at room temperature for 3 hours. The reaction was then quenched with water (100 mL) and extracted with diethyl ether (50 mL×3). The organic layer was dried and concentrated. The crude was purified by column chromatography on silica gel (PE:EA=10:1) to give the title compound D83 (1.2 g, 3.61 mmol, 33.5% yield) as yellow oil.

LCMS: 314 [M+H]$^+$. $t_R$=2.09 mins. (LCMS condition 2)

$^1$H NMR (400 MHz, DMSO-d$_6$): δ 8.91 (s, 1H), 8.31 (s, 1H), 4.56 (s, 2H), 3.30-3.45 (m, 3H), 2.55 (br. s., 1H), 1.60 (s, 6H), 0.79-0.94 (m, 2H), 0.00 (s, 9H).

Description D84

5-Chloro-1-(2-methyl-1-((2-(trimethylsilyl)ethoxy)methoxy)propan-2-yl)-4-nitro-1H-pyrazole (D84)

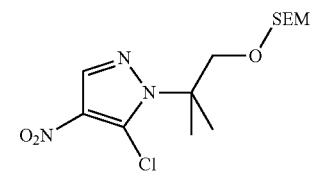 [SMILES: CC(C)(COCOCC[Si](C)(C)C)n1ncc([N+](=O)[O-])c1Cl]

To a solution of 1-(2-methyl-1-((2-(trimethylsilyl)ethoxy)methoxy)propan-2-yl)-4-nitro-1H-pyrazole (which may be prepared according to D83) (1.2 g, 3.80 mmol) in dry THF (30 mL) stirred under nitrogen at −70° C. was added a solution of lithium bis(trimethylsilyl)amide (11.41 mL, 11.41 mmol, 1M in THF) dropwise during 20 min. The reaction mixture was stirred at −78° C. for 30 min. A solution of perchloroethane (1.351 g, 5.71 mmol) was added and the mixture was stirred for 1 hour at −78° C. under nitrogen. The mixture was quenched with aq NH$_4$Cl. Then the mixture was extracted with EtOAc (2×100 mL), washed with brine, dried with Na$_2$SO$_4$, filtered and concentrated. The crude was purified by column chromatography on silica gel (PE:EA=30:1) to give the title compound D84 (1.2 g, 3.43 mmol, 90% yield) as a yellow solid.

LCMS: 322 [M+H]$^+$. $t_R$=2.17 mins. (LCMS condition 2)

$^1$H NMR (400 MHz, CHLOROFORM-d): δ 8.13 (s, 1H), 4.58-4.69 (m, 2H), 3.89-3.99 (m, 2H), 3.41-3.59 (m, 2H), 1.70-1.84 (m, 6H), 0.79-0.97 (m, 2H), 0.00 (s, 9H).

Description D85

5-methyl-1-(2-methyl-1-((2-(trimethylsilyl)-ethoxy)-methoxy)propan-2-yl)-4-nitro-1H-pyrazole (D85)

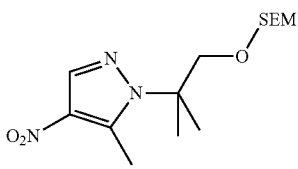 [SMILES: Cc1c([N+](=O)[O-])cnn1C(C)(C)COCOCC[Si](C)(C)C]

A solution of 2,4,6-trimethyl-1,3,5,2,4,6-trioxatriborinane (0.897 g, 7.15 mmol), 5-chloro-1-(2-methyl-1-((2-(trimethylsilyl)ethoxy)methoxy)propan-2-yl)-4-nitro-1H-pyrazole (which may be prepared according to D84) (1.0 g, 2.86 mmol), sodium carbonate (0.909 g, 8.57 mmol) and PdCl$_2$ (dppf)-CH$_2$Cl$_2$ adduct (0.467 g, 0.572 mmol) in 1,4-dioxane (2 mL) and water (0.400 mL) was combined in a thick-walled glass tube and stirred at 90° C. for 40 hours. Then the mixture was diluted with water (100 mL) and extracted with ethyl acetate (2×100 mL). The combined organic phase was washed with brine (20 mL), dried with Na$_2$SO$_4$, filtered and concentrated. The residue was purified by column chromatography on silica gel (PE:EA=30:1) to give the title compound D85 (530 g, 1.609 mmol, 56.3% yield) as yellow oil.

LCMS: 330 [M+H]$^+$. t$_R$=2.14 mins. (LCMS condition 2)
$^1$H NMR (400 MHz, CHLOROFORM-d): δ 8.06 (s, 1H), 4.62 (s, 2H), 3.82 (s, 2H), 3.34-3.56 (m, 2H), 2.71-2.95 (m, 3H), 1.72 (s, 6H), 0.79-0.95 (m, 2H), 0.00 (s, 9H).

Description D86

2-methyl-2-(5-methyl-4-nitro-1H-pyrazol-1-yl)propan-1-ol (D86)

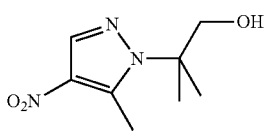

A solution of 5-methyl-1-(2-methyl-1-((2-(trimethylsilyl)-ethoxy)-methoxy)propan-2-yl)-4-nitro-1H-pyrazole (which may be prepared according to D85) (500 g, 1.518 mmol) and hydrogen chloride (15 mL, 60.0 mmol, 4M in water) was stirred at room temperature for 5 hours. The mixture was treated with saturated NaHCO$_3$ solution until the pH=8. The mixture was then extracted with EtOAc (2×50 mL). The organic layer was dried with Na$_2$SO$_4$, filtered and concentrated to give the title compound D86 (270 g, 1.355 mmol, 89% yield) as brown oil.

LCMS: 200 [M+H]$^+$. t$_R$=0.83 mins. (LCMS condition 2)
$^1$H NMR (400 MHz, CHLOROFORM-d): δ 8.06 (s, 1H), 7.26 (s, 1H), 3.94 (s, 2H), 2.83 (s, 3H), 1.46-1.75 (m, 6H).

Description D87

2-(4-amino-5-methyl-1H-pyrazol-1-yl)-2-methylpropan-1-ol (D87)

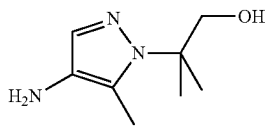

A solution of 2-methyl-2-(5-methyl-4-nitro-1H-pyrazol-1-yl)propan-1-ol (which may be prepared according to D86) (260 g, 1.305 mmol) and Pd/C (290 g, 2.73 mmol) in methanol (30 mL) was stirred under hydrogen at room temperature for 4 hours. The mixture was then filtered and the solution was concentrated to give the title compound D87 (200 g, 1.064 mmol, 81% yield) as brown oil.

LCMS: 170 [M+H]$^+$. t$_R$=0.72 mins. (LCMS condition 2)
$^1$H NMR (400 MHz, CHLOROFORM-d): δ 7.27 (s, 1H), 7.09 (s, 1H), 3.88 (s, 2H), 2.31 (s, 3H), 1.49 ppm (s, 6H).

Description D88

(±)-Trans-1-methyl-2-(4-nitro-1H-pyrazol-1-yl)-cyclopentanol (D88)

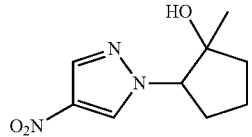

A solution of 4-nitro-1H-pyrazole (10 g, 88 mmol), 1-methyl-6-oxabicyclo-[3.1.0]-hexane (13.02 g, 133 mmol) (which may be prepared according to PCT Int. Appl. WO2013055577) and K$_2$CO$_3$ (24.44 g, 177 mmol) in DMF (200 mL) was stirred overnight at 120° C. The mixture was added to ice-water and then extracted with EtOAc. The organic layer was then concentrated and the crude was purified by chromatography on silica gel (PE:EA=5:1) to give the title compound D88 (4.0 g, 18.94 mmol, 21.41% yield) as yellow oil.

LCMS: 212 [M+H]$^+$. t$_R$=1.196 mins. (LCMS condition 2)
$^1$H NMR (400 MHz, CHLOROFORM-d): δ 8.20-8.23 (m, 1H), 8.09 (s, 1H), 4.47 (t, J=8.6 Hz, 1H), 2.09-2.24 (m, 2H), 1.79-1.91 (m, 2H), 1.51 (s, 3H), 1.19-1.25 (m, 2H).

Description D89

(±)-Trans-2-(5-chloro-4-nitro-1H-pyrazol-1-yl)-1-methylcyclopentanol (D89)

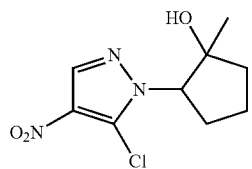 [SMILES: CC1(O)CCCC1n1ncc([N+](=O)[O-])c1Cl]

To a solution of (±)-Trans-1-methyl-2-(4-nitro-1H-pyrazol-1-yl)-cyclopentanol (which may be prepared according to D88) (6.5 g, 30.8 mmol) in dry THF (100 mL) under nitrogen at −78° C. was added lithium bis(trimethylsilyl) amide (92 mL, 92 mmol, 1M in THF) dropwise during 15 min. The reaction mixture was stirred at −78° C. for 30 min. Then, a solution of perchloroethane (18.21 g, 77 mmol) in dry THF (100 mL) was added and the mixture was stirred at −78° C. for 3 hours at −78° C. under nitrogen. The mixture was quenched with aq. NH$_4$Cl and extracted with EtOAc. The organic layer was concentrated and the crude was purified by chromatography on silica gel (PE:EA=5:1) to give the title compound D89 (5.0 g, 19.13 mmol, 62.2% yield) as yellow oil.

LCMS: 246 [M+H]$^+$. t$_R$=1.513 mins. (LCMS condition 2)
$^1$H NMR (400 MHz, CHLOROFORM-d): δ 8.19 (s, 1H), 4.77 (dd, J=5.6, 8.0 Hz, 1H), 2.33-2.49 (m, 2H), 1.94-2.08 (m, 3H), 1.75-1.87 (m, 1H), 1.02 (s, 3H).

Description D90

(±)-Trans-2-(5-cyclopropyl-4-nitro-1H-pyrazol-1-yl)-1-methylcyclopentanol (D90)

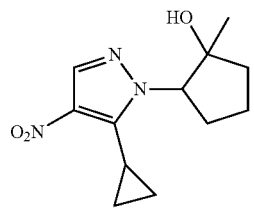 [SMILES: CC1(O)CCCC1n1ncc([N+](=O)[O-])c1C1CC1]

A solution of (±)-trans-2-(5-chloro-4-nitro-1H-pyrazol-1-yl)-1-methylcyclopentanol (which may be prepared according to D89) (1.5 g, 6.11 mmol), cyclopropylboronic acid (0.524 g, 6.11 mmol), PdCl$_2$(dppf) (4.47 g, 6.11 mmol) and Na$_2$CO$_3$ (0.647 g, 6.11 mmol) in 1,4-dioxane (20 mL) and water (2.000 mL) was stirred at 75° C. under nitrogen for 6 hours. The mixture was concentrated and the crude was directly purified by chromatography on silica gel (PE:EA=6:1) to give the title compound D90 (600 g, 2.388 mmol, 39.1% yield) as yellow oil.

LCMS: 252 [M+H]$^+$. t$_R$=1.540 mins. (LCMS condition 2)
$^1$H NMR (400 MHz, CHLOROFORM-d): δ 8.07 (s, 1H), 4.88-5.03 (m, 1H), 2.24-2.44 (m, 2H), 1.87-2.04 (m, 3H), 1.73-1.84 (m, 1H), 1.26-1.32 (m, 1H), 0.99 (s, 3H), 0.63-0.69 (m, 2H), 0.56 (qd, J=2.8, 5.6 Hz, 2H).

Description D91

(±)-Trans-2-(4-amino-5-cyclopropyl-1H-pyrazol-1-yl)-1-methylcyclopentanol (D91)

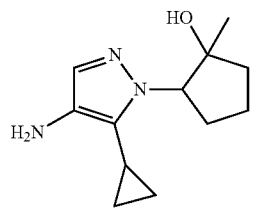

A solution of (±)-trans-2-(5-cyclopropyl-4-nitro-1H-pyrazol-1-yl)-1-methylcyclopentanol (which may be prepared according to D90) (550 g, 2.189 mmol) and Pd/C (116 mg, 0.109 mmol) in methanol (20 mL) was stirred overnight at room temperature under hydrogen. The mixture was filtered and the solution was concentrated to give the title compound D91 (400 g, 1.808 mmol, 83% yield) as yellow oil.

LCMS: 222 [M+H]$^+$. t$_R$=1.184 mins. (LCMS condition 2)

Description D92

(±)-Trans-2-(5-cyclopropyl-4-((4-ethoxy-7-tosyl-7H-pyrrolo-[2,3-d]-pyrimidin-2-yl)amino)-1H-pyrazol-1-yl)-1-methylcyclopentanol (D92)

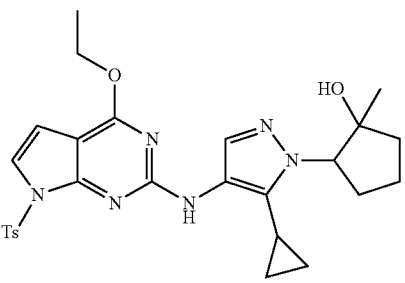 [SMILES: CCOc1nc(Nc2cnn(C3CCCC3(C)O)c2C2CC2)nc2c1ccn2S(=O)(=O)c1ccc(C)cc1]

A solution of 2-chloro-4-ethoxy-7-tosyl-7H-pyrrolo-[2,3-d]-pyrimidine (which may be prepared according to D2) (700 g, 1.990 mmol), (±)-trans-2-(4-amino-5-cyclopropyl-1H-pyrazol-1-yl)-1-methylcyclopentanol (which may be prepared according to D91) (440 g, 1.990 mmol), potassium carbonate (550 g, 3.98 mmol), (9,9-dimethyl-9H-xanthene-4,5-diyl)bis(diphenylphosphine) (173 g, 0.298 mmol) and Pd(dppf)Cl$_2$ (162 g, 0.199 mmol) in 1,4-dioxane (2.0 mL) and water (0.2 mL) was stirred at 90° C. for 6 hours. The mixture was diluted with EtOAc (25 mL) and washed with water (20 mL). The organic layer was dried and concentrated. The crude was purified by chromatography on silica gel (PE:EA=6:1) to give the title compound D92 (300 g, 0.498 mmol, 25.01% yield) as a white solid.

LCMS: 537 [M+H]$^+$. t$_R$=1.822 mins. (LCMS condition 2)
$^1$H NMR (400 MHz, CHLOROFORM-d): δ 8.00 (s, 1H), 7.93 (d, J=7.8 Hz, 2H), 7.18-7.24 (m, 3H), 6.45 (d, J=3.8 Hz, 1H), 4.88 (t, J=7.6 Hz, 1H), 4.45 (q, J=7.11 Hz, 2H), 2.34-2.53 (m, 5H), 1.88-2.13 (m, 3H), 1.80-1.85 (m, 1H), 1.45-1.56 (m, 1H), 1.39 (t, J=7.0 Hz, 3H), 0.96-1.10 (m, 5H), 0.83-0.91 (m, 1H), 0.63-0.72 (m, 1H).

Description D93

(±)-Trans-1-methyl-2-(5-methyl-4-nitro-1H-pyrazol-1-yl)cyclopentanol (D93)

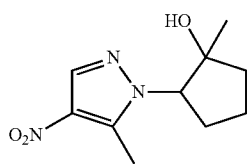 [SMILES: Cc1c([N+](=O)[O-])cnn1C1CCCC1(C)O]

A solution of (±)-trans-2-(5-chloro-4-nitro-1H-pyrazol-1-yl)-1-methylcyclopentanol (which may be prepared according to D89) (1.5 g, 6.11 mmol), methylboronic acid (0.366 g, 6.11 mmol), PdCl$_2$(dppf) (0.48 g, 0.611 mmol) and Na$_2$CO$_3$ (0.647 g, 6.11 mmol) in 1,4-dioxane (20 mL) and water (2.000 mL) was stirred at 75° C. under nitrogen for 6 hours. The mixture was concentrated and the crude was purified by chromatography on silica gel (PE:EA=6:1) to give the title compound D93 (500 g, 2.064 mmol, 33.8% yield) as yellow oil.

LCMS: 226 [M+H]$^+$. t$_R$=1.121 mins. (LCMS condition 2)
$^1$H NMR (400 MHz, CHLOROFORM-d): δ 8.10 (s, 1H), 4.52 (t, J=7.6 Hz, 1H), 2.74 (s, 3H), 2.41-2.55 (m, 1H), 2.24-2.39 (m, 1H), 1.75-2.05 (m, 4H), 0.98 (s, 3H).

Description D94

(±)-Trans-2-(4-amino-5-methyl-1H-pyrazol-1-yl)-1-methylcyclopentanol (D94)

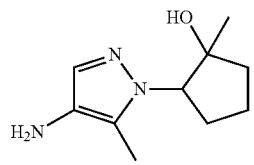

A mixture of (±)-trans-1-methyl-2-(5-methyl-4-nitro-1H-pyrazol-1-yl)cyclopentanol (D93) (500 g, 2.220 mmol) and Pd/C (118 g, 0.111 mmol) in methanol (20 mL) was stirred overnight at 20° C. under hydrogen. The mixture was filtered and the solution was concentrated to give the title compound D94 (350 g, 1.792 mmol, 81% yield) as yellow oil.

LCMS: 196 [M+H]$^+$. t$_R$=1.056 mins. (LCMS condition 2)

Description D95

(±)-Trans-2-(4-((4-ethoxy-7-tosyl-7H-pyrrolo-[2,3-d]pyrimidin-2-yl)amino)-5-methyl-1H-pyrazol-1-yl)-1-methylcyclopentanol (D95)

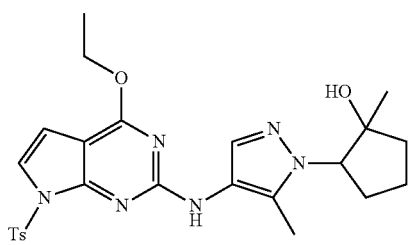 [SMILES: CCOc1nc(Nc2cnn(C3CCCC3(C)O)c2C)nc2c1ccn2S(=O)(=O)c1ccc(C)cc1]

A solution of 2-chloro-4-ethoxy-7-tosyl-7H-pyrrolo-[2,3-d]-pyrimidine (which may be prepared according to D2) (650 g, 1.848 mmol), (±)-trans-2-(4-amino-5-methyl-1H-pyrazol-1-yl)-1-methylcyclopentanol (which may be prepared according to D94) (350 g, 1.792 mmol), potassium carbonate (511 g, 3.70 mmol), (9,9-dimethyl-9H-xanthene-4,5-diyl)bis(diphenylphosphine) (160 g, 0.277 mmol) and Pd(dppf)Cl$_2$ (151 g, 0.185 mmol) in 1,4-dioxane (2.0 mL) and water (0.2 mL) was stirred at 90° C. for 6 hours. The mixture was diluted with EtOAc (25 mL) and washed with water (20 mL). The organic layer was dried and concentrated. The crude was purified by chromatography on silica gel (PE:EA=6:1) to give the title compound D95 (300 g, 0.505 mmol, 27.3% yield) as a white solid.

LCMS: 511 [M+H]$^+$. t$_R$=1.767 mins. (LCMS condition 2)

Description D96

1-(cyclopent-3-en-1-yl)-4-nitro-1H-pyrazole (D96)

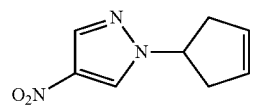 [SMILES: O=[N+]([O-])c1cnn(C2CC=CC2)c1]

A solution of 4-nitro-1H-pyrazole (750 g, 6.63 mmol), cyclopent-3-en-1-yl methanesulfonate (1614 g, 9.95 mmol) and K$_2$CO$_3$ (1375 g, 9.95 mmol) in DMF (20 mL) was stirred at 90° C. for 1 hour. The mixture was diluted with water and extracted with EA twice. The organic layer was then dried and concentrated. The crude was purified via column chromatography on silica gel (PE:EA=2:1) to give the title compound D96 (1.20 g, 6.54 mmol, 99% yield) as yellow oil.

LCMS: 180 [M+H]$^+$. t$_R$=2.750 mins. (LCMS condition 2)
$^1$H NMR (400 MHz, DMSO-d$_6$): δ 8.16 (s, 1H), 8.05 (s, 1H), 5.80-5.88 (m, 2H), 5.05 (tt, J=8.1, 3.9 Hz, 1H), 2.93-3.10 (m, 2H), 2.62-2.84 (m, 2H).

Description D97

5-chloro-1-(cyclopent-3-en-1-yl)-4-nitro-1H-pyrazole (D97)

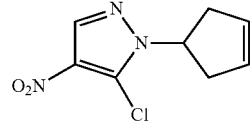 [SMILES: O=[N+]([O-])c1cnn(C2CC=CC2)c1Cl]

To a solution of 1-(cyclopent-3-en-1-yl)-4-nitro-1H-pyrazole (which may be prepared according to D96) (750 g, 4.19 mmol) in THF (20 mL) was added LHMDS (1M in THF) (9 mL, 9.00 mmol) at −78° C. under nitrogen. After stirring at −78° C. for 30 min, perchloroethane (1486 g, 6.28 mmol) in THF (20 mL) was added dropwise and the resulting mixture was stirred at −78° C. for another 2 hours. The reaction was quenched with saturated NH$_4$Cl solution (50 mL) and extracted with EA twice. The combined organic layer was then concentrated and purified via column chromatography on silica gel (PE:EA=1:1) to give the title compound D97 (704 g, 3.06 mmol, 73.2% yield) as yellow oil.

LCMS: 214 [M+H]$^+$. t$_R$=3.226 mins. (LCMS condition 2)
$^1$H NMR (400 MHz, DMSO-d$_6$): δ 8.11 (s, 1H), 5.65-5.78 (m, 2H), 5.10-5.24 (m, 1H), 2.71-2.94 (m, 4H).

Description D98

1-(cyclopent-3-en-1-yl)-5-cyclopropyl-4-nitro-1H-pyrazole (D98)

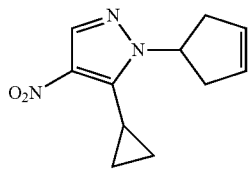 [SMILES: O=[N+]([O-])c1cnn(C2CC=CC2)c1C1CC1]

A solution of 5-chloro-1-(cyclopent-3-en-1-yl)-4-nitro-1H-pyrazole (which may be prepared according to D97) (500 g, 2.341 mmol), cyclopropylboronic acid (503 g, 5.85 mmol), sodium carbonate (744 g, 7.02 mmol) and PdCl$_2$(dppf)-CH$_2$Cl$_2$ adduct (96 g, 0.117 mmol) in 1,4-dioxane (10 mL) and water (1.00 mL) was stirred under nitrogen at 90° C. for overnight. The mixture was diluted with DCM, washed with water. The organic layer was dried and concentrated. The crude was purified by column chromatography on silica gel (PE:EA=1:1) to give the title compound D98 (386 g, 1.673 mmol, 71.5% yield) as yellow oil.

LCMS: 220 [M+H]$^+$. t$_R$=3.313 mins. (LCMS condition 2)

$^1$H NMR (400 MHz, DMSO-d$_6$): δ 8.09 (s, 1H), 5.77-5.88 (m, 2H), 5.39-5.53 (m, 1H), 2.74-3.02 (m, 4H), 1.88 (tt, J=8.4, 5.6 Hz, 1H), 1.21-1.34 (m, 2H), 0.77-0.92 (m, 2H).

Description D99

(±)-Trans-5-(5-cyclopropyl-4-nitro-1H-pyrazol-1-yl)cyclopent-2-enol (D99)

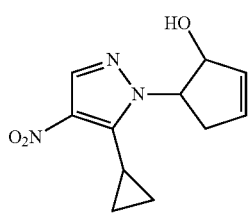 [SMILES: O=[N+]([O-])c1cnn(C2CC=CC2O)c1C1CC1]

A solution of 1-(cyclopent-3-en-1-yl)-5-cyclopropyl-4-nitro-1H-pyrazole (which may be prepared according to D98)(385 g, 1.756 mmol) and selenium dioxide (585 g, 5.27 mmol) in 1,4-dioxane (9 mL), water (0.2 mL) and pyridine (0.02 mL) was stirred at 80° C. for overnight. The mixture was filtered and the filtrate was evaporated. The crude was purified by column chromatography on silica gel (PE:EA=1: 1) to give the title compound D99 (91 g, 0.371 mmol, 21.15% yield) as yellow oil.

LCMS: 236 [M+H]$^+$. t$_R$=2.418 mins. (LCMS condition 2)

$^1$H NMR (400 MHz, DMSO-d$_6$): δ 8.03 (s, 1H), 5.73-5.98 (m, 2H), 5.19 (br. s., 1H), 5.10 (dt, J=5.59, 8.38 Hz, 1H), 2.83-2.97 (m, 1H), 2.58-2.79 (m, 1H), 1.85 (tt, J=5.53, 8.53 Hz, 1H), 1.16-1.27 (m, 4H).

Description D100

(±)-Trans-3-(5-cyclopropyl-4-nitro-1H-pyrazol-1-yl)bicycle-[3.1.0]-hexan-2-ol (D100)

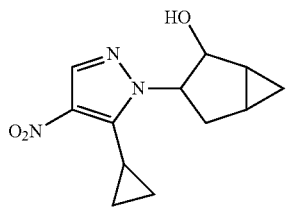

To a solution of (±)-Trans-5-(5-cyclopropyl-4-nitro-1H-pyrazol-1-yl)cyclopent-2-enol (which may be prepared according to D99) (85 g, 0.361 mmol) in DCM (5 mL) at 0° C. under nitrogen was added diethylzinc (1M in heptane) (1.807 mL, 1.807 mmol) dropwise. After 15 min, the mixture was treated with diiodomethane (0.292 mL, 3.61 mmol) dropwise at 0° C. The mixture was then warmed to room temperature and stirred for 2 hours. The reaction was quenched with saturated NH$_4$Cl solution (10 mL) and then extracted with DCM. The organic layer was dried and concentrated. The crude was purified by column chromatography on silica gel (PE:EA=1:1) to give the title compound D100 (45 g, 0.181 mmol, 50.0% yield) as yellow oil.

LCMS: 250 [M+H]$^+$. t$_R$=2.559 mins. (LCMS condition 2)

$^1$H NMR (400 MHz, DMSO-d$_6$): δ 8.02 (s, 1H), 4.94 (br. s., 1H), 4.44 (dt, J=7.64, 10.15 Hz, 1H), 2.31-2.44 (m, 1H), 2.14 (dd, J=7.70, 12.59 Hz, 1H), 1.70-1.79 (m, 1H), 1.60 (td, J=4.03, 7.27 Hz, 1H), 1.43-1.50 (m, 1H), 1.18 (d, 2H), 0.85-0.95 (m, 1H), 0.62-0.70 (m, 2H), 0.52-0.61 (m, 1H).

Description D101

(±)-Trans-3-(4-amino-5-cyclopropyl-1H-pyrazol-1-yl)bicycle-[3.1.0]-hexan-2-ol (D101)

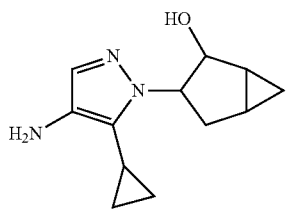 [SMILES: O=[N+]([O-])c1cnn(C2CC3CC3C2O)c1C1CC1]

A solution of (±)-Trans-3-(5-cyclopropyl-4-nitro-1H-pyrazol-1-yl)bicycle-[3.1.0]-hexan-2-ol (which may be prepared according to D100) (45 g, 0.181 mmol) and Pd/C (19.21 g, 0.018 mmol) in methanol (10 mL) was stirred at room temperature for 2 hours. The mixture was filtered and the filtrate was concentrated to give the title compound D101 (37.3 g, 0.170 mmol, 94% yield) as yellow oil, which used in next step without further purification.

LCMS: 220 [M+H]$^+$. t$_R$=1.359 mins. (LCMS condition 2)

Description D102

(±)-Trans-3-(5-cyclopropyl-4-((4-ethoxy-7-tosyl-7H-pyrrolo[2,3-d]pyrimidin-2-yl)amino)-1H-pyrazol-1-yl)bicycle-[3.1.0]-hexan-2-ol (D102)

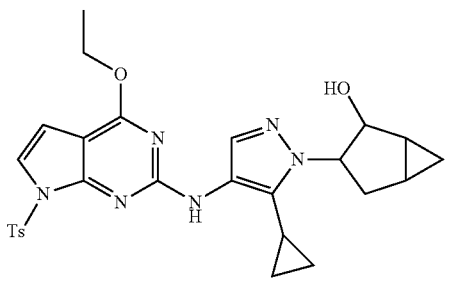 [SMILES: CCOc1nc(Nc2cnn(C3CC4CC4C3O)c2C2CC2)nc2c1ccn2S(=O)(=O)c1ccc(C)cc1]

A solution of (±)-trans-3-(4-amino-5-cyclopropyl-1H-pyrazol-1-yl)bicycle-[3.1.0]-hexan-2-ol (which may be prepared according to D101) (34 g, 0.155 mmol), 2-chloro-4-ethoxy-7-tosyl-7H-pyrrolo-[2,3-d]-pyrimidine (which may be prepared according to D2) (65.5 mg, 0.186 mmol), dicyclohexyl(2',4',6'-triisopropyl-[1,1'-biphenyl]-2-yl)phosphine (3.70 mg, 7.75 μmol), PdCl$_2$(dppf)-CH$_2$Cl$_2$ adduct (6.33 mg, 7.75 μmol) and potassium carbonate (64.3 mg, 0.465 mmol) in 1,4-dioxane (10 mL) and water (1 mL) was stirred at 100° C. under microwave for 2 hour. The mixture was directly concentrated to dryness and the crude was purified by column chromatography on silica gel (PE:EA=1:3) to give the title compound D102 (40 g, 0.071 mmol, 45.8% yield) as yellow oil.

LCMS: 535 [M+H]$^+$. $t_R$=3.075 mins. (LCMS condition 2)

Description D103 tert-butyl 3-fluoro-4-(4-nitro-1H-pyrazol-1-yl)piperidine-1-carboxylate (D103)

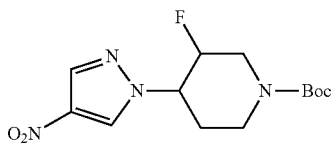

To a solution of tert-butyl 3-fluoro-4-((methylsulfonyl)oxy)piperidine-1-carboxylate (14.93 g, 50.2 mmol) (which may be prepared according to PCT Int. Appl., 2012062783) in DMF (25.0 mL) was added K$_2$CO$_3$ (13.88 g, 100 mmol) and 4-nitro-1H-pyrazole (5.68 g, 50.2 mmol). The reaction mixture was stirred at 90° C. for overnight. The reaction mixture was quenched with water and extracted with DCM (20 mL×3). The combined organic layers were dried over Na$_2$SO$_4$, filtered and concentrated in vacuum. The crude was purified by column chromatography on silica gel (PE:EA=4:1) to give the title compound D103 (10.0 g, 31.2 mmol, 62.1% yield) as yellow oil.

LCMS: 259.1 [M−56+H]$^+$. $t_R$=1.45 mins. (LCMS condition 2)

Description D104 tert-butyl 4-(5-chloro-4-nitro-1H-pyrazol-1-yl)-3-fluoropiperidine-1-carboxylate (D104)

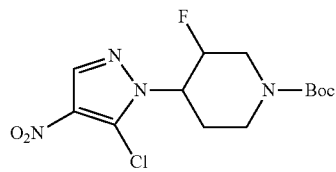

To a solution of tert-butyl-3-fluoro-4-(4-nitro-1H-pyrazol-1-yl)piperidine-1-carboxylate (which may be prepared according to D103) (10.0 g, 31.8 mmol) in dry THF (50.0 mL) under nitrogen at −70° C. was added lithium bis (trimethylsilyl)amide (127 mL, 127 mmol, 1M in THF) dropwise during 15 min. The reaction mixture was stirred at −78° C. for 30 min. A solution of perchloroethane (22.60 g, 95 mmol) in dry THF (50.0 mL) was added and the mixture was stirred for 2 hours at −78° C. under nitrogen. The mixture was quenched with aq NH$_4$Cl and extracted with EtOAc (2×100 mL). The organic layer was dried with Na$_2$SO$_4$, filtered and concentrated. The crude was purified by chromatography on silica gel (PE:EA=4:1) to give the title compound D104 (6.0 g, 15.31 mmol, 48.1% yield) as yellow oil.

LCMS: 293 [M−56+H]$^+$. $t_R$=1.55 mins. (LCMS condition 2)

Description D105 and 106 tert-butyl 3-fluoro-4-(5-methyl-4-nitro-1H-pyrazol-1-yl)piperidine-1-carboxylate (D105)

tert-butyl 3-fluoro-4-(4-nitro-1H-pyrazol-1-yl)piperidine-1-carboxylate (D106)

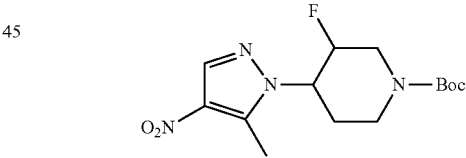

D105

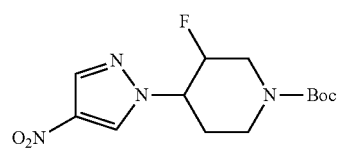 [SMILES: CC(C)(C)OC(=O)N1CCC(n2cc([N+](=O)[O-])cn2)C(F)C1]

D106

A solution of methylboronic acid (3.09 g, 51.6 mmol), tert-butyl 4-(5-chloro-4-nitro-1H-pyrazol-1-yl)-3-fluoropiperidine-1-carboxylate (which may be prepared according to D104) (D105 and D106 together, 6.0 g, 17.20 mmol), PdCl$_2$(dppf)-CH$_2$Cl$_2$ adduct (1.405 g, 1.720 mmol) and sodium carbonate (5.47 g, 51.6 mmol) in 1,4-dioxane (30 mL) and water (3.0 mL) was combined in a thick walled glass tube and stirred overnight at 75° C. The mixture was poured into water and extracted with DCM (20 mL×3). The combined organic layers were dried over Na$_2$SO$_4$, filtered and concentrated in vacuum. The crude was purified by column chromatography on silica (PE:EA=4:1) to give the mixture of title compounds D105 and
D106 (2.0 g, 6.09 mmol, 35.4% yield) as a yellow solid.
D105: LCMS: 273.1 [M−56+H]⁺. $t_R$=1.53 mins. (LCMS condition 2)

Description D107 and D108

3-fluoro-4-(5-methyl-4-nitro-1H-pyrazol-1-yl)piperidine (D107)

3-fluoro-4-(4-nitro-1H-pyrazol-1-yl)piperidine (D108)

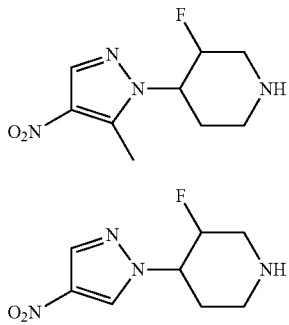

A solution of tert-butyl 3-fluoro-4-(5-methyl-4-nitro-1H-pyrazol-1-yl)piperidine-1-carboxylate (which may be prepared according to D105) and tert-butyl 3-fluoro-4-(4-nitro-1H-pyrazol-1-yl)piperidine-1-carboxylate (which may be prepared according to D106) (D105 and D106 together, 6.0 g, 18.27 mmol) in DCM (50 mL) was added TFA (14.08 mL, 183 mmol) was stirred at room temperature for 2 hours. The reaction mixture was quenched with aq. NaHCO₃ and extracted with DCM (20 mL×3). The combined organic layers were dried over Na₂SO₄, filtered and concentrated in vacuum. The crude was purified by column chromatography on silica gel (DCM:MeOH=20:1) to give the mixture of title compounds
D107 and D108 (4.0 g, 17.53 mmol, 96% yield) as a yellow solid.
D107: LCMS: 229.1 [M+H]⁺. $t_R$=1.11 mins. (LCMS condition 2)
D108: LCMS: 215. [M+H]⁺. $t_R$=1.04 mins. (LCMS condition 2)

Description D109 and D110

3-fluoro-1-methyl-4-(5-methyl-4-nitro-1H-pyrazol-1-yl)piperidine (D109)

3-fluoro-1-methyl-4-(4-nitro-1H-pyrazol-1-yl)piperidine (D110)

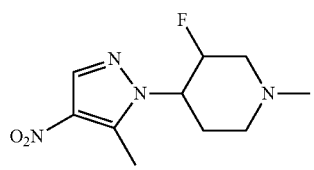

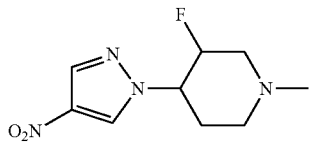

To a solution of 3-fluoro-4-(5-methyl-4-nitro-1H-pyrazol-1-yl)piperidine (which may be prepared according to D107) and 3-fluoro-4-(4-nitro-1H-pyrazol-1-yl)piperidine (which may be prepared according to D108) (D107 and D108 together, 4.0 g, 17.53 mmol) and formaldehyde (1.579 g, 52.6 mmol) in methanol (5.0 mL) was added AcOH (0.100 mL, 1.753 mmol). The reaction was stirred at 65° C. for 2 hours. The reaction mixture was then cooled to 0° C., sodium triacetoxyborohydride (3.71 g, 17.53 mmol) was added. The reaction was stirred at room temperature for 2 hours. The reaction mixture was quenched with water and extracted with mix solvent of DCM and MeOH (10:1, 20 mL×3). The combined organic layers were dried over Na₂SO₄, filtered and concentrated in vacuum. The crude was purified by column chromatography on silica gel (PE:EA=2:1) to give the title compound D109 and
D110 (3.0 g, 12.38 mmol, 70.7% yield) as a yellow solid.
D109: LCMS: 243.1 [M+H]⁺. $t_R$=1.47 mins. (LCMS condition 2)
D110: LCMS: 229 [M+H]⁺. $t_R$=1.41 mins. (LCMS condition 2)

Description D111 and D112

1-(3-fluoro-1-methylpiperidin-4-yl)-5-methyl-1H-pyrazol-4-amine (D111)

1-(3-fluoro-1-methylpiperidin-4-yl)-1H-pyrazol-4-amine (D112)

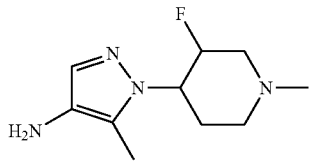

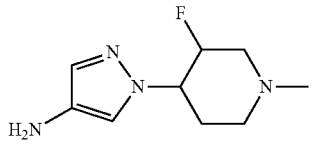

To a solution of 3-fluoro-1-methyl-4-(5-methyl-4-nitro-1H-pyrazol-1-yl)piperidine (which may be prepared according to D109) and 3-fluoro-1-methyl-4-(4-nitro-1H-pyrazol-1-yl)piperidine (which may be prepared according to D110) (D109 and D110 together, 3.0 g, 12.38 mmol) in ethanol (10.0 mL) and water (10.0 mL) was added iron (1.383 g, 24.77 mmol) and ammonium chloride (0.331 g, 6.19 mmol). The reaction was stirred overnight at room temperature. The mixture was filtered through a pad of Celite and washed with EtOH (10 mL×3). The filtrate was concentrated and the crude was purified by column chromatography on silica gel

89

(DCM:MeOH=20:1) to give the mixture of the title compound D111 and D112 (1.5 g, 7.07 mmol, 57.1% yield) as yellow oil.

D111: LCMS: 213.1 [M+H]+. $t_R$=0.94 mins. (LCMS condition 2)

D112: LCMS: 199.2 [M+H]+. $t_R$=0.67 mins. (LCMS condition 2)

Description D113 and D114

4-ethoxy-N-(1-(3-fluoro-1-methylpiperidin-4-yl)-5-methyl-1H-pyrazol-4-yl)-7-tosyl-7H-pyrrolo-[2,3-d]pyrimidin-2-amine (D113)

4-ethoxy-N-(1-(3-fluoro-1-methylpiperidin-4-yl)-1H-pyrazol-4-yl)-7-tosyl-7H-pyrrolo-[2,3-d]pyrimidin-2-amine (D114)

D113

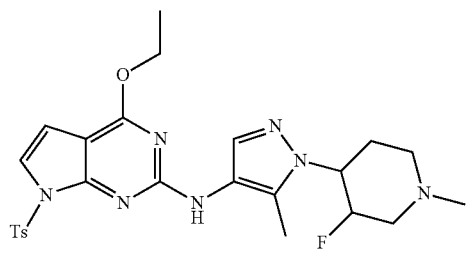

D114

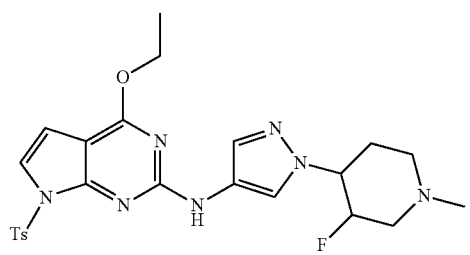

A solution of 2-chloro-4-ethoxy-7-tosyl-7H-pyrrolo-[2,3-d]-pyrimidine (which may be prepared according to D2) (180 g, 0.512 mmol), 1-(3-fluoro-1-methylpiperidin-4-yl)-5-methyl-1H-pyrazol-4-amine (which may be prepared according to D111) and 1-(3-fluoro-1-methylpiperidin-4-yl)-1H-pyrazol-4-amine (which may be prepared according to D112) (D111 and D112 together, 108 g, 0.512 mmol), K₂CO₃ (212 g, 1.535 mmol), X-Phos (73.2 g, 0.153 mmol) and PdCl₂(dppf)-CH₂Cl₂ adduct (84 g, 0.102 mmol) in 1,4-dioxane (1.50 mL) and water (0.20 mL) under nitrogen was stirred overnight at 90° C. The reaction mixture was poured into water and extracted with DCM (20 mL×3). The combined organic layers were dried over Na₂SO₄, filtered and concentrated in vacuum. The crude was purified by column chromatography on silica gel (PE:EA=2:1) to give the mixture of the title compound D113 and D114 (250 g, 0.256 mmol, 50.1% yield) as a yellow solid.

D113: LCMS: 528.3 [M+H]+. $t_R$=1.57 mins. (LCMS condition 2)

D114: LCMS: 514 [M+H]+. $t_R$=1.57 mins. (LCMS condition 2)

90

Description D115

(R)-3-methyl-4-(2-(5-methyl-4-nitro-1H-pyrazol-1-ylethyl)morpholine (D115)

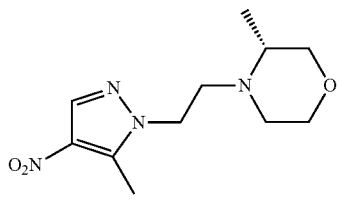 [SMILES: Cc1c([N+](=O)[O-])cnn1CCN1CCOC[C@H]1C]

To a solution of D15 (125 g, 0.502 mmol) in DMF (10 mL) was added (R)-3-methylmorpholine (50.7 g, 0.502 mmol) and K₂CO₃ (208 g, 1.505 mmol). The reaction mixture was stirred overnight and then quenched with water, extracted with DCM (20 mL×3). The combined extracts were dried over Na₂SO₄, filtered and concentrated. The crude was purified by column chromatography on silica gel (PE:EA=4:1) to give the title compound D115 (80.0 g, 0.315 mmol, 62.7% yield).

LCMS: 255 [M+H]+. $t_R$=1.13 mins. (LCMS condition 2)

Description D116

(R)-5-methyl-1-(2-(3-methylmorpholino)ethyl)-1H-pyrazol-4-amine (D116)

A solution of D115 (80.0 g, 0.315 mmol) and Pd/C (84 g, 0.079 mmol) in methanol (20 mL) was stirred under hydrogen overnight at room temperature. The suspension was filtered through a pad of Celite and the pad was washed with EtOH (10 mL×3). The combined filtrates were concentrated to give the title compound D116 (60 g, 0.267 mmol, 85% yield) as colorless oil.

Description D117

(S)-3-methyl-4-(2-(5-methyl-4-nitro-1H-pyrazol-1-yl)ethyl)morpholine (D117)

To a solution of D15 (120 g, 0.481 mmol) in acetonitrile (10 mL) was added (S)-3-methylmorpholine (80 g, 0.791 mmol) and K$_2$CO$_3$ (328 g, 2.373 mmol). The reaction was stirred overnight at 80° C. The mixture was concentrated and purified by column chromatography on silica gel to give the title compound D117 (90 g, 0.354 mmol, 44.7% yield) as colorless oil.

LCMS: 255 [M+H]$^+$. $t_R$=1.21 mins. (LCMS condition 2)

Description D118

(S)-5-methyl-1-(2-(3-methylmorpholino)ethyl)-1H-pyrazol-4-amine (D118)

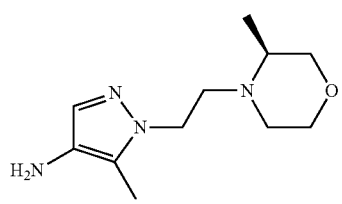 [SMILES: Cc1c([N+](=O)[O-])cnn1CCN1CCOC[C@@H]1C]

A solution of D117 (90 g, 0.354 mmol) and Pd/C (50 g, 0.047 mmol) in methanol (20 mL) was stirred under hydrogen overnight at room temperature. The mixture was filtered with diatomit, the filtrate was concentrated in vacuo to give the title compound D0118 (60 g, 0.118 mmol, 33.3% yield) as yellow oil.

Description D119

(R)-2-methyl-4-(2-(5-methyl-4-nitro-1H-pyrazol-1-yl)ethyl)morpholine (D119)

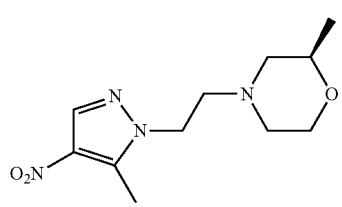

To a solution of D15 (200 g, 0.80 mmol) in DMF (10 mL) was added (R)-2-methylmorpholine (97 g, 0.963 mmol) and K$_2$CO$_3$ (333 g, 2.407 mmol). The mixture was stirred overnight at 90° C. The reaction mixture was quenched with water and extracted with DCM (20 mL×3). The combined extracts were dried over Na$_2$SO$_4$, filtered and concentrated in vacuum. The crude was purified by column chromatography on silica gel (PE:EA=1:1) to give the title compound D119 (180 g, 0.708 mmol, 88% yield).

LCMS: 255 [M+H]$^+$. $t_R$=1.19 mins. (LCMS condition 2)

Description D120

(R)-5-methyl-1-(2-(2-methylmorpholino)ethyl)-1H-pyrazol-4-amine (D120)

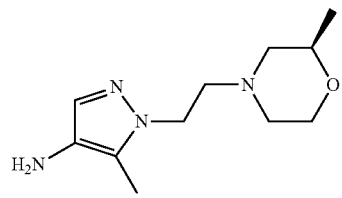 [SMILES: Cc1c([N+](=O)[O-])cnn1CCN1CCO[C@H](C)C1]

A solution of D119 (180 g, 0.708 mmol) and Pd/C (18.83 g, 0.018 mmol) in methanol (10 mL) was stirred under hydrogen overnight at room temperature. The suspension was filtered through a pad of Celite and the pad was washed with EtOH (10 mL×3). The combined filtrates were concentrated to give the title compound D120 (120 g, 0.535 mmol, 76% yield) as colorless oil.

LCMS: 225 [M+H]$^+$. $t_R$=0.89 mins. (LCMS condition 2)

Description D121

(S)-2-methyl-4-(2-(5-methyl-4-nitro-1H-pyrazol-1-yl)ethyl)morpholine (D121)

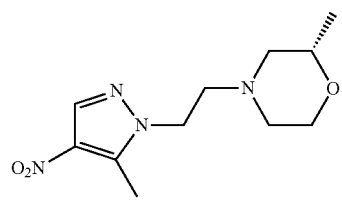 [SMILES: Cc1c([N+](=O)[O-])cnn1CCN1CCO[C@@H](C)C1]

To a solution of D15 (240 g, 0.963 mmol) in DMF (5 mL) was added (S)-2-methylmorpholine (146 g, 1.444 mmol) and K$_2$CO$_3$ (200 g, 1.444 mmol). The mixture was stirred overnight at 90° C. The mixture was extracted with EtOAc and purified by column chromatography on silica gel to give the title compound D121 (140 g, 0.551 mmol, 57.2% yield) as a yellow solid.

LCMS: 255 [M+H]$^+$. $t_R$=1.20 mins. (LCMS condition 2)

Description D122

(S)-5-methyl-1-(2-(2-methylmorpholino)ethyl)-1H-pyrazol-4-amine (D122)

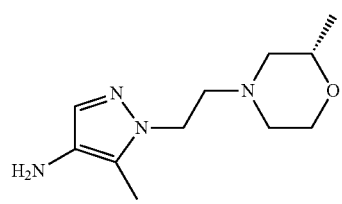

A solution of D121 (200 g, 0.787 mmol) and Pd/C (50 g, 0.047 mmol) in methanol (20 mL) was stirred under hydrogen overnight at room temperature. The mixture was filtered with diatomit, the filtrate was concentrated in vacuo to give the title compound D122 (120 g, 0.118 mmol, 14.96% yield) as yellow oil.

LCMS: 225 [M+H]$^+$. $t_R$=0.93 mins. (LCMS condition 2)

Description D123

(R)-tert-butyl 3-(4-nitro-1H-pyrazol-1-yl)pyrrolidine-1-carboxylate (D123)

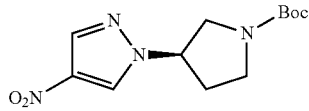

To a solution of 4-nitro-1H-pyrazole (1 g, 8.84 mmol), triphenylphosphine (2.78 g, 10.61 mmol) and (S)-tert-butyl 3-hydroxypyrrolidine-1-carboxylate (1.656 g, 8.84 mmol) in THF (60 mL) was added dropwise DIAD (2.264 mL, 11.50 mmol) at 0° C. under nitrogen. The mixture was then slowly warmed to room temperature and stirred for 2 hours. Solvent was evaporated and the crude was directly purified by column chromatography on silica gel (PE:EA=1:1) to give the title compound D123 (2.31 g, 8.18 mmol, 93% yield) as yellow oil.

LCMS: 227 [M−t−Bu+H]$^+$. $t_R$=3.136 mins. (LCMS condition 1)

$^1$H NMR (400 MHz, CHLOROFORM-d): δ 8.19 (s, 1H), 8.11 (s, 1H), 3.46-3.98 (m, 5H), 2.34-2.51 (m, 2H), 1.49 (s, 9H).

Description D124

(R)-4-nitro-1-(pyrrolidin-3-yl)-1H-pyrazole (D124)

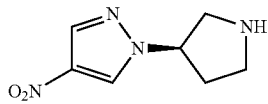

A solution of D123 (2.31 g, 8.18 mmol) and TFA (12.61 mL, 164 mmol) in DCM (50 mL) was stirred overnight at room temperature. The mixture was diluted with DCM and washed with 2N NaOH solution. The organic layer was dried over Na$_2$SO$_4$ and concentrated to give the title compound D124 (1.39 g, 7.63 mmol, 93% yield) as yellow oil.

LCMS: 183 [M+H]$^+$. $t_R$=0.58 mins. (LCMS condition 1)

$^1$H NMR (400 MHz, CHLOROFORM-d): δ 8.26 (s, 1H), 8.07 (s, 1H), 4.84 (d, J=1.96 Hz, 1H), 3.16-3.39 (m, 3H), 2.92-3.09 (m, 1H), 2.31-2.48 (m, 1H), 2.09-2.27 (m, 1H).

Description D125

(R)-1-(1-(2,2-difluoroethyl)pyrrolidin-3-yl)-4-nitro-1H-pyrazole (D125)

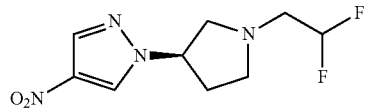 [SMILES: O=[N+]([O-])c1cnn([C@@H]2CCN(CC(F)F)C2)c1]

A solution of D124 (1.39 g, 7.63 mmol), 2,2-difluoroethyl 4-methylbenzenesulfonate (2.343 g, 9.92 mmol) and K$_2$CO$_3$ (3.16 g, 22.89 mmol) in DMF (20 mL) was stirred overnight at 90° C. The mixture was diluted with water and extracted with EA. The organic layer was dried and concentrated. The crude was purified by column chromatography on silica gel (PE:EA=1:1) to give the title compound D125 (1.508 g, 4.53 mmol, 59.4% yield) as yellow oil.

LCMS: 247 [M+H]$^+$. $t_R$=1.14 mins. (LCMS condition 1)

Description D126

(R)-5-chloro-1-(1-(2,2-difluoroethyl)pyrrolidin-3-yl)-4-nitro-1H-pyrazole (D126)

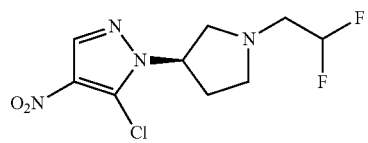 [SMILES: O=[N+]([O-])c1cnn([C@@H]2CCN(CC(F)F)C2)c1Cl]

To a solution of D121 (1.500 g, 4.51 mmol) in THF (25 mL) was added LHMDS (1M in THF, 9.02 mL, 9.02 mmol) at −78° C. under nitrogen. After stirring at −78° C. for 30 min, perchloroethane (1.601 g, 6.76 mmol) in THF (25 mL) was added dropwise and the resulting mixture was stirred at −78° C. for another 2 hours. The reaction was quenched with saturated NH$_4$Cl solution (100 mL) and extracted with EA twice. The combined organic layers were then concentrated and purified by column chromatography on silica gel (PE:EA=1:1) to give the title compound D126 (492 g, 1.753 mmol, 38.9% yield) as yellow oil.

LCMS: 281 [M+H]$^+$. $t_R$=1.526 mins. (LCMS condition 1)

$^1$H NMR (400 MHz, CHLOROFORM-d): δ 8.21 (s, 1H), 5.68-6.16 (m, 1H), 5.04-5.22 (m, 1H), 3.20-3.35 (m, 1H), 2.85-3.10 (m, 5H), 2.19-2.56 (m, 2H).

Description D127

(R)-1-(1-(2,2-difluoroethyl)pyrrolidin-3-yl)-5-methyl-4-nitro-1H-pyrazole (D127)

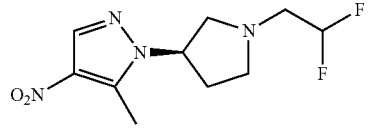

A solution of D126 (265 g, 0.944 mmol), methylboronic acid (0.329 mL, 4.72 mmol), Na$_2$CO$_3$ (300 g, 2.83 mmol) and PdCl$_2$(dppf)-CH$_2$Cl$_2$ adduct (77 g, 0.094 mmol) in 1,4-dioxane (10 mL) and water (1 mL) was stirred under nitrogen at 120° C. for 24 hours. The solution was diluted with EA and washed with water. The organic layer was dried and concentrated. The crude was purified by column chromatography on silica gel (PE:EA=1:1) to give the title compound D127 (223 g, 0.591 mmol, 62.6% yield) as yellow oil.

LCMS: 261 [M+H]$^+$. $t_R$=1.500 mins. (LCMS condition 1)

Description D128

(R)-1-(1-(2,2-difluoroethyl)pyrrolidin-3-yl)-5-methyl-1H-pyrazol-4-amine (D128)

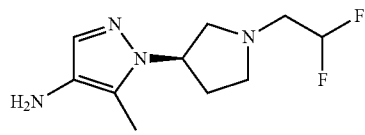 [SMILES: Cc1c([N+](=O)[O-])cnn1[C@@H]1CCN(CC(F)F)C1]

A solution of D127 (223 g, 0.591 mmol) and Pd/C (6.29 g, 0.059 mmol) in methanol (20 mL) was stirred under hydrogen for 2 hours at room temperature. The mixture was filtered and the solution was evaporated to give the crude product D128 (186.2 g, 0.518 mmol, 88% yield) as yellow oil.

LCMS: 231 [M+H]$^+$. $t_R$=2.390 mins. (LCMS condition 1)

Description D129

3-(4-((4-ethoxy-7-tosyl-7H-pyrrolo[2,3-d]pyrimidin-2-yl)amino)-5-methyl-1H-pyrazol-1-yl)cyclobutanol (D129)

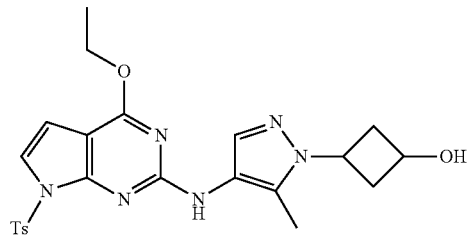 [SMILES: CCOc1nc(Nc2cnn(C3CC(O)C3)c2C)nc2c1ccn2S(=O)(=O)c1ccc(C)cc1]

A solution of D2 (315 g, 0.895 mmol), D62 (180 g, 1.074 mmol), K$_2$CO$_3$ (371 mg, 2.69 mmol), X-phos (64.0 g, 0.134 mmol) and PdCl$_2$(dppf)-CH$_2$Cl$_2$ adduct (73.1 g, 0.090 mmol) in 1,4-dioxane (0.8 mL) and water (0.2 mL) was stirred overnight at 90° C. The mixture was concentrated and purified by column chromatography on silica gel (PE:EA=1:1) to give the title compound D129 (311 g, 0.580 mmol, 64.8% yield) as yellow oil.

LCMS: 483 [M+H]$^+$. $t_R$=1.48 mins. (LCMS condition 2)

Description D130

3-(4-((4-ethoxy-7-tosyl-7H-pyrrolo[2,3-d]pyrimidin-2-yl)amino)-5-methyl-1H-pyrazol-1-yl)cyclobutyl methanesulfonate (D130)

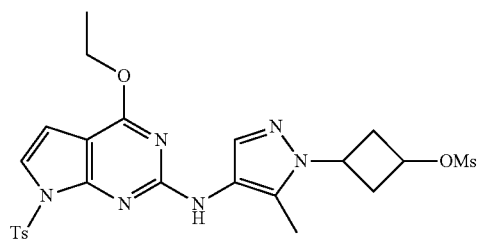 [SMILES: CCOc1nc(Nc2cnn(C3CC(OS(C)(=O)=O)C3)c2C)nc2c1ccn2S(=O)(=O)c1ccc(C)cc1]

To a solution of D129 (311 g, 0.644 mmol) in methanol (20 mL) was added DIPEA (0.113 mL, 0.644 mmol) and MsCl (0.050 mL, 0.644 mmol). The mixture was filtered with diatomit, the filtrate was concentrated to give the title compound D130 (360 g, 0.424 mmol, 65.8% yield) as a yellow solid.

LCMS: 561 [M+H]$^+$. $t_R$=1.568 mins. (LCMS condition 2)

Description D131

4-ethoxy-N-(5-methyl-1-(3-morpholinocyclobutyl)-1H-pyrazol-4-yl)-7-tosyl-7H-pyrrolo[2,3-d]pyrimidin-2-amine (D131)

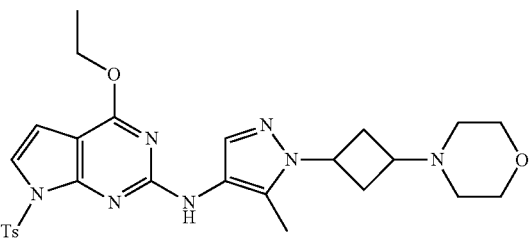 [SMILES: CCOc1nc(Nc2cnn(C3CC(N4CCOCC4)C3)c2C)nc2c1ccn2S(=O)(=O)c1ccc(C)cc1]

To a solution of D130 (360 g, 0.642 mmol) in acetonitrile (12 mL) was added morpholine (0.839 mL, 9.63 mmol). The mixture was stirred at 100° C. for 4 hours under microwave and then directly purified by column chromatography on silica gel by using EA to give the title compound D131 (200 g, 0.337 mmol, 52.5% yield) as yellow oil.

LCMS: 552 [M+H]$^+$. $t_R$=1.549 mins. (LCMS condition 2)

Description D132

(S)-tert-butyl 3-(4-nitro-1H-pyrazol-1-yl)pyrrolidine-1-carboxylate (D132)

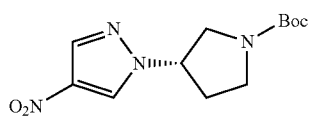 [SMILES: CC(C)(C)OC(=O)N1CC[C@H](n2cc([N+](=O)[O-])cn2)C1]

To a solution of 4-nitro-1H-pyrazole (1 g, 8.84 mmol), triphenylphosphine (2.78 g, 10.61 mmol) and (R)-tert-butyl 3-hydroxypyrrolidine-1-carboxylate (1.656 g, 8.84 mmol) in THF (50 mL) was added dropwise DIAD (2.264 mL, 11.50 mmol) at 0° C. under nitrogen. The mixture was then slowly warmed to room temperature and stirred overnight. Solvent was evaporated and the crude product was directly purified by column chromatography on silica gel (PE:EA=2:1) to give the title compound D132 (2.23 g, 7.90 mmol, 89% yield) as yellow oil.

LCMS: 227 [M-t-Bu+H]$^+$. $t_R$=2.295 mins. (LCMS condition 1)

$^1$H NMR (400 MHz, CHLOROFORM-d): δ 8.20 (s, 1H), 8.10 (s, 1H), 3.50-3.94 (m, 5H), 2.43 (d, J=6.36 Hz, 2H), 1.49 (s, 9H).

Description D133

(S)-4-nitro-1-(pyrrolidin-3-yl)-1H-pyrazole (D133)

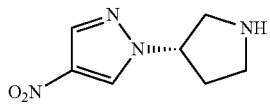 [SMILES: O=[N+]([O-])c1cnn([C@H]2CCNC2)c1]

A solution of D132 (2.23 g, 7.90 mmol) and TFA (12.17 mL, 158 mmol) in DCM (100 mL) was stirred at room temperature for 5 hours. The mixture was diluted with DCM and washed with water. The water layer was then added 2N NaOH solution and extracted with DCM. The combined organic layers were dried over $Na_2SO_4$ and concentrated to give the title compound D133 (1.39 g, 7.63 mmol, 97% yield) as yellow oil.

LCMS: 183 [M+H]$^+$. $t_R$=0.60 mins. (LCMS condition 1)
$^1$H NMR (400 MHz, CHLOROFORM-d): δ 8.26 (s, 1H), 8.08 (s, 1H), 4.99 (dt, J=6.14, 12.41 Hz, 1H), 4.84 (d, J=1.96 Hz, 1H), 3.19-3.45 (m, 3H), 2.89-3.13 (m, 1H), 2.31-2.50 (m, 1H), 2.10-2.27 (m, 1H).

Description D134

(S)-1-(1-(2,2-difluoroethyl)pyrrolidin-3-yl)-4-nitro-1H-pyrazole (D134)

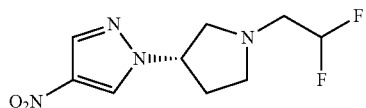

A solution of D133 (1.39 g, 7.63 mmol), 2,2-difluoroethyl4-methylbenzenesulfonate (2.343 g, 9.92 mmol) and $K_2CO_3$ (3.16 g, 22.89 mmol) in DMF (20 mL) was stirred overnight at 90° C. The mixture was diluted with water and extracted with EA. The combined organic layer was dried and concentrated. The crude was purified by column chromatography on silica gel (PE:EA=1:1) to give the title compound D134 (1.54 g, 5.07 mmol, 66.4% yield) as yellow oil.

LCMS: 247 [M+H]$^+$. $t_R$=0.954 mins. (LCMS condition 1)

Description D135

(S)-5-chloro-1-(1-(2,2-difluoroethyl)pyrrolidin-3-yl)-4-nitro-1H-pyrazole (D135)

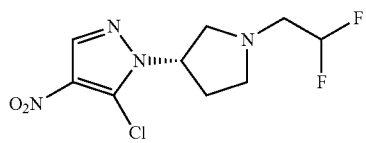 [SMILES: O=[N+]([O-])c1cnn([C@H]2CCN(CC(F)F)C2)c1Cl]

To a solution of D134 (1.64 g, 6.66 mmol) in THF (25 mL) was added LHMDS (1M in THF, 13.32 mL, 13.32 mmol) at −78° C. under nitrogen. After stirring at −78° C. for 30 min, perchloroethane (1.892 g, 7.99 mmol) in THF (25 mL) was added dropwise and the resulting mixture was stirred at −78° C. for another 2 hours. The reaction was quenched with saturated $NH_4Cl$ solution (100 mL) and extracted with EA twice. The combined organic layers were concentrated and purified by column chromatography on silica gel (PE:EA=1:1) to give the title compound D135 (552 g, 1.790 mmol, 26.9% yield) as yellow oil.

LCMS: 281 [M+H]$^+$. $t_R$=1.526 mins. (LCMS condition 1)
$^1$H NMR (400 MHz, CHLOROFORM-d): δ 8.22 (s, 1H), 5.73-6.10 (m, 1H), 5.05-5.17 (m, 1H), 3.28 (t, J=8.80 Hz, 1H), 2.91-3.07 (m, 5H), 2.29-2.49 (m, 2H).

Description D136

(S)-1-(1-(2,2-difluoroethyl)pyrrolidin-3-yl)-5-methyl-4-nitro-1H-pyrazole (D136)

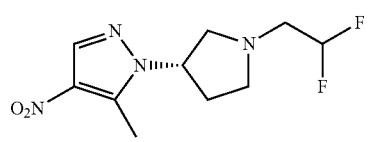 [SMILES: Cc1c([N+](=O)[O-])cnn1[C@H]1CCN(CC(F)F)C1]

A solution of D130 (552 g, 1.967 mmol), methylboronic acid (0.821 mL, 11.80 mmol), $K_2CO_3$ (1087 g, 7.87 mmol) and $PdCl_2$(dppf)-$CH_2Cl_2$ adduct (161 g, 0.197 mmol) in 1,4-dioxane (10 mL) and water (1 mL) was stirred under microwave at 120° C. for 3 hours. Solvent was evaporated and the crude was directly purified via column chromatography on silica gel (PE:EA=1:1) to give the title compound D136 (287 g, 1.079 mmol, 54.8% yield) as yellow oil.

LCMS: 261 [M+H]$^+$. $t_R$=1.436 mins. (LCMS condition 1)
$^1$H NMR (400 MHz, CHLOROFORM-d): δ 8.12 (s, 1H), 5.67-6.15 (m, 1H), 4.82-4.98 (m, 1H), 3.26 (t, J=8.68 Hz, 1H), 2.86-3.08 (m, 5H), 2.69 (s, 3H), 2.19-2.49 (m, 2H).

Description D137

(S)-1-(1-(2,2-difluoroethyl)pyrrolidin-3-yl)-5-methyl-1H-pyrazol-4-amine (D137)

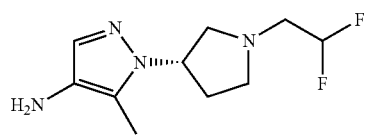

A solution of D136 (287 g, 1.103 mmol) and Pd/C (117 g, 0.110 mmol) in methanol (20 mL) was stirred under hydrogen for 2 hours. The mixture was filtered and the solution was evaporated to give the title compound D137 (176 g, 0.746 mmol, 67.6% yield) as yellow oil.

LCMS: 231 [M+H]$^+$. $t_R$=2.384 mins. (LCMS condition 1)
$^1$H NMR (400 MHz, CHLOROFORM-d): δ 7.20 (s, 1H), 5.66-6.12 (m, 1H), 4.75 (td, J=7.2, 14.61 Hz, 1H), 3.21 (t, J=8.44 Hz, 1H), 2.83-3.06 (m, 5H), 2.67 (br. s., 2H), 2.27-2.41 (m, 2H), 2.19 (s, 3H).

Description D138

2-methyl-2-morpholinopropan-1-ol (D138)

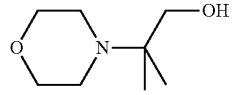

To a solution of ethyl 2-methyl-2-morpholinopropanoate (3.8 g, 18.88 mmol) in THF (30 mL) was added LiAlH$_4$ (2.87 g, 76 mmol) at 0° C. The reaction mixture was stirred overnight at 25° C. The reaction was quenched with water and 10% NaOH solution. The mixture was filtered through a pad of Celite and the pad was washed with THF (10 mL). The combined filtrates were concentrated and purified by column chromatography on silica gel (PE:EA=1:2) to give the title compound D138 (2.5 g, 15.70 mmol, 83% yield).

LCMS: 160 [M+H]$^+$. $t_R$=0.70 mins. (LCMS condition 2)
$^1$H NMR (400 MHz, CHLOROFORM-d): δ 3.72 (m, 4H), 3.33 (s, 2H), 2.55 (m, 4H), 1.03 (s, 6H).

Description D139

2-methyl-2-morpholinopropyl methanesulfonate (D139)

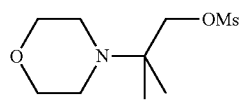

To a solution of D138 (2.2 g, 13.82 mmol) and DIPEA (4.83 mL, 27.6 mmol) in DCM (10 mL) was added methanesulfonyl chloride (1.283 mL, 16.58 mmol) at 0° C. The reaction was stirred at 0° C. for 2 hours. The mixture was quenched with aqueous NaHCO$_3$ and extracted with DCM (20 mL×3). The combined extracts were dried over Na$_2$SO$_4$, filtered and concentrated to give the title compound D139 (3.28 g, 13.82 mmol, 100% yield).

Description D140

4-(2-methyl-1-(4-nitro-1H-pyrazol-1-yl)propan-2-yl) morpholine (D140)

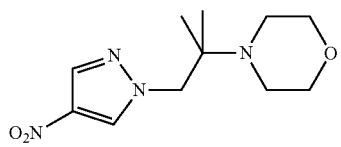 [SMILES: CC(C)(Cn1cc([N+](=O)[O-])cn1)N1CCOCC1]

To a solution of 4-nitro-1H-pyrazole (1.560 g, 13.80 mmol) and D139 (3.27 g, 13.80 mmol) in DMF (10 mL) was added K$_2$CO$_3$ (5.72 g, 41.4 mmol). The reaction was stirred overnight at 90° C. The mixture was quenched with water and extracted with DCM (20 mL×3). The combined extracts were dried over Na$_2$SO$_4$, filtered and concentrated in vacuum. The crude was purified by column chromatography on silica gel (PE:EA=4:1) to give the title compound D140 (1.50 g, 5.90 mmol, 42.7% yield).

LCMS: 255 [M+H]$^+$. $t_R$=1.19 mins. (LCMS condition 2)

Description D141

4-(1-(5-chloro-4-nitro-1H-pyrazol-1-yl)-2-methyl-propan-2-yl)morpholine (D141)

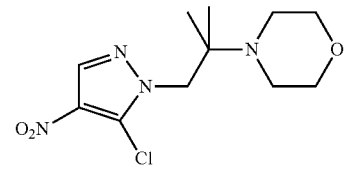 [SMILES: CC(C)(Cn1ncc([N+](=O)[O-])c1Cl)N1CCOCC1]

To a solution of D140 (1.50 g, 5.90 mmol) in THF (100 mL) was added LiHMDS (1M in THF, 23.60 mL, 23.60 mmol) at −78° C. under nitrogen. After stirring at −78° C. for 30 min, perchloroethane (4.19 g, 17.70 mmol) in THF (100 mL) was added and the mixture was stirred for another 2 hours at −78° C. under nitrogen. The reaction was quenched with aq. NH$_4$Cl. The mixture was extracted with EA (100 mL×2), washed with brine, dried with Na$_2$SO$_4$, filtered and concentrated. The crude was purified by column chromatography on silica gel (PE:EA=4:1) to give the title compound D141 (1.1 g, 3.15 mmol, 53.4% yield) as yellow oil.

LCMS: 289 [M+H]$^+$. $t_R$=1.34 mins. (LCMS condition 2)
$^1$H NMR (400 MHz, DMSO-d$_6$): δ 8.18 (s, 1H), 4.17 (s, 2H), 3.70 (m, 4H), 2.66 (m, 4H), 1.11 (s, 6H).

Description D142

4-(2-methyl-1-(5-methyl-4-nitro-1H-pyrazol-1-yl) propan-2-yl)morpholine (D142)

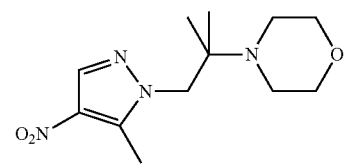

A solution of D141 (1.1 g, 3.81 mmol), methylboronic acid (0.684 g, 11.43 mmol), Na$_2$CO$_3$ (1.211 g, 11.43 mmol) and PdCl$_2$(dppf)-CH$_2$Cl$_2$ adduct (0.311 g, 0.381 mmol) in 1,4-dioxane (3 mL) and water (0.3 mL) was stirred under at 80° C. for 12 hours. Solvent was evaporated and the crude was directly purified via column chromatography on silica gel (PE:EA=4:1) to give the title compound D142 (800 g, 2.83 mmol, 74.3% yield).

LCMS: 269 [M+H]$^+$. $t_R$=1.10 mins. (LCMS condition 2)
$^1$H NMR (400 MHz, CHLOROFORM-d): δ 8.07 (s, 1H), 4.06 (s, 2H), 3.69 (m, 4H), 2.68 (s, 3H), 2.63 (m, 4H), 1.06 (s, 6H).

Description D143

4-(2-methyl-1-(5-methyl-4-nitro-1H-pyrazol-1-yl)propan-2-yl)morpholine (D143)

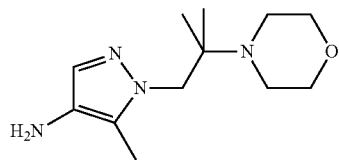 [SMILES: Cc1c([N+](=O)[O-])cnn1CC(C)(C)N1CCOCC1]

A solution of D142 (800 g, 2.98 mmol) and Pd/C (79 g, 0.075 mmol) in methanol (10 mL) was stirred overnight under hydrogen. The mixture was filtered and the solution was evaporated to give the title compound D143 (600 g, 2.439 mmol, 82% yield) as yellow oil.

LCMS: 239 [M+H]$^+$. $t_R$=0.75 mins. (LCMS condition 2)

$^1$H NMR (400 MHz, CHLOROFORM-d): δ 7.15 (s, 1H), 3.94 (s, 2H), 3.71 (m, 4H), 2.63 (m, 6H), 2.19 (s, 3H), 1.03 (s, 6H).

Description D144

1-(2-(3,3-difluoroazetidin-1-yl)ethyl)-5-methyl-4-nitro-1H-pyrazole (D144)

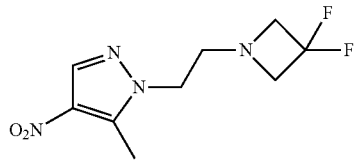 [SMILES: Cc1c([N+](=O)[O-])cnn1CCN1CC(F)(F)C1]

To a solution of D15 (40.2 g, 0.161 mmol) in DMF (8 mL) was added 3,3-difluoroazetidine (10 g, 0.107 mmol) and K$_2$CO$_3$ (44.5 g, 0.322 mmol). The reaction was stirred overnight at 90° C. The mixture was concentrated to give the title compound D144.

Description D145

1-(2-(3,3-difluoroazetidin-1-yl)ethyl)-5-methyl-1H-pyrazol-4-amine (D145)

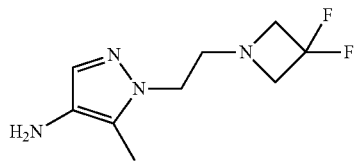

A solution of D144 (20 g, 0.081 mmol) and Pd/C (10 mg, 9.40 µmol) in methanol (20 mL) was stirred overnight under H$_2$ (excess). The mixture was filtered with diatomit and the solution was evaporated to get the title compound D145.

Description D146 ethyl 2-methyl-2-(4-nitro-1H-pyrazol-1-yl)propanoate (D146)

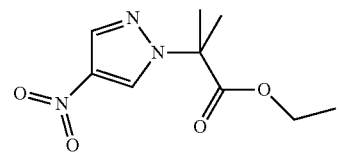 [SMILES: CCOC(=O)C(C)(C)n1cc([N+](=O)[O-])cn1]

A mixture of 4-nitro-1H-pyrazole (10.0 g, 8.85 mmol), ethyl 2-bromo-2-methylpropanoate (20.7 g, 10.6 mmol) and K$_2$CO$_3$ (24.4 g, 177 mmol) in DMF (100 mL) was stirred at 80° C. for 2 hours. The mixture was filtered through a celite pad and the filtrate was concentrated. The residue was diluted with EtOAc (300 mL), then washed with brine (100 mL), dried over Na$_2$SO$_4$, filtered and concentrated in vacuo. The residue was purified by column chromatography on silica gel (PE:EA=15:1 to 8:1) to give the title compound D146 (16.7 g, 83% yield) as yellow oil.

$^1$H NMR (400 MHz, CHLOROFORM-d): δ 8.31 (s, 1H), 8.06 (s, 1H), 4.18 (q, J=7.2 Hz, 2H), 1.86 (s, 6H), 1.20 (t, J=6.9 Hz, 3H).

Description D147

2-methyl-2-(4-nitro-1H-pyrazol-1-yl)propan-1-ol (D147)

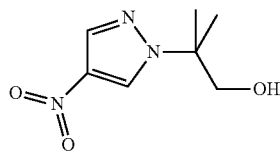

To a solution of D146 (17.0 g, 74.8 mmol) in THF (50 mL) and water (3 mL) was added NaBH$_4$ (5.66 g, 150 mmol) at 0° C. The reaction was stirred at room temperature for 2 hours. The mixture was quenched with aq. NaHCO$_3$ and extracted with DCM (20 mL×3). The combined extracts were dried over Na$_2$SO$_4$, filtered and concentrated in vacuum. The crude was purified by column chromatography on silica gel (DCM:CH$_3$OH=20:1) to give the title compound D147 (10.0 g, 54.0 mmol, 72.2% yield).

LCMS: 186 [M+H]$^+$. $t_R$=1.12 mins. (LCMS condition 2)

$^1$H NMR (300 MHz, DMSO-d$_6$): δ 8.79 (s, 1H), 8.26 (s, 1H), 5.09 (t, J=9.0 Hz, 1H), 3.57 (d, J=9.0 Hz, 2H), 1.48 (s, 6H).

Description D148

2-methyl-2-(4-nitro-1H-pyrazol-1-yl)propyl methanesulfonate (D148)

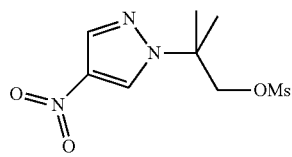 [SMILES: CC(C)(COS(C)(=O)=O)n1cc([N+](=O)[O-])cn1]

To a solution of D147 (5 g, 27.0 mmol) and DIPEA (9.43 mL, 54.0 mmol) in DCM (100 mL) at 0° C. was added a solution of MsCl (2.95 mL, 37.8 mmol) in DCM (10 mL) dropwise. The reaction was stirred at room temperature for 1 hour. Saturated NaHCO$_3$ solution was added and the mixture was extracted with DCM (100 mL×3). The combined organic layers were dried over Na$_2$SO$_4$ and concentrated to give the title compound D148 (6.2 g, 21.90 mmol, 81% yield) as a yellow solid.
LCMS: 264 [M+H]$^+$. t$_R$=1.52 mins. (LCMS condition 2)

Description D149

4-(2-methyl-2-(4-nitro-1H-pyrazol-1-yl)propyl)morpholine (D149)

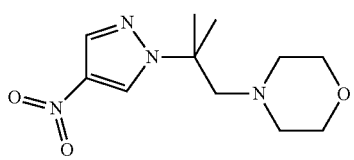 [SMILES: CC(C)(CN1CCOCC1)n1cc([N+](=O)[O-])cn1]

A mixture of D148 (6.2 g, 23.55 mmol) and morpholine (30 mL, 23.55 mmol) was stirred at 135° C. for 7 days. Then water (150 mL) was added and the aqueous phase was extracted with EA (100 mL×2). The combined organic phase was washed with brine (50 mL), dried over Na$_2$SO$_4$ and concentrated. The crude was purified by column chromatography on silica gel (PE:EA=10:1) to give the title compound D149 (3.7 g, 14.55 mmol, 61.8% yield) as a yellow solid.
LCMS: 255 [M+H]$^+$. t$_R$=1.35 mins. (LCMS condition 2)

Description D150

4-(2-methyl-2-(5-methyl-4-nitro-1H-pyrazol-1-yl)propyl)morpholine (D150)

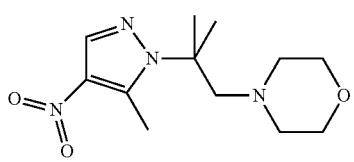 [SMILES: Cc1c([N+](=O)[O-])cnn1C(C)(C)CN1CCOCC1]

To a solution of D149 (1 g, 3.93 mmol) in THF (100 mL) was added LiHMDS (1M in THF) (1.974 g, 11.80 mmol) at −70° C. under nitrogen. After stirring at −70° C. for 30 min, iodomethane (1.675 g, 11.80 mmol) was added and the mixture was stirred for 30 min at −78° C. under nitrogen. The reaction was quenched with aq. NH$_4$Cl. Then the mixture was extracted with EA, washed with brine, dried over Na$_2$SO$_4$, filtered and concentrated. The crude was purified by prep-HPLC to give the title compound D150 (100 g, 0.373 mmol, 9.48% yield) as a white solid.
LCMS: 269 [M+H]$^+$. t$_R$=1.38 mins. (LCMS condition 2)

Description D151

5-methyl-1-(2-methyl-1-morpholinopropan-2-yl)-1H-pyrazol-4-amine (D151)

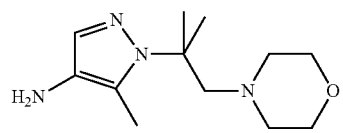 [SMILES: Cc1c(N)cnn1C(C)(C)CN1CCOCC1]

A solution of D150 (100 g, 0.373 mmol) and Pd/C (70 g, 0.658 mmol) in methanol (30 mL) was stirred overnight under hydrogen. The mixture was filtered with diatomit and the solution was evaporated to get the title compound D151 (70 g, 0.294 mmol, 79% yield) as oil.
LCMS: 239 [M+H]$^+$. t$_R$=1.43 mins. (LCMS condition 2)

Description D152

(±)-1-(4-nitro-1H-pyrazol-1-yl)propan-2-ol (D152)

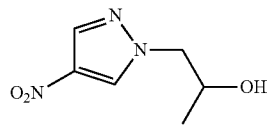

To a solution of 4-nitro-1H-pyrazole (5 g, 44.2 mmol) and 2-methyloxirane (5.14 g, 88 mmol) in DMF (50 mL) was added Cs$_2$CO$_3$ (18.73 g, 57.5 mmol). The reaction was stirred at 80° C. for 15 hours. Water was added (100 mL) and the mixture was extracted with EA. The organic phase was dried over Na$_2$SO$_4$, filtered and concentrated. The crude was purified by column chromatography on silica gel (PE:EA=3:1) to give the title compound D152 (6 g, 23.14 mmol, 52.3% yield) as oil.
LCMS: 172 [M+H]$^+$. t$_R$=0.846 mins. (LCMS condition 2)

Description D153

(±)-1-(4-nitro-1H-pyrazol-1-yl)propan-2-yl methanesulfonate (D153)

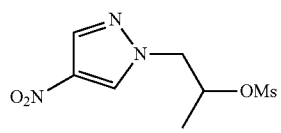 [SMILES: CC(Cn1cc([N+](=O)[O-])cn1)OS(C)(=O)=O]

To a solution of D152 (6 g, 35.1 mmol) and DIPEA (6.12 mL, 35.1 mmol) in THF (50 mL) was added hypochlorous methanesulfonic anhydride (6.30 mL, 35.1 mmol) and the resulting mixture was stirred at 0° C. for 30 min. The reaction was added aq. NaHCO$_3$ (20 mL), extracted with EA. The organic layer was dried over Na$_2$SO$_4$, concentrated to give the title compound D153 (6 g, 17.09 mmol, 48.8% yield) as oil.

LCMS: 250 [M+H]$^+$. t$_R$=1.396 mins. (LCMS condition 2)

Description D154

(±)-4-(1-(4-nitro-1H-pyrazol-1-yl)propan-2-yl)morpholine (D154)

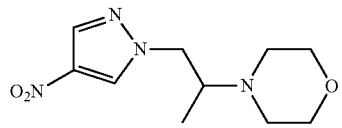 [SMILES: CC(Cn1cc([N+](=O)[O-])cn1)N1CCOCC1]

A solution of D153 (5.8 g, 23.27 mmol), Cs$_2$CO$_3$ (15.16 g, 46.5 mmol) and morpholine (4.05 g, 46.5 mmol) in acetonitrile (200 mL) was stirred overnight at 80° C. The mixture was concentrated and purified by column chromatography on silica gel (PE:EA=1:1) to give the title compound D154 (5.0 g, 16.65 mmol, 71.5% yield) as oil.

LCMS: 241 [M+H]$^+$. t$_R$=1.516 mins. (LCMS condition 2)

Description D155

(±)-4-(1-(5-chloro-4-nitro-1H-pyrazol-1-yl)propan-2-yl)morpholine (D155)

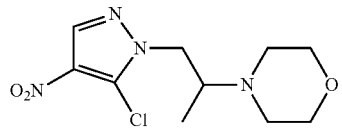 [SMILES: CC(Cn1ncc([N+](=O)[O-])c1Cl)N1CCOCC1]

To a solution of D154 (4 g, 16.65 mmol) in THF (50 mL) was added LiHMDS (1M in THF, 49.9 mL, 49.9 mmol) at −78° C. under nitrogen. After stirring at −78° C. for 30 min, perchloroethane (9.85 g, 41.6 mmol) in THF (50 mL) was added and the mixture was stirred for another 2 hours at −78° C. under nitrogen. The reaction was quenched with aq. NH$_4$Cl. The mixture was extracted with EA (100 mL×2), washed with brine, dried with Na$_2$SO$_4$, filtered and concentrated. The crude was purified by column chromatography on silica gel (PE:EA=4:1) to give the title compound D155 (2.0 g, 5.68 mmol, 34.1% yield) as yellow oil.

LCMS: 275 [M+H]$^+$. t$_R$=1.615 mins. (LCMS condition 2)

Description D156

(±)-4-(1-(5-methyl-4-nitro-1H-pyrazol-1-yl)propan-2-yl)morpholine (D156)

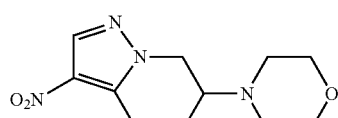

A solution of D155 (1.0 g, 3.64 mmol), methylboronic acid (0.218 g, 3.64 mmol), Na$_2$CO$_3$ (0.386 g, 3.64 mmol) and PdCl$_2$(dppf)-CH$_2$Cl$_2$ adduct (266 g, 0.364 mmol) in 1,4-dioxane (20 mL) and water (2 mL) was stirred under at 70° C. for 6 hours. Solvent was evaporated and the crude was directly purified via column chromatography on silica gel (PE:EA=1:1) to give the title compound D156 (250 g, 0.853 mmol, 23.44% yield) as oil.

LCMS: 255 [M+H]$^+$. t$_R$=1.198 mins. (LCMS condition 2)

Description D157

(±)-5-methyl-1-(2-morpholinopropyl)-1H-pyrazol-4-amine (D157)

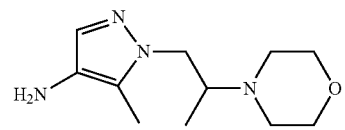

A solution of D156 (250 g, 0.983 mmol) and Pd/C (52.3 g, 0.049 mmol) in methanol (30 mL) was stirred overnight under H$_2$ (excess). The mixture was filtered with diatomit and the solution was evaporated to give the title compound D157 (200 g, 0.731 mmol, 74.4% yield) as oil.

LCMS: 225 [M+H]$^+$. t$_R$=0.86 mins. (LCMS condition 2)

Description D158

(±)-4-ethoxy-N-(5-methyl-1-(2-morpholinopropyl)-1H-pyrazol-4-yl)-7-tosyl-7H-pyrrolo[2,3-d]pyrimidin-2-amine (D158)

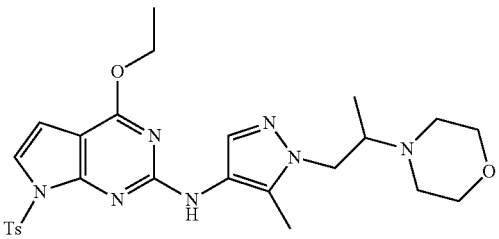 [SMILES: CCOc1nc(Nc2cnn(CC(C)N3CCOCC3)c2C)nc2c1ccn2S(=O)(=O)c1ccc(C)cc1]

A solution of D2 (300 g, 0.853 mmol), D157 (191 g, 0.853 mmol), K$_2$CO$_3$ (236 mg, 1.705 mmol), X-phos (74.0 g, 0.128 mmol) and PdCl$_2$(dppf)-CH$_2$Cl$_2$ adduct (69.6 g, 0.085 mmol) in 1,4-dioxane (8 mL) and water (2 mL) was stirred overnight at 90° C. The mixture was purified by column chromatography on silica gel (PE:EA=1:1) to give the title compound D158 (180 g, 0.260 mmol, 30.5% yield) as a yellow solid.

LCMS: 540 [M+H]$^+$. t$_R$=1.92 mins. (LCMS condition 1)

Description D159

2-(benzyloxy)-5,8-dioxaspiro[3.4]octane (D159)

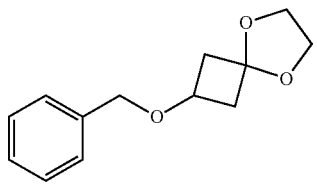 [SMILES: c1ccc(COC2CC3(C2)OCCO3)cc1]

To a solution of 3-(benzyloxy)cyclobutanone (5.000 g, 28.4 mmol) in toluene (100.0 mL) was added ethane-1,2-diol (3.17 mL, 56.7 mmol) and 4-methylbenzenesulfonic acid (0.489 g, 2.84 mmol). The reaction was stirred at 110° C. for 2 hours using Dean-Stark assembly. The mixture was quenched with water and extracted with mix solvent of DCM and MeOH (10:1, 20 mL×3). The combined extracts were dried over $Na_2SO_4$, filtered and concentrated. The crude was purified by column chromatography on silica gel (PE:EA=4:1) to give the title compound D159 (6.0 g, 27.2 mmol, 96% yield).
LCMS: 221 [M+H]$^+$. $t_R$=1.396 mins. (LCMS condition 2)
$^1$H NMR (300 MHz, DMSO-d$_6$): δ 7.33 (m, 5H), 4.35 (s, 2H), 3.88 (m, 1H), 3.78 (m, 4H), 2.48 (m, 2H), 2.19 (m, 2H).

Description D160

5,8-dioxaspiro[3.4]octan-2-ol (D160)

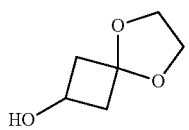

A solution of D159 (2.5 g, 11.35 mmol) and Pd/C (0.302 g, 0.284 mmol) in methanol (50 mL) was stirred overnight under H$_2$ (excess). The suspension was filtered through a pad of Celite and the solution was concentrated to give the title compound D160 (1.25 g, 9.60 mmol, 85% yield) as colorless oil.

Description D161

5,8-dioxaspiro[3.4]octan-2-yl 4-methylbenzenesulfonate (D161)

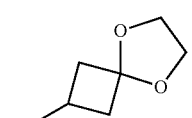

To a solution of D160 (2.5 g, 19.21 mmol) in DCM (10 mL) was added DIPEA (10.07 mL, 57.6 mmol) and 4-methylbenzene-1-sulfonyl chloride (4.39 g, 23.05 mmol) at 0° C. The reaction was stirred at 0° C. for 2 hours. The mixture was quenched with aqueous NaHCO$_3$ and extracted with DCM (20 mL×3). The combined extracts were dried over Na$_2$SO$_4$, filtered and concentrated to give the title compound D161 (5.46 g, 19.21 mmol, 100% yield).

Description D162

4-nitro-1-(5,8-dioxaspiro[3.4]octan-2-yl)-1H-pyrazole (D162)

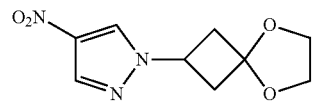

A solution of 4-nitro-1H-pyrazole (2.61 g, 23.05 mmol), K$_2$CO$_3$ (7.96 g, 57.6 mmol) and D161 (5.46 g, 19.21 mmol) in DMF (10 mL) was stirred overnight at 90° C. The reaction was quenched with water and extracted with DCM (20 mL×3). The combined extracts were dried over Na$_2$SO$_4$, filtered and concentrated. The crude was purified by column chromatography on silica gel (DCM: CH$_3$OH=20:1) to give the title compound D162 (2.2 g, 6.62 mmol, 34.4% yield).
LCMS: 226 [M+H]$^+$. $t_R$=1.03 mins. (LCMS condition 2)
$^1$H NMR (400 MHz, CHLOROFORM-d): δ 8.25 (s, 1H), 8.11 (s, 1H), 4.69 (m, 1H), 3.97 (m, 4H), 2.95 (m, 4H).

Description D163

5-chloro-4-nitro-1-(5,8-dioxaspiro[3.4]octan-2-yl)-1H-pyrazole (D163)

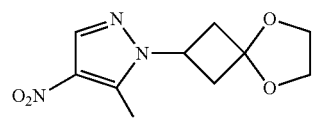

To a solution of D162 (2.2 g, 9.77 mmol) in THF (100 mL) was added LiHMDS (1M in THF, 39.1 mL, 39.1 mmol) at −78° C. under nitrogen. After stirring at −70° C. for 30 min, perchloroethane (6.94 g, 29.3 mmol) in THF (100 mL) was added and the mixture was stirred for another 2 hours at −78° C. under nitrogen. The reaction was quenched with aq. NH$_4$Cl. The mixture was extracted with EA (100 mL×2), washed with brine, dried with Na$_2$SO$_4$, filtered and concentrated. The crude was purified by column chromatography on silica gel (PE:EA=4:1) to give the title compound D163 (1.1 g, 4.09 mmol, 41.9% yield) as yellow oil.
LCMS: 260 [M+H]$^+$. $t_R$=1.17 mins. (LCMS condition 2)
$^1$H NMR (300 MHz, DMSO-d$_6$): δ 8.21 (s, 1H), 4.86 (m, 1H), 3.96 (m, 4H), 3.09 (m, 2H), 2.86 (m, 2H).

Description D164

5-methyl-4-nitro-1-(5,8-dioxaspiro[3.4]octan-2-yl)-1H-pyrazole (D164)

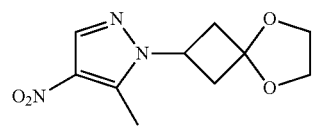

A solution of D163 (1.1 g, 4.24 mmol), methylboronic acid (0.761 g, 12.71 mmol), Na₂CO₃ (1.347 g, 12.71 mmol) and PdCl₂(dppf)-CH₂Cl₂ adduct (0.346 g, 0.424 mmol) in 1,4-dioxane (30 mL) and water (3 mL) was stirred under at 80° C. for 24 hours. Solvent was evaporated and the crude was directly purified via column chromatography on silica gel (PE:EA=4:1) to give the title compound D164 (600 g, 1.933 mmol, 45.6% yield).

LCMS: 240 [M+H]⁺. $t_R$=1.09 mins. (LCMS condition 2)

¹H NMR (400 MHz, CHLOROFORM-d): δ 8.12 (s, 1H), 1.61 (m, 1H), 3.97 (m, 4H), 3.11 (m, 2H), 2.82 (m, 2H), 2.64 (s, 3H).

Description D165

5-methyl-1-(5,8-dioxaspiro[3.4]octan-2-yl)-1H-pyrazol-4-amine (D165)

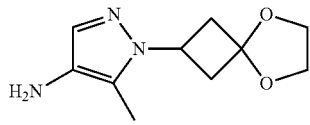 [SMILES: Cc1c([N+](=O)[O-])cnn1C1CC2(C1)OCCO2]

A solution of D164 (600 g, 2.508 mmol) and Pd/C (26.7 g, 0.251 mmol) in methanol (10 mL) was stirred overnight under H₂ (excess). The mixture was filtered with diatomit and the solution was evaporated to get the title compound D165 (350 g, 1.56 mmol, 62.3% yield) as colorless oil.

LCMS: 210 [M+H]⁺. $t_R$=0.91 mins. (LCMS condition 2)

Description D166

4-ethoxy-N-(5-methyl-1-(5,8-dioxaspiro[3.4]octan-2-yl)-1H-pyrazol-4-yl)-7-tosyl-7H-pyrrolo [2,3-d]pyrimidin-2-amine (D166)

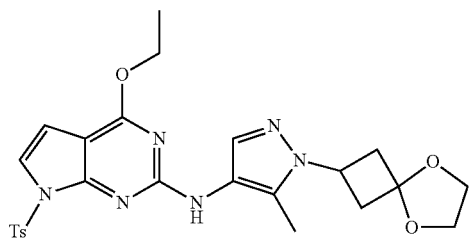 [SMILES: CCOc1nc(Nc2cnn(C3CC4(C3)OCCO4)c2C)nc2c1ccn2S(=O)(=O)c1ccc(C)cc1]

A solution of D2 (500 g, 1.421 mmol), D165 (357 g, 1.705 mmol), K₂CO₃ (589 mg, 4.26 mmol) and Pd₂(dba)₃ (65.1 g, 0.071 mmol) in 2-butanol (2 mL) was irradiated under microwave at 120° C. for 45 min. The mixture was purified by column chromatography on silica gel by using EA and further purified by pre-HPLC to give the title compound D166 (570 g, 1.039 mmol, 73.1% yield) as a white solid.

LCMS: 525 [M+H]⁺. $t_R$=1.429 mins. (LCMS condition 2)

¹H NMR (400 MHz, CHLOROFORM-d): δ 7.77 (s, 1H), 7.70 (s, 1H), 7.20 (m, 3H), 6.43 (s, 1H), 6.24 (s, 1H), 4.65 (m, 1H), 4.43 (dd, J=9.0 Hz, 2H), 3.96 (m, 4H), 3.16 (m, 2H), 2.82 (m, 2H), 2.36 (s, 3H), 2.29 (s, 3H), 1.38 (t, J=9.0 Hz, 3H).

Description D167

3-(4-((4-ethoxy-7-tosyl-7H-pyrrolo[2,3-d]pyrimidin-2-yl)amino)-5-methyl-1H-pyrazol-1-yl)cyclobutanone (D167)

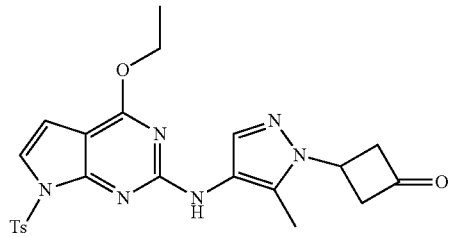 [SMILES: CCOc1nc(Nc2cnn(C3CC(=O)C3)c2C)nc2c1ccn2S(=O)(=O)c1ccc(C)cc1]

To a solution of D166 (550 g, 1.048 mmol) in acetone (10 mL) and water (1 mL) was added 4-methylbenzenesulfonic acid (18.05 g, 0.105 mmol). The reaction was stirred overnight at 55° C. The mixture was poured into water and extracted with DCM (20 mL×3). The combined extracts were dried over Na₂SO₄, filtered and concentrated. The crude was purified by column chromatography on silica gel (PE:EA=4:1) to give the title compound D167 (350 g, 0.553 mmol, 52.8% yield).

LCMS: 481 [M+H]⁺. $t_R$=1.46 mins. (LCMS condition 2)

¹H NMR (400 MHz, CHLOROFORM-d): δ 7.78 (m, 3H), 7.21 (m, 3H), 6.44 (m, 1H), 6.27 (m, 1H), 5.04 (m, 1H), 4.42 (dd, J=9.0 Hz, 2H), 3.96 (m, 2H), 3.56 (m, 2H), 2.36 (s, 6H), 1.39 (t, J=9.0 Hz, 3H).

Description D168

3-(4-((4-ethoxy-7-tosyl-7H-pyrrolo[2,3-d]pyrimidin-2-yl)amino)-5-methyl-1H-pyrazol-1-yl)-1-methylcyclobutanol (D168)

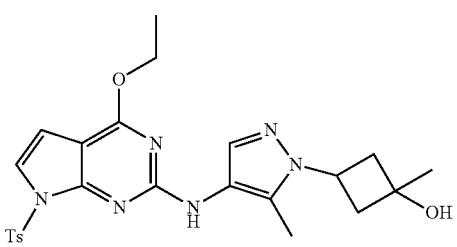 [SMILES: CCOc1nc(Nc2cnn(C3CC(C)(O)C3)c2C)nc2c1ccn2S(=O)(=O)c1ccc(C)cc1]

To a solution of D167 (350 g, 0.728 mmol) in THF (10 mL) was added methylmagnesium bromide (0.607 mL, 1.821 mmol) at 0° C. The reaction was stirred at room temperature for 2 hours. The mixture was quenched with aqueous NaHCO₃ and extracted with DCM (20 mL×3). The combined extracts were dried over Na₂SO₄, filtered and concentrated. The crude was purified by column chromatography on silica gel (DCM:CH₃OH=20:1) to give the title compound D168 (300 g, 0.604 mmol, 83% yield).

LCMS: 497 [M+H]⁺. $t_R$=1.41 mins. (LCMS condition 2)

Description D169

(R)-2-(difluoromethyl)-1-((R)-1-phenylethyl)-1,2-dihydropyridin-4-ol (D169)

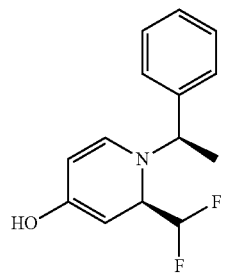 [SMILES: C[C@H](c1ccccc1)N1C=CC(O)=C[C@@H]1C(F)F]

ZnCl$_2$ (20 g) in SOCl$_2$ (10 mL) was kept stirring at 100° C. for 3 hours. Solvent was removed and the residue was redissolved in toluene (10 mL). Then toluene was removed, and dried under reduced pressure, then was kept under N$_2$. A solution of zinc (II) chloride (13.39 g, 98 mmol), (E)-N-(2,2-difluoroethylidene)-1-phenylethanamine (6 g, 32.8 mmol), (E)-((4-methoxybuta-1,3-dien-2-yl)oxy)trimethylsilane (5.64 g, 32.8 mmol) in THF (20 mL) was kept stirring overnight at room temperature. The mixture was poured into water (50 mL) and was extracted with EA (50 mL×3). The organic layer was concentrated and the crude was purified with column chromatography on silica gel (PE:EA=2:1 to 1:1) give the title compound D169 (2.8 g, 11.14 mmol, 34.0% yield).

Description D170

(±)-(2R)-2-(difluoromethyl)-1-((R)-1-phenylethyl)piperidin-4-ol (D170)

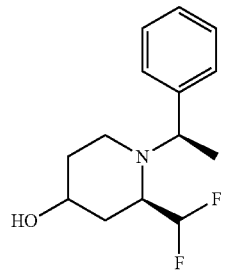 [SMILES: C[C@H](c1ccccc1)N1CCC(O)C[C@@H]1C(F)F]

A solution of NaBH$_4$ (1.518 g, 40.1 mmol) and D169 (2.8 g, 11.14 mmol) in ethanol (30 mL) was kept stirring at reflux for 4 hours. Solvent was removed. The residue was diluted with water (30 mL) and extracted with EA (20 mL×3). The combined organic layers were dried over Na$_2$SO$_4$ and concentrated to give the title compound D170 (2.7 g, 10.58 mmol, 95% yield).

LCMS: 256 [M+H]$^+$. $t_R$=1.41 mins. (LCMS condition 2)

Description D171

(±)-(2R)-2-(difluoromethyl)-1-((R)-1-phenylethyl)piperidin-4-yl methanesulfonate (D171)

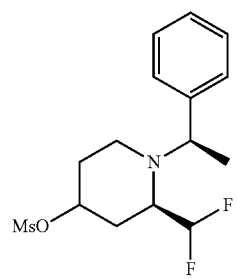 [SMILES: C[C@H](c1ccccc1)N1CCC(OS(C)(=O)=O)C[C@@H]1C(F)F]

To a solution of D170 (1.5 g, 5.88 mmol) and DIPEA (1.026 mL, 5.88 mmol) in THF (30 mL) was added hypochlorous methanesulfonic anhydride (1.057 mL, 5.88 mmol) and the mixture was stirred at 0° C. for 2 hours. The reaction mixture was added aq. NaHCO$_3$ (20 mL), extracted with EA. The organic layer was dried over Na$_2$SO$_4$ and concentrated to give the title compound D171 (1.5 g, 3.82 mmol, 65.1% yield) as oil.

LCMS: 334 [M+H]$^+$. $t_R$=1.524 mins. (LCMS condition 2)

Description D172

(±)-(2R)-2-(difluoromethyl)-4-(4-nitro-1H-pyrazol-1-yl)-1-((R)-1-phenylethyl)piperidine (D172)

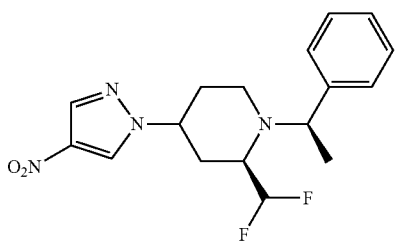 [SMILES: C[C@H](c1ccccc1)N1CCC(n2cc([N+](=O)[O-])cn2)C[C@@H]1C(F)F]

A solution of D171 (1.5 g, 4.50 mmol), Cs$_2$CO$_3$ (2.93 g, 9.00 mmol) and 4-nitro-1H-pyrazole (1.017 g, 9.00 mmol) in acetonitrile (20 mL) was stirred overnight at 80° C. The mixture was concentrated and purified by column chromatography on silica gel (PE:EA=10:1) to give the title compound D172 (600 g, 0.856 mmol, 19.03% yield) as oil.

LCMS: 351 [M+H]$^+$. $t_R$=1.450 mins. (LCMS condition 2)

Description D173 and D174

(2R,4R)-4-(5-chloro-4-nitro-1H-pyrazol-1-yl)-2-(difluoromethyl)-1-((R)-1-phenylethyl) piperidine (D173)

(2R,4S)-4-(5-chloro-4-nitro-1H-pyrazol-1-yl)-2-(difluoromethyl)-1-((R)-1-phenylethyl) piperidine (D174)

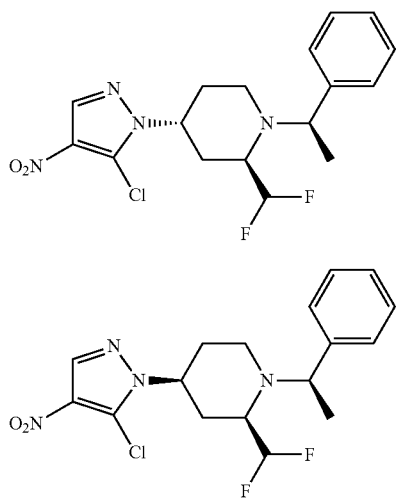

D173

D174

To a solution of D172 (600 g, 1.713 mmol) in THF (50 mL) was added LiHMDS (1M in THF, 5.14 mL, 5.14 mmol) at −78° C. under nitrogen. After stirring at −78° C. for 30 min, perchloroethane (1014 g, 4.28 mmol) in THF (50 mL) was added and the mixture was stirred for another 2 hours at −78° C. under nitrogen. The reaction was quenched with aq. NH$_4$Cl. The mixture was extracted with EA (100 mL×2), washed with brine, dried with Na$_2$SO$_4$, filtered and concentrated. The crude was purified by column chromatography on silica gel (PE:EA=20:1) to give the title compounds D173 (230 g, 0.586 mmol, 34.2% yield) and D174 (230 g, 0.598 mmol, 34.9% yield) as yellow solids.

D173: LCMS: 385 [M+H]$^+$. $t_R$=1.655 mins. (LCMS condition 2)

D174: LCMS: 385 [M+H]$^+$. $t_R$=1.703 mins. (LCMS condition 2)

Description D175

(2R,4R)-2-(difluoromethyl)-4-(5-methyl-4-nitro-1H-pyrazol-1-yl)-1-((R)-1-phenyl ethyl) piperidine (D175)

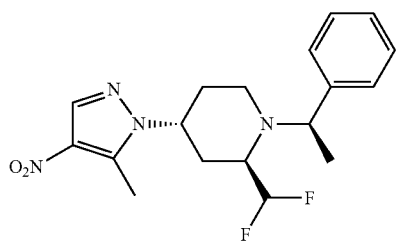 [SMILES: Cc1c([N+](=O)[O-])cnn1[C@@H]1CCN([C@H](C)c2ccccc2)[C@@H](C(F)F)C1]

A solution of D173 (200 g, 0.520 mmol), methylboronic acid (0.780 mL, 1.559 mmol), Na$_2$CO$_3$ (165 g, 1.559 mmol) and PdCl$_2$(dppf)-CH$_2$Cl$_2$ adduct (42.2 g, 0.052 mmol) in 1,4-dioxane (15 mL) and water (1.5 mL) was stirred overnight at 80° C. Solvent was evaporated and the crude was purified via column chromatography on silica gel (PE:EA=3:1) to give the title compound D175 (100 g, 0.198 mmol, 38.0% yield) as a white solid.

LCMS: 365 [M+H]$^+$. $t_R$=1.98 mins. (LCMS condition 1)

Description D176

1-((2R,4R)-2-(difluoromethyl)piperidin-4-yl)-5-methyl-1H-pyrazol-4-amine (D176)

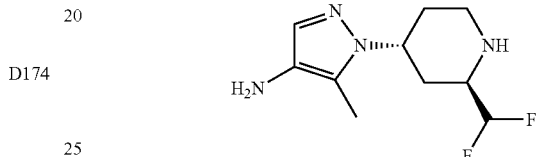

A solution of D175 (100 g, 0.274 mmol) and Pd/C (29.2 g, 0.027 mmol) in methanol (20 mL) was stirred under hydrogen for 2 hours. The mixture was filtered and the filtrate was evaporated to dryness to give the title compound D176 (40 g, 0.174 mmol, 63.3% yield) as yellow oil.

Description D177

(2R,4S)-2-(difluoromethyl)-4-(5-methyl-4-nitro-1H-pyrazol-1-yl)-1-((R)-1-phenylethyl) piperidine (D177)

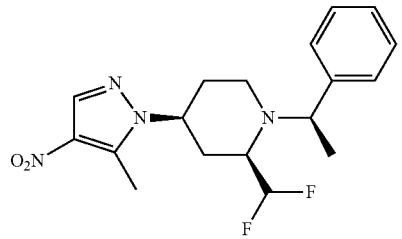 [SMILES: Cc1c([N+](=O)[O-])cnn1[C@H]1CCN([C@H](C)c2ccccc2)[C@@H](C(F)F)C1]

A solution of D174 (230 g, 0.598 mmol), methylboronic acid (0.125 mL, 1.793 mmol), Na$_2$CO$_3$ (190 g, 1.793 mmol) and PdCl$_2$(dppf)-CH$_2$Cl$_2$ adduct (48.8 g, 0.060 mmol) was stirred under microwave at 120° C. for 4 hours. The mixture was diluted with EA and concentrated. The crude was directly purified by column chromatography on silica gel (PE:EA=2:1) to give the title compound D177 (123 g, 0.338 mmol, 56.5% yield) as yellow oil.

LCMS: 365 [M+H]$^+$. $t_R$=2.614 mins. (LCMS condition 2)

Description D178

1-((2R,4S)-2-(difluoromethyl)piperidin-4-yl)-5-methyl-1H-pyrazol-4-amine (D178)

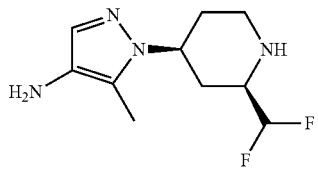 [SMILES: Cc1c(N)cnn1[C@H]1CCN[C@@H](C(F)F)C1]

A solution of D177 (123 g, 0.338 mmol) and Pd/C (35.9 g, 0.034 mmol) in methanol (20 mL) was stirred under hydrogen for 2 hours. The mixture was filtered and the filtrate was evaporated to give the title compound D178 (56 g, 0.243 mmol, 72.1% yield) as yellow oil.

LCMS: 231 [M+H]$^+$. $t_R$=0.244 mins. (LCMS condition 2)

Description D179 ethyl 2-methyl-2-(5-methyl-4-nitro-1H-pyrazol-1-yl)propanoate (D179)

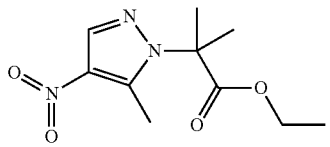 [SMILES: CCOC(=O)C(C)(C)n1ncc([N+](=O)[O-])c1C]

To a solution of ethyl D146 (14.0 g, 61.7 mmol) in THF (200 mL) was added LDA (2.0 M, 62 mL, 123.30 mmol) under −30° C. The mixture was stirred at −30° C. for 30 min. Then MeI (17.5 g, 7.7 mL, 123 mmol) was added and the mixture was stirred at 15° C. for 2 hours. The reaction was quenched with water (200 mL) and the mixture was extracted with EtOAc (300 mL×3). The combined organic layers were washed with brine (100 mL), dried over Na$_2$SO$_4$, filtered and evaporated in vacuo. The residue was purified by column chromatography on silica gel (PE:EA=30:1 to 15:1) to give the title compound D179 (5.0 g, 34% yield) as yellow oil.

LCMS: 242 [M+H]$^+$. $t_R$=1.61 mins. (LCMS condition 3)
$^1$H NMR (300 MHz, CHLOROFORM-d): δ 8.08 (s, 1H), 4.26 (q, J=5.7 Hz, 2H), 2.55 (s, 3H), 1.85 (s, 6H), 1.27 (t, J=5.4 Hz, 3H).

Description D180

2-methyl-2-(5-methyl-4-nitro-1H-pyrazol-1-yl)propanoic acid (D180)

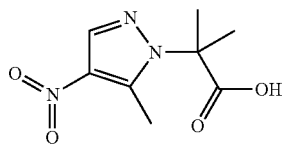

To a solution of D179 (5.00 g, 20.7 mmol) was added dropwise 1N NaOH (4.0 g, 100 mL, 0.104 mol). The reaction was stirred at room temperature for 16 hours and then adjusted to pH~1.0 with 1 N HCl (20 mL), and then extracted with EA (200 mL×3). The combined organic layers were washed with brine (200 mL), dried over Na$_2$SO$_4$, filtered and evaporated in vacuo to give the title compound D180 as a white solid.

LCMS: 212 [M+H]$^+$. $t_R$=1.30 mins. (LCMS condition 3)
$^1$H NMR (300 MHz, CHLOROFORM-d): δ 8.09 (s, 1H), 2.62 (s, 3H), 1.91 (s, 6H).

Description D181

2-methyl-2-(5-methyl-4-nitro-1H-pyrazol-1-yl)propanamide (D181)

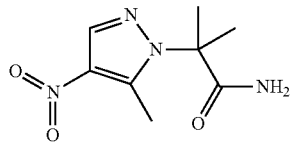

To a solution of D180 (4.10 g, 19.2 mmol) in DCM (100 mL) was added dropwise of oxalyl chloride (4.80 g, 3.7 mL, 38.5 mmol). The reaction was stirred at room temperature for 12 minutes. Then DMF (0.5 mL) was added dropwise and the mixture was stirred at room temperature for 2 hours. Solvent was evaporated, the residue was dissolved in THF (30 mL) and added dropwise into NH$_4$OH (60 mL). The reaction was stirred at room temperature for 1 hour. The solution was concentrated and the residue was portioned between EA (100 mL) and water (100 mL). The aqueous phase was extracted with EA (100 mL×3). The combined organic layers were washed with sat. NH$_4$Cl (100 mL), dried over Na$_2$SO$_4$, filtered and evaporated to give the title compound D181 (3.9 g, 95% yield) as a white solid.

LCMS: 211 [M+H]$^+$. $t_R$=0.52 mins. (LCMS condition 3)
$^1$H NMR (300 MHz, CHLOROFORM-d): δ 8.12 (s, 1H), 5.46 (br. s., 1H), 5.28 (br. s., 1H), 2.64 (s, 3H), 1.85 (s, 6H).

Description D182

2-(4-amino-5-methyl-1H-pyrazol-1-yl)-2-methylpropanamide (D182)

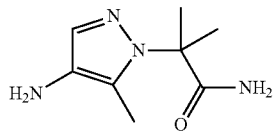

A mixture of D181 and Pd/C (400 mg, 20%) in MeOH (15 mL) was stirred under hydrogen for 2 hours at room temperature. The mixture was filtered and concentrated in vacuo. The residue was purified by column on C18 (ACN/H$_2$O=5:100) to give the title compound D182 (820 mg, 48% yield) as a yellow solid.

LCMS: 183 [M+H]$^+$. $t_R$=0.36 mins. (LCMS condition 3)
$^1$H NMR (300 MHz, CHLOROFORM-d): δ 7.20 (s, 1H), 5.34 (br s, 1H), 5.25 (br s, 1H), 2.73 (br s, 2H), 2.18 (s, 3H), 1.79 (s, 6H).

Description D183

2-(4-((4-ethoxy-7H-pyrrolo[2,3-d]pyrimidin-2-yl)amino)-5-methyl-1H-pyrazol-1-yl)-2-methylpropanamide (D183)

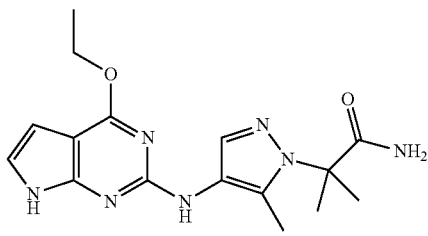 [SMILES: CCOc1nc(Nc2cnn(C(C)(C)C(N)=O)c2C)nc2[nH]ccc12]

A mixture of D182 (660 g, 3.63 mmol), D1 (786 g, 3.99 mmol), X-phos (345 mg, 0.730 mmol), Pd$_2$(dba)$_3$ (327 g, 0.357 mmol) and K$_2$CO$_3$ (1.5 g, 10.88 mmol) in dioxane (50 mL) was stirred at 100° C. for 16 hrs. The reaction mixture was cooled to room temperature and filtered through celite. The filtrate was concentrated and purified by column on C18 (ACN/H$_2$O=40/60) to give the title compound D183 (513 mg, 41% yield) as a yellow solid.

LCMS: 344 [M+H]$^+$. t$_R$=1.63 mins. (LCMS condition 3)

$^1$H NMR (300 MHz, DMSO-d$_6$): 11.16 (br. s., 1H), 8.03 (s, 1H), 7.65 (s, 1H), 7.29 (s, 1H), 7.00 (s, 1H), 6.85-6.87 (m, 1H), 6.19-6.22 (m, 1H), 4.41 (q, J=7.5 Hz, 2H), 2.12 (s, 3H), 1.64 (s, 6H), 1.34 (t, J=7.2 Hz, 3H).

Description D184

(±)-(trans)-3-fluoro-4-(5-methyl-4-nitro-1H-pyrazol-1-yl)-1-(oxetan-3-yl)piperidine (D184)

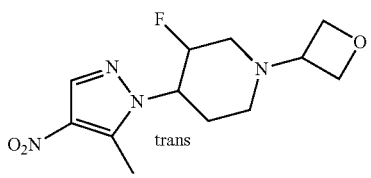 [SMILES: Cc1c([N+](=O)[O-])cnn1C1CCN(C2COC2)CC1F]

To a solution of D105 (1.00 g, 4.38 mmol), oxetan-3-one (785 g, 10.9 mmol) in DCE (40 mL) was added portions NaBH(OAc)$_3$ (2.78 g, 13.1 mmol) at room temperature. The reaction was stirred overnight at room temperature. Aq. Na$_2$CO$_3$ solution (30 mL) was added and the mixture was then extracted with DCM (50 mL×2). The combined organic layers were dried and concentrated. The crude was purified by column chromatography on silica gel (PE:EA=1:1) to give the title compound D184 (1.00 g, 80% yield) as a yellow solid.

LCMS: 285 [M+H]$^+$. t$_R$=1.53 mins. (LCMS condition 3)

$^1$H NMR (300 MHz, CHLOROFORM-d): δ 8.14 (s, 1H), 5.07-4.83 (m, 1H), 4.71-4.58 (m, 4H), 4.17-4.04 (m, 1H), 3.70-3.61 (m, 1H), 3.26-3.18 (m, 1H), 2.90-2.84 (m, 1H), 2.67 (s, 3H), 2.52-2.44 (m, 1H), 2.14-1.93 (m, 3H).

Description D185

(±)-(trans)-1-(3-fluoro-1-(oxetan-3-yl)piperidin-4-yl)-5-methyl-1H-pyrazol-4-amine (D185)

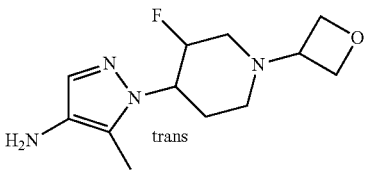

A solution of D184 (500 g, 1.76 mmol) and Pd/C (160 mg, 10%) in MeOH (20 mL) was stirred at 30° C. under H$_2$ for 2 hrs. The mixture was filtered and the filtrate was concentrated. The crude was purified by column (DCM:MeOH=15:1) to give the title compound D185 (420 mg, 94% yield) as a white solid.

LCMS: 255 [M+H]$^+$. t$_R$=1.32 mins. (LCMS condition 3)

$^1$H NMR (300 MHz, CHLOROFORM-d): δ 7.23 (s, 1H), 5.07-4.83 (m, 1H), 4.69-4.61 (m, 4H), 4.01-3.89 (m, 1H), 3.67-3.60 (m, 1H), 3.49 (s, 1H), 3.21-3.13 (m, 1H), 2.85-2.79 (m, 1H), 2.48-2.34 (m, 1H), 2.18 (s, 3H), 2.07-1.90 (m, 3H).

Description D186

(S)-tert-butyl 2-(hydroxymethyl)morpholine-4-carboxylate (D186)

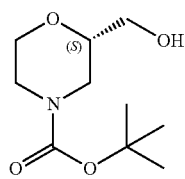

To a solution of (S)-4-(tert-butoxycarbonyl)morpholine-2-carboxylic acid (2.50 g, 10.8 mmol) in THF (25 mL) was added dropwise borane (1 M, 20 mL) at 0° C. over 15 min. After addition, the reaction mixture was warmed to room temperature and stirred for 2 hrs. The reaction was quenched with MeOH/AcOH (9:1, 10 mL) at 0° C. The mixture was then concentrated and the residue was poured into 35 mL of water and 35 mL of EtOAc. The organic layer was washed with saturated Na$_2$CO$_3$ (30 mL) aqueous solution, dried over Na$_2$SO$_4$ and concentrated to give the title compound D186 (2.6 g, 100%) as colorless oil.

LCMS: 118 [M−100+H]$^+$. t$_R$=1.96 mins. (LCMS condition 3)

$^1$H NMR (300 MHz, CHLOROFORM-d): δ 3.84-3.91 (m, 3H), 3.49-3.68 (m, 4H), 2.70-2.97 (m, 2H), 2.03 (t, 1H), 1.45 (s, 9H);

Description D187

(S)-morpholin-2-ylmethanol TFA salt (D187)

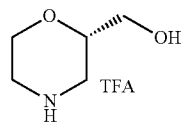

To a solution of D186 (2.6 g, 12 mmol) in DCM (25 mL) was added TFA (10 mL, 132 mmol). After stirred at room temperature for 2 days, the mixture was concentrated to give the title compound D187 (5.0 g, 100%) as yellow oil.

LCMS: 118 [M+H]$^+$. $t_R$=1.75 mins. (LCMS condition 3)

Description D188

(S)-benzyl 2-(hydroxymethyl)morpholine-4-carboxylate (D188)

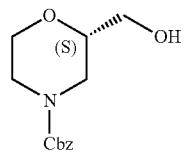

To a solution of D187 (700 g, 5.98 mmol), Na$_2$CO$_3$ (1.27 g, 12.0 mmol) in dioxane (12 mL) and H$_2$O (5 mL) was added CbzCl (1.53 g, 9.00 mmol). After stirred at room temperature for 2 hrs, the reaction mixture was poured into 200 mL of water and extracted with DCM (30 mL×3). The organic layer dried over Na$_2$SO$_4$ and concentrated. The crude was purified by column on C18 (ACN/H$_2$O=40%-60%) to give the title compound D188 (870 mg, 58%) as colorless oil.

LCMS: 252 [M+H]$^+$. $t_R$=2.73 mins. (LCMS condition 3)
$^1$H NMR (300 MHz, CHLOROFORM-d): δ 7.31-7.39 (m, 5H), 5.14 (s, 2H), 3.92-3.99 (m, 3H), 3.50-3.67 (m, 4H), 2.81-3.03 (m, 2H), 2.02 (t, J=6.3 Hz, 1H).

Description D189

(S)-benzyl 2-formylmorpholine-4-carboxylate (D189)

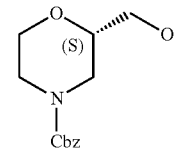

To a dry 100 mL of bottle was added (COCl)$_2$ and dry DCM (25 mL). After the solution was cooled to −78° C., DMSO (2.16 g, 27.7 mmol) in dry DCM (1.0 mL) was added dropwise. The reaction was stirred at −78° C. for 1 hour and a solution of D188 (870 g, 3.46 mmol) in DCM (1.0 mL) was added slowly. The mixture was stirred at −78° C. for 30 min and TEA (4.20 g, 41.5 mmol) was added. Then the reaction mixture was stirred at −78° C. for 30 min and 0° C. for 30 min. The mixture was diluted with DCM (100 mL), washed with water (30 mL), HCl (1 N, 30 mL), saturated NaHCO$_3$ (30 mL) and brine (30 mL), then dried over Na$_2$SO$_4$ and concentrated to give the title compound D189 (1.0 g, 100%) as colorless oil.

LCMS: 250 [M+H]$^+$. $t_R$=2.09 mins. (LCMS condition 3)
$^1$H NMR (300 MHz, DMSO-d$_6$): 9.57 (s, 1H), 7.30-7.38 (m, 5H), 5.75 (s, 1H), 5.10 (s, 2H), 3.55-4.15 (m, 4H), 3.13-3.43 (m, 2H), 2.73-2.92 (m, 1H)

Description D190

(S)-benzyl 2-(difluoromethyl)morpholine-4-carboxylate (D190)

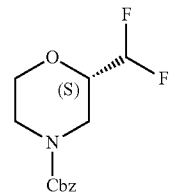

To a solution of D189 (1.0 g, 4.0 mmol) in DCM (15 mL) was added drop wise DAST (1.3 g, in 3 mL of DCM) at −78° C. under nitrogen. After stirred overnight at room temperature, the reaction mixture was cooled to 0° C. and 30 mL of saturated NaHCO$_3$ was added. The mixture was extracted with DCM (50 mL×2). The combined organic layer were washed with water (30 mL), dried over Na$_2$SO$_4$ and concentrated. The crude was purified by column chromatography on silica gel (PE:EA=1:20-1:15-1:10) to give the title compound D190 (240 mg, 25%).

LCMS: 138 [M−Cbz]$^+$. $t_R$=2.21 mins. (LCMS condition 3)
$^1$H NMR (300 MHz, DMSO-d$_6$): 7.32-7.38 (s, 5H), 5.72 (td, J=54.9, 3.9 Hz, 1H), 5.16 (s, 2H), 3.91-4.13 (m, 3H), 3.52-3.63 (m, 2H), 2.98-3.05 (m, 2H);

Description D191

(S)-2-(difluoromethyl)morpholine hydrochloride (D191)

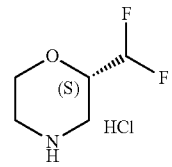

A solution of D190 (240 g, 0.88 mmol) and Pd/C (10%, 50 mg) in MeOH (20 mL) was stirred under H$_2$ at 40° C. for 16 hrs. The mixture was filtered and 3 drops of Conc. HCl was added, then the mixture was concentrated to give the title compound D191 (170 mg, 100%) as colorless oil.

LCMS: 138 [M+H]$^+$. $t_R$=1.93 mins. (LCMS condition 3)
$^1$H NMR (300 MHz, D$_2$O): 5.96 (td, J=53.4, 3.0 Hz, 1H), 4.11-4.22 (m, 2H), 3.84-3.93 (m, 1H), 3.13-3.49 (m. 4H).

Description D192

(S)—N-(1-(2-(2-(difluoromethyl)morpholino)ethyl)-5-methyl-1H-pyrazol-4-yl)-4-ethoxy-7-tosyl-7H-pyrrolo[2,3-d]pyrimidin-2-amine (D192)

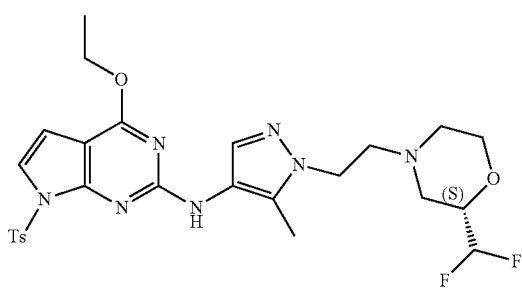

To a solution of D191 (170 g, 0.979 mmol), D80 (427 g, 0.800 mmol) in dioxane (10 mL) was added $K_2CO_3$ (550 g, 4 mmol) and $H_2O$ (3 drops). After stirred at 115° C. for 30 hrs, the reaction mixture was cooled to room temperature and concentrated. The residue was poured into 100 mL of water and extracted with EA (40 mL×3). The organic phase was dried over $Na_2SO_4$, concentrated and purified by column chromatography on silica gel (PE:EA=5:1-2:1-1:1) to give the title compound D192 (150 mg, 21%) as brown oil.

LCMS: 576 [M+H]$^+$. $t_R$=2.63 mins. (LCMS condition 3)

$^1$H NMR (300 MHz, DMSO-d$_6$): 8.66 (s, 1H), 7.65-7.79 (m, 2H), 7.65 (s, 1H), 7.25-7.30 (m, 3H), 6.51 (d, J=3.9 Hz, 1H), 5.97 (td, J=55.2, 3.9 Hz, 1H), 4.37-4.46 (m, 2H), 4.18-4.21 (m, 2H), 3.83 (d, J=10.8 Hz, 1H), 3.60-3.64 (m, 1H), 3.44-3.51 (m, 1H), 2.73-2.85 (m, 4H), 2.33 (s, 3H), 2.25 (s, 3H), 2.01-2.18 (m, 2H), 1.32 (t, J=6.9 Hz, 3H).

Description D193

(R)-tert-butyl 2-(hydroxymethyl)morpholine-4-carboxylate (D193)

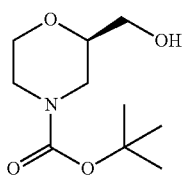

The title compound D193 (2.50 g, 83% yield) was prepared as colorless oil by a procedure similar to that described for D186 starting from (R)-4-(tert-butoxycarbonyl)morpholine-2-carboxylic acid (3.30 g, 14.3 mmol).

LCMS: 218 [M+H]$^+$. $t_R$=1.96 mins. (LCMS condition 3)

$^1$H NMR (300 MHz, CHLOROFORM-d): δ 3.84-3.91 (m, 3H), 3.49-3.68 (m, 4H), 2.70-2.97 (m, 2H), 2.03 (s, 1H), 1.45 (s, 9H);

Description D194

(R)-morpholin-2-ylmethanol TFA salt (D194)

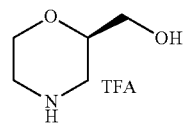

The title compound D194 (700 mg, 100% yield) was prepared as colorless oil by a procedure similar to that described for D187 starting from D193 (1.30 g, 5.99 mmol).

LCMS: 118 [M+H]$^+$. $t_R$=1.75 mins. (LCMS condition 3)

Description D195

(R)-benzyl 2-(hydroxymethyl)morpholine-4-carboxylate (D195)

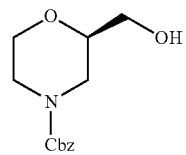 [SMILES: O=C(OCc1ccccc1)N1CCO[C@@H](CO)C1]

The title compound D195 (970 mg, 65% yield) was prepared as colorless oil by a procedure similar to that described for D188 starting from D194 (700 g, 5.98 mmol).

LCMS: 252 [M+H]$^+$. $t_R$=2.73 mins. (LCMS condition 3)

$^1$H NMR (300 MHz, DMSO-d$_6$): 7.30-7.41 (m, 5H), 5.09 (s, 2H), 4.78-4.81 (m, 1H), 3.76-3.95 (m, 3H), 3.31-3.43 (m, 4H), 2.62-2.93 (m, 2H);

Description D196

(R)-benzyl 2-formylmorpholine-4-carboxylate (D196)

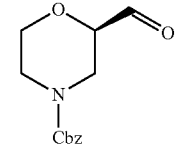 [SMILES: O=C[C@H]1CN(C(=O)OCc2ccccc2)CCO1]

The title compound D196 (800 mg, 100% yield) was prepared as colorless oil by a procedure similar to that described for D189 starting from D195 (820 g, 3.27 mmol).

LCMS: 250 [M+H]$^+$. $t_R$=2.09 mins. (LCMS condition 3)

$^1$H NMR (300 MHz, DMSO-d$_6$): 9.57 (s, 1H), 7.30-7.38 (m, 5H), 5.10 (s, 2H), 3.14-4.15 (m, 7H).

Description D197

(R)-benzyl 2-(difluoromethyl)morpholine-4-carboxylate (D197)

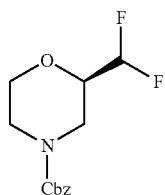 [SMILES: O=C(OCc1ccccc1)N1CCO[C@@H](C(F)F)C1]

The title compound D197 (340 mg, 39% yield) was prepared by a procedure similar to that described for D190 starting from D196 (800 g, 3.21 mmol).

LCMS: 272 [M+H]$^+$. $t_R$=2.20 mins. (LCMS condition 3)
$^1$H NMR (300 MHz, DMSO-d$_6$): 7.32-7.38 (s, 5H), 6.08 (td, J=54.9, 3.9 Hz, 1H), 5.11 (s, 2H), 3.72-3.93 (m, 4H), 3.45-3.54 (m, 1H), 2.95-3.02 (m, 2H).

Description D198

(R)-2-(difluoromethyl)morpholine hydrochloride (D198)

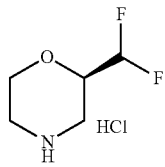

The title compound D198 (120 mg, 55% yield) was prepared as colorless oil by a procedure similar to that described for D191 starting from D197 (340 g, 1.25 mmol).

$^1$H NMR (300 MHz, DMSO-d$_6$): 9.94 (br s, 1H), 9.74 (br s, 1H), 6.14 (td, J=53.1, 3.3 Hz, 1H), 3.81-4.18 (m, 4H), 3.18-3.26 (m, 2H), 2.92-2.98 (m. 2H).

Description D199

(R)—N-(1-(2-(2-(difluoromethyl)morpholino)ethyl)-5-methyl-1H-pyrazol-4-yl)-4-ethoxy-7-tosyl-7H-pyrrolo[2,3-d]pyrimidin-2-amine (D199)

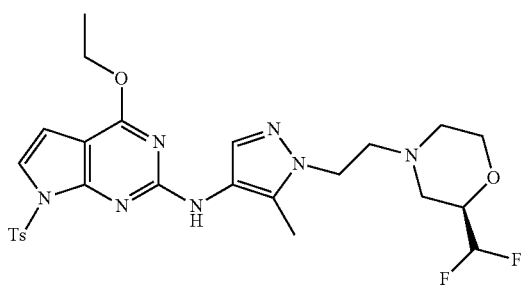 [SMILES: CCOc1nc(Nc2cnn(CCN3CCO[C@@H](C(F)F)C3)c2C)nc2c1ccn2S(=O)(=O)c1ccc(C)cc1]

The title compound D199 (125 mg, 31% yield) was prepared as a white solid by a procedure similar to that described for D192 starting from D198 (120 g, 0.667 mmol).

LCMS: 576 [M+H]$^+$. $t_R$=2.06 mins. (LCMS condition 3)
$^1$H NMR (300 MHz, DMSO-d$_6$): 8.66 (s, 1H), 7.65-7.79 (m, 2H), 7.65 (s, 1H), 7.25-7.30 (m, 3H), 6.51 (d, J=3.9 Hz, 1H), 5.97 (td, J=55.2, 3.9 Hz, 1H), 4.37-4.46 (m, 2H), 4.18-4.21 (m, 2H), 3.83 (d, J=10.8 Hz, 1H), 3.60-3.64 (m, 1H), 3.44-3.51 (m, 1H), 2.73-2.85 (m, 4H), 2.33 (s, 3H), 2.25 (s, 3H), 2.01-2.18 (m, 2H), 1.32 (t, J=6.9 Hz, 3H).

Description D200

(±)-3-(4-amino-5-chloro-1H-pyrazol-1-yl)cyclopentanol (D200)

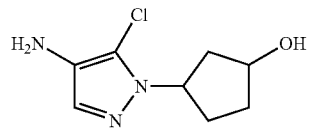 [SMILES: Nc1cnn(C2CCC(O)C2)c1Cl]

A mixture of D67 (400 g, 1.727 mmol), ammonium chloride (462 g, 8.63 mmol) and iron (482 g, 8.63 mmol) in water (10 mL) and ethanol (10 mL) was stirred at 80° C. for 1 hour. The mixture was filtered and the filtrate was concentrated. The crude was purified by reversed chromatography on C18 (CH$_3$CN/H$_2$O, 0.1% TFA) to give the title compound D200 (412 g, 0.959 mmol, 55.5% yield) as a yellow solid.

LCMS: 202 [M+H]$^+$. $t_R$=0.36 mins. (LCMS condition 1)

Description D201

(±)-cis-tert-butyl 3-fluoro-4-(4-nitro-1H-pyrazol-1-yl)piperidine-1-carboxylate (D201)

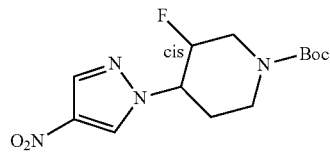 [SMILES: CC(C)(C)OC(=O)N1CCC(n2cc([N+](=O)[O-])cn2)C(F)C1]

To a solution of trans-tert-butyl 3-fluoro-4-hydroxypiperidine-1-carboxylate (2.0 g, 9.1 mmol), 4-nitro-1H-pyrazole (1.03 g, 9.11 mmol), PPh$_3$ (3.57 g, 13.6 mmol) in THF (50 mL) was added slowly DIAD (2.75 g, 13.6 mmol) at 0° C. The mixture was stirred overnight at room temperature. Solvent was evaporated and the residue was dissolved in DCM (30 mL) and n-hexane (60 mL) was added. The suspension was stirred vigorously for 1 h and then filtered. The filtrate was concentrated and the crude was purified by column chromatography on C18 (ACN:H$_2$O=4:1-1:1) to give the title compound D201 as yellow oil (2.4 g, 86% yield).

LCMS: 314 [M+H]$^+$. $t_R$=1.93 mins. (LCMS condition 3)
$^1$H NMR (300 MHz, CHLOROFORM-d): δ 8.25 (s, 1H), 8.10 (s, 1H), 5.03-4.86 (m, 1H), 4.55-4.39 (m, 3H), 3.13-2.85 (m, 2H), 2.38-2.24 (m, 1H), 2.08-2.00 (m, 1H), 1.48 (s, 9H).

Description D202

(±)-cis-tert-butyl 4-(5-chloro-4-nitro-1H-pyrazol-1-yl)-3-fluoropiperidine-1-carboxylate (D202)

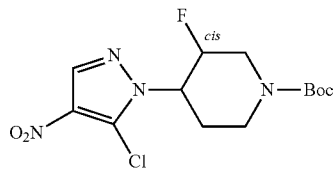 [SMILES: CC(C)(C)OC(=O)N1CCC(n2ncc([N+](=O)[O-])c2Cl)C(F)C1]

To a solution of DIPEA (0.98 g, 9.7 mmol) in THF (15 mL) was added n-BuLi (3.9 mL, 9.7 mmol) at −78° C. under $N_2$ atmosphere. The reaction mixture was stirred at this temperature for 30 min and then at 0° C. for 30 min. To a solution of D201 (1.7 g, 5.40 mmol) in THF (20 mL) was added above LDA solution at −78° C. The reaction mixture was stirred at this temperature for 1.5 h and perchloroethane (2.30 g, 9.72 mmol) was added. The reaction mixture was stirred at −78° C. for 30 min and then allowed warm to room temperature for 1 hour. $NH_4Cl$ aq. (40 mL) was added and the solution was extracted with EtOAc (50 mL×2). The organic layer was dried and concentrated. The crude was purified by chromatography on silica gel (PE:EA=8:1) to give the title compound D202 (640 mg, 36% yield) as a white solid.

$^1$H NMR (300 MHz, CHLOROFORM-d): δ 8.22 (s, 1H), 4.94-4.74 (m, 1H), 4.68-4.33 (m, 3H), 3.26-2.97 (m, 2H), 2.84-2.71 (m, 1H), 1.96-1.88 (m, 1H), 1.48 (s, 9H).

Description D203

(±)-cis-tert-butyl 3-fluoro-4-(5-methyl-4-nitro-1H-pyrazol-1-yl)piperidine-1-carboxylate (D203)

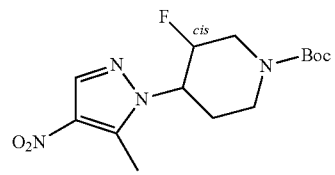 [SMILES: Cc1c([N+](=O)[O-])cnn1C1CCN(C(=O)OC(C)(C)C)CC1F]

A solution of D202 (640 g, 1.86 mmol), 2,4,6-trimethyl-cyclotriboroxane (224 mg, 1.77 mmol), Pd(dppf)Cl$_2$ (310 g, 0.37 mmol), Na$_2$CO$_3$ (297 g, 2.80 mmol) and KOAc (224 g, 2.80 mmol) in H$_2$O (2.8 mL) and acetonitrile (15 mL) was irradiated under microwave at 130° C. for 1.5 hours. The mixture was cooled to room temperature and filtered through a celite pad. The solution was concentrated and the crude was purified by column chromatography on silica gel (PE:EA=5:1) to give the title compound D203 (710 mg, 60% yield) as a yellow solid.

LCMS: 229 [M+H-100]$^+$. $t_R$=1.53 mins. (LCMS condition 3)

$^1$H NMR (300 MHz, CHLOROFORM-d): δ 8.11 (s, 1H), 4.84-4.69 (m, 1H), 4.52-4.26 (m, 3H), 3.33-3.10 (m, 2H), 2.77-2.64 (m, 1H), 2.71 (s, 3H), 1.99-1.92 (m, 1H), 1.47 (s, 9H).

Description D204

(±)-cis-3-fluoro-4-(5-methyl-4-nitro-1H-pyrazol-1-yl)piperidine (D204)

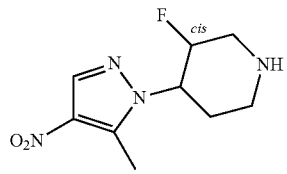 [SMILES: Cc1c([N+](=O)[O-])cnn1C1CCNCC1F]

To a solution of D203 (710 g, 2.16 mmol) in MeOH (7 mL) was added HCl/dioxane (5.7 M, 10 mL). The reaction was stirred at room temperature for 2 hrs. Solvent was removed, and the residue was dissolved in Na$_2$CO$_3$ aqueous solution (20 mL) and extracted with DCM/MeOH (10:1, 20 mL×5). The combined organic layers were dried and concentrated to give the title compound D204 (500 mg, 100% yield) as a yellow solid.

LCMS: 229 [M+H]$^+$. $t_R$=0.52 mins. (LCMS condition 3)

$^1$H NMR (300 MHz, CHLOROFORM-d): δ 8.12 (s, 1H), 4.78-4.61 (m, 1H), 4.44-4.32 (m, 1H), 3.47-3.35 (m, 3H), 2.87-2.63 (m, 2H), 2.71 (s, 3H), 1.91-1.85 (m, 1H), 1.64-1.57 (m, 1H).

Description D205 and D206

Enantiomer 1: cis-3-fluoro-4-(5-methyl-4-nitro-1H-pyrazol-1-yl)-1-(oxetan-3-yl)piperidine (D205)

Enantiomer 2: cis-3-fluoro-4-(5-methyl-4-nitro-1H-pyrazol-1-yl)-1-(oxetan-3-yl)piperidine (D206)

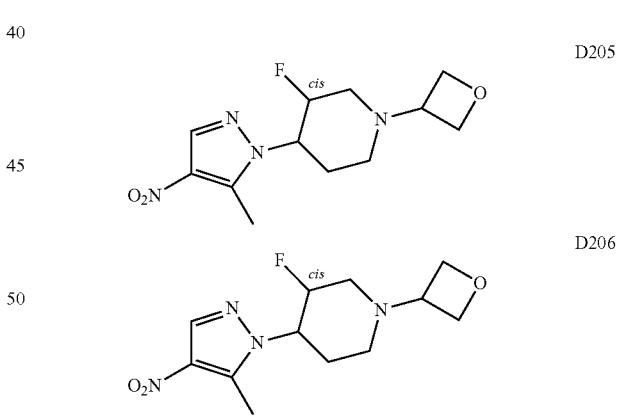

To a solution of D204 (500 g, 2.20 mmol), oxetan-3-one (395 g, 5.48 mmol) in DCE (20 mL) was added portions NaBH(OAc)$_3$ (1.4 g, 6.6 mmol) at room temperature. The reaction mixture was stirred overnight at room temperature. Na$_2$CO$_3$ aqueous solution (30 mL) was added and extracted with DCM (530 mL×5). The combined organic layer was dried and concentrated. The crude was purified by column chromatography on C18 (25-60% ACN in water) to afford desired product (470 mg, 75% yield) as a white solid, which was separated by chiral HPLC (chiralpak IA 5 um 4.6*250 mm, Hex/EtOH: 50/50, 1.0 mL/min) to give the title compounds D205 (200 mg, $t_R$=7.939 min) and D206 (180 mg, $t_R$=10.224 min) was prepared as white solids.

LCMS: 285 [M+H]$^+$. $t_R$=1.64 mins. (LCMS condition 3)

$^1$H NMR (300 MHz, CHLOROFORM-d): δ 8.09 (s, 1H), 4.93-4.76 (m, 1H), 4.70-4.60 (m, 4H), 4.50-4.37 (m, 1H), 3.74-3.68 (m, 1H), 3.09-2.96 (m, 2H), 2.77-2.75 (m, 1H), 2.70 (s, 3H), 2.50-2.27 (m, 2H), 2.09-2.00 (m, 1H).

Description D207

Enantiomer 1: cis-1-(3-fluoro-1-(oxetan-3-yl)piperidin-4-yl)-5-methyl-1H-pyrazol-4-amine (D207)

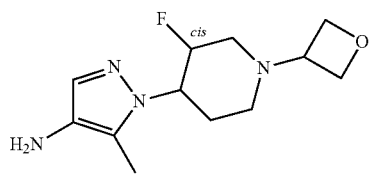 [SMILES: Cc1c(N)cnn1C1CCN(C2COC2)CC1F]

A solution of D205 (200 g, 0.70 mmol) and Pd/C (60 mg, 10%) in MeOH (8 mL) was stirred at 30° C. under hydrogen for 1 hour. The mixture was filtered and the filtrate was concentrated to give the title compound D207 (150 mg, 85% yield) as a white solid.

LCMS: 255 [M+H]$^+$. $t_R$=0.47 mins. (LCMS condition 3)

$^1$H NMR (300 MHz, CHLOROFORM-d): δ 7.18 (s, 1H), 4.89-4.61 (m, 5H), 4.32-4.18 (m, 1H), 3.73-3.64 (m, 1H), 3.10-3.02 (m, 2H), 2.78-2.74 (m, 1H), 2.66-2.61 (br. s., 2H), 2.40-2.17 (m, 2H), 2.21 (s, 3H), 2.01-1.93 (m, 1H).

Description D208

Enantiomer 2: cis-1-(3-fluoro-1-(oxetan-3-yl)piperidin-4-yl)-5-methyl-1H-pyrazol-4-amine (D208)

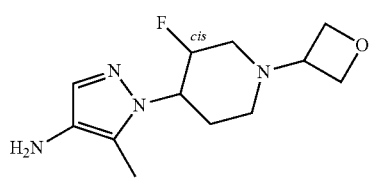 [SMILES: Cc1c(N)cnn1C1CCN(C2COC2)CC1F]

A solution of D206 (180 g, 0.63 mmol) and Pd/C (30 mg, 10%) in MeOH (8 mL) was stirred at 30° C. under H$_2$ balloon for 1 hour. The mixture was filtered and the filtrate was concentrated to give the title compound D208 (140 mg, 87% yield) as a white solid.

LCMS: 255 [M+H]$^+$. $t_R$=0.47 mins. (LCMS condition 3)

$^1$H NMR (300 MHz, CHLOROFORM-d): δ 7.18 (s, 1H), 4.89-4.61 (m, 5H), 4.32-4.18 (m, 1H), 3.73-3.64 (m, 1H), 3.10-3.02 (m, 2H), 2.78-2.74 (m, 1H), 2.66-2.61 (br. s., 2H), 2.40-2.17 (m, 2H), 2.21 (s, 3H), 2.01-1.93 (m, 1H).

Description D209

(3S,4S)-tert-butyl 3-fluoro-4-(4-nitro-1H-pyrazol-1-yl)piperidine-1-carboxylate (D209)

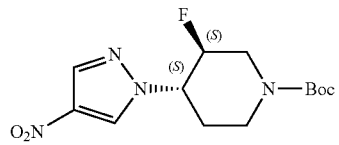

To a solution of (3S,4R)-tert-butyl 3-fluoro-4-hydroxypiperidine-1-carboxylate (3.40 g, 15.5 mmol), 4-nitro-1H-pyrazole (1.75 g, 15.5 mmol), PPh$_3$ (6.10 g, 23.3 mmol) in THF (100 mL) was added slowly DIAD (4.71 g, 23.3 mmol) at 0° C. The mixture was stirred overnight at room temperature. The mixture was concentrated, the residue was dissolved in EtOAc (50 mL) and then n-hexane (100 mL) was added. The suspension was stirred vigorously for 1 hour and then filtered. The filtrate was concentrated and the crude was purified by column chromatography on C18 (MeCN/water: 20% to 80%) to give the title compound D209 (4.05 g, 83% yield) as yellow oil.

$^1$H NMR (300 MHz, CHLOROFORM-d): δ 8.22 (s, 1H), 8.12 (s, 1H), 4.86-4.57 (m, 2H), 4.29-4.18 (m, 2H), 2.85 (br s, 2H), 2.28-2.12 (m, 2H), 1.48 (s, 9H).

Description D210

(3S,4S)-tert-butyl 4-(5-chloro-4-nitro-1H-pyrazol-1-yl)-3-fluoropiperidine-1-carboxylate (D210)

To a solution of D209 (2.7 g, 8.6 mmol) in THF (50 mL) was added LiHMDS (26 mL, 25.8 mmol, 1M in THF) at −78° C. under N$_2$. The reaction mixture was stirred at −78° C. for 40 min. A solution of hexachloroethane (4.07 g, 17.2 mmol) in THF (20 mL) was added and the reaction was stirred at −78° C. for 2 hrs under N$_2$. Aq. NH$_4$Cl solution (40 mL) was added and the solution was extracted with EtOAc (50 mL×2). The organic layers were dried and concentrated. The crude was purified by column chromatography on silica gel (PE:EA=5:1) to give the title compound D210 (1.2 g, 40% yield) as a yellow solid.

$^1$H NMR (300 MHz, CHLOROFORM-d): δ 8.23 (s, 1H), 4.99-4.75 (m, 1H), 4.61-4.48 (m, 2H), 4.32-4.22 (m, 1H), 2.99-2.83 (m, 2H), 2.31-2.16 (m, 1H), 2.03-1.96 (m, 1H), 1.48 (s, 9H).

Description D211

(3S,4S)-4-(5-chloro-4-nitro-1H-pyrazol-1-yl)-3-fluoropiperidine (D211)

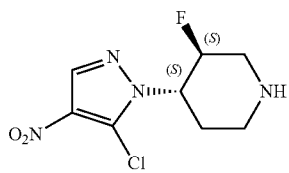

To a solution of D210 (1.2 g, 3.44 mmol) in MeOH (6 mL) was added HCl/dioxane (8 M, 6 mL). The reaction was stirred at room temperature for 2 hrs. Solvent was evaporated, and the residue was dissolved in Na$_2$CO$_3$ aqueous solution (20 mL) and extracted with DCM/MeOH (10:1, 50 mL×3). The combined organic layers were dried and concentrated to give the title compound D211 (820 mg, 96% yield).

$^1$H NMR (300 MHz, CHLOROFORM-d): δ 8.23 (s, 1H), 4.99-4.75 (m, 1H), 4.56-4.44 (m, 1H), 3.58-3.51 (m, 1H), 3.23-3.15 (m, 1H), 2.81-2.68 (m, 2H), 2.27-2.13 (m, 1H), 2.06-1.97 (m, 1H).

Description D212

(3S,4S)-4-(5-chloro-4-nitro-1H-pyrazol-1-yl)-3-fluoro-1-(oxetan-3-yl)piperidine (D212)

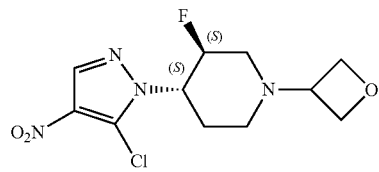

To a solution of D211 (400 g, 1.61 mmol), oxetan-3-one (290 g, 4.03 mmol) in DCE (15 mL) was added in portions NaBH(OAc)$_3$ (1.02 g, 4.83 mmol) at room temperature. The reaction mixture was stirred overnight at room temperature. Na$_2$CO$_3$ aqueous solution (30 mL) was added and extracted with DCM (30 mL×5). The combined organic layers were dried and concentrated. The crude was purified by column chromatography on silica gel (PE:EA=1:1) to give the title compound D212 (410 mg, 83% yield) as a light yellow solid.

LCMS: 305 [M+H]$^+$. t$_R$=1.02 mins. (LCMS condition 3)

$^1$H NMR (300 MHz, CHLOROFORM-d): δ 8.24 (s, 1H), 5.16-4.91 (m, 1H), 4.69 (t, J=6.6 Hz, 2H), 4.63-4.58 (m, 2H), 4.49-4.37 (m, 1H), 3.70-3.62 (m, 1H), 3.27-3.20 (m, 1H), 2.90-2.85 (m, 1H), 2.43-2.28 (m, 1H), 2.18-2.08 (m, 2H), 2.02-1.96 (m, 1H).

Description D213

5-chloro-1-((3S, 4S)-3-fluoro-1-(oxetan-3-yl)piperidin-4-yl)-1H-pyrazol-4-amine (D213)

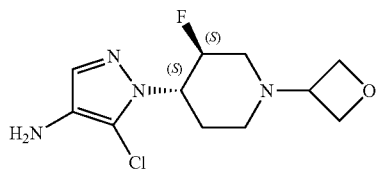

To a solution of D212 (410 g, 1.35 mmol) in EtOH/H$_2$O (4 mL/4 mL) was added iron powder (151 g, 2.70 mmol) and NH$_4$Cl (150 g, 2.70 mmol). The reaction was stirred overnight at room temperature. The solution was filtered through a celite pad and washed with MeOH (10 mL×3). The combined organic layers were concentrated and the crude was purified by column chromatography on C18 (20-50% acetonitrile in water, t$_R$=5 min) to give the title compound D213 (260 mg, 70% yield) as red oil.

LCMS: 275 [M+H]$^+$. t$_R$=1.55 mins. (LCMS condition 3)

$^1$H NMR (300 MHz, CHLOROFORM-d): δ 7.29 (s, 1H), 5.13-4.88 (m, 1H), 4.69-4.58 (m, 4H), 4.28-4.15 (m, 1H), 3.68-3.59 (m, 1H), 3.21-3.15 (m, 1H), 2.97-2.76 (m, 3H), 2.34-2.20 (m, 1H), 2.13-1.92 (m, 3H).

Description D214

(3R,4R)-tert-butyl 3-fluoro-4-(4-nitro-1H-pyrazol-1-yl)piperidine-1-carboxylate (D214)

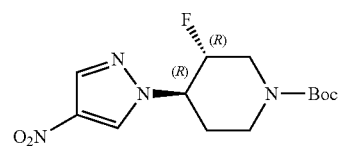

To a solution of (3R,4S)-tert-butyl 3-fluoro-4-hydroxypiperidine-1-carboxylate (2.2 g, 10.04 mmol), 4-nitro-1H-pyrazole (1.19 g, 10.5 mmol), PPh$_3$ (3.94 g, 15.06 mmol) in THF (50 mL) was added slowly DIAD (3.04 g, 15.06 mmol) under ice cooling. The mixture was stirred overnight at room temperature. Solvent was removed and the residue was dissolved in Et$_2$O (50 mL). The suspension was stirred vigorously for 30 min and then filtered. The filtrate was concentrated and the crude was purified by flash column chromatography on C18 (30-60% ACN in water) to give the title compound D214 (2.7 g, 85% yield) as yellow oil.

LCMS: 313 [M−H]$^+$. t$_R$=1.80 mins. (LCMS condition 3)

$^1$H NMR (300 MHz, CHLOROFORM-d): δ 8.23 (s, 1H), 8.13 (s, 1H), 4.87-4.62 (m, 2H), 4.29-4.17 (m, 2H), 2.93-2.80 (m, 2H), 2.33-2.12 (m, 2H), 1.47 (s, 9H).

Description D215

(3R, 4R)-tert-butyl 4-(5-chloro-4-nitro-1H-pyrazol-1-yl)-3-fluoropiperidine-1-carboxylate (D215)

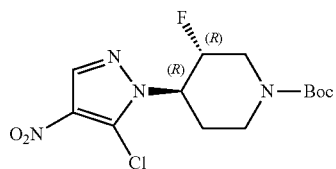

To a solution of D214 (2.7 g, 8.6 mmol) in THF (50 mL) was added dropwise LiHMDS (17 mL, 17.2 mmol, 1M in THF) at −78° C. under $N_2$. The reaction mixture was stirred at this temperature for 1 hour. A solution of hexachloroethane (4.07 g, 17.2 mmol) in THF (20 mL) was added at −78° C. The reaction mixture was stirred at −78° C. for 20 min under $N_2$. $NH_4Cl$ aq. solution (40 mL) was added and the solution was extracted with EA (50 mL×2). The organic layers were dried and concentrated. The crude was purified by column chromatography on silica gel (PE:EA=5:1) to give the title compound D215 (2.7 g, 90% yield) as a yellow solid.

$^1$H NMR (300 MHz, CHLOROFORM-d): δ 8.24 (s, 1H), 5.00-4.76 (m, 1H), 4.61-4.54 (m, 2H), 4.29-4.24 (m, 1H), 2.91-2.87 (m, 2H), 2.26-2.20 (m, 1H), 2.03-2.01 (m, 1H), 1.48 (s, 9H).

Description D216

(3R,4R)-4-(5-chloro-4-nitro-1H-pyrazol-1-yl)-3-fluoropiperidine (D216)

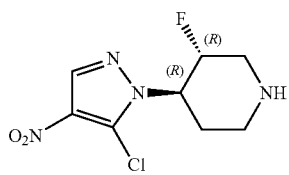

To a solution of D215 (2.7 g, 7.75 mmol) in MeOH (20 mL) was added HCl/dioxane (8 M, 20 mL). The reaction mixture was stirred at room temperature for 2 hrs. Solvent was removed and the residue was dissolved in $Na_2CO_3$ aqueous solution (30 mL) and extracted with DCM/MeOH (10:1, 50 mL×3). The combined organic layer were dried and concentrated to give the title compound D216 (1.83 g, 95% yield) as a yellow solid.

$^1$H NMR (300 MHz, CHLOROFORM-d): δ 8.23 (s, 1H), 5.00-4.74 (m, 1H), 4.56-4.44 (m, 1H), 3.56-3.51 (m, 1H), 3.20-3.16 (m, 1H), 2.81-2.66 (m, 2H), 2.27-2.12 (m, 1H), 2.05-1.97 (m, 2H).

Description D217

(3R,4R)-4-(5-chloro-4-nitro-1H-pyrazol-1-yl)-3-fluoro-1-(oxetan-3-yl)piperidine (D217)

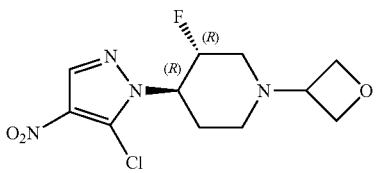

To a solution of D216 (500 g, 2.01 mmol), oxetan-3-one (363 g, 5.04 mmol) in DCE (16 mL) was added in portions $NaBH(OAc)_3$ (1.27 g, 6.03 mmol) at room temperature. The reaction mixture was stirred overnight at room temperature. $Na_2CO_3$ aqueous solution (60 mL) was added and extracted with DCM (80 mL×4). The combined organic layers were dried and concentrated. The crude was purified by column chromatography on silica gel (PE:EA=2:1) to give the title compound D217 (520 mg, 85% yield) as a colorless solid.

LCMS: 305 [M+H]$^+$. $t_R$=1.02 mins. (LCMS condition 3)

$^1$H NMR (300 MHz, CHLOROFORM-d): δ 8.24 (s, 1H), 5.12-4.94 (m, 1H), 4.71-4.58 (m, 4H), 4.48-4.38 (m, 1H), 3.69-3.63 (m, 1H), 3.25-3.22 (m, 1H), 2.89-2.85 (m, 1H), 2.41-2.30 (m, 1H), 2.16-2.03 (m, 2H), 2.01-1.99 (m, 1H).

Description D218

5-chloro-1-((3R, 4R)-3-fluoro-1-(oxetan-3-yl)piperidin-4-yl)-1H-pyrazol-4-amine (D218)

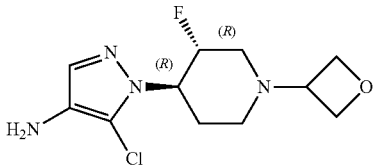

To a solution of D217 (5.90 g, 19.4 mmol) in EtOH/$H_2O$ (50 mL/50 mL) was added iron powder (5.4 g, 97 mmol) and $NH_4Cl$ (5.2 g, 97 mmol). The reaction mixture was stirred overnight at 50° C. The solution was filtered through a celite pad and washed with MeOH (50 mL×3). The combined organic layers were concentrated, dissolved in EtOAc (50 mL) and filtered. The organic solution was concentrated and purified by flash column chromatography on C18 (10-40% acetonitrile in water, $t_R$=20 min) to give the title compound D218 (3.5 g, 66% yield) as a white solid.

LCMS: 275 [M+H]$^+$. $t_R$=1.495 mins. (LCMS condition 3)

$^1$H NMR (300 MHz, CHLOROFORM-d): δ 7.29 (s, 1H), 5.13-4.88 (m, 1H), 4.69-4.57 (m, 4H), 4.28-4.15 (m, 1H), 3.68-3.59 (m, 1H), 3.21-3.14 (m, 1H), 2.90 (br s, 2H), 2.83-2.79 (m, 1H), 2.34-2.20 (m, 1H), 2.13-1.92 (m, 3H).

Description D219

(±)-(cis)-4-(5-chloro-4-nitro-1H-pyrazol-1-yl)-3-fluoropiperidine (D219)

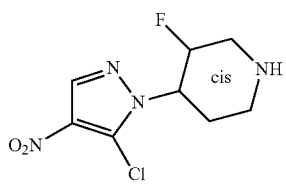 [SMILES: O=[N+]([O-])c1cnn(C2CCNCC2F)c1Cl]

To a solution of D202 (1.0 g, 2.87 mmol) in MeOH (10 mL) was added HCl/dioxane (5.7 M, 10 mL). The reaction mixture was stirred at room temperature for 1 hour. Solvent was removed and the residue was dissolved in $Na_2CO_3$ aqueous solution (40 mL) and extracted with EtOAc (50 mL×3). The combined organic layers were dried and concentrated to give the title compound D219 as a yellow solid (650 mg, 90% yield).

LCMS: 249 [M+H]$^+$. $t_R$=0.57 mins. (LCMS condition 3)

Description D220

(±)-(cis)-4-(5-chloro-4-nitro-1H-pyrazol-1-yl)-3-fluoro-1-(oxetan-3-yl)piperidine (D220)

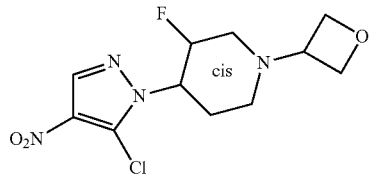 [SMILES: O=[N+]([O-])c1cnn(C2CCN(C3COC3)CC2F)c1Cl]

To a solution of D219 (650 g, 2.62 mmol), oxetan-3-one (472 g, 6.55 mmol) in DCE (30 mL) was added in portions $NaBH(OAc)_3$ (1.66 g, 7.86 mmol) at room temperature. The reaction mixture was stirred at room temperature for 2 hour. $Na_2CO_3$ aqueous solution (40 mL) was added and extracted with DCM (50 mL×3). The combined organic layers were dried and concentrated. The crude was purified by column chromatography on silica gel (PE:EA=1:2) to give the title compound D220 (640 mg, 84% yield) as a white solid.

LCMS: 305 [M+H]$^+$. $t_R$=1.96 mins. (LCMS condition 3)

$^1$H NMR (300 MHz, CHLOROFORM-d): δ 8.21 (s, 1H), 4.99-4.83 (m, 1H), 4.70-4.55 (m, 5H), 3.75-3.67 (m, 1H), 3.16-3.02 (m, 2H), 2.93-2.80 (m, 1H), 2.48-2.24 (m, 2H), 2.08-1.98 (m, 1H).

Description D221

(±)-(cis)-5-chloro-1-(3-fluoro-1-(oxetan-3-yl)piperidin-4-yl)-1H-pyrazol-4-amine (D221)

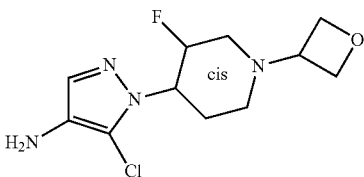

To a solution of D220 (640 g, 2.10 mmol) in EtOH/$H_2O$ (10 mL/10 mL) was added iron powder (707 g, 12.6 mmol) and $NH_4Cl$ (670 g, 12.6 mmol). The reaction mixture was stirred overnight at 50° C. The solution was filtered through a celite pad. The combined organic layer were concentrated and purified by flash column chromatography on C18 (0-20% acetonitrile in water) to give the title compound D221 (400 mg, 80% yield) as a red oil.

LCMS: 275 [M+H]$^+$. $t_R$=1.32 mins. (LCMS condition 3)

$^1$H NMR (300 MHz, CHLOROFORM-d): δ 7.27 (s, 1H), 4.93-4.77 (m, 1H), 4.72-4.64 (m, 4H), 4.38-4.25 (m, 1H), 3.74-3.65 (m, 1H), 3.15-2.78 (m, 5H), 2.41-2.18 (m, 2H), 1.99-1.94 (m, 1H).

Description D222

(±)-cis-3-(5-methyl-4-nitro-1H-pyrazol-1-yl)cyclopentyl methanesulfonate (D222)

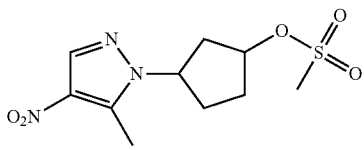 [SMILES: Cc1c([N+](=O)[O-])cnn1C1CCC(OS(C)(=O)=O)C1]

To a solution of D68 (1.00 g, 4.74 mmol) and TEA (2.39 g, 23.7 mmol) in DCM (15 mL) was added MsCl (1.09 g, 9.48 mmol) at 0° C. under nitrogen. The mixture was stirred overnight at room temperature. The mixture was poured into water (100 mL) and then extracted with DCM (40 mL×3). The combined organic layers were washed with brine (100 mL), dried over $Na_2SO_4$, filtered and concentrated. The crude was purified by flash chromatography on C18 (ACN:$H_2O$=1:4) to give the title compound D222 (630 mg, 48% yield) as a white solid.

LCMS: 290 [M+H]$^+$. $t_R$=1.76 mins. (LCMS condition 3)

$^1$H NMR (300 MHz, CHLOROFORM-d): δ 8.10 (s, 1H), 5.29-5.21 (m, 1H), 4.66-4.61 (m, 1H), 3.05 (s, 3H), 2.68 (s, 3H), 2.63-2.09 (m, 6H).

Description D223

(±)-(trans)-4-(3-(5-methyl-4-nitro-1H-pyrazol-1-yl)cyclopentyl)morpholine (D223)

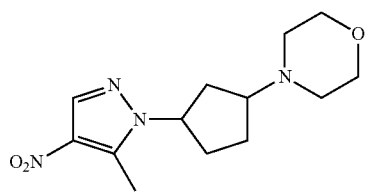 [SMILES: Cc1c([N+](=O)[O-])cnn1C1CCC(N2CCOCC2)C1]

A solution of D222 (630 g, 2.07 mmol), morpholine (541 g, 6.22 mmol) and K₂CO₃ (860 g, 6.22 mmol) in ACN/DMF (10 mL/3 mL) was stirred overnight at 90° C. The reaction mixture was poured into water (50 mL), extracted with EtOAc (30 mL×3). The combined organic layers were washed with brine (100 mL), dried over Na₂SO₄, filtered and concentrated. The crude was purified by column chromatography on silica gel (PE:EA=1:1) to give the title compound D223 (320 mg, 55% yield) as a brown solid.

¹H NMR (300 MHz, CHLOROFORM-d): δ 8.06 (s, 1H), 4.74-4.69 (m, 1H), 3.72-3.69 (m, 4H), 3.00-2.86 (m, 1H), 2.63 (s, 3H), 2.52-2.47 (m, 4H), 2.26-1.93 (m, 5H), 1.57-1.53 (m, 1H).

Description D224

(±)-(trans)-5-methyl-1-(3-morpholinocyclopentyl)-1H-pyrazol-4-amine (D224)

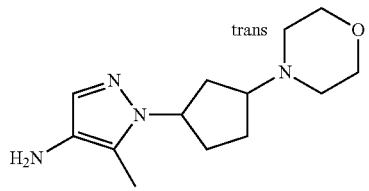 [SMILES: Cc1c(N)cnn1C1CCC(N2CCOCC2)C1]

A solution of D223 (315 g, 1.13 mmol) and Pd/C (300 mg, 10%) in MeOH (6 mL) was stirred overnight at room temperature under hydrogen. The mixture was filtered and concentrated to give the title product D224 (279 mg, 99%) as a white solid.

LCMS: 251 [M+H]⁺. t$_R$=1.46 mins. (LCMS condition 3)

¹H NMR (300 MHz, DMSO-d₆): δ 6.86 (s, 1H), 4.56-4.54 (m, 1H), 3.55-3.46 (m, 4H), 2.76-2.74 (m, 1H), 2.35 (s, 4H), 2.04-1.79 (m, 8H), 1.43-1.40 (m, 1H).

Description D225 cis/trans-3-(4-nitro-1H-pyrazol-1-yl)cyclopentyl methanesulfonate (D225)

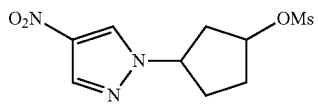 [SMILES: CS(=O)(=O)OC1CCC(n2cc([N+](=O)[O-])cn2)C1]

To a solution of D66 (3.10 g, 15.7 mmol) and TEA (7.95 g, 78.7 mmol) in DCM (45 mL) was added MsCl (3.60 g, 31.5 mmol) at 0° C. The mixture was stirred overnight at room temperature. The mixture was poured into water (50 mL), extracted with DCM (30 mL×3). The combined organic layers were washed with brine (100 mL), dried over Na₂SO₄, filtered and concentrated. The crude was purified by flash chromatography on C18 with ACN/H₂O (15%-55%) to give the title product D225 (2.00 g, >80% purity and 1.20 g crude) as an oil.

LCMS: 276 [M+H]⁺. t$_R$=2.196 mins. (LCMS condition 3)

Description D226 and D227

(±)-(trans)-4-[3-(4-nitro-pyrazol-1-yl)-cyclopentyl]-morpholine (D226)

(±)-(cis)-4-[3-(4-nitro-pyrazol-1-yl)-cyclopentyl]-morpholine (D227)

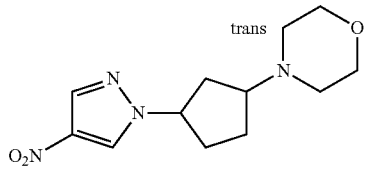

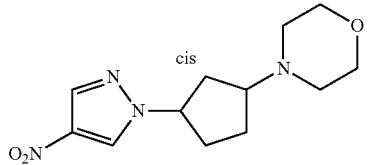

A solution of D225 (2.00 g, 7.27 mmol), morpholine (1.90 g, 21.8 mmol) and K₂CO₃ (3.00 g, 21.8 mmol) in DMF (50 mL) was stirred overnight at 115° C. The mixture was poured into water (50 mL), extracted with DCM (50 mL×3). The combined organic layers were washed with brine (100 mL), dried over Na₂SO₄, filtered and concentrated. The crude was purified by column chromatography on silica gel (PE:EA=1:1-0:1) to give the title compounds D226 (550 mg, yield 28%) and D227 (297 mg, yield 15%) as brown oil.

D226: LCMS: 267 [M+H]⁺. t$_R$=1.984 mins. (LCMS condition 3)

¹H NMR (300 MHz, CHLOROFORM-d): δ 8.15 (s, 1H), 8.08 (s, 1H), 4.81-4.72 (m, 1H), 3.73 (t, J=4.8 Hz, 4H), 2.98-2.87 (m, 1H), 2.52-2.48 (m, 4H), 2.42-2.03 (m, 6H);

D227: LCMS: 267 [M+H]⁺. t$_R$=1.999 mins. (LCMS condition 3)

¹H NMR (300 MHz, CHLOROFORM-d): δ 8.31 (s, 1H), 8.05 (s, 1H), 4.75-4.65 (m, 1H), 3.73 (t, J=4.8 Hz, 4H), 2.78-2.67 (m, 1H), 2.57-2.44 (m, 4H), 2.29-1.97 (m, 6H).

Description D228 and D229

Enantiomer 1: (trans)-4-(3-(5-chloro-4-nitro-1H-pyrazol-1-yl)cyclopentyl)morpholine (D228)

Enantiomer 2: (trans)-4-(3-(5-chloro-4-nitro-1H-pyrazol-1-yl)cyclopentyl)morpholine (D229)

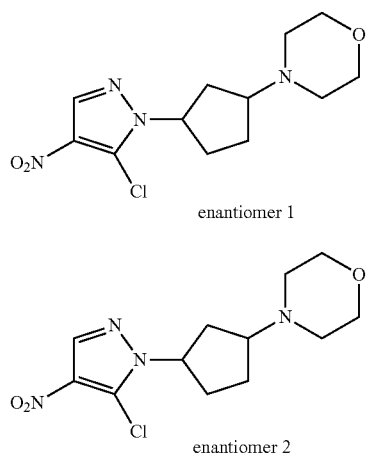

To a solution of D226 (550 g, 2.07 mmol) in THF (30 mL) was added dropwise LiHMDS (1 M in THF, 4.2 mL, 4.2 mmol) at −78° C. The mixture was stirred for 1 hour at −78° C. and then a solution of hexachloroethane (981 g, 4.14 mmol) in dry THF (4 mL) was added dropwise. The reaction was stirred for 2 hours at rt. The reaction was quenched with saturated NH$_4$Cl solution (30 mL). The mixture was extracted with EtOAc (30 mL×3). The combined organic layers were washed with brine (50 mL×2). The organic layers were concentrated in vacuo and purified by column chromatography on silica gel (PE:EA=3:1-0:1 and CH$_2$Cl$_2$:MeOH=20:1-10:1) to afford the racemate, which was separated by chiral HPLC (Chiral condition: chiralpak IF, 60-40 Hex-EtOH, Flow: 1.0 mL/Min, T=30° C.) to give the title compounds D228 (283 mg, t$_R$=10.208) and D229 (278 mg, t$_R$=13.517) as yellow solids.

LCMS: 301 [M+H]$^+$. t$_R$=20.199 mins. (LCMS condition 3)

$^1$H NMR (300 MHz, CHLOROFORM-d): δ 8.17 (s, 1H), 5.04-4.95 (m, 1H), 3.73 (t, J=4.8 Hz, 4H), 3.03-2.93 (m, 1H), 2.59-2.43 (m, 4H), 2.35-2.02 (m, 5H), 1.67-1.53 (m, 1H).

Description D230

Enantiomer 1: (trans)-5-chloro-1-(3-morpholinocyclopentyl)-1H-pyrazol-4-amine (D230)

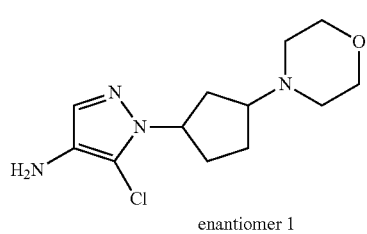

To a solution of D228 (283 g, 0.943 mmol) in EtOH/H$_2$O (4 mL/4 mL) was added iron power (216 g, 3.77 mmol) and NH$_4$Cl (101 g, 1.886 mmol). Then the reaction was stirred overnight at room temperature. The mixture was filtered and the filtrate was concentrated in vacuo to give a red solid, which was purified by flash column chromatography over C18 (5-45% CH$_3$CN in water) to give the title compound D230 (181 mg, 71% yield) as a red solid.

LCMS: 271 [M+H]$^+$. t$_R$=1.546 mins. (LCMS condition 3)

$^1$H NMR (300 MHz, CHLOROFORM-d): δ 7.22 (s, 1H), 4.86-4.77 (m, 1H), 3.73 (t, J=4.8 Hz, 1H), 2.98-2.88 (m, 3H), 2.54-2.45 (m, 4H), 2.67-1.93 (m, 5H), 1.57-1.51 (m, 1H).

Description D231

Enantiomer 2: (trans)-5-chloro-1-(3-morpholinocyclopentyl)-1H-pyrazol-4-amine (D231)

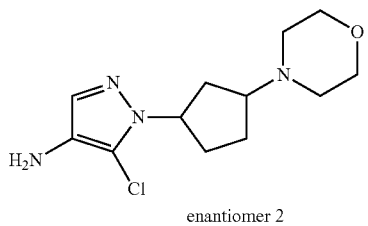

To a solution of D229 (278 g, 0.927 mmol) in EtOH/H$_2$O (4 mL/4 mL) was added iron power (208 g, 3.71 mmol) and NH$_4$Cl (99 g, 1.85 mmol). Then the reaction was stirred overnight at room temperature. The mixture was filtered and the filtrate was concentrated in vacuo to give crude as a red solid, which was purified by flash column chromatography over C18 (5~45% CH$_3$CN in water) to give the title compound D231 (162 mg, 69% yield) as a red solid.

LCMS: 271 [M+H]$^+$. t$_R$=1.547 mins. (LCMS condition 3)

$^1$H NMR (300 MHz, CHLOROFORM-d): δ 7.22 (s, 1H), 4.86-4.76 (m, 1H), 3.72 (t, J=4.8 Hz, 1H), 2.98-2.85 (m, 3H), 2.54-2.46 (m, 4H), 2.67-1.93 (m, 5H), 1.59-1.51 (m, 1H).

Description D232 and D233

Enantiomer 1: (cis)-4-(3-(5-chloro-4-nitro-1H-pyrazol-1-yl)cyclopentyl)morpholine (D232)

Enantiomer 2: (cis)-4-(3-(5-chloro-4-nitro-1H-pyrazol-1-yl)cyclopentyl)morpholine (D233)

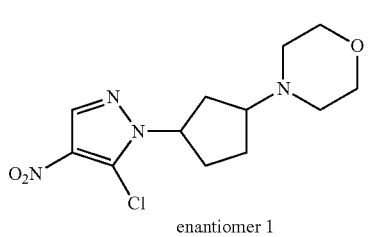

D233

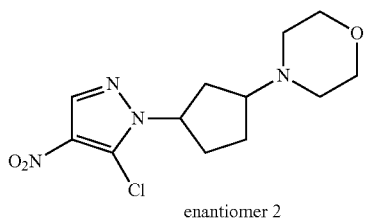

enantiomer 2

To a solution of D227 (297 g, 1.12 mmol) in THF (15 mL) was added dropwise LiHMDS (1 M in THF, 2.24 mL, 2.24 mmol) at −78° C. The mixture was stirred for 1 hour at −78° C. and then a solution of hexachloroethane (531 g, 2.24 mmol) in THF (2 mL) was added dropwise for 20 min. The reaction was stirred for 2 hours at room temperature. The reaction was quenched with saturated NH$_4$Cl solution (30 mL). The mixture was extracted with EtOAc (30 mL×3). The combined organic layers were washed with brine (50 mL×2). The organic layers were concentrated in vacuo and purified by column chromatography on silica gel (PE:EA=3:1-0:1 and CH$_2$Cl$_2$:MeOH=20:1-10:1) to afford the racemate, which was separated by chiral HPLC (Chiral condition: chiralpak IF, 60-40 Hex-EeOH, Flow: 1.0 mL/Min, T=30° C.) to give the title compounds D232 (66 mg, t$_R$=10.10) and D233 (67 mg, t$_R$=11.60) as yellow solids.

LCMS: 301 [M+H]$^+$. t$_R$=2.199 mins. (LCMS condition 3)

$^1$H NMR (300 MHz, CHLOROFORM-d): δ 8.17 (s, 1H), 4.92-4.81 (m, 1H), 3.73 (t, J=4.8 Hz, 4H), 2.79-2.68 (m, 1H), 2.59-2.44 (m, 4H), 2.41-2.35 (m, 1H), 2.25-2.06 (m, 1H), 2.02-1.87 (m, 2H).

Description D234

Enantiomer 2: (cis)-5-chloro-1-(3-morpholinocyclopentyl)-1H-pyrazol-4-amine (D234)

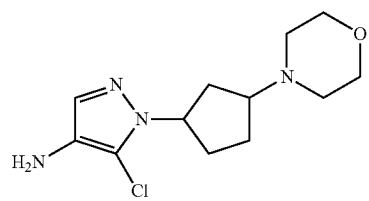 [SMILES: Nc1cnn(C2CCC(N3CCOCC3)C2)c1Cl]

To a solution of D233 (60 g, 0.20 mmol) in EtOH/H$_2$O (5 mL/5 mL) was added iron power (45 g, 0.8 mmol) and NH$_4$Cl (43 g, 0.8 mmol). Then the reaction was stirred at 50° C. for 2 hrs. The reaction mixture was filtered and the filtrate was concentrated. The residue was dissolved with EtOAc (5 mL) and washed with water (50 mL). The aqueous layer was extracted with EtOAc (10 mL). The combined organic layers were dried over Na$_2$SO$_4$ and concentrated to give the title compound D234 (30 mg, 56%) as brown oil.

LCMS: 271 [M+H]$^+$. t$_R$=1.723 mins. (LCMS condition 3)

$^1$H NMR (300 MHz, CHLOROFORM-d): δ 7.21 (s, 1H), 4.70-4.62 (m, 1H), 3.72 (t, J=4.8 Hz, 4H), 2.74-2.66 (m, 1H), 2.56-2.47 (m, 4H), 2.34-2.27 (m, 1H), 2.16-2.00 (m, 3H), 1.95-1.82 (m, 2H).

Description D235

(cis/trans)-3-methyltetrahydro-2H-pyran-4-ol (D235)

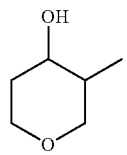

To a solution of 3-methyldihydro-2H-pyran-4(3H)-one (3.06 g, 26.8 mmol) in anhydrous THF (40 mL) was added to LiHBEt$_3$ (35 mL, 1M in THF) at 0° C. The reaction was stirred at 0° C. for 2 hrs, and then at room temperature for 2 hrs. Water (15 mL) and EtOH (22.5 mL) were added and the organic layer was oxidized with 6N NaOH (13.5 mL) and 36% H$_2$O$_2$ (18 mL) at 0° C. After stirring at room temperature for 30 min, the mixture was saturated with K$_2$CO$_3$ and the organic phase was separated. The aqueous phase was extracted with ether (150 mL×3). The combined organic layers were concentrated and the crude was purified by column chromatography on silica gel (EA:PE:MeOH=8:2:0.1) to give the title compound D235 (1.50 g, yield 48%) as colorless oil.

$^1$H NMR (300 MHz, CHLOROFORM-d): δ 4.01-3.92 (m, 1H), 3.86-3.76 (m, 1H), 3.64-3.57 (m, 0.5H), 3.52 (d, J=6.3 Hz, 1H), 3.45-3.27 (m, 1H), 2.99 (t, J=10.8 Hz, 0.5H), 1.94-1.51 (m, 4H), 0.94-0.90 (m, 3H)

Description D236

(cis/trans)-1-(3-methyltetrahydro-2H-pyran-4-yl)-4-nitro-1H-pyrazole (D236)

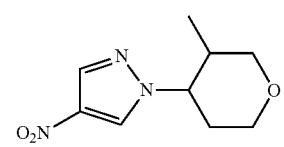

To a solution of D235 (1.50 g, 12.9 mmol), 4-nitro-1H-pyrazole (2.19 g, 19.4 mmol), PPh$_3$ (5.08 g, 19.4 mmol) in THF (15 mL) was added slowly DIAD (5.22 g, 25.9 mmol) at 0° C. After stirred overnight at room temperature, the mixture was concentrated. The crude was purified by column chromatography on silica gel (EA:PE=1:2) and flash column chromatography on C18 (15-50% CH$_3$CN in water) to give the title compound D236 (1.03 g, 38% yield) as colorless oil.

$^1$H NMR (300 MHz, CHLOROFORM-d): δ 8.15-8.09 (m, 2H), 4.58-4.50 (m, 0.5H), 4.25-4.10 (m, 1H), 4.00-3.85 (m, 1.5H), 3.71-3.54 (m, 1.5H), 3.15 (t, J=11.1 Hz, 0.5H), 2.45-2.32 (m, 1H), 2.23-2.14 (m, 1H), 2.14-1.90 (m, 1H), 0.81-0.70 (m, 3H).

Description D237

(cis/trans)-5-chloro-1-(3-methyltetrahydro-2H-pyran-4-yl)-4-nitro-1H-pyrazole (D237)

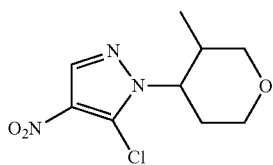 [SMILES: CC1COCCC1n1ncc([N+](=O)[O-])c1Cl]

To a solution of D236 (1.44 g, 6.82 mmol) in THF (20 mL) was added slowly LiHMDS (13 mL, 13 mmol) at −78° C. under $N_2$ atmosphere. The reaction was stirred at this temperature for 40 min. Perchloroethane (3.23 g, 13.6 mmol) in THF (8 mL) at −78° C. was added and the mixture was stirred at this temperature for 0.5 h and then quenched by $NH_4Cl$ aq. (15 mL). The solution was extracted with EtOAc (50 mL×2). The organic layer was dried and concentrated. The crude was purified by chromatography on silica gel (PE:EA=4:1) to give the title compound D237 (1.50 g, 89% yield) as a white solid.
$^1H$ NMR (400 MHz, CHLOROFORM-d): δ 8.22 (s, 0.4H), 8.18 (s, 0.6 Hz), 4.77-4.70 (m, 0.6H), 4.23-4.14 (m, 1.5H), 4.13-4.06 (m, 0.4H), 4.04-3.98 (m, 0.6H), 3.85-3.49 (m, 1.5H), 3.18 (t, J=11.1 Hz, 0.4H), 2.62-2.27 (m, 2H), 1.90-1.78 (m, 1H), 0.84 (d, J=6.9 Hz, 1.8H), 0.67 (d, J=6.6 Hz, 1.2H).

Description D238, D239, D240 and D241

Enantiomer 1: cis-5-methyl-1-(3-methyltetrahydro-2H-pyran-4-yl)-4-nitro-1H-pyrazole (D238)

Enantiomer 2: cis-5-methyl-1-(3-methyltetrahydro-2H-pyran-4-yl)-4-nitro-1H-pyrazole (D239)

Enantiomer 3: trans-5-methyl-1-(3-methyltetrahydro-2H-pyran-4-yl)-4-nitro-1H-pyrazole (D240)

Enantiomer 4: trans-5-methyl-1-(3-methyltetrahydro-2H-pyran-4-yl)-4-nitro-1H-pyrazole (D241)

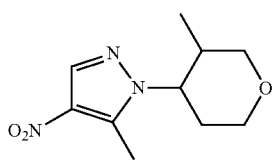

enantiomer 1 (cis)

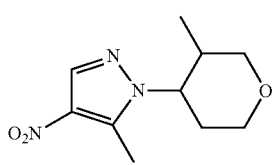

enantiomer 2 (cis)

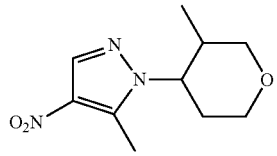

enantiomer 3 (trans)

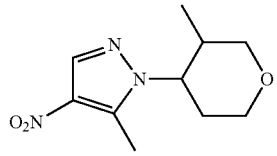

enantiomer 4 (trans)

A solution of D237 (1.50 g, 6.07 mmol), methylboronic acid (2.28 g, 38.0 mmol), Pd(dppf)$C_2$—$CH_2Cl_2$ (743 g, 0.91 mmol), $Na_2CO_3$ (1.93 g, 18.2 mmol) in dioxane (30 mL) and $H_2O$ (3 mL) was stirred overnight under $N_2$ at 100° C. The reaction was cooled to room temperature and filtered through a celite pad. The filtered cake was washed with DCM/MeOH (20:1, 60 mL). The filtrate was concentrated and purified by column chromatography on silica gel (PE:EA=5:1) and SFC (instrument method: 80-20-$CO_2$-MeOH; co-solvent: MeOH; column: IE; $CO_2$ flow rate: 2.4; co-solvent flow rate: 0.6; T=40.1° C.) to give cis isomer ($t_R$=2.98 min, 205 mg) and trans isomer ($t_R$=2.66 min, 147 mg), which were further separated by chiral-HPLC (chiral condition: Chiralpak AS-H 5 um 4.6*250 mm, Phase:Hex: EtOH=80:20, F: 1 mL/min, W: 230 nm, T: 30° C.) to give the title compounds D238 (80 mg, $t_R$=5.584), D239 (83 mg, $t_R$=6.002), D240 (41 mg, $t_R$=6.885) and D241 (40 mg, $t_R$=6.094) as brown oil.

Description D242

Enantiomer 1: (cis)-5-methyl-1-(3-methyltetrahydro-2H-pyran-4-yl)-1H-pyrazol-4-amine (D242)

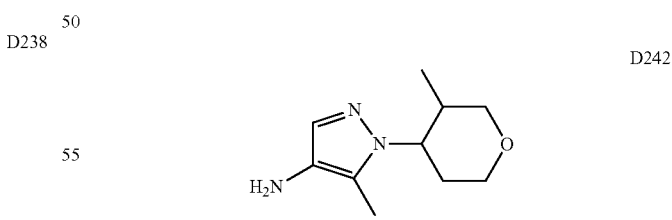

enantiomer 1 (cis)

To a solution of D238 (80 g, 0.35 mmol) in MeOH (15 mL) was added Pd/C (60 mg, 10% wet) at room temperature, then the reaction was stirred under $H_2$ balloon for 1 hour. The mixture was filtered. The filtrate was concentrated to give the title compound D242 (70 mg, 100% yield) as colorless oil.

Description D243

Enantiomer 2: (cis)-5-methyl-1-(3-methyltetra-hydro-2H-pyran-4-yl)-1H-pyrazol-4-amine (D243)

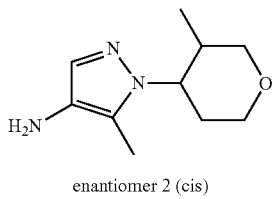

enantiomer 2 (cis)

To a solution of D239 (83 g, 0.37 mmol) in MeOH (15 mL) was added Pd/C (60 mg, 10% wet) at room temperature, and then the reaction was stirred under $H_2$ balloon for 1 hour. The mixture was filtered. The filtrate was concentrated to give the title compound D243 (66 mg, 92% yield) as colorless oil.

Description D244

Enantiomer 3: (trans)-5-methyl-1-(3-methyltetra-hydro-2H-pyran-4-yl)-1H-pyrazol-4-amine (D244)

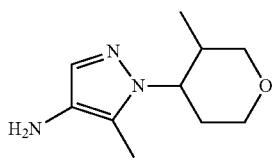

enantiomer 3 (trans)

To a solution of D239 (40 g, 178 mmol) in MeOH (20 mL) was added Pd/C (30 mg, 10% wet) at room temperature, and then the reaction was stirred under $H_2$ balloon for 1 hour. The mixture was filtered. The filtrate was concentrated to give the title compound D244 (35 mg, 100% yield) as colorless oil.

Description D245

Enantiomer 4: trans-5-methyl-1-(3-methyltetra-hydro-2H-pyran-4-yl)-4-nitro-1H-pyrazole (D245)

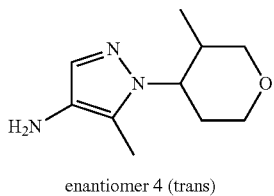

enantiomer 4 (trans)

To a solution of D241 (40 g, 178 mmol) in MeOH (20 mL) was added Pd/C (30 mg, 10% wet) at room temperature, then the reaction was stirred under $H_2$ balloon for 1 hour. The mixture was filtered. The filtrate was concentrated to give the title compound D245 (35 mg, 100% yield) as colorless oil.

Description D246

(±)-tert-butyl 3-(4-nitro-1H-pyrazol-1-yl)-4-oxopiperidine-1-carboxylate (D246)

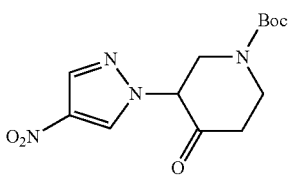 [SMILES: CC(C)(C)OC(=O)N1CCC(=O)C(n2cc([N+](=O)[O-])cn2)C1]

To a solution of tert-butyl 3-bromo-4-oxopiperidine-1-carboxylate (10.0 g, 35.9 mmol) and 4-nitro-1H-pyrazole (4.47 g, 39.5 mmol) in DMF (50 mL) was added $K_2CO_3$ (9.92 g, 71.9 mmol). The reaction was stirred overnight at room temperature. The mixture was poured into 500 mL of water and extracted with EA (300 mL×2). The extracts were concentrated and the residue was purified by column C18 (ACN/$H_2O$=35-57%) to give the title compound D246 (4.0 g, 36%) as a yellow oil.

LCMS: 211 [M+H-100]$^+$. $t_R$=1.92 mins. (LCMS condition 3)

$^1$H NMR (300 MHz, CHLOROFORM-d): δ 8.22 (s, 1H), 8.12 (s, 1H), 4.93-4.97 (m, 1H), 4.74 (br s, 1H), 4.43 (br s, 1H), 3.63 (t, J=11.4 Hz, 1H), 3.23-3.33 (m, 1H), 2.68-2.64 (m, 2H), 1.51 (s, 9H).

Description D247

(±)-tert-butyl 4,4-difluoro-3-(4-nitro-1H-pyrazol-1-yl)piperidine-1-carboxylate (D247)

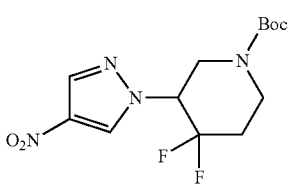 [SMILES: CC(C)(C)OC(=O)N1CCC(F)(F)C(n2cc([N+](=O)[O-])cn2)C1]

To a solution of D246 (2.00 g, 6.45 mmol) in DCM (20 mL) was added dropwise DAST (5.19 g, 32.3 mmol) at −78° C. under $N_2$ atmosphere. The reaction was allowed to warm to room temperature and stirred overnight. The reaction mixture was poured into 300 mL of saturated $NaHCO_3$ and extracted with DCM (150 mL×3). The extracts were dried over $Na_2SO_4$ and concentrated. The residue was purified by column C18 (ACN/$H_2O$=45-60%) to give the title compound D247 (2.20 g, 98%) as a white solid.

LCMS: 233 [M+H-100]$^+$. $t_R$=2.21 mins. (LCMS condition 3)

$^1$H NMR (300 MHz, CHLOROFORM-d): δ 8.29 (s, 1H), 8.11 (s, 1H), 4.50-4.56 (m, 1H), 4.36-4.42 (m, 1H), 4.05-4.12 (m, 1H), 3.61-3.68 (m, 1H), 3.24-3.32 (m, 1H), 2.26-2.40 (m, 1H), 1.96-2.13 (m, 1H), 1.49 (s, 9H).

Description D248

(±)-tert-butyl 3-(5-chloro-4-nitro-1H-pyrazol-1-yl)-4,4-difluoropiperidine-1-carboxylate (D248)

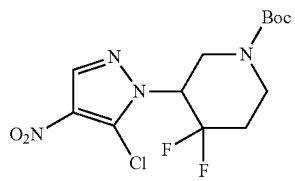 [SMILES: CC(C)(C)OC(=O)N1CCC(F)(F)C(n2ncc([N+](=O)[O-])c2Cl)C1]

To a solution of D247 (2.20 g, 6.60 mmol) in THF (30 mL) was added dropwise LiHDMS (1M in THF, 20 mL, 20.0 mmol) at −78° C. under N$_2$ atmosphere. The reaction was stirred at −78° C. for 1 h. Then C$_2$Cl$_6$ (3.12 g, 13.2 mmol) in THF (10 mL) was added dropwise and the mixture stirred at −78° C. for 1 h. NH$_4$Cl (aq., 30 mL) was added at −78° C. and the reaction mixture was allowed to warm to room temperature. The reaction mixture was concentrated and 30 mL of water was added. The mixture was extracted with EtOAc (100 mL×3). The extracts were concentrated and the residue was purified by column C18 (ACN/H$_2$O=57-67%) to give the title compound D248 (1.93 g, 80%) as yellow oil.

LCMS: 311 [M+H-56]$^+$. t$_R$=2.845 mins. (LCMS condition 3)

$^1$H NMR (300 MHz, CHLOROFORM-d): δ 8.21 (s, 1H), 4.59-4.70 (m, 1H), 4.04-4.06 (m, 2H), 3.75-3.89 (m, 1H), 3.51-3.60 (m, 1H), 2.38-2.61 (m, 1H), 1.97-2.15 (m, 1H), 1.47 (s, 9H).

Description D249 and D250

Enantiomer 1: tert-butyl 3-(5-chloro-4-nitro-1H-pyrazol-1-yl)-4,4-difluoropiperidine-1-carboxylate (D249)

Enantiomer 2: tert-butyl 3-(5-chloro-4-nitro-1H-pyrazol-1-yl)-4,4-difluoropiperidine-1-carboxylate (D250)

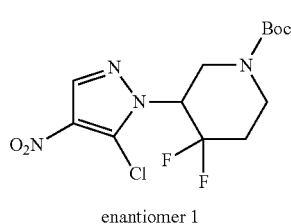

enantiomer 1
D249

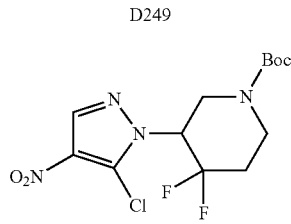

enantiomer 2
D250

The title compounds D249 (1.15 g) and D250 (1.35 g) were obtained as white solids by separation of D248 using chiral-HPLC (Chiralpak IB; 5 um 4.6*250 mm; Phase:Hex:IPA=80:20; F: 1.0 mL/min W: 230 nm T: 30).

LCMS: 267 [M+H-100]$^+$. t$_R$=2.31 mins. (LCMS condition 3)

$^1$H NMR (300 MHz, CHLOROFORM-d): δ 8.21 (s, 1H), 4.70-4.59 (m, 1H), 4.05 (m, 2H), 3.87-3.82 (m, 1H), 3.60-3.52 (m, 1H), 2.54-2.39 (m, 1H), 2.13-1.98 (m, 1H), 1.45 (s, 9H).

Description D251

(±)-tert-butyl 4,4-difluoro-3-(5-methyl-4-nitro-1H-pyrazol-1-yl)piperidine-1-carboxylate (D251)

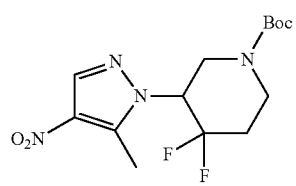 [SMILES: Cc1c([N+](=O)[O-])cnn1C1CN(C(=O)OC(C)(C)C)CCC1(F)F]

To a solution of D248 (3.2 g, 8.73 mmol) in DMF (8 mL) and water (2 mL) was added tripotassium phosphate (5.56 g, 26.2 mmol), methylboronic acid (3.66 g, 61.1 mmol) and PdCl$_2$(dppf)-CH$_2$Cl$_2$ adduct (0.713 g, 0.873 mmol). The resulting mixture was irradiated at 100° C. under microwave for 1 hour. The mixture was diluted with EA and water was added. The organic layer was washed with brine, dried over Na$_2$SO$_4$, filtered, and concentrated. The crude was purified by column chromatography on silica gel to give the title compound D251 (2.75 g, 7.94 mmol, 91% yield).

LCMS: 291 [M+H-56]$^+$. t$_R$=3.630 mins. (LCMS condition 1)

Description D252

(±)-tert-butyl 3-(4-amino-5-methyl-1H-pyrazol-1-yl)-4,4-difluoropiperidine-1-carboxylate (D252)

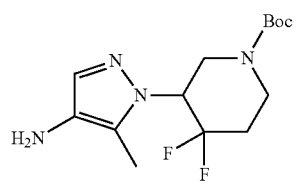

A mixture of D251 (1 g, 2.89 mmol), Pd/C (1.229 g, 1.155 mmol) in ethanol (15 mL) was stirred under hydrogen for 16 hours. After filtration, the filtrate was concentrated to give the title compound D252 (0.913 g, 2.89 mmol, 100% yield).

LCMS: 317 [M+H]$^+$. t$_R$=3.116 mins. (LCMS condition 1)

Description D253

(±)-tert-butyl 3-(4-((4-ethoxy-7H-pyrrolo[2,3-d]pyrimidin-2-yl)amino)-5-methyl-1H-pyrazol-1-yl)-4,4-difluoropiperidine-1-carboxylate (D253)

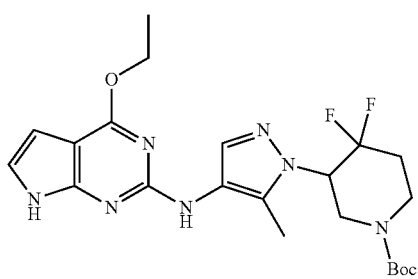 [SMILES: CCOc1nc(Nc2cnn(C3CN(C(=O)OC(C)(C)C)CCC3(F)F)c2C)nc2[nH]ccc12]

A mixture of D252 (898 g, 2.84 mmol), D1 (510 g, 2.58 mmol), X-phos (246 mg, 0.516 mmol), Pd$_2$dba$_3$ (236 g, 0.258 mmol), K$_2$CO$_3$ (1070 g, 7.74 mmol) in isobutanol (15 mL) was irradiated under microwave to 110° C. for 1 hour. EA was added and the solution was filtered. The filtrate was concentrated and the crude was purified by column chromatography on silica gel to give the title compound D253 (760 g, 1.592 mmol, 61.7% yield).

LCMS: 478 [M+H]$^+$. t$_R$=3.284 mins. (LCMS condition 1)

$^1$H NMR (400 MHz, DMSO-d$_6$): δ 11.20 (br. s., 1H), 8.09 (br. s., 1H), 7.62-7.76 (m, 1H), 6.87 (br. s., 1H), 6.22 (br. s., 1H), 4.73 (d, J=17.8 Hz, 1H), 4.33-4.53 (m, 2H), 4.03 (q, J=6.8 Hz, 2H), 3.86 (br. s., 2H), 2.31 (d, J=12.96 Hz, 1H), 2.22 (s, 3H), 2.11 (br. s., 1H), 1.31-1.47 (m, 12H).

Description D254

(±)-3-(5-chloro-4-nitro-1H-pyrazol-1-yl)-4,4-difluoropiperidine (D254)

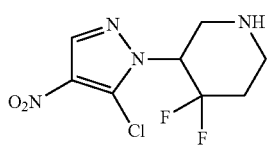 [SMILES: O=[N+]([O-])c1cnn(C2CNCCC2(F)F)c1Cl]

To a solution of D248 (1.93 g, 5.27 mmol) in MeOH (10 mL) was added HCl/EtOAc (10 mL, 4M). The reaction was stirred at room temperature for 1 hour. The mixture was concentrated below 40° C. and the residue was poured into 100 mL of saturated NaHCO$_3$. Then, the mixture was extracted with EtOAc (100 mL×2) and the extracts were concentrated. The crude was purified by column C18 (ACN/H$_2$O=35-50%) to give the title compound D254 (850 mg, 61%).

LCMS: 267 [M+H]$^+$. t$_R$=1.92 mins. (LCMS condition 3)

$^1$H NMR (300 MHz, CHLOROFORM-d): δ 8.23 (s, 1H), 4.59-4.68 (m, 1H), 3.54-3.61 (m, 1H), 3.30-3.36 (m, 1H), 3.13-3.22 (m, 1H), 3.00-3.08 (m, 1H), 2.13-2.32 (m, 1H), 2.00-2.09 (m, 1H).

Description D255 and D256

Enantiomer 1: 3-(5-chloro-4-nitro-1H-pyrazol-1-yl)-4,4-difluoro-1-(oxetan-3-yl)piperidine (D255)

Enantiomer 2: 3-(5-chloro-4-nitro-1H-pyrazol-1-yl)-4,4-difluoro-1-(oxetan-3-yl)piperidine (D256)

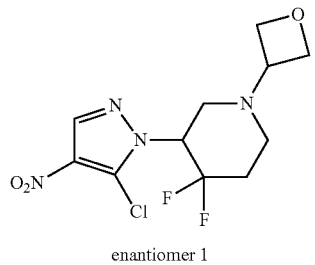

enantiomer 1

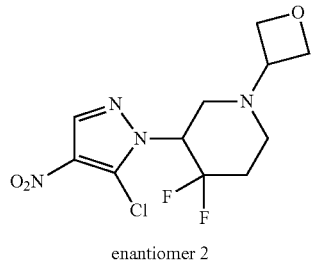

enantiomer 2

To a solution of D254 (850 g, 3.20 mmol) and oxetan-3-one (576 g, 7.99 mmol) in 1,2-dichloroethane (80 mL) was added NaBH(OAc)$_3$ (2.03 g, 9.60 mmol) as portions. After addition, the reaction mixture was stirred overnight at room temperature. The reaction mixture was poured into 50 mL of saturated Na$_2$CO$_3$ aqueous and extracted with DCM (70 mL×3). The extracts were dried over Na$_2$SO$_4$ and concentrated. The crude was purified by column chromatography (PE:EA=5:1-3:1-2:1) to afford the title racemate as a white solid (820 mg, 80%), which was separated by chiral-HPLC (Chiralpak IB 5 um 4.6*250 mm; Phase:Hex:EtOH=70:30; F: 1.0 mL/min; W: 230 nm; T: 30) to give the title compounds D255 (322 mg, 23% yield, t$_R$=8.401 min) and D256 (322 mg, 23% yield, t$_R$=9.439 min).

LCMS: 323 [M+H]$^+$. t$_R$=1.98 mins. (LCMS condition 3)

$^1$H NMR (300 MHz, CHLOROFORM-d): δ 8.23 (s, 1H), 4.79-4.90 (m, 1H), 4.56-4.71 (m, 4H), 3.67-3.75 (m, 1H), 3.04-3.12 (m, 1H), 2.91-2.98 (m, 1H), 2.82-2.87 (m, 1H), 2.13-2.38 (m, 3H).

Description D257

Enantiomer 1: 5-chloro-1-(4,4-difluoro-1-(oxetan-3-yl)piperidin-3-yl)-1H-pyrazol-4-amine (D257)

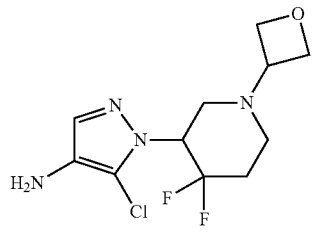

enantiomer 1

To a solution of D255 (322 g, 1.00 mmol) in EtOH/H₂O (5 mL/5 mL) was added iron power (224 g, 4.00 mmol) and NH₄Cl (212 g, 4.00 mmol). Then the reaction was stirred at 50° C. for 2 hours. The reaction mixture was filtered and the filtrate was concentrated. The residue was dissolved with EtOAc (50 mL) and washed with water (50 mL). The aqueous layer was extracted with EtOAc (50 mL). The combined organic layers were dried over Na₂SO₄ and concentrated to give the title compound D257 (280 mg, 90%) as red oil.

LCMS: 293 [M+H]⁺. $t_R$=0.62 mins. (LCMS condition 3)
¹H NMR (300 MHz, CHLOROFORM-d): δ 7.30 (s, 1H), 4.56-4.72 (m, 5H), 3.65-3.70 (m, 1H), 2.79-3.05 (m, 5H), 2.04-2.33 (m, 3H).

Description D258

Enantiomer 2: 5-chloro-1-(4,4-difluoro-1-(oxetan-3-yl)piperidin-3-yl)-1H-pyrazol-4-amine (D258)

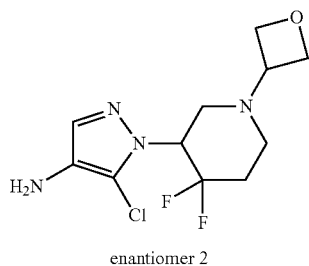

enantiomer 2

To a solution of D256 (322 g, 1.00 mmol) in EtOH/H₂O (5 mL/5 mL) was added iron power (224 g, 4.00 mmol) and NH₄Cl (212 g, 4.00 mmol). Then the reaction mixture was stirred at 50° C. for 2 hrs. The reaction mixture was cooled to room temperature and filtered. The filtrate was concentrated to give the title compound D258 (280 mg, 90%) as red oil.

LCMS: 293 [M+H]⁺. $t_R$=0.62 mins. (LCMS condition 3)
¹H NMR (300 MHz, CHLOROFORM-d): δ 7.30 (s, 1H), 4.59-4.72 (m, 5H), 3.65-3.72 (m, 1H), 2.79-3.05 (m, 5H), 2.04-2.33 (m, 3H).

Description D259

Enantiomer 1: tert-butyl 3-(4-amino-5-chloro-1H-pyrazol-1-yl)-4,4-difluoropiperidine-1-carboxylate (D259)

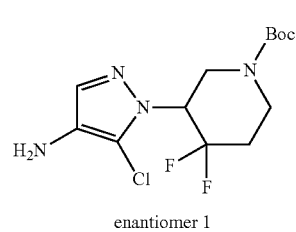

enantiomer 1

To a solution of D250 (200 g, 0.546 mmol) in EtOH/H₂O (5 mL/5 mL) was added iron powder (122 g, 2.18 mmol) and NH₄Cl (115 g, 2.18 mmol). After addition, the reaction mixture was stirred at 50° C. for 1.5 hrs. The reaction mixture was cooled to room temperature and filtered. The filtrate was concentrated and the residue was poured into 25 mL of water and extracted with EtOAc (20 mL×2). The extracts were dried over Na₂SO₄ and concentrated. The crude was purified by column C18 (ACN/H₂O=40-65%) to give the title compound D259 (145 mg, 79%).

LCMS: 237 [M+H-100]⁺. $t_R$=1.96 mins. (LCMS condition 3)
¹H NMR (300 MHz, CHLOROFORM-d): δ 7.29 (s, 1H), 4.49-4.37 (m, 1H), 4.20-3.85 (m, 3H), 3.47-3.38 (m, 1H), 3.00-2.88 (m, 2H), 2.48-2.35 (m, 1H), 2.09-1.91 (m, 1H), 1.45 (s, 9H).

Description D260

Enantiomer 2: tert-butyl 3-(4-amino-5-chloro-1H-pyrazol-1-yl)-4,4-difluoropiperidine-1-carboxylate (D260)

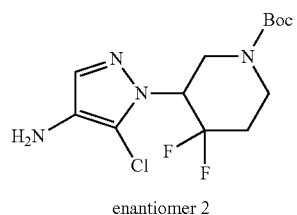

enantiomer 2

To a solution of D249 (480 g, 1.31 mmol) in EtOH/H₂O (10 mL/10 mL) was added iron powder (440 g, 7.86 mmol) and NH₄Cl (417 g, 7.86 mmol). After addition, the reaction mixture was stirred at 50° C. for 1.5 hrs. The reaction mixture was cooled to room temperature and filtered. The filtrate was concentrated and the residue was poured into 50 mL of water and extracted with EtoAc (50 mL×2). The extracts were dried over Na₂SO₄ and concentrated. The crude was purified by column C18 (ACN/H₂O=30-60%) to give the title compound D260 (400 mg, 90%).

LCMS: 237 [M+H-100]⁺. $t_R$=1.95 mins. (LCMS condition 3)
¹H NMR (300 MHz, CHLOROFORM-d): δ 7.29 (s, 1H), 4.49-4.38 (m, 1H), 4.08-3.85 (m, 3H), 3.47-3.38 (m, 1H), 2.99-2.91 (m, 2H), 2.48-2.34 (m, 1H), 2.09-1.91 (m, 1H), 1.45 (s, 9H).

Description D261

Enantiomer 1: tert-butyl 3-(5-chloro-4-((4-ethoxy-7H-pyrrolo[2,3-d]pyrimidin-2-yl)amino)-1H-pyrazol-1-yl)-4,4-difluoropiperidine-1-carboxylate (D261)

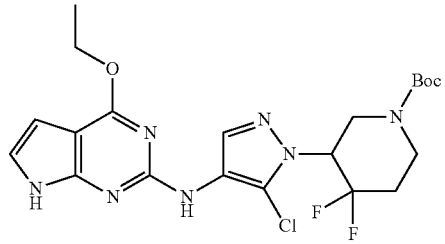

enantiomer 1

To a solution of D259 (80 g, 0.24 mmol), D1 (52 g, 0.26 mmol), K₂CO₃ (263 mg, 1.90 mmol) and X-phos (17 g, 0.036 mmol) in dioxane (6 mL) was added Pd₂(dba)₃ (22 g, 0.024 mmol) under N₂ atmosphere. After addition, the reaction mixture was stirred overnight at reflux. The reaction mixture was cooled to room temperature and filtered. The filtrate was concentrated and the crude was purified by column C18 (ACN/H₂O=35-60%) to give the title compound D261 (40 mg, 34%) as brown oil.

LCMS: 499 [M+H]⁺. $t_R$=2.30 mins. (LCMS condition 3)
¹H NMR (300 MHz, CHLOROFORM-d): δ 8.28 (s, 2H), 6.83 (s, 1H), 6.44 (s, 1H), 6.32 (s, 1H), 4.54-4.49 (m, 3H), 4.18-3.89 (m, 3H), 3.50-3.40 (m, 1H), 2.52-2.40 (m, 1H), 2.12-1.95 (m, 1H), 1.48-1.43 (m, 12H).

Description D262

Enantiomer 2: tert-butyl 3-(5-chloro-4-((4-ethoxy-7H-pyrrolo[2,3-d]pyrimidin-2-yl)amino)-1H-pyrazol-1-yl)-4,4-difluoropiperidine-1-carboxylate (D262)

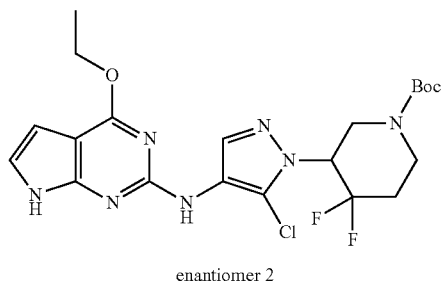

enantiomer 2

To a solution of D260 (150 g, 0.446 mmol), D1 (109 g, 0.536 mmol), K₂CO₃ (492 g, 3.57 mmol) and X-phos (32 g, 0.067 mmol) in dioxane (12 mL) was added Pd₂(dba)₃ (41 g, 0.045 mmol) under N₂ atmosphere. After addition, the reaction mixture was stirred at reflux for overnight. The reaction mixture was cooled to room temperature and filtered. The filtrate was concentrated and the residue was purified by column chromatography on silica gel (PE:EA=5:1-3:1) to give the title compound D262 (55 mg, 25%) as a yellow solid.

LCMS: 499 [M+H]⁺. $t_R$=2.30 mins. (LCMS condition 3)
¹H NMR (300 MHz, CHLOROFORM-d): δ 8.32 (s, 1H), 8.28 (s, 1H), 6.83 (dd, J=3.6, 2.1 Hz, 1H), 6.43 (dd, J=3.6, 2.1 Hz, 1H), 6.32 (s, 1H), 4.56-4.45 (m, 3H), 4.14-3.86 (m, 3H), 3.51-3.39 (m, 1H), 2.51-2.35 (m, 1H), 2.12-1.92 (m, 1H), 1.49-1.34 (m, 12H).

Description D263

1-(3,6-dihydro-2H-pyran-4-yl)-4-nitro-1H-pyrazole (D263)

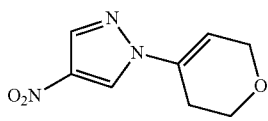 [SMILES: O=[N+]([O-])c1cnn(C2=CCOCC2)c1]

To a suspension of 4-nitro-1H-pyrazole (12.0 g, 106 mmol) and 2-(3,6-dihydro-2H-pyran-4-yl)-4,4,5,5-tetramethyl-1,3,2-dioxaborolane (16.0 g, 76.1 mmol), Cu(OAc)₂·H₂O (28.2 g, 141 mmol) in DMF (300 mL) was added pyridine (33.5 g, 423 mmol) at room temperature. The reaction was stirred overnight at 110° C. The mixture was poured in NH₃·H₂O (20%, 1000 mL), stirred for 20 minutes and then extracted with EtOAc (300 mL×3). The combined organic layers were washed with H₂O (150 mL), brine (130 mL), dried over Na₂SO₄ and concentrated. The crude was purified by column chromatography on silica gel (PE:EA=4:1-0:1) to give the title compound D258 (7.80 g, 52% yield) as a yellow solid.

¹H NMR (300 MHz, CHLOROFORM-d): δ 8.31 (s, 1H), 8.16 (s, 1H), 6.36-6.34 (m, 1H), 4.38-4.35 (m, 2H), 3.99 (t, J=5.4 Hz, 2H), 2.69-2.65 (m, 2H).

Description D264

(±)-4-(4-nitro-1H-pyrazol-1-yl)tetrahydro-2H-pyran-3-ol (D264)

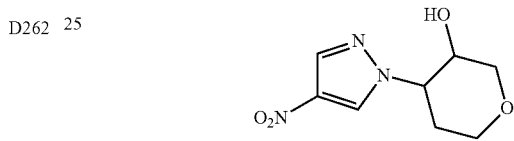

To a solution of D263 (5.80 g, 29.5 mmol) in THF (100 mL) was added BH₃·Me₂S (10 M, 15 mL, 150 mmol) at 0° C. The reaction was stirred at room temperature overnight under nitrogen. A solution of NaOH (2 M, 45 mL) was added at 0° C. dropwise followed by H₂O₂ (30%, 31 mL, 273 mmol). The mixture was stirred at room temperature for 2 hours and quenched with sat.Na₂SO₃ solution (50 mL). Solvent was removed and the residue was extracted with EA (80 mL×2). The combined organic layer was dried over Na₂SO₄ and concentrated. The crude was purified by column chromatography on silica gel (PE:EA=3:1-1:1) to give the title compound D264 (2.1 g, yield 34%) as a yellow solid.

¹H NMR (300 MHz, CD₃OD): δ 8.60 (s, 1H), 8.15 (s, 1H), 4.19-4.14 (m, 1H), 4.04-3.88 (m, 4H), 3.50 (td, J=12.3, 2.1 Hz, 1H), 3.19 (t, J=10.2 Hz, 1H), 2.29-2.23 (m, 1H), 2.07-2.00 (m, 1H).

Description D265

(±)-1-(3-fluorotetrahydro-2H-pyran-4-yl)-4-nitro-1H-pyrazole (D265)

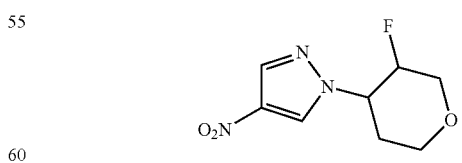

To a solution of D264 (1.90 g, 8.86 mmol) in DCM (70 mL) was added DAST (15 mL, 55.5 mmol) at −70° C. under nitrogen. The reaction was stirred overnight at room temperature. The mixture was quenched by dropping to a sat. NaHCO₃ solution (200 mL) and extracted with DCM (50 mL×2). The organic layer was dried over Na₂SO₄ and concentrated. The crude was purified by column chromatography on silica gel (PE:EA=2:1) to give the title compound D265 (570 mg, yield 31%) as a yellow solid.

$^1$H NMR (300 MHz, CHLOROFORM-d): δ 8.29 (s, 1H), 8.10 (s, 1H), 4.91 (d, J=48.9 Hz, 1H), 4.66-4.50 (m, 1H), 4.33-4.11 (m, 2H), 3.74-3.51 (m, 2H), 2.57-2.43 (m, 1H), 2.19-2.04 (m, 1H).

Description D266

(±)-5-chloro-1-(3-fluorotetrahydro-2H-pyran-4-yl)-4-nitro-1H-pyrazole (D266)

To a solution of D265 (650 g, 3.00 mmol) in THF (50 mL) was added LiHMDS (1.0 M, 6.5 mL, 6.5 mmol) with N$_2$ protection dropwise at −70° C. The reaction was stirred at −70° C. for 2 hours. C$_2$Cl$_6$ (3.07 g, 13.0 mmol) in THF (5 mL) was added and the mixture was stirred at −70° C. for another 2 hours. The reaction was quenched with sat. NH$_4$Cl solution (5 mL). The mixture was filtered and the filtrate was concentrated. The crude was purified by column chromatography on silica gel (PE:EA=3:1-1:1) to give the title compound D266 (500 mg, 67% yield) as a yellow solid.

$^1$H NMR (400 MHz, CD$_3$OD): δ 8.28 (s, 1H), 5.02-4.87 (m, 2H), 4.15-4.09 (m, 2H), 3.81-3.65 (m, 2H), 2.93-2.86 (m, 1H), 1.91-1.87 (m, 1H).

Description D267

(±)-1-(3-fluorotetrahydro-2H-pyran-4-yl)-5-methyl-4-nitro-1H-pyrazole (D267)

To a solution of D266 (500 g, 2.00 mmol), MeB(OH)$_2$ (360 g, 6.00 mmol) in dioxane (30 mL) was added Na$_2$CO$_3$ (636 g, 6.00 mmol), Pd(dppf)Cl$_2$ (250 g, 0.300 mmol) at room temperature under N$_2$ atmosphere. The mixture was stirred overnight at 100° C. The mixture was filtered and the filtrate was concentrated. The crude was purified by column chromatography on silica gel (PE:EA=3:1-1:1) to give the title compound D267 (330 mg, yield 72%) as a yellow solid $^1$H NMR (300 MHz, CHLOROFORM-d): δ 8.14 (s, 1H), 4.75 (d, J=60.0 Hz, 1H), 4.68-4.48 (m, 1H), 4.33-4.16 (m, 2H), 3.76-3.61 (m, 2H), 2.98-2.90 (m, 1H), 2.73 (s, 3H), 2.04-1.94 (m, 1H).

Description D268

(±)-1-(3-fluorotetrahydro-2H-pyran-4-yl)-5-methyl-1H-pyrazol-4-amine (D268)

A solution of D267 (310 g, 1.35 mmol) and Pd/C (120 mg, 10%) in MeOH (15 mL) and THF (10 mL) was stirred at room temperature under H$_2$ for 3 hours. The mixture was filtered and washed with MeOH (5 mL). The filtrate was concentrated to give the title compound D268 (250 mg, yield 93%) as a yellow solid.

$^1$H NMR (300 MHz, CD$_3$OD): δ 7.14 (s, 1H), 4.81-4.43 (m, 2H), 4.12-4.04 (m, 2H), 3.78-3.61 (m, 2H), 2.87-2.70 (m, 1H), 2.27 (s, 3H), 2.04-1.94 (m, 1H).

Description D269

(±)-(trans)-tert-butyl 3-fluoro-4-(4-nitro-5-vinyl-1H-pyrazol-1-yl)piperidine-1-carboxylate (D269)

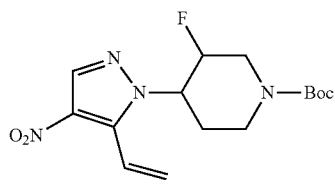 [SMILES: C=Cc1c([N+](=O)[O-])cnn1C1CCN(C(=O)OC(C)(C)C)CC1F]

A solution of D104 (700 g, 2.01 mmol), 4,4,5,5-tetramethyl-2-vinyl-1,3,2-dioxaborolane (775 g, 5.03 mmol), Na$_2$CO$_3$ (640 g, 6.03 mmol) and PdCl$_2$(dppf) (180 g, 0.22 mmol) in dioxane (10 mL) and water (2 mL) was stirred at 120° C. under nitrogen for 2 days. The mixture was cooled to room temperature and filtered. The filtrate was concentrated. The residue was poured into 50 mL of water and extracted with EtOAc (50 mL×3). The extracts were dried over Na$_2$SO$_4$ and concentrated. The crude was purified by column chromatography on silica gel (PE:EA=5:1) to give the title compound D269 (400 mg, 58%) as red oil.

LCMS: 241 [M+H-100]$^+$. t$_R$=2.24 mins. (LCMS condition 3)

$^1$H NMR (300 MHz, CHLOROFORM-d): δ 8.16 (s, 1H), 6.85-6.95 (m, 1H), 5.80-5.97 (m, 2H), 4.82-5.06 (m, 1H), 4.42-4.65 (m, 2H), 4.19-4.26 (m, 1H), 2.72-2.93 (m, 2H), 2.23-2.37 (m, 1H), 1.90-1.95 (m, 1H), 1.48 (s, 9H).

Description D270

(±)-(trans)-3-fluoro-4-(4-nitro-5-vinyl-1H-pyrazol-1-yl)piperidine (D270)

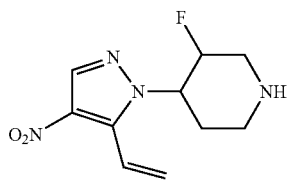 [SMILES: C=Cc1c([N+](=O)[O-])cnn1C1CCNCC1F]

To a solution of D269 (400 g, 1.18 mmol) in MeOH (5 mL) added HCl/dioxane (4 M, 5 mL). After addition, the reaction mixture was stirred overnight at room temperature. The reaction was concentrated and the residue was poured into 40 mL of water and extracted with EtOAc (40 mL×2). The aqueous layer was basified with NaOH (aq., 2N, 10 mL) to pH=9 and extracted with EtOAc (40 mL×3). The extracts were dried over $Na_2SO_4$ and concentrated to give the title compound D270 (200 mg, yield 70%) as brown oil.

LCMS: 241 [M+H]$^+$. $t_R$=1.86 mins. (LCMS condition 3)

$^1$H NMR (300 MHz, CHLOROFORM-d): δ 8.17 (s, 1H), 6.85-6.95 (m, 1H), 5.81-5.96 (m, 2H), 4.81-5.07 (m, 1H), 4.38-4.52 (m, 1H), 3.51-3.56 (m, 1H), 3.15-3.19 (m, 1H), 2.62-2.76 (m, 2H), 2.04-2.30 (m, 1H), 1.93-1.98 (m, 1H).

Description D271

(±)-(trans)-3-fluoro-4-(4-nitro-5-vinyl-1H-pyrazol-1-yl)-1-(oxetan-3-yl)piperidine (D271)

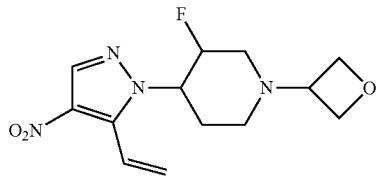 [SMILES: C=Cc1c([N+](=O)[O-])cnn1C1CCN(C2COC2)CC1F]

To a solution of D270 (200 g, 0.83 mmol) and oxetan-3-one (150 g, 2.08 mmol) in 1,2-dichloroethane (10 mL) was added NaBH(OAc)$_3$ at room temperature as portions. Then the reaction was stirred at room temperature for 2 hrs. The mixture was poured 40 mL of saturated Na$_2$CO$_3$ aqueous solution and extracted with DCM (40 mL×3). The extracts were dried over Na$_2$SO$_4$ and concentrated. The crude was purified by column C18 (30-60% ACN/H$_2$O) to give the title compound D271 (150 mg, 61% yield) as colorless oil.

LCMS: 297 [M+H]$^+$. $t_R$=1.94 mins. (LCMS condition 3)

$^1$H NMR (300 MHz, CHLOROFORM-d): δ 8.18 (s, 1H), 6.84-6.94 (m, 1H), 5.79-5.95 (m, 2H), 4.98-5.22 (m, 1H), 4.60-4.69 (m, 5H), 4.31-4.44 (m, 1H), 3.61-3.69 (m, 1H), 3.21-3.27 (m, 1H), 2.83-2.87 (m, 1H), 2.36-2.50 (m, 1H), 1.90-2.12 (m, 2H).

Description D272

(±)-(trans)-5-ethyl-1-(3-fluoro-1-(oxetan-3-yl)piperidin-4-yl)-1H-pyrazol-4-amine (D272)

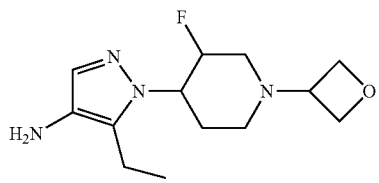 [SMILES: CCc1c(N)cnn1C1CCN(C2COC2)CC1F]

A solution of D271 (150 g, 0.51 mmol) and Pd/C (10%, 50 mg) in MeOH (5 mL) was stirred under H$_2$ at room temperature for 2 hrs. The reaction mixture was filtered and the filtrate was concentrated to give the title product D272 (125 mg, 91% yield) as colorless oil.

LCMS: 269 [M+H]$^+$. $t_R$=1.94 mins. (LCMS condition 3)

$^1$H NMR (300 MHz, CHLOROFORM-d): δ 7.23 (s, 1H), 4.88-5.13 (m, 1H), 4.61-4.67 (m, 4H), 3.88-3.98 (m, 1H), 3.60-3.69 (m, 1H), 3.15-3.21 (m, 1H), 2.79-2.84 (m, 1H), 2.61-2.64 (m, 2H), 2.32-2.46 (m, 1H), 1.98-2.11 (m, 2H), 1.89-1.95 (m, 1H), 1.16 (t, J=7.5 Hz, 3H).

Description D273 tert-butyl 3-hydroxy-4-(4-nitro-1H-pyrazol-1-yl)piperidine-1-carboxylate (D273)

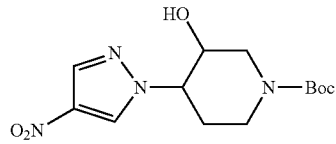 [SMILES: CC(C)(C)OC(=O)N1CCC(n2cc([N+](=O)[O-])cn2)C(O)C1]

To a solution of 4-nitro-1H-pyrazole (8.43 g, 74.62 mmol) in DCM (500 mL) was added Cs$_2$CO$_3$ and tert-butyl 7-oxa-3-azabicyclo[4.1.0]heptane-3-carboxylate (13.5 g, 67.84 mmol). The mixture was stirred at 100° C. The mixture was concentrated in vacuo and poured into water (100 mL), extracted with EtOAc (100 mL×3). The combined organic layers were washed with brine (500 mL×2), dried over Na$_2$SO$_4$ and concentrated. The crude was purified by column chromatography on silica gel (PE:EA=3:1-2:1) to give the title compound D273 (8.7 g, 41% yield) as a white solid.

$^1$H NMR (300 MHz, CHLOROFORM-d): δ 8.24 (s, 1H), 8.12 (s, 1H), 4.50-4.20 (m, 2H), 4.05-3.92 (m, 2H), 2.99-2.65 (m, 2H), 2.15-2.08 (m, 2H), 1.46 (s, 9H).

Description D274

(±)-tert-butyl 4-(4-nitro-1H-pyrazol-1-yl)-3-oxopiperidine-1-carboxylate (D274)

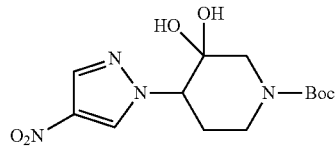

To a suspension of D273 (6.00 g, 19.2 mmol) in DCM (200 mL) was added DMP (10.6 g, 25.0 mmol) portionwise at room temperature. The reaction was stirred for 2 hours. The mixture was filtered through celite and the filtrate was washed with water (50 mL), brine (50 mL), dried over Na$_2$SO$_4$ and concentrated. The crude was purified by flash column chromatography over C18 (mobile phase: from 95% water and 5% CH$_3$CN to 20% water and 80% CH$_3$CN) to give the title compound D274 (4.0 g, 66% yield) as a yellow solid.

Description D275

(±)-tert-butyl 3,3-difluoro-4-(4-nitro-1H-pyrazol-1-yl)piperidine-1-carboxylate (D275)

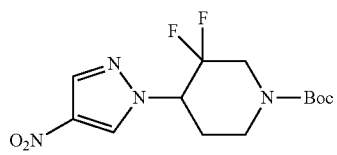

To a solution of D274 (4.00 g, 12.9 mmol) in DCM (60 mL) was added DAST (8.31 g, 51.6 mmol) at −78° C. under N$_2$. The reaction was stirred for 2 hrs at 0° C. and then overnight at room temperature. The mixture was quenched with sat.NaHCO$_3$ solution (50 mL) at 5° C. followed by 50 mL of water and then extracted with DCM (50 mL×3). The combined organic layers were washed with brine (75 mL), dried over Na$_2$SO$_4$ and concentrated. The crude was purified by column chromatography on silica gel (PE:EA=30:1-5:1) to give the title compound D275 (1.65 g, 38% yield) as yellow foam.

LCMS: 233 [M+H-100]$^+$. $t_R$=2.08 mins. (LCMS condition 3)

$^1$H NMR (300 MHz, CHLOROFORM-d): δ 8.29 (s, 1H), 8.12 (s, 1H), 4.29-4.71 (m, 3H), 2.94-3.31 (m, 2H), 2.18-2.42 (m, 2H), 1.49 (s, 9H).

Description D276

(±)-tert-butyl 4-(5-chloro-4-nitro-1H-pyrazol-1-yl)-3,3-difluoropiperidine-1-carboxylate (D276)

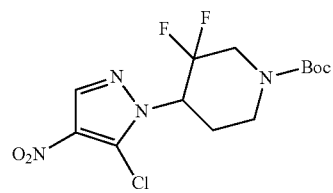 [SMILES: CC(C)(C)OC(=O)N1CCC(n2ncc([N+](=O)[O-])c2Cl)C(F)(F)C1]

To a solution of D275 (1.40 g, 4.22 mmol) in dry THF (25 mL) was added LiHMDS (1 M in THF, 7.6 mL, 7.6 mmol) dropwise at −78° C. under N$_2$. The mixture was stirred for 1 hour at the temperature and then a solution of hexachloroethane (2.50 g, 10.6 mmol) in dry THF (5 mL) was added dropwise. The reaction was further stirred for 30 min at −78° C. The reaction was quenched with sat. NH$_4$Cl solution (30 mL) followed by 50 mL of water after dry ice-bath was removed. The mixture was extracted with EtOAc (50 mL×3). The combined organic layers were washed with brine (50 mL), dried over Na$_2$SO$_4$, and filtered. The solvent was evaporated in vacuo and purified by column chromatography on silica gel (PE:EA=30:1-5:1) to give the title compound D276 (1.13 g, 73% yield) as a yellow foam.

LCMS: 267 [M+H-100]$^+$. $t_R$=1.77 mins. (LCMS condition 3)

$^1$H NMR (300 MHz, CHLOROFORM-d): δ 8.25 (s, 1H), 4.69-4.83 (m, 1H), 4.17-4.42 (m, 2H), 3.34-3.55 (m, 1H), 3.20-3.30 (m, 1H), 2.54-2.68 (m, 1H), 2.07-2.18 (m, 1H), 1.48 (s, 9H).

Description D277

(±)-tert-butyl 3,3-difluoro-4-(5-methyl-4-nitro-1H-pyrazol-1-yl)piperidine-1-carboxylate (D277)

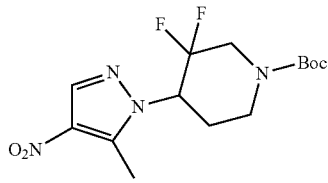 [SMILES: Cc1c([N+](=O)[O-])cnn1C1CCN(C(=O)OC(C)(C)C)CC1(F)F]

To a mixture of D276 (750 g, 2.05 mmol), methylboronic acid (1.1 g, 18 mmol) in dioxane (12 mL) was added Pd(dppf)Cl$_2$ (155 g, 0.210 mmol), followed by Na$_2$CO$_3$ (2M, 3.1 mL, 6.2 mmol) under N$_2$. The mixture was stirred for 1 day at reflux. The reaction was cooled to room temperature and filtered through celite. The filtrated was diluted with water (50 mL) and extracted with EtOAc (40 mL×3). The combined organic layers were washed with brine (30 mL), dried over Na$_2$SO$_4$ and filtered. The solvent was evaporated in vacuo and purified by column chromatography over silica gel (PE:EA=30:1-5:1) to give the title compound D277 (480 mg, 67% yield) as a yellow foam.

LCMS: 247 [M+H-100]$^+$. $t_R$=1.74 mins. (LCMS condition 3)

$^1$H NMR (300 MHz, CHLOROFORM-d): δ 8.15 (s, 1H), 4.40-4.55 (m, 1H), 4.18-4.35 (m, 1H), 3.43-3.56 (m, 1H), 3.22-3.38 (m, 1H), 2.56-2.73 (m, 4H), 2.11-2.21 (m, 1H), 1.48 (s, 9H).

Description D278 and D279

Enantiomer 1: 3,3-difluoro-4-(5-methyl-4-nitro-1H-pyrazol-1-yl)-1-(oxetan-3-yl)piperidine (D278)

Enantiomer 2: 3,3-difluoro-4-(5-methyl-4-nitro-1H-pyrazol-1-yl)-1-(oxetan-3-yl)piperidine (D279)

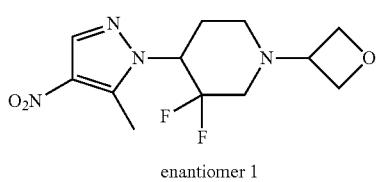

enantiomer 1

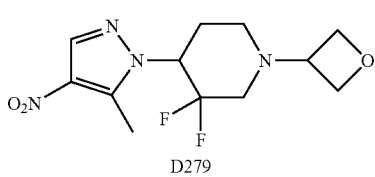

D279 enantiomer 2

A mixture of D277 (480 g, 1.39 mmol) in HCl/dioxane (4M, 10 mL) was stirred for 1 hour at room temperature and then evaporated in vacuo to give a white solid (LCMS: 247 [M+H]$^+$. $t_R$=1.79 mins. (LCMS condition 3) $^1$H NMR (300 MHz, DMSO-d$_6$): δ 9.90 (br s, 2H), 8.35 (s, 1H), 5.38-5.46 (m, 1H), 3.70-3.97 (m, 2H), 3.45-3.49 (m, 1H), 3.12-3.22 (m, 1H), 2.64-2.77 (m, 4H), 2.24-2.33 (m, 1H).) A mixture of the intermediate (350 g, 1.24 mmol) and oxetan-3-one (786 g, 10.9 mmol) in DCM (15 mL) was stirred for 30 min at room temperature. NaBH(OAc)$_3$ (1.18 g, 5.56 mmol) was added portionwise. The mixture was stirred for 2 hrs. The reaction was quenched with sat. NaHCO$_3$ solution (50 mL) and then extracted with DCM (40 mL×3). The combined organic layers were washed with brine (50 mL), dried over Na$_2$SO$_4$, and filtered. The solvent was evaporated in vacuo and purified by column chromatography on silica gel (PE:EA=5:1-1:1) to give the title compound as a yellow foam (250 mg, 66% yield), which was separated by chiral HPLC to give the title compounds D278 (75 mg, $t_R$=6.627, 100% ee) and D279 (130 mg, $t_R$=7.895, 100% ee) as white foam.

LCMS: 303 [M+H]$^+$. $t_R$=1.82 mins. (LCMS condition 3)
$^1$H NMR (300 MHz, CHLOROFORM-d): δ 8.15 (s, 1H), 4.61-4.72 (m, 4H), 4.33-4.42 (m, 1H), 3.75-3.81 (m, 1H), 3.05-3.15 (m, 2H), 2.77-2.85 (m, 1H). 2.70 (s, 3H), 2.43-2.56 (m, 1H), 2.34 (t, J=11.4 Hz, 1H), 2.10-2.17 (m, 1H).

Description D280

Enantiomer 1: 1-(3,3-difluoro-1-(oxetan-3-yl)piperidin-4-yl)-5-methyl-1H-pyrazol-4-amine (D280)

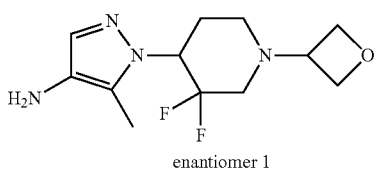

D280 enantiomer 1

A mixture of D278 (100 g, 0.330 mmol) and Pd/C (10%, 20 mg) in MeOH (5 mL) was stirred for 3 hrs under H$_2$ atmosphere (balloon). The reaction was filtered and the filtrate was evaporated in vacuo to give the title compounds D280 as a white solid (70 mg, 78% yield).

LCMS: 273 [M+H]$^+$. $t_R$=1.63 mins. (LCMS condition 3)
$^1$H NMR (300 MHz, CD$_3$OD): δ 7.20 (s, 1H), 4.42-4.70 (m, 5H), 3.68-3.76 (m, 1H), 2.96-3.13 (m, 2H), 2.59-2.73 (m, 1H), 2.38-2.52 (m, 1H), 2.21-2.31 (m, 4H), 1.93-2.02 (m, 1H).

Description D281

Enantiomer 2: 1-(3,3-difluoro-1-(oxetan-3-yl)piperidin-4-yl)-5-methyl-1H-pyrazol-4-amine (D281)

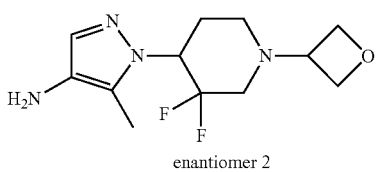

D281 enantiomer 2

A mixture of D279 (170 g, 0.560 mmol) and Pd/C (10%, 50 mg) in MeOH (5 mL) was stirred for 2 hrs under H$_2$ atmosphere (balloon). The reaction was filtered and the filtrate was evaporated in vacuo to give the title compounds D281 (80 mg, 52% yield) as a white solid.

LCMS: 273 [M+H]$^+$. $t_R$=1.63 mins. (LCMS condition 3)
$^1$H NMR (300 MHz, CD$_3$OD): δ 7.20 (s, 1H), 4.41-4.70 (m, 5H), 3.66-3.78 (m, 1H), 2.90-3.15 (m, 2H), 2.58-2.75 (m, 1H), 2.38-2.51 (m, 1H), 2.21-2.36 (m, 4H), 1.90-2.03 (m, 1H).

Description D282

(±)-4-(5-chloro-4-nitro-1H-pyrazol-1-yl)-3,3-difluoropiperidine (D282)

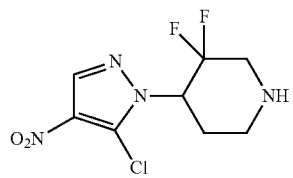 [SMILES: O=[N+]([O-])c1cnn(C2CCNCC2(F)F)c1Cl]

To a stirring solution of D276 (750 g, 2.05 mmol) in MeOH (5 mL) was added HCl/dioxane solution (4N, 10 mL). Then the reaction mixture was stirred at room temperature for 1 hour. The reaction mixture was concentrated to give the title compounds D282 (650 mg) as a yellow solid.

LCMS: 267 [M+H]$^+$. $t_R$=1.30 mins. (LCMS condition 3)

Description D283 and D284

Enantiomer 1: 4-(5-chloro-4-nitro-1H-pyrazol-1-yl)-3,3-difluoro-1-(oxetan-3-yl)piperidine (D283)

Enantiomer 2: 4-(5-chloro-4-nitro-1H-pyrazol-1-yl)-3,3-difluoro-1-(oxetan-3-yl)piperidine (D284)

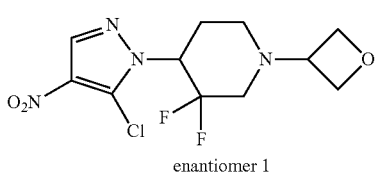

D283 enantiomer 1

-continued

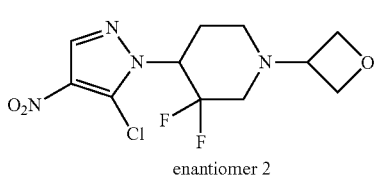

D284 enantiomer 2

In two separate preparations to a stirring solution of D282 (100 g, 0.376 mmol and 550 g, 2.07 mmol) and oxetan-3-one (135 g, 1.88 mmol and 1.50 g, 20.7 mmol) in DCE (10 mL and 50 mL) was added sodium triacetoxyborohydride (238 g, 1.13 mmol and 2.18 g, 10.35 mmol). The reactions were stirred at room temperature (overnight and for 15 hrs). The mixtures were quenched by NaHCO$_3$ solution (50 mL and 100 mL), and extracted with CH$_2$Cl$_2$ (50 mL×3 and 50 mL×4). The combined organic layers were dried and concentrated. The crudes were purified by column chromatography on silica gel (PE:EA=4:1 to 1:1) to afford desired product (60 mg and 350 mg) as a colorless to yellow solid. The two preparations were then joined together and separated by chiral HPLC (chiralpak IA 5 um 4.6*250 mm, MeOH/EtOH: 50/50, 1.0 mL/min) to give the title compounds D283 (120 mg, $t_R$=9.694) and D284 (120 mg, $t_R$=1.664) as yellow solids.

LCMS: 323 [M+H]$^+$. $t_R$=1.85 mins. (LCMS condition 3)

$^1$H NMR (300 MHz, CHLOROFORM-d): δ 8.24 (s, 1H), 4.72-4.60 (m, 4H), 3.81-3.72 (m, 1H), 3.24-3.02 (m, 2H), 2.84-2.71 (m, 1H), 2.57-2.44 (m, 1H), 2.38-2.30 (m, 1H), 2.17-2.04 (m, 1H).

Description D285

Enantiomer 1: 5-chloro-1-(3,3-difluoro-1-(oxetan-3-yl)piperidin-4-yl)-1H-pyrazol-4-amine (D285)

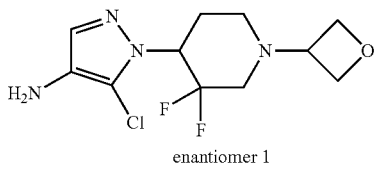

D285 enantiomer 1

To a solution of D283 (120 g, 0.373 mmol) in EtOH (20 mL) and H$_2$O (20 mL) was added iron powder (104 g, 1.86 mmol) and NH$_4$Cl (100 g, 1.86 mmol). Then the reaction was heated to 45° C. and stirred overnight. The reaction mixture was cooled to room temperature, filtered, washed with EtOH (80 mL). The combined filtrate was concentrated to give the title compound D285 (100 mg) as red solid.

LCMS: 293 [M+H]$^+$. $t_R$=1.57 mins. (LCMS condition 3)

$^1$H NMR (300 MHz, CHLOROFORM-d): δ 7.31 (s, 1H), 4.67-4.63 (m, 4H), 4.49-4.43 (m, 1H), 3.77-3.73 (m, 1H), 3.12-2.97 (m, 2H), 2.69-2.62 (m, 1H), 2.53-2.41 (m, 1H), 2.35-2.27 (m, 1H), 2.10-2.03 (m, 1H).

Description D286

Enantiomer 2: 5-chloro-1-(3,3-difluoro-1-(oxetan-3-yl)piperidin-4-yl)-1H-pyrazol-4-amine (D286)

D286 enantiomer 2

To a solution of D284 (120 g, 0.373 mmol) in EtOH (20 mL) and H$_2$O (20 mL) was added iron powder (104 g, 1.86 mmol) and NH$_4$Cl (100 g, 1.86 mmol). Then the reaction was heated to 45° C. and stirred overnight. The reaction mixture was cooled to room temperature, filtered, washed with EtOH (80 mL). The combined filtrate was concentrated to give the title compound D286 (100 mg) as red solid.

LCMS: 293 [M+H]$^+$. $t_R$=1.57 mins. (LCMS condition 3)

Description D287

(R)-tert-butyl 3-(4-nitro-1H-pyrazol-1-yl)piperidine-1-carboxylate (D287)

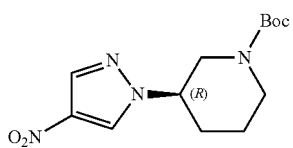

To a solution of (S)-tert-butyl 3-hydroxypiperidine-1-carboxylate (4.50 g, 22.4 mmol), 4-nitro-1H-pyrazole (2.53 g, 22.4 mmol), PPh$_3$ (11.7 g, 44.8 mmol) in THF (100 mL) was added slowly DIAD (9.05 g, 44.8 mmol) at room temperature under N$_2$. The reaction was stirred overnight at room temperature. The mixture was quenched with H$_2$O (100 mL) and concentrated. The residue was extracted with EtOAc (100 mL×3), drier over Na$_2$SO$_4$ and concentrated. The crude was purified by column chromatography on silica gel (PE:EA=10:1) and then column chromatography on C18 to give the title compound D287 (2.67 g, 40% yield) as red oil.

$^1$H NMR (300 MHz, CHLOROFORM-d): δ 8.26 (s, 1H), 8.08 (s, 1H), 4.28-4.19 (m, 1H), 4.17-4.07 (m, 1H), 3.82-3.74 (m, 1H), 3.49-3.43 (m, 1H), 3.17-3.08 (m, 1H), 2.20-2.13 (m, 2H), 1.79-1.60 (m, 2H), 1.47 (s, 9H).

Description D288

(R)-tert-butyl 3-(5-chloro-4-nitro-1H-pyrazol-1-yl)piperidine-1-carboxylate (D288)

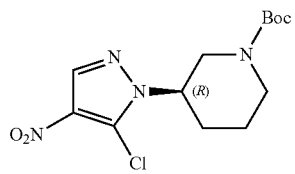

To a solution of D287 (1.20 g, 4.05 mmol) in THF (30 mL) was added slowly LiHMDS (1M in THF, 8 mL, 8 mmol) at −70° C. under N$_2$. The reaction was stirred at −70° C. for 45 mins and a solution of hexachloroethane (1.80 g, 7.60 mmol) in THF (5 mL) was added at −78° C. The reaction was stirred at −70° C. for 1 hour and then quenched by NH$_4$Cl aq. (5 mL). The mixture was filtered and the filtrate was concentrated. The crude was purified by chromatography on silica gel (PE:EA=10:1) to give the title compound D288 (1.2 g, 90% yield) as colorless oil.

$^1$H NMR (300 MHz, CHLOROFORM-d): δ 8.17 (s, 1H), 4.40-4.06 (m, 3H), 3.18 (t, J=11.4 Hz, 1H), 2.82 (td, J=11.4, 2.4 Hz, 1H), 2.17-2.09 (m, 2H), 1.94-1.88 (m, 1H), 1.71-1.60 (m, 1H), 1.46 (s, 9H).

Description D289

(R)-tert-butyl 3-(5-methyl-4-nitro-1H-pyrazol-1-yl)piperidine-1-carboxylate (D289)

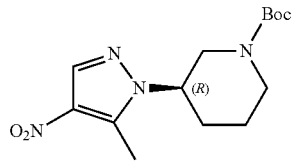

A mixture of D288 (1.20 g, 3.62 mmol), methylboronic acid (2.17 g, 36.2 mmol), Na$_2$CO$_3$ (3.84 g, 36.2 mmol) and Pd(dppf)Cl$_2$ (440 g, 0.543 mmol) in dioxane (40 mL) and H$_2$O (5 mL) was stirred overnight under N$_2$ at 100° C. The reaction was cooled to room temperature and filtered through a celite pad. The filtrate was concentrated and purified by column chromatography on silica gel (PE:EA=5:1) to give the title compound D289 (900 mg, 90% yield) as colorless oil.

$^1$H NMR (300 MHz, CHLOROFORM-d): δ 8.09 (s, 1H), 4.27-4.03 (m, 3H), 3.15 (t, J=11.4 Hz, 1H), 2.78 (t, J=12.4 Hz, 1H), 2.69 (s, 3H), 2.28-2.18 (m, 1H), 2.16-2.02 (m, 1H), 1.92-1.86 (m, 1H), 1.68-1.54 (m, 1H).

Description D290

(R)-3-(5-methyl-4-nitro-1H-pyrazol-1-yl)piperidine hydrochloride (D290)

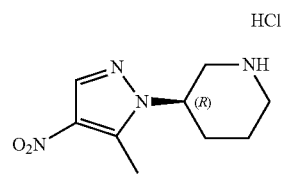

To a solution of 3N HCl/dioxane (15 mL) was added D289 (900 g, 8.98 mmol) at room temperature. The reaction was stirred for 2 hours at room temperature and then concentrated to give the title product D290 (700 mg 98%) as a white solid.

$^1$H NMR (300 MHz, DMSO-d$_6$): δ 9.25 (br s, 2H), 8.33 (s, 1H), 4.79 (br s, 1H), 3.45 (dd, J=11.1, 3.3 Hz, 1H), 3.28-3.20 (m, 2H), 3.02-2.92 (m, 1H), 2.66 (s, 3H), 2.09-1.90 (m, 4H).

Description D291

(R)-3-(5-methyl-4-nitro-1H-pyrazol-1-yl)-1-(oxetan-3-yl)piperidine (D291)

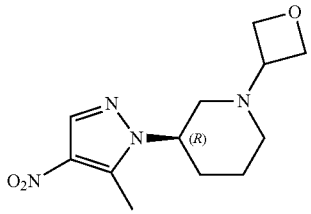

To a solution of D290 (500 g, 2.03 mmol) and oxetan-3-one (1.46 g, 20.3 mmol) in DCM (30 mL) was added NaBH(OAc)$_3$ (2.16 g, 10.2 mmol) in portions. The reaction was stirred overnight at room temperature. The reaction was quenched with NaHCO$_3$ solution (15 mL) and extracted with DCM (30 mL×2). The DCM was dried over Na$_2$SO$_4$ and concentrated. The crude was purified by column chromatography on silica gel (EtOAc) to give the title product D291 (400 mg, yield 74%) as a white solid.

$^1$H NMR (300 MHz, CHLOROFORM-d): δ 8.07 (s, 1H), 4.70-4.55 (m, 4H), 4.35-4.25 (m, 1H), 3.61-3.52 (m, 1H), 2.86-2.76 (m, 2H), 2.68 (s, 3H), 2.40 (t, J=10.5 Hz, 1H), 2.02-1.71 (m, 5H).

Description D292

(R)-5-methyl-1-(1-(oxetan-3-yl)piperidin-3-yl)-1H-pyrazol-4-amine (D292)

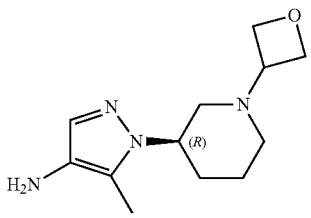

A solution of D291 (400 g, 1.50 mmol) and Pd/C (200 mg, 10% wet) in MeOH (30 mL) was stirred at 30° C. under H$_2$. The mixture was filtered and washed with MeOH (5 mL). The filtrate was concentrated to give the title compound D292 (300 mg, 85% yield) as yellow oil.

$^1$H NMR (300 MHz, CHLOROFORM-d): δ 7.15 (s, 1H), 4.69-4.56 (m, 4H), 4.18-4.08 (m, 1H), 3.58-3.51 (m, 1H), 2.85-2.74 (m, 2H), 2.32 (t, J=10.8 Hz, 1H), 2.18 (s, 3H), 1.97-1.71 (m, 5H).

Description D293

(S)-tert-butyl 3-(4-nitro-1H-pyrazol-1-yl)piperidine-1-carboxylate (D293)

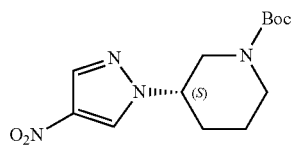

To a solution of (R)-tert-butyl 3-hydroxypiperidine-1-carboxylate (5.00 g, 24.7 mmol), 4-nitro-1H-pyrazole (2.80 g, 24.7 mmol), PPh$_3$ (13.0 g, 49.4 mmol) in THF (100 mL) was added slowly DIAD (10.0 g, 49.4 mmol) at room temperature with N$_2$ protection. The mixture was stirred overnight at room temperature. The mixture was quenched with H$_2$O (100 mL) and concentrated. The residue was extracted with EA (100 mL×3), dried over Na$_2$SO$_4$ and concentrated. The crude was purified by column chromatography on silica gel (PE:EA=10:1) and flash column chromatography on C18 to give the title compound D293 as red oil (3.10 g, 42% yield).

$^1$H NMR (300 MHz, CHLOROFORM-d): δ 8.26 (s, 1H), 8.08 (s, 1H), 4.28-4.19 (m, 1H), 4.14-4.07 (m, 1H), 3.82-3.74 (m, 1H), 3.49-3.42 (m, 1H), 3.16-3.07 (m, 1H), 2.20-2.13 (m, 2H), 1.79-1.60 (m, 2H), 1.47 (s, 9H).

Description D294

(S)-tert-butyl 3-(5-chloro-4-nitro-1H-pyrazol-1-yl)piperidine-1-carboxylate (D294)

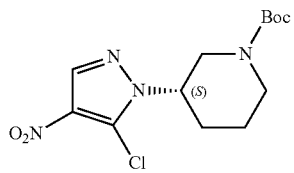

To a solution of D293 (1.20 g, 4.05 mmol) in THF (30 mL) was added slowly LiHMDS (1M in THF, 8 mL, 8 mmol) at −70° C. under N$_2$ atmosphere. The reaction was stirred at this temperature for 45 mins. Hexachloroethane (1.80 g, 7.60 mmol) in THF (5 mL) was added at −78° C. The reaction was stirred at this temperature for 1 hour and then quenched by NH$_4$Cl aq. (5 mL). The mixture was filtered and the filtrate was concentrated. The crude was purified by chromatography on silica gel (PE:EA=10:1) to give the title compound D294 (1.1 g, 83% yield) as colorless oil.

$^1$H NMR (300 MHz, CHLOROFORM-d): δ 8.17 (s, 1H), 4.42-4.07 (m, 3H), 3.18 (t, J=12.0 Hz, 1H), 2.82 (td, J=12.0, 2.4 Hz, 1H), 2.17-2.09 (m, 2H), 1.94-1.88 (m, 1H), 1.71-1.57 (m, 1H), 1.46 (s, 9H).

Description D295

(S)-tert-butyl 3-(5-methyl-4-nitro-1H-pyrazol-1-yl)piperidine-1-carboxylate (D295)

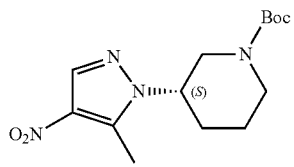

To a solution of D294 (1.10 g, 3.32 mmol), methylboronic acid (1.72 g, 33.2 mmol), Na$_2$CO$_3$ (3.50 g, 33.2 mmol) in dioxane (40 mL) and H$_2$O (5 mL) was added Pd(dppf)Cl$_2$ (407 g, 0.498 mmol). The mixture was stirred overnight under N$_2$ at 100° C. The reaction was cooled to room temperature and filtered through a celite pad. The filtrate was concentrated and purified by column chromatography on silica gel (PE:EA=5:1) to give the title compound D295 (830 mg, 81% yield) as colorless oil.

$^1$H NMR (300 MHz, CHLOROFORM-d): δ 8.09 (s, 1H), 4.23-4.03 (m, 3H), 3.15 (t, J=11.7 Hz, 1H), 2.78 (t, J=11.7 Hz, 1H), 2.69 (s, 3H), 2.26-2.19 (m, 1H), 2.18-2.02 (m, 1H), 1.93-1.86 (m, 1H), 1.68-1.53 (m, 1H).

Description D296

(S)-3-(5-methyl-4-nitro-1H-pyrazol-1-yl)piperidine hydrochloride (D296)

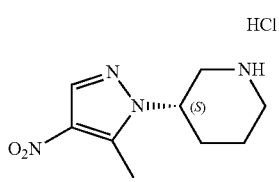

To a solution of 3N HCl/dioxane (15 mL) was added D295 (830 g, 2.68 mmol) at room temperature. The reaction was stirred for 2 hours at room temperature and then concentrated to give the title compound D296 (600 mg 91%) as a white solid.

$^1$H NMR (300 MHz, DMSO-$d_6$): δ 9.39 (br s, 2H), 8.32 (s, 1H), 4.91-4.77 (m, 1H), 3.44 (dd, J=11.4, 3.0 Hz, 1H), 3.32-3.14 (m, 2H), 3.02-2.88 (m, 1H), 2.66 (s, 3H), 2.09-1.90 (m, 4H).

Description D297

(S)-3-(5-methyl-4-nitro-1H-pyrazol-1-yl)-1-(oxetan-3-yl)piperidine (D297)

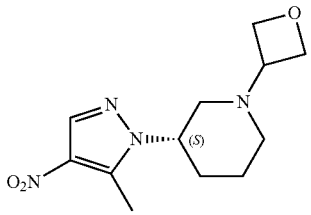

To a solution of D296 (500 g, 2.03 mmol) and oxetan-3-one (1.46 g, 20.3 mmol) in DCM (30 mL) was added NaBH(OAc)$_3$ (2.16 g, 10.2 mmol) in portions. The reaction was stirred overnight at room temperature and, then quenched with NaHCO$_3$ (15 mL) and extracted with DCM (30 mL×2). The combined organic layers were dried over Na$_2$SO$_4$ and concentrated. The crude was purified by column (EA) to give the title compound D297 (400 mg, yield 74%) as a white solid.

$^1$H NMR (300 MHz, CHLOROFORM-d): δ 8.07 (s, 1H), 4.70-4.55 (m, 4H), 4.35-4.25 (m, 1H), 3.61-3.52 (m, 1H), 2.86-2.76 (m, 2H), 2.68 (s, 3H), 2.40 (t, J=10.5 Hz, 1H), 2.02-1.86 (m, 5H).

Description D298

(S)-5-methyl-1-(1-(oxetan-3-yl)piperidin-3-yl)-1H-pyrazol-4-amine (D298)

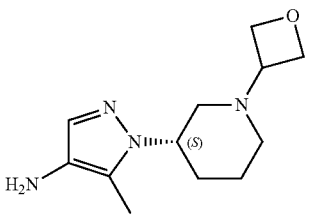

To a solution of D297 (350 g, 1.31 mmol) in MeOH (30 mL) was added Pd/C (200 mg, 10% wet). The reaction was stirred at room temperature with 1 atm H$_2$ for 2 hrs. The mixture was filtered and washed with MeOH (5 mL). The filtrate was concentrated to give the title compound D298 (283 mg, 91% yield) as yellow oil.

$^1$H NMR (300 MHz, CHLOROFORM-d): δ 57.15 (s, 1H), 4.69-4.56 (m, 4H), 4.19-4.09 (m, 1H), 3.58-3.49 (m, 1H), 2.85-2.74 (m, 2H), 2.33 (t, J=10.5 Hz, 1H), 2.18 (s, 3H), 1.97-1.73 (m, 5H).

Description D299

3-(benzyloxy)-1-methylcyclobutanol (D299)

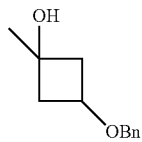

Methylmagnesium bromide (34.0 mL, 34.0 mmol) was added dropwise to a solution of 3-(benzyloxy)cyclobutanone (4 g, 22.70 mmol) in toluene (40 mL) and THF (4.00 mL) at −78° C. The mixture was stirred at −78° C. for 1 hour. The reaction was then quenched by aqueous NH$_4$Cl solution. The aqueous layer was extracted with ethyl acetate and the combined organic layers were washed with brine, dried over Na$_2$SO$_4$ and concentrated. The crude was purified by column chromatography on C18 (0.05% TFA in water) to give the title compound D299 (800 g, 4.16 mmol, 18.33% yield).

Description D300

1-(3-(benzyloxy)-1-methylcyclobutyl)-4-nitro-1H-pyrazole (D300)

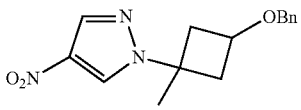 [SMILES: CC1(n2cc([N+](=O)[O-])cn2)CC(OCc2ccccc2)C1]

To a solution of 4-nitro-1H-pyrazole (471 g, 4.16 mmol), triphenylphosphine (2183 g, 8.32 mmol), D299 (800 g, 4.16 mmol) in THF (20 mL) was added DIAD (1.618 mL, 8.32 mmol) and the mixture was stirred at room temperature for 3 days. Solvent was evaporated and the crude was purified by column chromatography on silica gel (20% EA in PE) to give the title compound D300.

LCMS: 288 [M+H]⁺. $t_R$=3.742 mins. (LCMS condition 1)

Description D301

1-(3-(benzyloxy)-1-methylcyclobutyl)-5-chloro-4-nitro-1H-pyrazole (D301)

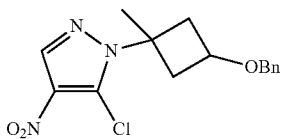

To a solution of D300 (1200 g, 4.18 mmol) in THF (30 mL) was added LiHMDS (6.26 mL, 6.26 mmol, 1M in THF) dropwise at −78° C. for 1 hour. Perchloroethane (1483 g, 6.26 mmol) in THF (5 mL) was then added and the reaction was stirred at −78° C. for 2 hours. The reaction solution was poured into saturated NH₄Cl (30 mL) and extracted with ethyl acetate (15 mL×2). The combined extracts were washed with brine, dried over Na₂SO₄, filtered and concentrated. The crude was purified by column chromatography on silica gel (20% EA in PE) to give the title compound D301 (1 g, 3.11 mmol, 74.4% yield).

LCMS: 322 [M+H]⁺. $t_R$=4.090 mins. (LCMS condition 1)

¹H NMR (400 MHz, DMSO-d₆): δ 8.47 (s, 1H), 7.34 (m, 5H), 4.85 (m, 1H), 4.44 (s, 2H), 4.10 (m, 1H), 3.16 (m, 2H), 1.70 (s, 3H).

Description D302

1-(3-(benzyloxy)-1-methylcyclobutyl)-5-methyl-4-nitro-1H-pyrazole (D302)

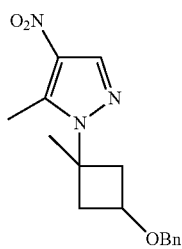 [SMILES: Cc1c([N+](=O)[O-])cnn1C1(C)CC(OCc2ccccc2)C1]

A mixture of D301 (900 g, 2.80 mmol), methylboronic acid (1172 g, 19.58 mmol), potassium phosphate (1781 g, 8.39 mmol) and PdCl₂(dtbpf) (182 g, 0.280 mmol) in DMF (8 mL) and water (2 mL) was irradiated by microwave to 100° C. for 1 h. The mixture was diluted with ethyl acetate and water was added. The layers were separated, and the organic layer was washed with brine, dried over sodium sulfate, filtered, and concentrated. The crude was purified using column chromatography on silica gel (20% EA in PE) to give the title compound D302 (1050 g, 3.48 mmol).

LCMS: 302 [M+H]⁺. $t_R$=3.87 mins. (LCMS condition 1)

Description D303

3-(4-amino-5-methyl-1H-pyrazol-1-yl)-3-methylcyclobutanol (D303)

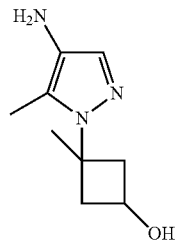

A mixture of D302 (230 mg, 0.763 mmol) and Pd/C (81 g, 0.076 mmol) in methanol (10 mL) was stirred at room temperature under hydrogen for 16 hours. After filtration, the filtrate was concentrated to give the title compound D303 (120 g, 0.662 mmol, 87% yield).

LCMS: 182 [M+H]⁺. $t_R$=3.32 mins. (LCMS condition 1)

Description D304

3-(4-((4-ethoxy-7H-pyrrolo[2,3-d]pyrimidin-2-yl)amino)-5-methyl-1H-pyrazol-1-yl)-3-methylcyclobutanol (D304)

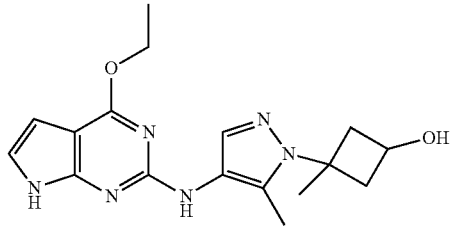 [SMILES: CCOc1nc(Nc2cnn(C3(C)CC(O)C3)c2C)nc2[nH]ccc12]

To a solution of D303 (431 g, 2.378 mmol) in isobutanol (12 mL) was added potassium carbonate (986 g, 7.13 mmol), Pd₂dba₃ (218 g, 0.238 mmol), D1 (470 g, 2.378 mmol), X-phos (227 g, 0.476 mmol). The resulting reaction mixture was irradiated by microwave to 110° C. for 1 hr. The reaction mixture was diluted with ethyl acetate (15 mL) and filtered. The filtrate was concentrated and the crude was purified by flash chromatography on silica gel (30% MeOH in DCM) to give the title compound D304 (650 g, 1.898 mmol, 80% yield).

LCMS: 343 [M+H]⁺. $t_R$=2.25 mins. (LCMS condition 1)

Description D305 tert-butyl 1-methyl-7-oxa-3-azabicyclo[4.1.0]heptane-3-carboxylate (D305)

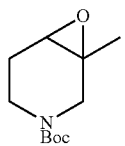

To a solution of tert-butyl 3-methyl-5,6-dihydropyridine-1(2H)-carboxylate (13.5 g, 68.5 mmol) in DCM (200 mL) was added m-CPBA (23.6 g, 137 mmol) at 0° C. for 40 min. The mixture was stirred overnight at room temperature. The reaction was poured into sat Na₂CO₃ (50 mL) solution and then was extracted with DCM (50 mL×3). The combined organic layers were washed with brine (100 mL) and concentrated. The crude was purified by column chromatography on silica gel (PE:EA=10:1-6:1) to give the title compound D305 (9.70 g, yield 66%) as yellow oil.

$^1$H NMR (300 MHz, CHLOROFORM-d): δ 3.69-3.54 (m, 2H), 3.32-3.20 (m, 2H), 3.09 (t, J=1.8 Hz, 1H), 2.06-1.81 (m, 2H), 1.43 (s, 9H), 1.33 (s, 3H).

Description D306

(±)-(trans)-tert-butyl 3-hydroxy-3-methyl-4-(4-nitro-1H-pyrazol-1-yl)piperidine-1-carboxylate (D306)

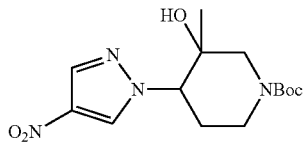 [SMILES: CC(C)(C)OC(=O)N1CCC(n2cc([N+](=O)[O-])cn2)C(C)(O)C1]

To a solution of 4-nitro-1H-pyrazole (5.66 g, 50.1 mmol) in DMF (500 mL) was added Cs₂CO₃ (29.7 g, 91.1 mmol) and D305 (9.70 g, 45.5 mmol). The reaction was stirred at 100° C. for 48 hours. The mixture was concentrated in vacuo, poured into water (100 mL), extracted with DCM (100 mL×3). The combined organic layers were washed with brine (300 mL×2), dried over Na₂SO₄ and concentrated. The crude was triturate with diethyl ether (200 mL) to give the title compound D306 (8.1 g, yield 54%) as a white solid.

$^1$H NMR (300 MHz, CHLOROFORM-d): δ 8.22 (s, 1H), 8.13 (s, 1H), 4.53-4.35 (m, 1H), 4.23 (t, J=8.4 Hz, 1H), 4.16-4.04 (m, 1H), 3.78-3.66 (br s, 1H), 3.00-2.85 (m, 2H), 2.17-2.12 (m, 2H), 1.48 (s, 9H), 0.96 (s, 3H).

Description D307

(±)-(cis)-tert-butyl 3-fluoro-3-methyl-4-(4-nitro-1H-pyrazol-1-yl)piperidine-1-carboxylate (D307)

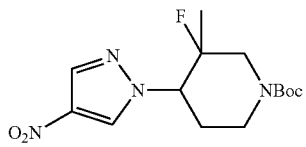 [SMILES: CC(C)(C)OC(=O)N1CCC(n2cc([N+](=O)[O-])cn2)C(C)(F)C1]

To a solution of D306 (8.10 g, 24.8 mmol) in DCM (500 mL) was added DAST (12.0 g, 74.55 mmol) at −78° C. under N₂ for 30 min. The reaction was stirred overnight at room temperature. The resulting mixture was quenched with sat.NaHCO₃ solution (300 mL) at 5° C., and then was extracted with DCM (200 mL×3). The combined organic layers were concentrated in vacuo. The crude was purified by column chromatography on silica gel (PE:EA=8:1 to 5:1) to give the title compound D307 (4.5 g, 55% yield) as a white solid.

LCMS: 273 [M+H-55]⁺. $t_R$=2.622 mins. (LCMS condition 3)

$^1$H NMR (300 MHz, CHLOROFORM-d): δ 8.23 (s, 1H), 8.10 (s, 1H), 4.40-4.18 (m, 3H), 3.08-2.91 (m, 2H), 2.47-2.33 (m, 1H), 2.19-2.10 (m, 1H), 1.48 (s, 9H), 1.15 (d, J=22.8 Hz, 3H).

Description D308

(±)-(cis)-tert-butyl 4-(5-chloro-4-nitro-1H-pyrazol-1-yl)-3-fluoro-3-methylpiperidine-1-carboxylate (D308)

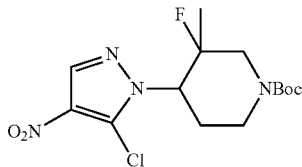 [SMILES: CC(C)(C)OC(=O)N1CCC(n2ncc([N+](=O)[O-])c2Cl)C(C)(F)C1]

To a solution of D307 (4.2 g, 12.8 mmol) in dry THF (100 mL) was added LiHMDS (1 M in THF, 19.2 mL, 19.2 mmol) dropwise at −78° C. under N₂ for 1 hour. Then a solution of hexachloroethane (6.06 g, 25.6 mmol) in dry THF (5 mL) was added dropwise. The reaction was stirred for 2 hours at room temperature. The reaction was quenched with sat. NH₄Cl solution (100 mL), and then was extracted with EtOAc (100 mL×3). The combined organic layers were washed with brine (100 mL), and concentrated to give a yellow solid, which was purified by column chromatography on silica gel (PE:EA=8:1-5:1) to give the title compound D308 (4.2 g, yield 85%) as a yellow solid.

$^1$H NMR (300 MHz, CHLOROFORM-d): δ 8.21 (s, 1H), 4.74-4.63 (m, 1H), 4.26-4.09 (m, 2H), 3.24-3.08 (m, 2H), 2.42-2.30 (m, 1H), 2.05-1.94 (m, 1H), 1.48 (s, 9H), 1.26 (d, J=22.8 Hz, 3H).

Description D309

(±)-(cis)-tert-butyl 3-fluoro-3-methyl-4-(5-methyl-4-nitro-1H-pyrazol-1-yl)piperidine-1-carboxylate (D309)

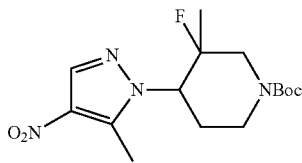 [SMILES: Cc1c([N+](=O)[O-])cnn1C1CCN(C(=O)OC(C)(C)C)CC1(C)F]

To a mixture of D308 (2.10 g, 5.8 mmol), methylboronic acid (0.696 g, 11.6 mmol) in dioxane/H₂O (12 mL/8 mL) was added Pd(dppf)Cl₂ (0.520 g, 0.580 mmol), followed by Na₂CO₃ (1.84 g, 17.4 mmol) under N₂. The mixture was stirred overnight at 100° C. The mixture was concentrated in vacuo and purified by column chromatography on silica gel (PE:EA=8:1-5:1) to give the title compound D309 (1.7 g, yield 89%) as a white solid.

LCMS: 287 [M−55]⁺. $t_R$=2.458 mins. (LCMS condition 3)

¹H NMR (300 MHz, CHLOROFORM-d): δ 8.11 (s, 1H), 4.41-4.17 (m, 3H), 3.13-2.95 (m, 2H), 2.70 (s, 3H), 2.59-2.43 (m, 1H), 2.01-1.93 (m, 1H), 1.48 (s, 9H), 1.23 (d, J=23.1 Hz, 3H).

Description D310

(±)-(cis)-3-fluoro-3-methyl-4-(5-methyl-4-nitro-1H-pyrazol-1-yl)piperidine (D310)

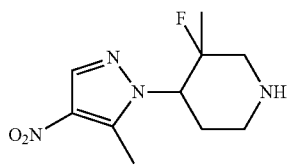 [SMILES: Cc1c([N+](=O)[O-])cnn1C1CCNCC1(C)F]

To a solution of D309 (1.00 g, 2.92 mmol) in MeOH (24 mL) was added conc. HCl (12 mL). The mixture was stirred for 30 min at room temperature and then was acidified with Na₂CO₃ to pH=10. The mixture was extracted with EA (30 mL×3), concentrated in vacuo to give the title compound D310 (700 mg, yield 99%) as yellow oil.

LCMS: 243 [M+H]⁺. $t_R$=0.645 mins. (LCMS condition 3)
¹H NMR (300 MHz, CHLOROFORM-d): δ 8.11 (s, 1H), 4.38-4.29 (m, 1H), 3.29-3.15 (m, 2H), 2.89-2.71 (m, 2H), 2.69 (d, J=1.5 Hz, 3H), 2.52-2.38 (m, 1H), 1.97-1.91 (m, 1H), 1.29 (d, J=23.7 Hz, 3H).

Description D311 and D312

Enantiomer 1: (cis)-3-fluoro-3-methyl-4-(5-methyl-4-nitro-1H-pyrazol-1-yl)-1-(oxetan-3-yl)piperidine (D311)

Enantiomer 2: (cis)-3-fluoro-3-methyl-4-(5-methyl-4-nitro-1H-pyrazol-1-yl)-1-(oxetan-3-yl)piperidine (D312)

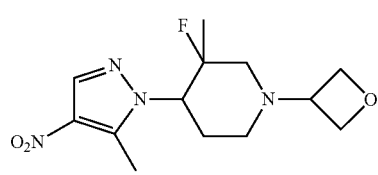
enantiomer 1

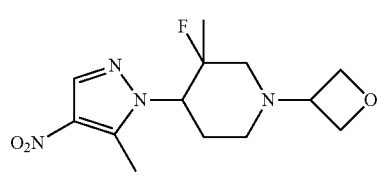
enantiomer 2

A mixture of D310 (700 g, 2.89 mmol) and oxetan-3-one (500 g, 6.93 mmol) in DCE (20 mL) was added portionwise NaBH(OAc)₃ (3.10 g, 14.4 mmol). The mixture was stirred overnight. The reaction was quenched with sat. NaHCO₃ solution (20 mL) and then extracted with DCM (20 mL×3). The combined organic layers were concentrated in vacuo and purified by column chromatography on silica gel (PE:EA=3:1-1:1) to give the racemate, which was further separated by chiral HPLC to give the title compounds D311 ($t_R$=5.953 min, 260 mg) and D312 ($t_R$=6.759 min, 250 mg) as white solids.

LCMS: 299 [M+H]⁺. $t_R$=2.276 mins. (LCMS condition 3)
¹H NMR (300 MHz, CHLOROFORM-d): δ 8.12 (s, 1H), 4.71-4.57 (m, 4H), 4.31-4.21 (m, 1H), 3.66-3.56 (m, 1H), 2.97-2.90 (m, 1H), 2.83-2.80 (m, 1H), 2.68 (d, J=1.5 Hz, 3H), 2.22-2.04 (m, 2H), 1.97-1.93 (m, 1H), 1.36 (d, J=23.7 Hz, 3H).

Description D313

Enantiomer 1: (cis)-1-(3-fluoro-3-methyl-1-(oxetan-3-yl)piperidin-4-yl)-5-methyl-1H pyrazol-4-amine (D313)

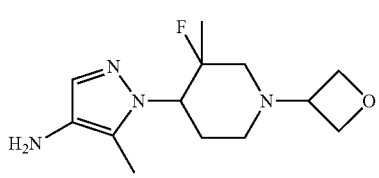
enantiomer 1

A mixture of D311 (210 g, 0.705 mmol) and Pd/C (10%, 42 mg) in MeOH/THF (10 mL/10 mL) was stirred for overnight under H₂ atmosphere (balloon). The reaction was filtered and the filtrate was concentrated in vacuo to give the title compound D313 as a white solid (189 mg, yield 99%).

LCMS: 269 [M+H]⁺. $t_R$=1.726 mins. (LCMS condition 3)
¹H NMR (300 MHz, CHLOROFORM-d): δ 7.19 (s, 1H), 4.69-4.56 (m, 4H), 4.15-4.05 (m, 1H), 3.64-3.55 (m, 1H), 2.93-2.85 (m, 1H), 2.80-2.74 (m, 1H), 2.66-2.49 (m, 3H), 2.18 (d, J=0.9 Hz, 3H), 2.17-1.91 (m, 3H), 1.30 (d, J=23.7 Hz, 3H).

Description D314

Enantiomer 2: (cis)-1-(3-fluoro-3-methyl-1-(oxetan-3-yl)piperidin-4-yl)-5-methyl-1H pyrazol-4-amine (D314)

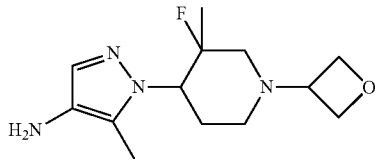
enantiomer 2

A mixture of D312 (250 g, 0.84 mmol) and Pd/C (10%, 50 mg) in MeOH/THF (10 mL/10 mL) was stirred for overnight under H₂ atmosphere (balloon). The reaction was filtered and the filtrate was concentrated in vacuo to give the title compound D314 as a white solid (240 mg, yield 99%).

LCMS: 269 [M+H]⁺. $t_R$=1.726 mins. (LCMS condition 3)

¹H NMR (300 MHz, CHLOROFORM-d): δ 7.17 (s, 1H), 4.69-4.54 (m, 4H), 4.13-4.02 (m, 1H), 3.61-3.53 (m, 1H), 2.90-2.85 (m, 1H), 2.77-2.75 (m, 1H), 2.72-2.46 (m, 3H), 2.16 (d, J=0.9 Hz, 3H), 2.13-1.90 (m, 3H), 1.28 (d, J=23.7 Hz, 3H).

Description D315

(±)-tert-butyl 2-hydroxymorpholine-4-carboxylate (D315)

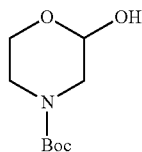 [SMILES: CC(C)(C)OC(=O)N1CCOC(O)C1]

To the suspension of morpholin-2-ol hydrochloride (2.00 g, 14.3 mmol) in ethyl acetate (80 mL) was added (Boc)₂O (4.65 g, 21.5 mmol) and DIPEA (5.53 g, 42.9 mmol). The resulting mixture was refluxed overnight under N₂. Water (50 mL) was added and the reaction was stirred at room temperature for 10 min. The aqueous layer was extracted with ethyl acetate (50 mL×2). The combined organic layers were washed with brine (30 mL×2), then dried over anhydrous Na₂SO₄, filtered and concentrated to give the title compound D315 (3.45 g) as a light yellow solid.

¹H NMR (300 MHz, CHLOROFORM-d): δ 4.91-4.87 (m, 1H), 4.03-3.96 (m, 1H), 3.68 (dd, J=13.2, 2.4 Hz, 1H), 3.62-3.45 (m, 2H), 3.36-3.28 (m, 1H), 3.18 (dd, J=13.2 and 5.4 Hz, 1H), 2.99 (d, J=5.4 Hz, 1H), 1.47 (s, 9H).

Description D316

(±)-tert-butyl 2-(4-nitro-1H-pyrazol-1-yl)morpholine-4-carboxylate (D316)

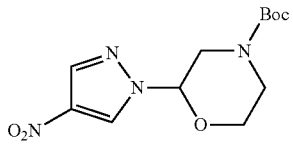 [SMILES: CC(C)(C)OC(=O)N1CCOC(n2cc([N+](=O)[O-])cn2)C1]

To a solution of D315 (3.27 g, 16.1 mmol), 4-nitro-1H-pyrazole (1.82 g, 16.1 mmol), PPh₃ (6.33 g, 24.2 mmol) in anhydrous THF (65 mL) was added DIAD (4.89 g, 24.2 mmol) at 0° C. under N₂. The resulting yellow mixture was stirred at room temperature for 2 days. The reaction was quenched with water (100 mL) and extracted with ethyl acetate (80 mL×3). The combined organic layers were washed with brine (50 mL×2), then dried over anhydrous Na₂SO₄, filtered and concentrated. The crude was purified by column chromatography on silica gel (PE:EA=12:1) and further purified C18 (20-40% CH₃CN/H₂O) to give the title compound D316 (2.4 g, yield 50%) as white thick oil.

¹H NMR (300 MHz, CHLOROFORM-d): δ 8.39 (s, 1H), 8.12 (s, 1H), 5.48 (dd, J=7.2, 3.3 Hz, 1H), 4.18-4.12 (m, 1H), 3.96-3.90 (m, 1H), 3.82-3.72 (m, 2H), 3.61 (dd, J=13.5, 7.2 Hz, 1H), 3.38-3.30 (m, 1H), 1.48 (s, 9H).

Description D317

(±)-tert-butyl 2-(5-chloro-4-nitro-1H-pyrazol-1-yl) morpholine-4-carboxylate (D317)

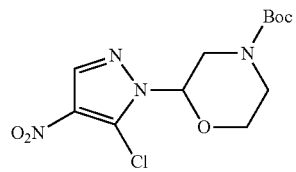 [SMILES: CC(C)(C)OC(=O)N1CCOC(n2ncc([N+](=O)[O-])c2Cl)C1]

To a solution of D316 (474 g, 1.59 mmol) in THF (10 mL) was added LiHMDS (3.18 mL, 1M) at −70° C. under N₂. The resulting yellow solution was stirred below −65° C. for 1 hour. Then a solution of C₂Cl₆ (753 g, 3.18 mmol) in THF (2 mL) was added at −65° C. and the mixture was stirred below −65° C. for another 1 hour. The reaction was quenched with NH₄Cl (20 mL, sat.) and extracted with ethyl acetate (30 mL×3). The combined organic layers were washed with brine (30 mL×2), dried over anhydrous Na₂SO₄, filtered and concentrated. The crude was purified by column chromatography on silica gel (PE:EA=10:1) to give the title compound D317 (470 mg, yield 89%) as a white solid.

LCMS: $t_R$=2.04 mins. (LCMS condition 3)

¹H NMR (300 MHz, CHLOROFORM-d): δ 8.21 (s, 1H), 5.56 (dd, J=8.4, 3.3 Hz, 1H), 4.17-4.06 (m, 1H), 4.03-3.97 (m, 1H), 3.87-3.72 (m, 3H), 3.31-3.22 (m, 1H), 1.49 (s, 9H).

Description D318

(±)-2-(5-chloro-4-nitro-1H-pyrazol-1-yl)morpholine (D318)

To a solution of D317 (160 g, 0.48 mmol) in anhydrous DCM (4 mL) was added ZnBr₂ (216 g, 0.96 mmol). The resulting mixture was stirred overnight at room temperature under N₂. The reaction was quenched with Cs₂CO₃ solution (10 mL, pH~12) and extracted with ethyl acetate (20 mL×3). The combined organic layers were dried over anhydrous Na₂SO₄, filtered and concentrated to give the title compound D318 (110 mg, yield 100%) as light yellow oil.

LCMS: 233 [M+H]⁺. $t_R$=1.88 mins. (LCMS condition 3)

¹H NMR (300 MHz, CHLOROFORM-d): δ 8.22 (s, 1H), 5.66 (dd, J=5.4, 3.3 Hz, 1H), 3.83-3.77 (m, 2H), 3.61 (dd, J=13.5, 5.4 Hz, 1H), 3.34 (dd, J=13.5 and 3.3 Hz, 1H), 3.05 (t, J=4.8 Hz, 2H).

Description D319

(±)-2-(5-chloro-4-nitro-1H-pyrazol-1-yl)-4-(oxetan-3-yl)morpholine (D319)

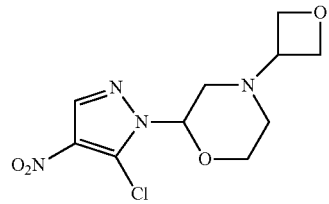 [SMILES: Nc1cnn(C2CN(C3COC3)CCO2)c1Cl]

To a solution of D318 (110 g, 0.48 mmol) in DCM (3 mL) and MeOH (5 mL) was added oxetan-3-one (0.3 mL). The resulting mixture was stirred at room temperature for 2 hrs. Then NaBH$_3$CN (151 g, 2.4 mmol) was added and the mixture was stirred at room temperature for 2 days. The reaction was worked up with Cs$_2$CO$_3$ solution (20 mL, pH~12) and extracted with DCM (30 mL×3). The combined organic layers were dried over anhydrous Na$_2$SO$_4$, filtered and concentrated. The crude was purified with C18 (15-40% CH$_3$CN in H$_2$O) to give the title compound D319 (26 mg, yield 19%) as light yellow oil.

LCMS: 289 [M+H]$^+$. $t_R$=2.05 mins. (LCMS condition 3)

$^1$H NMR (300 MHz, CHLOROFORM-d): δ 8.19 (s, 1H), 5.71-5.67 (m, 1H), 4.73-4.59 (m, 4H), 4.09-4.05 (m, 1H), 3.97-3.89 (m, 1H), 3.70-3.62 (m, 1H), 2.88 (d, J=6.3 Hz, 2H), 2.65 (d, J=11.4 Hz, 1H), 2.28 (td, J=11.4, 3.3 Hz, 1H).

Description D320

(±)-5-chloro-1-(4-(oxetan-3-yl)morpholin-2-yl)-1H-pyrazol-4-amine (D320)

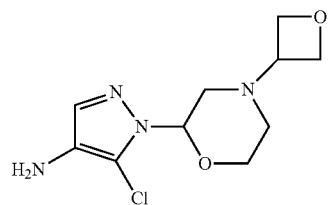

To a solution of D319 (105 g, 0.36 mmol) in EtOH (3 mL) was added iron powder (101 g, 1.80 mmol) and NH$_4$Cl (39 g, 0.72 mmol) in water (3 mL). The resulting mixture was stirred overnight at 50° C. The mixture was filtered and the filtrate was concentrated. The crude was purified with C18 (10-25% CH$_3$CN in H$_2$O) to give the title compound D320 (70 mg, yield 75%) as colorless oil.

LCMS: 259 [M+H]$^+$. $t_R$=1.492 mins. (LCMS condition 3)

$^1$H NMR (300 MHz, CHLOROFORM-d): δ 7.29 (s, 1H), 5.52-5.48 (m, 1H), 4.71-4.61 (m, 4H), 4.04-3.99 (m, 1H), 3.94-3.86 (m, 1H), 3.67-3.58 (m, 1H), 2.96-2.84 (m, 4H), 2.64-2.59 (m, 1H), 2.28-2.19 (m, 1H).

Description D321 cis/trans-4-(benzyloxy)-2-bromocyclohexanone (D321)

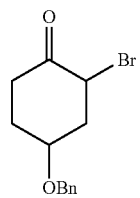 [SMILES: O=C1CCC(OCc2ccccc2)CC1Br]

To a cooled solution of 4-(benzyloxy)cyclohexanone (8.4 g, 41.1 mmol) in diethyl ether (200 mL) was added bromine (2.119 mL, 41.1 mmol) under ice-water cooling. After stirred for 1 h, saturated aq. sodium thiosulfate was added and the mixture was extracted with ethyl acetate. The combined organic phases were dried, concentrated and purified by flash chromatography on silica gel (15-25% EA in PE) to give the title compound D321 (10 g, 35.3 mmol, 86% yield).

LCMS: 305 [M+Na]$^+$. $t_R$=3.537 mins. (LCMS condition 1)

Description D322 cis/trans-4-(benzyloxy)-2-(4-nitro-1H-pyrazol-1-yl)cyclohexa none (D322)

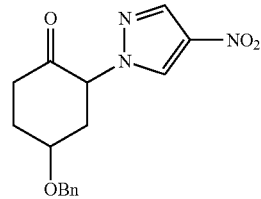 [SMILES: O=C1CCC(OCc2ccccc2)CC1n1cc([N+](=O)[O-])cn1]

A solution of 4-nitro-1H-pyrazole (4.0 g, 35.4 mmol), D321 (10.02 g, 35.4 mmol), potassium carbonate (9.78 g, 70.7 mmol) in DMF (70 mL) was heated to 40° C. for 16 hours. After cooling to room temperature, the mixture was diluted with ethyl acetate and water was added. The organic layer was washed with brine, dried over Na$_2$SO$_4$, filtered, and concentrated. The crude was purified by column chromatography on silica gel (40-45% EA in PE) to give the title compound D322 (7.59 g, 24.07 mmol, 68.0% yield).

LCMS: 316 [M+H]$^+$. $t_R$=3.824 mins. (LCMS condition 1)

Description D323 cis/trans-1-(5-(benzyloxy)-2,2-difluorocyclohexyl)-4-nitro-1H-pyrazole (D323)

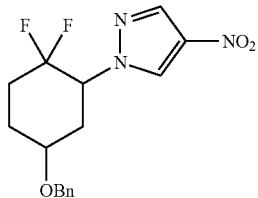 [SMILES: O=[N+]([O-])c1cnn(C2CC(OCc3ccccc3)CCC2(F)F)c1]

To a solution of D322 (7.59 g, 24.07 mmol) in DCM (90 mL) was added DAST (15.90 mL, 120 mmol) dropwise at −78° C. After the addition, the reaction was allowed to warm to room temperature and stirred for another 16 hours. The mixture was poured into saturated aq. NaHCO$_3$ and extracted with DCM. The organic layer was dried over Na$_2$SO$_4$, concentrated and purified by column chromatography on silica gel (25-30% EA in PE) to give the title compound D323 (6.32 g, 18.74 mmol, 78% yield).

LCMS: 338 [M+H]$^+$. t$_R$=3.824 mins. (LCMS condition 1)

Description D324 cis/trans-4,4-difluoro-3-(4-nitro-1H-pyrazol-1-yl)cyclohexanol (D324)

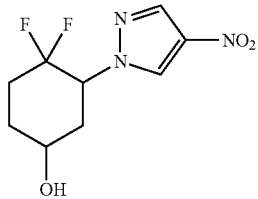 [SMILES: O=[N+]([O-])c1cnn(C2CC(O)CCC2(F)F)c1]

A solution of D323 (6.32 g, 18.74 mmol), triphenylphosphine (11.57 g, 33.7 mmol) in acetonitrile (15 mL) was heated to 100° C. in a sealed tube for 16 hours. After cooling to room temperature, the reaction was diluted with ethyl acetate, washed with brine, dried and concentrated. The crude was purified by column chromatography on silica gel (75-85% EA in PE) to give the title compound D324 (4.61 g, 99% yield).

LCMS: 248 [M+H]$^+$. t$_R$=2.460 mins. (LCMS condition 1)

$^1$H NMR (400 MHz, DMSO-d$_6$): δ 9.05 (s, 1H), 8.33 (s, 1H), 5.05 (m, 2H), 4.17 (br. s., 1H), 2.46 (m, 1H), 2.20 (m, 3H), 1.83 (m, 1H), 1.70 (m, 1H).

Description D325

(±)-4,4-difluoro-3-(4-nitro-1H-pyrazol-1-yl)cyclohexanone (D325)

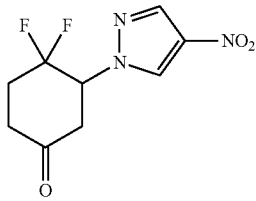 [SMILES: O=C1CCC(F)(F)C(n2cc([N+](=O)[O-])cn2)C1]

To a solution of D324 (1.82 g, 7.36 mmol) in DCM (50 mL) was added dess-martinperiodinane (6.25 g, 14.72 mmol) at 0° C. and the reaction was allowed to warm to room temperature and stirred for 16 hours. The mixture was poured into saturated aq. NaHCO$_3$ and extracted with DCM. The organic layer was dried, concentrated and purified by column chromatography on silica gel (60-70% EA in PE) to give the title compound D325 (1.6 g, 6.53 mmol, 89% yield).

LCMS: 246 [M+H]$^+$. t$_R$=3.112 mins. (LCMS condition 1)

$^1$H NMR (400 MHz, DMSO-d$_6$): δ 9.08 (s, 1H), 8.39 (s, 1H), 5.45 (dt, J=6.11, 13.69 Hz, 1H), 3.12-3.21 (m, 1H), 2.97-3.06 (m, 1H), 2.55-2.62 (m, 2H), 2.33-2.48 (m, 2H).

Description D326 and D327

(±)-trans-4-(4,4-difluoro-3-(4-nitro-1H-pyrazol-1-yl)cyclohexyl)morpholine (D326)

(±)-cis-4-(4,4-difluoro-3-(4-nitro-1H-pyrazol-1-yl)cyclohexyl)morpholine (D327)

D326

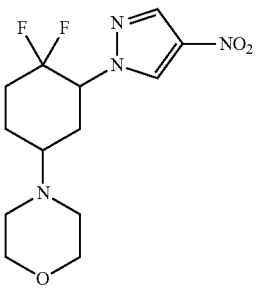

D327

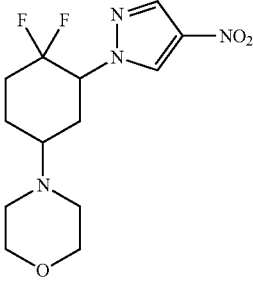

A solution of D325 (2.7 g, 11.01 mmol), morpholine (1.919 mL, 22.02 mmol), acetic acid (0.630 mL, 11.01 mmol) in DCE (150 mL) was stirred at room temperature for 16 hours. Then sodium triacetoxyborohydride (4.67 g, 22.02 mmol) was added and the mixture was stirred for another 5 hours. The reaction was quenched with water, and extracted with DCM. The organic layer was dried, concentrated and purified by column chromatography on silica gel (100% EA) to give the title compounds D326 (1.71 g, 5.41 mmol, 49.1% yield) and D327 (240 g, 0.759 mmol, 6.89% yield).

D321: LCMS: 317 [M+H]$^+$. $t_R$=2.011 mins. (LCMS condition 1)

D322: LCMS: 317 [M+H]$^+$. $t_R$=1.929 mins. (LCMS condition 1)

Description D328

(±)-trans-4-(3-(5-chloro-4-nitro-1H-pyrazol-1-yl)-4,4-difluorocyclohexyl)morpholine (D328)

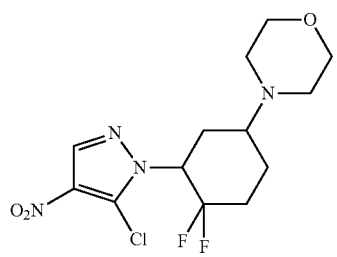

To a solution of D326 (1.71 g, 5.41 mmol) in THF (50 mL) was added LiHMDS (8.11 mL, 8.11 mmol, 1M in THF) dropwise at −78° C. for 1 hour. Perchloroethane (1.920 g, 8.11 mmol) in THF (5 mL) was then added and the reaction was stirred at −78° C. for 2 hours. The mixture was poured into saturated NH$_4$Cl (20 mL) and extracted with EA (30 mL×2). The combined organic layers were washed with brine, dried over Na$_2$SO$_4$, filtered and concentrated. The crude was purified by column chromatography on silica gel (100% EA) to give the title compound D328 (1.69 g, 4.82 mmol, 89% yield).

LCMS: 351 [M+H]$^+$. $t_R$=2.205 mins. (LCMS condition 1)

Description D329

(±)-trans-5-chloro-1-(2,2-difluoro-5-morpholinocyclohexyl)-1H-pyrazol-4-amine (D329)

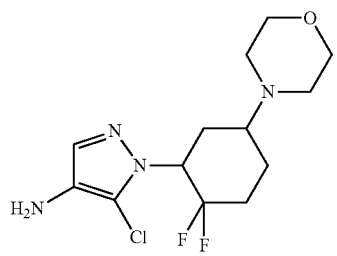

To a solution of D328 (1.69 g, 4.82 mmol) in water (27 mL) was added ammonium chloride (1.289 g, 24.09 mmol), iron (1.614 g, 28.9 mmol) and ethanol (18.00 mL). The reaction was then stirred at 70° C. for 1 hour and diluted with DCM. The mixture was filtered through celite and sat aqueous sodium bicarbonate was added. The aqueous layer was further extracted with DCM and the combined organic layer was dried and concentrated to give the title compound D329 (1.58 g, 4.93 mmol).

LCMS: 321 [M+H]$^+$. $t_R$=1.153 mins. (LCMS condition 1)

Description D330

(±)-cis-4-(3-(5-chloro-4-nitro-1H-pyrazol-1-yl)-4,4-difluorocyclohexyl)morpholine (D330)

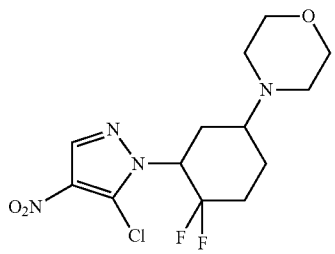 [SMILES: O=[N+]([O-])c1cnn(C2CC(N3CCOCC3)CCC2(F)F)c1Cl]

To a solution of D327 (240 g, 0.759 mmol) in THF (8 mL) was added LiHMDS (1.138 mL, 1.138 mmol, 1M in THF) dropwise at −78° C. for 1 hour. Perchloroethane (269 mg, 1.138 mmol) in THF (2 mL) was then added and the reaction was stirred at −78° C. for 2 hours. The mixture was poured into sat. NH$_4$Cl (5 mL) and extracted with EA (8 mL×2). The combined organic layers were washed with brine, dried over Na$_2$SO$_4$, filtered and concentrated. The crude was purified by column chromatography on silica gel (55-60% EA in PE) to give the title compound D330 (200 g, 0.570 mmol, 75% yield).

LCMS: 351 [M+H]$^+$. $t_R$=2.509 mins. (LCMS condition 1)

Description D331

(±)-cis-5-chloro-1-(2,2-difluoro-5-morpholinocyclohexyl)-1H-pyrazol-4-amine (D331)

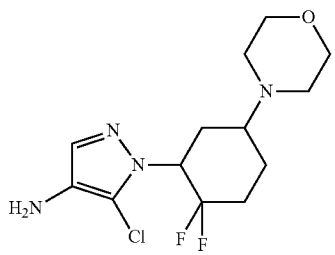 [SMILES: O=[N+]([O-])c1cnn(C2CC(N3CCOCC3)CCC2(F)F)c1Cl]

To a solution of D330 (200 g, 0.570 mmol) in water (9 mL) was added ammonium chloride (153 g, 2.85 mmol), iron (191 g, 3.42 mmol) and ethanol (6 mL). The reaction was then stirred at 70° C. for 1 hour and diluted with DCM. The mixture was filtered through celite and sat aqueous sodium bicarbonate was added. The aqueous layer was further extracted with DCM and the combined organic layer was dried and concentrated to give the title compound D331 (160 g, 0.499 mmol, 87%, yield).

LCMS: 321 [M+H]$^+$. $t_R$=1.020 mins. (LCMS condition 1)

Description D332

4-nitro-1-(1,4-dioxaspiro[4.5]deACN-8-yl)-1H-pyrazole (D332)

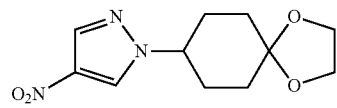

To a solution of 4-nitro-1H-pyrazole (2 g, 17.69 mmol), DIAD (6.88 mL, 35.4 mmol) and 1,4-dioxaspiro[4.5]decan-8-ol (3.08 g, 19.46 mmol) in THF (50 mL) was added Ph$_3$P (9.28 g, 35.4 mmol). The reaction was stirred overnight at room temperature. Solvent was removed and the residue was re-dissolved in EA. The organic layer was washed with water, dried over anhydrous sodium sulphate and concentrated. The crude was purified by column chromatography on silica gel to give the title compound D332 (4.48 g, 17.69 mmol, 100% yield).

LCMS: 254 [M+H]$^+$. $t_R$=2.641 mins. (LCMS condition 1)

Description D333

4-(4-nitro-1H-pyrazol-1-yl)cyclohexanone (D333)

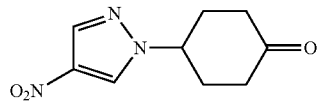

To a solution of D332 (4.48 g, 17.69 mmol) in acetone (30 mL) was added HCl (15 mL, 17.69 mmol). The reaction was stirred at room temperature for 5 hours. Aqueous NaHCO$_3$ solution was added to the mixture until pH~8.0 and then solvent was evaporated. The residue was diluted with water (15 mL) and extracted with EA (10 mL×3). The combined organic layer were dried over anhydrous Na$_2$SO$_4$ and concentrated. The crude was purified by column chromatography on silica gel to give the title compound D333 (623.2 mg, 2.98 mmol, 16.84% yield).

LCMS: 210 [M+H]$^+$. $t_R$=2.020 mins. (LCMS condition 2)

Description D334

4-(4-nitro-1H-pyrazol-1-yl)cyclohexanone (D334)

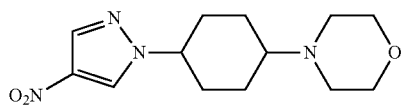

A solution of D333 (500 g, 2.390 mmol), morpholine (416 g, 4.78 mmol) and HOAc (5 drops) in DCM (10 mL) was stirred overnight at room temperature. Then sodium triacetoxyborohydride (557 g, 2.63 mmol) was added and the mixture was stirred for another 4 hours. The reaction was basicified using saturated aqueous NaHCO$_3$ solution until pH~8.0. The mixture was then diluted with water (15 mL) and extracted with DCM (10 mL×2). The combined organic layers were dried over Na$_2$SO$_4$ and concentrated. The crude was purified by column chromatography on silica gel to give the title compound D334 (402.5 g, 1.436 mmol, 60.1% yield).

LCMS: 281 [M+H]$^+$. $t_R$=1.225 mins. (LCMS condition 1)

Description D335

4-(4-(5-chloro-4-nitro-1H-pyrazol-1-yl)cyclohexyl)morpholine (D335)

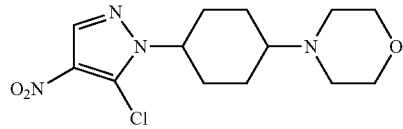

To a solution of D334 (458 g, 1.634 mmol) in THF (10 mL) was added LiHMDS (2.451 mL, 2.451 mmol) dropwise at −78° C. under nitrogen. After stirring for 1 hour at −78° C., perchloroethane (580 g, 2.451 mmol) was added and the reaction was stirred at −78° C. for another 2 hours. Water (15 mL) was added and the mixture was warmed to room temperature. The mixture was extracted with EA (10 mL×3). The combined organic phase was dried over anhydrous sulphate and concentrated. The crude was purified by column chromatography on silica gel (EA/PE: 0 to 40%) to give the title compound D335 (253.8 g, 0.806 mmol, 49.4% yield).

LCMS: 315 [M+H]$^+$. $t_R$=1.955 mins. (LCMS condition 1)

$^1$H NMR (400 MHz, DMSO-d$_6$): δ 8.48 (s, 1H), 4.57-4.47 (m, 1H), 3.60 (t, J=4.6 Hz, 4H), 2.39 (br. s., 3H), 2.20-1.98 (m, 5H), 1.70-1.60 (m, 2H), 1.55 (t, J=13.0 Hz, 2H).

Description D336

5-chloro-1-(4-morpholinocyclohexyl)-1H-pyrazol-4-amine (D336)

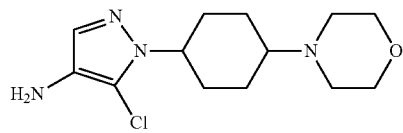 [SMILES: O=[N+]([O-])c1cnn(C2CCC(N3CCOCC3)CC2)c1Cl]

A solution of D335 (253.8 g, 0.806 mmol), iron (270 g, 4.84 mmol) and ammonium chloride (216 g, 4.03 mmol) in ethanol (10 mL) and water (15.00 mL) was stirred at 70° C. for 19 hours. The mixture was filtered through celite and extracted with DCM. The organic phase was dried over anhydrous sodium sulphate and concentrated to give the title compound D336 (202.1 g, 0.710 mmol, 88% yield).

LCMS: 285 [M+H]$^+$. $t_R$=0.54 mins. (LCMS condition 1)

Description D337

(2S, 4R)-methyl 1-benzyl-4-hydroxypyrrolidine-2-carboxylate (D337)

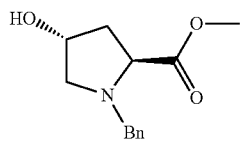 [SMILES: COC(=O)[C@@H]1C[C@@H](O)CN1Cc1ccccc1]

To a solution of (2S, 4R)-methyl 4-hydroxypyrrolidine-2-carboxylate hydrochloride (50.0 g, 276 mmol) and BnBr (48.0 g, 276 mmol) in DCM (500 mL) was added TEA (92.0 g, 911 mmol). The resulting mixture was stirred overnight at 50° C. Solvent was evaporated and the crude product was purified by column chromatography on silica gel (PE:EA=1:1) to give the title compound D337 (40.0 g, 62%) as colorless oil.

$^1$H NMR (300 MHz, CHLOROFORM-d): δ 7.31-7.22 (m 5H), 4.45-4.41 (m, 1H), 3.89 (d, J=12.9 Hz, 1H), 3.67-3.57 (m, 5H), 3.31 (dd, J=10.2, 5.4 Hz, 1H), 2.46 (dd, J=10.2, 3.6 Hz, 1H), 2.28-2.19 (m, 1H), 2.10-2.02 (m, 2H).

Description D338

(3R,5S)-1-benzyl-5-(hydroxymethyl)pyrrolidin-3-ol (D338)

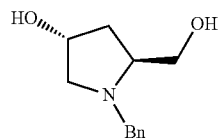 [SMILES: OC[C@@H]1C[C@@H](O)CN1Cc1ccccc1]

A suspension of LiAlH$_4$ (26.0 g, 680 mmol) in THF (500 mL) under ice-bath was added a solution of D337 (40.0 g, 0.170 mmol) in THF (240 mL) dropwise. After addition, the resulting mixture was stirred overnight at room temperature. Water was added carefully at 0° C. and the mixture was filtered. The filtrate was extracted with EtOAc (300 mL×3). The combined organic layer were washed with brine, dried over Na$_2$SO$_4$ and concentrated to give the title compound D338 (22.0 g, 63%) as colorless oil.

LCMS: 208 [M+H]$^+$. $t_R$=1.486 mins. (LCMS condition 3)

$^1$H NMR (300 MHz, CHLOROFORM-d): δ 7.34-7.23 (m, 5H), 4.36-4.29 (m, 1H), 3.98 (d, J=9.9 Hz, 1H), 3.67 (dd, J=10.8, 3.0 Hz, 1H), 3.47 (d, J=13.2 Hz, 1H), 3.40 (d, J=11.4 Hz, 1H), 3.24 (dd, J=10.2, 5.4 Hz, 1H), 3.10-3.05 (m, 1H), 2.67 (br s, 1H), 2.37 (dd, J=10.2, 5.1 Hz, 1H), 2.19-2.04 (m, 1H), 1.91-1.79 (m, 2H)

Description D339

(3R, 5R)-1-benzylpiperidine-3,5-diol (D339)

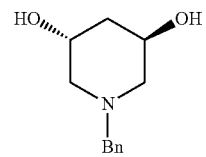 [SMILES: O[C@@H]1C[C@@H](O)CN(Cc2ccccc2)C1]

Trifluoroacetic anhydride (19.6 mL, 138 mmol) was added dropwise to a solution of D338 (22.0 g, 106 mmol) in THF (900 mL) and then cooled to 0° C. After 1 hour, TEA (66.0 mL, 476 mmol) was added dropwise at −78° C. The reaction mixture was stirred at 0° C. for 20 min and then heated at reflux for 60 hrs. After the addition of aqueous 2.5M NaOH solution (900 mL), the mixture was stirred for 2 hrs at room temperature. The mixture was extracted with EtOAc (400 mL×3), dried over Na$_2$SO$_4$ and concentrated. The crude was purified by column chromatography on silica gel (DCM:MeOH=20:1 to 10:1) to give the title compound D339 (16.5 g, 75%) as yellow oil.

LCMS: 208 [M+H]$^+$. $t_R$=2.052 mins. (LCMS condition 3)

$^1$H NMR (300 MHz, CHLOROFORM-d): δ 7.34-7.26 (m, 5H), 4.03-3.96 (m, 2H), 3.56 (d, J=2.7 Hz, 2H), 2.60 (d, J=9.0 Hz, 2H), 2.37-2.31 (m, 2H), 2.16 (br s, 2H), 1.76-1.73 (m, 2H).

Description D340

(3R,5R)-tert-butyl 3,5-dihydroxypiperidine-1-carboxylate (D340)

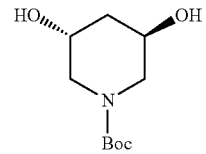

To a solution of D339 (9.00 g, 43.0 mmol) and (Boc)$_2$O (12.2 g, 56.5 mmol) in EtOH (100 mL) was added Pd/C (10%, 200 mg) under N$_2$ atmosphere. Then the reaction mixture was stirred overnight under H$_2$ atmosphere at room temperature. The reaction mixture was filtered and the filtrate was concentrated. The crude was purified by column chromatography on silica gel (PE:EA=1:1 to 0:1) to give the title compound D340 as a white solid (9.00 g, 95%).

LCMS: 118 [M+H-100]$^+$. $t_R$=1.858 mins. (LCMS condition 3)

$^1$H NMR (300 MHz, CHLOROFORM-d): δ 4.08-4.05 (m, 2H), 3.52 (br s, 2H), 3.29 (br s, 2H), 1.83 (br s, 2H), 1.45 (s, 9H).

Description D341

(3R,5R)-tert-butyl 3-((tert-butyldimethylsilyl)oxy)-5-hydroxypiperidine-1-carboxylate (D341)

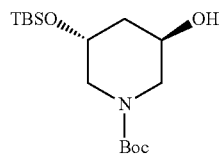 [SMILES: CC(C)(C)OC(=O)N1C[C@H](O)C[C@@H](O[Si](C)(C)C(C)(C)C)C1]

To a solution of D340 (9.00 g, 41.5 mmol) and imidazole (14.1 g, 207 mmol) in DCM (500 mL) was added TBSCl (18.7 g, 124 mmol). The reaction was stirred overnight at 55° C. The mixture was concentrated and the residue was purified by column chromatography (PE) to give the intermediate as colorless oil, which was dissolved in DCM (200 mL) and was treated with TBAF (1.0 M in THF, 40 mL). The mixture was stirred at room temperature for 1 hour and concentrated. The residue was poured into water (150 mL) and extracted with EtOAc (100 mL×3). The extracts were dried over Na$_2$SO$_4$ and concentrated. The crude was purified by column chromatography on silica gel (PE:EA=8:1) to give the title compound D341 as colorless oil (5.0 g, 40%).

LCMS: 232 [M+H-100]$^+$. $t_R$=3.319 mins. (LCMS condition 3)

Description D342

(3R,5R)-tert-butyl 3-((tert-butyldimethylsilyl)oxy)-5-((methylsulfonyl)oxy)piperidine-1-carboxylate (D342)

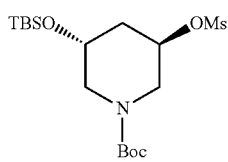 [SMILES: CC(C)(C)OC(=O)N1C[C@H](O[Si](C)(C)C(C)(C)C)C[C@@H](OS(C)(=O)=O)C1]

To a solution of D341 (2.12 g, 6.3 mmol) and TEA (3.2 g, 31.7 mmol) in DCM (60 mL) was added dropwise MsCl (1.45 g, 12.7 mmol) at 0° C. under N$_2$ atmosphere. After addition, the reaction mixture was stirred overnight at room temperature. The reaction mixture was washed with HCl (1N, 50 mL) and water (50 mL). Then the organic layer was dried over Na$_2$SO$_4$ and concentrated to give the title compound D342 (2.2 g, 85% yield) as yellow oil.

LCMS: 310 [M+H-100]$^+$. $t_R$=3.265 mins. (LCMS condition 3)

$^1$H NMR (300 MHz, CHLOROFORM-d): δ 4.94 (br s, 1H), 3.96 (br s, 1H), 3.79 (br s, 1H), 3.69 (br s, 1H), 3.44-3.39 (m, 1H), 3.05-3.00 (m, 4H), 2.09 (br s, 1H), 1.87-1.83 (m, 1H), 1.46 (s, 9H), 0.88 (s, 9H), 0.09 (s, 6H).

Description D343

(3R,5S)-tert-butyl 3-((tert-butyldimethylsilyl)oxy)-5-(4-nitro-1H-pyrazol-1-yl)piperidine-1-carboxylate (D343)

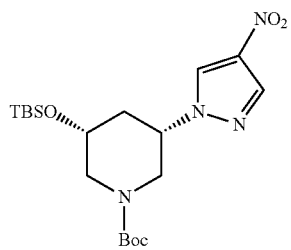 [SMILES: CC(C)(C)OC(=O)N1C[C@H](O[Si](C)(C)C(C)(C)C)C[C@H](n2cc([N+](=O)[O-])cn2)C1]

To a solution of D342 (2.6 g, 6.3 mmol) and 4-nitro-1H-pyrazole (10.0 g, 88.0 mmol) in DMF (30 mL) was added Cs$_2$CO$_3$ (8.50 g, 26.0 mmol). The reaction was stirred at 100° C. for 2 hrs. The mixture was poured into 100 mL of water and extracted with EtOAc (100 mL×2). The combined extracts were dried over Na$_2$SO$_4$ and concentrated. The crude was purified by column chromatography on silica gel (PE:EA=10:1-8:1) to give the title compound D343 (1.1 g, 41% yield) as colorless oil.

LCMS: 371 [M+H-56]$^+$. $t_R$=2.245 mins. (LCMS condition 3)

$^1$H NMR (300 MHz, CHLOROFORM-d): δ 8.31 (s, 1H), 8.08 (m, 1H), 4.31-4.25 (m, 1H), 4.22-4.16 (m, 1H), 3.95-3.92 (m, 1H), 3.78 (br s, 1H), 3.28 (t, J=10.0 Hz, 1H), 2.91 (dd, J=13.6, 9.2 Hz, 1H), 2.36-2.33 (m, 1H), 2.17-2.06 (m, 1H), 1.48 (s, 9H), 0.86 (s, 9H), 0.09 (s, 3H), 0.06 (s, 3H).

Description D344

(3R,5S)-tert-butyl 3-hydroxy-5-(4-nitro-1H-pyrazol-1-yl)piperidine-1-carboxylate (D344)

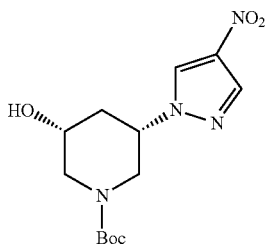 [SMILES: CC(C)(C)OC(=O)N1C[C@H](O)C[C@H](n2cc([N+](=O)[O-])cn2)C1]

To a solution of D343 (1.37 g, 3.21 mmol) in THF (25 mL) was added TBAF (1.01 g, 3.86 mmol). The reaction was stirred at room temperature for 0.5 h. The mixture was concentrated and the residue was poured into 50 mL of water. The mixture was extracted with EtOAc (50 mL×2). The extracts were dried over Na$_2$SO$_4$ and concentrated. The crude was purified by column chromatography on silica gel (PE:EA=1:1) to give the title compound D344 (1.0 g, 100% yield).

LCMS: 257 [M+H-56]$^+$. $t_R$=1.52 mins. (LCMS condition 3)

$^1$H NMR (300 MHz, CHLOROFORM-d): δ 8.33 (s, 1H), 8.09 (m, 1H), 4.38-4.33 (m, 1H), 3.97 (dd, J=13.6, 4.2 Hz,

1H), 3.90-3.80 (m, 2H), 3.52 (dd, J=13.6, 7.2 Hz, 1H), 3.29-3.21 (m, 2H), 2.50-2.39 (m, 1H), 2.24-2.14 (m, 1H), 1.43 (s, 9H).

Description D345

(3S,5S)-tert-butyl 3-fluoro-5-(4-nitro-1H-pyrazol-1-yl)piperidine-1-carboxylate (D345)

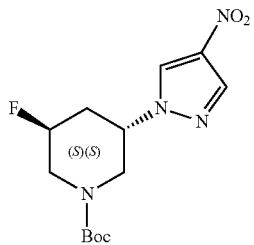

To a solution of D344 (1.06 g, 3.40 mmol) in DCM (20 mL) was added dropwise DAST (1.09 g, 6.80 mmol) under N₂ atmosphere at −78° C. The reaction was allowed to warm to room temperature and stirred at room temperature for 4 hrs. The mixture was poured into 150 mL of saturated NaHCO₃ aqueous and extracted with EtOAc (100 mL×2). The extracts were dried over Na₂SO₄ and concentrated. The crude was purified by column chromatography on silica gel (PE:EA=8:1-6:1-4/1) to give the title compound D345 (500 mg, 50% yield).

LCMS: 259 [M+H-56]⁺. $t_R$=1.86 mins. (LCMS condition 3)

¹H NMR (300 MHz, CHLOROFORM-d): δ 8.38 (s, 1H), 8.09 (m, 1H), 4.79-4.64 (m, 1H), 4.43-4.36 (m, 1H), 3.97-3.89 (m, 1H), 3.86-3.75 (m, 2H), 3.61-3.51 (m, 2H), 2.56-2.40 (m, 2H), 1.48 (s, 9H).

Description D346

(3S,5S)-tert-butyl 3-(5-chloro-4-nitro-1H-pyrazol-1-yl)-5-fluoropiperidine-1-carboxylate (D346)

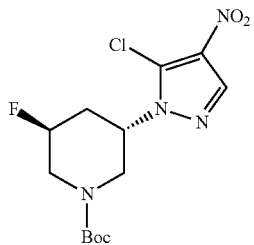 [SMILES: CC(C)(C)OC(=O)N1C[C@@H](F)C[C@H](n2ncc([N+](=O)[O-])c2Cl)C1]

To a solution of D345 (500 g, 1.59 mmol) in THF (5 mL) was added dropwise LiHDMS (1M in THF, 3.18 mL, 3.18 mmol) at −78° C. under N₂ atmosphere. The reaction was stirred at −78° C. for 40 min. Then C₂Cl₆ (754 g, 3.18 mmol) in THF (2 mL) was added dropwise and the mixture was stirred at −78° C. for 40 min. The saturated NH₄Cl aqueous (20 mL) was added and the mixture was concentrated. The residue was poured into 20 mL of water and was extracted with EtOAc (30 mL×3). The extracts were dried over Na₂SO₄ and concentrated. The crude was purified by column C18 (0-100%, ACN/H₂O) to give the title product D346 (440 mg, 80% yield) as yellow oil.

LCMS: 293 [M+H-56]⁺. $t_R$=1.80 mins. (LCMS condition 3)

¹H NMR (300 MHz, CHLOROFORM-d): δ 8.20 (s, 1H), 4.72-4.54 (m, 1H), 4.50-4.41 (m, 2H), 4.29 (br s, 1H), 3.07 (t, J=12.0 Hz, 1H), 2.84-2.75 (m, 1H), 2.57-2.53 (m, 1H), 2.42-2.31 (m, 1H), 1.48 (s, 9H).

Description D347

(3S,5S)-3-(5-chloro-4-nitro-1H-pyrazol-1-yl)-5-fluoropiperidine (D347)

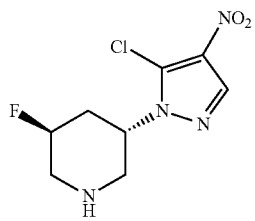 [SMILES: O=[N+]([O-])c1cnn([C@@H]2CNC[C@@H](F)C2)c1Cl]

To a solution of D346 (190 g, 0.546 mmol) in MeOH (3 mL) was added HCl/dioxane (7 mL, 4M) and the mixture was stirred at room temperature for 1 hour. The mixture was concentrated and the residue was poured into saturated NaHCO₃ aqueous (15 mL). The mixture was extracted with EtOAc (15 mL×2) and the extracts were dried over Na₂SO₄, and then concentrated to give the title compound D347 (135 mg, 99% yield) as a yellow solid.

LCMS: 249 [M+H]⁺. $t_R$=0.48 mins. (LCMS condition 3)

¹H NMR (300 MHz, CHLOROFORM-d): δ 8.19 (s, 1H), 4.73-4.54 (m, 1H), 4.48-4.41 (m, 1H), 3.36-3.29 (m, 1H), 3.19-3.16 (m, 1H), 3.09 (dd, J=12.4, 8.8 Hz, 1H), 2.81-2.74 (m, 1H), 2.49-2.43 (m, 1H), 2.42-2.34 (m, 1H).

Description D348

(3S,5S)-3-(5-chloro-4-nitro-1H-pyrazol-1-yl)-5-fluoro-1-(oxetan-3-yl)piperidine (D348)

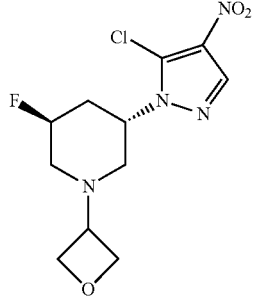 [SMILES: O=[N+]([O-])c1cnn([C@H]2C[C@H](F)CN(C3COC3)C2)c1Cl]

To a solution of D347 (135 g, 0.54 mmol) and oxetan-3-one (148 g, 2.05 mmol) in 1,2-dichloroethane (10 mL) was added NaBH(OAc)₃ (536 g, 2.57 mmol) as portions at room temperature. After addition, the reaction was stirred overnight at room temperature. The mixture was poured into saturated Na₂CO₃ aqueous (40 mL) and extracted with EtOAc (45 mL×2). The extracts were dried over Na₂SO₄ and concentrated. The crude was purified by column chromatography on silica gel (PE:EA=4:1) to give the title compound D348 (110 mg, 66% yield) as a white solid.

LCMS: 305 [M+H]⁺. $t_R$=1.38 mins. (LCMS condition 3)

¹H NMR (300 MHz, CHLOROFORM-d): δ 8.18 (s, 1H), 4.91-4.80 (m, 0.5H), 4.73-4.54 (m, 4.5H), 3.74-3.65 (m, 1H), 3.17-3.14 (m, 1H), 2.88-2.85 (m, 1H), 2.56-2.50 (m, 1H), 2.40 (t, J=10.5 Hz, 1H), 2.27-2.17 (m, 1H), 2.11-2.03 (m, 1H).

Description D349

5-chloro-1-((3S,5S)-5-fluoro-1-(oxetan-3-yl)piperidin-3-yl)-1H-pyrazol-4-amine (D349)

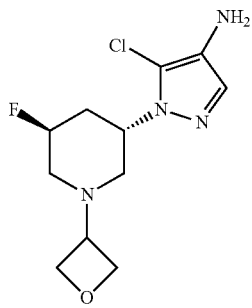

To a solution of D348 (110 mg, 0.361) in EtOH/H₂O (8 mL/8 mL) was added iron powder (80 g, 1.44 mmol) and NH₄Cl (76 g, 1.44 mmol) at room temperature. The reaction was stirred at 50° C. for 1.5 hrs. The mixture was filtered and the filtrate was concentrated. The crude was purified by column C18 (ACN/H₂O=5-100%) to give the title compound D349 (60 mg, 60% yield) as colorless oil.

LCMS: 275 [M+H]⁺. $t_R$=0.54 mins. (LCMS condition 3)

Description D350

(2R,4R)-methyl 4-hydroxypyrrolidine-2-carboxylate hydrochloride (D350)

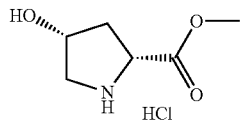

To a suspension of (2R,4R)-4-hydroxypyrrolidine-2-carboxylic acid (100 g, 0.763 mol) in MeOH (1 L) was added SOCl₂ (115 g, 0.966 mol) slowly at 10° C. Then the reaction was heated at 65° C. for 2 hrs. The mixture was concentrated under high vacuum. The residue was washed with ether, filtered to give the title compound D350 (138 g, 100% yield) as a yellow solid.

LCMS: 146 [M+H]⁺. $t_R$=0.366 mins. (LCMS condition 3)

Description D351

(2R,4R)-methyl 1-benzyl-4-hydroxypyrrolidine-2-carboxylate (D351)

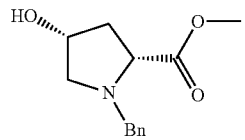 [SMILES: COC(=O)[C@H]1C[C@@H](O)CN1Cc1ccccc1]

To a suspension of D350 (128 g, 0.707 mol), triethylamine (236 g, 2.34 mol) in DCM (1.1 L) was added BnBr (121 g, 0.708 mol) slowly. The reaction was refluxed for 4 hrs. The reaction was concentrated under high vacuum, then purified by column chromatography (PE:EA=10:1 to 5:1) to give the title compound D351 (140 g, 78% yield) as yellow oil.

¹H NMR (300 MHz, CHLOROFORM-d): δ 7.31-7.22 (m, 5H), 4.27-4.21 (m, 1H), 3.86 (d, J=13.2 Hz, 1H), 3.70 (d, J=13.2 Hz, 1H), 3.63 (s, 3H), 3.35 (dd, J=10.0, 4.0 Hz, 1H), 3.17 (d, J=11.2 Hz, 1H), 3.01 (d, J=11.2 Hz, 1H), 2.62 (dd, J=9.6 Hz, 4.0 Hz, 1H), 2.42-2.34 (m, 1H), 1.96-1.92 (m, 1H)

Description D352

(2R,4R)-methyl 1-benzyl-4-((tert-butyldimethylsilyl)oxy)pyrrolidine-2-carboxylate (D352)

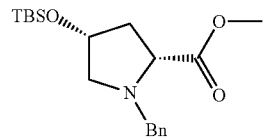 [SMILES: COC(=O)[C@H]1C[C@@H](O[Si](C)(C)C(C)(C)C)CN1Cc1ccccc1]

To a solution of D351 (30.0 g, 128 mmol), imidazole (26.4 g, 383 mmol) in DCM (250 mL) was added TBSCl (28.5 g, 191 mmol) dropwise at 0° C. The reaction was stirred at 0° C. for 2 hrs. The reaction was then quenched with saturated NH₄Cl solution (250 mL), extracted with DCM (200 mL×3). The combined organic layers were washed with brine, dried over anhydrous Na₂SO₄, filtered and concentrated under high vacuum. The crude was purified by column chromatography on silica gel (PE:EA=50:1-8:1) to give the title compound D352 (42.9 g, 96% yield) as light yellow oil.

LCMS: 350 [M+H]⁺. $t_R$=3.072 mins. (LCMS condition 3)

¹H NMR (300 MHz, CHLOROFORM-d): δ 7.32-7.21 (m, 5H), 4.38-4.30 (m, 1H), 3.96 (d, J=13.5 Hz, 1H), 3.68 (s, 3H), 3.62 (d, J=13.5 Hz, 1H), 3.35 (t, J=7.5 Hz, 1H), 2.94 (dd, J=9.9, 3.6 Hz, 1H), 2.69 (dd, J=9.9, 6.6 Hz, 1H), 2.44-2.35 (m, 1H), 2.03-1.94 (m, 1H), 0.85 (s, 9H), 0.01 (s, 3H), 0.00 (s, 3H)

Description D353

((2R,4R)-1-benzyl-4-((tert-butyldimethylsilyl)oxy)pyrrolidin-2-yl)methanol (D353)

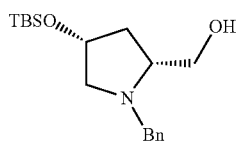 [SMILES: CC(C)(C)[Si](C)(C)O[C@@H]1C[C@H](CO)N(Cc2ccccc2)C1]

To a solution of D352 (22.8 g, 65.2 mmol) in THF (340 mL) was added LiBH$_4$ (2.20 g, 100 mmol) in small portions at 00° C. The reaction was stirred at 0° C. for 0.5 hour and then room temperature for 2 days. NaHCO$_3$ (200 mL) saturated solution was added. The mixture was then concentrated, extracted with EtOAc (200 mL×3). The organic layers were combined, washed with brine, concentrated under high vacuum. The crude was purified by column chromatography on silica gel (PE:EA=5:1) to give the title compound D353 (12.6 g, 60% yield) as colorless oil.

$^1$H NMR (300 MHz, CHLOROFORM-d): δ 7.34-7.22 (m, 5H), 4.27-4.25 (m, 1H), 4.02 (d, J=14.0 Hz, 1H), 3.72 (dd, J=10.8, 2.8 Hz, 1H), 3.46 (dd, J=10.8, 1.2 Hz, 1H), 3.40 (d, J=14.0 Hz, 1H), 2.91-2.86 (m, 1H), 2.43 (dd, J=10.0, 4.0 Hz, 1H), 2.25-2.18 (m, 1H), 1.90-1.85 (m, 1H), 0.88 (s, 9H), 0.04 (s, 3H), 0.00 (s, 3H)

Description D354

(3S,5R)-1-benzyl-5-((tert-butyldimethylsilyl)oxy)piperidin-3-ol (D354)

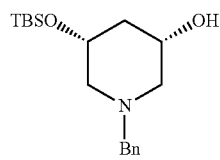 [SMILES: CC(C)(C)[Si](C)(C)O[C@@H]1C[C@H](O)CN(Cc2ccccc2)C1]

To a solution of D353 (16.0 g, 49.8 mmol) in THF (415 mL) was added trifluoroacetic anhydride (20.9 g, 99.7 mmol) dropwise at room temperature. The mixture was stirred at 0° C. for 3 hrs. The reaction was then cooled to −70° C. and triethylamine (22.7 g, 224 mmol) was added dropwise. The reaction was stirred at −70° C. for 0.5 hour and then refluxed for 3 days. NaOH solution (4M, 300 mL) was added and the reaction was stirred at room temperature for 1 hour, and then concentrated under high vacuum. The residue was extracted with EtOAc (300 mL×3). The organic layers were combined, washed with brine, concentrated under high vacuum. The crude was purified by column chromatography (PE:EA=10:1-3:1) to give the title compound D354 (16.0 g, 100% yield) as yellow oil.

$^1$H NMR (300 MHz, CHLOROFORM-d): δ 7.38-7.25 (m, 5H), 3.96 (br s, 1H), 3.85 (br s, 1H), 3.68 (d, J=13.2 Hz, 1H), 3.47 (d, J=13.2 Hz, 1H), 2.98 (d, J=21.6 Hz, 1H), 2.70-2.32 (m, 4H), 1.82-1.73 (m, 2H), 0.91 (s, 9H), 0.06 (s, 3H), 0.00 (s, 3H)

Description D355

(3R,5S)-tert-butyl 3-((tert-butyldimethylsilyl)oxy)-5-hydroxypiperidine-1-carboxylate (D355)

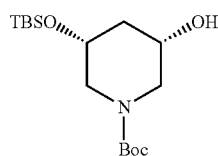 [SMILES: CC(C)(C)OC(=O)N1C[C@@H](O)C[C@@H](O[Si](C)(C)C(C)(C)C)C1]

To a mixture of D354 (16.0 g, 49.8 mmol) and Boc$_2$O (14.0 g, 64.8 mmol) in EtOH (114 mL) was added Pd/C (10%, 2.00 g) under N$_2$ atmosphere. Then the reaction was stirred under H$_2$ atmosphere at room temperature for 2 days. The mixture was filtered and the filtrate was concentrated. The crude was purified by column chromatography (PE:EA=5:1) to give the title compound D355 (15.1 g, 92%) as yellow oil.

$^1$H NMR (300 MHz, CHLOROFORM-d): δ 4.01-3.76 (m, 4H), 3.15-3.07 (m, 2H), 1.96-1.72 (m, 2H), 1.52 (s, 1H), 1.46 (s, 9H), 0.90 (s, 9H), 0.12 (s, 3H), 0.11 (s, 3H)

Description D356

(3R,5S)-tert-butyl 3-((tert-butyldimethylsilyl)oxy)-5-((methylsulfonyl)oxy)piperidine-1-carboxylate (D356)

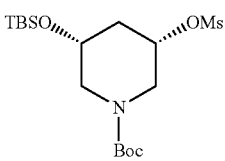

To a solution of D355 (5.00 g, 15.1 mmol), triethylamine (7.60 g, 75.4 mmol) in DCM (67 mL) was added MsCl (3.50 g, 30.0 mmol) at 0° C. The reaction was stirred at room temperature for 3 hrs. The reaction was diluted with DCM (200 mL), washed with 1M HCl (200 mL×2), brine, concentrated to give the title compound D356 (6.2 g, 100% yield) as yellow oil.

$^1$H NMR (300 MHz, CHLOROFORM-d): δ 4.59-4.49 (m, 1H), 4.30-4.25 (m, 1H), 4.02 (br s, 1H), 3.69-3.58 (m, 1H), 3.14 (s, 3H), 2.76 (t, J=10.5 Hz, 1H), 2.59-2.53 (m, 1H), 2.42-2.39 (m, 1H), 1.71-1.57 (m, 1H), 1.46 (s, 9H), 0.88 (s, 9H), 0.09 (s, 3H), 0.08 (s, 3H).

Description D357

(3R,5R)-tert-butyl 3-((tert-butyldimethylsilyl)oxy)-5-(4-nitro-1H-pyrazol-1-yl)piperidine-1-carboxylate (D357)

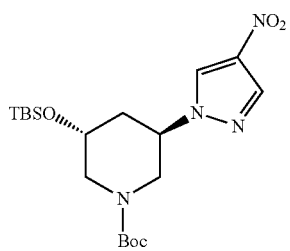 [SMILES: CC(C)(C)OC(=O)N1C[C@H](O[Si](C)(C)C(C)(C)C)C[C@@H](n2cc([N+](=O)[O-])cn2)C1]

To a solution of D356 (6.17 g, 15.0 mmol) and 4-nitro-1H-pyrazole (3.40 g, 30.0 mmol) in DMF (82 mL) was added Cs$_2$CO$_3$ (20.2 g, 61.8 mmol). The reaction was stirred overnight at 90° C. The mixture was poured into water (400 mL) and extracted with EtOAc (400 mL×2). The combined organic layers were washed with brine and concentrated. The crude was purified by column chromatography (PE:EA=10:1-8:1) to give the title compound D357 (3.8 g, 59%) as yellow oil.

$^1$H NMR (300 MHz, CHLOROFORM-d): δ 8.22 (s, 1H), 8.08 (s, 1H), 4.62-4.53 (m, 1H), 4.36-4.12 (m, 1H), 4.04 (br s, 1H), 3.86-3.80 (m, 1H), 3.44-3.22 (m, 1H), 3.13 (dd, J=13.5 Hz, 1H), 2.34-2.25 (m, 1H), 2.14-2.07 (m, 1H), 1.46 (s, 9H), 0.90 (s, 9H), 0.10 (s, 3H), 0.08 (s, 3H).

Description D358

(3R,5R)-tert-butyl 3-hydroxy-5-(4-nitro-1H-pyrazol-1-yl)piperidine-1-carboxylate (D358)

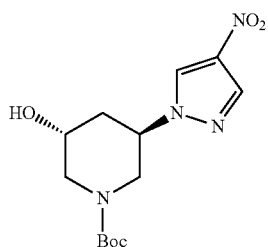 [SMILES: CC(C)(C)OC(=O)N1C[C@H](O)C[C@@H](n2cc([N+](=O)[O-])cn2)C1]

To a solution of D357 (3.7 g, 8.7 mmol) in THF (68 mL) was added TBAF solution (1M in THF (10.4 mL, 10.4 mmol). The reaction was stirred overnight at room temperature. The reaction mixture was concentrated and the residue was diluted with EtOAc (400 mL). The organic layer was washed with water (200 mL), brine, concentrated. The crude was purified by column chromatography on silica gel (PE:EA=1:1) to give the title compound D358 (2.7 g, 100% yield) as an off-white solid.

$^1$H NMR (300 MHz, CHLOROFORM-d): δ 8.24 (s, 1H), 8.08 (s, 1H), 4.67-4.60 (m, 1H), 4.23-4.17 (m, 2H), 3.97-3.91 (m, 1H), 3.37 (dd, J=13.2, 10.2 Hz, 1H), 3.19 (d, J=14.4 Hz, 1H), 2.35-2.21 (m, 2H), 1.46 (s, 9H).

Description D359

(3S,5R)-tert-butyl 3-fluoro-5-(4-nitro-1H-pyrazol-1-yl)piperidine-1-carboxylate (D359)

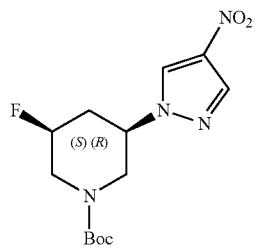

To a solution of D358 (2.8 g, 9.0 mmol) in DCM (53 mL) was added dropwise DAST (3.60 g, 22.4 mmol) under N$_2$ atmosphere at −70° C. The reaction was allowed to warm to room temperature and stirred at room temperature for 4 hrs. The mixture was poured into 200 mL of saturated NaHCO$_3$ aqueous and extracted with DCM (200 mL×2). The organic layers were combined, washed with brine and concentrated. The crude was purified by column chromatography on silica gel (PE:EA=10:1 to 8:1) to give the title compound D359 (250 mg, 25% yield) as a white solid.

$^1$H NMR (300 MHz, CHLOROFORM-d): δ 8.22 (s, 1H), 8.10 (s, 1H), 5.02-4.86 (m, 1H), 4.61-4.51 (m, 1H), 4.41-4.30 (m, 2H), 3.23-3.01 (m, 2H), 2.55-2.26 (m, 2H), 1.48 (s, 9H).

Description D360

(3R,5S)-tert-butyl 3-(5-chloro-4-nitro-1H-pyrazol-1-yl)-5-fluoropiperidine-1-carboxylate (D360)

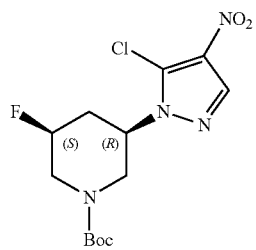

To a solution of D359 (600 g, 1.91 mmol) in THF (6 mL) was added drop wise LiHDMS (3.82 mL, 3.82 mmol, 1M in THF) at −78° C. under N$_2$ atmosphere. After addition, the reaction mixture was stirred at −78° C. for 40 min. Then C$_2$Cl$_6$ (900 g, 3.18 mmol) in 2 mL of THF was added dropwise and the mixture was stirred at −78° C. for 40 min. The saturated NH$_4$Cl aqueous (10 mL) was added at −78° C. and the mixture was concentrated. The residue was poured into 20 mL of water and was extracted with EtOAc (50 mL×3). The extracts were dried over Na$_2$SO$_4$ and concentrated. The crude was purified by column chromatography on silica gel (PE:EA=13:1) to give the title compound D360 (510 mg, 77% yield) as yellow oil.

LCMS: 294 [M+H-55]$^+$. t$_R$=2.09 mins. (LCMS condition 3)

¹H NMR (300 MHz, CHLOROFORM-d): δ 8.18 (s, 1H), 5.14-4.89 (m, 1H), 4.86-4.75 (m, 1H), 4.48-4.23 (m, 2H), 3.26-2.97 (m, 2H), 2.51-2.30 (m, 2H), 1.48 (s, 9H)

Description D361

(3R,5S)-3-(5-chloro-4-nitro-1H-pyrazol-1-yl)-5-fluoropiperidine hydrochloride (D361)

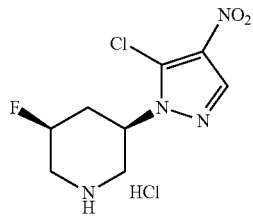 [SMILES: O=[N+]([O-])c1cnn([C@H]2CNC[C@@H](F)C2)c1Cl ; Cl]

To a solution of D360 (510 g, 0.546 mmol) in MeOH (5 mL) was added HCl/dioxane (5 mL, 4M) and the reaction was stirred at room temperature for 1 hour. The mixture was concentrated to give the title compound D361 (363 mg) as white solid.

LCMS: 249 [M+H]⁺. $t_R$=0.48 mins. (LCMS condition 3)

Description D362

(3R,5S)-3-(5-chloro-4-nitro-1H-pyrazol-1-yl)-5-fluoro-1-(oxetan-3-yl)piperidine (D362)

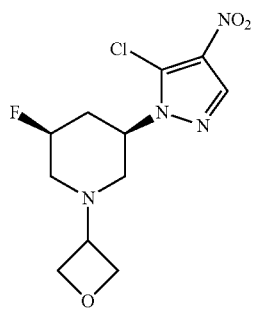

To a solution of D361 (363 g, 1.45 mmol) and oxetan-3-one (528 g, 7.30 mmol) in 1,2-dichloroethane (30 mL) was added NaBH(OAc)₃ (1.84 g, 8.70 mmol) at room temperature. The reaction was stirred at room temperature for 2 hrs. The mixture was poured into 20 ml of saturated Na₂CO₃ aqueous and extracted with DCM (30 mL×2). The extracts were dried over Na₂SO₄ and concentrated. The crude was purified by column chromatography on silica gel (PE:EA=3:1-2:1) to give the title compound D362 (350 mg, 80% yield) as a white solid.

LCMS: 305 [M+H]⁺. $t_R$=1.63 mins. (LCMS condition 3)

¹H NMR (300 MHz, CHLOROFORM-d): δ 8.17 (s, 1H), 5.10-4.92 (m, 2H), 4.71-4.57 (m, 4H), 3.75-3.67 (m, 1H), 3.16-3.07 (m, 1H), 3.02-2.97 (m, 1H), 2.51-2.16 (m, 4H).

Description D363

5-chloro-1-((3R,5S)-5-fluoro-1-(oxetan-3-yl)piperidin-3-yl)-1H-pyrazol-4-amine (D363)

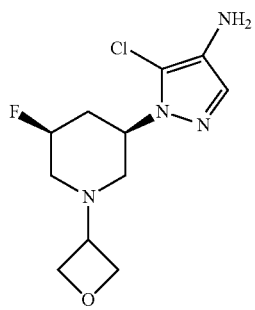 [SMILES: O=[N+]([O-])c1cnn([C@@H]2C[C@H](F)CN(C3COC3)C2)c1Cl]

To a solution of D362 (350 mg, 0.361) in EtOH/H₂O (5 mL/5 mL) was added iron powder (322 g, 5.76 mmol) and NH₄Cl (305 g, 5.76 mmol) at room temperature and the reaction was stirred at 45° C. for 1 hour. The mixture was filtered and the filtrate was concentrated. The crude was purified by column C18 (ACN/H₂O=5-30%) to give the title compound D363 (230 mg, 73%) as colorless oil.

LCMS: 275 [M+H]⁺. $t_R$=0.70 mins. (LCMS condition 3)

¹H NMR (300 MHz, CHLOROFORM-d): δ 7.22 (s, 1H), 5.07-4.92 (m, 1H), 4.81-4.61 (m, 4H), 3.71-3.63 (m, 1H), 3.07 (t, J=12.0 Hz, 1H), 2.98-2.90 (m, 2H), 2.43-2.10 (m, 4H).

Description D364

(±)-tert-butyl 2-(4-amino-5-chloro-1H-pyrazol-1-yl)morpholine-4-carboxylate (D364)

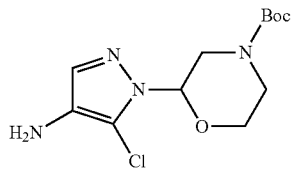

To a solution of D317 (1.0 g, 3.0 mmol) in EtOH (35 mL) was added iron powder (840 g, 15.0 mmol) and NH₄Cl (321 g, 60 mmol) in water (35 mL). The resulting mixture was stirred at 50° C. for 3 hrs. The reaction mixture was filtered and the filtrate was concentrated. The residue was added ethyl acetate (50 mL) and stirred at rt for 10 min, then separated. The aqueous layer was extracted with ethyl acetate (30 mL×3). The combined organic layers were dried over anhydrous Na₂SO₄, filtered and concentrated. The crude was purified with C18 (25-40% CH₃CN in H₂O) to give the title compound D364 (650 mg, yield 72%) as red oil.

LCMS: 303 [M+H]⁺. $t_R$=2.15 mins. (LCMS condition 3)

¹H NMR (400 MHz, CHLOROFORM-d): δ 7.30 (s, 1H), 5.33 (dd, J=9.6, 2.8 Hz, 1H), 4.14-4.09 (m, 1H), 3.97 (d, J=11.2 Hz, 1H), 3.88 (d, J=12.4 Hz, 1H), 3.75-3.69 (m, 2H), 3.11 (t, J=13.2 Hz, 1H), 2.94 (br s, 2H), 1.47 (s, 9H).

Description D365 and D366

Enantiomer 1: tert-butyl 2-(5-chloro-4-((4-ethoxy-7H-pyrrolo[2,3-d]pyrimidin-2-yl)amino)-1H-pyrazol-1-yl) morpholine-4-carboxylate (D365)

Enantiomer 2: tert-butyl 2-(5-chloro-4-((4-ethoxy-7H-pyrrolo[2,3-d]pyrimidin-2-yl)amino)-1H-pyrazol-1-yl) morpholine-4-carboxylate (D366)

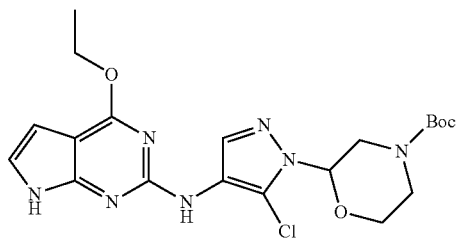

D365

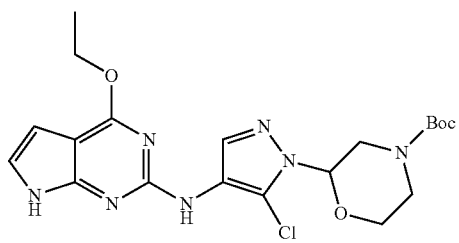

D366

To a solution of D364 (650 g, 2.15 mmol) in dioxane (90 mL) was added D1 (1.06 g, 5.38 mmol), $Pd_2(dba)_3$ (394 g, 0.43 mmol), X-phos (409 g, 0.86 mmol) and $K_2CO_3$ (890 g, 6.45 mmol). The reaction was stirred overnight at 100° C. under $N_2$. The mixture was filtered and concentrated. The residue was dissolved in water (100 mL) and ethyl acetate (100 mL). The aqueous layer was extracted with ethyl acetate (50 mL×2). The combined organic layers were washed with brine (50 mL×2), dried over anhydrous $Na_2SO_4$, filtered and concentrated. The crude was purified with C18 (35-50% $CH_3CN/H_2O$) and further separated by chiral HPLC (chiralpak IC 5 um 4.6*250 mm, phase: Hex:EtOH=60:40, F: 1.0 mL/min, W: 230 nm, T=30° C.) to give the title compounds D365 (182 mg, yield 46%, $t_R$=6.84 min, 100% ee) and D366 (185 mg, yield 46%, $t_R$=12.48 min, 100% ee) as white solids.

LCMS: 464 [M+H]$^+$. $t_R$=2.63 mins. (LCMS condition 3)

$^1$H NMR (400 MHz, CHLOROFORM-d): δ 8.47 (s, 1H), 8.27 (s, 1H), 6.82 (dd, J=3.6 and 2.0 Hz, 1H), 6.43 (dd, J=3.6 and 2.0 Hz, 1H), 6.33 (s, 1H), 5.43 (dd, J=9.2 and 2.4 Hz, 1H), 4.52 (q, J=7.2 Hz, 2H), 4.27-4.16 (m, 1H), 4.14 (d, J=11.2 Hz, 1H), 3.96-3.73 (m, 3H), 3.16 (J=12.0 Hz, 1H), 1.49 (s, 9H), 1.45 (t, J=7.2 Hz, 3H).

Example 1

N-(1,3-dimethyl-1H-pyrazol-4-yl)-4-ethoxy-7H-pyrrolo[2,3-d]pyrimidin-2-amine (E1)

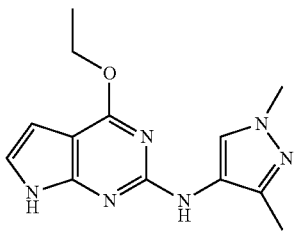 [SMILES: CCOc1nc(Nc2cn(C)nc2C)nc2[nH]ccc12]

A solution of N-(1,3-dimethyl-1H-pyrazol-4-yl)-4-ethoxy-7-tosyl-7H-pyrrolo[2,3-d]pyrimidin-2-amine (which may be prepared according to D3)(100 g, 0.234 mmol) and sodium hydroxide (0.586 mL, 1.172 mmol) in isopropanol (10 mL) was stirred overnight at 50° C. The reaction mixture was concentrated in vacuum. The residue was poured into water and extracted with EtOAc (20 mL×3). The combined organic layer was dried over $Na_2SO_4$, filtered and concentrated in vacuum. The crude was purified by prep-HPLC to give the title compound E1 (12 g, 0.042 mmol, 18.12% yield) as a yellow solid.

LCMS: 273.1 [M+H]$^+$. $t_R$=1.10 min. (LCMS condition 2)

$^1$H NMR (400 MHz, CHLOROFORM-d): δ 8.66-9.05 (m, 1H), 7.80 (s, 1H), 6.69 (d, J=1.5 Hz, 1H), 6.41 (d, J=1.8 Hz, 1H), 6.24 (s, 1H), 4.53 (q, J=7.1 Hz, 2H), 3.82 (s, 3H), 2.27 (s, 3H), 1.47 (t, J=7.0 Hz, 3H).

Example 2 and 3

1-(4-((4-ethoxy-7H-pyrrolo-[2,3-d]pyrimidin-2-yl)amino)-3-methyl-1H-pyrazol-1-yl)-2-methylpropan-2-ol (E2)

1-(4-((4-ethoxy-7H-pyrrolo-[2,3-d]pyrimidin-2-yl)amino)-5-methyl-1H-pyrazol-1-yl)-2-methylpropan-2-ol (E3)

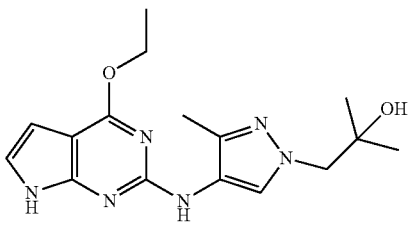

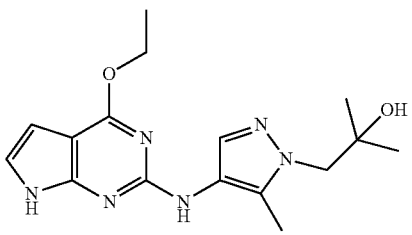

A solution of 2-chloro-4-ethoxy-7H-pyrrolo[2,3-d]pyrimidine (which may be prepared according to D1) (200 g, 1.012 mmol), a mixture of 1-(4-amino-3-methyl-1H-pyrazol-1-yl)-2-methylpropan-2-ol and 1-(4-amino-5-methyl-1H-pyrazol-1-yl)-2-methylpropan-2-ol (206 g, 1.214 mmol), Pd₂(dba)₃ (46.3 g, 0.051 mmol), (9,9-dimethyl-9H-xanthene-4,5-diyl)bis-(diphenylphosphine) (58.6 g, 0.101 mmol) and potassium carbonate (420 g, 3.04 mmol) in 2-butanol (2.0 mL) was irradiated by microwave at 120° C. for 45 min. The reaction mixture was quenched with water and extracted with EtOAc (20 mL×3). The combined organic layer was dried over Na₂SO₄, filtered and concentrated in vacuum. The crude was purified by column chromatography on silica gel (DCM:MeOH=20:1) to get a mixture, which was further purified by chiral-HPLC (Co-Solvent MeOH (0.1% DEA); Column AY-H (4.6*250 mm, 5 um); Column Temperature 40; CO₂ Flow Rate 2.4; Co-Solvent Flow Rate 0.6; Co-Solvent % 20; Back Pressure 120; Total Flow 31; PDA Start Wavelength 214; PDA Stop Wavelength 359) to give the title compounds E2 (30 g, 0.086 mmol, 8.53% yield) and E3 (20 g, 0.058 mmol, 5.76% yield) as grey solids. The structure of E3 was determined by NOE effect between methyl group on position 5 of pyrazole (CH₃, 2.23 ppm) and methylene group on position N1 of pyrazole (CH₂, 3.96 ppm).

E2: LCMS: 331.1[M+H]⁺, $t_R$=1.09 min. (LCMS condition 2)

¹H NMR (400 MHz, CHLOROFORM-d): δ 8.69 (s, 1H), 7.92 (s, 1H), 6.79 (m, 1H), 6.43 (m, 1H), 6.30 (s, 1H), 4.53 (dd, J=9.0 Hz, 9.0 Hz, 2H), 3.98 (s, 2H), 2.29 (s, 3H), 1.75 (s, 1H), 1.47 (t, J=9.0 Hz, 3H), 1.20 (s, 6H).

E3: LCMS: 331.1 [M+H]⁺, $t_R$=1.31 min. (LCMS condition 2)

¹H NMR (400 MHz, CHLOROFORM-d): δ 9.04 (s, 1H), 7.75 (s, 1H), 6.71 (d, J=4.0 Hz, 1H), 6.41 (d, J=4.5 Hz, 1H), 6.15 (s, 1H), 4.50 (dd, J=9.0 Hz, 9.0 Hz, 2H), 3.96, (s, 2H), 2.23 (s, 3H), 1.89 (s, 1H), 1.45 (t, J=9.0 Hz, 3H), 1.20 (s, 6H).

Example 4

N-(5-chloro-1-methyl-1H-pyrazol-4-yl)-4-ethoxy-7H-pyrrolo-[2,3-d]-pyrimidin-2-amine (E4)

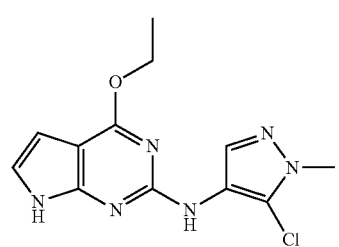 [SMILES: CCOc1nc(Nc2cnn(C)c2Cl)nc2[nH]ccc12]

A solution of N-(5-chloro-1-methyl-1H-pyrazol-4-yl)-4-ethoxy-7-tosyl-7H-pyrrolo-[2,3-d]-pyrimidin-2-amine (which may be prepared according to D4) (50 g, 0.112 mmol) and sodium hydroxide (1 mL, 2.0 mmol, 2M in water) in methanol (3 mL) was stirred at 50° C. for 2 hours. The mixture was extracted with ethyl acetate. The organic layer was dried and evaporated. The crude was purified by prep-HPLC to give the title compound E4 (19 g, 0.065 mmol, 58.0% yield) as a white solid.

LCMS: 293 [M+H]⁺. $t_R$=1.278 mins. (LCMS condition 2)

¹H NMR (400 MHz, METHANOL-d₄): δ 7.82-8.01 (m, 1H), 6.86 (d, J=3.5 Hz, 1H), 6.32 (d, J=3.5 Hz, 1H), 4.51 (q, J=7.0 Hz, 2H), 3.85 (s, 3H), 1.44 (t, J=7.2 Hz, 3H).

Example 5

1-(4-((4-ethoxy-7H-pyrrolo[2,3-d]pyrimidin-2-yl)amino)-3,5-dimethyl-1H-pyrazol-1-yl)-2-methylpropan-2-ol (E5)

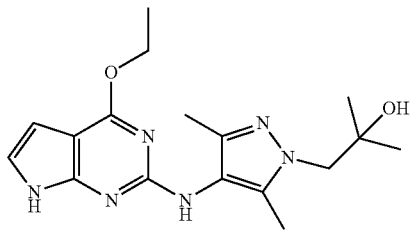 [SMILES: CCOc1nc(Nc2c(C)nn(CC(C)(C)O)c2C)nc2[nH]ccc12]

A solution of 2-chloro-4-ethoxy-7H-pyrrolo[2,3-d]pyrimidine (which may be prepared according to D1) (150 g, 0.759 mmol), 1-(4-amino-3,5-dimethyl-1H-pyrazol-1-yl)-2-methylpropan-2-ol (D6) (167 g, 0.911 mmol), Pd₂(dba)₃ (35.4 g, 0.039 mmol), (9,9-dimethyl-9H-xanthene-4,5-diyl)bis(diphenylphosphine) (44.4 g, 0.077 mmol) and potassium carbonate (319 g, 2.307 mmol) in 2-butanol (2.0 mL) was irradiated by microwave at 120° C. for 45 min. The reaction mixture was quenched with water and extracted with EtOAc (20 mL×3). The combined organic layer was dried over Na₂SO₄, filtered and concentrated in vacuum. The crude was purified by column chromatography on silica gel (DCM:MeOH=20:1) to give the title compound E5 (121 g, 0.351 mmol, 46.3% yield) as a white solid.

LCMS: 344.9 [M+H]⁺. $t_R$=1.16 mins. (LCMS condition 2)

¹H NMR (400 MHz, DMSO-d₆): δ 11.20 (s, 1H), 7.70 (s, 1H), 6.80 (m, 1H), 6.16 (m, 1H), 4.70 (s, 1H), 4.38 (s, 2H), 3.83 (s, 2H), 2.06 (s, 3H), 1.96 (s, 3H), 1.30 (t, J=9.0 Hz, 3H), 1.08 (s, 6H).

Example 6

4-ethoxy-N-(1,3,5-trimethyl-1H-pyrazol-4-yl)-7H-pyrrolo-[2,3-d]-pyrimidin-2-amine (E6)

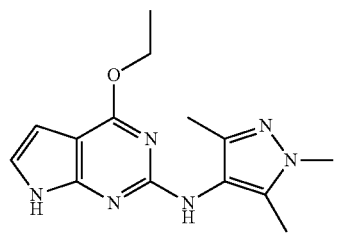 [SMILES: CCOc1nc(Nc2c(C)nn(C)c2C)nc2[nH]ccc12]

A solution of 2-chloro-4-ethoxy-7H-pyrrolo[2,3-d]pyrimidine (which may be prepared according to D1) (150 g, 0.759 mmol), 1,3,5-trimethyl-1H-pyrazol-4-amine (which may be prepared according to D8) (114 g, 0.911 mmol), Pd₂(dba)₃ (35.4 g, 0.039 mmol), (9,9-dimethyl-9H-xanthene-4,5-diyl)bis(diphenylphosphine) (44.4 g, 0.077 mmol) and potassium carbonate (319 g, 2.307 mmol) in 2-butanol (3.0 mL) was irradiated by microwave at 120° C. for 45 min. The reaction mixture was quenched with water and extracted with EtOAc (20 mL×3). The combined organic layer was dried over Na₂SO₄, filtered and concentrated in vacuum. The crude was purified by column chromatography on silica gel (DCM:MeOH=20:1) to give the title compound E6 (65 g, 0.227 mmol, 29.9% yield) as a white solid.

LCMS: 286.9 [M+H]⁺. $t_R$=1.13 mins. (LCMS condition 2)

¹H NMR (400 MHz, DMSO-d₆): δ 11.19 (s, 1H), 7.68 (s, 1H), 7.80 (d, J=4.5 Hz, 1H), 6.17 (d, J=4.5 Hz, 1H), 4.41 (dd, J=9.0 Hz, 2H), 3.62 (s, 3H), 2.02 (s, 3H), 1.93 (s, 3H), 1.33 (t, J=9.0 Hz, 3H).

Example 7

1-(3-chloro-4-((4-ethoxy-7H-pyrrolo-[2,3-d]-pyrimidin-2-yl)amino)-1H-pyrazol-1-yl)-2-methylpropan-2-ol (E7)

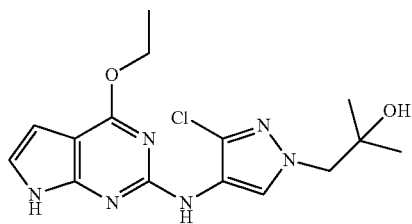 [SMILES: CCOc1nc(Nc2cn(CC(C)(C)O)nc2Cl)nc2[nH]ccc12]

A solution of 2-chloro-4-ethoxy-7H-pyrrolo[2,3-d]pyrimidine (which may be prepared according to D1) (60 g, 0.304 mmol), 1-(4-amino-3-chloro-1H-pyrazol-1-yl)-2-methylpropan-2-ol (which may be prepared according to D11) (60 g, 0.316 mmol), Pd₂(dba)₃ (13.90 g, 0.015 mmol), (9,9-dimethyl-9H-xanthene-4,5-diyl)bis(diphenylphosphine) (17.57 g, 0.030 mmol) and potassium carbonate (126 g, 0.911 mmol) in 2-butanol (3.0 mL) was irradiated by microwave at 120° C. for 45 min. The reaction mixture was quenched with water and extracted with EtOAc (20 mL×3). The combined organic layer was dried over Na₂SO₄, filtered and concentrated in vacuum. The crude was purified by chromatography on silica gel (DCM:MeOH=20:1) to give the title compound E7 (2.6 mg, 6.80 μmol, 2.241% yield) as a white solid.

LCMS: 351 [M+H]⁺. $t_R$=1.635 mins. (LCMS condition 2)

¹H NMR (400 MHz, CHLOROFORM-d): δ 8.33-8.55 (m, 1H), 8.15 (s, 1H), 6.85 (d, J=1.3 Hz, 1H), 6.57 (br. s., 1H), 6.44 (d, J=3.3 Hz, 1H), 4.53 (q, J=7.0 Hz, 2H), 4.02 (s, 2H), 1.47 (t, J=7.2 Hz, 3H), 1.23 (s, 6H).

Example 8 and 9

4-ethoxy-N-(1-(2-methoxyethyl)-3-methyl-1H-pyrazol-4-yl)-7H-pyrrolo-[2,3-d]-pyrimidin-2-amine (E8)

4-ethoxy-N-(1-(2-methoxyethyl)-5-methyl-1H-pyrazol-4-yl)-7H-pyrrolo-[2,3-d]-pyrimidin-2-amine (E9)

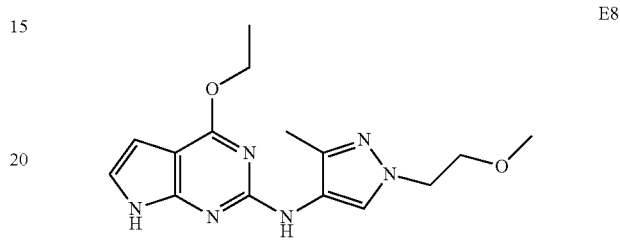

E8

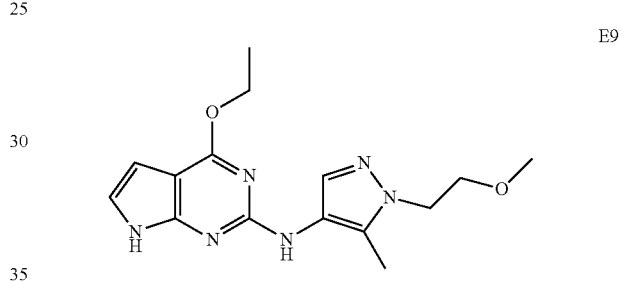

E9

A solution of the mixture of 4-ethoxy-N-(1-(2-methoxyethyl)-3-methyl-1H-pyrazol-4-yl)-7-tosyl-7H-pyrrolo-[2,3-d]-pyrimidin-2-amine (which can be prepared according to D12) and 4-ethoxy-N-(1-(2-methoxyethyl)-5-methyl-1H-pyrazol-4-yl)-7-tosyl-7H-pyrrolo-[2,3-d]-pyrimidin-2-amine (which may be prepared according to D13) (300 g, 0.191 mmol), sodium hydroxide (3 mL, 6.00 mmol, 2M in water) in methanol (15 mL) was stirred at 50° C. for 2 hours. The mixture was concentrated and saturated NaHCO₃ was added until pH=8. The mixture was extracted with EtOAc (50 mL×3). The organic layer was dried over Na₂SO₄, filtered and concentrated. The crude was purified by chromatography on silica gel (DCM:MeOH=20:1) to give the title compounds E8 (100 g, 0.316 mmol, 70.8% yield) and E9 (25 g, 0.079 mmol, 17.71% yield) as white solids.

E8: LCMS: 316.9 [M+H]⁺. $t_R$=1.26 mins. (LCMS condition 2)

¹H NMR (400 MHz, CHLOROFORM-d): δ 9.69 (br. s., 1H), 7.85 (s, 1H), 6.50-6.64 (m, 1H), 6.37 (d, J=2.0 Hz, 1H), 6.23 (s, 1H), 4.52 (q, J=7.1 Hz, 2H), 4.16 (t, J=5.3 Hz, 2H), 3.68 (t, J=5.3 Hz, 2H), 3.23-3.39 (m, 3H), 2.26 (s, 3H), 1.46 (t, J=7.2 Hz, 3H).

E9: LCMS: 316.9 [M+H]⁺. $t_R$=1.25 mins. (LCMS condition 2)

¹H NMR (400 MHz, CHLOROFORM-d): δ 10.05-10.33 (m, 1H), 7.64 (s, 1H), 6.41 (br. s., 1H), 6.25-6.34 (m, 1H), 6.12 (s, 1H), 4.49 (q, J=7.0 Hz, 2H), 4.11 (t, J=5.5 Hz, 2H), 3.66 (t, J=5.5 Hz, 2H), 3.25 (s, 3H), 2.21 (s, 3H), 1.44 (t, J=7.0 Hz, 3H).

Example 10

N-(1-(2-(3-aza-bicyclo-[3.1.0]hexan-3-yl)ethyl)-5-methyl-1H-pyrazol-4-yl)-4-ethoxy-7H-pyrrolo-[2,3-d]-pyrimidin-2-amine (E10)

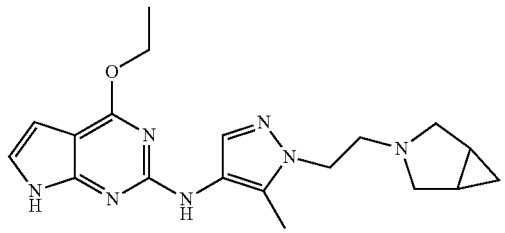 [SMILES: CCOc1nc(Nc2cnn(CCN3CC4CC4C3)c2C)nc2[nH]ccc12]

A solution of N-(1-(2-(3-azabicyclo-[3.1.0]-hexan-3-yl)ethyl)-5-methyl-1H-pyrazol-4-yl)-4-ethoxy-7-tosyl-7H-pyrrolo[2,3-d]pyrimidin-2-amine (which may be prepared according to D18) (150 g, 0.288 mmol) and sodium hydroxide (0.431 mL, 0.863 mmol, 2M in water) in isopropanol (5 mL) was stirred at 60° C. for overnight. The mixture was concentrated and 2N HCl was added until pH=7. The product was extracted with EtOAc twice. The combined organic layer was dried and evaporated. The crude was purified by prep-HPLC to give the title compound E10 (40 g, 0.109 mmol, 37.9% yield) as a white solid.

LCMS: 368 [M+H]$^+$. $t_R$=1.233 mins. (LCMS condition 2)

$^1$H NMR (400 MHz, DMSO-d$_6$): δ 11.00-11.25 (m, 1H), 8.00 (s, 1H), 7.55 (s, 1H), 6.85 (d, J=3.0 Hz, 1H), 6.20 (d, J=3.3 Hz, 1H), 4.43 (q, J=6.9 Hz, 2H), 4.02 (t, J=6.8 Hz, 2H), 2.94 (d, J=8.5 Hz, 2H), 2.64-2.78 (m, 2H), 2.28 (d, J=8.0 Hz, 2H), 2.15 (s, 3H), 1.27-1.47 (m, 5H), 0.53 (q, J=3.5 Hz, 1H), 0.28 (td, J=7.7, 3.8 Hz, 1H).

Example 11 and 12

4-ethoxy-N-(5-methyl-1-(tetrahydro-2H-pyran-4-yl)-1H-pyrazol-4-yl)-7H-pyrrolo-[2,3-d]-pyrimidin-2-amine (E11)

4-ethoxy-N-(3-methyl-1-(tetrahydro-2H-pyran-4-yl)-1H-pyrazol-4-yl)-7H-pyrrolo-[2,3-d]-pyrimidin-2-amine (E12)

E11

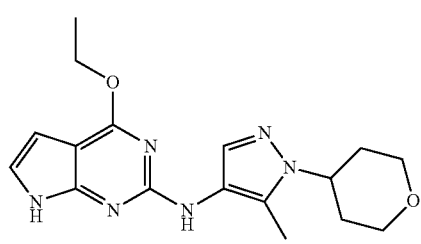

E12

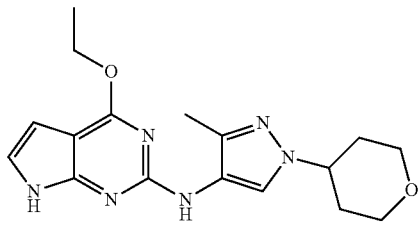

A solution of 2-chloro-4-ethoxy-7H-pyrrolo[2,3-d]pyrimidine (which may be prepared according to D1) (90 g, 0.455 mmol), a mixture of 5-methyl-1-(tetrahydro-2H-pyran-4-yl)-1H-pyrazol-4-amine and 3-methyl-1-(tetrahydro-2H-pyran-4-yl)-1H-pyrazol-4-amine (41.3 g, 0.228 mmol) (which may be prepared according to PCT Int. Appl. WO2012062783), Pd$_2$(dba)$_3$ (41.7 g, 0.046 mmol), (9,9-dimethyl-9H-xanthene-4,5-diyl)bis-(diphenylphosphine) and potassium carbonate (189 g, 1.366 mmol) in 2-butanol (3.0 mL) was irradiated by microwave at 120° C. for 45 min. The reaction mixture was quenched with water, partitioned between ethyl acetate (25 mL) and water (5 mL). The organic layer was washed with water, and then saturated NaHCO$_3$ solution. The resulting organic layer was then dried over Na$_2$SO$_4$, filtered and concentrated. The crude was purified by prep-HPLC to give the title compounds E11 (16 g, 0.047 mmol, 10.26% yield) and E12 (40 mg, 0.117 mmol, 25.7% yield) as brown solids.

E11: LCMS: 343 [M+H]$^+$. $t_R$=1.478 mins. (LCMS condition 2)

$^1$H NMR (400 MHz, DMSO-d$_6$): δ 10.94-11.33 (m, 1H), 8.01 (s, 1H), 7.60 (s, 1H), 6.85 (d, J=3.3 Hz, 1H), 6.20 (d, J=3.0 Hz, 1H), 4.44 (q, J=6.9 Hz, 2H), 4.20-4.39 (m, 1H), 3.96 (dd, J=10.9, 3.6 Hz, 2H), 3.48 (t, J=11.4 Hz, 2H), 2.20 (s, 3H), 2.03 (qd, J=12.2, 4.5 Hz, 2H), 1.76 (dd, J=12.4, 1.9 Hz, 2H), 1.35 (t, 3H).

E12: LCMS: 343 [M+H]$^+$. $t_R$=1.121 mins. (LCMS condition 2)

$^1$H NMR (400 MHz, DMSO-d$_6$): δ 11.23 (br. s., 1H), 8.09 (s, 1H), 7.93 (s, 1H), 6.74-7.02 (m, 1H), 6.22 (d, J=1.3 Hz, 1H), 4.47 (q, J=7.0 Hz, 2H), 4.12-4.32 (m, 1H), 3.84-4.05 (m, 2H), 3.45 (td, J=11.3, 2.3 Hz, 2H), 2.12 (s, 3H), 1.81-2.02 (m, 4H), 1.37 (t, J=7.0 Hz, 3H).

Example 13 and 14

Enantiomer 1: 4-ethoxy-N-(5-methyl-1-(1-methyl-pyrrolidin-3-yl)-1H-pyrazol-4-yl)-7H-pyrrolo-[2,3-d]-pyrimidin-2-amine (E13)

Enantiomer 2: 4-ethoxy-N-(5-methyl-1-(1-methyl-pyrrolidin-3-yl)-1H-pyrazol-4-yl)-7H-pyrrolo-[2,3-d]-pyrimidin-2-amine (E14)

E13

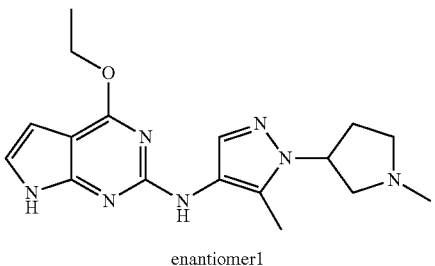

enantiomer1

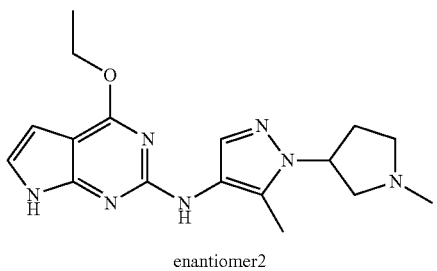

enantiomer2

A solution of (±)-4-ethoxy-N-(5-methyl-1-(1-methyl-pyrrolidin-3-yl)-1H-pyrazol-4-yl)-7-tosyl-7H-pyrrolo-[2,3-d]-pyrimidin-2-amine (which may be prepared according to D19) (240 g, 0.484 mmol) and sodium hydroxide (3 mL, 6.00 mmol) in methanol (15 mL) was stirred at 50° C. for 2 hours. The mixture was concentrated and saturated NaHCO$_3$ was added until pH=8. The mixture was extracted with EtOAc (50 mL×3). The organic layer was dried over Na$_2$SO$_4$, filtered and concentrated. The crude was purified by chromatography on silica gel (DCM:MeOH=8:1) to give the racemic product, which was further purified by chiral-HPLC (Co-Solvent MeOH (0.1% DEA); Column AD-H (4.6*250 mm, 5 um); Column Temperature 39.8; CO$_2$ Flow Rate 1.95; Co-Solvent Flow Rate 1.05; Co-Solvent % 35; Back Pressure 120; Total Flow 3; PDA Start Wavelength 214; PDA Stop Wavelength 359) to give the title compounds E13 (30 g, 0.088 mmol, 18.15% yield) and E14 (30 g, 0.088 mmol, 18.15% yield) as white solids.

E13: LCMS: 342 [M+H]$^+$. $t_R$=1.244 mins. (LCMS condition 2)

Chiral HPLC: $t_R$=3.2 mins. (Conditions: Column AD-H (4.6*250 mm, 5 um); Co-Solvent MeOH (0.1% DEA)) The absolute stereochemistry was not determined.

$^1$H NMR (400 MHz, DMSO-d$_6$): δ 8.01 (s, 1H), 7.58 (s, 1H), 6.63-6.96 (m, 1H), 6.20 (d, J=1.3 Hz, 1H), 4.71-4.96 (m, 1H), 4.44 (q, J=7.0 Hz, 2H), 3.00 (t, J=8.3 Hz, 1H), 2.64-2.76 (m, 1H), 2.53-2.61 (m, 2H), 2.26-2.31 (m, 2H), 2.13-2.26 (m, 5H), 1.35 (t, J=7.0 Hz, 3H)

E14: LCMS: 342 [M+H]$^+$. $t_R$=1.237 mins. (LCMS condition 2)

Chiral HPLC: $t_R$=4.9 mins. (Conditions: Column AD-H (4.6*250 mm, 5 um); Co-Solvent MeOH (0.1% DEA)) The absolute stereochemistry was not determined.

$^1$H NMR (400 MHz, DMSO-d$_6$): δ 11.18 (br. s., 1H), 8.00 (s, 1H), 7.58 (s, 1H), 6.85 (br. s., 1H), 6.21 (d, J=1.0 Hz, 1H), 4.83 (m, 1H), 4.44 (q, J=6.9 Hz, 2H), 3.00 (t, J=8.3 Hz, 1H), 2.65-2.74 (m, 1H), 2.53-2.61 (m, 2H), 2.28 (s, 3H), 2.12-2.26 (m, 5H), 1.35 (t, J=7.0 Hz, 3H).

Example 15

1-(5-chloro-4-((4-ethoxy-7H-pyrrolo-[2,3-d]pyrimidin-2-yl)amino)-1H-pyrazol-1-yl)-2-methylpropan-2-ol (E15)

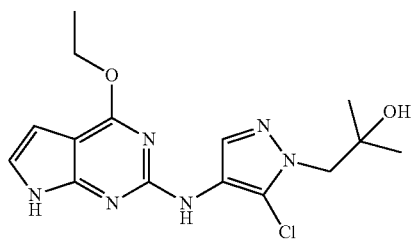 [SMILES: CCOc1nc(Nc2cnn(CC(C)(C)O)c2Cl)nc2[nH]ccc12]

A solution of 1-(5-chloro-4-((4-ethoxy-7-tosyl-7H-pyrrolo-[2,3-d]-pyrimidin-2-yl)amino)-1H-pyrazol-1-yl)-2-methylpropan-2-ol (which may be prepared according to D20)(40 mg, 0.079 mmol) and sodium hydroxide (1 mL, 2.000 mmol, 2M in water) in methanol (3 mL) was stirred at 20° C. for 2 hours. The mixture was extracted with ethyl acetate. The organic layer was dried with Na$_2$SO$_4$ and evaporated. The crude was purified by prep-HPLC to give the title compound E15 (9 g, 0.026 mmol, 32.4% yield) as a white solid.

LCMS: 352 [M+H]$^+$. $t_R$=1.62 mins. (LCMS condition 2)

$^1$H NMR (400 MHz, METHANOL-d$_4$): δ 7.99 (s, 1H), 6.85 (d, J=3.5 Hz, 1H), 6.13-6.37 (m, 1H), 4.50 (q, J=7.0 Hz, 2H), 4.12 (s, 2H), 1.42 (t, J=7.0 Hz, 3H), 1.24 (s, 6H).

Example 16 and 17

Enantiomer 1: 4-ethoxy-N-(5-methyl-1-(tetrahydro-furan-3-yl)-1H-pyrazol-4-yl)-7H-pyrrolo-[2,3-d]-pyrimidin-2-amine (E16)

Enantiomer 2: 4-ethoxy-N-(5-methyl-1-(tetrahydro-furan-3-yl)-1H-pyrazol-4-yl)-7H-pyrrolo-[2,3-d]-pyrimidin-2-amine (E17)

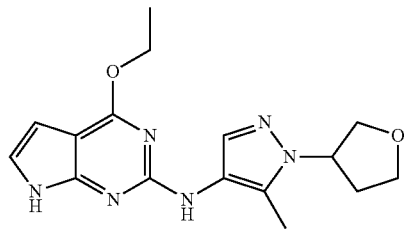

enantiomer1

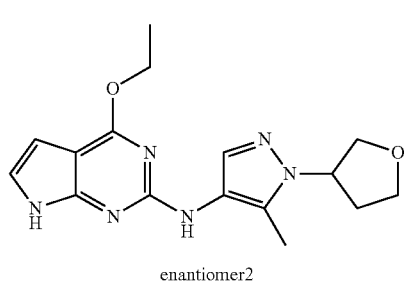

enantiomer2

A solution of 2-chloro-4-ethoxy-7H-pyrrolo[2,3-d]pyrimidine (which can be prepared according to D1) (49 g, 0.248 mmol), 5-methyl-1-(tetrahydrofuran-3-yl)-1H-pyrazol-4-amine (49.8 g, 0.298 mmol) (which may be prepared according to PCT Int. Appl., WO2012062783), Pd$_2$(dba)$_3$ (11.35 g, 0.012 mmol), potassium carbonate (103 mg, 0.744 mmol) and (9,9-dimethyl-9H-xanthene-4,5-diyl)-bis(diphenylphosphine) (11.82 mg, 0.025 mmol) in 2-butanol (5 mL) was irradiated by microwave at 120° C. for 45 min. The reaction mixture was quenched with water, partitioned between ethyl acetate (25 mL) and water (5 mL). The organic layer was washed with water, and then saturated NaHCO$_3$. Then, the resulting organic phase was dried over Na$_2$SO$_4$, filtered and concentrated. The crude was purified by chiral-HPLC (Co-Solvent MeOH (0.1% DEA); Column OJ-H (4.6*250 mm, 5 um); Column Temperature 39.8; CO$_2$ Flow Rate 2.4; Co-Solvent Flow Rate 0.6; Co-Solvent % 20; Back Pressure 120; Total Flow 3; PDA Start Wavelength 214; PDA Stop Wavelength 359) to give the title compounds E16 (18 mg, 24.56% yield) and E17 (10 mg, 15.43% yield) as white solids.

E16: LCMS: 329 [M+H]$^+$. $t_R$=1.267 mins. (LCMS condition 2)

Chiral HPLC: $t_R$=2.85 mins. (Conditions: Column OJ-H (4.6*250 mm, 5 um); Co-Solvent MeOH (0.1% DEA)) The absolute stereochemistry was not determined.

$^1$H NMR (400 MHz, DMSO-$d_6$): δ 10.95-11.29 (m, 1H), 8.02 (s, 1H), 7.60 (s, 1H), 6.84 (d, J=2.3 Hz, 1H), 6.20 (d, J=2.8 Hz, 1H), 4.88-5.00 (m, 1H), 4.43 (d, J=7.0 Hz, 2H), 3.90-4.13 (m, 2H), 3.68-3.90 (m, 2H), 2.23-2.32 (m, 2H), 2.18 (s, 3H), 1.34 (t, 3H).

E17: LCMS: 329 [M+H]$^+$. $t_R$=1.255 mins. (LCMS condition 2)

Chiral HPLC: $t_R$=4.28 mins. (Conditions: Column OJ-H (4.6*250 mm, 5 um); Co-Solvent MeOH (0.1% DEA)) unknown absolute stereochemistry $^1$H NMR (400 MHz, DMSO-$d_6$): δ 11.20 (br. s., 1H), 8.06 (s, 1H), 7.61 (s, 1H), 6.78-6.96 (m, 1H), 6.00-6.34 (m, 1H), 4.89-5.05 (m, 1H), 4.44 (q, J=6.9 Hz, 2H), 3.92-4.10 (m, 2H), 3.66-3.89 (m, 2H), 2.29 (q, J=6.6 Hz, 2H), 2.20 (s, 3H), 1.36 (t, 3H).

Example 18 and 19

4-ethoxy-N-(5-methyl-1-(1-methylpiperidin-4-yl)-1H-pyrazol-4-yl)-7H-pyrrolo-[2,3-d]-pyrimidin-2-amine (E18)

4-ethoxy-N-(3-methyl-1-(1-methylpiperidin-4-yl)-1H-pyrazol-4-yl)-7H-pyrrolo-[2,3-d]-pyrimidin-2-amine (E19)

E18

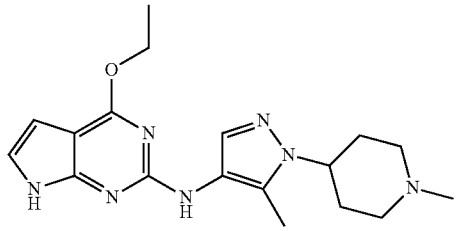

E19

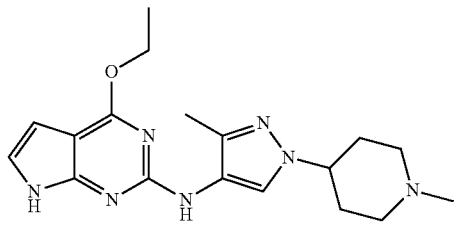

A solution of a mixture of 4-ethoxy-N-(5-methyl-1-(1-methylpiperidin-4-yl)-1H-pyrazol-4-yl)-7-tosyl-7H-pyrrolo-[2,3-d]pyrimidin-2-amine (which may be prepared according to D21) and 4-ethoxy-N-(3-methyl-1-(1-methylpiperidin-4-yl)-1H-pyrazol-4-yl)-7-tosyl-7H-pyrrolo-[2,3-d]pyrimidin-2-amine (which can be prepared according to D22) (260 g, 0.510 mmol), sodium hydroxide (0.510 mL, 1.020 mmol, 2M in water) in THF (5 mL) was stirred at 60° C. for 1 hour. The reaction mixture was poured into EtOAc (20 mL) and extracted with water (3×30 mL). The organic layer was evaporated in vacuum and purified by prep-HPLC to give the title compounds E18 (16 g, 0.045 mmol, 8.82% yield) and E19 (5 g, 0.014 mmol, 2.76% yield) as white solids.

E18: LCMS: 356.3 [M+H]$^+$. $t_R$=1.10 mins. (LCMS condition 2)

$^1$H NMR (400 MHz, CHLOROFORM-d): δ 9.12 (br. s., 1H), 7.91 (s, 1H), 6.67 (m, 1H), 6.38 (d, J=1.8 Hz, 1H), 6.23 (s, 1H), 4.51 (q, J=7.0 Hz, 2H), 3.88-4.14 (m, 1H), 2.97 (d, J=11.3 Hz, 2H), 2.33 (s, 3H), 2.26 (s, 3H), 1.96-2.18 (m, 6H), 1.45 (t, J=7.0 Hz, 3H).

E19: LCMS: 356.2 [M+H]$^+$. $t_R$=1.27 mins. (LCMS condition 2)

$^1$H NMR (400 MHz, CHLOROFORM-d): δ 9.16 (br. s., 1H), 7.69 (s, 1H), 6.60 (m, 1H), 6.35 (d, J=1.8 Hz, 1H), 6.06 (s, 1H), 4.49 (q, J=7.0 Hz, 2H), 4.00 (m, 1H), 3.05 (m, 2H), 2.10-2.44 (m, 10H), 1.90 (m, 2H), 1.43 (t, J=7.0 Hz, 3H).

Example 20

4-ethoxy-N-(5-methoxy-1-(tetrahydro-2H-pyran-4-yl)-1H-pyrazol-4-yl)-7H-pyrrolo-[2,3-d]-pyrimidin-2-amine (E20)

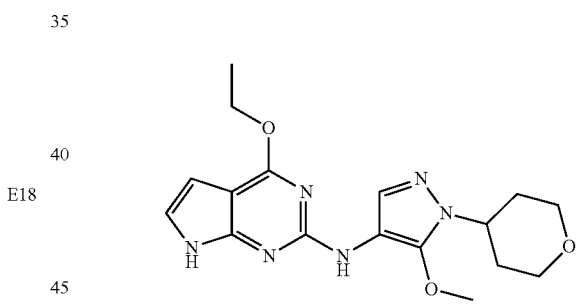

A solution of 4-ethoxy-N-(5-methoxy-1-(tetrahydro-2H-pyran-4-yl)-1H-pyrazol-4-yl)-7-tosyl-7H-pyrrolo-[2,3-d]pyrimidin-2-amine (which may be prepared according to D25)(40 g, 0.078 mmol) and sodium hydroxide (1 mL, 2.000 mmol, 2M in water) in methanol (3 mL) was stirred at 20° C. for 2 hours. The mixture was extracted with ethyl acetate. The organic layer was dried with Na$_2$SO$_4$ and evaporated. The crude was purified by prep-HPLC to give the title compound E20 (4 mg, 10.83 μmol, 13.87% yield) as a white solid.

LCMS: 359 [M+H]$^+$. $t_R$=1.587 mins. (LCMS condition 2)

$^1$H NMR (400 MHz, CHLOROFORM-d): δ 8.47-8.87 (m, 1H), 7.53 (s, 1H), 6.75 (dd, J=3.4, 1.9 Hz, 1H), 6.39 (dd, J=3.3, 1.8 Hz, 1H), 5.98 (m., 1H), 4.48 (q, J=7.1 Hz, 2H), 4.29 (tt, J=11.6, 4.0 Hz, 1H), 4.06-4.16 (m, 2H), 3.99 (s, 3H), 3.45-3.58 (m, 2H), 2.15-2.32 (m, 2H), 1.85 (dd, J=12.7, 2.1 Hz, 2H), 1.42 (t, J=7.0 Hz, 3H).

Example 21

N-(5-chloro-1-(2-methoxyethyl)-1H-pyrazol-4-yl)-4-ethoxy-7H-pyrrolo-[2,3-d]-pyrimidin-2-amine (E21)

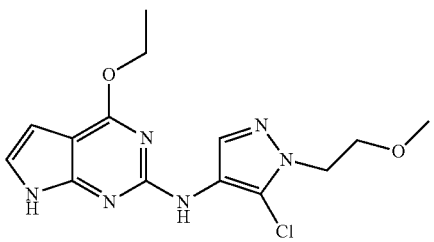 [SMILES: CCOc1nc(Nc2cnn(CCOC)c2Cl)nc2[nH]ccc12]

A solution of 2-chloro-4-ethoxy-7H-pyrrolo[2,3-d]pyrimidine (which can be prepared according to D1) (120 g, 0.607 mmol), 5-chloro-1-(2-methoxyethyl)-1H-pyrazol-4-amine (128 g, 0.729 mmol) (which may be prepared according to PCT Int. Appl. WO2012062783), $Pd_2(dba)_3$ (27.8 g, 0.030 mmol), potassium carbonate (168 g, 1.214 mmol) and (9,9-dimethyl-9H-xanthene-4,5-diyl)bis(diphenylphosphine) (35.1 g, 0.061 mmol) in 2-butanol (3 mL) was irradiated by microwave at 120° C. for 70 min. The reaction mixture was poured into EtOAc (50 mL) and extracted with water (50 mL). The organic layer was evaporated in vacuum and purified by prep-HPLC to give the title compound E21 (50 g, 0.148 mmol, 24.45% yield) as a white solid.

LCMS: 337[M+H]$^+$. $t_R$=1.37 mins. (LCMS condition 2)

$^1$H NMR (400 MHz, CHLOROFORM-d): δ 8.40 (br. s., 1H), 8.16 (s, 1H), 6.81 (dd, J=3.4, 2.1 Hz, 1H), 6.43 (dd, J=3.4, 2.1 Hz, 1H), 6.27 (s, 1H), 4.53 (q, J=7.0 Hz, 2H), 4.30 (t, J=5.6 Hz, 2H), 3.78 (t, J=5.8 Hz, 2H), 3.35 (s, 3H), 1.46 (t, J=7.2 Hz, 3H).

Example 22

N-(5-chloro-1-(tetrahydro-2H-pyran-4-yl)-1H-pyrazol-4-yl)-4-ethoxy-7H-pyrrolo-[2,3-d]-pyrimidin-2-amine (E22)

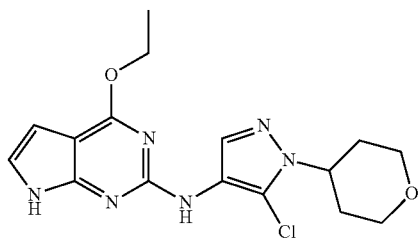 [SMILES: CCOc1nc(Nc2cnn(C3CCOCC3)c2Cl)nc2[nH]ccc12]

A solution of 2-chloro-4-ethoxy-7H-pyrrolo[2,3-d]pyrimidine (which may be prepared according to D1) (70 g, 0.354 mmol), 5-chloro-4-nitro-1-(tetrahydro-2H-pyran-4-yl)-1H-pyrazole (79 g, 0.390 mmol) (which may be prepared according to PCT Int. Appl. WO2012062783), $Pd_2(dba)_3$ (32.4 g, 0.035 mmol), potassium carbonate (147 mg, 1.063 mmol) and (9,9-dimethyl-9H-xanthene-4,5-diyl)bis(diphenylphosphine) (30.7 g, 0.053 mmol) in 2-butanol (1 mL) was irradiated by microwave at 120° C. for 45 min. The reaction mixture was partitioned between ethyl acetate (25 mL) and water (25 mL). The organic layer was washed with water, $NaHCO_3$ solution and brine, dried over $Na_2SO_4$ and evaporated. The crude was purified by prep-HPLC to give the title compound E22 (15 g, 0.041 mmol, 11.67% yield) as a white solid.

LCMS: 343[M+H]$^+$. $t_R$=1.121 mins. (LCMS condition 2)

$^1$H NMR (400 MHz, DMSO-d$_6$) δ: 11.29 (br. s., 1H), 8.16 (s, 1H), 7.82 (s, 1H), 6.90 (d, J=3.5 Hz, 1H), 6.23 (d, J=3.3 Hz, 1H), 4.33-4.60 (m, 3H), 3.98 (dd, J=11.2, 3.6 Hz, 2H), 3.51 (t, J=11.2 Hz, 2H), 1.92-2.12 (m, 2H), 1.83 (dd, J=12.5, 2.0 Hz, 2H), 1.35 (t, 3H).

Example 23

1-(4-((4-ethoxy-3-methyl-1H-pyrazolo-[3,4-d]-pyrimidin-6-yl)amino)-3-methyl-1H-pyrazol-1-yl)-2-methylpropan-2-ol (E23)

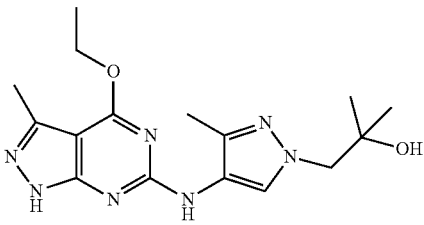 [SMILES: CCOc1nc(Nc2cn(CC(C)(C)O)nc2C)nc2[nH]nc(C)c12]

A solution of 6-chloro-4-ethoxy-3-methyl-1H-pyrazolo[3,4-d]pyrimidine (which may be prepared according to D28)(200 g, 0.941 mmol), 1-(4-amino-3-methyl-1H-pyrazol-1-yl)-2-methyl propan-2-ol (159 g, 0.941 mmol) (which may be prepared according to PCT Int. Appl., WO2012062783), $Pd_2(dba)_3$ (60.3 g, 0.066 mmol), dicyclohexyl(2',4',6'-triisopropyl-[1,1'-biphenyl]-2-yl)phosphine (62.8 g, 0.132 mmol) and potassium carbonate (390 g, 2.82 mmol) in 2-butanol (15 mL) was irradiated by microwave at 100° C. for 2 hours. Then, the reaction mixture was filtered, and then was purified via biotage with reverse phase column (0.1% NH$_4$OH in water/acetonitrile) to give the mixture, which was further purified by chiral-HPLC (Co-Solvent MeOH (0.1% DEA); Column AS-H (4.6*250 mm, 5 um); Column Temperature 40.4; CO$_2$ Flow Rate 2.25; Co-Solvent Flow Rate 0.45; Co-Solvent % 15; Back Pressure 120; Total Flow 3; PDA Start Wavelength 214; PDA Stop Wavelength 359) to give the title compound E23 (17 g, 0.049 mmol, 31.5% yield) as a white solid.

LCMS: 346[M+H]$^+$. $t_R$=1.04 mins. (LCMS condition 2)

$^1$H NMR (400 MHz, CHLOROFORM-d): δ 7.89 (s, 1H), 6.49 (s, 1H), 4.51 (q, J=7.0 Hz, 2H), 4.11 (br. s., 1H), 3.98 (s, 2H), 3.96 (s, 2H), 2.51 (s, 3H), 2.27 (s, 3H), 1.46 (t, J=7.0 Hz, 3H), 1.19 (s, 6H).

Example 24 and 25

1-(4-((4-(cyclopropylmethoxy)-1H-pyrazolo-[3,4-d]-pyrimidin-6-yl)amino)-5-methyl-1H-pyrazol-1-yl)-2-methylpropan-2-ol (E24)

1-(4-((4-(cyclopropylmethoxy)-1H-pyrazolo-[3,4-d]-pyrimidin-6-yl)amino)-3-methyl-1H-pyrazol-1-yl)-2-methylpropan-2-ol (E25)

Example 26 and 27

4-ethoxy-N-(1-(2-fluoroethyl)-5-methyl-1H-pyrazol-4-yl)-7H-pyrrolo-[2,3-d]-pyrimidin-2-amine (E26)

4-ethoxy-N-(1-(2-fluoroethyl)-3-methyl-1H-pyrazol-4-yl)-7H-pyrrolo-[2,3-d]-pyrimidin-2-amine (E27)

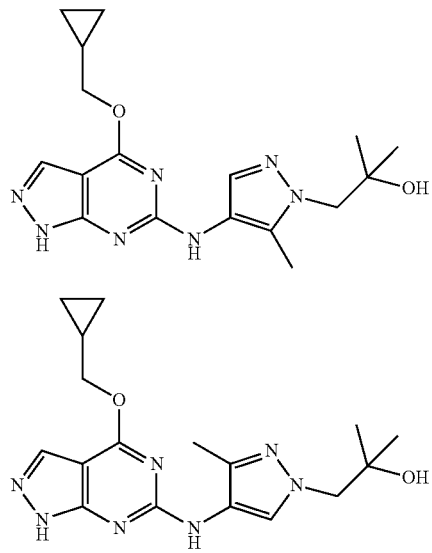

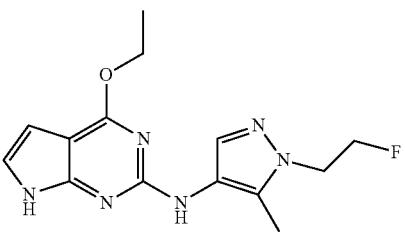

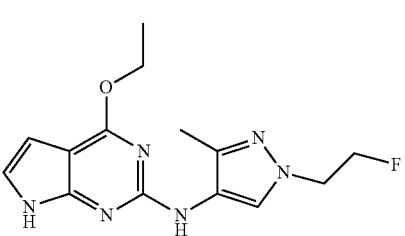

A solution of 6-chloro-4-(cyclopropylmethoxy)-1H-pyrazolo[3,4-d]pyrimidine (which may be prepared according to D29)(200 g, 0.890 mmol), a mixture of 1-(4-amino-3-methyl-1H-pyrazol-1-yl)-2-methylpropan-2-ol, 1-(4-amino-5-methyl-1H-pyrazol-1-yl)-2-methylpropan-2-ol (151 g, 0.890 mmol) (which may be prepared according to PCT Int. Appl., WO2012062783), Pd$_2$(dba)$_3$ (40.8 g, 0.045 mmol), dicyclohexyl(2',4',6'-triisopropyl-[1,1'-biphenyl]-2-yl)phosphine (42.4 g, 0.089 mmol) and potassium carbonate (369 mg, 2.67 mmol) in 2-butanol (24 mL) was irradiated by microwave at 100° C. for 2 hours. Then, the reaction mixture was filtered, purified via biotage with reverse phase column (0.1% NH$_4$OH in water/acetonitrile) to give a mixture, which was further purified by chiral-HPLC (Co-Solvent MeOH (0.1% DEA); Column OZ-H (4.6*250 mm, 5 um); Column Temperature 39; CO$_2$ Flow Rate 2.1; Co-Solvent Flow Rate 0.9; Co-Solvent % 30; Back Pressure 119; Total Flow 3; PDA Start Wavelength 214; PDA Stop Wavelength 359) to give the title compounds E24 (25 mg, 35.6%) and E25 (38 mg, 50.4%) as white solids.

E24: LCMS: 358[M+H]$^+$. $t_R$=1.07 mins. (LCMS condition 2)

$^1$H NMR (400 MHz, CHLOROFORM-d): δ 7.89 (s, 1H), 7.70 (s, 1H), 4.51 (m, 1H), 4.26 (d, J=7.0 Hz, 2H), 3.98 (s, 2H), 2.24 (s, 3H), 1.32 (m, 1H), 1.21 (s, 7H), 0.58-0.72 (m, 2H), 0.37 (d, J=4.8 Hz, 2H).

E25: LCMS: 358[M+H]$^+$. $t_R$=1.06 mins. (LCMS condition 2)

$^1$H NMR (400 MHz, CHLOROFORM-d) δ: 7.91 (s, 1H), 7.86 (br. s., 1H), 4.29 (d, J=7.3 Hz, 2H), 4.15 (m, 1H), 3.98 (s, 2H), 2.26 (s, 3H), 1.27-1.45 (m, 1H), 1.20 (s, 6H), 0.59-0.75 (m, 2H), 0.39 (q, J=4.8 Hz, 2H).

A solution of 2-chloro-4-ethoxy-7H-pyrrolo[2,3-d]pyrimidine (which may be prepared according to D1) (200 g, 1.012 mmol), a mixture of 1-(2-fluoroethyl)-5-methyl-1H-pyrazol-4-amine (which may be prepared according to D32) and 1-(2-fluoroethyl)-3-methyl-1H-pyrazol-4-amine (which may be prepared according to D33)(200 g, 0.838 mmol), Pd$_2$(dba)$_3$ (46.3 g, 0.051 mmol), (9,9-dimethyl-9H-xanthene-4,5-diyl)bis(diphenylphosphine) and potassium carbonate (280 g, 2.024 mmol) in 2-butanol (10 mL) was irradiated by microwave at 100° C. for 2 hours. Then water (100 mL) was added and the aqueous phase was extracted with ethyl acetate (3×50 mL). The combined organic layer was washed with brine (20 mL), dried with Na$_2$SO$_4$, filtered and concentrated. The crude was purified by chromatography on silica gel (PE:EA=1:3) and further purified via Biotage (2M NH$_4$OH in Methanol; 40+M Biotage column) to give the title compound E26 (35 g, 0.115 mmol, 11.36% yield) and E27 (100 g, 0.329 mmol, 32.5% yield) as white solids.

E26: LCMS: 305 [M+H]$^+$. $t_R$=1.263 mins. (LCMS condition 2)

$^1$H NMR (400 MHz, CHLOROFORM-d): δ 9.70 (br. s., 1H), 7.70 (s, 1H), 6.44-6.58 (m, 1H), 6.28-6.40 (m, 1H), 6.09 (s, 1H), 4.76 (t, J=4.9 Hz, 1H), 4.64 (t, J=4.9 Hz, 1H), 4.49 (q, J=7.0 Hz, 2H), 4.26-4.34 (m, 1H), 4.14-4.25 (m, 1H), 2.18-2.28 (m, 3H), 1.69 (s, 3H), 1.43 (t, J=7.0 Hz, 3H).

E27: LCMS: 305 [M+H]$^+$. $t_R$=1.274 mins. (LCMS condition 2)

$^1$H NMR (400 MHz, CHLOROFORM-d): δ 8.98 (br. s., 1H), 7.94 (s, 1H), 6.64-6.73 (m, 1H), 6.40 (dd, J=3.3, 2.0 Hz, 1H), 6.23 (s, 1H), 4.78 (t, J=4.8 Hz, 1H), 4.66 (t, J=4.8 Hz, 1H), 4.52 (q, J=7.1 Hz, 2H), 4.34 (t, J=4.8 Hz, 1H), 4.28 (t, J=4.8 Hz, 1H), 2.22-2.32 (m, 3H), 1.46 (t, 3H).

Example 28

N-(5-chloro-1-(oxetan-3-yl-methyl)-1H-pyrazol-4-yl)-4-ethoxy-7H-pyrrolo-[2,3-d]pyrimidin-2-amine (E28)

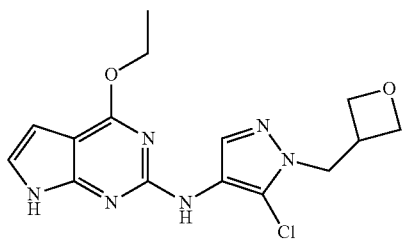 [SMILES: CCOc1nc(Nc2cnn(CC3COC3)c2Cl)nc2[nH]ccc12]

A solution of 2-chloro-4-ethoxy-7H-pyrrolo[2,3-d]pyrimidine (which may be prepared according to D1) (120 g, 0.607 mmol), 5-chloro-1-(oxetan-3-yl-methyl)-1H-pyrazol-4-amine (which may be prepared according to D34)(125 g, 0.668 mmol), $Pd_2(dba)_3$ (55.6 g, 0.061 mmol), (9,9-dimethyl-9H-xanthene-4,5-diyl)bis(diphenylphosphine) (52.7 mg, 0.091 mmol) and potassium carbonate in 2-butanol (1 mL) was irradiated by microwave at 130° C. for 90 min. The reaction mixture was partitioned between ethyl acetate (25 mL) and water (25 mL). The organic layer was washed with water, saturated $NaHCO_3$ and brine, dried over $Na_2SO_4$, filtered and concentrated. The crude was purified by prep-HPLC to give the title compound E28 (50 g, 0.143 mmol, 23.61% yield) as a yellow solid.

LCMS: 349 [M+H]$^+$. $t_R$=1.170 mins. (LCMS condition 2)

$^1$H NMR (400 MHz, DMSO-d): δ 11.29 (br. s., 1H), 8.16 (s, 1H), 7.77 (s, 1H), 6.90 (dd, J=3.3, 2.3 Hz, 1H), 6.23 (dd, J=3.4, 1.9 Hz, 1H), 4.66 (dd, J=7.5, 6.3 Hz, 2H), 4.31-4.52 (m, 6H), 3.38-3.49 (m, 1H), 1.35 (t, 3H).

Example 29

4-ethoxy-N-(5-methyl-1-(oxetan-3-yl-methyl)-1H-pyrazol-4-yl)-7H-pyrrolo-[2,3-d]pyrimidin-2-amine (E29)

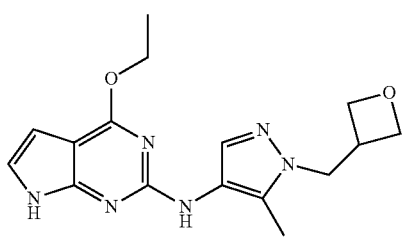 [SMILES: CCOc1nc(Nc2cnn(CC3COC3)c2C)nc2[nH]ccc12]

A solution of 2-chloro-4-ethoxy-7H-pyrrolo[2,3-d]pyrimidine (which may be prepared according to D1) (120 g, 0.607 mmol), 5-methyl-1-(oxetan-3-ylmethyl)-1H-pyrazol-4-amine (which may be prepared according to D36) (112 g, 0.668 mmol), $Pd_2(dba)_3$ (55.6 g, 0.061 mmol), (9,9-dimethyl-9H-xanthene-4,5-diyl)bis(diphenylphosphine) (52.7 mg, 0.091 mmol) and potassium carbonate in 2-butanol (1 mL) was irradiated by microwave at 130° C. for 90 min. The reaction mixture was partitioned between ethyl acetate (25 mL) and water (25 mL). The organic layer was washed with water, saturated $NaHCO_3$ and brine, dried over $Na_2SO_4$, filtered and concentrated. The crude was purified by prep-HPLC to give the title compound E29 (66 g, 0.201 mmol, 33.1% yield)) as a yellow solid.

LCMS: 329 [M+H]$^+$. $t_R$=1.441 mins. (LCMS condition 2)

$^1$H NMR (400 MHz, DMSO-d$_6$): δ 11.17 (br. s., 1H), 7.99 (s, 1H), 7.55 (s, 1H), 6.83-6.87 (m, 1H), 6.20 (dd, J=3.3, 1.8 Hz, 1H), 4.65 (dd, J=7.8, 6.3 Hz, 2H), 4.38-4.47 (m, 4H), 4.24-4.33 (m, 2H), 3.36-3.45 (m, 1H), 2.14-2.21 (m, 3H), 1.35 (t, 3H).

Example 30-31-32-33

Enantiomer 1: 4-ethoxy-N-(5-methyl-1-(tetrahydro-2H-pyran-3-yl)-1H-pyrazol-4-yl)-7H-pyrrolo-[2,3-d]pyrimidin-2-amine (E30)

Enantiomer 2: 4-ethoxy-N-(5-methyl-1-(tetrahydro-2H-pyran-3-yl)-1H-pyrazol-4-yl)-7H-pyrrolo-[2,3-d]pyrimidin-2-amine (E31)

Enantiomer 1: 4-ethoxy-N-(3-methyl-1-(tetrahydro-2H-pyran-3-yl)-1H-pyrazol-4-yl)-7H-pyrrolo-[2,3-d]pyrimidin-2-amine (E32)

Enantiomer 2: 4-ethoxy-N-(3-methyl-1-(tetrahydro-2H-pyran-3-yl)-1H-pyrazol-4-yl)-7H-pyrrolo-[2,3-d]pyrimidin-2-amine (E33)

E30

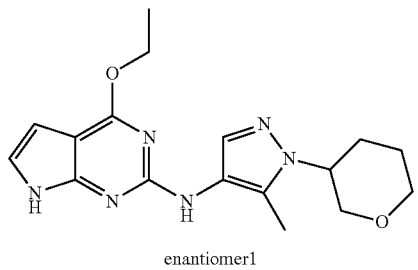

enantiomer1

E31

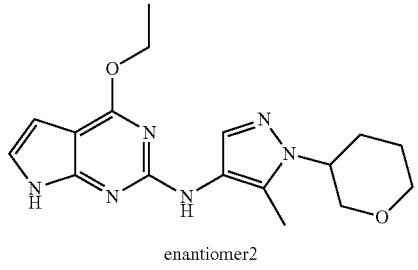

enantiomer2

E32

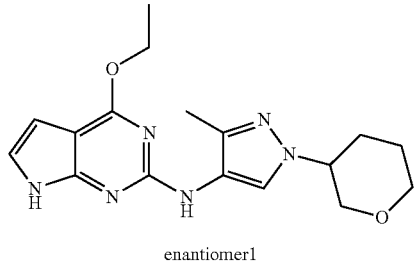

enantiomer1

217

-continued

E33

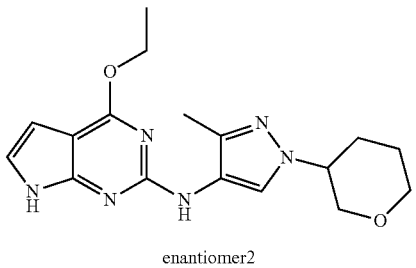

enantiomer2

A solution of 2-chloro-4-ethoxy-7H-pyrrolo[2,3-d]pyrimidine (which may be prepared according to D1) (126 g, 0.638 mmol), a mixture of (±)-5-methyl-1-(tetrahydro-2H-pyran-3-yl)-1H-pyrazol-4-amine (which may be prepared according to D39) and (±)-3-methyl-1-(tetrahydro-2H-pyran-3-yl)-1H-pyrazol-4-amine (which may be prepared according to D40) (139 g, 0.765 mmol), $Pd_2(dba)_3$ (55.6 g, 0.061 mmol), potassium carbonate (264 g, 1.913 mmol) and (9,9-dimethyl-9H-xanthene-4,5-diyl)bis(diphenylphosphine) (30.4 g, 0.064 mmol) in 2-butanol (4 mL) was irradiated by microwave at 120° C. for 45 min. After filtration, the filtrate was concentrated and the crude was purified by chiral-HPLC (Co-Solvent MeOH (0.1% DEA); Column AD-H (4.6*250 mm, 5 um); Column Temperature 39.8; $CO_2$ Flow Rate 2.1; Co-Solvent Flow Rate 0.9; Co-Solvent % 30; Back Pressure 120; Total Flow 3; PDA Start Wavelength 214; PDA Stop Wavelength 359) to give the title compounds E30 (21 g, 0.061 mmol, 9.62% yield) and E31 (21 g, 0.061 mmol, 9.62% yield) as white solids, E32 (13 g, 0.038 mmol, 5.95% yield) and E33 (19 g, 0.055 mmol, 8.70% yield) as yellow solids.

E30: LCMS: 343 [M+H]$^+$. $t_R$=1.329 mins. (LCMS condition 2)

Chiral HPLC: $t_R$=3.53 mins. (Condition: Column AD-H (4.6*250 mm, 5 um); (Co-Solvent MeOH (0.1% DEA)) The absolute stereochemistry was not determined.

$^1$H NMR (400 MHz, DMSO-d$_6$): δ 11.17 (br. s., 1H), 8.00 (s, 1H), 7.61 (s, 1H), 6.78-6.93 (m, 1H), 6.20 (dd, J=3.3, 2.0 Hz, 1H), 4.37-4.51 (m, 2H), 4.09-4.26 (m, 1H), 3.87 (dd, J=10.8, 2.3 Hz, 2H), 3.46-3.61 (m, 1H), 3.33-3.38 (m, 1H), 2.20 (s, 3H), 1.92-2.16 (m, 2H), 1.63-1.82 (m, 2H), 1.30-1.44 (m, 3H).

E31: LCMS: 343 [M+H]$^+$. $t_R$=1.330 mins. (LCMS condition 2)

Chiral HPLC: $t_R$=4.15 mins. (Condition: Column AD-H (4.6*250 mm, 5 um); (Co-Solvent MeOH (0.1% DEA)) The absolute stereochemistry was not determined.

$^1$H NMR (400 MHz, DMSO-d$_6$): δ 11.17 (br. s., 1H), 8.00 (s, 1H), 7.61 (s, 1H), 6.85 (br. s., 1H), 6.21 (br. s., 1H), 4.44 (q, J=6.9 Hz, 2H), 4.05-4.29 (m, 2H), 3.87 (d, J=10.3 Hz, 2H), 3.54 (t, J=10.5 Hz, 1H), 3.41 (m, 1H), 2.20 (s, 3H), 1.94-2.14 (m, 2H), 1.65-1.83 (m, 2H), 1.35 (t, J=7.0 Hz, 3H).

E32: LCMS: 343 [M+H]$^+$. $t_R$=1.338 mins. (LCMS condition 2)

Chiral HPLC: $t_R$=5.69 mins. (Condition: Column AD-H (4.6*250 mm, 5 um); (Co-Solvent MeOH (0.1% DEA)) The absolute stereochemistry was not determined.

$^1$H NMR (400 MHz, DMSO-d$_6$): δ 11.20 (br. s., 1H), 8.06 (s, 1H), 7.95 (s, 1H), 6.75-6.95 (m, 1H), 6.22 (d, J=1.5 Hz, 1H), 4.47 (q, J=7.0 Hz, 2H), 4.08-4.23 (m, 1H), 3.95 (dd, J=10.7, 3.1 Hz, 1H), 3.69-3.85 (m, 1H), 3.55 (t, J=10.0 Hz, 1H), 3.40-3.44 (m, 1H), 1.91-2.22 (m, 5H), 1.55-1.82 (m, 2H), 1.37 (t, J=7.0 Hz, 3H).

218

E33: LCMS: 343 [M+H]$^+$. $t_R$=1.339 mins. (LCMS condition 2)

Chiral HPLC: $t_R$=7.64 mins. (Condition: Column AD-H (4.6*250 mm, 5 um); (Co-Solvent MeOH (0.1% DEA)) The absolute stereochemistry was not determined.

$^1$H NMR (400 MHz, DMSO-d$_6$): δ 11.20 (br. s., 1H), 8.06 (s, 1H), 7.95 (s, 1H), 6.77-6.95 (m, 1H), 6.22 (d, J=1.5 Hz, 1H), 4.47 (q, J=7.0 Hz, 2H), 4.07-4.21 (m, 1H), 3.95 (dd, J=10.7, 3.1 Hz, 1H), 3.71-3.85 (m, 1H), 3.55 (t, J=10.0 Hz, 1H), 3.40-3.45 (m, 1H), 1.94-2.19 (m, 5H), 1.57-1.80 (m, 2H), 1.37 (t, 3H).

Example 34

4-ethoxy-N-(5-methyl-1-(oxetan-3-yl)-1H-pyrazol-4-yl)-7H-pyrrolo[2,3-d]pyrimidin-2-amine (E34)

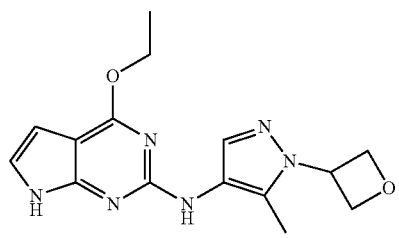 [SMILES: CCOc1nc(Nc2cnn(C3COC3)c2C)nc2[nH]ccc12]

A solution of 2-chloro-4-ethoxy-7H-pyrrolo[2,3-d]pyrimidine (which may be prepared according to D1) (120 g, 0.607 mmol), 5-methyl-1-(oxetan-3-yl)-1H-pyrazol-4-amine (102 g, 0.668 mmol) (which may be prepared according to PCT Int. Appl., WO2012062783), $Pd_2(dba)_3$ (55.6 g, 0.061 mmol), (9,9-dimethyl-9H-xanthene-4,5-diyl)bis-(diphenylphosphine) (52.7 g, 0.091 mmol) and potassium carbonate (252 g, 1.822 mmol) in 2-butanol (1 mL) was irradiated by microwave at 130° C. for 90 min. The reaction mixture was partitioned between ethyl acetate (25 mL) and water (25 mL). The organic layer was washed with water, saturated $NaHCO_3$ and brine, dried over $Na_2SO_4$, filtered and concentrated. The crude was purified by prep-HPLC to give the title compound E34 (60 g, 0.191 mmol, 31.4% yield) as a white solid.

LCMS: 315 [M+H]$^+$. $t_R$=1.445 mins. (LCMS condition 2)

$^1$H NMR (400 MHz, DMSO-d$_6$): δ 11.18 (br. s., 1H), 8.07 (s, 1H), 7.75 (s, 1H), 6.80-6.92 (m, 1H), 6.21 (dd, J=3.3, 1.8 Hz, 1H), 5.37-5.62 (m, 1H), 4.92-4.99 (m, 2H), 4.84-4.91 (m, 2H), 4.45 (q, J=7.1 Hz, 2H), 2.13 (s, 3H), 1.36 (t, J=7.0 Hz, 3H).

Example 35

N-(5-chloro-1-(oxetan-3-yl)-1H-pyrazol-4-yl)-4-ethoxy-7H-pyrrolo-[2,3-d]pyrimidin-2-amine (E35)

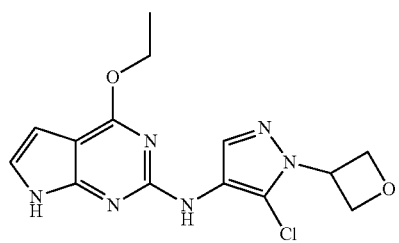 [SMILES: CCOc1nc(Nc2cnn(C3COC3)c2Cl)nc2[nH]ccc12]

A solution of 2-chloro-4-ethoxy-7H-pyrrolo[2,3-d]pyrimidine (which may be prepared according to D1) (120 g, 0.607 mmol), 5-chloro-1-(oxetan-3-yl)-1H-pyrazol-4-amine (116 g, 0.668 mmol) (which may be prepared according to PCT Int. Appl., WO2012062783), Pd$_2$(dba)$_3$ (55.6 g, 0.061 mmol), (9,9-dimethyl-9H-xanthene-4,5-diyl)bis(diphenylphosphine) (52.7 g, 0.091 mmol) and potassium carbonate (252 g, 1.822 mmol) in 2-butanol (1 mL) was irradiated by microwave at 130° C. for 90 min. The reaction mixture was partitioned between ethyl acetate (25 mL) and water (25 mL). The organic layer was washed with water, saturated NaHCO$_3$ and brine, dried over Na$_2$SO$_4$, filtered and concentrated. The crude was purified by prep-HPLC to give the title compound E35 (40 g, 0.119 mmol, 19.68% yield) as a white solid.

LCMS: 335 [M+H]$^+$. $t_R$=1.121 mins. (LCMS condition 2)

$^1$H NMR (400 MHz, DMSO-d$_6$): δ 11.30 (br. s., 1H), 8.24 (s, 1H), 7.97 (s, 1H), 6.75-7.06 (m, 1H), 6.24 (dd, J=3.3, 1.8 Hz, 1H), 5.64 (q, J=6.9 Hz, 1H), 4.90-4.98 (m, 4H), 4.45 (q, J=7.0 Hz, 2H), 1.36 (t, J=6.9 Hz, 3H).

Example 36

(±)-2-(5-chloro-4-((4-ethoxy-7H-pyrrolo-[2,3-d]-pyrimidin-2-yl)amino)-1H-pyrazol-1-yl)cyclopentanol (E36)

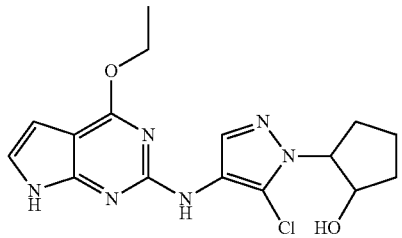 [SMILES: CCOc1nc(Nc2cnn(C3CCCC3O)c2Cl)nc2[nH]ccc12]

A solution of (±)-trans-2-(5-chloro-4-((4-ethoxy-7-tosyl-7H-pyrrolo-[2,3-d]-pyrimidin-2-yl)amino)-1H-pyrazol-1-yl)cyclopentanol (which may be prepared according to D46) (350 g, 0.677 mmol) and sodium hydroxide (1.015 mL, 2.031 mmol, 2M in water) in isopropanol (5 mL) was stirred at 60° C. for overnight. The mixture was evaporated and 2N HCl was added until pH=7. The product was extracted with EtOAc. The organic layer was dried with MgSO$_4$ and evaporated. The crude was purified by prep-HPLC to give the title compound E36 (200 g, 0.551 mmol, 81% yield) as a white solid.

LCMS: 363 [M+H]$^+$. $t_R$=1.548 mins. (LCMS condition 2)

$^1$H NMR (400 MHz, METHANOL-d$_4$): δ 7.99 (s, 1H), 6.86 (d, J=3.5 Hz, 1H), 6.32 (d, J=3.5 Hz, 1H), 4.58-4.68 (m, 1H), 4.44-4.56 (m, 3H), 2.00-2.28 (m, 3H), 1.84-1.97 (m, 2H), 1.64-1.77 (m, 1H), 1.44 (t, J=7.0 Hz, 3H).

Example 37 and 38

Enantiomer 1: trans-2-(5-chloro-4-((4-ethoxy-7H-pyrrolo-[2,3-d]-pyrimidin-2-yl)amino)-1H-pyrazol-1-yl)-cyclopentanol (E37)

Enantiomer 2: trans-2-(5-chloro-4-((4-ethoxy-7H-pyrrolo-[2,3-d]-pyrimidin-2-yl)amino)-1H-pyrazol-1-yl)cyclopentanol (E38)

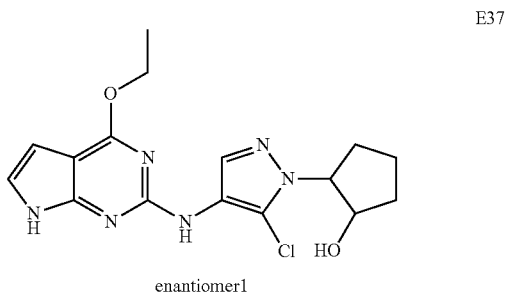

enantiomer1

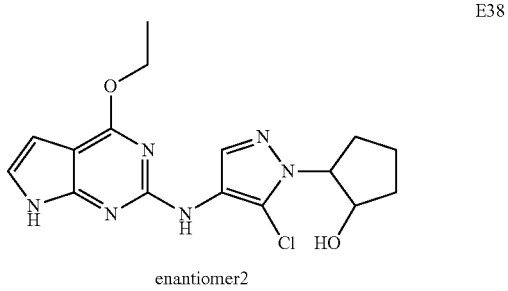

enantiomer2

The title compounds E37 (50 g, 0.132 mmol, 25.9% yield) and E38 (30 g, 0.081 mmol, 15.89% yield) were prepared from chiral-HPLC separation of E36 (Co-Solvent MeOH; Column IC (4.6*250 mm, 5 um); Column Temperature 40.1; CO$_2$ Flow Rate 2.55; Co-Solvent Flow Rate 0.45; Co-Solvent % 15; Back Pressure 119; Total Flow 3; PDA Start Wavelength 214; PDA Stop Wavelength 359) as white solids.

E37: LCMS: 363 [M+H]$^+$. $t_R$=1.563 mins. (LCMS condition 2)

Chiral HPLC: $t_R$=5.21 mins. (Condition: Column IC (4.6*250 mm, 5 um); (Co-Solvent MeOH)

The absolute stereochemistry was not determined.

$^1$H NMR (400 MHz, METHANOL-d$_4$): δ 7.99 (s, 1H), 6.85 (d, J=3.5 Hz, 1H), 6.32 (d, J=3.5 Hz, 1H), 4.59-4.67 (m, 1H), 4.45-4.55 (m, 3H), 2.02-2.29 (m, 3H), 1.83-1.98 (m, 2H), 1.65-1.77 (m, 1H), 1.44 (t, 3H).

E38: LCMS: 363 [M+H]$^+$. $t_R$=1.349 mins. (LCMS condition 2)

Chiral HPLC: $t_R$=6.28 mins. (Condition: Column IC (4.6*250 mm, 5 um); (Co-Solvent MeOH) The absolute stereochemistry was not determined.

$^1$H NMR (400 MHz, METHANOL-d$_4$): δ 7.99 (s, 1H), 6.85 (d, J=3.5 Hz, 1H), 6.32 (d, J=3.5 Hz, 1H), 4.59-4.69 (m, 1H), 4.42-4.56 (m, 3H), 2.02-2.29 (m, 3H), 1.83-1.99 (m, 2H), 1.63-1.77 (m, 1H), 1.44 (t, 3H).

Example 39

(±)-2-(4-((4-ethoxy-7H-pyrrolo[2,3-d]pyrimidin-2-yl)amino)-5-methyl-1H-pyrazol-1-yl)cyclopentanol (E39)

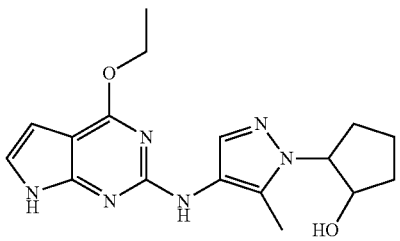 [SMILES: CCOc1nc(Nc2cnn(C3CCCC3O)c2C)nc2[nH]ccc12]

A solution of (±)-trans-2-(4-((4-ethoxy-7-tosyl-7H-pyrrolo-[2,3-d]-pyrimidin-2-yl)amino)-5-methyl-1H-pyrazol-1-yl)cyclopentanol (which may be prepared according to D47) (250 g, 0.503 mmol) and sodium hydroxide (0.755 mL, 1.510 mmol, 2M in water) in isopropanol (5 mL) was stirred at 60° C. for overnight. The mixture was concentrated and 2N HCl was added until pH=7. The product was extracted with EtOAc twice. The combined organic layer was dried and evaporated. The crude was purified by prep-HPLC to give the title compound E39 (120 g, 0.343 mmol, 68.2% yield) as a white solid.

LCMS: 343 [M+H]$^+$. $t_R$=1.258 mins. (LCMS condition 2)

$^1$H NMR (400 MHz, DMSO-d$_6$): δ 11.20 (br. s., 1H), 7.98 (br. s., 1H), 7.58 (s, 1H), 6.85 (br. s., 1H), 6.11-6.25 (m, 1H), 4.98 (d, J=5.4 Hz, 1H), 4.45 (q, J=6.9 Hz, 2H), 4.27-4.35 (m, 1H), 4.15-4.25 (m, 1H), 2.20 (s, 3H), 1.90-2.13 (m, 3H), 1.70-1.83 (m, 2H), 1.50-1.62 (m, 1H), 1.36 (t, 3H).

Example 40 and 41

Enantiomer 1: trans-2-(4-((4-ethoxy-7H-pyrrolo-[2,3-d]pyrimidin-2-yl)amino)-5-methyl-1H-pyrazol-1-yl)-cyclopentanol (E40)

Enantiomer 2: trans-2-(4-((4-ethoxy-7H-pyrrolo-[2,3-d]pyrimidin-2-yl)amino)-5-methyl-1H-pyrazol-1-yl)-cyclopentanol (E41)

E40

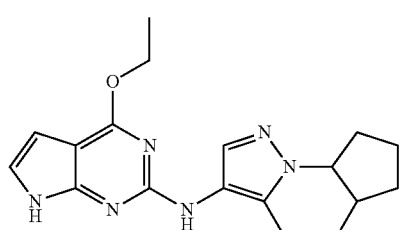

enantiomer1

-continued

E41

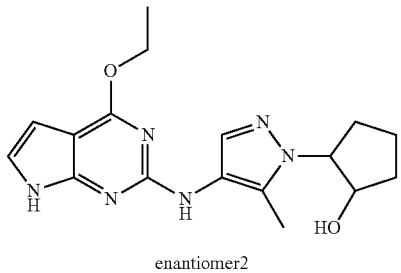

enantiomer2

The title compounds E40 (23 g, 0.066 mmol, 20.49% yield) and E41 (25 g, 0.073 mmol, 22.73% yield) were prepared from chiral-HPLC separation of E39 (Co-Solvent MeOH; Column IC (4.6*250 mm, 5 um); Column Temperature 39.9; CO$_2$ Flow Rate 2.4; Co-Solvent Flow Rate 0.6; Co-Solvent % 20; Back Pressure 120; Total Flow 3; PDA Start Wavelength 214; PDA Stop Wavelength 359) as white solids.

E40: LCMS: 343 [M+H]$^+$. $t_R$=1.489 mins. (LCMS condition 2)

Chiral HPLC: $t_R$=2.82 mins. (Condition: Column IC (4.6*250 mm, 5 um); (Co-Solvent MeOH)

The absolute stereochemistry was not determined.

$^1$H NMR (400 MHz, DMSO-d$_6$): δ 11.18 (br. s., 1H), 7.96 (s, 1H), 7.56 (s, 1H), 6.76-6.89 (m, 1H), 6.19 (dd, J=3.3, 1.8 Hz, 1H), 4.96 (d, J=5.0 Hz, 1H), 4.44 (q, J=7.0 Hz, 2H), 4.24-4.34 (m, 1H), 4.19 (m, J=5.8 Hz, 1H), 2.18 (s, 3H), 1.88-2.12 (m, 3H), 1.70-1.80 (m, 2H), 1.50-1.61 (m, 1H), 1.35 (t, 3H).

E41: LCMS: 343 [M+H]$^+$. $t_R$=1.486 mins. (LCMS condition 2)

Chiral HPLC: $t_R$=4.06 mins. (Condition: Column IC (4.6*250 mm, 5 um); (Co-Solvent MeOH) The absolute stereochemistry was not determined.

$^1$H NMR (400 MHz, DMSO-d$_6$): δ 11.20 (br. s., 1H), 8.03 (br. s., 1H), 7.56 (s, 1H), 6.85 (d, J=2.3 Hz, 1H), 6.18-6.23 (m, 1H), 4.44 (q, J=7.0 Hz, 2H), 4.25-4.35 (m, 1H), 4.19 (q, J=6.2 Hz, 1H), 2.18 (s, 3H), 1.88-2.13 (m, 3H), 1.70-1.81 (m, 2H), 1.50-1.62 (m, 1H), 1.35 (t, 3H).

Example 42 and 43

Enantiomer 1: cis-4-ethoxy-N-(5-methyl-1-((2S,4S)-2-methyl-tetrahydro-2H-pyran-4-yl)-1H-pyrazol-4-yl)-7H-pyrrolo-[2,3-d]-pyrimidin-2-amine (E42)

Enantiomer 2: cis-4-ethoxy-N-(5-methyl-1-((2S,4S)-2-methyl-tetrahydro-2H-pyran-4-yl)-1H-pyrazol-4-yl)-7H-pyrrolo-[2,3-d]-pyrimidin-2-amine (E43)

E42

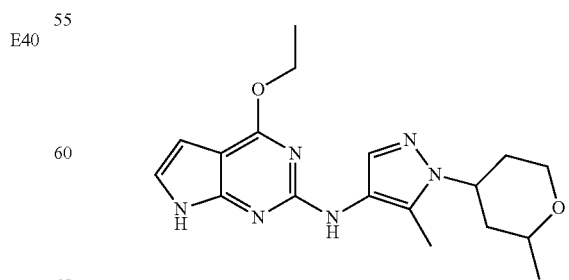

enantiomer1

-continued

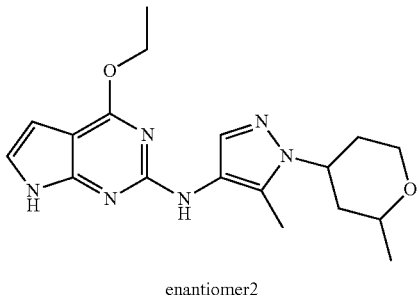

enantiomer2

E43

A solution of (±)-4-ethoxy-N-(5-methyl-1-(2-methyl-tetrahydro-2H-pyran-4-yl)-1H-pyrazol-4-yl)-7-tosyl-7H-pyrrolo [2,3-d]pyrimidin-2-amine (which may be prepared according to D51) (300 g, 0.588 mmol) and sodium hydroxide (0.588 mL, 1.175 mmol, 2M in water) in THF (2 mL) and methanol (0.500 mL) was stirred at 50° C. for 3 hours. After cooling, the reaction mixture was poured into water (50 mL) and extracted with EtOAc (40 mL×3). The combined organic layer was dried and evaporated in vacuum. The crude was purified by prep-HPLC to give the product (150 g, 0.391 mmol, 66.6% yield), which was further purified by chiral-HPLC (Column AY-H (4.6*250 mm, 5 um); Mobile Phase: n-Hexane (0.1% DEA):EtOH (0.1% DEA)=85:15) to give the title compounds E42 (44 g, 0.123 mmol, 29.3% yield) and E43 (50 g, 0.140 mmol, 33.3% yield) as white solids.

E42: LCMS: 357 [M+H]$^+$. $t_R$=1.21 mins. (LCMS condition 2)

Chiral HPLC: $t_R$=6.61 mins. (Condition: Column AY-H (4.6*250 mm, 5 um); Co-Solvent MeOH) The absolute stereochemistry was not determined.

$^1$H NMR (400 MHz, CHLOROFORM-d): δ 9.99 (br. s., 1H), 7.66 (s, 1H), 6.42 (br. s., 1H), 6.30 (d, J=2.2 Hz, 1H), 6.10 (s, 1H), 4.49 (q, J=7.3 Hz, 2H), 4.43 (t, J=4.3 Hz, 1H), 4.21 (t, J=6.1 Hz, 1H), 4.07-4.16 (m, 1H), 3.81 (dt, J=11.4, 4.2 Hz, 1H), 2.22 (s, 3H), 1.95-2.05 (m, 2H), 1.85-1.95 (m, 1H), 1.64-1.75 (m, 3H), 1.43 (t, J=7.1 Hz, 3H), 1.16 (d, 3H).

E43: LCMS: 357 [M+H]$^+$. $t_R$=1.21 mins. (LCMS condition 2)

Chiral HPLC: $t_R$=7.99 mins. (Condition: Column AY-H (4.6*250 mm, 5 um); Co-Solvent MeOH) The absolute stereochemistry was not determined.

$^1$H NMR (400 MHz, CHLOROFORM-d): δ 9.66 (br. s., 1H), 7.68 (s, 1H), 6.49 (br. s., 1H), 6.32 (br. s., 1H), 6.08 (s, 1H), 4.41-4.54 (m, 3H), 4.18-4.28 (m, 1H), 4.13 (td, J=11.0, 2.7 Hz, 1H), 3.82 (dt, J=11.5, 4.2 Hz, 1H), 2.22 (s, 3H), 1.97-2.07 (m, 2H), 1.87-1.97 (m, 1H), 1.71 (ddd, J=14.0, 9.2, 4.9 Hz, 3H), 1.43 (t, J=7.1 Hz, 3H), 1.17 (d, 3H).

Example 44

N-(5-cyclopropyl-1-(tetrahydro-2H-pyran-4-yl)-1H-pyrazol-4-yl)-4-ethoxy-7H-pyrrolo-[2,3-d]pyrimidin-2-amine (E44)

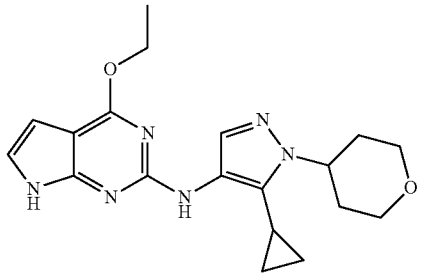 [SMILES: CCOc1nc(Nc2cnn(C3CCOCC3)c2C2CC2)nc2[nH]ccc12]

A solution of N-(5-cyclopropyl-1-(tetrahydro-2H-pyran-4-yl)-1H-pyrazol-4-yl)-4-ethoxy-7-tosyl-7H-pyrrolo-[2,3-d]-pyrimidin-2-amine (which may be prepared according to D54) (40 g, 0.077 mmol) and sodium hydroxide (1 mL, 2.000 mmol, 2M in water) in methanol (3 mL) was stirred at 20° C. for 2 hours. The mixture was extracted with ethyl acetate. The organic layer was dried with Na$_2$SO$_4$ and concentrated. The crude was purified by prep-HPLC to give the title compound E44 (10 g, 0.027 mmol, 35.5% yield) as a white solid.

LCMS: 369 [M+H]$^+$. $t_R$=1.67 mins. (LCMS condition 2)

$^1$H NMR (400 MHz, DMSO-d$_6$): δ 11.22 (br. s., 1H), 7.61 (s, 1H), 7.48 (s, 1H), 6.85 (br. s., 1H), 6.21 (br. s., 1H), 4.61 (br. s., 1H), 4.43 (q, J=6.9 Hz, 2H), 3.92-4.06 (m, 2H), 3.50 (t, J=11.8 Hz, 2H), 1.99-2.18 (m, 2H), 1.61-1.88 (m, 3H), 1.35 (t, J=6.9 Hz, 3H), 0.85 (m, 2H), 0.68 (m, 2H).

Example 45

4-ethoxy-N-(5-methyl-1-(2-morpholinoethyl)-1H-pyrazol-4-yl)-7H-pyrrolo-[2,3-d]pyrimidin-2-amine (E45)

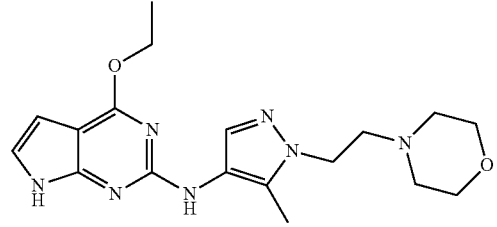 [SMILES: CCOc1nc(Nc2cnn(CCN3CCOCC3)c2C)nc2[nH]ccc12]

A solution of 4-ethoxy-N-(5-methyl-1-(2-morpholinoethyl)-1H-pyrazol-4-yl)-7-tosyl-7H-pyrrolo[2,3-d]pyrimidin-2-amine (which may be prepared according to D57)(70 mg, 0.133 mmol) and sodium hydroxide (0.200 mL, 0.400 mmol) in isopropanol (2 mL) was stirred overnight at 60° C. The mixture was concentrated and 2N HCl was added until pH=7. The mixture was then extracted with EtOAc twice. The combined organic layer was dried and evaporated. The crude was purified by prep-HPLC to give the title compound E45 (25 g, 0.065 mmol, 49.0% yield) as a white solid.

LCMS: 372 [M+H]$^+$. $t_R$=1.223 mins. (LCMS condition 2)

$^1$H NMR (400 MHz, DMSO-d$_6$): δ 11.17 (br. s., 1H), 7.98 (s, 1H), 7.55 (s, 1H), 6.66-6.94 (m, 1H), 6.19 (dd, J=3.3, 1.8 Hz, 1H), 4.42 (q, J=7.0 Hz, 2H), 4.09 (t, J=6.7 Hz, 2H), 3.55 (t, J=4.5 Hz, 4H), 2.56-2.73 (m, 2H), 2.41 (br. s., 4H), 2.18 (s, 3H), 1.34 (t, J=7.0 Hz, 3H).

Example 46

4-ethoxy-2-((5-methyl-1-(tetrahydro-2H-pyran-4-yl)-1H-pyrazol-4-yl)-amino)-7H-pyrrolo-[2,3-d]-pyrimidine-5-carbonitrile (E46)

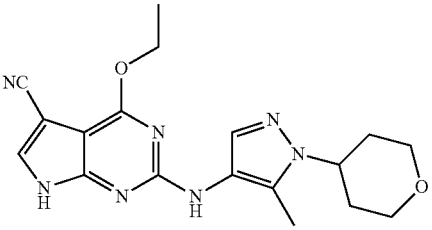 [SMILES: CCOc1nc(Nc2cnn(C3CCOCC3)c2C)nc2[nH]cc(C#N)c12]

A solution of 2-chloro-4-ethoxy-7H-pyrrolo-[2,3-d]pyrimidine-5-carbonitrile (which may be prepared according to D27) (120 g, 0.539 mmol), 5-methyl-1-(tetrahydro-2H-pyran-4-yl)-1H-pyrazol-4-amine (117 g, 0.647 mmol), potassium carbonate (223 g, 1.617 mmol), $Pd_2(dba)_3$ (24.68 g, 0.027 mmol) and dicyclohexyl(2',4',6'-triisopropyl-[1,1'-biphenyl]-2-yl)-phosphine (25.7 g, 0.054 mmol) in 2-butanol (5 mL) was irradiated by microwave at 120° C. for 1 hour. After filtration, the filtrate was concentrated and the crude was purified by MDAP (base mobile phase) to give the title compound E46 (13 g, 0.035 mmol, 6.56% yield) as a white solid.

LCMS: 368[M+H]$^+$. $t_R$=2.637 mins. (LCMS condition 1)

$^1$H NMR (400 MHz, DMSO-d$_6$): δ 12.15 (br. s., 1H), 8.33 (br. s., 1H), 7.78 (s, 1H), 7.51 (s, 1H), 4.41 (q, J=6.7 Hz, 2H), 4.27 (tt, J=11.2, 4.0 Hz, 1H), 3.89 (dd, J=11.0, 3.9 Hz, 2H), 3.41 (t, J=11.2 Hz, 2H), 2.13 (s, 3H), 1.88-1.99 (m, 2H), 1.62-1.75 (m, 2H), 1.30 (t, J=6.7 Hz, 3H).

Example 47 and 48

4-ethoxy-2-((1-(2-methoxyethyl)-5-methyl-1H-pyrazol-4-yl)-amino)-7H-pyrrolo-[2,3-d]-pyrimidine-5-carbonitrile (E47)

4-ethoxy-2-((1-(2-methoxyethyl)-3-methyl-1H-pyrazol-4-yl)-amino)-7H-pyrrolo-[2,3-d]-pyrimidine-5-carbonitrile (E48)

E47

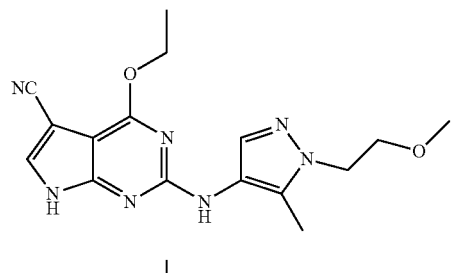

E48

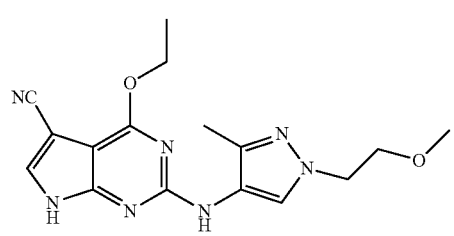

A solution of 2-chloro-4-ethoxy-7H-pyrrolo-[2,3-d]pyrimidine-5-carbonitrile (which may be prepared according to D27) (170 g, 0.764 mmol), a mixture 1-(2-methoxyethyl)-5-methyl-1H-pyrazol-4-amine and 1-(2-methoxyethyl)-3-methyl-1H-pyrazol-4-amine (142 mg, 0.916 mmol) (which may be prepared according to PCT Int. Appl., WO2012062783 as a mixture) potassium carbonate (317 g, 2.291 mmol), $Pd_2(dba)_3$ (35.0 g, 0.038 mmol) and dicyclohexyl (2',4',6'-triisopropyl-[1,1'-biphenyl]-2-yl)phosphine (36.4 g, 0.076 mmol) in 2-butanol (5 mL) was irradiated by microwave at 120° C. for 1 hour. After filtration, the filtrate was concentrated and the crude was purified by reversed column chromatography to give the mixture of the title compound E47 and E48 (150 g, 0.439 mmol, 57.5% yield), which further purified by chiral-HPLC (Co-Solvent MeOH (0.1% DEA); Column OZ-H (4.6*250 mm, 5 um); Column Temperature 40.3; $CO_2$ Flow Rate 2.25; Co-Solvent Flow Rate 075; Co-Solvent % 25; Back Pressure 120; Total Flow 3; PDA Start Wavelength 214; PDA Stop Wavelength 359) to give E47 (10 g, 0.029 mmol, 13.33% yield) as a yellow solid and E48 (45 g, 0.132 mmol, 60.0% yield) as a brown solid.

E47: LCMS: 342[M+H]$^+$. $t_R$=1.554 mins. (LCMS condition 2)

$^1$H NMR (400 MHz, METHANOL-d$_4$): δ 7.66 (s, 1H), 7.56 (s, 1H), 4.53 (q, J=7.0 Hz, 2H), 4.23 (t, J=5.3 Hz, 2H), 3.71 (t, J=5.3 Hz, 2H), 2.25 (s, 3H), 1.43 (t, J=7.0 Hz, 3H).

E48: LCMS: 342[M+H]$^+$. $t_R$=1.434 mins. (LCMS condition 2)

$^1$H NMR (400 MHz, DMSO-d$_6$): δ 12.27 (br. s., 1H), 8.46 (br. s., 1H), 7.87 (d, J=2.3 Hz, 1H), 7.82 (s, 1H), 4.51 (q, J=7.0 Hz, 2H), 4.13 (t, J=5.3 Hz, 2H), 3.65 (t, J=5.3 Hz, 2H), 3.24 (s, 3H), 2.10 (s, 3H), 1.38 (t, J=7.0 Hz, 3H).

Example 49

(S)-4-ethoxy-2-((5-methyl-1-(1-methyl-pyrrolidin-3-yl)-1H-pyrazol-4-yl)-amino)-7H-pyrrolo-[2,3-d]pyrimidine-5-carbonitrile (E49)

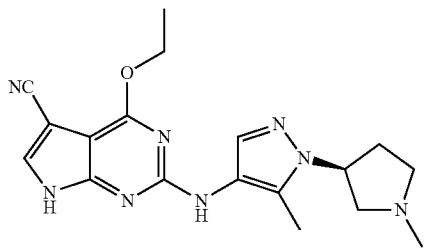 [SMILES: CCOc1nc(Nc2cnn([C@H]3CCN(C)C3)c2C)nc2[nH]cc(C#N)c12]

A solution of 2-chloro-4-ethoxy-7H-pyrrolo-[2,3-d]pyrimidine-5-carbonitrile (which may be prepared according to D27) (100 g, 0.449 mmol), (S)-5-methyl-1-(1-methylpyrrolidin-3-yl)-1H-pyrazol-4-amine (97 g, 0.539 mmol), potassium carbonate (186 g, 1.348 mmol), $Pd_2(dba)_3$ (20.57 g, 0.022 mmol) and dicyclohexyl(2',4',6'-triisopropyl-[1,1'-biphenyl]-2-yl)-phosphine (21.41 g, 0.045 mmol) in 2-butanol (8 mL) was irradiated by microwave at 120° C. for 1 hour. After filtration, the filtrate was concentrated and the crude was purified by MDAP (base mobile phase) to give the title compound E49 (35 g, 0.096 mmol, 21.27% yield) as a white solid.

LCMS: 367[M+H]$^+$. $t_R$=2.066 mins. (LCMS condition 1)

$^1$H NMR (400 MHz, DMSO-d$_6$): δ 12.16 (br. s., 1H), 8.34 (br. s., 1H), 7.78 (s, 1H), 7.49 (s, 1H), 4.69-4.84 (m, 1H), 4.41 (q, J=7.0 Hz, 2H), 2.94 (t, J=8.3 Hz, 1H), 2.59-2.70 (m, 1H), 2.47-2.57 (m, 2H), 2.22 (s, 3H), 2.12-2.21 (m, 2H), 2.11 (s, 3H), 1.30 (t, 3H).

Example 50

4-ethoxy-2-((1-(2-fluoroethyl)-5-methyl-1H-pyrazol-4-yl)-amino)-7H-pyrrolo-[2,3-d]-pyrimidine-5-carbonitrile (E50)

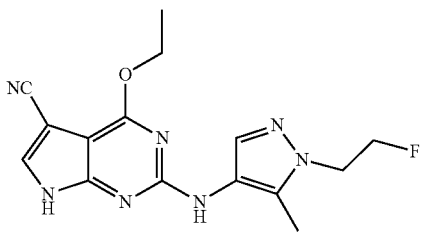 [SMILES: CCOc1nc(Nc2cnn(CCF)c2C)nc2[nH]cc(C#N)c12]

A solution of 2-chloro-4-ethoxy-7H-pyrrolo-[2,3-d]pyrimidine-5-carbonitrile (which may be prepared according to D27) (220 g, 0.988 mmol), 1-(2-fluoroethyl)-5-methyl-1H-pyrazol-4-amine (170 g, 1.186 mmol) (which may be prepared according to PCT Int. Appl., WO2012062783), potassium carbonate (410 g, 2.96 mmol), $Pd_2(dba)_3$ (45.2 mg, 0.049 mmol) and dicyclohexyl(2',4',6'-triisopropyl-[1,1'-biphenyl]-2-yl)phosphine (47.1 mg, 0.099 mmol) in 2-butanol (8 mL) was irradiated by microwave at 100° C. for 40 min. After filtration, the filtrate was concentrated and the crude was purified by MDAP (base mobile phase) to give the title compound E50 (17 g, 0.052 mmol, 5.22% yield) as a white solid.

LCMS: 330[M+H]$^+$. $t_R$=11.858 mins. (LCMS condition 1)

$^1$H NMR (400 MHz, DMSO-$d_6$): δ 12.18 (br. s., 1H), 8.37 (br. s., 1H), 7.78 (s, 1H), 7.52 (s, 1H), 4.73 (t, J=4.8 Hz, 1H), 4.61 (t, J=4.6 Hz, 1H), 4.41 (q, J=6.7 Hz, 2H), 4.30 (t, J=4.8 Hz, 1H), 4.23 (t, J=4.6 Hz, 1H), 2.10 (s, 3H), 1.30 (t, 3H).

Example 51

(R)-4-ethoxy-2-((5-methyl-1-(1-methyl-pyrrolidin-3-yl)-1H-pyrazol-4-yl)-amino)-7H-pyrrolo-[2,3-d]pyrimidine-5-carbonitrile (E51)

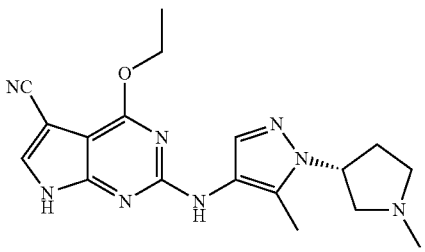 [SMILES: CCOc1nc(Nc2cnn([C@@H]3CCN(C)C3)c2C)nc2[nH]cc(C#N)c12]

A solution of 2-chloro-4-ethoxy-7H-pyrrolo-[2,3-d]pyrimidine-5-carbonitrile (which may be prepared according to D27)(100 g, 0.449 mmol), (R)-5-methyl-1-(1-methylpyrrolidin-3-yl)-1H-pyrazol-4-amine (97 g, 0.539 mmol) (which may be prepared according to PCT Int. Appl., WO2012062783), potassium carbonate (186 g, 1.348 mmol), $Pd_2(dba)_3$ (20.57 g, 0.022 mmol) and dicyclohexyl(2',4',6'-triisopropyl-[1,1'-biphenyl]-2-yl)phosphine (21.41 g, 0.045 mmol) in 2-butanol (8 mL) was irradiated by microwave to 120° C. for 1 hour. After filtration, the filtrate was concentrated and the crude was purified by MDAP (base mobile phase) to give the title compound E51 (26 g, 0.071 mmol, 15.80% yield) as a white solid.

LCMS: 367[M+H]$^+$. $t_R$=2.184 mins. (LCMS condition 1)

$^1$H NMR (400 MHz, DMSO-$d_6$): δ 12.16 (br. s., 1H), 8.34 (br. s., 1H), 7.78 (s, 1H), 7.49 (s, 1H), 4.70-4.88 (m, 1H), 4.24-4.51 (m, 2H), 2.94 (t, J=8.3 Hz, 1H), 2.64 (td, J=7.9, 5.4 Hz, 1H), 2.47-2.58 (m, 2H), 2.22 (s, 3H), 2.12-2.20 (m, 2H), 2.11 (s, 3H), 1.30 (t, 3H).

Example 52

3-(4-((4-ethoxy-7H-pyrrolo-[2,3-d]-pyrimidin-2-yl)-amino)-5-methyl-1H-pyrazol-1-yl)cyclo-butanol (E52)

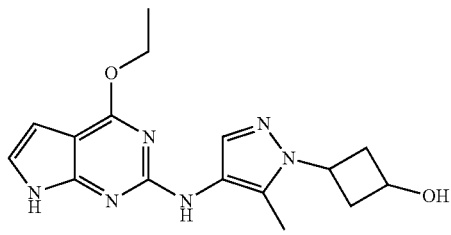 [SMILES: CCOc1nc(Nc2cnn(C3CC(O)C3)c2C)nc2[nH]ccc12]

A solution of 2-chloro-4-ethoxy-7H-pyrrolo[2,3-d]pyrimidine (which may be prepared according to D1) (90 g, 0.455 mmol), 3-(4-amino-5-methyl-1H-pyrazol-1-yl)cyclobutanol (which may be prepared according to D62) (91 g, 0.546 mmol), (9,9-dimethyl-9H-xanthene-4,5-diyl)bis(diphenylphosphine) (21.71 g, 0.046 mmol), potassium carbonate (189 g, 1.366 mmol) and $Pd_2(dba)_3$ (20.85 g, 0.023 mmol) in 2-butanol (2 mL) was irradiated by microwave at 120° C. for 45 min. The mixture was concentrated and purified by pre-HPLC to give the title compound E52 (35 g, 0.106 mmol, 23.17% yield) as a white solid.

LCMS: 329[M+H]$^+$. $t_R$=1.180 mins. (LCMS condition 2)

$^1$H NMR (400 MHz, DMSO-$d_6$): δ 11.17 (br. s., 1H), 7.99 (s, 1H), 7.61 (s, 1H), 6.73-6.95 (m, 1H), 6.20 (dd, J=3.3, 2.0 Hz, 1H), 5.15 (d, J=5.0 Hz, 1H), 4.77-4.97 (m, 1H), 4.44 (q, J=6.9 Hz, 3H), 2.57-2.72 (m, 2H), 2.31 (ddd, J=12.4, 8.3, 3.9 Hz, 2H), 2.12 (s, 3H), 1.29-1.41 (m, 3H).

Example 53

4-ethoxy-N-(5-methyl-1-(1-(oxetan-3-yl)-piperidin-4-yl)-1H-pyrazol-4-yl)-7H-pyrrolo-[2,3-d]-pyrimidin-2-amine (E53)

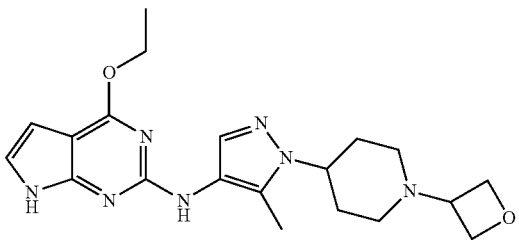 [SMILES: CCOc1nc(Nc2cnn(C3CCN(C4COC4)CC3)c2C)nc2[nH]ccc12]

229

A solution of 2-chloro-4-ethoxy-7H-pyrrolo[2,3-d]pyrimidine (which may be prepared according to D1) (15 g, 0.076 mmol), 5-methyl-1-(1-(oxetan-3-yl)piperidin-4-yl)-1H-pyrazol-4-amine (21.52 g, 0.091 mmol)(which may be prepared according to PCT Int. Appl., WO2012062783), (9,9-dimethyl-9H-xanthene-4,5-diyl)bis(diphenylphosphine) (3.62 mg, μmol), potassium carbonate (31.5 g, 0.228 mmol) and Pd$_2$(dba)$_3$ (3.48 mg, 3.80 μmol) in 2-butanol (2 mL) was irradiated by microwave at 120° C. for 45 min. The mixture was concentrated and purified by pre-HPLC to give the title compound E53 (4 mg, 10.06 μmol, 13.26% yield) as a white solid.

LCMS: 398 [M+H]$^+$. $t_R$=1.245 mins. (LCMS condition 2)

$^1$H NMR (400 MHz, DMSO-d$_6$): δ 11.18 (br. s., 1H), 7.98 (s, 1H), 7.59 (s, 1H), 6.81-6.87 (m, 1H), 6.16-6.22 (m, 1H), 4.52-4.59 (m, 2H), 4.37-4.49 (m, 4H), 4.00-4.15 (m, 1H), 3.40-3.46 (m, 1H), 2.81 (d, J=10.8 Hz, 2H), 2.18 (s, 3H), 1.91-2.06 (m, 4H), 1.80 (d, J=11.0 Hz, 2H), 1.35 (t, J=7.2 Hz, 3H).

Example 54 cis-4-(4-((4-ethoxy-7H-pyrrolo[2,3-d]pyrimidin-2-yl)amino)-5-methyl-1H-pyrazol-1-yl)-cyclohexanol (E54)

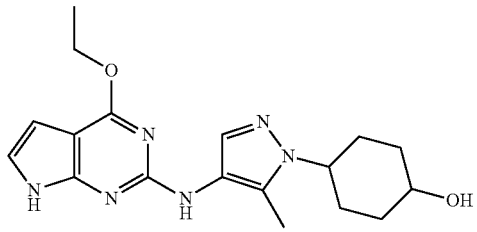 [SMILES: CCOc1nc(Nc2cnn(C3CCC(O)CC3)c2C)nc2[nH]ccc12]

A solution of (±)-4-(4-((4-ethoxy-7-tosyl-7H-pyrrolo-[2,3-d]pyrimidin-2-yl)amino)-5-methyl-1H-pyrazol-1-yl)cyclohexanol (which may be prepared according to D65)(100 g, 0.196 mmol) and sodium hydroxide (0.196 mL, 0.392 mmol, 2M in water) in THF (5 mL) and methanol (1.250 mL) was stirred at 50° C. for 2 hours. After cooling, the reaction mixture was poured into water (50 mL) and extracted with EtOAc (40 mL×3). The combined organic layer was dried over MgSO$_4$ and concentrated in vacuum. The crude was purified by prep-HPLC to give the title compound E54 (4 g, 0.011 mmol, 8.00% yield) as a white solid.

LCMS: 357 [M+H]$^+$. $t_R$=1.48 mins. (LCMS condition 2)

$^1$H NMR (400 MHz, CHLOROFORM-d): 8.66 (br. s., 1H), 7.73 (s, 1H), 6.70 (br. s., 1H), 6.38 (br. s., 1H), 6.05 (s, 1H), 4.49 (q, J=7.0 Hz, 2H), 4.10 (br. s., 1H), 3.90-4.06 (m, 1H), 2.29-2.51 (m, 2H), 2.23 (s, 3H), 1.91-2.07 (m, 2H), 1.65-1.81 (m, 4H), 1.43 (t, J=7.0 Hz, 3H).

Example 55 and 56

Enantiomer 1: cis-3-(4-((4-ethoxy-7H-pyrrolo[2,3-d]pyrimidin-2-yl)amino)-5-methyl-1H-pyrazol-1-yl) cyclopentanol (E55)

Enantiomer 2: cis-3-(4-((4-ethoxy-7H-pyrrolo[2,3-d]pyrimidin-2-yl)amino)-5-methyl-1H-pyrazol-1-yl) cyclopentanol (E56)

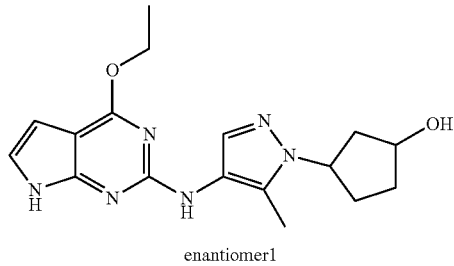

enantiomer1

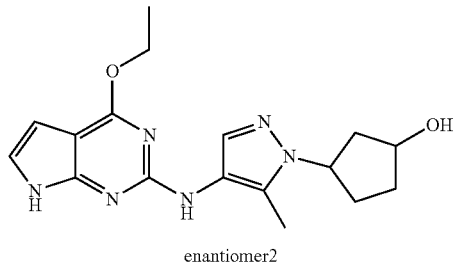

enantiomer2

A solution of 2-chloro-4-ethoxy-7H-pyrrolo[2,3-d]pyrimidine (which may be prepared according to D1) (230 g, 1.164 mmol), (±)-cis-3-(4-amino-5-methyl-1H-pyrazol-1-yl)cyclopentanol (which may be prepared according to D70) (260 g, 1.435 mmol), xantphos (101 g, 0.175 mmol), Pd$_2$(dba)$_3$ (53.3 g, 0.058 mmol) and potassium carbonate (322 g, 2.328 mmol) in 2-butanol (10 mL) was irradiated by microwave at 120° C. for 1 hour. Water (10 mL) was then added and the mixture was extracted with ethyl acetate (2×50 mL). The combined organic layer was washed with brine (20 mL), dried with Na$_2$SO$_4$, filtered and concentrated. The crude was purified by chromatography on silica gel (PE:EA=1:2) to get the racemic product, which was further purified by chiral-HPLC to give the title compounds E55 (65 g, 0.190 mmol, 16.31% yield) and E56 (65 g, 0.190 mmol, 16.31% yield) as white solids. (chiral-HPLC condition: Co-Solvent MeOH (0.1% DEA); Column AD-H (4.6*250 mm, 5 um); Column Temperature 39.9; CO$_2$ Flow Rate 2.1; Co-Solvent Flow Rate 0.9; Co-Solvent % 30; Back Pressure 118; Total Flow 3; PDA Start Wavelength 214; PDA Stop Wavelength 359) E55: LCMS: 343 [M+H]$^+$. $t_R$=1.48 mins. (LCMS condition 2)

Chiral HPLC: $t_R$=4.59 mins. (Condition: Column AD-H (4.6*250 mm, 5 um); Co-Solvent MeOH (0.1% DEA)) The absolute stereochemistry was not determined.

$^1$H NMR (400 MHz, DMSO-d$_6$): δ 11.19 (br. s., 1H), 8.01 (s, 1H), 7.61 (s, 1H), 6.76-6.92 (m, 1H), 6.21 (br. s., 1H), 5.05 (d, J=6.0 Hz, 1H), 4.57-4.69 (m, 1H), 4.44 (q, J=7.0 Hz, 2H), 4.02-4.22 (m, 1H), 2.22-2.36 (m, 2H), 2.17 (s, 3H), 1.96-2.06 (m, 2H), 1.91 (dt, J=12.9, 6.3 Hz, 1H), 1.64-1.86 (m, 2H), 1.36 (t, J=7.0 Hz, 3H).

E56: LCMS: 343[M+H]$^+$. $t_R$=1.48 mins. (LCMS condition 2)

Chiral HPLC: $t_R$=5.60 mins. (Condition: Column AD-H (4.6*250 mm, 5 um); Co-Solvent MeOH (0.1% DEA)) The absolute stereochemistry was not determined.

$^1$H NMR (400 MHz, DMSO-d$_6$): δ 11.19 (br. s., 1H), 8.01 (s, 1H), 7.60 (s, 1H), 6.67-6.97 (m, 1H), 6.21 (br. s., 1H), 5.04 (d, J=6.0 Hz, 1H), 4.57-4.69 (m, 1H), 4.44 (q, J=7.0 Hz, 2H), 4.06-4.22 (m, 1H), 2.21-2.34 (m, 1H), 1.96-2.06 (m, 2H), 1.91 (dt, J=12.9, 6.3 Hz, 1H), 1.64-1.86 (m, 2H), 1.36 (t, J=7.0 Hz, 3H).

Example 57 and 58

Enantiomer 1: trans-3-(4-((4-ethoxy-7H-pyrrolo[2,3-d]pyrimidin-2-yl)amino)-5-methyl-1H-pyrazol-1-yl)cyclopentanol (E57)

Enantiomer 2: trans-3-(4-((4-ethoxy-7H-pyrrolo[2,3-d]pyrimidin-2-yl)amino)-5-methyl-H-pyrazol-1-yl)cyclopentanol (E58)

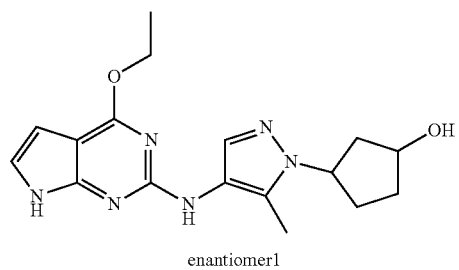

enantiomer1

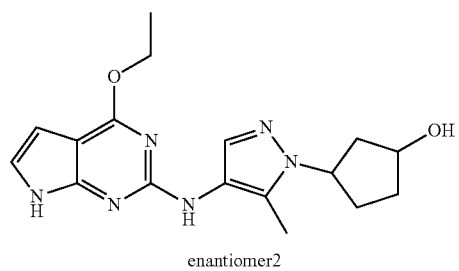

enantiomer2

A solution of 2-chloro-4-ethoxy-7H-pyrrolo[2,3-d]pyrimidine (which may be prepared according to D1) (60 g, 0.304 mmol), (±)-3-(5-methyl-4-nitro-1H-pyrazol-1-yl)cyclopentanol (which may be prepared according to D69) (50 g, 0.276 mmol), xantphos (26.4 mg, 0.046 mmol), Pd$_2$(dba)$_3$ (13.90 g, 0.015 mmol) and potassium carbonate (84 g, 0.607 mmol) in 2-butanol (3 mL) was irradiated by microwave at 120° C. for 1 hour. Water (10 mL) was then added and the mixture was extracted with ethyl acetate (3×30 mL). The combined organic layer was washed with brine (20 mL), dried with Na$_2$SO$_4$, filtered and concentrated. The crude was purified by chromatography on silica gel (PE:EA=1:4) to give the racemic product, which was further purified by chiral-HPLC to give the title compounds E57 (6 mg, 0.017 mmol, 5.66% yield) as a white solid and E58 (4 g, 0.011 mmol, 3.66% yield) as a yellow solid. (HPLC conditions: Co-Solvent MeOH (0.1% DEA); Column AD-H (4.6*150 mm, 5 um); Column Temperature 40.1; CO$_2$ Flow Rate 2.55; Co-Solvent Flow Rate 0.45; Co-Solvent % 15; Back Pressure 120; Total Flow 3; PDA Start Wavelength 214; PDA Stop Wavelength 359)

E57: LCMS: 343 [M+H]$^+$. $t_R$=1.426 mins. (LCMS condition 2)

Chiral HPLC: $t_R$=9.78 mins. (Condition: Column AD-H (4.6*250 mm, 5 um); Co-Solvent MeOH (0.1% DEA)) The absolute stereochemistry was not determined.

$^1$H NMR (400 MHz, DMSO-d$_6$): δ 11.17 (br. s., 1H), 7.97 (s, 1H), 7.55 (s, 1H), 6.71-7.01 (m, 1H), 6.20 (dd, J=3.4, 1.9 Hz, 1H), 4.74-4.85 (m, 1H), 4.64 (d, J=3.5 Hz, 1H), 4.43 (q, J=7.0 Hz, 2H), 4.34 (d, J=3.0 Hz, 1H), 2.08-2.23 (m, 5H), 1.77-2.07 (m, 3H), 1.56 (d, J=9.3 Hz, 1H), 1.35 (t, J=7.0 Hz, 3H).

E58: LCMS: 343 [M+H]$^+$. $t_R$=1.425 mins. (LCMS condition 2)

Chiral HPLC: $t_R$=10.97 mins. (Condition: Column AD-H (4.6*250 mm, 5 um); Co-Solvent MeOH (0.1% DEA)) The absolute stereochemistry was not determined.

$^1$H NMR (400 MHz, DMSO-d$_6$): δ 11.17 (br. s., 1H), 7.97 (s, 1H), 7.55 (s, 1H), 6.80-6.87 (m, 1H), 6.20 (dd, J=3.3, 1.8 Hz, 1H), 4.80 (m, 1H), 4.65 (d, J=3.5 Hz, 1H), 4.43 (q, J=7.0 Hz, 2H), 4.34 (d, J=3.0 Hz, 1H), 2.08-2.22 (m, 5H), 1.77-2.07 (m, 3H), 1.50-1.64 (m, 1H), 1.35 (t, J=7.0 Hz, 3H).

Example 59-61

Enantiomer 1: 4-ethoxy-N-(1-(4-fluoro-1-methylpyrrolidin-3-yl)-5-methyl-1H-pyrazol-4-yl)-7H-pyrrolo-[2,3-d]pyrimidin-2-amine (E59)

Enantiomer 2: 4-ethoxy-N-(1-(4-fluoro-1-methylpyrrolidin-3-yl)-5-methyl-1H-pyrazol-4-yl)-7H-pyrrolo-[2,3-d]pyrimidin-2-amine (E60)

Enantiomer 3: 4-ethoxy-N-(1-(4-fluoro-1-methylpyrrolidin-3-yl)-5-methyl-1H-pyrazol-4-yl)-7H-pyrrolo-[2,3-d]pyrimidin-2-amine (E61)

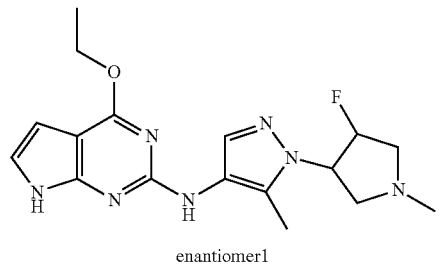

enantiomer1

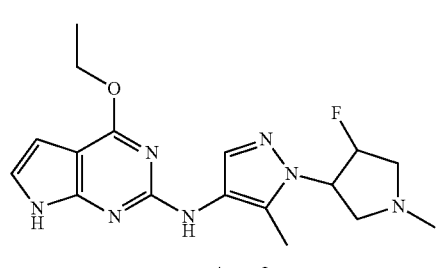

enantiomer2

E61

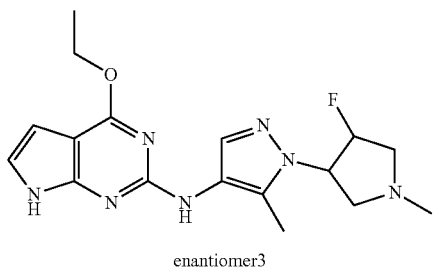

enantiomer3

A solution of (±)-4-ethoxy-N-(1-(4-fluoro-1-methylpyr-rolidin-3-yl)-5-methyl-1H-pyrazol-4-yl)-7-tosyl-7H-pyrrolo[2,3-d]pyrimidin-2-amine (which may be prepared according to D74) (100 g, 0.195 mmol) and sodium hydroxide (0.292 mL, 0.584 mmol, 2M in water) in isopropanol (2 mL) was stirred overnight at 60° C. Solvent was evaporated and 2N HCl was added until pH=7. The mixture was then extracted with EA twice. The combined organic layer was dried with MgSO₄ and evaporated. The crude was purified by prep-HPLC column to give the racemic compound, which was further purified by chiral-HPLC to give the title compounds E59 (3 mg, 7.85 μmol), E60 (3 mg, 8.35 μmol) and E61 (1.5 mg, 4.17 μmol) as gray solids. (HPLC conditions: Co-Solvent EtOH (0.1% DEA); Column OZ-H (4.6*150 mm, 5 um); Column Temperature 40; CO₂ Flow Rate 2.4; Co-Solvent Flow Rate 0.6; Co-Solvent % 20; Back Pressure 120; Total Flow 3; PDA Start Wavelength 214; PDA Stop Wavelength 359)

E59: LCMS: 360 [M+H]⁺. $t_R$=1.300 mins. (LCMS condition 2)

Chiral HPLC: $t_R$=3.20 mins. (Conditions: Column OZ-H (4.6*150 mm, 5 um); Co-Solvent EtOH (0.1% DEA)) The absolute stereochemistry was not determined.

¹H NMR (400 MHz, METHANOL-d₄): δ 7.71 (s, 1H), 6.82 (d, J=3.5 Hz, 1H), 6.30 (d, J=3.5 Hz, 1H), 5.23-5.45 (m, 1H), 4.49 (q, J=7.2 Hz, 2H), 3.41-3.47 (m, 1H), 3.16-3.29 (m, 1H), 2.67-2.95 (m, 3H), 2.45 (s, 3H), 2.29 (s, 3H), 1.42 (t, J=7.2 Hz, 3H).

E60: LCMS: 360 [M+H]⁺. $t_R$=1.320 mins. (LCMS condition 2)

Chiral HPLC: $t_R$=5.09 mins. (Conditions: Column OZ-H (4.6*150 mm, 5 um); Co-Solvent EtOH (0.1% DEA)) The absolute stereochemistry was not determined.

¹H NMR (400 MHz, METHANOL-d₄): δ 7.71 (s, 1H), 6.82 (d, J=3.5 Hz, 1H), 6.30 (d, J=3.5 Hz, 1H), 5.23-5.45 (m, 1H), 4.49 (q, J=7.2 Hz, 2H), 3.40-3.49 (m, 1H), 3.18-3.28 (m, 1H), 2.67-2.96 (m, 3H), 2.45 (s, 3H), 2.29 (s, 3H), 1.42 (t, J=7.2 Hz, 3H).

E61: LCMS: 360 [M+H]⁺. $t_R$=1.301 mins. (LCMS condition 2)

Chiral HPLC: $t_R$=4.03 mins. (Conditions: Column OZ-H (4.6*150 mm, 5 um); Co-Solvent EtOH (0.1% DEA)) The absolute stereochemistry was not determined.

¹H NMR (400 MHz, METHANOL-d₄): δ 8.07 (s, 1H), 6.85 (d, J=3.5 Hz, 1H), 6.32 (d, J=3.3 Hz, 1H), 5.12-5.43 (m, 1H), 4.52 (q, J=7.0 Hz, 2H), 3.35-3.42 (m, 1H), 3.05-3.18 (m, 1H), 2.72-3.01 (m, 3H), 2.44 (s, 3H), 2.24 (s, 3H), 1.45 (t, J=7.0 Hz, 3H).

Example 62

3-(4-((4-ethoxy-7H-pyrrolo-[2,3-d]pyrimidin-2-yl)amino)-5-methyl-1H-pyrazol-1-yl)-2,2-dimethylpropanenitrile (E62)

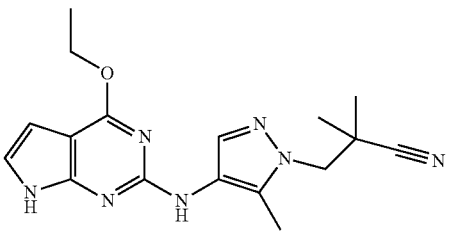 [SMILES: CCOc1nc(Nc2cnn(CC(C)(C)C#N)c2C)nc2[nH]ccc12]

A solution of 3-(4-((4-ethoxy-7-tosyl-7H-pyrrolo-[2,3-d]pyrimidin-2-yl)amino)-5-methyl-1H-pyrazol-1-yl)-2,2-dimethylpropanenitrile (which may be prepared according to D78)(80 g, 0.162 mmol) and N, N-dibutyl-N-propylbutan-1-aminium (185 g, 0.810 mmol) in THF (10 mL) was heated at reflux for 1 hour. The mixture was then concentrated and purified by pre-HPLC to get the title compound E62 (27 g, 0.076 mmol, 46.6% yield) as a white solid.

LCMS: 340 [M+H]⁺. $t_R$=1.334 mins. (LCMS conditions 2)

¹H NMR (400 MHz, DMSO-d₆): δ 11.19 (br. s., 1H), 8.05 (s, 1H), 7.67 (s, 1H), 6.85 (d, J=2.5 Hz, 1H), 6.20 (d, J=3.0 Hz, 1H), 4.42 (q, J=7.0 Hz, 2H), 4.20 (s, 2H), 2.24 (s, 3H), 1.30-1.40 (m, 9H).

Example 63

(R)-4-ethoxy-N-(1-(2-(3-fluoropyrrolidin-1-yl)-ethyl)-5-methyl-1H-pyrazol-4-yl)-7H-pyrrolo[2,3-d]pyrimidin-2-amine (E63)

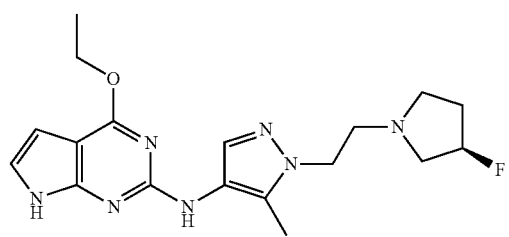 [SMILES: CCOc1nc(Nc2cnn(CCN3CC[C@@H](F)C3)c2C)nc2[nH]ccc12]

A solution of (R)-4-ethoxy-N-(1-(2-(3-fluoropyrrolidin-1-yl)ethyl)-5-methyl-1H-pyrazol-4-yl)-7-tosyl-7H-pyrrolo[2,3-d]pyrimidin-2-amine (which may be prepared according to D81) (150 g, 0.284 mmol) and sodium hydroxide (5.00 mL, 10.00 mmol, 2N in water) in isopropanol (5 mL) was stirred overnight at 60° C. Solvent was evaporated and 2N HCl was added until pH=7. The mixture was then extracted with EtOAc twice. The combined organic layer was dried with MgSO₄ and evaporated. The crude was purified by prep-HPLC to give the title compound E63 (40 g, 0.107 mmol, 37.7% yield) as a white solid.

LCMS: 374 [M+H]⁺. $t_R$=1.303 mins. (LCMS conditions 2)

¹H NMR (400 MHz, DMSO-d₆): δ 11.19 (br. s., 1H), 8.00 (s, 1H), 7.56 (s, 1H), 6.81-6.88 (m, 1H), 6.20 (dd, J=3.3, 1.8 Hz, 1H), 5.07-5.29 (m, 1H), 4.43 (q, J=7.0 Hz, 2H), 4.10 (t,

J=6.8 Hz, 2H), 2.72-2.93 (m, 4H), 2.53-2.68 (m, 1H), 2.34 (q, J=7.9 Hz, 1H), 2.18 (s, 3H), 2.00-2.15 (m, 1H), 1.72-1.95 (m, 1H), 1.35 (t, J=7.2 Hz, 3H).

Example 64

(S)-4-ethoxy-N-(1-(2-(3-fluoropyrrolidin-1-yl)ethyl)-5-methyl-1H-pyrazol-4-yl)-7H-pyrrolo[2,3-d]pyrimidin-2-amine (E64)

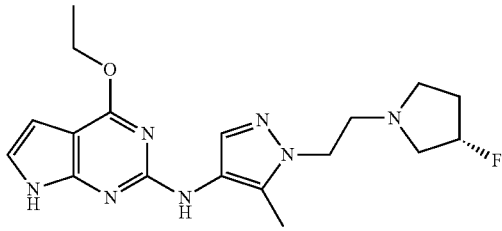 [SMILES: CCOc1nc(Nc2cnn(CCN3CC[C@H](F)C3)c2C)nc2[nH]ccc12]

A solution of (S)-4-ethoxy-N-(1-(2-(3-fluoropyrrolidin-1-yl)ethyl)-5-methyl-1H-pyrazol-4-yl)-7-tosyl-7H-pyrrolo[2,3-d]pyrimidin-2-amine (which may be prepared according to D82)(150 g, 0.284 mmol) and sodium hydroxide (5.00 mL, 10.00 mmol, 2N in water) in isopropanol (5 mL) was stirred overnight at 60° C. Solvent was evaporated and 2N HCl was added until pH=7. The mixture was then extracted with EtOAc twice. The combined organic layer was dried with MgSO₄ and evaporated. The crude was purified by prep-HPLC to give the title compound E63 (30 g, 0.080 mmol, 28.3% yield) as a white solid.

LCMS: 374 [M+H]⁺. $t_R$=1.299 mins. (LCMS conditions 2)

¹H NMR (400 MHz, DMSO-$d_6$): δ 11.19 (br. s., 1H), 7.99 (s, 1H), 7.56 (s, 1H), 6.77-6.94 (m, 1H), 6.20 (dd, J=3.1, 1.6 Hz, 1H), 5.04-5.33 (m, 1H), 4.43 (q, J=7.0 Hz, 2H), 4.10 (t, J=6.8 Hz, 2H), 2.73-2.92 (m, 4H), 2.53-2.69 (m, 1H), 2.27-2.39 (m, 1H), 2.18 (s, 3H), 2.00-2.17 (m, 1H), 1.74-1.96 (m, 1H), 1.35 (t, J=6.8 Hz, 3H).

Example 65

2-(4-((4-ethoxy-7H-pyrrolo-[2,3-d]pyrimidin-2-yl)amino)-5-methyl-1H-pyrazol-1-yl)-2-methylpropan-1-ol (E65)

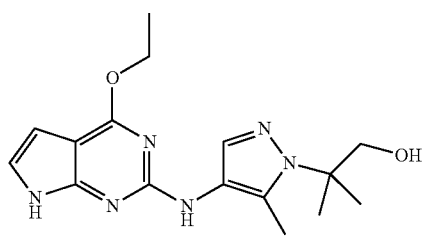 [SMILES: CCOc1nc(Nc2cnn(C(C)(C)CO)c2C)nc2[nH]ccc12]

A solution of 2-chloro-4-ethoxy-7H-pyrrolo[2,3-d]pyrimidine (which may be prepared according to D1) (60 g, 0.304 mmol), 2-(4-amino-5-methyl-1H-pyrazol-1-yl)-2-methylpropan-1-ol (which may be prepared according to D87) (46.2 g, 0.273 mmol), xantphos (26.4 g, 0.046 mmol), K₂CO₃ (84 g, 0.607 mmol) and Pd₂(dba)₃ (27.8 mg, 0.030 mmol) in 2-butanol (2 mL) was irradiated by microwave at 120° C. for 1 hour. The mixture was filtered and concentrated. The crude was then purified by prep-HPLC to give the title compound E65 (30 g, 0.091 mmol, 29.9% yield) as a white solid.

LCMS: 331 [M+H]⁺. $t_R$=1.16 mins. (LCMS conditions 2)

¹H NMR (400 MHz, CHLOROFORM-d): δ 9.45 (br. s., 1H), 7.61 (s, 1H), 6.48-6.64 (m, 1H), 6.35 (dd, J=3.3, 2.0 Hz, 1H), 6.04 (s, 1H), 4.42-4.59 (m, 3H), 3.89 (br. s., 2H), 2.35 (s, 3H), 1.41-1.49 (m, 9H).

Example 66

4-Ethoxy-N-(5-methyl-1-(1-(oxetan-3-yl)pyrrolidin-3-yl)-1H-pyrazol-4-yl)-7H-pyrrolo[2,3-d]pyrimidin-2-amine (E66)

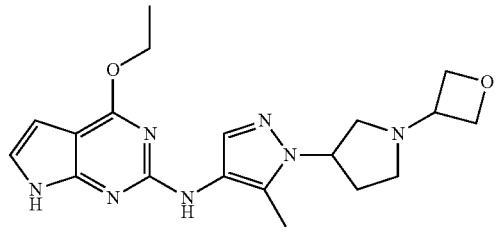 [SMILES: CCOc1nc(Nc2cnn(C3CCN(C4COC4)C3)c2C)nc2[nH]ccc12]

A solution of 2-chloro-4-ethoxy-7H-pyrrolo[2,3-d]pyrimidine (which may be prepared according to D1) (180 g, 0.911 mmol), 5-methyl-1-(1-(oxetan-3-yl)-pyrrolidin-3-yl)-1H-pyrazol-4-amine (182 g, 0.820 mmol)(which may be prepared according to PCT Int. Appl., WO2012062783), xantphos (79 g, 0.137 mmol), Pd₂(dba)₃ (83 g, 0.091 mmol) and K₂CO₃ (252 g, 1.822 mmol) in 2-butanol (8 mL) was irradiated by microwave at 120° C. for 1 hour. The mixture was filtered and the solution was concentrated. The crude was purified by prep-HPLC to give the title compound E66 (45 g, 0.113 mmol, 12.37% yield) as a white solid.

LCMS: 384 [M+H]⁺. $t_R$=1.08 mins. (LCMS conditions 2)

¹H NMR (400 MHz, CHLOROFORM-d): δ 9.75 (br. s., 1H), 7.68 (s, 1H), 6.47 (br. s., 1H), 6.23-6.34 (m, 1H), 6.08 (s, 1H), 4.58-4.80 (m, 5H), 4.50 (q, J=7.0 Hz, 2H), 3.73 (quin, J=6.2 Hz, 1H), 3.00 (t, J=8.4 Hz, 1H), 2.78-2.92 (m, 1H), 2.64 (dq, J=16.2, 8.1 Hz, 2H), 2.26-2.41 (m, 2H), 2.22 (s, 3H), 1.44 (t, J=7.2 Hz, 3H).

Example 67 and 68

Enantiomer 1: 4-ethoxy-N-(5-methyl-1-(1-(oxetan-3-yl)-pyrrolidin-3-yl)-1H-pyrazol-4-yl)-7H-pyrrolo-[2,3-d]pyrimidin-2-amine (E67)

Enantiomer 2: 4-ethoxy-N-(5-methyl-1-(1-(oxetan-3-yl)-pyrrolidin-3-yl)-1H-pyrazol-4-yl)-7H-pyrrolo-[2,3-d]pyrimidin-2-amine (E68)

E67

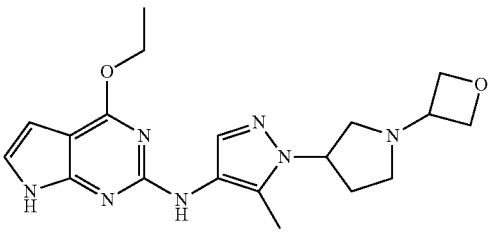

Enantiomer1

-continued

E68

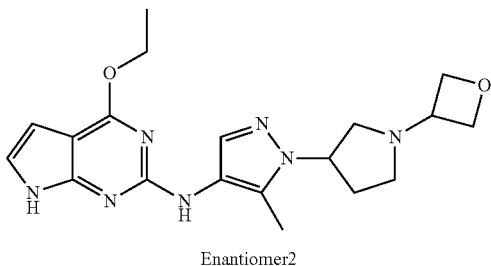

Enantiomer2

The title compounds E67 (30 g, 0.078 mmol, 25.8% yield) and E68 (30 g, 0.078 mmol, 25.8% yield) were prepared from chiral-HPLC separation of E66 as white solid (Co-Solvent MeOH (0.1% DEA); Column AD-H (4.6*250 mm, 5 um); Column Temperature 39.6; CO2 Flow Rate 2.55; Co-Solvent Flow Rate 0.45; Co-Solvent % 15; Back Pressure 120; Total Flow 3; PDA Start Wavelength 214; PDA Stop Wavelength 359).

E67: LCMS: 384 [M+H]$^+$. $t_R$=1.08 mins. (LCMS condition 2)

Chiral HPLC: $t_R$=4.08 mins. (Condition: Column AD-H (4.6*250 mm, 5 um); (Co-Solvent MeOH) The absolute stereochemistry was not determined.

$^1$H NMR (400 MHz, CHLOROFORM-d): δ 9.73 (br. s., 1H), 7.68 (s, 1H), 6.48 (br. s., 1H), 6.31 (br. s., 1H), 6.08 (s, 1H), 4.57-4.78 (m, 5H), 4.50 (q, J=7.0 Hz, 2H), 3.72 (quin, J=6.3 Hz, 1H), 2.99 (t, J=8.5 Hz, 1H), 2.87 (td, J=8.1, 4.9 Hz, 1H), 2.54-2.73 (m, 2H), 2.25-2.42 (m, 2H), 2.22 (s, 3H), 1.44 (t, J=7.0 Hz, 3H).

E68: LCMS: 384 [M+H]$^+$. $t_R$=1.08 mins. (LCMS condition 2)

Chiral HPLC: $t_R$=5.96 mins. (Condition: Column AD-H (4.6*250 mm, 5 um); (Co-Solvent MeOH) The absolute stereochemistry was not determined.

$^1$H NMR (400 MHz, CHLOROFORM-d): δ 9.65 (br. s., 1H), 7.69 (s, 1H), 6.49 (br. s., 1H), 6.31 (br. s., 1H), 6.07 (s, 1H), 4.57-4.82 (m, 5H), 4.50 (q, J=7.0 Hz, 2H), 3.72 (quin, J=6.2 Hz, 1H), 3.00 (t, J=8.4 Hz, 1H), 2.87 (td, J=8.2, 4.8 Hz, 1H), 2.53-2.72 (m, 2H), 2.28-2.40 (m, 2H), 2.22 (s, 3H), 1.44 (t, J=7.2 Hz, 3H).

Example 69

Trans-2-(5-cyclopropyl-4-((4-ethoxy-7H-pyrrolo-[2,3-d]pyrimidin-2-yl)amino)-1H-pyrazol-1-yl)-1-methylcyclopentanol (E69)

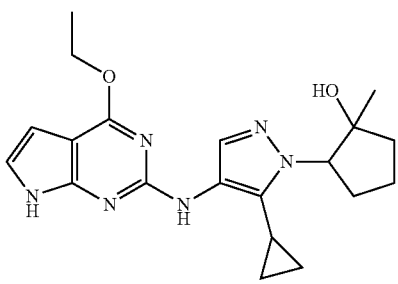 [SMILES: CCOc1nc(Nc2cnn(C3CCCC3(C)O)c2C2CC2)nc2[nH]ccc12]

A solution of (±)-Trans-2-(5-cyclopropyl-4-((4-ethoxy-7-tosyl-7H-pyrrolo-[2,3-d]-pyrimidin-2-yl)amino)-1H-pyrazol-1-yl)-1-methylcyclopentanol (which may be prepared according to D92) (300 g, 0.559 mmol) and N,N-dibutyl-N-propylbutan-1-aminium (639 g, 2.80 mmol) in THF (10 mL) was heated to reflux for 1 hour. The mixture was concentrated and purified by pre-HPLC to give the title compound E69 (150 g, 0.377 mmol, 67.4% yield) as a white solid.

LCMS: 383 [M+H]$^+$. $t_R$=1.08 mins. (LCMS condition 2)

$^1$H NMR (400 MHz, DMSO-d$_6$): δ 11.17 (br. s., 1H), 7.62 (s, 1H), 7.34-7.48 (m, 1H), 6.74-6.89 (m, 1H), 6.18 (dd, J=3.3, 1.8 Hz, 1H), 4.61-4.75 (m, 2H), 4.37 (q, J=6.9 Hz, 2H), 2.09-2.31 (m, 2H), 1.59-1.90 (m, 5H), 1.30 (t, J=7.0 Hz, 3H), 0.75-0.88 (m, 6H), 0.41-0.58 (m, 1H).

Example 70

Trans-2-(4-((4-ethoxy-7H-pyrrolo-[2,3-d]pyrimidin-2-yl)amino)-5-methyl-1H-pyrazol-1-yl)-1-methylcyclopentanol (E70)

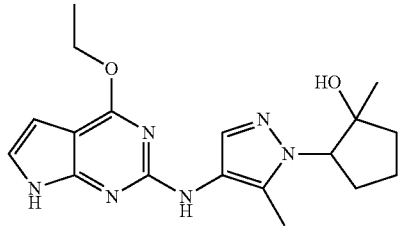 [SMILES: CCOc1nc(Nc2cnn(C3CCCC3(C)O)c2C)nc2[nH]ccc12]

A mixture of (±)-Trans-2-(4-((4-ethoxy-7-tosyl-7H-pyrrolo-[2,3-d]pyrimidin-2-yl)amino)-5-methyl-1H-pyrazol-1-yl)-1-methylcyclopentanol (which may be prepared according to D95) (400 g, 0.783 mmol) and N,N-dibutyl-N-propylbutan-1-aminium (895 g, 3.92 mmol) in THF (10 mL) was heated to reflux for 1 hour. The mixture was concentrated and purified by pre-HPLC to give the title compound E70 (150 g, 0.421 mmol, 53.7% yield) as a white solid.

LCMS: 357 [M+H]$^+$. $t_R$=1.150 mins. (LCMS condition 2)

$^1$H NMR (400 MHz, DMSO-d$_6$): δ 10.77-11.42 (m, 1H), 8.00 (s, 1H), 7.57 (s, 1H), 6.84 (br. s., 1H), 6.19 (br. s., 1H), 4.70 (s, 1H), 4.27-4.46 (m, 3H), 2.14-2.31 (m, 5H), 1.79 (br. s., 3H), 1.63 (br. s., 1H), 1.32 (t, J=7.03 Hz, 3H), 0.73 (s, 3H).

Example 71 and 72

Enantiomer 1: 3-(5-cyclopropyl-4-((4-ethoxy-7H-pyrrolo-[2,3-d]pyrimidin-2-yl)amino)-1H-pyrazol-1-yl)bicyclo-[3.1.0]-hexan-2-ol (E71)

Enantiomer 2: 3-(5-cyclopropyl-4-((4-ethoxy-7H-pyrrolo-[2,3-d]pyrimidin-2-yl)amino)-1H-pyrazol-1-yl)bicyclo-[3.1.0]-hexan-2-ol (E72)

E71

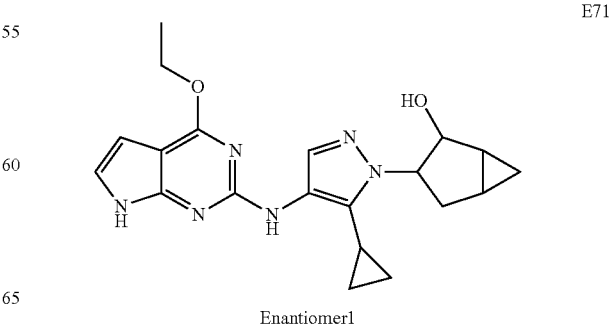

Enantiomer1

-continued

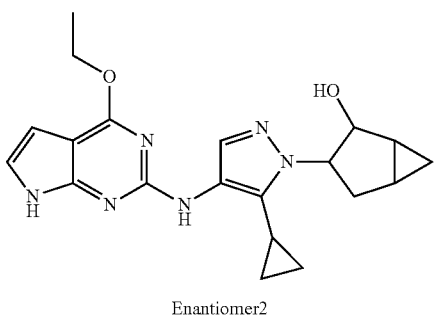

Enantiomer2

A solution of (±)-Trans-3-(5-cyclopropyl-4-((4-ethoxy-7-tosyl-7H-pyrrolo[2,3-d]pyrimidin-2-yl)amino)-1H-pyrazol-1-yl)bicycle-[3.1.0]-hexan-2-ol (which may be prepared according to D102) (30 g, 0.056 mmol) and TBAF (1M in THF) (0.561 mL, 0.561 mmol) in THF (10 mL) was stirred at 60° C. for 4 hours. Solvent was evaporated and the residue was dissolved in EA, washed with water twice. The organic layer was dried and concentrated. The crude was purified by reversed chromatography on C18 (base phase) to give the mixture, which was further purified by chiral-HPLC (Co-Solvent MeOH (0.1% DEA); Column IC (4.6*250 mm, 5 um); Column Temperature 39.9; CO2 Flow Rate 2.1; Co-Solvent Flow Rate 0.9; Co-Solvent % 30; Back Pressure 120; Total Flow 3; PDA Start Wavelength 214; PDA Stop Wavelength 359) to give the title compounds E71 (4 mg, 10.51 μmol, 21.05% yield) and E72 (5 g, 0.013 mmol, 26.3% yield) as white solids.

E71: LCMS: 381 [M+H]$^+$. $t_R$=1.544 mins. (LCMS condition 2)

Chiral HPLC: $t_R$=3.22 mins. (Condition: Column IC (4.6*250 mm, 5 um); (Co-Solvent MeOH) The absolute stereochemistry was not determined.

$^1$H NMR (400 MHz, CHLOROFORM-d): δ 9.45 (br. s., 1H), 7.79 (s, 1H), 6.62 (br. s., 1H), 6.37 (br. s., 1H), 6.21 (s, 1H), 4.88-5.05 (m, 1H), 4.51 (q, J=7.0 Hz, 2H), 4.26-4.43 (m, 1H), 2.36-2.55 (m, 1H), 2.17 (dd, J=12.4, 7.7 Hz, 1H), 1.56-1.66 (m, 2H), 1.45 (t, J=7.2 Hz, 4H), 0.72-0.94 (m, 4H), 0.52-0.64 (m, 2H).

E72: LCMS: 381 [M+H]$^+$. $t_R$=1.543 mins. (LCMS condition 2)

Chiral HPLC: $t_R$=3.97 mins. (Condition: Column IC (4.6*250 mm, 5 um); (Co-Solvent MeOH) The absolute stereochemistry was not determined.

$^1$H NMR (400 MHz, CHLOROFORM-d): δ 9.14-9.36 (m, 1H), 7.81 (s, 1H), 6.66 (d, J=3.3 Hz, 1H), 6.37 (d, J=3.3 Hz, 1H), 6.21 (s, 1H), 4.86-5.09 (m, 1H), 4.52 (q, J=7.0 Hz, 2H), 4.23-4.42 (m, 1H), 2.36-2.53 (m, 1H), 2.18 (dd, J=12.7, 7.7 Hz, 1H), 1.57-1.65 (m, 2H), 1.45 (t, J=7.0 Hz, 4H), 0.72-0.96 (m, 4H), 0.48-0.66 (m, 2H).

Example 73 and 74, E75 and E76

Enantiomer 1: trans-4-ethoxy-N-(1-(3-fluoro-1-methylpiperidin-4-yl)-5-methyl-1H-pyrazol-4-yl)-7H-pyrrolo[2,3-d]pyrimidin-2-amine (E73)

Enantiomer 2: trans-4-ethoxy-N-(1-(3-fluoro-1-methylpiperidin-4-yl)-5-methyl-1H-pyrazol-4-yl)-7H-pyrrolo[2,3-d]pyrimidin-2-amine (E74)

Enantiomer 1: trans-4-ethoxy-N-(1-(3-fluoro-1-methylpiperidin-4-yl)-1H-pyrazol-4-yl)-7H-pyrrolo[2,3-d]pyrimidin-2-amine (E75)

Enantiomer 2: trans-4-ethoxy-N-(1-(3-fluoro-1-methylpiperidin-4-yl)-1H-pyrazol-4-yl)-7H-pyrrolo[2,3-d]pyrimidin-2-amine (E76)

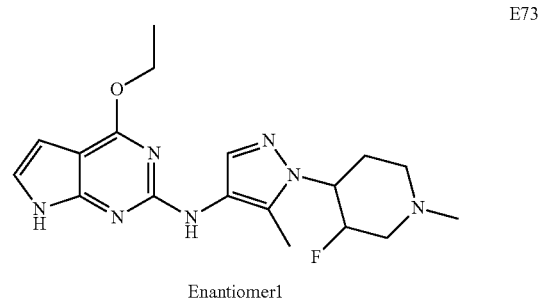

Enantiomer1

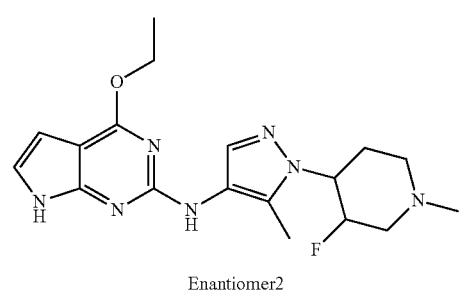

Enantiomer2

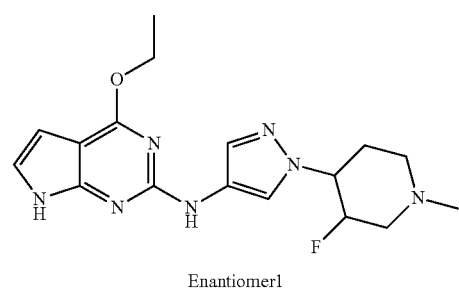

Enantiomer1

-continued

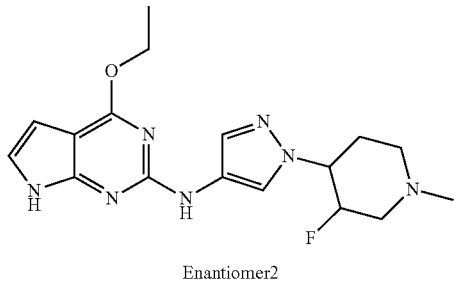

Enantiomer2

A solution of 3-fluoro-1-methyl-4-(5-methyl-4-nitro-1H-pyrazol-1-yl)piperidine (which may be prepared according to D109) (750 g, 1.421 mmol) and TBAF (1858 g, 7.11 mmol, 1M in THF) in THF (10.0 mL) was stirred at 80° C. for 2 hours. The mixture was quenched with aqueous NH$_4$Cl and extracted with DCM (20 mL×3). The combined organic layers were dried over Na$_2$SO$_4$, filtered and concentrated in vacuum The residue was purified by column chromatography on silica gel (DCM:MeOH=20:1) to give the mixture (220 g, 0.554 mmol, 39.0% yield), which was further purified by chiral-HPLC (Co-Solvent MeOH (0.1% DEA); Column OJ-H (4.6*250 mm, 5 um); Column Temperature 40; CO$_2$ Flow Rate 2.25; Co-Solvent Flow Rate 0.45; Co-Solvent % 15; Back Pressure 120; Total Flow 3; PDA Start Wavelength 214; PDA Stop Wavelength 359) to give the title compounds E73 (19.0 g, 0.051 mmol, 8.64% yield), E74 (13.6 g, 0.036 mmol, 6.18% yield), E75 (2.0 mg, 5.36 μmol, 0.909% yield) and E76 (1.0 mg, 2.68 μmol, 0.455% yield) as white solids.

E73: LCMS: 374.2 [M+H]$^+$. $t_R$=1.21 mins. (LCMS condition 2)

Chiral HPLC: $t_R$=3.27 mins. (Condition: Column OJ-H (4.6*250 mm, 5 um); (Co-Solvent MeOH) The absolute stereochemistry was not determined.

$^1$H NMR (400 MHz, CHLOROFORM-d): δ 9.10 (br. s., 1H), 7.77 (s, 1H), 6.54-6.74 (m, 1H), 6.35 (dd, J=3.4, 1.9 Hz, 1H), 6.06 (s, 1H), 4.82-5.07 (m, 1H), 4.42-4.54 (m, J=7.2, 7.2, 7.2 Hz, 2H), 3.85-4.07 (m, 1H), 3.18-3.37 (m, 1H), 2.79-3.01 (m, 1H), 2.41-2.52 (m, 1H), 2.37 (s, 3H), 2.23 (s, 3H), 2.05-2.19 (m, 2H), 1.91 (dd, J=7.5, 5.0 Hz, 1H), 1.42 (t, J=7.0 Hz, 3H).

E74: LCMS: 374.2 [M+H]$^+$. $t_R$=1.21 mins. (LCMS condition 2)

Chiral HPLC: $t_R$=3.85 mins. (Condition: Column OJ-H (4.6*250 mm, 5 um); (Co-Solvent MeOH) The absolute stereochemistry was not determined.

$^1$H NMR (400 MHz, CHLOROFORM-d): δ 7.77 (s, 1H), 6.63 (d, J=3.0 Hz, 1H), 6.36 (d, J=1.8 Hz, 1H), 6.06 (s, 1H), 4.83-5.08 (m, 1H), 4.48 (q, J=7.2 Hz, 2H), 3.87-4.05 (m, 1H), 3.21-3.35 (m, 1H), 2.92 (d, J=9.8 Hz, 1H), 2.40-2.52 (m, 1H), 2.38 (s, 3H), 2.23 (s, 3H), 2.04-2.20 (m, 2H), 1.92 (dd, J=7.8, 5.3 Hz, 1H), 1.42 (t, J=7.0 Hz, 3H).

E75: LCMS: 360 [M+H]$^+$. $t_R$=1.90 mins. (LCMS condition 2)

Chiral HPLC: $t_R$=6.72 mins. (Condition: Column OJ-H (4.6*250 mm, 5 um); (Co-Solvent MeOH) The absolute stereochemistry was not determined.

$^1$H NMR (400 MHz, CHLOROFORM-d): δ 8.65 (br. s., 1H), 7.95 (s, 1H), 7.62 (s, 1H), 6.79 (d, J=3.3 Hz, 1H), 6.68 (br. s., 1H), 6.41 (d, J=3.0 Hz, 1H), 4.73-5.00 (m, 1H), 4.45-4.58 (m, 2H), 4.01-4.16 (m, 1H), 3.19-3.36 (m, 1H), 2.81-3.00 (m, 1H), 2.38 (s, 3H), 2.11-2.32 (m, 4H), 1.42-1.50 (m, 3H).

E76: LCMS: 360 [M+H]$^+$. $t_R$=1.90 mins. (LCMS condition 2)

Chiral HPLC: $t_R$=7.8 mins. (Condition: Column OJ-H (4.6*250 mm, 5 um); (Co-Solvent MeOH) The absolute stereochemistry was not determined.

$^1$H NMR (400 MHz, CHLOROFORM-d): δ 8.52 (br. s., 1H), 7.96 (s, 1H), 7.61 (s, 1H), 6.79 (dd, J=3.3, 2.0 Hz, 1H), 6.56 (s, 1H), 6.41 (dd, J=3.3, 2.0 Hz, 1H), 4.73-5.06 (m, 1H), 4.39-4.58 (m, 2H), 4.01-4.17 (m, 1H), 3.24-3.36 (m, 1H), 2.92 (d, J=9.8 Hz, 1H), 2.38 (s, 3H), 2.11-2.32 (m, 4H), 1.46 (t, J=7.2 Hz, 3H).

Example 77 and 78

Enantiomer 1: trans-2-(4-((4-ethoxy-7H-pyrrolo-[2,3-d]pyrimidin-2-yl)amino)-5-methyl-1H-pyrazol-1-yl)-1-methylcyclopentanol (E77)

Enantiomer 1: trans-2-(4-((4-ethoxy-7H-pyrrolo-[2,3-d]pyrimidin-2-yl)amino)-5-methyl-1H-pyrazol-1-yl)-1-methylcyclopentanol (E78)

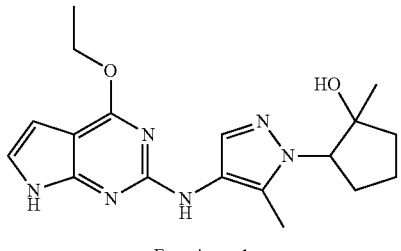

Enantiomer1

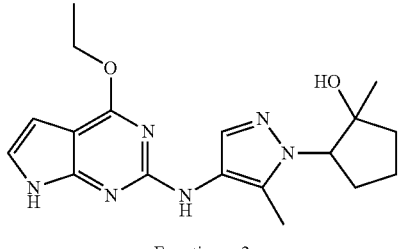

Enantiomer2

The title compounds E77 (63 g, 0.177 mmol, 43.4% yield) and E78 (66 g, 0.185 mmol, 45.5% yield) were prepared from chiral-HPLC separation of E70 (Co-Solvent MeOH (0.1% DEA); Column IC (4.6*250 mm, 5 um); Column Temperature 40.2; CO$_2$ Flow Rate 2.4; Co-Solvent Flow Rate 0.6; Co-Solvent % 20; Back Pressure 120; Total Flow 3; PDA Start Wavelength 214; PDA Stop Wavelength 359) as white solids.

E77: LCMS: 357 [M+H]$^+$. $t_R$=1.149 mins. (LCMS condition 2)

Chiral HPLC: $t_R$=2.31 mins. (Condition: Column IC (4.6*250 mm, 5 um); (Co-Solvent MeOH) The absolute stereochemistry was not determined.

$^1$H NMR (400 MHz, DMSO-d$_6$): δ 11.16 (br. s., 1H), 8.00 (s, 1H), 7.57 (s, 1H), 6.78-6.90 (m, 1H), 6.19 (dd, J=3.3, 1.8 Hz, 1H), 4.70 (s, 1H), 4.19-4.48 (m, 3H), 2.12-2.36 (m, 5H), 1.73-1.85 (m, 3H), 1.57-1.69 (m, 1H), 1.32 (t, J=7.0 Hz, 3H), 0.73 (s, 3H).

E78: LCMS: 357 [M+H]⁺. t_R=1.153 mins. (LCMS condition 2)

Chiral HPLC: t_R=2.53 mins. (Condition: Column IC (4.6*250 mm, 5 um); (Co-Solvent MeOH) The absolute stereochemistry was not determined.

¹H NMR (400 MHz, DMSO-d₆): δ 11.16 (br. s., 1H), 8.00 (s, 1H), 7.57 (s, 1H), 6.78-6.90 (m, 1H), 6.19 (dd, J=3.3, 1.8 Hz, 1H), 4.70 (s, 1H), 4.19-4.48 (m, 3H), 2.12-2.36 (m, 5H), 1.73-1.85 (m, 3H), 1.57-1.69 (m, 1H), 1.32 (t, J=7.0 Hz, 3H), 0.73 (s, 3H).

Example 79 and 80

Enantiomer 1: trans-2-(5-cyclopropyl-4-((4-ethoxy-7H-pyrrolo-[2,3-d]pyrimidin-2-yl)amino)-1H-pyrazol-1-yl)-1-methylcyclopentanol (E79)

Enantiomer 2: trans-2-(5-cyclopropyl-4-((4-ethoxy-7H-pyrrolo-[2,3-d]pyrimidin-2-yl)amino)-1H-pyrazol-1-yl)-1-methylcyclopentanol (E80)

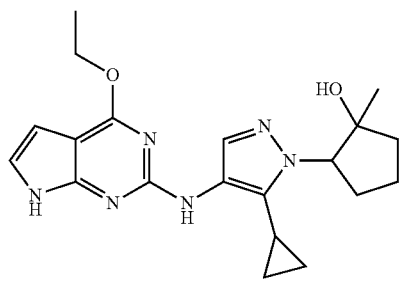

Enantiomer1

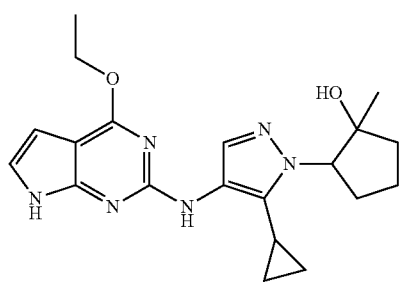

Enantiomer2

The title compounds E79 (70 g, 0.183 mmol, 48.3% yield) and E80 (62 g, 0.162 mmol, 42.8% yield) were prepared from chiral-HPLC separation of E69 (Co-Solvent MeOH (0.1% DEA); Column IC (4.6*250 mm, 5 um); Column Temperature 40.1; CO₂ Flow Rate 2.4; Co-Solvent Flow Rate 0.6; Co-Solvent % 20; Back Pressure 120; Total Flow 3; PDA Start Wavelength 214; PDA Stop Wavelength 359) as white solids.

E79: LCMS: 383 [M+H]⁺. t_R=1.217 mins. (LCMS condition 2)

Chiral HPLC: t_R=2.19 mins. (Condition: Column IC (4.6*250 mm, 5 um); (Co-Solvent MeOH) The absolute stereochemistry was not determined.

¹H NMR (400 MHz, DMSO-d₆): δ 11.17 (br. s., 1H), 7.62 (s, 1H), 7.43 (s, 1H), 6.69-7.03 (m, 1H), 6.18 (dd, J=3.2, 1.8 Hz, 1H), 4.63-4.72 (m, 2H), 4.37 (q, J=7.0 Hz, 2H), 2.06-2.34 (m, 2H), 1.58-1.92 (m, 5H), 1.30 (t, J=7.0 Hz, 3H), 0.75-0.90 (m, 5H), 0.46-0.57 (m, 1H).

E80: LCMS: 383 [M+H]⁺. t_R=1.221 mins. (LCMS condition 2)

Chiral HPLC: t_R=2.42 mins. (Condition: Column IC (4.6*250 mm, 5 um); (Co-Solvent MeOH) The absolute stereochemistry was not determined.

¹H NMR (400 MHz, DMSO-d₆): δ 11.17 (br. s., 1H), 7.62 (s, 1H), 7.43 (s, 1H), 6.75-6.92 (m, 1H), 6.18 (dd, J=3.2, 1.8 Hz, 1H), 4.55-4.77 (m, 2H), 4.37 (q, J=6.9 Hz, 2H), 2.07-2.33 (m, 2H), 1.57-1.91 (m, 5H), 1.30 (t, J=7.0 Hz, 3H), 0.73-0.89 (m, 6H), 0.42-0.59 (m, 1H).

Example 81

(R)-4-ethoxy-N-(5-methyl-1-(2-(3-methylmorpholino)ethyl)-1H-pyrazol-4-yl)-7H-pyrrolo [2,3-d]pyrimidin-2-amine (E81)

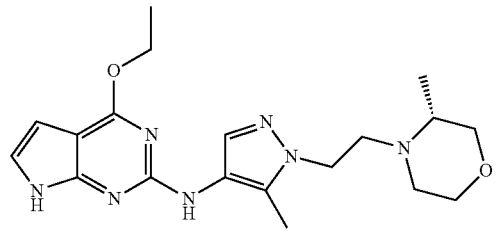 [SMILES: CCOc1nc(Nc2cnn(CCN3CCOC[C@H]3C)c2C)nc2[nH]ccc12]

A solution of D1 (50 g, 0.253 mmol), D116 (68.1 g, 0.304 mmol), X-phos (12.6 mg, 0.025 mmol), K₂CO₃ (105 g, 0.759 mmol) and Pd₂(dba)₃ (11.58 g, 0.013 mmol) in 2-butanol (2 mL) was irradiated by microwave at 120° C. for 45 min. The mixture was filtered and concentrated. The crude was then purified by prep-HPLC to give the title compound E81 (5.0 g, 0.013 mmol, 5.13% yield) as a white solid.

LCMS: 386 [M+H]⁺. t_R=1.18 mins. (LCMS conditions 2)

¹H NMR (400 MHz, CHLOROFORM-d): δ 8.79 (br. s., 1H), 7.66 (s, 1H), 6.66-6.72 (m, 1H), 6.37 (dd, J=2.0, 3.2 Hz, 1H), 6.03 (s, 1H), 4.49 (q, J=7.11 Hz, 2H), 4.10 (t, J=7.0 Hz, 2H), 3.78 (d, J=11.29 Hz, 1H), 3.56-3.70 (m, 2H), 3.20 (d, J=2.0 Hz, 2H), 2.58-2.77 (m, 2H), 2.38-2.52 (m, 2H), 2.24 (s, 3H), 1.44 (t, J=7.0 Hz, 3H), 0.93 (d, J=6.4 Hz, 3H).

Example 82

(S)-4-ethoxy-N-(5-methyl-1-(2-(3-methylmorpholino)ethyl)-1H-pyrazol-4-yl)-7H-pyrrolo [2,3-d]pyrimidin-2-amine (E82)

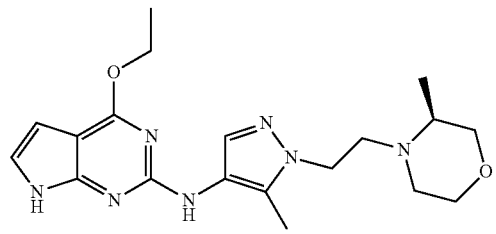 [SMILES: CCOc1nc(Nc2cnn(CCN3CCOC[C@@H]3C)c2C)nc2[nH]ccc12]

A solution of D1 (29 g, 0.147 mmol), D118 (39.5 g, 0.176 mmol), X-phos (7 mg, 0.015 mmol), K₂CO₃ (60.8 g, 0.440 mmol) and Pd₂(dba)₃ (6.72 mg, 7.34 μmol) in 2-butanol (2 mL) was irradiated by microwave at 120° C. for 45 min. The mixture was filtered and concentrated. The crude was then purified by prep-HPLC to give the title compound E82 (5 mg, 0.013 mmol, 8.84% yield) as a white solid.

LCMS: 386 [M+H]$^+$. $t_R$=1.256 mins. (LCMS conditions 2)

$^1$H NMR (400 MHz, METHANOL-d$_4$): δ 7.56 (s, 1H), 6.71 (d, J=3.51 Hz, 1H), 6.19 (d, J=3.51 Hz, 1H), 4.37 (q, J=7.11 Hz, 2H), 4.08 (t, J=6.65 Hz, 2H), 3.66 (d, J=11.29 Hz, 1H), 3.43-3.58 (m, 2H), 2.97-3.10 (m, 2H), 2.67 (br. s., 1H), 2.49-2.58 (m, 1H), 2.29-2.43 (m, 2H), 2.18 (s, 3H), 1.31 (t, J=7.15 Hz, 3H), 0.82 (d, J=6.27 Hz, 3H).

Example 83

(R)-4-ethoxy-N-(5-methyl-1-(2-(2-methylmorpholino)ethyl)-1H-pyrazol-4-yl)-7H-pyrrolo[2,3-d]pyrimidin-2-amine (E83)

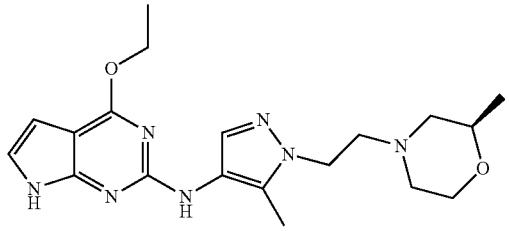 [SMILES: CCOc1nc(Nc2cnn(CCN3CCO[C@H](C)C3)c2C)nc2[nH]ccc12]

A solution of D1 (100 g, 0.506 mmol), D120 (136 g, 0.607 mmol), X-phos (24.12 g, 0.051 mmol), K$_2$CO$_3$ (210 g, 1.518 mmol) and Pd$_2$(dba)$_3$ (23.17 g, 0.025 mmol) in 2-butanol (2 mL) was irradiated by microwave at 120° C. for 45 min. The mixture was filtered and concentrated. The crude was then purified by prep-HPLC to give the title compound E83 (60.0 g, 0.156 mmol, 30.8% yield) as a white solid.

LCMS: 386 [M+H]$^+$. $t_R$=1.25 mins. (LCMS conditions 2)

$^1$H NMR (400 MHz, CHLOROFORM-d): δ 9.88 (s, 1H), 7.62 (s, 1H), 6.48 (m, 1H), 6.32 (m, 1H), 6.08 (m, 1H), 4.51 (dd, J=9.0 Hz, 2H), 4.09 (t, J=9.0 Hz, 2H), 3.83 (m, 1H), 3.63 (m, 2H), 2.63 (m, 4H), 2.21 (s, 3H), 2.16 (m, 1H), 1.84 (m, 1H), 1.44 (t, J=9.0 Hz, 3H), 1.14 (d, J=9.0 Hz, 3H).

Example 84

(S)-4-ethoxy-N-(5-methyl-1-(2-(2-methylmorpholino)ethyl)-1H-pyrazol-4-yl)-7H-pyrrolo[2,3-d]pyrimidin-2-amine (E84)

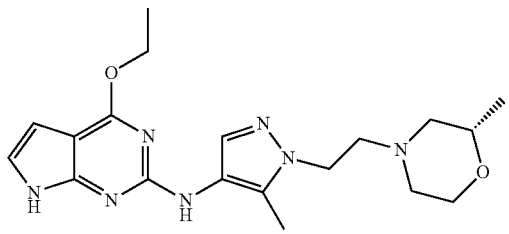 [SMILES: CCOc1nc(Nc2cnn(CCN3CCO[C@@H](C)C3)c2C)nc2[nH]ccc12]

A solution of D1 (75 g, 0.380 mmol), D122 (120 g, 0.535 mmol), X-phos (18.09 mg, 0.038 mmol), K$_2$CO$_3$ (157 g, 1.139 mmol) and Pd$_2$(dba)$_3$ (17.38 g, 0.019 mmol) in 2-butanol (2 mL) was irradiated by microwave at 120° C. for 45 min. The mixture was filtered and concentrated. The crude was then purified by prep-HPLC to give the title compound E84 (13 g, 0.034 mmol, 8.89% yield) as a white solid.

LCMS: 386 [M+H]$^+$. $t_R$=1.27 mins. (LCMS conditions 2)

$^1$H NMR (400 MHz, DMSO-d$_6$): 11.20 (br. s., 1H), 8.02 (s, 1H), 7.55 (s, 1H), 6.75-6.92 (m, 1H), 6.20 (dd, J=1.88, 3.39 Hz, 1H), 4.43 (q, J=7.03 Hz, 2H), 4.10 (t, J=6.78 Hz, 2H), 3.65-3.79 (m, 1H), 3.40-3.52 (m, 2H), 2.66-2.81 (m, 2H), 2.62 (t, J=6.78 Hz, 2H), 2.18 (s, 3H), 1.97-2.09 (m, 1H), 1.75 (t, J=10.54 Hz, 1H), 1.35 (t, J=7.03 Hz, 3H), 1.03 (d, J=6.27 Hz, 3H).

Example 85

(R)—N-(1-(1-(2,2-difluoroethyl)pyrrolidin-3-yl)-5-methyl-1H-pyrazol-4-yl)-4-ethoxy-7H-pyrrolo[2,3-d]pyrimidin-2-amine (E85)

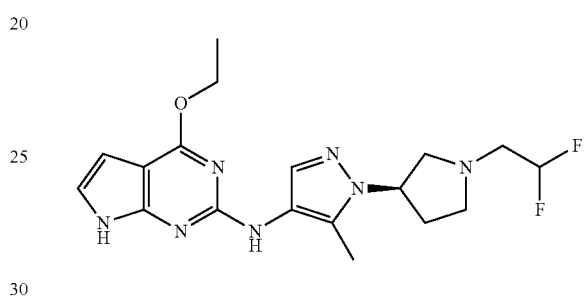

A solution of D1 (239 g, 1.212 mmol), D128 (186 g, 0.808 mmol), X-phos (7.70 g, 0.016 mmol), Pd$_2$(dba)$_3$ (22.19 g, 0.024 mmol) and K$_2$CO$_3$ (335 g, 2.423 mmol) in 2-butanol (12 mL) was stirred under microwave at 120° C. for 1 hour. The reaction was then filtered and the filtrate was concentrated. The crude was the purified via MDAP (base) to give the title compound E85 (75 g, 0.192 mmol, 23.72% yield) as a white solid.

LCMS: 392 [M+H]$^+$. $t_R$=2.177 mins. (LCMS conditions 1)

$^1$H NMR (400 MHz, CHLOROFORM-d): δ 8.87 (br. s., 1H), 7.75 (s, 1H), 6.62-6.73 (m, 1H), 6.39 (br. s., 1H), 5.68-6.14 (m, 2H), 4.74-4.86 (m, 1H), 4.51 (q, J=6.85 Hz, 2H), 3.20 (t, J=8.44 Hz, 1H), 2.84-3.06 (m, 5H), 2.30-2.46 (m, 2H), 2.25 (s, 3H), 1.46 (t, J=7.09 Hz, 3H).

Example 86

4-ethoxy-N-(5-methyl-1-(3-morpholinocyclobutyl)-1H-pyrazol-4-yl)-7H-pyrrolo[2,3-d]pyrimidin-2-amine (E86)

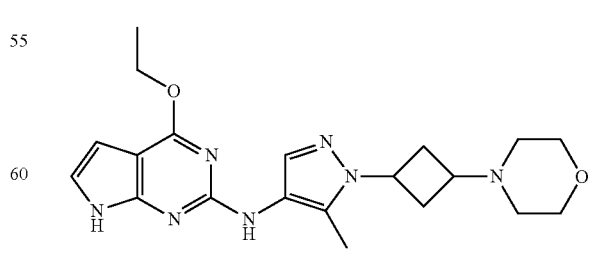

A solution of D131 (200 g, 0.363 mmol) and sodium hydroxide (5.00 mL, 10.00 mmol, 2M in water) in isopropanol (5 mL) was stirred overnight at 60° C. The mixture was concentrated and 2N HCl was added until pH=7. The mixture was extracted with EtOAc. The aqueous phase was extracted with EtOAc and the combined organic extracts were dried over MgSO₄ and concentrated. The crude was purified by prep-HPLC to give the title compound E86 (46 g, 0.116 mmol, 31.9% yield) as white solid.

LCMS: 398 [M+H]⁺. $t_R$=1.30 mins. (LCMS conditions 2)
¹H NMR (400 MHz, DMSO-de): 11.20 (br. s., 1H), 8.02 (s, 1H), 7.51-7.69 (m, 1H), 6.78-6.91 (m, 1H), 6.20 (dd, J=1.76, 3.26 Hz, 1H), 4.38-4.59 (m, 3H), 3.59 (t, J=4.14 Hz, 4H), 2.53-2.62 (m, 1H), 2.43-2.48 (m, 2H), 2.24-2.39 (m, 6H), 2.14 (s, 3H), 1.36 (t, J=7.03 Hz, 3H)

Example 87

(S)—N-(1-(1-(2,2-difluoroethyl)pyrrolidin-3-yl)-5-methyl-1H-pyrazol-4-yl)-4-ethoxy-7H-pyrrolo[2,3-d]pyrimidin-2-amine (E87)

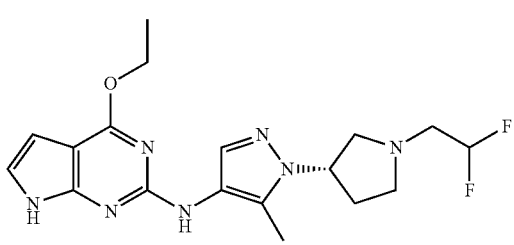 [SMILES: CCOc1nc(Nc2cnn([C@H]3CCN(CC(F)F)C3)c2C)nc2[nH]ccc12]

A solution of D1 (227 g, 1.147 mmol), D137 (176 g, 0.764 mmol), X-phos (7.29 g, 0.015 mmol), Pd₂(dba)₃ (21.00 g, 0.023 mmol) and K₂CO₃ (317 g, 2.293 mmol) in 2-butanol (12 mL) was stirred under microwave at 120° C. for 1 hour. The reaction was then filtered and the filtrate was concentrated. The crude was purified via MDAP (base) to give the title compound E87 (130 g, 0.332 mmol, 43.5% yield) as a yellow solid.

LCMS: 392 [M+H]⁺. $t_R$=2.019 mins. (LCMS conditions 1)
¹H NMR (400 MHz, CHLOROFORM-d): δ 9.19 (br. s., 1H), 7.74 (s, 1H), 6.60 (br. s., 1H), 6.37 (br. s., 1H), 5.71-6.12 (m, 2H), 4.78 (br. s., 1H), 4.51 (q, J=7.09 Hz, 2H), 3.17 (t, J=8.68 Hz, 1H), 2.79-3.04 (m, 5H), 2.28-2.43 (m, 2H), 2.24 (s, 3H), 1.46 (t, J=7.09 Hz, 3H).

Example 88

4-ethoxy-N-(5-methyl-1-(2-methyl-2-morpholinopropyl)-1H-pyrazol-4-yl)-7H-pyrrolo[2,3-d]pyrimidin-2-amine (E88)

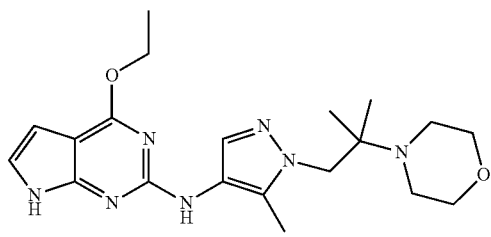 [SMILES: CCOc1nc(Nc2cnn(CC(C)(C)N3CCOCC3)c2C)nc2[nH]ccc12]

A solution of D1 (100 g, 0.506 mmol), D143 (145 g, 0.607 mmol), X-phos (18.09 g, 0.038 mmol), K₂CO₃ (210 g, 1.518 mmol) and Pd₂(dba)₃ (24.12 g, 0.051 mmol) in 2-butanol (2 mL) was irradiated by microwave at 120° C. for 45 min. The mixture was filtered and concentrated. The crude was then purified by prep-HPLC to give the title compound E88 (105 g, 0.263 mmol, 51.9% yield) as a white solid.

LCMS: 400 [M+H]⁺. $t_R$=1.28 mins. (LCMS conditions 2)
¹H NMR (300 MHz, CHLOROFORM-d): δ 11.20 (s, 1H), 8.00 (s, 1H), 7.57 (s, 1H), 6.86 (d, J=3.5 Hz, 1H), 6.21 (d, J=3.5 Hz, 1H), 4.42 (dd, J=9.0 Hz, 2H), 3.97 (s, 2H), 3.57 (m, 4H), 2.58 (m, 4H), 2.19 (s, 3H), 1.34 (t, J=9.0 Hz, 3H), 0.97 (s, 6H).

Example 89

N-(1-(2-(3,3-difluoroazetidin-1-yl)ethyl)-5-methyl-1H-pyrazol-4-yl)-4-ethoxy-7H-pyrrolo [2,3-d]pyrimidin-2-amine (E89)

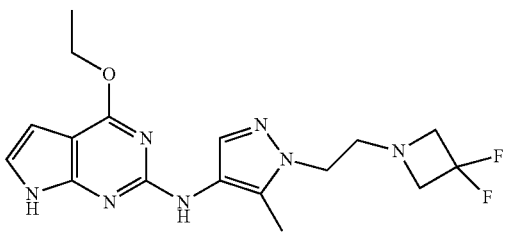 [SMILES: CCOc1nc(Nc2cnn(CCN3CC(F)(F)C3)c2C)nc2[nH]ccc12]

A solution of D1 (15 g, 0.076 mmol), D145 (19.70 g, 0.091 mmol), X-phos (3.62 mg, 7.59 μmol), K₂CO₃ (31.5 g, 0.228 mmol) and Pd₂(dba)₃ (3.48 mg, 3.80 μmol) in 2-butanol (2 mL) was irradiated by microwave at 120° C. for 45 min. The mixture was filtered and concentrated. The crude was then purified by prep-HPLC to give the title compound E89 (3 mg, 7.95 μmol, 10.47% yield) as a white solid.

LCMS: 378 [M+H]⁺. $t_R$=1.30 mins. (LCMS conditions 2)
¹H NMR (400 MHz, METHANOL-d₄): δ 7.67 (s, 1H), 6.82 (d, J=3.51 Hz, 1H), 6.30 (d, J=3.51 Hz, 1H), 4.47 (q, J=7.03 Hz, 2H), 4.14 (t, J=6.15 Hz, 2H), 3.55 (t, J=12.17 Hz, 4H), 3.02 (t, J=6.15 Hz, 2H), 2.27 (s, 3H), 1.41 (t, J=7.03 Hz, 3H).

Example 90

4-ethoxy-N-(5-methyl-1-(2-methyl-1-morpholinopropan-2-yl)-1H-pyrazol-4-yl)-7H-pyrrolo[2,3-d]pyrimidin-2-amine (E90)

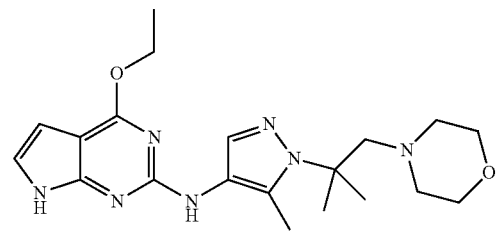

A solution of D1 (50 g, 0.253 mmol), D151 (70 g, 0.294 mmol), X-phos (14.64 mg, 0.025 mmol), K₂CO₃ (69.9 g, 0.506 mmol) and Pd₂(dba)₃ (23.17 g, 0.025 mmol) in 2-butanol (1.5 mL) was irradiated by microwave at 120° C. for 45 min. The mixture was filtered and concentrated. The crude was then purified by prep-HPLC to give the title compound E90 (45 g, 0.113 mmol, 44.5% yield) as a white solid.

LCMS: 400 [M+H]$^+$. $t_R$=1.75 mins. (LCMS conditions 2)
$^1$H NMR (300 MHz, CHLOROFORM-d): δ 7.63 (s, 1H), 6.56 (br. s., 1H), 6.34 (dd, J=2.01, 3.26 Hz, 1H), 6.02 (s, 1H), 4.48 (q, J=7.03 Hz, 2H), 3.51-3.67 (m, 4H), 2.60 (s, 2H), 2.43 (s, 3H), 2.18-2.30 (m, 4H), 1.61 (s, 6H), 1.43 (t, J=7.15 Hz, 3H).

Example 91 and 92

Enantiomer 1: 4-ethoxy-N-(5-methyl-1-(2-methyl-1-morpholinopropan-2-yl)-1H-pyrazol-4-yl)-7H-pyrrolo[2,3-d]pyrimidin-2-amine (E91)

Enantiomer 2: 4-ethoxy-N-(5-methyl-1-(2-methyl-1-morpholinopropan-2-yl)-1H-pyrazol-4-yl)-7H-pyrrolo[2,3-d]pyrimidin-2-amine (E92)

E91

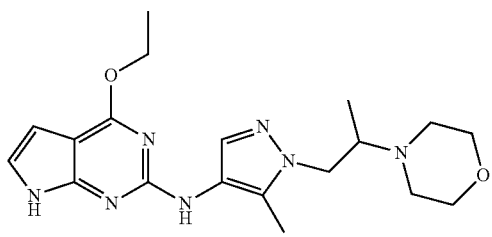

E92

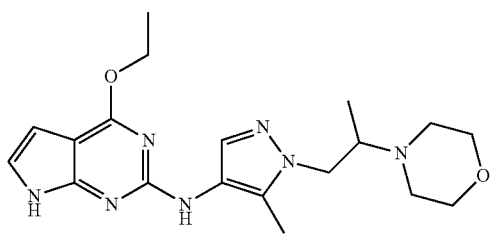

A mixture of D158 (180 g, 0.334 mmol) and TBAF (381 g, 1.668 mmol) in THF (10 mL) was heated to reflux for 1 hour. The mixture was concentrated and purified by pre-HPLC and further purified by chiral-HPLC to give the title compounds E91 (21 g, 0.054 mmol, 14.48% yield) and E92 (16 g, 0.042 mmol, 11.03% yield) as white solids.

E91: LCMS: 386 [M+H]$^+$. $t_R$=1.270 mins. (LCMS condition 2)

Chiral HPLC: $t_R$=5.56 mins. (Conditions: Column OZ-H (4.6*250 mm, 5 um); Co-Solvent MeOH (0.1% DEA)) The absolute stereochemistry was not determined.

$^1$H NMR (400 MHz, DMSO-d$_6$): 11.19 (br. s., 1H), 8.00 (s, 1H), 7.56 (s, 1H), 6.75-6.96 (m, 1H), 6.20 (dd, J=1.76, 3.26 Hz, 1H), 4.42 (q, J=7.03 Hz, 2H), 4.14 (dd, J=5.90, 13.93 Hz, 1H), 3.84 (dd, J=7.91, 13.93 Hz, 1H), 3.54 (t, J=4.39 Hz, 4H), 2.93-3.03 (m, 1H), 2.53-2.60 (m, 2H), 2.41-2.48 (m, 2H), 2.18 (s, 3H), 1.34 (t, J=7.03 Hz, 3H), 0.89 (d, J=6.78 Hz, 1H).

E92: LCMS: 386 [M+H]$^+$. $t_R$=1.277 mins. (LCMS condition 2)

Chiral HPLC: $t_R$=7.55 mins. (Conditions: Column OZ-H (4.6*250 mm, 5 um); Co-Solvent MeOH (0.1% DEA)) The absolute stereochemistry was not determined.

$^1$H NMR (400 MHz, DMSO-d$_6$): 11.19 (br. s., 1H), 8.02 (s, 1H), 7.57 (s, 1H), 6.80-6.90 (m, 1H), 6.20 (dd, J=1.76, 3.26 Hz, 1H), 4.42 (q, J=6.86 Hz, 2H), 4.14 (dd, J=6.02, 13.80 Hz, 1H), 3.84 (dd, J=7.91, 13.93 Hz, 1H), 3.55 (t, J=4.39 Hz, 4H), 2.99 (q, J=6.61 Hz, 1H), 2.54-2.61 (m, 2H), 2.42-2.48 (m, 2H), 2.18 (s, 3H), 1.34 (t, J=7.03 Hz, 3H), 0.89 (d, J=6.78 Hz, 3H)

Example 93

3-(4-((4-ethoxy-7H-pyrrolo[2,3-d]pyrimidin-2-yl)amino)-5-methyl-1H-pyrazol-1-yl)-1-methylcyclobutanol (E93)

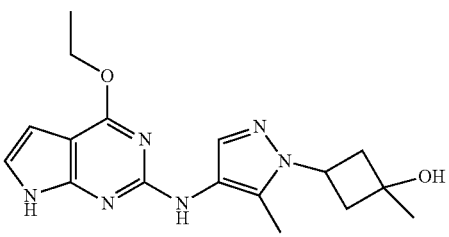 [SMILES: CCOc1nc(Nc2cnn(C3CC(C)(O)C3)c2C)nc2[nH]ccc12]

A mixture of D168 (300 g, 0.604 mmol) and TBAF (790 g, 3.02 mmol) in THF (10 mL) was heated to reflux for 2 hours. The mixture was concentrated and purified by column chromatography on silica gel (DCM:CH$_3$OH=20:1) to give the title compound E93 (64.0 g, 0.182 mmol, 30.2% yield) as a white solid.

LCMS: 343 [M+H]$^+$. $t_R$=1.07 mins. (LCMS condition 2)
$^1$H NMR (300 MHz, DMSO-d$_6$): δ 11.17 (s, 1H), 7.98 (s, 1H), 7.58 (s, 1H), 6.84 (d, J=4.5 Hz, 1H), 6.18 (d, J=4.5 Hz, 1H), 5.16 (s, 1H), 4.43 (dd, J=9.6 Hz, 2H), 4.35 (dd, J=10.0 Hz, 1H), 2.56 (m, 2H), 2.37 (m, 2H), 2.12 (s, 3H), 1.34 (m, 6H).

Example 94

N-(1-((2R,4R)-2-(difluoromethyl)piperidin-4-yl)-5-methyl-1H-pyrazol-4-yl)-4-ethoxy-7H-pyrrolo[2,3-d]pyrimidin-2-amine (E94)

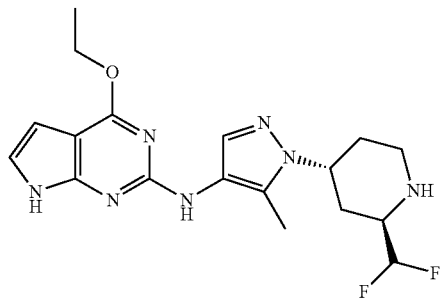 [SMILES: CCOc1nc(Nc2cnn([C@@H]3CCN[C@@H](C(F)F)C3)c2C)nc2[nH]ccc12]

A solution of D1 (51.5 g, 0.261 mmol), D176 (40 g, 0.174 mmol), X-phos (1.656 mg, 3.47 μmol), Pd$_2$(dba)$_3$ (4.77 mg, 5.21 μmol) and K$_2$CO$_3$ (72.0 g, 0.521 mmol) in 2-butanol (12 mL) was stirred under microwave at 120° C. for 2 hours. The reaction was then filtered and the filtrate was concentrated. The crude was the purified via MDAP (base) to give the title compound E94 (17 g, 0.043 mmol, 25.00% yield) as a white solid.

LCMS: 392 [M+H]+. $t_R$=2.030 mins. (LCMS conditions 1)

$^1$H NMR (600 MHz, METHANOL-$d_4$): δ 7.64 (s, 1H), 6.83 (d, J=3.30 Hz, 1H), 6.31 (d, J=3.67 Hz, 1H), 5.89-6.15 (m, 1H), 4.63 (qd, J=3.97, 7.89 Hz, 1H), 4.50 (q, J=7.21 Hz, 2H), 3.61 (dt, J=5.32, 14.21 Hz, 1H), 3.17-3.24 (m, 1H), 3.02 (ddd, J=3.48, 8.34, 12.38 Hz, 1H), 2.26 (s, 3H), 2.20 (ddd, J=4.95, 8.16, 13.66 Hz, 1H), 1.95-2.11 (m, 3H), 1.43 (t, J=7.15 Hz, 3H).

Example 95

N-(1-((2R,4S)-2-(difluoromethyl)piperidin-4-yl)-5-methyl-1H-pyrazol-4-yl)-4-ethoxy-7H-pyrrolo[2,3-d]pyrimidin-2-amine (E95)

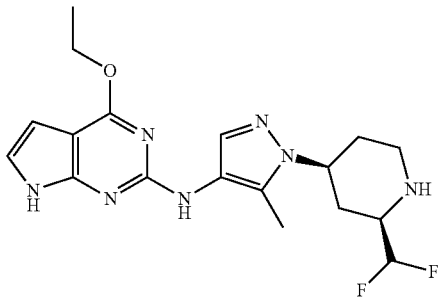 [SMILES: CCOc1nc(Nc2cnn([C@H]3CCN[C@@H](C(F)F)C3)c2C)nc2[nH]ccc12]

A solution of D1 (57.7 g, 0.292 mmol), D178 (56 g, 0.243 mmol), X-phos (2.319 mg, 4.86 μmol), Pd$_2$(dba)$_3$ (6.68 mg, 7.30 μmol) and K$_2$CO$_3$ (101 g, 0.730 mmol) in 2-butanol (12 mL) was stirred under microwave at 120° C. for 2 hours. The reaction was then filtered and the filtrate was concentrated. The crude was the purified via MDAP (base) to give the title compound E95 (51 g, 0.127 mmol, 52.1% yield) as a white solid.

LCMS: 392 [M+H]+. $t_R$=1.895 mins. (LCMS conditions 1)

$^1$H NMR (600 MHz, METHANOL-$d_4$): δ 7.60-7.72 (m, 1H), 6.83 (d, J=3.30 Hz, 1H), 6.31 (d, J=3.30 Hz, 1H), 5.70-5.94 (m, 1H), 4.50 (q, J=7.21 Hz, 2H), 4.34-4.44 (m, 1H), 3.30 (d, J=13.20 Hz, 1H), 3.16-3.26 (m, 1H), 2.89 (br. s., 1H), 2.28 (s, 3H), 1.92-2.13 (m, 4H), 1.43 (t, J=7.15 Hz, 3H).

Example 96

2-(4-((4-ethoxy-7H-pyrrolo[2,3-d]pyrimidin-2-yl)amino)-5-methyl-1H-pyrazol-1-yl)-2-methylpropanenitrile (E96)

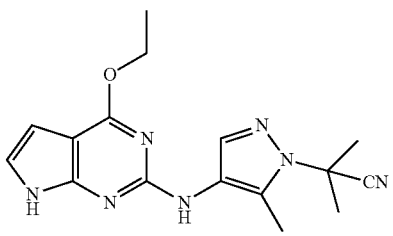 [SMILES: CCOc1nc(Nc2cnn(C(C)(C)C#N)c2C)nc2[nH]ccc12]

A solution of D183 (510 g, 1.49 mmol) in POCl$_3$ (50 mL) was stirred at 90° C. for 1 hour. POCl$_3$ was removed by evaporation and the mixture was added into ice water (100 mL). Sat. Na$_2$CO$_3$ was added until pH to 8 and the organic layer was extracted with EtOAc (100 mL×3). The combined organic layers were washed with brine (200 mL), dried over Na$_2$SO$_4$, filtered and concentrated. The crude was purified by column on C18 (ACN/H$_2$O: 45/55) to give the title compound E96 (380 mg, 78% yield) as a white solid.

LCMS: 326 [M+H]+. $t_R$=3.836 mins. (LCMS conditions 3)

$^1$H NMR (300 MHz, DMSO-$d_6$): δ 11.23 (br s, 1H), 8.17 (s, 1H), 7.71 (s, 1H), 6.86-6.89 (m, 1H), 6.21-6.23 (m, 1H), 4.42 (q, J=7.2 Hz, 2H), 2.41 (s, 3H), 1.94 (s, 6H), 1.34 (t, J=7.2 Hz, 3H).

Example 97 and 98

4-ethoxy-N-(1-((3S,4S)-3-fluoro-1-(oxetan-3-yl)piperidin-4-yl)-5-methyl-1H-pyrazol-4-yl)-7H-pyrrolo[2,3-d]pyrimidin-2-amine (E97)

4-ethoxy-N-(1-((3R,4R)-3-fluoro-1-(oxetan-3-yl)piperidin-4-yl)-5-methyl-1H-pyrazol-4-yl)-7H-pyrrolo[2,3-d]pyrimidin-2-amine (E98)

E97

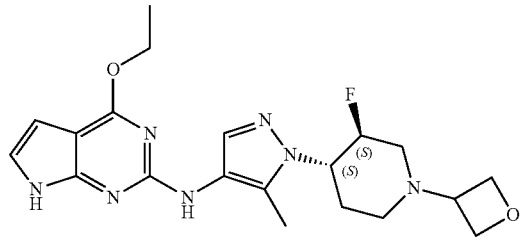

E98

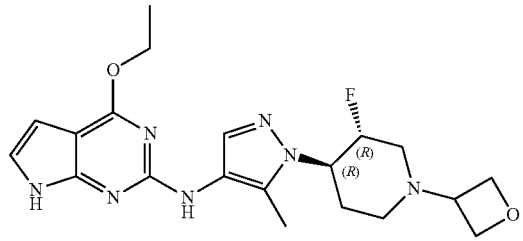

A solution of D1 (390 g, 1.98 mmol), D185 (420 g, 1.65 mmol), X-phos (157 mg, 0.33 mmol), Pd$_2$(dba)$_3$ (144 g, 0.16 mmol) and K$_2$CO$_3$ (683 g, 4.95 mmol) in dioxane (20 mL) was stirred overnight at 100° C. under N$_2$. The mixture was filtered and the filtrate was concentrated. The crude was purified by column chromatography on silica gel (DCM:MeOH=40:1) to give the racemate (320 mg, 49% yield) as a light yellow solid, which was further separated by chiral-HPLC and purified by prep-HPLC [Waters Xbridge™ C18, 5 um, 19*150 mm; Flowing phase: H$_2$O (0.1% NH$_4$HCO$_3$)/MeCN: MeCN form 10% to 95%, 15 ml/min, T=6 min] to give the title compounds E97 and E98.

E97: LCMS: 416 [M+H]+. $t_R$=3.50 mins. (LCMS condition 3)

Chiral HPLC: $t_R$=6.688 mins. (Chiralpak OD-H 5 um 4.6*250 nm, Hex:EtOH:DEA=70:30:0.2, Flow: 1.0 ml/min, 230 nm, T=30° C.)

¹H NMR (300 MHz, DMSO-d₆): δ 11.20 (s, 1H), 8.03 (s, 1H), 7.67 (s, 1H), 6.85 (s, 1H), 6.20 (s, 1H), 5.03-4.77 (m, 1H), 4.58-4.55 (m, 2H), 4.50-4.40 (m, 4H), 4.30-4.24 (m, 1H), 3.59-3.55 (m, 1H), 3.20-3.15 (m, 1H), 2.78-2.75 (m, 1H), 2.18 (s, 3H), 2.12-2.04 (m, 3H), 1.96-1.87 (m, 1H), 1.35 (t, J=6.6 Hz, 3H).

¹⁹F NMR (376 MHz, DMSO-d₆): δ −186.1.

E98: LCMS: 416 [M+H]⁺. $t_R$=2.98 mins. (LCMS condition 3)

Chiral HPLC: $t_R$=5.96 mins. (Chiralpak OD-H 5 um 4.6*250 nm, Hex:EtOH:DEA=70:30:0.2, Flow: 1.0 ml/min, 230 nm, T=30° C.)

¹H NMR (300 MHz, DMSO-d₆): 511.20 (s, 1H), 8.03 (s, 1H), 7.67 (s, 1H), 6.85 (s, 1H), 6.20 (s, 1H), 5.03-4.77 (m, 1H), 4.58-4.55 (m, 2H), 4.50-4.40 (m, 4H), 4.30-4.24 (m, 1H), 3.59-3.55 (m, 1H), 3.20-3.15 (m, 1H), 2.78-2.75 (m, 1H), 2.18 (s, 3H), 2.12-2.04 (m, 3H), 1.96-1.87 (m, 1H), 1.35 (t, J=6.6 Hz, 3H).

¹⁹F NMR (376 MHz, DMSO-d₆): δ −186.1.

Example 99

(R)—N-(1-(2-(2-(difluoromethyl)morpholino)ethyl)-5-methyl-1H-pyrazol-4-yl)-4-ethoxy-7H-pyrrolo[2,3-d]pyrimidin-2-amine (E99)

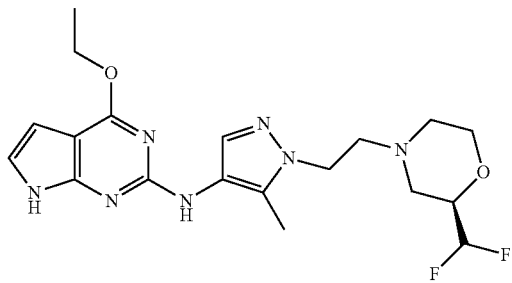 [SMILES: CCOc1nc(Nc2cnn(CCN3CCO[C@@H](C(F)F)C3)c2C)nc2[nH]ccc12]

To a solution of D199 (125 g, 0.217 mmol) in H₂O (2 mL), dioxane (3 mL) and EtOH (5 mL) was added Cs₂CO₃ (847 g, 2.60 mmol). The reaction was heated to 105° C. and stirred for 16 hours. The mixture was concentrated in vacuo. Water (50 mL) was added to the residue. The mixture was extracted with EtOAc (50 mL×3). The combined organic layers were washed with brine (50 mL), dried over Na₂SO₄, and concentrated. The crude was purified by column on C18 (ACN/H₂O=40-60%) and further purified by chiral HPLC (chiral condition: Chiralpak IC 5 um 4.6*250 nm, Hex: EtOH=80:20, Flow: 1.0 ml/min, 230 nm, T=30° C. Rt=9.195 min) to give the title compound E100 (13 mg, 85% ee, yield 14%) as off white solid.

LCMS: 422 [M+H]⁺. $t_R$=3.278 mins. (LCMS condition 3)

¹H NMR (300 MHz, CD₃OD): δ 7.66 (s, 1H), 6.81 (d, J=3.6 Hz, 1H), 6.29 (d, J=3.6 Hz, 1H), 5.76 (td, J=55.5, 4.2 Hz, 1H), 4.47 (q, J=7.2 Hz, 2H), 4.22 (t, J=6.9 Hz, 2H), 3.89 (d, J=10.5 Hz, 1H), 3.59-3.76 (m, 2H), 2.69-2.87 (m, 4H), 2.22-2.32 (m, 4H), 2.19 (t, J=10.5 Hz, 1H), 1.41 (t, J=7.2 Hz, 3H);

¹⁹F NMR (376 MHz, CD₃OD): δ −130.1 (d, J=295 Hz, 1F); −132.7 (d, J=295 Hz, 1F).

Example 100

(S)—N-(1-(2-(2-(difluoromethyl)morpholino)ethyl)-5-methyl-1H-pyrazol-4-yl)-4-ethoxy-7H-pyrrolo[2,3-d]pyrimidin-2-amine (E100)

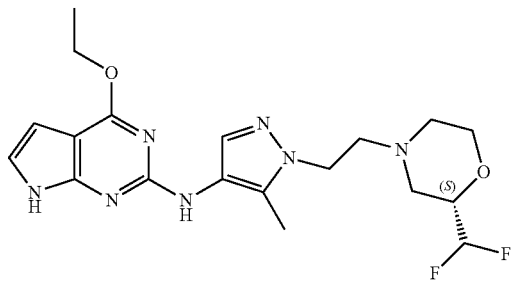

To a solution of D192 (150 g, 0.260 mmol) in H₂O (2 mL), dioxane (3 mL) and EtOH (5 mL) was added Cs₂CO₃ (1.00 g, 3.07 mmol). The reaction was heated to 105° C. and stirred overnight. The mixture was concentrated and the residue was poured into 15 mL of water, extracted with EtOAc (10 mL×2). The organic layer was dried over Na₂SO₄ and concentrated. The crude was purified by prep-HPLC (SunFire C18 5 um 19*15 mm, 15-70% B, A:H₂O (0.1% NH₄HCO₃), B: ACN, UV 214 nm, Flowrate 15 mL/min, RT: 80 min) and chiral HPLC (Chiral condition: Chiralpak IC 5 um 4.6*250 nm, Hex:EtOH=80:20, Flow: 1.0 ml/min, 230 nm, T=30° C. Rt=8.417 min) to give the title compound E100 as a yellow solid (15 mg, 98.7% ee, yield 14%).

LCMS: 422 [M+H]⁺. $t_R$=3.332 mins. (LCMS condition 3)

¹H NMR (400 MHz, CD₃OD): δ 7.66 (s, 1H), 6.80 (d, J=3.6 Hz, 1H), 6.29 (d, J=3.6 Hz, 1H), 5.77 (td, J=54.8, 3.0 Hz, 1H), 4.47 (q, J=7.2 Hz, 2H), 4.22 (t, J=6.8 Hz, 2H), 3.89 (d, J=11.2 Hz, 1H), 3.60-3.72 (m, 2H), 2.78-2.86 (m, 3H), 2.71 (d, J=11.2 Hz, 1H), 2.21-2.31 (m, 4H), 2.18 (t, J=10.8 Hz, 1H), 1.41 (t, J=7.2 Hz, 3H);

¹⁹F NMR (376 MHz, CD₃OD): δ −130.1 (d, J=295 Hz, 1F); −132.7 (d, J=295 Hz, 1F).

Example 101

(±)-trans-3-(5-chloro-4-((4-ethoxy-7H-pyrrolo[2,3-d]pyrimidin-2-yl)amino)-1H-pyrazol-1-yl) cyclopentanol (E101)

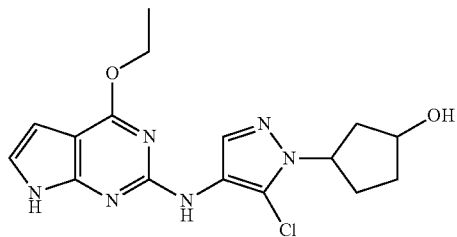 [SMILES: CCOc1nc(Nc2cnn(C3CCC(O)C3)c2Cl)nc2[nH]ccc12]

A solution of D200 (320 g, 0.745 mmol), D1 (177 g, 0.894 mmol), X-phos (7.10 g, 0.015 mmol), K₂CO₃ (618 g, 4.47 mmol) and Pd₂(dba)₃ (20.46 g, 0.022 mmol) in 2-butanol (10 mL) was stirred under microwave for 120 min. Solvent was evaporated and the crude was directly purified by column chromatography on silica gel (PE:EA=1:0-0:1) and then further purified by MDAP (base phase, 30-70% CH₃CN in water) to give the title compound E101 (75 g, 0.207 mmol, 27.8% yield) as a yellow solid.

LCMS: 363 [M+H]⁺. t$_R$=2.529 mins. (LCMS condition 1)

¹H NMR (400 MHz, CHLOROFORM-d): δ 8.75 (br. s., 1H), 8.15 (s, 1H), 6.79 (br. s., 1H), 6.44 (br. s., 1H), 6.31 (s, 1H), 5.08 (quin, J=7.27 Hz, 1H), 4.65 (br. s., 1H), 4.56 (q, J=7.09 Hz, 2H), 2.31-2.48 (m, 2H), 2.21-2.30 (m, 1H), 2.12-2.20 (m, 1H), 1.99-2.11 (m, 1H), 1.76 (d, J=6.36 Hz, 1H), 1.48 (t, J=6.97 Hz, 3H).

Example 102

Enantiomer 1: cis-4-ethoxy-N-(1-(3-fluoro-1-(oxetan-3-yl)piperidin-4-yl)-5-methyl-1H-pyrazol-4-yl)-7H-pyrrolo[2,3-d]pyrimidin-2-amine (E102)

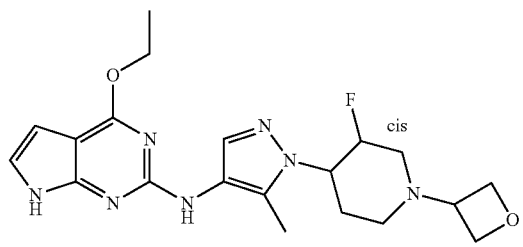 [SMILES: CCOc1nc(Nc2cnn(C3CCN(C4COC4)CC3F)c2C)nc2[nH]ccc12]

A solution of D1 (128 g, 0.648 mmol), D207 (150 g, 0.590 mmol), X-phos (60 mg, 0.11 mmol), Pd₂(dba)₃ (53 g, 0.058 mmol), K₂CO₃ (244 g, 1.77 mmol) in dioxane (10 mL) was stirred at 110° C. under N₂ for 8 hrs. The mixture was filtered and the filtrate was concentrated. The crude was purified by column chromatography on C18 (20-50% ACN in water) and further purified by prep-HPLC (Instrument: Column: Boston C18, 5 um, 21*150 mm; Mobile phase: H₂O (0.1% NH₄HCO₃)/MeCN: MeCN form 20% to 70%, 20 ml/min, T=15 min, rt=7.2 min) to give the title compound E102 (30 mg, 100% ee) as a light yellow solid.

LCMS: 416 [M+H]⁺. t$_R$=3.29 mins. (LCMS condition 3)

Chiral HPLC: t$_R$=6.73 mins. (Chiral condition: OD-H; 5 um 4.6*250 nm, Hex:EtOH:DEA=70:30:0.2, Flow: 1.0 ml/min, 230 nm, T=30° C.) The absolute stereochemistry was not determined.

¹H NMR (300 MHz, DMSO-d₆): δ 11.20 (s, 1H), 8.03 (s, 1H), 7.59 (s, 1H), 6.85 (m, 1H), 6.20 (m 1H), 4.89-4.77 (m, 1H), 4.57-4.36 (m, 7H), 3.57-3.52 (m, 1H), 2.99-2.89 (m, 2H), 2.67-2.58 (m, 2H), 2.21 (s, 3H), 2.35-2.07 (m, 2H), 1.82-1.78 (m, 1H), 1.35 (t, J=6.6 Hz, 3H).

¹⁹F NMR (376 MHz, DMSO-d₆): δ −198.1.

Example 103

Enantiomer 2: cis-4-ethoxy-N-(1-(3-fluoro-1-(oxetan-3-yl)piperidin-4-yl)-5-methyl-1H-pyrazol-4-yl)-7H-pyrrolo[2,3-d]pyrimidin-2-amine (E103)

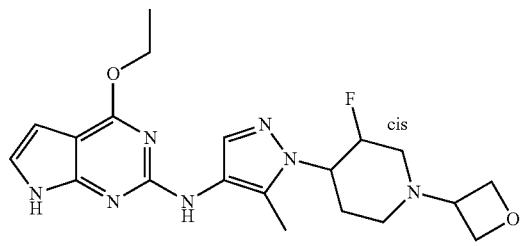 [SMILES: CCOc1nc(Nc2cnn(C3CCN(C4COC4)CC3F)c2C)nc2[nH]ccc12]

A solution of D1 (119 g, 0.602 mmol), D208 (140 g, 0.550 mmol), X-phos (52 mg, 0.10 mmol), Pd₂(dba)₃ (50 g, 0.05 mmol) and K₂CO₃ (227 g, 1.65 mmol) in dioxane (10 mL) was stirred at 110° C. under N₂ for 8 hrs. The mixture was filtered and the filtrate was concentrated. The crude was purified by column chromatography on C18 (20-50% ACN in water) and further purified by prep-HPLC (Instrument: Column: Boston C18, 5 um, 21*150 mm; Mobile phase: H₂O (0.1% NH₄HCO₃)/MeCN: MeCN form 20% to 70%, 20 ml/min, T=15 min, rt=7.2 min) to give the title compound E103 (20 mg, 11.5% yield, 100% ee) as a light yellow solid.

LCMS: 416 [M+H]⁺. t$_R$=3.29 mins. (LCMS condition 3)

Chiral HPLC: t$_R$=7.61 mins. (Chiral condition: OD-H 5 um; 4.6*250 nm, Hex:EtOH:DEA=70:30:0.2, Flow: 1.0 ml/min, 230 nm, T=30° C.) The absolute stereochemistry was not determined.

¹H NMR (300 MHz, DMSO-d₆): δ 11.20 (s, 1H), 8.03 (s, 1H), 7.59 (s, 1H), 6.85 (m, 1H), 6.20 (m 1H), 4.89-4.77 (m, 1H), 4.57-4.36 (m, 7H), 3.57-3.52 (m, 1H), 2.99-2.89 (m, 2H), 2.67-2.58 (m, 2H), 2.21 (s, 3H), 2.35-2.07 (m, 2H), 1.82-1.78 (m, 1H), 1.35 (t, J=6.6 Hz, 3H).

¹⁹F NMR (376 MHz, DMSO-d₆): δ −198.

Example 104

N-(5-chloro-1-((3S, 4S)-3-fluoro-1-(oxetan-3-yl)piperidin-4-yl)-1H-pyrazol-4-yl)-4-ethoxy-7H-pyrrolo[2,3-d]pyrimidin-2-amine (E104)

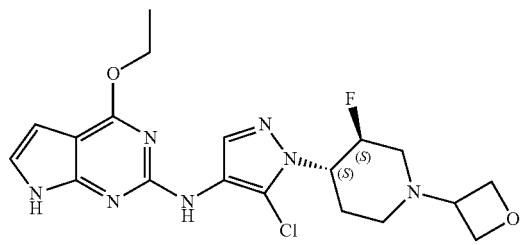

A mixture of D1 (181 g, 0.92 mmol), D213 (210 g, 0.76 mmol), X-phos (71 mg, 0.15 mmol), Pd₂(dba)₃ (70 g, 0.07 mmol) and K₂CO₃ (314 g, 2.28 mmol) in dioxane (20 mL) was stirred at 110° C. under N₂ for 8 hrs. The mixture was cooled to room temperature and filtered. The filter was concentrated and the crude was purified by flash chromatography on C18 (20-50% acetonitrile in water) to give crude product (100 mg, 30% yield) as a light yellow solid, which was further purified by prep-HPLC [Welch XB C18 5 um 21.2*150 mm, 10-70% acetonitrile in H₂O, UV: 214 nm, Flow rate: 20 mL/min, $t_R$=10.8 min] to give the title compound E104 (60 mg, 99.7% ee) as a white solid.

LCMS: 436 [M+H]⁺. $t_R$=3.85 mins. (LCMS condition 3)

Chiral HPLC: $t_R$=8.92 mins. (ID, CO₂:MEOH=70:30, Flow: CO₂ Flow rate: 2.1, Co-solvent: 0.899, back pressure: 100, T=39.9° C.) The absolute stereochemistry was not determined.

¹H NMR (400 MHz, DMSO-d₆): δ 11.31 (s, 1H), 8.20 (s, 1H), 7.90 (s, 1H), 6.90 (d, J=2.8 Hz, 1H), 6.23 (d, J=2.8 Hz, 1H), 5.00-4.86 (m, 1H), 4.58-4.54 (m, 2H), 4.51-4.39 (m, 5H), 3.60-3.57 (m, 1H), 3.21-3.18 (m, 1H), 2.79-2.77 (m, 1H), 2.16-2.07 (m, 3H), 1.96-1.94 (m, 1H), 1.35 (t, J=6.8 Hz, 3H).

¹⁹F NMR (376 MHz, DMSO-d₆): δ −186.6.

E104 [α]_D=−6.63° (Concentration=1.660 g/100 mL, CHCl₃, T: 20.2° C.)

Example 105

N-(5-chloro-1-((3R,4R)-3-fluoro-1-(oxetan-3-yl)piperidin-4-yl)-1H-pyrazol-4-yl)-4-ethoxy-7H-pyrrolo[2,3-d]pyrimidin-2-amine (E105)

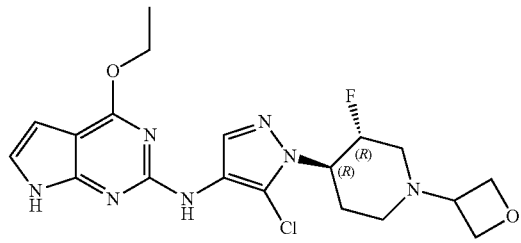

A mixture of D1 (258 g, 1.31 mmol), D218 (300 g, 1.09 mmol), X-phos (99 mg, 0.21 mmol), Pd₂(dba)₃ (90 g, 0.10 mmol) and K₂CO₃ (451 g, 3.27 mmol) in dioxane (30 mL) was stirred overnight at 110° C. under N₂. The mixture was cooled to room temperature and filtered. The filter was concentrated and the crude was purified by flash chromatography on C18 (20-50% acetonitrile in water) to give crude product (200 mg, 50% yield) as a light yellow solid, which was further purified by prep-HPLC [Welch XB C18 5 um 21.2*150 mm, 10-70% Acetonitrile in H₂O, UV: 214 nm, Flow rate: 20 mL/min, $t_R$=11.0 min] to give the title compound E105 as a white solid (100 mg, 99.5% ee).

LCMS: 436 [M+H]⁺. $t_R$=3.85 mins. (LCMS condition 3)

Chiral HPLC: $t_R$=6.87 mins. (ID, CO₂:MEOH=70:30, Flow: CO₂ Flow rate: 2.1, Co-solvent: 0.899, back pressure: 100, T=39.9° C.) The absolute stereochemistry was not determined.

¹H NMR (400 MHz, DMSO-d₆): δ 11.31 (s, 1H), 8.21 (s, 1H), 7.90 (s, 1H), 6.90 (d, J=2.8 Hz, 1H), 6.23 (d, J=2.8 Hz, 1H), 5.00-4.86 (m, 1H), 4.58-4.55 (m, 2H), 4.51-4.41 (m, 5H), 3.61-3.57 (m, 1H), 3.23-3.17 (m, 1H), 2.79-2.77 (m, 1H), 2.16-2.09 (m, 3H), 1.97-1.94 (m, 1H), 1.34 (t, J=6.8 Hz, 3H).

¹⁹F NMR (376 MHz, DMSO-d₆): δ −186.6;

[α]_D=+6.020 (Concentration=1.629 g/100 mL, CHCl₃, T: 20.3° C.)

Example 106 and 107

Enantiomer 1: cis-N-(5-chloro-1-(3-fluoro-1-(oxetan-3-yl)piperidin-4-yl)-1H-pyrazol-4-yl)-4-ethoxy-7H-pyrrolo[2,3-d]pyrimidin-2-amine (E106)

Enantiomer 2: cis-N-(5-chloro-1-(3-fluoro-1-(oxetan-3-yl)piperidin-4-yl)-1H-pyrazol-4-yl)-4-ethoxy-7H-pyrrolo[2,3-d]pyrimidin-2-amine (E107)

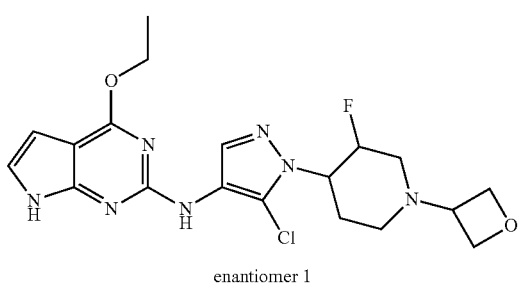

enantiomer 1

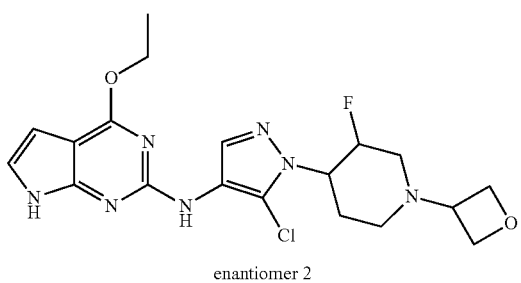

enantiomer 2

A mixture of D1 (345 g, 1.75 mmol), D221 (400 g, 1.46 mmol), X-phos (139 mg, 0.29 mmol), Pd₂(dba)₃ (132 g, 0.14 mmol) and K₂CO₃ (604 g, 4.38 mmol) in dioxane (30 mL) was stirred overnight at 105° C. under N₂. The mixture was cooled to room temperature and filtered. The filter was concentrated and the crude was purified by flash chromatography on C18 (20-50% acetonitrile in water) to give title product (150 mg, 24% yield) as a light yellow solid, which was further separated by SFC to give the title compounds E106 (40 mg, $t_R$=5.5 min, 100% ee) and E107 (40 mg, $t_R$=6.5 min, 99% ee)

E106: LCMS: 436 [M+H]⁺. $t_R$=3.61 mins. (LCMS condition 3)

Chiral HPLC: $t_R$=5.5 mins. (Chiralpak OD-H 5 um 250 mm*4.6 mm, CO₂: MeOH (0.2% DEA)=70:30, Flow: CO₂ Flow rate: 2.1, Co-solvent: 0.899, back pressure: 100, T=39.9° C. Time=10 min.) The absolute stereochemistry was not determined.

¹H NMR (400 MHz, DMSO-d₆): δ 11.30 (s, 1H), 8.20 (s, 1H), 7.82 (s, 1H), 6.90 (t, J=2.8 Hz, 1H), 6.23 (dd, J=3.2, 1.6 Hz, 1H), 4.95-4.83 (m, 1H), 4.61-4.40 (m, 7H), 3.58-3.52 (m, 1H), 3.04-2.90 (m, 2H), 2.67-2.57 (m, 1H), 2.38-2.18 (m, 2H), 1.90-1.87 (m, 1H), 1.35 (t, J=7.2 Hz, 3H).

¹⁹F NMR (376 MHz, DMSO-d₆): δ −198.6.

E107: LCMS: 436 [M+H]⁺. $t_R$=3.615 mins. (LCMS condition 3)

Chiral HPLC: $t_R$=6.5 mins. (Chiralpak OD-H 5 um 250 mm*4.6 mm, CO₂:MeOH (0.2% DEA)=70:30, Flow: CO₂

Flow rate: 2.1, Co-solvent: 0.899, back pressure: 100, T=39.9° C. Time=10 min.) The absolute stereochemistry was not determined.

$^1$H NMR (400 MHz, DMSO-d$_6$): δ 11.30 (s, 1H), 8.20 (s, 1H), 7.82 (s, 1H), 6.90 (t, J=2.8 Hz, 1H), 6.23 (dd, J=3.2, 1.6 Hz, 1H), 4.95-4.83 (m, 1H), 4.61-4.40 (m, 7H), 3.58-3.52 (m, 1H), 3.04-2.90 (m, 2H), 2.67-2.58 (m, 1H), 2.38-2.16 (m, 2H), 1.90-1.87 (m, 1H), 1.35 (t, J=7.2 Hz, 3H).

$^{19}$F NMR (376 MHz, DMSO-d$_6$): δ −198.6.

Example 108 and 109

Enantiomer 1: (trans)-4-ethoxy-N-(5-methyl-1-(3-morpholinocyclopentyl)-1H-pyrazol-4-yl)-7H-pyrrolo[2,3-d]pyrimidin-2-amine (E108)

Enantiomer 2: (trans)-4-ethoxy-N-(5-methyl-1-(3-morpholinocyclopentyl)-1H-pyrazol-4-yl)-7H-pyrrolo[2,3-d]pyrimidin-2-amine (E109)

E108

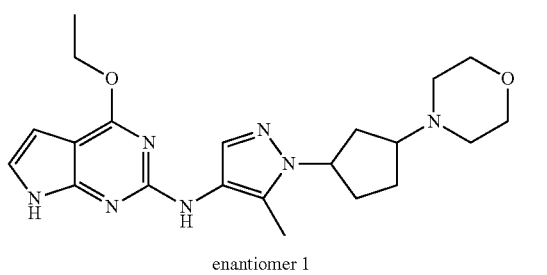

enantiomer 1

E109

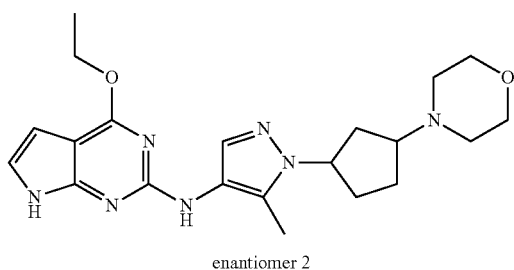

enantiomer 2

A solution of D224 (279 g, 1.12 mmol), D1 (242 g, 1.23 mmol), X-phos (107 mg, 0.224 mmol), Pd$_2$(dba)$_3$ (101 g, 0.113 mmol) and K$_2$CO$_3$ (464 g, 3.36 mmol) in 1,4-dioxane (10 mL) was stirred overnight at 105° C. under N$_2$ atmosphere. The mixture was filtered and diluted with DCM (50 mL), washed with water (50 mL), brine (50 mL), dried over Na$_2$SO$_4$, filtered and concentrated. The residue was purified by column chromatography on silica gel (PE:EA=1:1) to give racemate (243 mg) as brown oil, which was separated by Chiral-HPLC and C18 column (MeCN/H$_2$O=30:70) to give the title compounds E108 (t$_R$=5.753 min, 30 mg, 95.9% ee) and E109 (t$_R$=7.195 min, 26 mg, 99.7% ee).

E108: LCMS: 412 [M+H]$^+$. t$_R$=2.970 mins. (LCMS condition 3)

Chiral HPLC: t$_R$=5.573 mins. (IC 5 um 4.6×250 mm; Injection: 8 ul; Mobile Phase: Hex: EtOH:DEA=50:50:0.2, Flow: 1.0 ml/min, 254 nm, T=30° C.) The absolute stereochemistry was not determined.

$^1$H NMR (300 MHz, DMSO-d$_6$): δ 11.15 (s, 1H), 7.96 (s, 1H), 7.55 (s, 1H), 6.84-6.82 (m, 1H), 6.18-6.17 (m, 1H), 4.70 (br s, 1H), 4.41 (q, J=7.2 Hz, 2H), 3.58-3.56 (m, 4H), 2.85-2.79 (m, 1H), 2.38 (br s, 4H), 2.15-1.92 (m, 8H), 1.47-1.40 (m, 1H), 1.33 (t, J=6.9 Hz, 3H).

E109: LCMS: 412 [M+H]$^+$. t$_R$=3.510 mins. (LCMS condition 3) Chiral HPLC: t$_R$=7.195 mins. (IC 5 um 4.6×250 mm; Injection: 8 ul; Mobile Phase: Hex: EtOH:DEA=50:50:0.2, Flow: 1.0 ml/min, 254 nm, T=30° C.) The absolute stereochemistry was not determined.

$^1$H NMR (300 MHz, DMSO-d$_6$): δ 11.15 (s, 1H), 7.96 (s, 1H), 7.55 (s, 1H), 6.84-6.82 (m, 1H), 6.18-6.17 (m, 1H), 4.70 (br s, 1H), 4.41 (q, J=7.2 Hz, 2H), 3.58-3.56 (m, 4H), 2.85-2.79 (m, 1H), 2.38 (br s, 4H), 2.15-1.92 (m, 8H), 1.47-1.40 (m, 1H), 1.33 (t, J=6.9 Hz, 3H).

Example 110

Enantiomer 1: (trans)-N-(5-chloro-1-(3-morpholinocyclopentyl)-1H-pyrazol-4-yl)-4-ethoxy-7H-pyrrolo[2,3-d]pyrimidin-2-amine (E110)

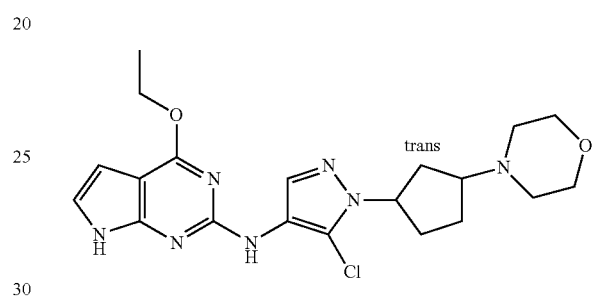

To a solution of D230 (181 g, 0.67 mmol), D1 (198 g, 1.01 mmol), X-phos (64 mg, 0.134 mmol) and K$_2$CO$_3$ (290 g, 2.11 mmol) in dioxane (30 mL) was added Pd$_2$(dba)$_3$ (62 g, 0.067 mmol) under N$_2$. The reaction was stirred overnight at 100° C. The mixture filtered and the filtrate was concentrated. The crude was purified by prep-TLC (eluent: EtOAc) and prep-HPLC to give the title compound E110 (23 mg, 10% yield, 97.5% ee) as a white solid.

LCMS: 432 [M+H]$^+$. t$_R$=3.936 mins. (LCMS condition 3)

Chiral HPLC: t$_R$=11.753 mins. (IF 5 um, 4.6*250 mm, phase: Hex:EtOH=60:40, F: 1.0 ml/min, W: 230 nm, T=30° C.) The absolute stereochemistry was not determined.

$^1$H NMR (300 MHz, CHLOROFORM-d): δ 8.59 (s, 1H), 8.14 (s, 1H), 6.78 (dd, J=3.3, 2.1 Hz, 1H), 6.42 (dd, J=3.3, 2.1 Hz, 1H), 6.27 (s, 1H), 4.94-4.85 (m, 1H), 4.53 (q, J=6.9 Hz, 2H), 3.74 (t, J=4.8 Hz, 1H), 3.03-2.92 (m, 1H), 2.59-2.46 (m, 4H), 2.31-2.14 (m, 4H), 2.06-1.96 (m, 1H), 1.60-1.53 (m, 1H), 1.45 (t, J=6.9 Hz, 3H).

Example 111

Enantiomer 2: (trans)-N-(5-chloro-1-(3-morpholinocyclopentyl)-1H-pyrazol-4-yl)-4-ethoxy-7H-pyrrolo[2,3-d]pyrimidin-2-amine (E111)

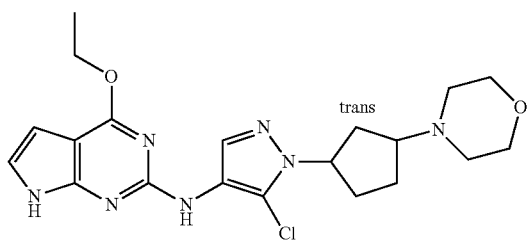 [SMILES: CCOc1nc(Nc2cnn(C3CCC(N4CCOCC4)C3)c2Cl)nc2[nH]ccc12]

To a solution of D231 (162 g, 0.60 mmol), D1 (178 g, 0.90 mmol), X-phos (58 mg, 0.12 mmol) and $K_2CO_3$ (250 g, 1.80 mmol) in dioxane (30 mL) was added $Pd_2(dba)_3$ (55 g, 0.060 mmol) under $N_2$. The reaction was stirred overnight at 100° C. The mixture filtered and the filtrate was concentrated. The crude was purified by prep-TLC (EtOAc) and prep-HPLC to give the title compound E111 (62 mg, 20% yield, 100% ee) as a white solid.

LCMS: 432 [M+H]$^+$. $t_R$=3.401 mins. (LCMS condition 3)

Chiral HPLC: $t_R$=8.594 mins. (IF 5 um, 4.6*250 mm, phase: Hex:EtOH=60:40, F: 1.0 ml/min, W: 230 nm, T=30° C.) The absolute stereochemistry was not determined.

$^1$H NMR (300 MHz, CHLOROFORM-d): δ 8.85 (s, 1H), 8.12 (s, 1H), 6.75 (dd, J=3.3, 2.1 Hz, 1H), 6.40 (dd, J=3.3, 2.1 Hz, 1H), 6.27 (s, 1H), 4.93-4.84 (m, 1H), 4.53 (q, J=7.2 Hz, 2H), 3.73 (t, J=4.5 Hz, 1H), 3.01-2.91 (m, 1H), 2.58-2.45 (m, 4H), 2.29-2.11 (m, 4H), 2.06-1.95 (m, 1H), 1.62-1.51 (m, 1H), 1.45 (t, J=7.2 Hz, 3H).

Example 112

(cis)-N-(5-chloro-1-(3-morpholinocyclopentyl)-1H-pyrazol-4-yl)-4-ethoxy-7H-pyrrolo[2,3-d]pyrimidin-2-amine (E112)

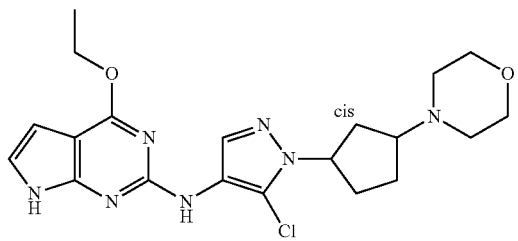 [SMILES: CCOc1nc(Nc2cnn(C3CCC(N4CCOCC4)C3)c2Cl)nc2[nH]ccc12]

To a solution of D234 (20 g, 0.074 mmol), D1 (16 g, 0.081 mmol), X-phos (5.3 mg, 0.011 mmol) and $K_2CO_3$ (82 g, 0.59 mmol) in dioxane (5 mL) was added $Pd_2(dba)_3$ (7 mg, 0.007 mmol) at room temperature under $N_2$ atmosphere. The reaction was stirred overnight at 120° C. The mixture was cooled to room temperature and filtered. The filtrate was concentrated and the residue was purified by column C18 (ACN/$H_2O$=40-60%) to give the title compound E112 (1.7 mg, 5%) as a white solid.

LCMS: 432 [M+H]$^+$. $t_R$=3.37 mins. (LCMS condition 3)

$^1$H NMR (300 MHz, CHLOROFORM-d): δ 8.46 (s, 1H), 8.13 (s, 1H), 6.80 (dd, J=3.6, 1.8 Hz, 1H), 6.42 (dd, J=3.6, 1.8 Hz, 1H), 6.29 (s, 1H), 4.80-4.70 (m, 1H), 4.53 (q, J=7.2 Hz, 2H), 3.73 (t, J=4.8 Hz, 4H), 2.78-2.66 (m, 1H), 2.59-2.46 (m, 4H), 2.39-2.30 (m, 1H), 2.25-2.06 (m, 3H), 1.97-1.85 (m, 2H), 1.47 (t, J=7.2 Hz, 3H).

Example 113

Enantiomer 1: (cis)-4-ethoxy-N-(5-methyl-1-(3-methyltetrahydro-2H-pyran-4-yl)-1H-pyrazol-4-yl)-7H-pyrrolo[2,3-d]pyrimidin-2-amine (E113)

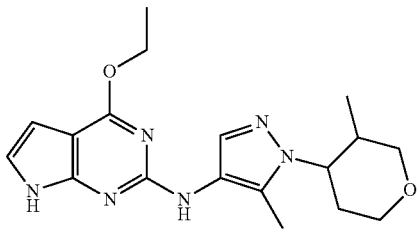 [SMILES: CCOc1nc(Nc2cnn(C3CCOCC3C)c2C)nc2[nH]ccc12]

A solution of D242 (70 g, 0.36 mmol), D1 (109 g, 0.43 mmol), X-phos (34 mg, 0.072 mmol), $Pd_2(dba)_3$ (32 g, 0.036 mmol) and $K_2CO_3$ (148 g, 1.08 mmol) in dioxane (6 mL) was stirred overnight at 110° C. under $N_2$. The mixture was filtered and the filtrate was concentrated. The crude was purified by pre-TLC (DCM:MeOH=10:1) to give the title compound E113 (22.0 mg, yield 17%, 100% ee).

LCMS: 357 [M+H]$^+$. $t_R$=3.801 mins. (LCMS condition 3)

Chiral HPLC: $t_R$=4.54 mins. (column: ID; co-solvent: MeOH (0.2 DEA); CO2 flow rate: 2.1; co-solvent flow rate: 0.899; T=40° C.) The absolute stereochemistry was not determined.

$^1$H NMR (300 MHz, CHLOROFORM-d): δ 7.63 (s, 1H), 6.80 (d, J=3.6 Hz, 1H), 6.28 (d, J=3.6 Hz, 1H), 4.62-4.55 (m, 1H), 4.45 (q, J=7.2 Hz, 2H), 4.20-4.13 (m, 1H), 3.83-3.74 (m, 2H), 3.73-3.60 (m, 1H), 2.69-2.57 (m, 1H), 2.26 (s, 3H), 2.16-2.08 (m, 1H), 1.82-1.73 (m, 1H), 1.39 (t, J=6.9 Hz, 3H), 0.86 (d, J=7.2 Hz, 3H).

Example 114

Enantiomer 2: (cis)-4-ethoxy-N-(5-methyl-1-(3-methyltetrahydro-2H-pyran-4-yl)-1H-pyrazol-4-yl)-7H-pyrrolo[2,3-d]pyrimidin-2-amine (E114)

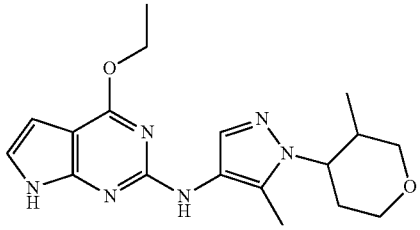 [SMILES: CCOc1nc(Nc2cnn(C3CCOCC3C)c2C)nc2[nH]ccc12]

A solution of D243 (66 g, 0.36 mmol), D1 (109 g, 0.43 mmol), X-phos (34 mg, 0.072 mmol), $Pd_2(dba)_3$ (32 g, 0.036 mmol) and $K_2CO_3$ (148 g, 1.08 mmol) in dioxane (6 mL) was stirred overnight at 110° C. under $N_2$. The mixture was filtered and the filtrate was concentrated. The crude was purified by pre-TLC (DCM:MeOH=10:1) to give the title compound E114 (55.8 mg, yield 44%, 100% ee).

LCMS: 357 [M+H]$^+$. $t_R$=3.802 mins. (LCMS condition 3)

Chiral HPLC: $t_R$=3.76 mins. (column: ID; co-solvent: MeOH (0.2 DEA); CO2 flow rate: 2.1; co-solvent flow rate: 0.899; T=40° C.) The absolute stereochemistry was not determined.

¹H NMR (300 MHz, CD₃OD): δ 7.63 (s, 1H), 6.80 (d, J=3.6 Hz, 1H), 6.28 (d, J=3.6 Hz, 1H), 4.61-4.56 (m, 1H), 4.45 (q, J=7.2 Hz, 2H), 4.20-4.12 (m, 1H), 3.80-3.73 (m, 2H), 3.73-3.60 (m, 1H), 2.69-2.57 (m, 1H), 2.26 (s, 3H), 2.16-2.10 (m, 1H), 1.82-1.75 (m, 1H), 1.39 (t, J=6.9 Hz, 3H), 0.85 (d, J=7.2 Hz, 3H).

Example 115

Enantiomer 1: (trans)-4-ethoxy-N-(5-methyl-1-(3-methyltetrahydro-2H-pyran-4-yl)-1H-pyrazol-4-yl)-7H-pyrrolo[2,3-d]pyrimidin-2-amine (E115)

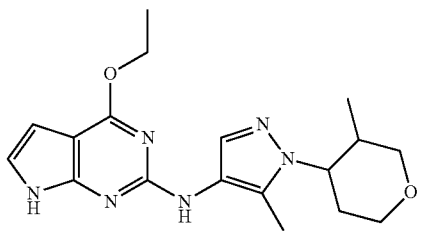 [SMILES: CCOc1nc(Nc2cnn(C3CCOCC3C)c2C)nc2[nH]ccc12]

A solution of D244 (35 g, 0.18 mmol), D1 (55 g, 0.22 mmol), X-phos (17 mg, 0.036 mmol), Pd₂(dba)₃ (16 g, 0.018 mmol) and K₂CO₃ (74 g, 0.54 mmol) in dioxane (6 mL) was stirred overnight at 110° C. under N₂. The mixture was filtered and the filtrate was concentrated. The crude was purified by pre-TLC (DCM/MeOH=10:1) to give the title compound E115 (22.6 mg, yield 35%, 100% ee).

LCMS: 357 [M+H]⁺. $t_R$=3.791 mins. (LCMS condition 3)
Chiral HPLC: $t_R$=6.87 mins. (column: IE; co-solvent: MeOH (0.2 DEA); CO₂ flow rate: 2.1; co-solvent flow rate: 0.899; T=40° C.) The absolute stereochemistry was not determined.

¹H NMR (300 MHz, CD₃OD): δ 7.68 (s, 1H), 6.80 (d, J=3.6 Hz, 1H), 6.28 (d, J=3.6 Hz, 1H), 4.45 (q, J=7.2 Hz, 2H), 4.10-3.92 (m, 3H), 3.64-3.55 (m, 1H), 3.22 (t, J=11.1 Hz, 1H), 2.41-2.33 (m, 1H), 2.25 (s, 3H), 2.21-2.15 (m, 1H), 1.87-1.78 (m, 1H), 1.39 (t, J=7.2 Hz, 3H), 0.66 (d, J=6.6 Hz, 3H).

Example 116

Enantiomer 2: (trans)-4-ethoxy-N-(5-methyl-1-(3-methyltetrahydro-2H-pyran-4-yl)-1H-pyrazol-4-yl)-7H-pyrrolo[2,3-d]pyrimidin-2-amine (E116)

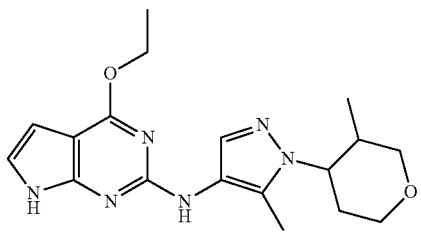 [SMILES: CCOc1nc(Nc2cnn(C3CCOCC3C)c2C)nc2[nH]ccc12]

A solution of D245 (35 g, 0.18 mmol), D1 (55 g, 0.22 mmol), X-phos (17 mg, 0.036 mmol), Pd₂(dba)₃ (16 g, 0.018 mmol), K₂CO₃ (74 g, 0.54 mmol) in dioxane (6 mL) was stirred overnight at 110° C. under N₂. The mixture was filtered and the filtrate was concentrated. The crude was purified by pre-TLC (DCM:MeOH=10:1) to give the title compound E116 (15.0 mg, yield 24%, 97.3% ee).

LCMS: 357 [M+H]⁺. $t_R$=3.791 mins. (LCMS condition 3)
Chiral HPLC: $t_R$=6.12 mins. (column: IE; co-solvent: MeOH (0.2 DEA); CO₂ flow rate: 2.1; co-solvent flow rate: 0.899; T=40° C.) The absolute stereochemistry was not determined.

¹H NMR (300 MHz, CD₃OD): δ 7.68 (s, 1H), 6.80 (d, J=3.6 Hz, 1H), 6.28 (d, J=3.6 Hz, 1H), 4.45 (q, J=6.9 Hz, 2H), 4.10-4.06 (m, 1H), 4.06-3.98 (m, 2H), 3.64-3.55 (m, 1H), 3.22 (t, J=11.1 Hz, 1H), 2.41-2.35 (m, 1H), 2.32 (s, 3H), 2.23-2.16 (m, 1H), 1.88-1.80 (m, 1H), 1.39 (t, J=6.9 Hz, 3H), 0.66 (d, J=6.9 Hz, 3H).

Example 117 and 118

Enantiomer 1: N-(1-(4,4-difluoropiperidin-3-yl)-5-methyl-1H-pyrazol-4-yl)-4-ethoxy-7H-pyrrolo[2,3-d]pyrimidin-2-amine (E117)

Enantiomer 2: N-(1-(4,4-difluoropiperidin-3-yl)-5-methyl-1H-pyrazol-4-yl)-4-ethoxy-7H-pyrrolo[2,3-d]pyrimidin-2-amine (E118)

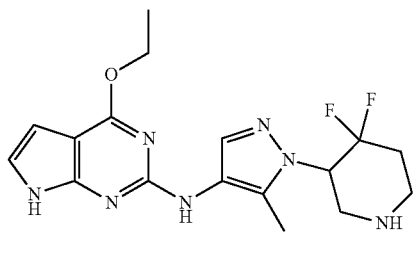

enantiomer 1

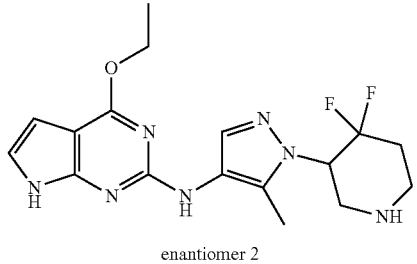

enantiomer 2

To a solution of D253 (760 g, 1.592 mmol) in isopropanol (10 mL) was added HCl (7.64 mL, 38.2 mmol). The reaction was stirred at room temperature for 16 hours. Solvent was evaporated to give the racemate (601 g, 1.592 mmol, 100% yield), 200 mg of which was separated by SFC and purified by prep-TLC (CH₂Cl₂:methanol=10:1) to give the title compounds E117 (30 mg, yield 15%, 100% ee) and E118 (45 mg, yield 23%, 99.1% ee) as white solids.

E117: LCMS: 378 [M+H]⁺. $t_R$=3.568 mins. (LCMS condition 3) Chiral HPLC: $t_R$=2.1 mins. (IC column, CO₂: MeOH:DEA=60:40:0.2, Flow: 1.799 ml/min, 230 nm) The absolute stereochemistry was not determined.

¹H NMR (300 MHz, CD₃OD): δ 7.71 (s, 1H), 6.80 (d, J=3.9 Hz, 1H), 6.28 (d, J=3.9 Hz, 1H), 4.57-4.42 (m, 3H), 3.58-3.50 (m, 1H), 3.27-3.22 (m, 1H), 3.07-3.02 (m, 2H), 2.34-2.18 (m, 4H), 2.09-1.96 (m, 1H), 1.39 (t, J=7.2 Hz, 3H).

E118: LCMS: 378 [M+H]$^+$. $t_R$=3.025 mins. (LCMS condition 3)

Chiral HPLC: $t_R$=3.66 mins. (IC column, CO$_2$:MeOH:DEA=60:40:0.2, Flow: 1.799 ml/min, 230 nm) The absolute stereochemistry was not determined.

$^1$H NMR (300 MHz, CD$_3$OD): δ 7.73 (s, 1H), 6.80 (d, J=3.6 Hz, 1H), 6.28 (d, J=3.6 Hz, 1H), 4.59-4.42 (m, 3H), 3.58-3.51 (m, 1H), 3.31-3.23 (m, 1H), 3.07-3.03 (m, 2H), 2.33-2.20 (m, 4H), 2.09-2.10 (m, 1H), 2.10-1.92 (m, 1H), 1.39 (t, J=7.2 Hz, 3H);

Example 119 and 120

Enantiomer 1: N-(1-(4,4-difluoro-1-(oxetan-3-yl)piperidin-3-yl)-5-methyl-1H-pyrazol-4-yl)-4-ethoxy-7H-pyrrolo[2,3-d]pyrimidin-2-amine (E119)

Enantiomer 2: N-(1-(4,4-difluoro-1-(oxetan-3-yl)piperidin-3-yl)-5-methyl-1H-pyrazol-4-yl)-4-ethoxy-7H-pyrrolo[2,3-d]pyrimidin-2-amine (E120)

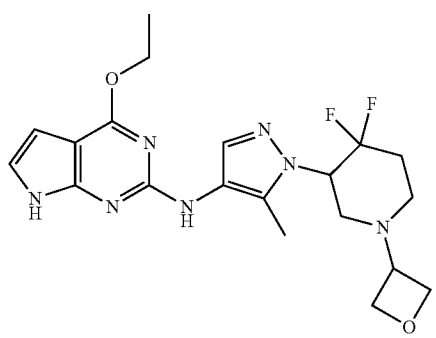

enantiomer 1

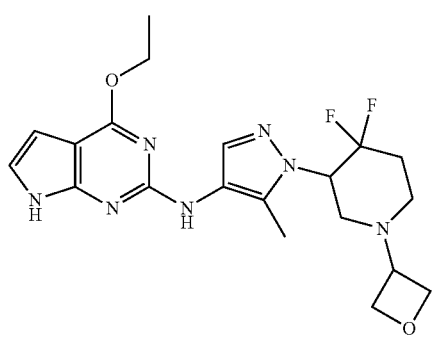

enantiomer 2

To a solution of N-(1-(4,4-difluoropiperidin-3-yl)-5-methyl-1H-pyrazol-4-yl)-4-ethoxy-7H-pyrrolo[2,3-d]pyrimidin-2-amine (200 g, 0.530 mmol) in DMF (10 mL) was added oxetan-3-one (764 g, 10.60 mmol) portionwise, followed by sodium triacetoxyborohydride (337 g, 1.590 mmol). The reaction was stirred at room temperature for 16 hours. Solvent was evaporated and the crude was purified by C18 reverse column to give the racemic (200 g, 0.461 mmol, 87% yield), which was further purified by chiral HPLC to give the title compounds E119 (9.2 mg, yield 7.7%, 96.5% ee) and E120 (8.1 mg, yield 6.8%, 70.9% ee) as white solids.

E119: LCMS: 433 [M+H]$^+$. $t_R$=3.714 mins. (LCMS condition 3)

Chiral HPLC: $t_R$=6.097 mins. (OD-H 5 um 4.6*250 nm, Hex:EtOH=70:30, Flow: 1.0 ml/min, 230 nm, T=30° C.) The absolute stereochemistry was not determined.

$^1$H NMR (300 MHz, CD$_3$OD): δ 7.72 (s, 1H), 6.79 (s, 1H), 6.28 (s, 1H), 4.77-4.70 (m, 3H), 4.66-4.58 (m, 2H), 4.46 (q, J=7.2 Hz, 2H), 3.76-3.67 (m, 1H), 3.03-2.93 (m, 2H), 2.91-2.86 (m, 1H), 2.31-2.15 (m, 6H), 1.39 (t, J=7.2 Hz, 3H).

E120: LCMS: 433 [M+H]$^+$. $t_R$=3.714 mins. (LCMS condition 3)

Chiral HPLC: $t_R$=7.588 mins. (OD-H 5 um 4.6*250 nm, Hex:EtOH=70:30, Flow: 1.0 ml/min, 230 nm, T=30° C.) The absolute stereochemistry was not determined.

$^1$H NMR (300 MHz, CD$_3$OD): δ 7.72 (s, 1H), 6.79 (s, 1H), 6.28 (s, 1H), 4.75-4.68 (m, 3H), 4.63-4.58 (m, 2H), 4.46 (q, J=7.2 Hz, 2H), 3.73-3.69 (m, 1H), 3.00-2.93 (m, 2H), 2.90-2.85 (m, 1H), 2.27-2.16 (m, 6H), 1.39 (t, J=7.2 Hz, 3H).

Example 121 and 122

Enantiomer 1: N-(1-(4,4-difluoro-1-methylpiperidin-3-yl)-5-methyl-1H-pyrazol-4-yl)-4-ethoxy-7H-pyrrolo[2,3-d]pyrimidin-2-amine (E121)

Enantiomer 2: N-(1-(4,4-difluoro-1-methylpiperidin-3-yl)-5-methyl-1H-pyrazol-4-yl)-4-ethoxy-7H-pyrrolo[2,3-d]pyrimidin-2-amine (E122)

enantiomer 1 enantiomer 2

To a solution of N-(1-(4,4-difluoropiperidin-3-yl)-5-methyl-1H-pyrazol-4-yl)-4-ethoxy-7H-pyrrolo[2,3-d]pyrimidin-2-amine (122 g, 0.323 mmol), formaldehyde (0.241 mL, 3.23 mmol) in DMF (5 mL) was added sodium triacetoxyborohydride (206 g, 0.970 mmol) at −10° C. and the reaction was stirred for 5 hours. The mixture was poured into sat. aq. NaHCO$_3$ and extracted with ethyl acetate. The organic layer was washed with brine, dried over Na$_2$SO$_4$, filtered, and concentrated. The crude was purified by C18 column, SFC and prep-TLC (CH₂Cl₂:methanol=12:1) to give the title compounds E121 (15 mg, yield 17%, 100% ee) and E122 (14 mg, yield 16%, 98.5% ee) as white solids.

E121: LCMS: 391 [M+H]⁺. $t_R$=3.236 mins. (LCMS condition 3)

Chiral HPLC: $t_R$=2.96 mins. (Chiral condition: IC column, CO₂:MeOH:DEA=75:25:0.2, Flow: 2.25 ml/min, 230 nm) The absolute stereochemistry was not determined.

¹H NMR (300 MHz, CHLOROFORM-d): δ 9.93 (s, 1H), 7.75 (s, 1H), 6.47 (d, J=5.1 Hz, 1H), 6.30 (d, J=5.1 Hz, 1H), 6.17 (s, 1H), 4.51-4.32 (m, 3H), 3.20-3.12 (m, 1H), 2.93-2.83 (m, 2H), 2.46-2.42 (m, 1H), 2.38 (s, 3H), 2.25-2.15 (m, 4H), 2.13-2.10 (m, 1H), 1.41 (t, J=7.2 Hz, 3H);

¹⁹F NMR (282 MHz, CDCl₃): δ −102.79, −103.62, −116.14, −116.98.

E122: LCMS: 391 [M+H]⁺. $t_R$=3.235 mins. (LCMS condition 3)

Chiral HPLC: $t_R$=4.08 mins. (Chiral condition: IC column, CO₂:MeOH:DEA=75:25:0.2, Flow: 2.25 ml/min, 230 nm) The absolute stereochemistry was not determined.

¹H NMR (300 MHz, CHLOROFORM-d): δ 10.44 (s, 1H), 7.73 (s, 1H), 6.38-6.36 (m, 1H), 6.28-6.26 (m, 1H), 6.23 (s, 1H), 4.51-4.30 (m, 3H), 3.13 (t, J=11.4 Hz, 1H), 2.88-2.84 (m, 2H), 2.46-2.41 (m, 1H), 2.37 (m, 3H), 2.27-2.04 (m, 5H), 1.40 (t, J=7.2 Hz, 3H);

¹⁹F NMR (282 MHz, CDCl₃): δ −102.83, −103.72, −116.09, −116.94.

Example 123

Enantiomer 1: N-(5-chloro-1-(4,4-difluoro-1-(oxetan-3-yl)piperidin-3-yl)-1H-pyrazol-4-yl)-4-ethoxy-7H-pyrrolo[2,3-d]pyrimidin-2-amine (E123)

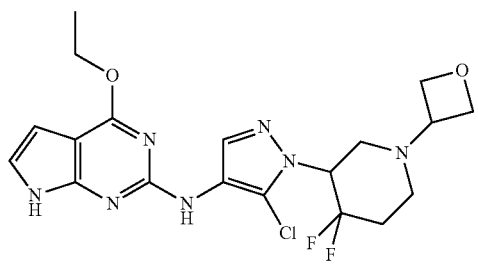 [SMILES: CCOc1nc(Nc2cnn(C3CN(C4COC4)CCC3(F)F)c2Cl)nc2[nH]ccc12]

To a solution of D257 (280 g, 0.96 mmol), D1 (208 g, 1.05 mmol), X-phos (69 mg, 0.14 mmol) and K₂CO₃ (795 g, 5.76 mmol) in dioxane (20 mL) was added Pd₂(dba)₃ (88 g, 0.096 mmol) at room temperature under N₂ atmosphere. The reaction was stirred overnight at 115° C. and then cooled to room temperature. The mixture was filtered and the filtrate was concentrated. The crude was purified by column C18 (ACN/H₂O=40-60%) and further purified by prep-HPLC (Sunfire 19×150 mm; 25-65% B; A: H₂O (0.1% NH₄HCO₃) B: ACN; V=20 mL/min; $t_R$=12.6 min) to give the title compound E123 (55 mg, 13%, 100% ee) as a white solid.

LCMS: 455 [M+H]⁺. $t_R$=2.06 mins. (LCMS condition 3)

Chiral HPLC: $t_R$=9.737 mins. (Chiralpak OD-H 5 um, 4.6*250 mm, phase: Hex:EtOH=70:30, F: 1.0 ml/min, W: 230 nm, T: 30) The absolute stereochemistry was not determined.

¹H NMR (400 MHz, CHLOROFORM-d): δ 8.63 (s, 1H), 8.27 (s, 1H), 6.79 (s, 1H), 6.43 (s, 1H), 6.32 (s, 1H), 4.52-4.79 (m, 7H), 3.68-3.72 (m, 1H), 3.04-3.10 (m, 1H), 2.95 (m, 1H), 2.81-2.84 (m, 1H), 2.13-2.35 (m, 3H), 1.45 (t, J=7.2 Hz, 3H).

Example 124

Enantiomer 2: N-(5-chloro-1-(4,4-difluoro-1-(oxetan-3-yl)piperidin-3-yl)-1H-pyrazol-4-yl)-4-ethoxy-7H-pyrrolo[2,3-d]pyrimidin-2-amine (E124)

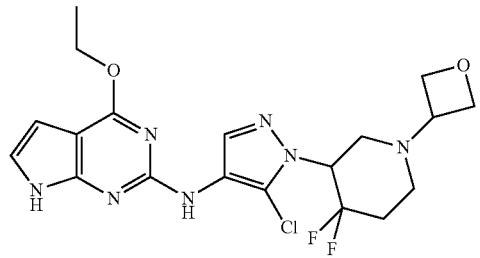 [SMILES: CCOc1nc(Nc2cnn(C3CN(C4COC4)CCC3(F)F)c2Cl)nc2[nH]ccc12]

To a solution of D258 (280 g, 0.96 mmol), D1 (208 g, 1.05 mmol), X-phos (69 mg, 0.14 mmol) and K₂CO₃ (795 g, 5.76 mmol) in dioxane (20 mL) was added Pd₂(dba)₃ (88 g, 0.096 mmol) at room temperature under N₂ atmosphere. The reaction was stirred overnight at 115° C. and then cooled to room temperature. The mixture was concentrated and the crude was purified by column C18 (ACN/H₂O=40-60%) and further purified by prep-HPLC (Sunfire 19×150 mm; 25-65% B; A: H₂O (0.1% NH₄HCO₃) B: ACN; V=20 mL/min; $t_R$=12.6 min) to give the title compound E124 (42 mg, 10%, 100% ee) as a yellow solid.

LCMS: 455 [M+H]⁺. $t_R$=2.06 mins. (LCMS condition 3)

Chiral HPLC: $t_R$=7.823 mins. (Chiralpak OD-H 5 um, 4.6*250 mm, phase: Hex:EtOH=70:30, F: 1.0 ml/min, W: 230 nm, T: 30) The absolute stereochemistry was not determined.

¹H NMR (400 MHz, CHLOROFORM-d): δ 8.65 (s, 1H), 8.26 (s, 1H), 6.78 (s, 1H), 6.41 (s, 1H), 6.32 (s, 1H), 4.52-4.71 (m, 7H), 3.68-3.72 (m, 1H), 3.04-3.10 (m, 1H), 2.95 (m, 1H), 2.81-2.84 (m, 1H), 2.13-2.35 (m, 3H), 1.45 (t, J=7.2 Hz, 3H).

Example 125

Enantiomer 1: N-(5-chloro-1-(4,4-difluoropiperidin-3-yl)-1H-pyrazol-4-yl)-4-ethoxy-7H-pyrrolo[2,3-d]pyrimidin-2-amine (E125)

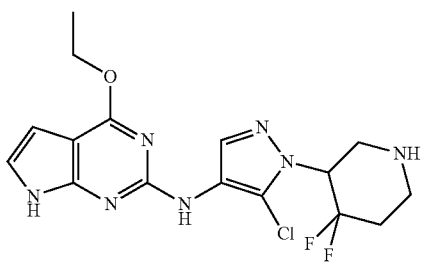 [SMILES: CCOc1nc(Nc2cnn(C3CNCCC3(F)F)c2Cl)nc2[nH]ccc12]

To a solution of D261 (40 g, 0.080 mmol) in MeOH (3 mL) was added HCl/dioxane (2 mL, 4 M). The mixture stirred at room temperature for 2 hrs. The mixture was concentrated and the residue was poured into 5 mL of saturated NaHCO$_3$ aqueous. The aqueous layer was extracted with EtOAc (10 mL×2). The extracts were concentrated and the crude was purified by column C18 (ACN/H$_2$O=30-50%) to give the title compound E125 (9 mg, yield 28%, 100% ee) as a white solid.

LCMS: 398 [M+H]$^+$. $t_R$=3.31 mins. (LCMS condition 3)

Chiral HPLC: $t_R$=7.523 mins. (Chiralpak OD-H 5 um 4.6*250 mm, Phase: Hex:EtOH=70:30; F: 1.0 mL/min; W: 230 nm; T: 30) The absolute stereochemistry was not determined.

$^1$H NMR (400 MHz, CHLOROFORM-d): δ 8.39 (s, 1H), 8.24 (s, 1H), 6.82 (dd, J=4.0, 2.0 Hz, 1H), 6.44 (dd, J=4.0, 2.0 Hz, 1H), 6.31 (s, 1H), 4.56-4.48 (m, 3H), 3.58-3.53 (m, 1H), 3.30 (dd, J=14.0, 4.0 Hz, 1H), 3.23-3.19 (m, 1H), 3.03-2.99 (m, 1H), 2.37-2.22 (m, 1H), 2.04-1.95 (m, 1H), 1.46 (t, J=7.2 Hz, 3H).

Example 126

Enantiomer 2: N-(5-chloro-1-(4,4-difluoropiperidin-3-yl)-1H-pyrazol-4-yl)-4-ethoxy-7H-pyrrolo [2,3-d]pyrimidin-2-amine (E126)

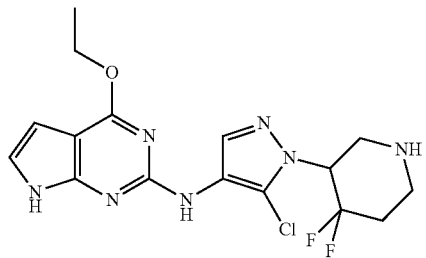

To a solution of D262 (55 g, 0.110 mmol) in MeOH (5 mL) was added HCl/dioxane (4 mL, 4M). The reaction was stirred at room temperature for 2 hrs. The mixture was concentrated and the residue was poured into 50 mL of saturated NaHCO$_3$ aqueous. The aqueous layer was extracted with EtOAc (50 mL×2). The extracts were concentrated and the crude was purified by column C18 (ACN/H$_2$O=35-50%) to give the title compound E126 (17 mg, 39% yield, 100% ee) as a white solid.

LCMS: 398 [M+H]$^+$. $t_R$=2.99 mins. (LCMS condition 3)

Chiral HPLC: $t_R$=5.391 mins. (Chiralpak OD-H 5 um 4.6*250 mm, Phase: Hex:EtOH=70:30; F: 1.0 mL/min; W: 230 nm; T: 30) The absolute stereochemistry was not determined.

$^1$H NMR (400 MHz, CHLOROFORM-d): δ 8.77 (s, 1H), 8.22 (s, 1H), 6.78 (dd, J=3.2, 2.0 Hz, 1H), 6.42 (dd, J=3.2, 2.0 Hz, 1H), 6.35 (s, 1H), 4.56-4.48 (m, 3H), 3.56-3.53 (m, 1H), 3.30 (dd, J=14.0, 4.0 Hz, 1H), 3.23-3.19 (m, 1H), 3.04-2.97 (m, 1H), 2.37-2.22 (m, 1H), 2.03-1.95 (m, 1H), 1.46 (t, J=7.2 Hz, 3H).

Example 127 and 128

Enantiomer 1: (cis)-4-ethoxy-N-(1-(3-fluorotetrahydro-2H-pyran-4-yl)-5-methyl-1H-pyrazol-4-yl)-7H-pyrrolo[2,3-d]pyrimidin-2-amine (E127)

Enantiomer 2: (cis)-4-ethoxy-N-(1-(3-fluorotetrahydro-2H-pyran-4-yl)-5-methyl-1H-pyrazol-4-yl)-7H-pyrrolo[2,3-d]pyrimidin-2-amine (E128)

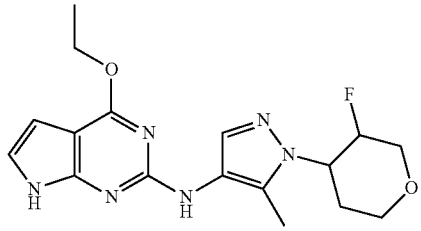

enantiomer 1

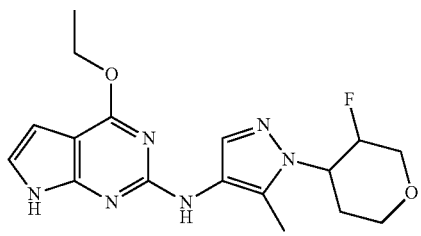

enantiomer 2

To a solution of D268 (250 g, 1.26 mmol) in dioxane (30 mL) was added D1 (311 mg, 1.58 mmol), Pd$_2$(dba)$_3$ (115 g, 0.126 mmol), X-phos (120 g, 0.252 mmol) and K$_2$CO$_3$ (520 g, 3.78 mmol) at room temperature under N$_2$ atmosphere. The mixture was stirred overnight at 100° C. The mixture was filtered and the filtrate was concentrated. The crude was purified by column (PE:EA=1:1 to 0:1) to give the racemate as a yellow solid (200 mg, yield 44%), which was further separated by SFC to give the title compound E127 (11.1 mg, $t_R$=4.72 min) and E128 (13.0 mg, $t_R$=5.92 min).

E127: LCMS: 361 [M+H]$^+$. $t_R$=3.506 mins. (LCMS condition 3)

Chiral HPLC: $t_R$=4.72 mins. (Chiral condition: Chiralpak IE, 80-20-CO$_2$-MeOH, Flow: 2.4, T=39.9° C.) The absolute stereochemistry was not determined.

$^1$H NMR (400 MHz, DMSO-d$_6$): δ 11.18 (s, 1H), 8.02 (s, 1H), 7.60 (s, 1H), 6.85 (s, 1H), 6.21 (s, 1H), 4.83-4.58 (m, 2H), 4.44 (q, J=7.2 Hz, 2H), 4.05-3.96 (m, 2H), 3.74-3.56 (m, 2H), 2.76-2.67 (m, 1H), 2.24 (s, 3H), 1.77-1.73 (m, 1H), 1.36 (t, J=7.2 Hz, 3H).

$^{19}$F NMR (DMSO-d$_6$, 376 MHz): δ −203.4.

E128: LCMS: 361 [M+H]$^+$. $t_R$=3.522 mins. (LCMS condition 3)

Chiral HPLC: $t_R$=5.92 mins. (Chiral condition: Chiralpak IE, 80-20-CO$_2$-MeOH, Flow: 2.4, T=39.9° C.) The absolute stereochemistry was not determined.

$^1$H NMR (400 MHz, DMSO-d$_6$): δ 11.19 (s, 1H), 8.02 (s, 1H), 7.60 (s, 1H), 6.85 (s, 1H), 6.21 (s, 1H), 4.83-4.58 (m, 2H), 4.44 (q, J=7.2 Hz, 2H), 4.05-3.96 (m, 2H), 3.74-3.56 (m, 2H), 2.76-2.67 (m, 1H), 2.24 (s, 3H), 1.76-1.74 (m, 1H), 1.36 (t, J=7.2 Hz, 3H).

$^{19}$F NMR (DMSO-d$_6$, 376 MHz): δ −203.4.

Example 129 and 130

Enantiomer 1: (trans)-4-ethoxy-N-(5-ethyl-1-(3-fluoro-1-(oxetan-3-yl)piperidin-4-yl)-1H-pyrazol-4-yl)-7H-pyrrolo[2,3-d]pyrimidin-2-amine (E129)

Enantiomer 2: (trans)-4-ethoxy-N-(5-ethyl-1-(3-fluoro-1-(oxetan-3-yl)piperidin-4-yl)-1H-pyrazol-4-yl)-7H-pyrrolo[2,3-d]pyrimidin-2-amine (E130)

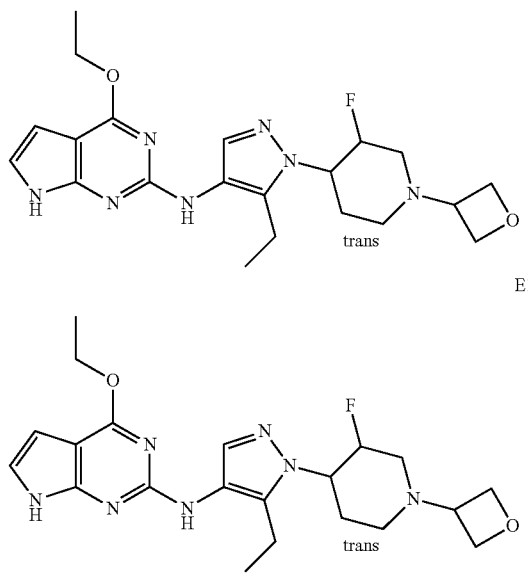

To a solution of D272 (125 g, 0.47 mmol), D1 (101 g, 0.51 mmol), K$_2$CO$_3$ (259 mg, 1.88 mmol) and X-phos (41 g, 0.071 mmol) in dioxane (15 mL) was added Pd$_2$(dba)$_3$ (42 g, 0.047 mmol) at room temperature under N$_2$ atmosphere. The reaction was stirred at 120° C. for 16 hrs. The mixture was filtered and the filtrate was concentrated. The residue was purified by column chromatography (DCM:MeOH=50:1) to afford the desired racemate (80 mg, 75%), which was separated by chiral HPLC (OJ-H 5 um 4.6*250 mm phase: Hex/EtOH=70/30, F: 1 ml/min w: 230 nm T: 30) and column on C18 (MeCN/H$_2$O=35-55%) to give the title compounds E129 (14 mg, t$_R$=8.735 min, 100% ee) and E130 (10 mg, t$_R$=11.262 min, 97.5% ee) as white solids.

E129: LCMS: 430 [M+H]$^+$. t$_R$=3.298 mins. (LCMS condition 3)

Chiral HPLC: t$_R$=8.735 mins. (Chiralcel OJ-H 5 um 4.6*250 mm phase: Hex/EtOH=70/30, F: 1 ml/min w: 230 nm T: 30) The absolute stereochemistry was not determined.

$^1$H NMR (400 MHz, CD$_3$OD): δ 7.74 (s, 1H), 6.80 (d, J=3.6 Hz, 1H), 6.28 (d, J=3.6 Hz, 1H), 5.09-4.90 (m, 1H), 4.71 (t, J=6.4 Hz, 2H), 4.63 (q, J=6.4 Hz, 2H), 4.47 (q, J=7.2 Hz, 2H), 4.30-4.20 (m, 1H), 3.72-3.65 (m, 1H), 3.25-3.23 (m, 1H), 2.89-2.86 (m, 1H), 2.73 (q, J=7.6 Hz, 2H), 2.38-2.28 (m, 1H), 2.18-2.10 (m, 2H), 2.03-1.97 (m, 1H), 1.40 (t, J=7.2 Hz, 3H), 1.17 (t, J=7.6 Hz, 3H).

$^{19}$F NMR (CD$_3$OD, 376 MHz): δ −189.1.

E130: LCMS: 430 [M+H]$^+$. t$_R$=3.298 mins. (LCMS condition 3)

Chiral HPLC: t$_R$=11.262 mins. (Chiralcel OJ-H 5 um 4.6*250 mm phase: Hex/EtOH=70/30, F: 1 ml/min w: 230 nm T: 30) The absolute stereochemistry was not determined.

$^1$H NMR (400 MHz, CD$_3$OD): δ 7.74 (s, 1H), 6.80 (d, J=3.6 Hz, 1H), 6.28 (d, J=3.6 Hz, 1H), 5.08-4.90 (m, 1H), 4.71 (t, J=6.4 Hz, 2H), 4.63 (q, J=6.4 Hz, 2H), 4.47 (q, J=7.2 Hz, 2H), 4.30-4.20 (m, 1H), 3.72-3.65 (m, 1H), 3.25-3.23 (m, 1H), 2.89-2.86 (m, 1H), 2.73 (q, J=7.6 Hz, 2H), 2.38-2.28 (m, 1H), 2.18-2.10 (m, 2H), 2.03-1.96 (m, 1H), 1.40 (t, J=7.2 Hz, 3H), 1.17 (t, J=7.6 Hz, 3H).

$^{19}$F NMR (CD$_3$OD, 376 MHz): δ −189.1.

Example 131

Enantiomer 1: N-(1-(3,3-difluoro-1-(oxetan-3-yl)piperidin-4-yl)-5-methyl-1H-pyrazol-4-yl)-4-ethoxy-7H-pyrrolo[2,3-d]pyrimidin-2-amine (E131)

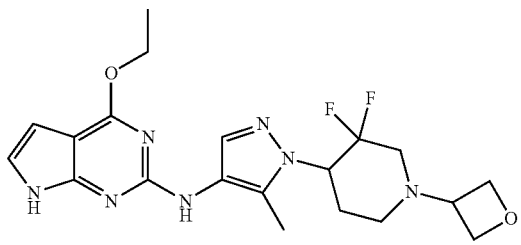 [SMILES: CCOc1nc(Nc2cnn(C3CCN(C4COC4)CC3(F)F)c2C)nc2[nH]ccc12]

To a mixture of D280 (70 g, 0.26 mmol), D1 (76 g, 0.39 mmol) and K$_2$CO$_3$ (108 g, 0.780 mmol) in dioxane (5 mL) was added X-phos (45 g, 0.090 mmol), followed by Pd$_2$(dba)$_3$ (42 g, 0.050 mmol) under N$_2$ atmosphere. The reaction was stirred overnight at reflux and then concentrated. The residue was diluted in DCM and filtered. The filtrate was concentrated and the crude was purified by prep-HPLC and prep-TLC (EA:MeOH=20:1) to give the title compound E131 as a white solid (20 mg, 17% yield, 99.5% ee).

LCMS: 434 [M+H]$^+$. t$_R$=3.60 mins. (LCMS condition 3)

Chiral HPLC: t$_R$=7.39 mins. (Chiralpak ID 5 um 4.6*250 mm, Co-solvent: MeOH F: 2.1 mL/min; rate: 0.899) The absolute stereochemistry was not determined.

$^1$H NMR (300 MHz, CD$_3$OD): δ 7.73 (s, 1H), 6.81 (d, J=3.3 Hz, 1H), 2.28 (d, J=3.3 Hz, 1H), 4.60-4.71 (m, 5H), 4.46 (q, J=6.9 Hz, 2H), 3.72-3.76 (m, 1H), 3.00-3.17 (m, 2H), 2.67-2.80 (m, 1H), 2.42-2.56 (m, 1H), 2.26-2.36 (m, 4H), 2.03-2.07 (m, 1H), 1.39 (t, J=6.9 Hz, 3H).

$^{19}$F NMR (376 MHz, CD$_3$OD): δ −107.3 (d, J=242 Hz, 1F), −116.1 (d, J=242, 1F).

Example 132

Enantiomer 2: N-(1-(3,3-difluoro-1-(oxetan-3-yl)piperidin-4-yl)-5-methyl-1H-pyrazol-4-yl)-4-ethoxy-7H-pyrrolo[2,3-d]pyrimidin-2-amine (E132)

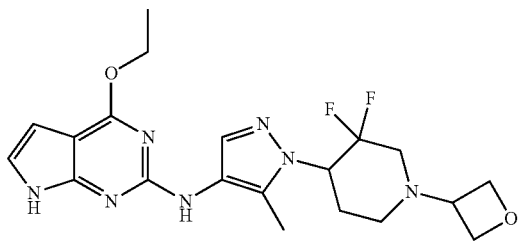 [SMILES: CCOc1nc(Nc2cnn(C3CCN(C4COC4)CC3(F)F)c2C)nc2[nH]ccc12]

A solution of D281 (80 g, 0.29 mmol), D1 (90 g, 0.45 mmol), X-phos (50 g, 0.10 mmol), Pd$_2$(dba)$_3$ (42 g, 0.050 mmol) and K$_2$CO$_3$ (120 g, 0.870 mmol) in 1,4-dioxane (5 mL) was stirred overnight at reflux under nitrogen. The mixture was evaporated and the residue was suspended in DCM and filtered. Solvent was evaporated and the crude was purified by prep-HPLC and further purified by prep-TLC (EA:MeOH=20:1) to give the title compound E132 (20 mg, 15% yield) as a white solid.

LCMS: 434 [M+H]$^+$. t$_R$=3.60 mins. (LCMS condition 3)

Chiral HPLC: t$_R$=6.10 mins. (Condition: Column ID (4.6*250 mm, 5 um); (Co-Solvent MeOH) The absolute stereochemistry was not determined.

$^1$H NMR (300 MHz, METHANOL-d$_4$): δ 7.73 (s, 1H), 6.81 (d, J=3.6 Hz, 1H), 6.28 (d, J=3.6 Hz, 1H), 4.60-4.71 (m, 5H), 4.46 (q, J=7.2 Hz, 2H), 3.70-3.79 (m, 1H), 3.01-3.16 (m, 2H), 2.69-2.81 (m, 1H), 2.42-2.60 (m, 1H), 2.26-2.35 (m, 4H), 2.03-2.09 (m, 1H), 1.39 (t, J=7.2 Hz, 3H).

$^{19}$F NMR (376 MHz, CD$_3$OD): δ −107.3 (d, J=242 Hz, 1F), −116.1 (d, J=242, 1F).

Example 133

Enantiomer 1: N-(5-chloro-1-(3,3-difluoro-1-(oxetan-3-yl)piperidin-4-yl)-1H-pyrazol-4-yl)-4-ethoxy-7H-pyrrolo[2,3-d]pyrimidin-2-amine (E133)

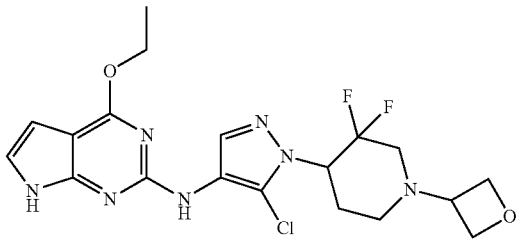

To a solution of D285 (100 g, 0.342 mmol) in dioxane (15 mL) was added D1 (101 g, 0.514 mmol), Pd$_2$(dba)$_3$ (63 g, 0.068 mmol), X-phos (57 g, 0.12 mmol) and K$_2$CO$_3$ (142 g, 1.03 mmol) at room temperature under N$_2$ atmosphere. The reaction was stirred overnight at 100° C. The mixture was filtered and the filtrate was concentrated. The crude product was purified by pre-TLC (EA:PE=3:1) and prep-HPLC to give the title compound E133 (11 mg, yield 7.1%, 100% ee) as a white solid.

LCMS: 454 [M+H]$^+$. t$_R$=3.353 mins. (LCMS condition 3)

Chiral HPLC: t$_R$=6.08 mins. (Condition: Column ID (4.6*250 mm, 5 um); Co-Solvent MeOH; Flow rate: 0.899; Temp.: 40.2) The absolute stereochemistry was not determined.

$^1$H NMR (300 MHz, CHLOROFORM-d): δ 8.59 (s, 1H), 8.27 (s, 1H), 6.81 (s, 1H), 6.42 (s, 1H), 6.33 (s, 1H), 4.69-4.59 (m, 4H), 4.57-4.50 (m, 3H), 3.82-3.73 (m, 1H), 3.16-3.01 (m, 2H), 2.81-2.67 (m, 1H), 2.57-2.45 (m, 1H), 2.39-2.31 (m, 1H), 2.19-2.08 (m, 1H), 1.46 (t, J=6.9 Hz, 3H).

$^{19}$F NMR (376 MHz, CD$_3$OD): δ −107.2 (d, J=241.0 Hz, 1F), −115.8 (d, J=241.0, 1F).

Example 134

Enantiomer 2: N-(5-chloro-1-(3,3-difluoro-1-(oxetan-3-yl)piperidin-4-yl)-1H-pyrazol-4-yl)-4-ethoxy-7H-pyrrolo[2,3-d]pyrimidin-2-amine (E134)

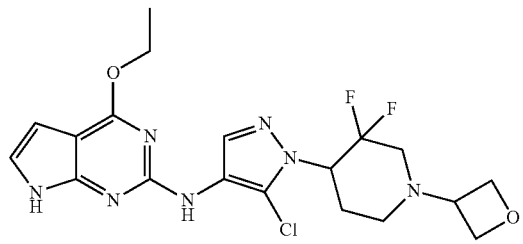 [SMILES: CCOc1nc(Nc2cnn(C3CCN(C4COC4)CC3(F)F)c2Cl)nc2[nH]ccc12]

To a solution of D286 (100 g, 0.514 mmol) and D1 (101 g, 0.514 mmol) in dioxane (15 mL) was added K$_2$CO$_3$ (142 g, 1.03 mmol), followed by Pd$_2$(dba)$_3$ (63 g, 0.068 mmol) and X-phos (57 g, 0.12 mmol) at room temperature under N$_2$. The reaction was heated to reflux and stirred overnight. The mixture was diluted with CH$_2$Cl$_2$ (100 mL) and filtered. The filtrate was concentrated and the crude was purified by pre-TLC (EA:PE=3:1) and prep-HPLC to give the title compound E134 (10 mg, yield 7.0%, 99.7% ee) as a white solid.

LCMS: 454 [M+H]$^+$. t$_R$=3.353 mins. (LCMS condition 3)

Chiral HPLC: t$_R$=7.12 mins. (Condition: Column ID (4.6*250 mm, 5 um); Co-Solvent MeOH; Flow rate: 0.899; Temp.: 40.2) The absolute stereochemistry was not determined.

$^1$H NMR (300 MHz, CHLOROFORM-d): δ 8.53 (s, 1H), 8.27 (s, 1H), 6.81 (s, 1H), 6.42 (s, 1H), 6.32 (s, 1H), 4.72-4.62 (m, 4H), 4.56-4.50 (m, 3H), 3.80-3.75 (m, 1H), 3.16-3.01 (m, 2H), 2.81-2.68 (m, 1H), 2.57-2.45 (m, 1H), 2.38-2.31 (m, 1H), 2.19-2.07 (m, 1H), 1.46 (t, J=6.9 Hz, 3H).

$^{19}$F NMR (376 MHz, CD$_3$OD): δ −107.2 (d, J=241.0 Hz, 1F), −115.8 (d, J=241.0, 1F).

[α]$_D$=+42.760 (Concentration=0.29 g/100 mL, CHCl$_3$, T: 21.4° C.)

Example 135

(R)-4-ethoxy-N-(5-methyl-1-(1-(oxetan-3-yl)piperidin-3-yl)-1H-pyrazol-4-yl)-7H-pyrrolo[2,3-d]pyrimidin-2-amine (E135)

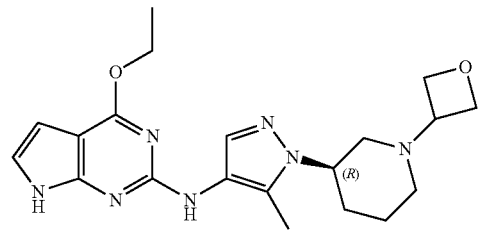

A solution of D1 (376 g, 1.91 mmol), D292 (300 g, 1.27 mmol), X-phos (121 mg, 0.254 mmol), K$_2$CO$_3$ (525 g, 3.81 mmol) and Pd$_2$(dba)$_3$ (116 g, 0.127 mmol) in 1,4-dioxane (40 mL) was stirred overnight at 110° C. under nitrogen. The mixture was filtered and the filtrate was concentrated. The crude was purified by prep-HPLC to give the title compound E135 (40 mg, 8% yield) as a white solid LCMS: 398 [M+H]$^+$. $t_R$=3.50 mins. (LCMS condition 3)

$^1$H NMR (300 MHz, METHANOL-d$_4$): δ 7.63 (s, 1H), 6.76 (d, J=3.6 Hz, 1H), 6.28 (d, J=3.6 Hz, 1H), 4.73-4.61 (m, 4H), 4.48 (q, J=7.2 Hz, 2H), 4.36-4.26 (m, 1H), 3.61-3.53 (m, 1H), 2.89-2.80 (m, 2H), 2.30-2.23 (m, 1H), 2.26 (s, 3H), 2.05-1.74 (m, 4H), 1.41 (t, J=7.2 Hz, 3H).

Example 136

(S)-4-ethoxy-N-(5-methyl-1-(1-(oxetan-3-yl)piperidin-3-yl)-1H-pyrazol-4-yl)-7H-pyrrolo[2,3-d]pyrimidin-2-amine (E136)

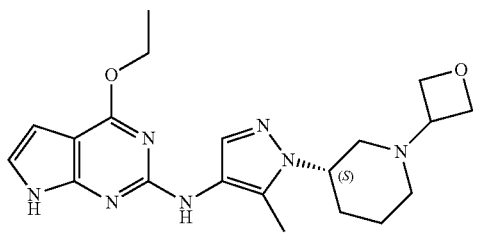

A solution of D1 (360 g, 1.82 mmol), D298 (280 g, 1.19 mmol), X-phos (140 mg, 0.294 mmol), K$_2$CO$_3$ (500 g, 3.62 mmol) and Pd$_2$(dba)$_3$ (121 g, 0.132 mmol) in 1,4-dioxane (40 mL) was stirred overnight at 100° C. under nitrogen. The mixture was filtered and the filtrate was concentrated. The crude was purified by prep-HPLC to give the title compound E136 (67.1 mg, 14% yield) as a white solid.

LCMS: 398 [M+H]$^+$. $t_R$=3.50 mins. (LCMS condition 3)

$^1$H NMR (300 MHz, METHANOL-d$_4$): δ 7.63 (s, 1H), 6.76 (d, J=3.6 Hz, 1H), 6.27 (d, J=3.6 Hz, 1H), 4.73-4.56 (m, 4H), 4.48 (q, J=7.2 Hz, 2H), 4.34-4.27 (m, 1H), 3.61-3.53 (m, 1H), 2.89-2.81 (m, 2H), 2.30-2.23 (m, 1H), 2.25 (s, 3H), 2.03-1.77 (m, 4H), 1.40 (t, J=7.2 Hz, 3H).

Example 137

4-ethoxy-N-(5-methyl-1-(1-methyl-3-morpholinocyclobutyl)-1H-pyrazol-4-yl)-7H-pyrrolo[2, 3-d]pyrimidin-2-amine (E137)

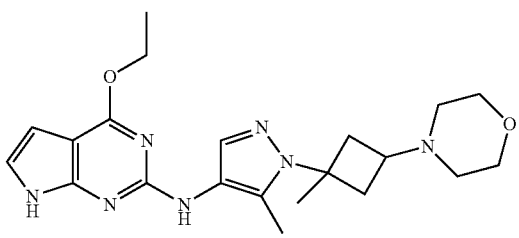 [SMILES: CCOc1nc(Nc2cnn(C3(C)CC(N4CCOCC4)C3)c2C)nc2[nH]ccc12]

To a solution of D304 (440 g, 1.285 mmol), DIPEA (0.673 mL, 3.86 mmol) in DCM (15 mL) was added Ms-Cl (0.120 mL, 1.542 mmol) at 0° C. The resulting mixture was stirred at 0° C. for 30 min. Water was added and the organic phase was dried and concentrated. The residue was dissolved in DMF (10 mL), potassium carbonate (887 g, 6.42 mmol) and morpholine (2.238 mL, 25.7 mmol) was added. The mixture was irradiated under microwave at 150° C. for 1 hour. After filtration, the filtrate was purified by MDAP to give the title compound E137 (10 g, 0.024 mmol, 1.892% yield) as a white solid.

LCMS: 412 [M+H]$^+$. $t_R$=2.060 mins. (LCMS condition 1)

$^1$H NMR (300 MHz, DMSO-d$_6$): δ 11.18 (brs., 1H), 7.97 (br. s., 1H), 7.53 (s, 1H), 6.86 (br. s., 1H), 6.21 (br. s., 1H), 4.44 (d, J=6.6 Hz, 2H), 3.56 (br. s., 4H), 2.74 (t, J=7.2 Hz, 1H), 2.38-2.48 (m, 4H), 2.27 (br. s., 4H), 2.14 (s, 3H), 1.47 (s, 3H), 1.36 (t, J=6.4 Hz, 3H).

Example 138

Enantiomer 1: (4-ethoxy-7H-pyrrolo[2,3-d]pyrimidin-2-yl)-[1-(3-fluoro-3-methyl-1-oxetan-3-yl-piperidin-4-yl)-5-methyl-1H-pyrazol-4-yl]-amine (E138)

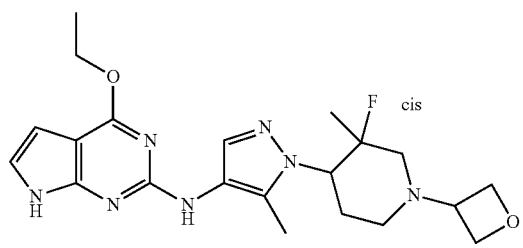 [SMILES: CCOc1nc(Nc2cnn(C3CCN(C4COC4)CC3(C)F)c2C)nc2[nH]ccc12]

To a solution of D313 (230 g, 0.86 mmol), D1 (254 g, 1.29 mmol) and K$_2$CO$_3$ (356 g, 2.58 mmol) in dioxane (30 mL) was added X-phos (82 g, 0.172 mmol), followed by Pd$_2$(dba)$_3$ (79 g, 0.086 mmol) under N$_2$ atmosphere. The reaction was stirred overnight at 100° C. The mixture was filtered and concentrated in vacuo to afford yellow oil, which was purified by prep-HPLC to give the title compound E138 (12.9 mg, yield 5%, 100% ee) as a white solid.

LCMS: 430 [M+H]$^+$. $t_R$=3.361 mins. (LCMS condition 3)

Chiral HPLC: $t_R$=5.756 mins. (Chiralpak OD-H 5 um 4.6*250 mm, Phase: Hex:EtOH=70/30, F: 1.0 mL/min, W: 230 nm, T: 30) The absolute stereochemistry was not determined.

$^1$H NMR (300 MHz, CHLOROFORM-d): δ 9.09 (s, 1H), 7.76 (s, 1H), 6.64 (s, 1H), 6.35 (s, 1H), 6.19 (s, 1H), 4.68-4.57 (m, 4H), 4.47 (q, J=6.9 Hz, 2H), 4.21-4.12 (m, 1H), 3.66-3.57 (m, 1H), 2.93-2.89 (m, 1H), 2.81-2.78 (m, 1H), 2.67-2.55 (m, 1H), 2.24 (s, 3H), 2.20-1.96 (m, 3H), 1.44 (t, J=6.9 Hz, 3H), 1.35 (d, J=23.7 Hz, 3H).

$^{19}$F NMR (376 MHz, CDCl$_3$): δ −142.8.

Example 139

Enantiomer 2: (4-ethoxy-7H-pyrrolo[2,3-d]pyrimidin-2-yl)-[1-(3-fluoro-3-methyl-1-oxetan-3-yl-piperidin-4-yl)-5-methyl-1H-pyrazol-4-yl]-amine (E139)

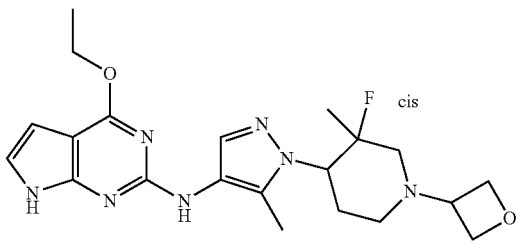 [SMILES: CCOc1nc(Nc2cnn(C3CCN(C4COC4)CC3(C)F)c2C)nc2[nH]ccc12]

To a mixture of D314 (240 g, 0.90 mmol), D1 (266 g, 1.35 mmol) and K$_2$CO$_3$ (372 g, 2.7 mmol) in dioxane (30 mL) was added X-phos (86.0 g, 0.18 mmol), followed by Pd$_2$(dba)$_3$ (83 g, 0.090 mmol) under N$_2$ atmosphere. The reaction was stirred overnight at 100° C. The mixture was filtered and concentrated in vacuo to afford yellow oil, which was purified by column chromatography on silica gel (DCM:MeOH=10:1) and prep-HPLC to give the title compound E139 (21.8 mg, yield 6%, 100% ee) as a white solid.

LCMS: 430 [M+H]$^+$. t$_R$=0.892 mins. (LCMS condition 3)
Chiral HPLC: t$_R$=7.305 mins. (Chiralpak OD-H 5 um 4.6*250 mm, Phase: Hex:EtOH=70/30, F: 1.0 mL/min, W: 230 nm, T: 30) The absolute stereochemistry was not determined.

$^1$H NMR (300 MHz, CHLOROFORM-d): δ 9.08 (s, 1H), 7.76 (s, 1H), 6.62 (s, 1H), 6.35 (s, 1H), 6.11 (s, 1H), 4.70-4.51 (m, 4H), 4.47 (q, J=6.9 Hz, 2H), 4.20-4.11 (m, 1H), 3.65-3.58 (m, 1H), 2.94-2.88 (m, 1H), 2.80-2.75 (m, 1H), 2.66-2.53 (m, 1H), 2.24 (s, 3H), 2.20-1.97 (m, 3H), 1.44 (t, J=6.9 Hz, 3H), 1.35 (d, J=23.1 Hz 3H).

$^{19}$F NMR (376 MHz, CDCl$_3$): δ −142.8 (s, 1F),

Example 140

(±)-N-(5-chloro-1-(4-(oxetan-3-yl)morpholin-2-yl)-1H-pyrazol-4-yl)-4-ethoxy-7H-pyrrolo [2,3-d]pyrimidin-2-amine (E140)

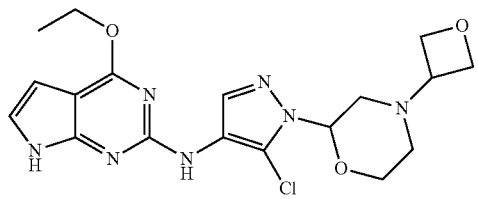 [SMILES: CCOc1nc(Nc2cnn(C3CN(C4COC4)CCO3)c2Cl)nc2[nH]ccc12]

To a solution of D320 (70 g, 0.27 mmol) in dioxane (15 mL) was added D1 (106 mg, 0.54 mmol), Pd$_2$(dba)$_3$ (25 g, 0.027 mmol), X-phos (26 g, 0.054 mmol) and K$_2$CO$_3$ (112 g, 0.81 mmol). The resulting mixture was stirred overnight at 100° C. Another D1 (106 mg, 0.54 mmol), Pd$_2$(dba)$_3$ (25 g, 0.027 mmol), X-phos (26 g, 0.054 mmol) and K$_2$CO$_3$ (112 g, 0.81 mmol) were added the resulting mixture was stirred overnight at 100° C. under N$_2$. The mixture was filtered and the filtrated was concentrated. The crude was purified with prep-TLC (PE:EA=1:10) and then C18 (10-20% CH$_3$CN/H$_2$O) to give the title E140 (18 mg, yield 16%) as colorless oil.

LCMS: 420 [M+H]$^+$. t$_R$=3.17 mins. (LCMS condition 3)
$^1$H NMR (300 MHz, CHLOROFORM-d): δ 8.92 (s, 1H), 8.23 (s, 1H), 6.77 (d, J=5.7 Hz, 1H), 6.41-6.39 (m, 1H), 5.59 (t, J=6.0 Hz, 1H), 4.73-4.61 (m, 4H), 4.51 (q, J=7.2 Hz, 2H), 4.05 (dd, J=11.4, 2.4 Hz, 1H), 3.92 (dt, J=11.4, 2.4 Hz, 1H), 3.65 (t, J=6.3 Hz, 1H), 2.89 (d, J=6.3 Hz, 2H), 2.64 (d, J=11.4 Hz, 1H), 2.26 (dt, J=11.4, 3.6 Hz, 1H), 1.44 (t, J=7.2 Hz, 3H).

Alternatively, E140 could be also prepared following below procedure:

To a solution of D320 (205 g, 0.79 mmol) in dioxane (80 mL) was added D1 (391 mg, 1.99 mmol), Pd$_2$(dba)$_3$ (145 g, 0.16 mmol), X-phos (150 g, 0.32 mmol) and K$_2$CO$_3$ (327 g, 2.37 mmol). The resulting mixture was stirred overnight at 100° C. The mixture was filtered and the filtrated was concentrated. The residue was dissolved in water (20 mL), EA (20 mL) and then separated. The aqueous layer was extracted with EA (20 mL×3). The combined organic layer were washed with brine (20 mL×2), dried over Na$_2$SO$_4$, filtered and concentrated. The crude was purified with C18 (25-50% CH$_3$CN/H$_2$O) and column chromatography on silica gel (PE:EA=5:1 to 1:10) to give the title E140 (149 mg) as colorless oil.

Example 141 and 142

Enantiomer 1: N-(5-chloro-1-(4-(oxetan-3-yl)morpholin-2-yl)-1H-pyrazol-4-yl)-4-ethoxy-7H-pyrrolo[2,3-d]pyrimidin-2-amine (E141)

Enantiomer 2: N-(5-chloro-1-(4-(oxetan-3-yl)morpholin-2-yl)-1H-pyrazol-4-yl)-4-ethoxy-7H-pyrrolo[2,3-d]pyrimidin-2-amine (E142)

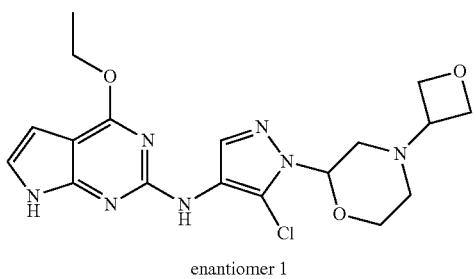

enantiomer 1

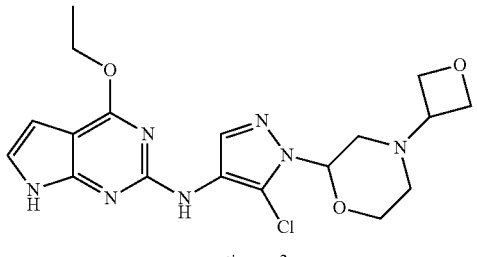

enantiomer 2

The title compounds E141 (39.8 mg, yield 19%, t$_R$=5.885 min, 100% ee) and E142 (31.5 mg, yield 15%, t$_R$=7.295 min, 94.1% ee) were obtained as white solids by separation of E140 (147 mg) using Chiral HPLC (chiralpak IC 5 um 4.6*250 mm, phase: MeOH:EtOH=50:50, F: 1.0 mL/min, W: 230 nm, T=30° C.).

E141: LCMS: 420 [M+H]⁺. $t_R$=3.729 mins. (LCMS condition 3)

Chiral HPLC: $t_R$=5.89 mins. (chiralpak IC 5 um 4.6*250 mm, phase: MeOH:EtOH=50:50, F: 1.0 mL/min, W: 230 nm, T=30° C.) The absolute stereochemistry was not determined.

¹H NMR (300 MHz, CHLOROFORM-d): δ 8.71 (s, 1H), 8.23 (s, 1H), 6.76 (dd, J=3.6, 2.4 Hz, 1H), 6.40 (dd, J=3.6, 2.4 Hz, 1H), 6.34 (s, 1H), 5.59 (t, J=6.0 Hz, 1H), 4.73-4.61 (m, 4H), 4.51 (q, J=7.2 Hz, 2H), 4.05 (dd, J=11.4, 2.4 Hz, 1H), 3.92 (dt, J=11.4, 2.4 Hz, 1H), 3.69-3.61 (m, 1H), 2.90 (d, J=6.6 Hz, 2H), 2.64 (d, J=11.4 Hz, 1H), 2.26 (dt, J=11.4, 3.6 Hz, 1H), 1.45 (t, J=7.2 Hz, 3H).

[α]$_D$=+59.5° (Concentration=0.447 g/100 mL, CHCl₃, T: 18.5° C.).

E142: LCMS: 420 [M+H]⁺. $t_R$=3.712 mins. (LCMS condition 3)

Chiral HPLC: $t_R$=7.29 mins. (chiralpak IC 5 um 4.6*250 mm, phase: MeOH:EtOH=50:50, F: 1.0 mL/min, W: 230 nm, T=30° C.) The absolute stereochemistry was not determined.

¹H NMR (300 MHz, CHLOROFORM-d): δ 9.03 (s, 1H), 8.23 (s, 1H), 6.75 (dd, J=3.6, 2.4 Hz, 1H), 6.40 (dd, J=3.6, 2.4 Hz, 1H), 6.35 (s, 1H), 5.58 (t, J=5.7 Hz, 1H), 4.73-4.61 (m, 4H), 4.51 (q, J=7.2 Hz, 2H), 4.05 (dd, J=11.4, 3.6 Hz, 1H), 3.92 (dt, J=11.4, 2.4 Hz, 1H), 3.69-3.61 (m, 1H), 2.90 (d, J=6.9 Hz, 2H), 2.64 (d, J=11.4 Hz, 1H), 2.26 (dt, J=11.4, 3.6 Hz, 1H), 1.45 (t, J=7.2 Hz, 3H).

Example 143

Enantiomer 1: N-(5-chloro-1-(morpholin-2-yl)-1H-pyrazol-4-yl)-4-ethoxy-7H-pyrrolo[2,3-d]pyrimidin-2-amine (E143)

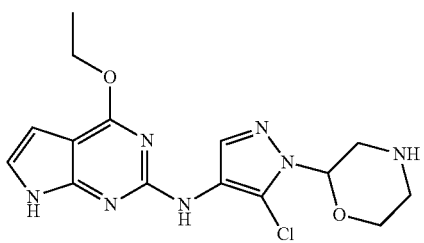 [SMILES: CCOc1nc(Nc2cnn(C3CNCCO3)c2Cl)nc2[nH]ccc12]

To a solution of D365 (90 g, 0.19 mmol) in anhydrous DCM (9 mL) was added ZnBr₂ (224 g, 0.98 mmol). The resulting mixture was stirred at room temperature for 7 hrs. The reaction was quenched with NaHCO₃ (20 mL, sat.). The suspension was stirred at room temperature for 20 min, then extracted with DCM (6×15 mL). The combined organic layers were dried over anhydrous Na₂SO₄, filtered and concentrated. The residue was purified with C18 (20-30% CH₃CN/H₂O) to give the title compound E143 (53 mg, yield 75%, 92.2% ee) as a white solid.

LCMS: 364 [M+H]⁺. $t_R$=3.52 mins. (LCMS condition 3)

Chiral HPLC: $t_R$=6.15 mins. (chiralpak IC 5 um 4.6*250 mm, phase: Hex:EtOH=60:40, F: 1.0 mL/min, W: 230 nm, T=30° C.) The absolute stereochemistry was not determined.

¹H NMR (400 MHz, CHLOROFORM-d): δ 8.67 (s, 1H), 8.25 (s, 1H), 6.80 (dd, J=3.2, 2.0 Hz, 1H), 6.42 (dd, J=3.2, 2.0 Hz, 1H), 6.35 (s, 1H), 5.50 (dd, J=5.6, 3.6 Hz, 1H), 4.53 (q, J=7.2 Hz, 2H), 3.84-3.79 (m, 1H), 3.72-3.60 (m, 2H), 3.27 (dd, J=13.2, 3.6 Hz, 1H), 2.99 (t, J=4.8 Hz, 2H), 1.46 (t, J=7.2 Hz, 3H).

Example 144

Enantiomer 2: N-(5-chloro-1-(morpholin-2-yl)-1H-pyrazol-4-yl)-4-ethoxy-7H-pyrrolo[2,3-d]pyrimidin-2-amine (E144)

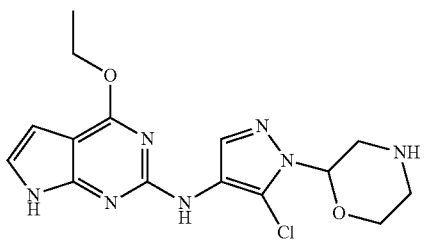 [SMILES: CCOc1nc(Nc2cnn(C3CNCCO3)c2Cl)nc2[nH]ccc12]

To a solution of D366 (180 g, 0.388 mmol) in anhydrous DCM (20 mL) was added ZnBr₂ (530 g, 2.356 mmol). The resulting mixture was stirred at room temperature for 9 hrs. The reaction was quenched with NaHCO₃ (50 mL, sat.) and the mixture was stirred at room temperature for 30 min. The organic layer was separated and the aqueous layer was extracted with DCM (30 mL×3). The combined organic layers were dried over anhydrous Na₂SO₄, filtered and concentrated. The crude was purified with C18 (20-30% CH₃CN/H₂O) to give the title compound E144 (105 mg, yield 74%, 100% ee) as a white solid.

LCMS: 364 [M+H]⁺. $t_R$=3.52 mins. (LCMS condition 3)

Chiral HPLC: $t_R$=11.59 mins. (chiralpak IC 5 um 4.6*250 mm, phase: Hex:EtOH=60:40, F: 1.0 mL/min, W: 230 nm, T=30° C.) The absolute stereochemistry was not determined.

¹H NMR (400 MHz, CHLOROFORM-d): δ 8.78 (s, 1H), 8.25 (s, 1H), 6.79 (d, J=3.2 Hz, 1H), 6.42 (d, J=3.2 Hz, 1H), 6.35 (s, 1H), 5.50 (dd, J=5.6, 3.6 Hz, 1H), 4.53 (q, J=7.2 Hz, 2H), 3.84-3.79 (m, 1H), 3.72-3.60 (m, 2H), 3.27 (dd, J=13.2, 3.6 Hz, 1H), 2.99 (t, J=4.8 Hz, 2H), 1.46 (t, J=7.2 Hz, 3H).

Example 145

(±)-trans-N-(5-chloro-1-(2,2-difluoro-5-morpholino-cyclohexyl)-1H-pyrazol-4-yl)-4-ethoxy-7H-pyrrolo[2,3-d]pyrimidin-2-amine (E145)

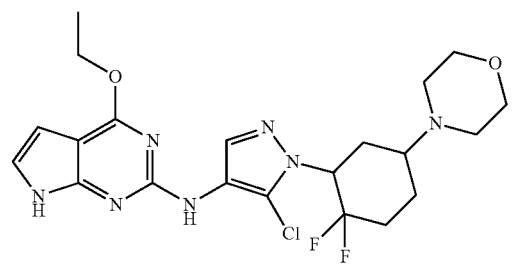 [SMILES: CCOc1nc(Nc2cnn(C3CC(N4CCOCC4)CCC3(F)F)c2Cl)nc2[nH]ccc12]

To a solution of D329 (130 g, 0.405 mmol) in isobutanol (10 mL) was added K₂CO₃ (280 g, 2.026 mmol), Pd₂dba₃ (37.1 g, 0.041 mmol), D1 (96 g, 0.486 mmol) and X-phos (38.6 g, 0.081 mmol). The reaction was irritated under microwave to 110° C. for 1 hr. After filtration, the filtrate was concentrated and purified by MDAP to give the title compound E145 (31 g, 0.052 mmol, 12.84% yield).

LCMS: 482 [M+H]$^+$. $t_R$=2.472 mins. (LCMS condition 1)
$^1$H NMR (400 MHz, DMSO-d$_6$): δ 11.30 (br. s., 1H), 8.22 (s, 1H), 7.90 (s, 1H), 6.92 (dd, J=2.32, 3.30 Hz, 1H), 6.24 (dd, J=1.83, 3.30 Hz, 1H), 4.76-4.96 (m, 1H), 4.44 (q, J=6.85 Hz, 2H), 3.58 (t, J=4.28 Hz, 4H), 2.84 (t, J=11.62 Hz, 1H), 2.52-2.59 (m, 4H), 2.31-2.44 (m, 1H), 1.98-2.24 (m, 3H), 1.89 (d, J=13.45 Hz, 1H), 1.44-1.62 (m, 1H), 1.35 (t, J=6.97 Hz, 3H).

Example 146

(±)-cis-N-(5-chloro-1-(2,2-difluoro-5-morpholinocyclohexyl)-1H-pyrazol-4-yl)-4-ethoxy-7H-pyrrolo[2,3-d]pyrimidin-2-amine (E146)

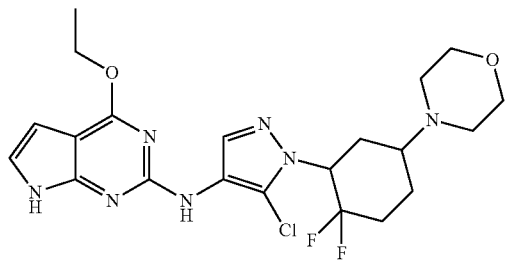 [SMILES: CCOc1nc(Nc2cnn(C3CC(N4CCOCC4)CCC3(F)F)c2Cl)nc2[nH]ccc12]

To a solution of D331 (160 g, 0.499 mmol) in 1,4-dioxane (10 mL) was added K$_2$CO$_3$ (345 g, 2.494 mmol), Pd$_2$dba$_3$ (45.7 g, 0.050 mmol), D1 (99 g, 0.499 mmol), X-phos (47.6 g, 0.100 mmol). The reaction mixture was heated to reflux for 1 hour. After filtration, the filtrate was concentrated and purified by MDAP to give the title compound D146 (7 g, 0.015 mmol, 2.91% yield).

LCMS: 482 [M+H]$^+$. $t_R$=2.731 mins. (LCMS condition 1)
$^1$H NMR (400 MHz, DMSO-d$_6$): δ 11.30 (br. s., 1H), 8.26 (s, 1H), 7.92 (s, 1H), 6.92 (dd, J=2.32, 3.30 Hz, 1H), 6.24 (dd, J=1.96, 3.42 Hz, 1H), 4.82-4.99 (m, 1H), 4.44 (q, J=7.01 Hz, 2H), 3.63 (t, J=4.03 Hz, 4H), 2.66 (br. s., 1H), 2.44 (br. s., 4H), 2.37 (d, J=11.49 Hz, 1H), 1.99-2.30 (m, 4H), 1.60-1.76 (m, 1H), 1.35 (t, J=6.97 Hz, 3H).

Example 147 and 148

Enantiomer 1: trans-N-(5-chloro-1-(2,2-difluoro-5-morpholinocyclohexyl)-1H-pyrazol-4-yl)-4-ethoxy-7H-pyrrolo[2,3-d]pyrimidin-2-amine (E147)

Enantiomer 2: trans-N-(5-chloro-1-(2,2-difluoro-5-morpholinocyclohexyl)-1H-pyrazol-4-yl)-4-ethoxy-7H-pyrrolo[2,3-d]pyrimidin-2-amine (E148)

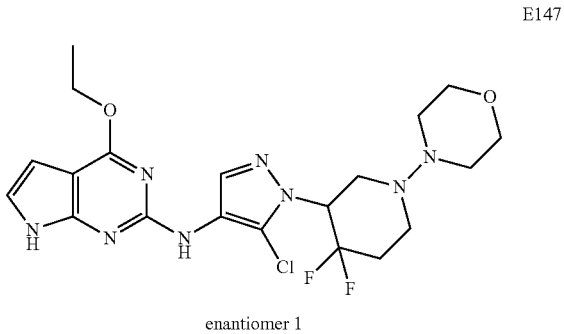

enantiomer 1

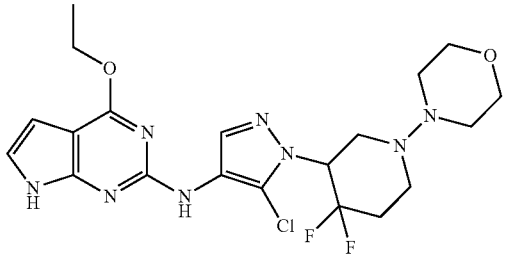

enantiomer 2

The title compounds E147 (36 mg, yield 18%, 100% ee) and E148 (33 mg, yield 17%, 98.7% ee) was obtained as white solids by separation of E145 (198 g, 0.410 mmol) using chiral prep-HPLC and prep-TLC (CH$_2$Cl$_2$:methanol=12:1).

E147: LCMS: 482 [M+H]$^+$. $t_R$=3.608 mins. (LCMS condition 3)

Chiral HPLC: $t_R$=6.636 mins. (Chiral condition: IC column: 5 um, 4.6*250 mm, Phase: Hex:EtOH=60:40, Flow rate: 1 ml/min, 230 nm) The absolute stereochemistry was not determined.

$^1$H NMR (400 MHz, CHLOROFORM-d): δ 8.68 (s, 1H), 8.27 (s, 1H), 6.79 (s, 1H), 6.42 (s, 1H), 6.35 (s, 1H), 4.59-4.47 (m, 3H), 3.74-3.71 (m, 4H), 2.75-2.57 (m, 6H), 2.40-2.30 (m, 1H), 2.24-2.16 (m, 1H), 2.03-1.77 (m, 3H), 1.45 (t, J=6.9 Hz, 3H);
$^{19}$F NMR (376 MHz, CDCl$_3$): δ −102.74, −103.37, −115.36, −115.99.

E148: LCMS: 482 [M+H]$^+$. $t_R$=4.067 mins. (LCMS condition 3)

Chiral HPLC: $t_R$=7.961 mins. (Chiral condition: IC column: 5 um, 4.6*250 mm, Phase: Hex:EtOH=60:40, Flow rate: 1 ml/min, 230 nm) The absolute stereochemistry was not determined.

$^1$H NMR (400 MHz, CHLOROFORM-d): δ 8.39 (s, 1H), 8.29 (s, 1H), 6.83-6.81 (m, 1H), 6.44-6.42 (m, 1H), 6.33 (s, 1H), 4.57-4.51 (m, 3H), 3.74-3.71 (m, 4H), 2.71-2.64 (m, 6H), 2.38-2.31 (m, 1H), 2.24-2.17 (m, 1H), 2.03-1.74 (m, 3H), 1.45 (t, J=7.2 Hz, 3H);
$^{19}$F NMR (376 MHz, CDCl$_3$): δ −102.74, −103.37, −115.39, −116.02.

Example 149

N-(5-chloro-1-(4-morpholinocyclohexyl)-1H-pyrazol-4-yl)-4-ethoxy-7H-pyrrolo[2,3-d]pyrimidin-2-amine (E149)

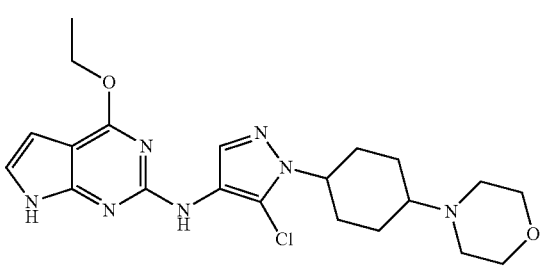 [SMILES: CCOc1nc(Nc2cnn(C3CCC(N4CCOCC4)CC3)c2Cl)nc2[nH]ccc12]

A solution of D1 (168 g, 0.852 mmol), D336 (202.1 g, 0.710 mmol), X-phos (67.7 g, 0.142 mmol), K$_2$CO$_3$ (490 g, 3.55 mmol) and Pd$_2$(dba)$_3$ (65.0 g, 0.071 mmol) in 1,4-dioxane (10 mL) was stirred at 120° C. for 5 hours. After cooled to room temperature, the reaction mixture was diluted with water (20 mL). Then the mixture was extracted with EA (10 mL×3). The combined organic phase was dried over anhydrous sodium sulphate, filtrated and concentrated. The crude was purified by column chromatography on silica gel (MeOH/DCM: 0 to 15%) and then MDAP (base) to give the title compound E149 (8.6 g, 0.019 mmol, 2.72% yield).

LCMS: 446[M+H]$^+$. $t_R$=2.446 mins. (LCMS condition 1)

$^1$H NMR (400 MHz, DMSO-d$_6$): δ 11.28 (br. s., 1H), 8.12 (s, 1H), 7.79 (s, 1H), 6.90 (br. s., 1H), 6.24 (br. s., 1H), 4.44 (q, J=7.01 Hz, 2H), 4.34 (br. s., 1H), 3.62 (br. s., 4H), 2.41 (br. s., 4H), 1.98-2.21 (m, 5H), 1.46-1.68 (m, 4H), 1.35 (t, J=7.09 Hz, 3H).

Example 150

N-(5-chloro-1-((3S,5S)-5-fluoro-1-(oxetan-3-yl)piperidin-3-yl)-1H-pyrazol-4-yl)-4-ethoxy-7H-pyrrolo[2,3-d]pyrimidin-2-amine (E150)

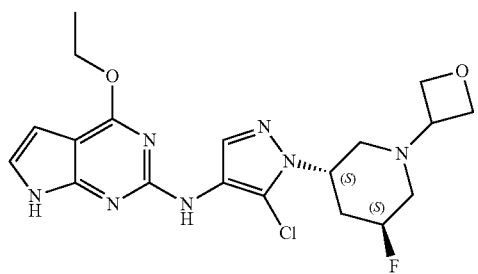

To a solution of D349 (60 g, 0.22 mmol), D1 (51 g, 0.263 mmol), X-phos (15 mg, 0.033 mmol) and K$_2$CO$_3$ (181 g, 1.30 mmol) in dioxane (10 mL) was added Pd$_2$(dba)$_3$ (20 g, 0.022 mmol) under N$_2$ atmosphere. The reaction was stirred overnight at 115° C. The mixture was then filtered, and the filtrate was concentrated. The crude was purified by column C18 (ACN/H$_2$O=35-55%) to give the title compound D150 (9.5 mg, 11%) as a white solid.

LCMS: 436 [M+H]$^+$. $t_R$=4.233 mins. (LCMS condition 3)

$^1$H NMR (400 MHz, CHLOROFORM-d): δ 8.47 (s, 1H), 8.17 (s, 1H), 6.80 (dd, J=3.2, 2.4 Hz, 1H), 6.42 (dd, J=3.2, 2.4 Hz, 1H), 6.28 (s, 1H), 4.88-4.81 (m, 0.5H), 4.75-4.55 (m, 7.5H), 3.70-3.63 (m, 1H), 3.15-3.12 (m, 1H), 2.88-2.85 (m, 1H), 2.57-2.53 (m, 1H), 2.35 (m, 2H), 2.05 (t, J=10.8 Hz, 1H), 2.26-2.20 (m, 1H), 2.08-2.00 (m, 1H), 1.46 (t, J=7.2 Hz, 3H).

$^{19}$F NMR (386 MHz, CDCl$_3$): δ −183.4.

Example 151

N-(5-chloro-1-((3R,5S)-5-fluoro-1-(oxetan-3-yl)piperidin-3-yl)-1H-pyrazol-4-yl)-4-ethoxy-7H-pyrrolo[2,3-d]pyrimidin-2-amine (E151)

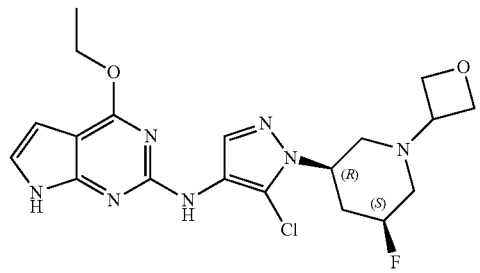

To a solution of D363 (230 g, 0.839 mmol), D1 (249 g, 1.26 mmol), X-phos (120 g, 0.252 mmol) and K$_2$CO$_3$ (463 g, 3.36 mmol) in dioxane (10 mL) was added Pd$_2$(dba)$_3$ (155 g, 0.168 mmol) under nitrogen. The reaction was stirred at 115° C. for 4 hrs. The mixture was filtered and the filtrate was concentrated. The crude was purified by column C18 (ACN/H$_2$O=35-50%) to give the title compound E151 (94 mg, 26%) as a white solid.

LCMS: 436 [M+H]$^+$. $t_R$=3.937 mins. (LCMS condition 3)

$^1$H NMR (400 MHz, CHLOROFORM-d): δ 11.28 (s, 1H), 8.23 (s, 1H), 7.85 (s, 1H), 6.90 (dd, J=3.2, 2.0 Hz, 1H), 6.23 (dd, J=3.2, 2.0 Hz, 1H), 5.13-5.01 (m, 1H), 4.67-4.61 (m, 1H), 4.54 (q, J=7.2 Hz, 2H), 4.48-4.40 (m, 4H), 3.63-3.57 (m, 1H), 3.01-2.87 (m, 2H), 2.34-2.13 (m, 4H), 1.35 (t, J=7.2 Hz, 3H).

F. Biological Data

As stated above, the compounds of present invention are LRRK2 kinase inhibitors, and are useful in the treatment of diseases mediated by LRRK2. The biological activities of the compounds of present invention can be determined using any suitable assay for determining the activity of a candidate compound as a LRRK2 kinase inhibitor, as well as tissue and in vivo models.

Production of 6His-Tev-LRRK2 (1326-2527)

A LRRK2 cDNA encoding residues 1326-2527 was received from Dundee University (described in M. Jaleel et al., 2007, Biochem J, 405: 407-417). This gene fragment was subcloned into pFB-HTb (Invitrogen) using BamHI and NotI restriction sites. The LRRK2 plasmid was recombined into the baculovirus genome according to the BAC-to-BAC protocol described by Invitrogen. Transfection into Spodoptera frugiperda (Sf9) insect cells was performed using Cellfectin (Invitrogen), according to the manufacturer's protocol to generate P1 and P2 baculovirus stocks.

Sf9 cells were grown in HyClone SFX (Thermo Scientific) growth media at 27° C., 80 rpm in shake flask until of a sufficient volume to inoculate a bioreactor. The cells were grown in a 20 liter working volume Wave bioreactor (GE Healthcare) at 27° C., 50% dissolved oxygen and an agitation rate 22 rocks per minute, 10 degree rock angle, 200 ml/min air with a cell concentration of approximately 6×e6 cells/ml. The cells were infected with P2 Baculovirus at a multiplicity of infection (MOI) of 3. The cultivation was continued for a 48 hour expression phase. The infected cells were removed from the growth media by centrifugation at 2500 g using a Sorvall RC 3C Plus centrifuge at 2500 g for 20 minutes. The cell pellet was immediately frozen and subsequently supplied for purification.

A 260 g pellet was allowed to thaw in a water bath at 27° C. with 800 ml lysis buffer/buffer A (50 mm Tris-HCl pH 8.5, 300 mM NaCl, 1 mm DTT, 10% glycerol, 1 ml/L calbiochem complete protease inhibitor cocktail and benzonase (50 ul/800 ml)) before being dounce homogenised on ice using 20 strokes per 100 ml. The suspension was packed in ice and sonicated at 50% amplitude for 3 min 10 sec on/off using a ¾" probe. The suspension was then centrifuged at 100,000 g for 90 min, at 4° C.

The lysate (700 ml) was decanted from the insoluble pellet and contacted for 3 h at 4 C with 10 ml His bind Ni NTA resin by end over end mixing. The resin was recovered by centrifugation, 3000 g, 5 min at 4 C, and packed in an XK16 column. The column was then washed with 10 column volumes buffer A, 10 column volumes buffer B (buffer A+1M NaCl) and 10 column volumes buffer C (buffer A+20 mM imidazole). The column was then eluted with 15 column volumes buffer D (buffer A+300 mM imidazole) collecting 2 ml fractions. All washes and elution were conducted at 4 ml/min.

Fractions identified by SDS-PAGE as containing protein of interest were pooled and loaded directly onto a 320 ml SEC Superdex 200 pg column that was pre-equilibrated with buffer E (50 mM Tris-HCl pH 8.5, 300 mM NaCl, 10% glycerol, 1 mM DTT). The column was loaded and eluted with 1.2 column volumes buffer E at 2 ml/min collecting 2 ml fractions. Fractions identified by SDS-PAGE as containing protein of interest were tested for activity.

Production of Biotin-Longer LRRKtide

The peptide (biotin-RLGRDKYKTLRQIRQGNTKQR-OH) was assembled at a 0.2 mM scale using FMOC solid phase peptide synthesis on an ACT 357 MPS automated peptide synthesizer. The resulting crude peptide was cleaved from the resin using a 95:2.5:2.5 mix of trifluoroacetic acid: triisopropylsilane: water. The crude cleaved peptide was purified by reverse phase HPLC, eluting with a 5-35% gradient of 0.1% trifluoroacetic acid/acetonitrile in 0.1% trifluoroacetic acid/water.

Production of LRRKtide for LRRK2 Inhibition Mass Spectrometry Assay

The 'LRRKtide' peptide H-RLGRDKYKTLRQIRQ-OH was synthesized as follows. The protected peptide was assembled on a solid-phase synthesiser using preloaded Wang resin and utilising standard Fmoc synthesis protocols. The crude peptide was obtained after cleavage from the resin with a mixture of trifluoroacetic acid (TFA), triisopropylsilane and water (95:2.5:2.5) for 3 hours at room temperature and was then purified using a C18 reverse-phase column utilising a 0.1% TFA-buffered water/acetonitrile gradient. The resulting fractions were analysed and fractions which were >95% pure by analytical HPLC and giving the correct molecular weight (mw) (by MALDiTOF mass spectroscopy) were pooled and freeze dried. The final material was analysed by HPLC and MALDiTOF mass spectroscopy.

Recombinant LRRK2 Enzyme Peptide Substrate TR-FRET Assay

This assay for LRRK2 inhibition is based on the detection of phosphorylation of the peptide 'longer LRRKtide' (biotin-RLGRDKYKTLRQIRQGNTKQR-OH) using a time resolved-fluorescence resonance energy transfer (TR-FRET) assay. It uses an antibody labelled europium chelate donor, W-1024 (Eu) and Streptavidin-Surelight APC acceptor (APC). When in close proximity, the excitation of Eu at 330 nm leads to energy transfer to APC with emission of light at 665 nm, Assay Protocol
1. A 10 mM test compound was dissolved in 100% DMSO and serially diluted 1 in 4. 100 nL was then added to a 384 well low volume black plate, excluding columns 6 and 18. 100 nL of DMSO was added to columns 6 and 18 as controls wells. Assay dilution gave a top final assay concentration of test compound of 166.67 µM
2. 3 uL of 'enzyme solution' containing 120 nM of purified recombinant 6HIS-Tev-LRRK2 (1326-2527) in assay buffer (50 mM Hepes (pH 7.2), 10 mM $MgCl_2$, 150 mM NaCl, 5% glycerol, 0.0025% triton X-100 and 1 mM DTT) was added to all wells except column 18 using a multidrop combi dispenser, giving a final assay concentration of 60 nM LRRK2 enzyme. 3 uL assay buffer only was added to column 18 using a multidrop combi dispenser as a 100% inhibition, no enzyme control. Column 6 (enzyme plus DMSO) gave was 0% inhibition. Test plates were then incubated for 30 minutes at room temperature.
3. 3 uL 'substrate solution' containing 2 uM Biotin-longer LRRKtide peptide substrate and 20 uM ATP was added to all wells of the plate using a multidrop combi dispenser giving a final assay concentration of 1 uM Biotin-longer LRRKtide and 10 uM ATP. Test plates were then incubated for 2 hours at room temperature. (Incubation may vary depending on rate and linearity of reaction with different enzyme batches).
4. 6 uL of 'detection solution' containing 200 nM Streptavidin SureLight® APC, 2 nM Eu-W1024 labelled anti-rabbit IgG antibody and 1:500 dilution of Phospho-Ezrin (Thr567)/Radixin (Thr564)/Moesin (Thr558) Polyclonal Antibody in 'stop' assay buffer (50 mM Hepes (pH 7.2), 60 mM EDTA, 10 mM $MgCl_2$, 150 mM NaCl, 5% glycerol and 0.0025% triton X) was added to all wells of the plate using a multidrop combi dispenser. Test plates were then incubated for a further 2 hours at room temperature and then read on a suitable plate reader (Excitation 330 nm, emission 620 nm (Eu) and 665 nm (APC)). Data is analysed using ActivityBase software (IDBS). Dilutions and concentrations of reagents determined on a batch to batch basis LRRK2 Inhibition Mass Spectrometry Assay This assay for Leucine Rich Repeat Kinase 2 (LRRK2) inhibition is based on the direct measurement of the peptide 'LRRKtide' (LRRKtide: RLGRDKYKT*LRQIRQ (H-RL-GRDKYKTLRQIRQ-OH used for this screen)) and phosphorylated 'LRRKtide' using a high throughput RapidFire mass spectrometry assay. Inhibitors are defined as compounds which reduce the conversion of LRRKtide to Phospho-LRRKtide.

Assay Protocol
1. A 10 mM test compound was dissolved in 100% DMSO and serially diluted 1 in 4. 100 nL of this dilution series was then added to a 384 well, v bottom polypropylene plate, excluding columns 6 and 18. 100 nL of DMSO was added to columns 6 and 18 as controls wells. Assay dilution gave a top final assay concentration of test compound of 166.67 µM
2. 5 uL of 'enzyme solution' containing 120 nM of purified recombinant 6HIS-Tev-LRRK2 (1326-2527) in assay buffer (50 mM Hepes (pH 7.2), 10 mM MgCl2, 150 mM NaCl, 5% glycerol, 0.0025% triton X-100 and 1 mM DTT) was added to all wells except column 18 using a multidrop combi dispenser, giving a final assay concentration of 60 nM LRRK2 enzyme. 5 uL assay buffer only was added to column 18 using a multidrop combi dispenser as a 100% inhibition control, column 6 (enzyme plus DMSO) gave 0% inhibition. Test plates were then incubated for 30 minutes at room temperature.

3. 5 uL 'substrate solution' containing 50 uM LRRKtide peptide substrate and 40 uM ATP was added to all wells of the plate using a multidrop combi dispenser giving a final assay concentration of 25 uM LRRKtide and 20 uM ATP. Test plates were then incubated for 1 hour at room temperature. (Incubation may vary depending on rate and linearity of reaction with different enzyme batches).

5. 50 ul of 1% formic acid in laboratory grade water was added to all wells to quench the reaction, and plates were centrifuged at 3000 rpm for 10 minutes. Test plates were then analysed on an Agilent RapidFire High Throughput solid phase extraction system coupled to AB Sciex API 4000 triple quadropole mass spectrometer with the following setting:

Dilutions and concentrations of reagents determined on a batch to batch basis

RapidFire Settings:
Sip Height=2 mm, Aspirate=500 ms, Load time=3000 ms, Elution time=3000 ms, Requilibration=500 ms,
Flow rates: pump 1=1.5 mL/min, pump 2 1.25 mL/min pump 3=0.8 mL/min Mass Spectrometer Settings
LRRKtide Detection settings: Q1 mass 644.8 Da, Q3 mass 638.8, declustering potential 76 volts, collision energy 37 volts, CXP 34 volts
Phospho-LRRKtide Detection settings: Q1 mass 671.4 Da, Q3 mass 638.8, Declustering potential 76 volts, Collision energy 37 volts, CXP 34 volts.
A C4 cartridge was used and running buffers were: A (aqueous) 0.1% formic acid in water B (organic) 0.1% formic acid, 80% acetonitrile, 20% water 5. Data was analysed using ActivityBase software (IDBS). A percent conversion from LRRKtide to Phospho-LRRKtide was calculated using the following formula:

% conversion=(Phospho-LRRKtide product peak area/(Phospho-LRRKtide product peak area+ LRRKtide substrate peak area))*100

Recombinant Cellular LRRK2 AlphaScreen Assay

To determine the activity of compounds against LRRK2 kinase activity in cells, the observed LRRK2 kinase-dependent modulation of LRRK2 Ser 935 phosphorylation (Dzamko et al., 2010, Biochem. J. 430: 405-413) was utilized to develop a quantitative 384 well plate-based immunoassay of LRRK2 Ser935 phosphorylation in the human neuroblastoma cell line SH-SY5Y, engineered to over-express recombinant full length LRRK2 protein.

A BacMam virus expressing full length recombinant LRRK2 was purchased from Invitrogen and amplified by inoculation of SF-9 cells at MOI 0.3 for 4-5 days in Sf-900 III SFM medium supplemented with 3% fetal bovine serum. Infected cell cultures were then centrifuged at 2000 g for 20 minutes, viral supernatant titer determined by anti-gp64 plaque assay and stored at 4° C.

Affinity-purified anti-phospho LRRK2 Ser935 sheep polyclonal antibody (Dzamko et al., 2010, Biochem. J. 430: 405-413) was biotinylated by standard methods (PerkinElmer). Anti-LRRK2 rabbit polyclonal antibody was purchased from Novus Biologicals. AlphaScreen Protein A IgG Kit (including acceptor and donor beads) was purchased from Perkin Elmer.

SH-SY5Y cells were grown in DMEM/F12 medium with 10% dialysed fetal bovine serum and harvested by treatment with 0.5% trypsin-EDTA for 5 minutes at 37° C. followed by centrifugation at 1000 rpm for 4 minutes. The cell pellet was resuspended in Opti-MEM reduced serum media (Invitrogen) at 200,000 cells/ml and mixed with the BacMam LRRK2 virus at MOI=50. 50 µl cell solutions were then dispensed to each well of a 384-well plate and incubated at 37° C., 5% $CO_2$ for 24 hours.

Serial dilutions of test compounds were prepared in Opti-MEM reduced serum media (Invitrogen) and 5.6 ul transferred from compound plate to cell assay plate to achieve a top final assay concentration of 10 uM. DMSO was used in certain wells as controls. Cells were incubated at 37° C., 5% $CO_2$ for 60 minutes. The medium was then removed and cells lysed by addition of 20 ul cell lysis buffer (Cell Signaling Technology) and incubation at 4° C. for 20 minutes. 10 ul of antibody/acceptor bead mix [(1/1000 biotinylated-pS935 LRRK2 antibody, 1/1000 total-LRRK2 antibody, 1/100 Acceptor beads in AlphaScreen detection buffer (25 mM Hepes (pH 7.4), 0.5% Triton X-100, 1 mg/ml Dextran 500 and 0.1% BSA)] was then added to each well and plates incubated for 2 hours at ambient temperature in the dark. 10 µl of donor beads solution (1/33.3 donor beads in AlphaScreen detection buffer) was then added to each well. Following incubation for a further 2 hours at ambient temperature in the dark, plates were read on an EnVision™ plate reader at emission 520-620 nm with excitation 680 nm. Dose response curve data was based on sigmoidal dose-response model.

Pharmacological Data

Compounds of Examples E1-E151 were tested in the recombinant LRRK2 enzyme peptide substrate TR-FRET assay, the recombinant cellular LRRK2 alphaScreen assay, and/or LRRK2 Inhibition Mass Spectrometry Assay. The compounds of Examples E1-E151 were found to inhibit LRRK2 kinase activity in at least one assay.

The $pIC_{50}$ value for each compound was either reported in at least one experiment or the average of multiple experiments. It is understood that the data described herein may have reasonable variations depending on the specific conditions and procedures used by the person conducting the experiments.

The compounds of Examples E1-E151 were tested in the recombinant cellular LRRK2 alphaScreen assay and exhibited a $pIC_{50} \geq 5.0$. The compounds of examples E1, E3, E4, E8-E11, E14-E18, E21, E22, E26-E31, E34-E59, E62-E68, E70, E73-E78, E81-88, E92-111, E113-117, E119-125, E128, E130-E143, E145-E146, and E148-E151 exhibited $pIC_{50} \geq 7.0$.

The compounds of Examples E1-E6, E9-E17, E19, E21, E23-E38, E40-E52, E56, E62-E65, E67, E68, E70, E74, E78, E83-E88, and E90-97 were tested in the recombinant LRRK2 enzyme peptide substrate TR-FRET assay and exhibited a $pIC_{50} \geq 5.0$. The compounds of Examples E1-E4, E9-E17, E19, E21, E24, E28-E38, E40-E52, E56, E62-E65, E67, E68, E70, E74, E78, E83-E88, and E90-E97 exhibited $\geq 7.0$.

The compounds of Examples E11, E31, E53, E54, E58-E60, E65, E74, E86, E98, E100, E102-109, E113-121, E123-E124, E127-E128, E131, E134-E137, E139, and E150 were tested in the LRRK2 Inhibition Mass Spectrometry Assay and exhibited a $pIC_{50} \geq 7.0$.

For example, the pIC50 values of recombinant cellular LRRK2 alphaScreen assay and recombinant LRRK2 enzyme peptide substrate TR-FRET assay for following examples are:

| Example No | recombinant cellcular LRRK2 alphaScreen assay (pIC50) | recombinant LRRK2 enzyme peptide substrate TR-FRET assay (pIC50) |
|---|---|---|
| E3 | 7.1 | 7.9 |
| E14 | 7.2 | 7.9 |
| E37 | 7.6 | 9 |
| E38 | 7.6 | 9.1 |
| E40 | 7.8 | 8.3 |
| E41 | 7.8 | 8 |
| E44 | 7.2 | 8.1 |
| E45 | 7.7 | 8 |
| E52 | 7.9 | 8.1 |
| E56 | 7.8 | 8.1 |

For example, the pIC50 values of recombinant cellular LRRK2 alphaScreen assay and LRRK2 Inhibition Mass Spectrometry Assay for following examples are:

| Example No | recombinant cellcular LRRK2 alphaScreen assay (pIC50) | LRRK2 Inhibition Mass Spectrometry Assay (pIC50) |
|---|---|---|
| E86 | 7.4 | 8 |
| E100 | 7.5 | 8.1 |
| E104 | 7.5 | 8.1 |
| E105 | 7.6 | 8.1 |
| E113 | 7.6 | 8 |
| E117 | 8.6 | 7.9 |
| E 121 | 9.2 | 8 |
| E123 | 7 | 7.9 |
| E124 | 9.1 | 8 |
| E 134 | 8.3 | 8.1 |
| E141 | 7.8 | 8.1 |
| E150 | 7.5 | 7.9 |

What is claimed is:

1. A compound which is (R)-N-(5-chloro-1-(3,3-difluoro-1-(oxetan-3-yl)piperidin-4-yl)-1H-pyrazol-4-yl)-4-ethoxy-7H-pyrrolo[2,3-d]pyrimidin-2-amine, or a pharmaceutically acceptable salt thereof.

2. A pharmaceutical composition comprising the compound, or pharmaceutically acceptable salt thereof, according to claim 1, and one or more pharmaceutically acceptable excipients.

3. A method of treatment of Parkinson's disease which comprises administering to a subject in need thereof a therapeutically effective amount of the compound, or pharmaceutically acceptable salt thereof, according to claim 1.

4. The method of claim 3, wherein the subject is human.

5. The method of claim 3 wherein the Parkinson's disease is familial Parkinson's disease and the subject expresses LRRK2 kinase bearing G2019S mutation.

6. A compound having the formula:

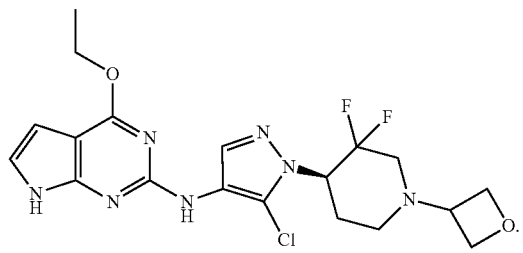 [SMILES: CCOc1nc(Nc2cnn([C@@H]3CCN(C4COC4)CC3(F)F)c2Cl)nc2[nH]ccc12]

7. A pharmaceutical composition comprising the compound according to claim 6, and one or more pharmaceutically acceptable excipients.

8. A method of treatment of Parkinson's disease which comprises administering to a subject in need thereof a therapeutically effective amount of the compound according to claim 6.

9. The method of claim 8, wherein the subject is human.

10. The method of claim 8, wherein the Parkinson's disease is familial Parkinson's disease and the subject expresses LRRK2 kinase bearing G2019S mutation.

11. A pharmaceutically acceptable salt of a compound having the formula:

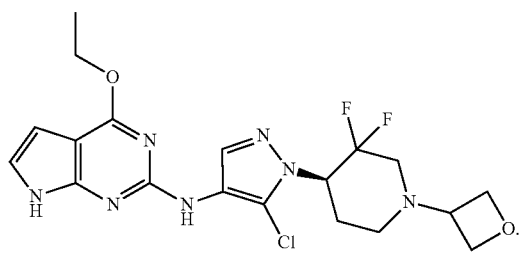 [SMILES: CCOc1nc(Nc2cnn([C@@H]3CCN(C4COC4)CC3(F)F)c2Cl)nc2[nH]ccc12]

12. A pharmaceutical composition comprising the pharmaceutically acceptable salt according to claim 11, and one or more pharmaceutically acceptable excipients.

13. A method of treatment of Parkinson's disease which comprises administering to a subject in need thereof a therapeutically effective amount of the pharmaceutically acceptable salt according to claim 11.

14. The method of claim 13, wherein the subject is a human.

15. The method of claim 13 wherein the Parkinson's disease is familial Parkinson's disease and the subject expresses LRRK2 kinase bearing G2019S mutation.

* * * * *